United States Patent
Hirst et al.

(10) Patent No.: US 7,332,497 B2
(45) Date of Patent: *Feb. 19, 2008

(54) PYRAZOLOPYRIMIDINES AS THERAPEUTIC AGENTS

(75) Inventors: Gavin C. Hirst, Marlborough, MA (US); Paul Rafferty, Westborough, MA (US); Kurt Ritter, Frankfurt (DE); David Calderwood, Framingham, MA (US); Neil Wishart, Holden, MA (US); Lee D. Arnold, Westborough, MA (US); Michael M. Friedman, Newton, MA (US)

(73) Assignee: Abbott GmbH & Co KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/104,140

(22) Filed: Mar. 22, 2002

(65) Prior Publication Data
US 2004/0006083 A1   Jan. 8, 2004

Related U.S. Application Data

(60) Provisional application No. 60/278,047, filed on Mar. 22, 2001.

(51) Int. Cl.
*C07D 487/04* (2006.01)
*A61K 31/519* (2006.01)

(52) U.S. Cl. .................. 514/262.1; 544/262
(58) Field of Classification Search ............ 544/262; 514/262.1
See application file for complete search history.

(56) References Cited

U.S. PATENT DOCUMENTS

| | | | | |
|---|---|---|---|---|
| 4,966,849 | A | 10/1990 | Vallee et al. | 435/199 |
| 5,217,999 | A | 6/1993 | Levitzki et al. | 514/613 |
| 5,302,606 | A | 4/1994 | Spada et al. | 514/357 |
| 5,330,992 | A | 7/1994 | Eissenstat et al. | 514/312 |
| 5,593,997 | A | 1/1997 | Dow et al. | |
| 6,383,790 | B1* | 5/2002 | Shokat | 435/194 |
| 6,660,744 | B1* | 12/2003 | Hirst et al. | 514/262.1 |
| 6,921,763 | B2* | 7/2005 | Hirst et al. | 514/262.1 |
| 2002/0156081 | A1* | 10/2002 | Hirst et al. | 514/247 |

FOREIGN PATENT DOCUMENTS

| | | |
|---|---|---|
| EP | 0566226 | 10/1993 |
| WO | 91/15495 | 10/1991 |
| WO | 92/20642 | 11/1992 |
| WO | 92/21660 | 12/1992 |
| WO | 94/03427 | 2/1994 |
| WO | 94/10202 | 5/1994 |
| WO | 94/14808 | 7/1994 |
| WO | 97/22596 | 6/1997 |
| WO | 97/34876 | 9/1997 |
| WO | 97/40830 | 11/1997 |
| WO | 97/40831 | 11/1997 |
| WO | 97/42187 | 11/1997 |
| WO | 98/07832 | 2/1998 |
| WO | 00/42042 | 7/2000 |
| WO | 01/19829 | 3/2001 |
| WO | WO 02/080926 | 10/2002 |

OTHER PUBLICATIONS

Tanaka et al., PubMed Abstract (Cell. 108(3):317-29), Feb. 2002.*
Rogers et al., PubMed Abstract (J. Cell Biol. 157(2):219-29), Apr. 2002.*
Casanova et al., PubMed Abstract (Rev Neurol. 28(9):909-15), May 1999.*
Traxler, Review: Oncologic, Endocrine & Metabolic Protein Tyrosine Kinase inhibitors in cancer treatment, Exp. Opin. Ther. Patents, 7(6):571-588, 1997.*
Simone, Oncology: Introduction, Cecil Textbook of Medicine, 20th Edition, vol. 1, pp. 1004-1010, 1996.*
Amato et al., PubMed Abstract (Best Pract Res Clin Obstet Gynaecol. 18(5):707-18) Oct. 2004.*
Suh et al., PubMed Abstract (J Biol Chem. 278(24):21960-71) Epub Mar. 2003.*
Iovino et al., PubMed Abstract (Clin J Oncol Nurs. 7(5):535-40) Sep.-Oct. 2003.*
Baba, PubMed Abstract (Curr Top Med Chem. 4(9):871-82) 2004.*
Carmeliet et al., Angiogenesis in cancer and other diseases, Nature, vol. 407, pp. 249-257, Sep. 2000.*
Schlessinger and Ulrich, "Growth Facotr Signaling by Receptor Tyrosine Kinases", (1992), Neuron, 9:383-391.
Armstrong, "Treatment of Opportunistic Fungal Infections", (1993), Clinical Infectious Diseases, 16:1-7.
Stacker, S.A., Vitali, A., Domagala, T., Nice, E., and Wilks, A.F., "Mutations in the V3 Domain of the Cysteine-Knot Motif of Mouse Vascular Endothelial Growth Factor (VEGF) Modulate the Interaction with VEGFR2 (FLK-1) but do not Inhibit Vascular Permeability", Angiogenesis and Cancer Conference, Amer. Assoc. Cancer Res., Jan. 1998, Orlando, FL.

(Continued)

*Primary Examiner*—Deepak Rao
(74) *Attorney, Agent, or Firm*—Kenneth P. Zwicker; Gayle B. O'Brien

(57) ABSTRACT

The present invention provides compounds of Formula I,

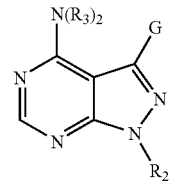

(I)

including pharmaceutically acceptable salts and/or prodrugs thereof, where G, $R_a$, $R_2$, and $R_3$ are defined as described herein.

24 Claims, No Drawings

OTHER PUBLICATIONS

Williams, "Factors regulating the Expression of Vascular Permeability/Vascular Endothelial Growth Factor by Human Vascular Tissues", (1997), Diabetelogia, 40:S118-120.

Zindy et al., "Cyclin A is Required in S Phase in Normal Epithelial Cells", (1992), Biochemical & Biophysical Research Communications, 182:1144-1154.

Buchdunger et al., "Selective Inhibition of the Platelet-Derived Growth Factor Signal Transduction Pathway by a Protein-Tyrosine Kinase Inhibitor of the 2-Phenylaminopyrimidine Class", (1995), Proceedings of the National Academy of Science USA, 92:2558-2562.

Borthwick et al., "Inhibition of Glycogen Synthase Kinase-3 by Insulin in Cultured Human Skeletal Muscle Myoblasts", (1995), Biochemical & Biophysical Research Communications, 210(3):738-745.

Badger et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function", (1996), The Journal of Pharmacology and Experimental Therapeutics, 279:1453-1461.

Vousden, "Interactions of Human Papillomavirus Transforming Proteins with the Products of Tumor Suppressor Genes", (1993), FASEB Journal, 7:8720879.

Olofsson et al, "Vacsular Endothelial Growth Factor B (VEGF-B) Binds to VEGF Receptor-1 and Regulates Plasminogen Activator Activity in Endothelial Cells", 1998), Proc. Natl. Acad. Sci. U. S. A., 95(20): 11709-11714.

Shoelson, "SH2 and TB Domain Interactions in Tyrosine Kinase Signal Transduction", (1997), Curr. Opin. Chem. Biol., 1(2), 227-234.

Meyer et al, "A Novel Vascular Endothelial Growth Factor Encoded by Orf Virus, VEGF-E, Mediates Angiogenesis Via Signaling Through VEGFR-2 (KDR) but not VEGFR-1 (Flt-1) Receptor Tyrosine Kinases", (1999), EMBO J., 18(2), 363-374.

"4-Anilinoquinazoline Derivatives", (1998), Expert Opin. Ther. Pat., 8(4): 475-478.

Witzenbichler et al, "Vascular Endothelial Growth Factor-C (VEGF-C/VEGF-2) Promotes Angiogenesis in the Setting of Tissue Ischemia", (1998), Am. J. Pathol., 153(2), 381-394.

Lymboussaki et al, "Expression of the Vascular Endothelial Growth Factor C Receptor VEGFR-3 in Lymphatic Endothelium of the Skin and in Vascular Tumors", (1998), Am. J. Pathol., 153(2): 395-403.

Achen et al, "Vascular Endothelial Growth Factor D (VEGF-D) is a Ligand for the Tyrosine Kinases VEGF Receptor 2 (Flk1) and VEGF Receptor 3 (Flt4)", Proc. Natl. Acad. Sci. U. S. A., 95(2), 548-553.

Cowburn, "Peptide Recognition by PTB and PDZ Domains", (1997), Curr. Opin. Struct. Biol., 7(6), 835-838.

Solomon et al., "Cyclin Activation of p34cdc2", (1990), Cell, 63:1013-1024.

Oelrichs et al, "NYK/FLK-1: A Putative Receptor Protein Tyrosine Kinase Isolated From E10 Embryonic Neuroepithelium is Expressed in Endothelial Cells of the Developing Embryo", (1993), Oncogene, 8(1):11-15.

Ferrara et al., "The Biology of Vascular Endothelial Growth Factor", (1997), Endocrine Reviews, 18(1);4-25.

Shawver et al., "Receptor Tyrosine Kinases as Targets for Inhibition of Angiogenesis", (1997), Drug Discovery Today, 2:50-63.

Kohn et al., "Cell Cycle Control and Cancer Chemotherapy", (1994), Journal of Cellular Biochemistry, 54:440-452.

Powis, "Signalling Pathways as Targets for Anticancer Drug Development", (1994), Pharmacology & Therapeutics, 62:57-95.

Pines, "Cell Proliferation and Control", (1992), Current Opinion in Cell Biology, 4:144-148.

Korpelainen and Alitalo, "Signaling Angiogenesis and Lymphangiogenesis", (1998), Curr. Opin. Cell Biol., 159-164.

Kolch et al., "Regulation of the Expression of the VEGF/VPS and its Receptors: Rile in Tumor Angiogenesis", (1995), Breast Cancer Research and Treatment, 36: 139-155.

Pines, "Cyclins and Cyclin-dependent Kinases: Take Your Partners", (1993), Trends in Biochemical Sciences, 18:195-197.

Courtneidge, "Protein Tyrosine Kinases, with Emphasis on the Src Family", (1994), Seminars in Cancer Biology, 5:236-246.

Ferrara et al., "The Vascular Endothelial Growth Factor Family of Polypeptides", (1991), J. Cell. Biochem., 47:211-218.

Klagsburn and D'Amore, "Vascular Endothelial Growth Factor and its Receptors", (1996), Cytokine & Growth Factor Reviews, 7: 259-270.

Draetta, "Cdc2 Activation: The Interplay of Cyclin Binding and Thr161 Phosphorylation", (1993), Trends in Cell Biology, 3:287-289.

Staunton et al, "The Arrangement of the Immunoglobulin-like Domains of ICAM-1 and the Binding Sites for LFA-1 and Rhinovirus", (1990), Cell, 61:243-254.

Osmani et al., "Parallel Activation of the NIMA and P34cdc2 Cell Cycle-Regulated Protein Kinases is Required to Initiate Mitosis in *A. nidulans*", (1991), Cell, 67:283-291.

Brickell, "The p60c-src Family of Protein-Tyrosine Kinases: Structure, Regulation and Function", (1992), Critical Reviews in Oncogenesis, 3(4):401-406.

Myers et al., "The Preparation and SAR of 4-(Anilino), 4(Phenoxy), and 4-(Thiophenoxy)-Quinazolines: Inhibitors of p561ck and EGF-R Tyrosine Kinase Activity", (1997), Bioorganic & Medicinal Chemistry Letters, 7(4):417-420.

He et al., "The Human Cytomegalovirus UL97 Protein is a Protein Kinase That Autophosphorylates on Serine and Threonines", (1997), Journal of Virology, 71:405-411.

Yarden and Ullrich, Growth Factor receptor Tyrosine Kinases:, (1988), Ann. Rev. Biochem., 57:433-478.

Shibuya et al., "Nucleotide Seuence and Expression of a Novel Human Receptor-Type Tyrosine Kinase Gene (flt) Closely Related to the fms Family", (1990), Oncogene, 5:519-524.

Murray and Kirschner, "Cyclin Synthesis Drives the Early Embryonic Cell Cycle", (1989), Nature, 339:275-280.

Hunter and Pines, "Cyclins and Cancer II: Cyclin D and CDK Inhibitors Come of Age", (1994), Cell, 79:573-582.

Aplin et al., "In Vitro Phosphorylation of the Cytoplamic Domain of the Amyloid Precursor Protein by Glycogen Synthase Kinase-3β", (1996), Journal of Neurochemistry, 67:699-707.

Lees, "Cyclin Dependent Kinase Regulation", (1995), Current Opinion in Cell Biology, 7:773-780.

Perkins et al., "Regulation of NF-kB by Cyclin-Dependent Kinases Associated with the p300 Coactivator", (1997), Science, 275:523-527.

Hosoi et al., "Evidence for cdk5 as a Major Activity Phosphorylating Tau Protein in Porcine Brain Extract", (1995), Journal of Biochemistry (Tokyo), 117:741-749.

Millauer et al., "High Affinity VEGF Binding and Developmental Expression Suggest Flk-1 as a Major Regulator of Vasculogenesis and Angiogenesis", (1993), Cell, 72:835-846.

Tanaka et al., "c-Cbl is Downstream of c-Src in a Signalling Pathway Necessary for Bone Resorption", (1996), Nature, 383:528-531.

Maglione et al. "Two Alternative mRNAs Coding for the Angiogenic Factor, Placenta Growth Factor (PIGF), are Transcribed from a Single Gene of Chromosome 14" (1993), Oncogene, 8:925-31.

Jakeman et al., "Developemtn Expression of Binding Sites and Messenger Ribonucleic Acid for Vascular Endothelial Growth Factor Suggest a Rile for This Protein in Vasculogenesis and Angiogenesis", (1993), Endocrinology, 133(2):848-859.

Mustonen and Alitalo, "Endothelial Receptor Tyrosine Kinases Involved in Angiogenesis", (1995), J. Cell Biol. 129:895-898.

Beg and Baltimore, "An Essential Role for NF-kB in Preventing TNF-a-Induced Cell Death", (1996), Science, 274:782-784.

Wang et al., "TNF- and Cancer Therapy-Induced Apoptosis: Potentiation by Inhibition of NF-kB", (1996), Science, 274:784-787.

Van Antwerp et al., "Suppression of TNF-a-Induced Apoptosis by NF-kB", (1996), Science, 274:787-789.

Sherr, "Mammalian G1 Cyclins", (1993), Cell, 73:1059-1065.

Girard et al., Cyclin A is Required for the Onset of DNA Replication in Mammalian Fibroblasts, (1991), Cell, 67, 1169-1179.

Pagano et al., "Cyclin A is Required at Two Points in the Human Cell Cycle", (1992), EMBO Journal, 11:961-971.

Rosenblatt et al., "Human Cyclin-Dependent Kinase 2 is Activated During the S and G2 Phases of the Cycle and Associates with Cyclin A", (1992), Proceedings of the National Academy of Science USA, 89:2824-2828.

Walker and Maller, "Role for Cyclin A in the Dependence of Mitosis on Completion of DNA Replication", (1991), Nature, 354:314-317.

DeVries et al., "The fms-Like Tyrosine Kinase, a Receptor for Vascular Endothelial Growth Factor", (1992) Science, 255;989-991.

Quelle et al., "Overexpression of Mouse D-Type Cyclins Accelerates GI Phase in Rodent Fibroblasts", (1993), Genes & Development, 7:1559-1571.

Terman et al., "Identification of a New Endothelial Cell Growth Factor Receptor Tyrosine Kinase", (1991), Oncogene, 6:1677-83.

Resnitzky et al., "Acceleration of the GI/S Phase Transition by Expression of Cyclins D1 and E with an Inducible System", (1994), Molecular & Cellular Biology, 14:1669-1679.

Terman et al., "Identification of the KDR Tyrosine Kinase as a Receptor for Vascular Endothelial Cell Growth Factor", (1992), Biochem. Biophys. Res. Comm., 187:1579-86.

Matsushime et al., "D-Type Cyclin-Dependent Kinase Activity in Mammalian Cells", (1994), Molecular & Cellular Biology, 14:2066-2076.

Ohtsubo and Roberts, "Cyclin-Dependent Regulation of G1 in Mammalian Fibroblasts", (1993), Science, 259:1908-1912.

Kinsella, et al. "Protein Kinases C Regulates Endothelial Cell Tube Formation on Basement Membrane Matrix, Matrigel", (1992), Exp. Cell Res., 199:56-62.

Ullrich & Schlessinger, "Signal Transduction by Receptors with Tyrosine Kinase Activity", (1990), Cell, 61:203-212.

Takano, et al., "Inhibition of Angiogenesis by a Novel Diaminoanthraquinone that Inhibits Protein Kinases C.", (1993), Mol. Bio. Cell, 4:358A.

Fantl et al., "Distinct Phosphotyrosines on a Growth Factor Receptor Bind to Specific Molecules that Mediate Different Signaling Pathways", (1992), Cell, 69:413-423.

Wright, et al., "Inhibition of Angiogenesis In Vitro and In Ovo with an Inhibitor of Cellular Protein Kinases, MDL 27032", (1992), J. Cellular Phys., 152:448-57.

Osmani et al., "Activation of the nimA Protein Kinase Plays a Unique Role During Mitosis that Canot be Bypassed by Absence of the bimE Checkpoint", (1991), EMBO Journal, 10:2669-2679.

Songyang et al., "SH2 Domains Recognize Specific Phosphopeptide Sequences", (1993), Cell, 72:767-778.

Koch et al., "SH2 and SH3 Domains: Elements that Control Interactions of Cytoplasmic Signaling Proteins", (1991), Science, 252:668-678.

Kim et al., "Inhibition of Vascular Endothelial Growth Factor-Induced Angiogenesis Suppresses Tumor Growth in vivo", (1993), Nature, 362:841-844.

Stone et al., "Reversible. P16-mediated Cell Cycle Arrest as Protection from Chemotherapy", (1996), Cancer Research, 56:3199-3202.

Ducommun et al., "Cdc2 Phosphorylation is Required for its Interaction with Cyclin", (1991), EMBO Journal, 10(11):3311-3319.

Gautier et al., "Dephosphorylation and Activation of Xenopus p34cdc2 Protein Kinase During the Cell Cycle", (1989), Nature, 339:626-629.

Gould and Nurse, "Tyrosine Phosphorylation of the Fission Yeast cdc2+ Protein Kinase Regulates Entry into Mitosis", (1989), Nature, 342:39-45.

Krek and Nigg, "Mutations of p34cdc2 Phosphorylation Sites Induce Premature Mitotic Events in HeLa Cells: Evidence for a Double Block to p34cdc2 Kinase Activation in Vertebrates", (1991), EMBO Journal, 10(11):3331-3341.

* cited by examiner

PYRAZOLOPYRIMIDINES AS THERAPEUTIC AGENTS

CROSS REFERENCE TO RELATED APPLICATION

This application claims the benefit of U.S. Provisional Application No. 60/278,047, filed Mar. 22, 2001, now abandoned.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383-391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433-478, 1988; Ullrich and Schlessinger, *Cell* 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1-20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413-423; Songyang et al., 1994, *Mol. Cell. Biol.* 14:2777-2785; Songyang et al., 1993, *Cell* 72:767-778; and Koch et al., 1991, *Science* 252:668-678; Shoelson, *Curr. Opin. Chem. Biol.* (1997), 1(2), 227-234; Cowburn, *Curr. Opin. Struct. Biol.* (1997), 7(6), 835-838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767-778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767-778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895-898, 1995). One such receptor tyrosine kinase, known as □fetal liver kinase 1□ (FLK-1), is a member of the type III subclass of RTKs. An alternative designation for human FLK-1 is "kinase insert domain-containing receptor" (KDR) (Terman et al., *Oncogene* 6:1677-83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1):11-15, 1993). DNAs encoding mouse, rat and human FLK-1 have been isolated, and the nucleotide and encoded amino acid sequences reported (Matthews et al., *Proc. Natl. Acad. Sci. USA*, 88:9026-30, 1991; Terman et al., 1991, supra; Terman et al., *Biochem. Biophys. Res. Comm.* 187:1579-86, 1992; Sarzani et al., supra; and Millauer et al., *Cell* 72:835-846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255;989-991, 1992; Shibuya et al., *Oncogene* 5:519-524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259-270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848-859, 1993; Kolch et al., *Breast Cancer Research and Treatment* 36: 139-155, 1995; Ferrara et al., *Endocrine Reviews* 18(1); 4-25, 1997; Ferrara et al., *Regulation of Angiogenesis* (ed. L. D. Goldberg and E. M. Rosen), 209-232, 1997). In addition, VEGF has been implicated in the control and enhancement of vascular permeability (Connolly, et al., *J. Biol. Chem.* 264: 20017-20024, 1989; Brown et al., *Regulation of Angiogenesis* (ed. L. D. Goldberg and E. M. Rosen), 233-269, 1997). Different forms of VEGF arising from alternative splicing of mRNA have been reported, including the four species described by Ferrara et al. (*J. Cell. Biochem.* 47:211-218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.*, 159-164, 1998 and references cited therein).

Placenta growth factor (PlGF) has an amino acid sequence that exhibits significant homology to the VEGF sequence (Park et al., *J. Biol. Chem.* 269:25646-54, 1994; Maglione et al. *Oncogene* 8:925-31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272-22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709-11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol.* (1998), 153(2): 395-403; Witzenbichler et al, *Am. J. Pathol.* (1998), 153(2), 381-394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14),8413-8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S.A.* (1998), 95(2), 548-553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363-374; Ogawa et al, *J. Biol. Chem.* (1998), 273(47), 31273-31282.). VEGF-E sequences possess 25% homology to mammalian VEGF and are encoded by the parapoxyirus Orf virus (OV). This parapoxyirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular $Ca2+$ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118-120 (1997)).

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7-10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, thereful, useful in treating such disorders, and in other situations of inappropriate neovascularization.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, *Oncogene* 8:2025-2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Application No. WO 94/10202; Kendall & Thomas, 1994, *Proc. Natl. Acad. Sci* 90:10705-09; Kim et al., 1993, *Nature* 362:841-844), RNA ligands (Jellinek, et al., *Biochemistry* 33:10450-56; Takano, et al., 1993, *Mol. Bio. Cell* 4:358A; Kinsella, et al. 1992, *Exp. Cell Res.* 199:56-62; Wright, et al., 1992, *J. Cellular Phys.* 152:448-57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475-478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases.

High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is also known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The regulation of CDK activation is complex, but requires the association of the CDK with a member of the cyclin family of regulatory subunits (Draetta, *Trends in Cell Biology*, 3:287-289 (1993)); Murray and Kirschner, *Nature*, 339:275-280 (1989); Solomon et al., *Molecular Biology of the Cell*, 3:13-27 (1992)). A further level of regulation occurs through both activating and inactivating phosphorylations of the CDK subunit (Draetta, *Trends in Cell Biology*, 3:287-289 (1993)); Murray and Kirschner, *Nature*, 339:275-280 (1989); Solomon et al., *Molecular Biology of the Cell*, 3:13-27 (1992); Ducommun et al., *EMBO Journal*, 10:3311-3319 (1991); Gautier et al., *Nature* 339:626-629 (1989); Gould and Nurse, *Nature*, 342:39-45 (1989); Krek and Nigg, *EMBO Journal*, 10:3331-3341 (1991); Solomon et al., *Cell*, 63:1013-1024 (1990)). The coordinate activation and inactivation of different cyclin/CDK complexes is necessary for normal progression through the cell cycle (Pines, *Trends in Biochemical Sciences*, 18:195-197 (1993); Sherr, *Cell*, 73:1059-1065 (1993)). Both the critical G1-S and G2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066-2076 (1994); Ohtsubo and Roberts, Science, 259:1908-1912 (1993); Quelle et al., *Genes & Development*, 7:1559-1571 (1993); Resnitzky et al., *Molecular & Cellular Biology*, 14:1669-1679 (1994)). Progression through S-phase requires the activity of cyclin A/CDK2 (Girard et al., *Cell*, 67:1169-1179 (1991); Pagano et al., *EMBO Journal*, 11:961-971 (1992); Rosenblatt et al., *Proceedings of the National Academy of Science USA*, 89:2824-2828 (1992); Walker and Maller, *Nature*, 354:314-317 (1991); Zindy et al., *Biochemical & Biophysical Research Communications*, 182:1144-1154 (1992)) whereas the activation of cyclin A/cdc2 (CDK1) and cyclin B/cdc2 are required for the onset of metaphase (Draetta, *Trends in Cell Biology*, 3:287-289 (1993)); Murray and Kirschner, *Nature*, 339:275-280 (1989); Solomon et al., *Molecular Biology of the Cell*, 3:13-27 (1992); Girard et al., *Cell*, 67:1169-1179 (1991); Pagano et al., *EMBO Journal*, 11:961-971 (1992); Rosenblatt et al., *Proceedings of the National Academy of Science USA*, 89:2824-2828 (1992); Walker and Maller, *Nature*, 354:314-317 (1991); Zindy et al., *Biochemical & Biophysical Research Communications*, 182:1144-1154 (1992)). It is not surprising, therefore, that the loss of control of CDK regulation is a frequent event in hyperproliferative diseases and cancer. (Pines, *Current Opinion in Cell Biology*, 4:144-148 (1992); Lees, *Current Opinion in Cell Biology*, 7:773-780 (1995); Hunter and Pines, *Cell*, 79:573-582 (1994)).

Inhibitors of kinases involved in mediating or maintaining disease states represent novel therapies for these disorders. Examples of such kinases include, but are not limited to: (1) inhibition of c-Src (Brickell, *Critical Reviews in Oncogenesis*, 3:401-406 (1992); Courtneidge, *Seminars in Cancer Biology*, 5:236-246 (1994), raf (Powis, *Pharmacology & Therapeutics*, 62:57-95 (1994)) and the cyclin-dependent kinases (CDKs) 1, 2 and 4 in cancer (Pines, *Current Opinion in Cell Biology*, 4:144-148 (1992); Lees, *Current Opinion in Cell Biology*, 7:773-780 (1995); Hunter and Pines, Cell, 79:573-582 (1994)), (2) inhibition of CDK2 or PDGF-R kinase in restenosis (Buchdunger et al., *Proceedings of the National Academy of Science USA*, 92:2258-2262 (1995)), (3) inhibition of CDK5 and GSK3 kinases in Alzheimers (Hosoi et al., *Journal of Biochemistry* (Tokyo), 117:741-749 (1995); Aplin et al., *Journal of Neurochemistry*, 67:699-707 (1996), (4) inhibition of c-Src kinase in osteoporosis (Tanaka et al., *Nature*, 383:528-531 (1996), (5) inhibition of GSK-3 kinase in type-2 diabetes (Borthwick et al., *Biochemical & Biophysical Research Communications*, 210: 738-745 (1995), (6) inhibition of the p38 kinase in inflammation (Badger et al., *The Journal of Pharmacology and Experimental Therapeutics*, 279:1453-1461 (1996)), (7) inhibition of VEGF-R 1-3 and TIE-1 and -2 kinases in diseases which involve angiogenesis (Shawver et al., *Drug Discovery Today*, 2:50-63 (1997)), (8) inhibition of UL97 kinase in viral infections (He et al., *Journal of Virology*, 71:405-411 (1997)), (9) inhibition of CSF-1R kinase in bone and hematopoetic diseases (Myers et al., *Bioorganic & Medicinal Chemistry Letters*, 7:421-424 (1997), and (10) inhibition of Lck kinase in autoimmune diseases and transplant rejection (Myers et al., *Bioorganic & Medicinal Chemistry Letters*, 7:417-420 (1997).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199-3202 (1996); Kohn et al., *Journal of Cellular Biochemistry*, 54:44-452 (1994)). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB. Inhibition of CDK2 activity stimulates NF-kB-dependent gene expression, an event mediated through interactions with the p300 coactivator (Perkins et al., *Science*, 275:523-527 (1997)). NF-kB regulates genes involved in inflammatory responses (such as hematopoetic growth factors, chemokines and leukocyte adhesion molecules) (Baeuerle and Henkel, *Annual Review of Immunology*, 12:141-179 (1994)) and may be involved in the suppression of apoptotic signals within the cell (Beg and Baltimore, *Science*, 274: 782-784 (1996); Wang et al., *Science*, 274:784-787 (1996); Van Antwerp et al., *Science*, 274:787-789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-KB plays a role in etiology of disease. A further example may be take from fungal infections: Aspergillosis is a common infection in immune-compromised patients (Armstrong, *Clinical Infectious Diseases,* 16:1-7 (1993)). Inhibition of the Aspergillus kinases Cdc2/CDC28 or Nim A (Osmani et al., *EMBO Journal,* 10:2669-2679 (1991); Osmani et al., *Cell,* 67:283-291 (1991)) may cause arrest or death in the fungi, improving the therapeutic outcome for patients with these infections.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides compounds of Formula (I)

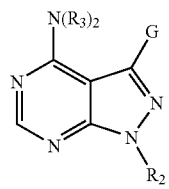

(I)

racemic-diastereomeric mixtures, optical isomers, pharmaceutically-acceptable salts, prodrugs or biologically active metabolites thereof wherein:

G is

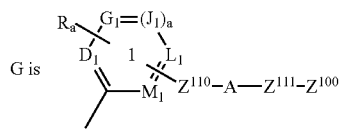

where $Z^{100}$ is

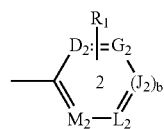

or a group optionally substituted with $R_1$ selected from the group consisting of alkyl; cycloalkyl; pyrrolidinyl; a bicyclic aromatic nitrogen containing heterocycle in which each ring has six atoms such as quinolinyl, quinoxalinyl, quinazolinyl, isoquinolinyl and phthalazinyl; a bicyclic aromatic nitrogen containing heterocycle in which nitrogen is in a bridging position and one aromatic ring has five member and the other aromatic ring has six members such as imidazo[1,2-a]pyrimidinyl; 1H-imidazo[1,2-a]imidazolyl; imidazo[2,1-b][1,3]thiazolyl; naphthyl; tetrahydronaphthyl; benzothienyl; furanyl; thienyl; benzoxazolyl; benzoisoxazolyl; benzothiazolyl;

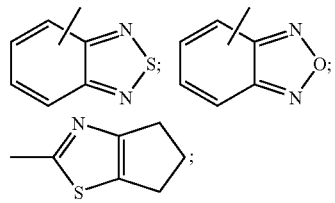

thiazolyl; benzofuranyl; 2,3-dihydrobenzofuranyl; indolyl; isoxazolyl; tetrahydropyranyl; tetrahydrofuranyl; piperidinyl; pyrazolyl; pyrrolyl; pyrrolopyridinyl; H-pyridinone; oxazolyl; isothiazolyl; oxadiazolyl; thiadiazolyl; indolinyl; indazolyl; imidazo[1,2-a]pyridinyl; benzoisothiazolyl; 1,1-dioxybenzoisothiazolyl; pyrido-oxazolyl; pyrido-thiazolyl; pyrimido-oxazolyl; pyrimido-thiazolyl; and benzimidazolyl;

$Z^{110}$ is a covalent bond, or an optionally substituted $(C_1-C_6)$ which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted $(C_1-C_6)$ or an optionally substituted $-(CH_2)_n$-cycloalkyl-$(CH_2)_n-$; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-S(O)$_p$—, substituted or unsubstituted alkyl-S—, substituted or unsubstituted aryl-S(O)$_p$—, substituted or unsubstituted heteroaryl-S(O)$_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, -$Z^{105}$—C(O)N(R)$_2$, -$Z^{105}$—N(R)—C(O)-$Z^{200}$, -$Z^{105}$—N(R)—S(O)$_2$-$Z^{200}$, -$Z^{105}$—N(R)—C(O)—N(R)-$Z^{200}$, $R_c$ and $CH_2OR_c$;

$R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—O-alkyl, —W—$(CH_2)_t$—S-alkyl, or —W—$(CH_2)_t$—OH;

$Z^{105}$ for each occurrence is independently a covalent bond or $(C_1-C_6)$;

$Z^{200}$ for each occurrence is independently a substituted or unsubstituted $(C_1-C_6)$, substituted or unsubstituted phenyl or substituted or unsubstituted $-(C_1-C_6)-$ phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$ wherein $R_f$ for each occurrence is independently H or alkyl; or $R_1$ is a substituted or unsubstituted carbocyclic or heterocyclic ring fused with ring 2;

$R_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

A is $-(C_1-C_6)-$, $-O-$; $-S-$; $-S(O)_p-$; $-N(R)-$; $-N(C(O)OR)-$; $-N(C(O)R)-$; $-N(SO_2R)-$; $-CH_2O-$; $-CH_2S-$; $-CH_2N(R)-$; $-CH(NR)-$; $-CH_2N(C(O)R))-$; $-CH_2N(C(O)OR)-$; $-CH_2N(SO_2R)-$; $-CH(NHR)-$; $-CH(NHC(O)R)-$; $-CH(NHSO_2R)-$; $-CH(NHC(O)OR)-$; $-CH(OC(O)R)-$; $-CH(OC(O)NHR)-$; $-CH=CH-$; $-C(=NOR)-$; $-C(O)-$; $-CH(OR)-$; $-C(O)N(R)-$; $-N(R)C(O)-$; $-N(R)S(O)_p-$; $-OC(O)N(R)-$; $-N(R)-C(O)-(CH_2)_n-N(R)-$, $-N(R)C(O)O-$; $-N(R)-(CH_2)_{n+1}-C(O)-$, $-S(O)_pN(R)-$; $-O-(CR_2)_{n+1}-C(O)-$, $-O-(CR_2)_{n+1}-O-$, $-N(C(O)R)S(O)_p-$; $-N(R)S(O)_pN(R)-$; $-N(R)-C(O)-(CH_2)_n-O-$, $-C(O)N(R)C(O)-$; $-S(O)_pN(R)C(O)-$; $-OS(O)_pN(R)-$; $-N(R)S(O)_pO-$; $-N(R)S(O)_pC(O)-$; $-SO_2N(C(O)R)-$; $-N(R)SO_pN(R)-$; $-C(O)O-$; $-N(R)P(OR_b)O-$; $-N(R)P(OR_b)-$; $-N(R)P(O)(OR_b)O-$; $-N(R)P(O)(OR_b)-$; $-N(C(O)R)P(OR_b)O-$; $-N(C(O)R)P(OR_b)-$; $-N(C(O)R)P(O)(OR_b)O-$, or $-N(C(O)R)P(OR_b)-$;

R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and $R_b$ together form a five- or six-membered heterocyclic ring; or A is $NRSO_2$ and R, $R_a$ and the nitrogen atom together form a substituted or unsubstituted five or -six-membered heterocyclic ring fused to ring 1; or $Z^{110}$-A-$Z^{111}$ taken together is a covalent bond; and $R_2$ is H or a group of the formula $Z^{101}$-$Z^{102}$;

$Z^{101}$ is a covalent bond, $-(C_1-C_6)-$, $-(C_1-C_6)-O-$, $-(C_1-C_6)-C(O)-$, $-(C_1-C_6)-C(O)O-$, $-(C_1-C_6)-C(O)-NH-$, $-(C_1-C_6)-C(O)-N((C_1-C_6))-$ or a substituted or unsubstituted phenyl group;

$Z^{102}$ is hydrogen; a substituted or unsubstituted alkyl group; a substituted or unsubstituted cycloalkyl group; a substituted or unsubstituted cycloalkenyl, a substituted or unsubstituted, saturated or unsaturated heterocyclic group; or a substituted or unsubstituted, saturated or unsaturated heterobicyclic group; wherein said substituted alkyl, substituted cycloalkyl, substituted cycloalkenyl, substituted heterocyclic and substituted heterobicyclic group having one or more substituents each independently selected from the group consisting of hydroxyl, cyano, nitro, halo, substituted or unsubstituted $(C_1-C_6)$, substituted or unsubstituted aryl, substituted or unsubstituted —C(O)-alkyl, substituted or unsubstituted alkoxy, substituted or unsubstituted —N(R)—$(C_1-C_6)$—OR, substituted or unsubstituted —N((C_1-C_6)—OR)_2$, substituted or unsubstituted —N(R)—$(C_1-C_6)$—C(O)_2 R, substituted or unsubstituted —$(C_1-C_6)$—N(R)—$(C_1-C_6)$—OR, substituted or unsubstituted —$(C_1-C_6)$—N(R)—$(C_1-C_6)$—N(R)_2$, substituted or unsubstituted —$(C_1-C_6)$—C(O)N(R)—$(C_1-C_6)$—N(R)_2$, substituted or unsubstituted sulfonamido, substituted or unsubstituted ureido, substituted or unsubstituted carboxamido, substituted or unsubstituted amino, substituted or unsubstituted —N(R)—$(C_1-C_6)$—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)_2$, substituted or unsubstituted —C(O)—$(C_1-C_6)$—N(R)_2$, —C(O)-alkyl, —C(O)-aryl, —C(O)-heteroaryl, substituted or unsubstituted arylalkyl group, or substituted or unsubstituted heteroarylalkyl; or $R_2$ is a group of the formula -B-E, wherein B is a substituted or unsubstituted cycloalkyl, substituted or unsubstituted aryl, substituted or unsubstituted heteroaryl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted alkyl, a substituted or unsubstituted cycloalkyl, substituted or unsubstituted azacycloalkyl, a substituted or unsubstituted heterocycloalkyl, substituted or unsubstituted $(C_1-C_6)$-azacycloalkyl-, substituted or unsubstituted azacycloalkylcarbonyl, substituted or unsubstituted azacycloalkylsulfonyl, substituted or unsubstituted azacycloalkylalkyl, substituted or unsubstituted heteroaryl-N(R)—$(C_1-C_6)$—, substituted or unsubstituted aryl-N(R)—$(C_1-C_6)$—, substituted or unsubstituted alkyl-N(R)—$(C_1-C_6)$—, substituted or unsubstituted heteroaryl-$(C_1-C_6)$—N(R)—, substituted or unsubstituted aryl-$(C_1-C_6)$—N(R)—, substituted or unsubstituted alkyl-$(C_1-C_6)$—N(R)—, substituted or unsubstituted heteroaryl, substituted or unsubstituted heteroarylcarbonyl, substituted or unsubstituted alkylcarbonyl, substituted or unsubstituted arylcarbonyl, substituted or unsubstituted heteroarylsulfonyl, substituted or unsubstituted alkylsulfonyl, substituted or unsubstituted arylsulfonyl, substituted or unsubstituted heteroarylalkyl, substituted or unsubstituted arylalkyl, substituted or unsubstituted azacycloalkylcarbonylamino, substituted or unsubstituted heteroarylcarbonylamino, substituted or unsubstituted arylcarbonylamino, substituted or unsubstituted alkylcarbonylamino or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

provided that when A is —N(R)—, $Z^{110}$ and $Z^{111}$ are each a covalent bond, and $R_2$ is a 3,4-dihydroxytetrahydrofur-2-yl or a 3,4-diacyloxytetrahydrofur-2-yl, then $Z^{100}$ is not alkyl, tetrahydropyranyl, tetrahydrofuranyl, piperidinyl or pyrrolidinyl;

provided that when $Z^{110}$ and $Z^{111}$ are each a covalent bond, and $R_2$ is a 3,4-dihydroxytetrahydrofur-2-yl or a 3,4-diacyloxytetrahydrofur-2-yl, $Z^{100}$ is a substituted or unsubstituted alkyl, then A is not alkyl, —O—, —C(O)—, —NHC(O)— or —C(O)O—;

provided that when $Z^{110}$-A-$Z^{111}$ taken together are a covalent bond, then $Z^{100}$ is not alkyl;

provided that when $Z^{110}$-A-$Z^{111}$ taken together are a $C_1$-$C_6$ alkyl, then $Z^{100}$ is not phenyl, pyrrolyl, imidazolyl, pyrazolyl, pyridinyl, pyrimidinyl, pyrazinyl, pyridazinyl, furyl or thienyl; and provided that when $R_2$ is a substituted or unsubstituted cyclopentyl, $Z^{100}$ is an substituted or unsubstituted alkyl, $Z^{110}$ and $Z^{111}$ are each a covalent bond, then A is not —O—, —C(O)O—, or —N(R)—.

In a first embodiment, $R_2$ in the compounds of formula I is a) hydrogen; b) substituted or unsubstituted trityl; c) substituted or unsubstituted cycloalkenyl; d) azaheteroaryl substituted with a substituted or unsubstituted alkyl; e) azacycloalkyl which is substituted with one or more substituents selected from substituted or unsubstituted —($C_1$-$C_6$)-alkyl, substituted or unsubstituted —$C_1$-$C_6$-alkyl-OR, substituted or unsubstituted —C(O)—$C_1$-$C_6$-alkyl-N(R)$_2$, substituted or unsubstituted—$C_1$-$C_6$-alkyl-N(R)$_2$, substituted or unsubstituted —$C_1$-$C_6$-alkyl-cycloalkyl, substituted or unsubstituted tetrahydrothienyl, and substituted or unsubstituted tetrahydrothiopyranyl; or f) a group of the formula (a)

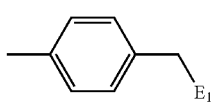

wherein $E_1$ is piperidinyl, piperazinyl, imidazolyl, morpholinyl, pyrrolidinyl, amino, amido, or tetrahydrothiazolyl, and wherein E is optionally substituted with one or more substituents selected from —$C_0$-$C_6$-alkyl-OR, —$C_1$-$C_6$-alkyl-C(O)OR, —$C_1$-$C_6$-alkyl-heteroaryl, —$C_1$-$C_6$-alkyl-heterocycloalkyl, and —$C_1$-$C_6$-alkyl-N(R)$_2$.

In a second embodiment, $R_2$ in the compounds of formula I is a group represented by formula (a) in which $E_1$ is selected from the group consisting of —amino-$C_1$-$C_6$-alkyl-morpholino, -piperidino-$C_1$-$C_6$-alkyl-OR, -imidazolyl-$C_1$-$C_6$-alkyl-C(O)OR, -piperazino-$C_1$-$C_6$-alkyl-OR, -amino-$C_1$-$C_6$-alkyl-OR, -pyrrolidino-OR, -amino-$C_1$-$C_6$-alkyl-imidazolo, -amino-$C_1$-$C_6$-alkyl-N(R)$_2$, -amido-$C_1$-$C_6$-alkyl-N(R)$_2$, tetrahydrothiazolyl, N,N-di-(hydroxy-$C_1$-$C_6$-alkyl) amino-, and -piperizino-OR.

In a third embodiment, $R_2$ in the compounds of formula I is a group represented by formula (a) in which $E_1$ is selected from the group consisting of 4-(2-hydroxyethyl)morpholino, 3-hydroxymethylpiperidino, 2-[3-(methylcarboxy)propyl]imidizol-4-yl, 4-(2-hydroxyethyl)piperazino, 2-hydroxyethylamino, 3-hydroxypyrrolidino, 3-imidazolopropylamino, 4-hydroxybutylamino, 3-methoxypropylamino, 3-(N,N-dimethylamino)propylamino, N-[2-(N,N-dimethyl)ethyl]amido, tetrahydrothiazolyl, N,N-di-(2-hydroxyethyl)amino, 4-hydroxypiperizino, and 4-hydroxymethylpiperizino.

In fourth embodiment, $Z^{110}$-A-$Z^{111}$ is —NHC(O)— in the compounds of formula I or in any one of embodiments 1-3.

In a fifth embodiment, G in the compounds of formula I or in any one of embodiments 1-4 is a group represented by the following structural formula

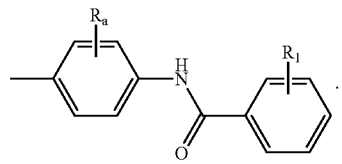

In a sixth embodiment, G in the compounds of formula I or in any one of embodiments 1-5 is a group represented by the following structural formula

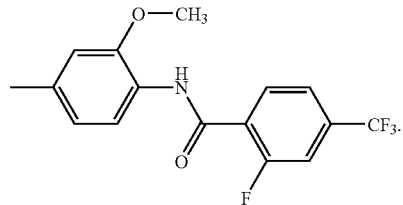

In a seventh embodiment, $R_2$ in the compounds of formula I is an azaheteroaryl substituted with a $C_1$-$C_6$ alkyl, wherein the alkyl is optionally substituted with with one or more substitutents selected form RO—, —C(O)OR, —C(O)N(R)$_2$, and —N(R)$_2$.

In an eighth embodiment, $R_2$ in the compounds of formula I is 4-(2-hydroxyethyl)pyridin-2-yl, 3-aminomethylpyridin-4-yl or 2-methylimidazol-4-yl.

In a ninth embodiment, G in the compounds of formula I or in embodiments 7 or 8 is a group represented by the following formula

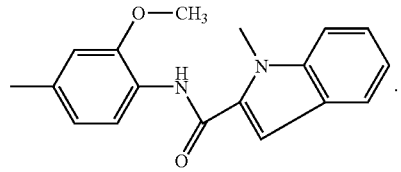

In a tenth embodiment, $R_2$ in the compounds of formula I is a pyrrolidinyl which is substituted with 2-methoxyethyl, N,N-dimethylaminomethyl, N,N-dimethylamino-1-oxoethyl, or 2-(N-methylamino)-1-oxopropyl.

In an eleventh embodiment, G in the compounds of formula I or in embodiment 10 is a group represented by the following formula

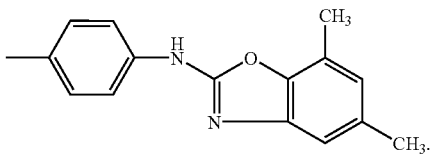

In a twelfth embodiment, $R_2$ in the compounds of formula I is a piperidinyl which is substituted with a tetrahydrothiopyranyl, tetrahydrothienyl, 2-(N-methylamino)-2-methyl-1-oxopropyl, 2-methoxyethyl, or cyclopropylmethyl.

In a thirteenth embodiment, $Z^{100}$ in the compounds of formula I is pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, H-pyridinone, 1,1-dioxybenzoisothiazolyl, benzoisoxazolyl, alkyl, imidazo[1,2-a]pyridinyl, pyrrolopyridinyl or

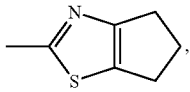

wherein all of the foregoing $Z^{100}$ groups can be optionally substituted with $R_1$.

In a fourteenth embodiment, $Z^{100}$ in the compounds of formula I or in embodiment 13 is 2-pyrrolidinyl, 1,2-dihydro-2-oxopyridin-3-yl, benzoisoxazol-3-yl, 1,1-dioxybenzoisothiazol-3-yl, imidazo[1,2-a]pyridin-2-yl or

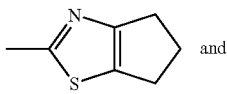 and $R_2$ is 4-(4-methylpiperazino)-cyclohexyl.

In a fifteenth embodiment, $Z^{110}$-A-$Z^{111}$ in the compounds of formula I or embodiments 13 or 14 is —NH—.

In a sixteenth embodiment, $Z^{100}$ in formula I or in embodiment 13 is a pyrrolopyridinyl selected from

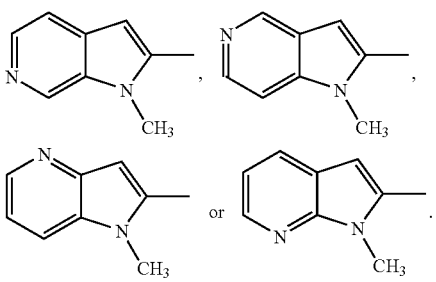

In a seventeenth embodiment, $Z^{110}$-A-$Z^{111}$ in embodiments 13 or 16 is —NHC(O)—.

In an eighteenth embodiment, $R_2$ in formula I or in embodiments 13, 16 or 17 is piperdin-4-yl, N-methylpiperidin-4-yl, N-(prop-2-yl)piperidin-4-yl, N-(imidazol-4-yl-methyl)piperidin-4-yl, N-(2-methylimidazol-4-yl-methyl)piperidin-4-yl, N-(pyrazol-4-yl-methyl)piperidin-4-yl, N-(2-methoxyethyl)piperidin-4-yl, N-(fur-3-yl-methyl)piperidin-4-yl, N-(tetrahydropyran-4-yl-methyl)piperidin-4-yl, N-(pyrrol-2-yl-methyl)piperidin-4-yl, or N-(2-difluoroethyl)piperidin-4-yl.

In a nineteenth embodiment, $R_a$ and $R_1$ in the compounds of formula I each represent one or more substituents for each occurrence independently selected from the group consisting of hydrogen, —C(O)O-aryl, —C(O)O-heteroaryl, —C(O)-alkyl, —C(O)-aryl, —C(O)-heteroaryl, substituted or unsubstituted cycloalkyl, substituted or unsubstituted heteroaryl, substituted or unsubstituted heteroarylalkoxy, substituted or unsubstituted arylalkoxy, substituted or unsubstituted alkyl-S(O)$_p$—, substituted or unsubstituted alkyl-S—, substituted or unsubstituted aryl-S(O)$_p$—, substituted or unsubstituted heteroaryl-S(O)$_p$—, and wherein at least one of $R_a$ and R, is not hydrogen.

In a twentieth embodiment, A in the compounds of formula I is —(C$_1$-C$_6$)—.

In a twenty-first embodiment, $Z^{110}$-A-$Z^{111}$ taken together is a covalent bond in the compounds represented by formula I.

In a twenty-second embodiment, $R_3$ for each occurrence in the compounds represented by formula I is, independently, substituted or unsubstituted —C(O)-alkyl, a substituted or unsubstituted —C(O)-aryl, or a substituted or unsubstituted —C(O)-heteroaryl.

In a twenty-third embodiment, $R_2$ is a group of the formula -$Z^{101}$-$Z^{102}$, wherein $Z^{101}$ is a covalent bond, —(C$_1$-C$_6$)—, —(C$_1$-C$_6$)—O—, —(C$_1$-C$_6$)—C(O)—, —(C$_1$-C$_6$)—C(O)O—, —(C$_1$-C$_6$)—C(O)—NH—, —(C$_1$-C$_6$)—C(O)—N((C$_1$-C$_6$))— or a substituted or unsubstituted phenyl group; and wherein $Z^{102}$ is a substituted or unsubstituted cycloalkenyl, wherein said substituted cycloalkenyl has one or more substituents each independently selected from the group consisting of hydroxyl, cyano, nitro, halo, substituted or unsubstituted (C$_1$-C$_6$), substituted or unsubstituted aryl, substituted or unsubstituted —C(O)-alkyl, substituted or unsubstituted alkoxy, substituted or unsubstituted —N(R)—(C$_1$-C$_6$)—OR, substituted or unsubstituted —N((C$_1$-C$_6$)—OR)$_2$, substituted or unsubstituted —N(R)—(C$_1$-C$_6$)—C(O)$_2$R, substituted or unsubstituted —(C$_1$-C$_6$)—N(R)—(C$_1$-C$_6$)—OR, substituted or unsubstituted —(C$_1$-C$_6$)—N(R)—(C$_1$-C$_6$)—N(R)$_2$, substituted or unsubstituted —(C$_1$-C$_6$)—C(O)N(R)—(C$_1$-C$_6$)—N(R)$_2$, substituted or unsubstituted sulfonamido, substituted or unsubstituted ureido, substituted or unsubstituted carboxamido, substituted or unsubstituted amino, substituted or unsubstituted —N(R)—(C$_1$-C$_6$)—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—(C$_1$-C$_6$)—N(R)$_2$, —C(O)-alkyl, —C(O)-aryl, —C(O)-heteroaryl, substituted or unsubstituted arylalkyl group, or substituted or unsubstituted heteroarylalkyl.

In a twenty-forth embodiment, $R_2$ is a group of the formula $Z^{101}$-$Z^{102}$; $Z^{101}$ is a covalent bond, —(C$_1$-C$_6$)—, —(C$_1$-C$_6$)—O—, —(C$_1$-C$_6$)—C(O)—, —(C$_1$-C$_6$)—

—C(O)O—, —(C$_1$-C$_6$)—C(O)—NH—, —(C$_1$-C$_6$)—C(O)—N((C$_1$-C$_6$))— or a substituted or unsubstituted phenyl group; Z$^{102}$ is a substituted, saturated or unsaturated heterocyclic group; or a substituted, saturated or unsaturated heterobicyclic group; wherein said substituted heterocyclic and substituted heterobicyclic group have one or more substituents each independently selected from the group consisting of nitro, halo, substituted or unsubstituted (C$_1$-C$_6$), substituted or unsubstituted aryl, substituted or unsubstituted—C(O)-alkyl, substituted or unsubstituted —N(R)—(C$_1$-C$_6$)—OR, substituted or unsubstituted —N((C$_1$-C$_6$)—OR)$_2$, substituted or unsubstituted —N(R)—(C$_1$-C$_6$)—C(O)$_2$ R, substituted or unsubstituted —(C$_1$-C$_6$)—N(R)—(C$_1$-C$_6$)—OR, substituted or unsubstituted —(C$_1$-C$_6$)—N(R)—(C$_1$-C$_6$)—N(R)$_2$, substituted or unsubstituted —(C$_1$-C$_6$)—C(O)N(R)—(C$_1$-C$_6$)—N(R)$_2$, substituted or unsubstituted —N(R)—(C$_1$-C$_6$)—OR, and a substituted or unsubstituted heterocyclic group comprising one or more heteroatoms selected from the group consisting of O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—(C$_1$-C$_6$)—N(R)$_2$, —C(O)-alkyl, —C(O)-aryl, —C(O)-heteroaryl, substituted or unsubstituted arylalkyl group, or substituted or unsubstituted heteroarylalkyl.

A preferred compound of Formula (I) is wherein R$_3$ is H; R, for each occurrence is independently selected from the group consisting of F, Cl, Br, I, CH$_3$, NO$_2$, OCF$_3$, OCH$_3$, CN, CO$_2$CH$_3$, CF$_3$, —CH$_2$NR$_d$R$_e$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

Another preferred compound of Formula (I) is wherein R$_3$ is H; R$_a$ for each occurrence is independently selected from the group consisting of F, Cl, Br, I, CH$_3$, NO$_2$, OCF$_3$, OCH$_3$, CN, CO$_2$CH$_3$, CF$_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

Another preferred compound of Formula (I) is wherein R$_3$ is H; R$_2$ is of the formula

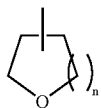

wherein n is 1, 2 or 3.

Another preferred compound of Formula (I) is wherein R$_3$ is H; R$_2$ is of the formula

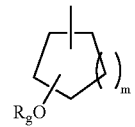

wherein m is 0, 1, 2 or 3 and

R$_g$ is H or —(CH$_2$)$_p$N(R$_4$)R$_5$, wherein p is an integer from 2 to 6 and R$_4$ and R$_5$ are each, independently, H, azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6; and r is 0, 1 or 2; and Z is a substituted or unsubstituted moiety selected from the group consisting of alkyl, alkoxy, amino, aryl, heteroaryl and heterocycloalkyl group or R$_4$, R$_5$ and the nitrogen atom to which they are attached together form a 3, 4, 5, 6 or 7-membered, substituted or unsubstituted heterocyclic or heterobicyclic group.

Another preferred compound of Formula (I) is wherein R$_3$ is H; R$_2$ is of the formula

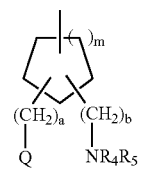

wherein m is 0, 1, 2 or 3;
a and b are each, independently, an integer from 0 to 6;
Q is —OR$_6$ or —NR$_4$R$_5$;
each R$_4$ and R$_5$ is, independently, H, azabicycloalkyl or Y-Z, wherein Y is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein q is an integer from 0 to 6; and r is 0, 1 or 2; and Z is a substituted or unsubstituted alkyl, substituted or unsubstituted alkoxy, amino, aryl, heteroaryl or heterocycloalkyl group; or R$_4$, R$_5$ and the nitrogen atom to which they are attached together form a 3, 4, 5, 6 or 7-membered, substituted or unsubstituted heterocyclic or heterobicyclic group; and R$_6$ is hydrogen or a substituted or unsubstituted alkyl group.

Another preferred compound of Formula (I) is wherein R$_3$ is H; R$_2$ is of the formula

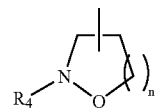

wherein n is 1, 2 or 3; and
R$_4$ is H, azabicycloalkyl or Y-Z, wherein Y is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein q is an integer 0 to 6; and r is 0, 1 or 2; and Z is a substituted or unsubstituted alkyl, substituted or unsubstituted amino, aryl, substituted or unsubstituted heteroaryl or substituted or unsubstituted heterocycloalkyl group.

Another preferred compound of Formula (I) is wherein $R_3$ is H; $R_2$ is of the formula

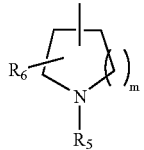

where m is 0, 1, 2 or 3;

$R_5$ is H, azabicycloalkyl or Y-Z, wherein Y is selected from the group consisting of a covalent bond, —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, —(CH$_2$)$_q$C(O)—, —C(O)(CH$_2$)$_q$— and —(CH$_2$)$_q$S(O)$_r$—, where the alkyl portion of —(CH$_2$)$_q$—, —(CH$_2$)$_q$O—, —(CH$_2$)$_q$NH—, —(CH$_2$)$_q$C(O)—, —C(O)(CH$_2$)$_q$—and —(CH$_2$)$_q$S(O)$_r$ is optionally substituted by a halogen, hydroxy or an alkyl group; wherein q is an integer from 0 to 6; and r is 0, 1 or 2; and Z is a substituted or unsubstituted alkyl, substituted or unsubstituted amino, substituted or unsubstituted alkoxy, substituted or unsubstituted aryl, substituted or unsubstituted heteroaryl or substituted or unsubstituted heterocycloalkyl group;

or Y and Z together are a natural or unnatural amino acid, which may be mono- or di-alkylated at the amine nitrogen; and $R_6$ represents one or more substituents each independently selected from the group consisting of hydrogen, hydroxy, oxo, substituted or unsubstituted alkyl, substituted or unsubstituted aryl, substituted or unsubstituted heterocyclyl, substituted or unsubstituted alkoxycarbonyl, substituted or unsubstituted alkoxyalkyl, substituted or unsubstituted aminocarbonyl, substituted or unsubstituted alkylcarbonyl, substituted or unsubstituted arylcarbonyl, substituted or unsubstituted heterocyclylcarbonyl, substituted or unsubstituted aminoalkyl and substituted or unsubstituted arylalkyl; provided that the carbon atoms adjacent to the nitrogen atom are not substituted by a hydroxy group.

Another preferred compound of Formula (I) is wherein $R_3$ is H; $R_2$ is of the formula

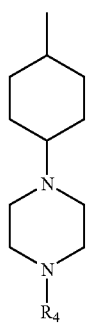

wherein $R_4$ is H, substituted or unsubstituted alkyl, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6, and r is 0, 1 or 2; and Z is hydrogen, substituted or unsubstituted alkyl, substituted or unsubstituted amino, substituted or unsubstituted aryl, substituted or unsubstituted heteroaryl or substituted or unsubstituted heterocycloalkyl.

Another preferred compound of Formula (I) is wherein $R_3$ is H; $R_2$ is of the formula

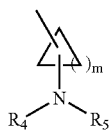

wherein m is an integer from 1 to 6; and $R_4$ and $R_5$ are each, independently, H, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6; and r is 0, 1 or 2; and Z is a substituted or unsubstituted alkyl, substituted or unsubstituted amino, substituted or unsubstituted aryl, substituted or unsubstituted heteroaryl or substituted or unsubstituted heterocycloalkyl group; or $R_4$, $R_5$ and the nitrogen atom to which they are attached together form a 3, 4, 5, 6 or 7-membered, substituted or unsubstituted heterocyclic or substituted or unsubstituted heterobicyclic group.

Another preferred compound of Formula (I) is wherein $R_3$ is H; $R_2$ is of the formula

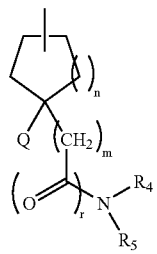

where n is an integer from 0 to 4;

r is 0 and m is an integer from 1 to 6; or r is 1 and m is an integer from 0 to 6;

Q is —OR$_6$ or —NR$_4$R$_5$;

each $R_4$ and $R_5$ is, independently, H, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; q is an integer from 0 to 6; and r is 0, 1 or 2; and Z is a substituted or unsubstituted alkyl, substituted or unsubstituted alkoxy, substituted or unsubstituted amino, substituted or unsubstituted aryl, substituted or unsubstituted heteroaryl or substituted or unsubstituted heterocycloalkyl group; or $R_4$, $R_5$ and the nitrogen atom to which they are attached together form a 3, 4, 5 or 6-membered, substituted or unsubstituted heterocyclic group; and $R_6$ is hydrogen or a substituted or unsubstituted alkyl group.

Another preferred compound of Formula (I) is wherein $R_3$ is H; $R_2$ is of the formula

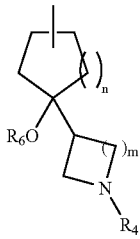

n is an integer from 0 to 4;

m is an integer from 0 to 6;

$R_4$ is H, substituted or unsubstituted azabicycloalkyl or Y-Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, (CH$_2$)$_q$NH—, and —(CH$_2$)$_q$S(O)$_r$—; wherein q is an integer from 0 to 6; and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl; and $R_6$ is hydrogen or a substituted or unsubstituted alkyl group.

A more preferred compound of Formula (a) is where in any of the applicable foregoing preferred compounds $R_4$, $R_5$ and the nitrogen atom together form a heterocyclic group of the formula

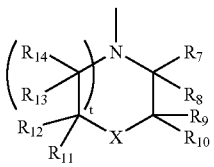

wherein $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, CONHR$_{15}$, COOR$_{15}$, CH$_2$OR$_{15}$ or CH$_2$NR$_{15}$(R$_{16}$), wherein $R_{15}$ and $R_{16}$ are each, independently, H, azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or $R_{15}$, $R_{16}$ and the nitrogen atom together form a 3, 4, 5, 6 or 7-membered, substituted or unsubstituted heterocyclic or a substituted or unsubstituted heterobicyclic group;

X is O, S, SO, SO$_2$, CH$_2$, CHOR$_{17}$ or NR$_{17}$, wherein $R_{17}$ is hydrogen, substituted or unsubstituted alkyl, substituted or unsubstituted aryl, substituted or unsubstituted arylalkyl, —C(NH)NH$_2$, —C(O)R$_{17}$, or —C(O)OR$_{18}$, wherein $R_{18}$ is hydrogen, substituted or unsubstituted alkyl, substituted or unsubstituted aryl or substituted or unsubstituted arylalkyl; and t is 0 or 1.

A more preferred compound of Formula (I) is where in any of the applicable foregoing preferred compounds $R_4$, $R_5$ and the nitrogen atom together form a heterocycle of the formula

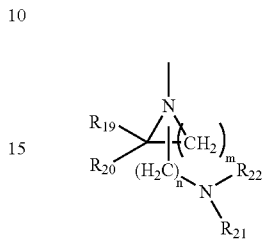

wherein $R_{19}$ and $R_{20}$ are each, independently, hydrogen or lower alkyl; or $R_{19}$ and $R_{20}$ together are an oxygen atom;

$R_{21}$ and $R_{22}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or $R_{21}$, $R_{22}$ and the nitrogen atom together form a 3, 4, 5 or 6-membered, substituted or unsubstituted heterocyclic group;

m is an integer from 1 to 6; and n is an integer from 0 to 6.

A more preferred compound of Formula (I) is where in any of the applicable foregoing preferred compounds $R_4$, $R_5$ and the nitrogen atom together form a heterocyclic group of the formula

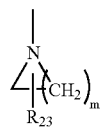

wherein m is an integer from 1 to 6; and $R_{23}$ is CH$_2$OH, NRR', C(O)NRR' or COOR, wherein R and R' are each, independently, hydrogen or substituted or unsubstituted alkyl, substituted or unsubstituted aryl or substituted or unsubstituted arylalkyl.

A more preferred compound of Formula (I) is where in any of the applicable foregoing preferred compounds $R_4$, $R_5$ and the nitrogen atom together form a heterocyclic group of the formula

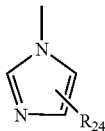

wherein R$_{24}$ is substituted or unsubstituted alkyl, substituted or unsubstituted aryl or substituted or unsubstituted arylalkyl, carboxyl, cyano, C(O)OR$_{25}$, CH$_2$OR$_{25}$, CH$_2$NR$_{26}$R$_{27}$ or C(O)NHR$_{26}$, wherein R$_{25}$ is substituted or unsubstituted alkyl, substituted or unsubstituted aryl, substituted or unsubstituted arylalkyl, substituted or unsubstituted heterocyclic or substituted or unsubstituted heterocycloaryl; and R$_{26}$ and R$_{27}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or R$_{26}$, R$_{27}$ and the nitrogen atom together form a 3, 4, 5 or 6-membered, substituted or unsubstituted heterocyclic group.

A more preferred compound of Formula (I) is where in any of the applicable foregoing preferred compounds at least one of R$_4$ and R$_5$ is of the formula Y-Z, wherein Z is of the formula

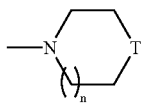

wherein

T is C(O), S, SO, SO$_2$, CHOR or NR, wherein R is hydrogen or a substituted or unsubstituted alkyl, substituted or unsubstituted aryl or substituted or unsubstituted arylalkyl group; and n is 0, 1 or 2.

A more preferred compound of Formula (I) is where in any of the applicable foregoing preferred compounds at least one of R$_4$ and R$_5$ is of the formula Y-Z, wherein Z is of the formula —N(R$_{28}$)R$_{29}$, wherein R$_{28}$ and R$_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or R$_{28}$ and R$_{29}$, together with the nitrogen atom, form a five- or six-membered substituted or unsubstituted heterocyclic group.

A more preferred compound of Formula (I) is where in any of the applicable foregoing preferred compounds R$_4$, R$_5$ and the nitrogen atom together form a heterocycle of the formula

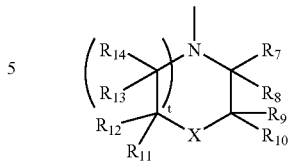

wherein

R$_7$, R$_8$, R$_9$, R$_{10}$, R$_{11}$, R$_{12}$, R$_{13}$ and R$_{14}$ are each, independently, lower alkyl or hydrogen; or at least one pair of substituents R$_7$ and R$_8$; R$_9$ and R$_{10}$; R$_{11}$, and R$_{12}$; or R$_{13}$ and R$_{14}$ together are an oxygen atom; or at least one of R$_7$ and R$_9$ is cyano, CONHR$_{15}$, COOR$_{15}$, CH$_2$OR$_{15}$ or CH$_2$NR$_{15}$(R$_{16}$), wherein R$_{15}$ and R$_{16}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or R$_{15}$, R$_{16}$ and the nitrogen atom together form a 3, 4, 5, 6 or 7-membered, substituted or unsubstituted heterocyclic or heterobicyclic group;

X is O, S, SO, SO$_2$, CH$_2$, CHOR$_{17}$ or NR$_{17}$, wherein R$_{17}$ is hydrogen, substituted or unsubstituted alkyl, substituted or unsubstituted aryl, substituted or unsubstituted arylalkyl, —C(NH)NH$_2$, —C(O)R$_{18}$, or —C(O)OR$_{18}$, wherein R$_{18}$ is hydrogen, substituted or unsubstituted alkyl, substituted or unsubstituted aryl or substituted or unsubstituted arylalkyl; and t is 0 or 1.

A more preferred compound of Formula (I) is where in any of the applicable foregoing preferred compounds R$_4$, R$_5$ and the nitrogen atom together form a heterocycle of the formula

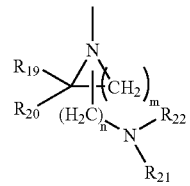

wherein

R$_{19}$ and R$_{20}$ are each, independently, hydrogen or lower alkyl; or R$_{19}$ and R$_{20}$ together are an oxygen atom;

R$_{21}$ and R$_{22}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or $R_{21}$, $R_{22}$ and the nitrogen atom together form a 3, 4, 5 or 6-membered, substituted or unsubstituted heterocyclic group;

m is an integer from 1 to 6; and n is an integer from 0 to 6.

A more preferred compound of Formula (I) is where in any of the applicable foregoing preferred compounds $R_4$, $R_5$ and the nitrogen atom together form a heterocyclic group of the formula

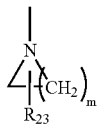

wherein m is an integer from 1 to 6; and $R_{23}$ is $CH_2OH$, NRR', C(O)NRR' or COOR, wherein R is hydrogen or a substituted or unsubstituted alkyl, substituted or unsubstituted aryl or substituted or unsubstituted arylalkyl group.

A more preferred compound of Formula (I) is where in any of the applicable foregoing preferred compounds $R_4$, $R_5$ and the nitrogen atom together form a heterocyclic group of the formula

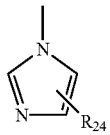

wherein $R_{24}$ is substituted or unsubstituted alkyl, substituted or unsubstituted aryl or substituted or unsubstituted arylalkyl, carboxyl, cyano, $C(O)OR_{25}$, $CH_2OR_{25}$, $CH_2NR_{26}R_{27}$ or $C(O)NHR_{26}$, wherein $R_{25}$ is substituted or unsubstituted alkyl, substituted or unsubstituted aryl, substituted or unsubstituted arylalkyl, substituted or unsubstituted heterocyclic or substituted or unsubstituted heterocycloaryl group; and $R_{26}$ and $R_{27}$ are each, independently, H, substituted or unsubstituted azabicycloalkyl or V-L, wherein V is selected from the group consisting of —C(O)—, —(CH$_2$)$_r$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or $R_{26}$, $R_{27}$ and the nitrogen atom together form a 3, 4, 5 or 6-membered, substituted or unsubstituted heterocyclic group.

A more preferred compound of Formula (I) is where in any of the applicable foregoing preferred compounds at least one of $R_4$ and $R_5$ is of the formula Y-Z, wherein Z is of the formula

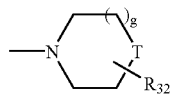

wherein g is 0 or 1;

T is C(O), O, S, SO, SO$_2$, CH$_2$, CHOR$_{17}$ or NR$_{17}$, wherein $R_{17}$ is hydrogen, substituted or unsubstituted alkyl, substituted or unsubstituted aryl, substituted or unsubstituted arylalkyl, —C(NH)NH$_2$, —C(O)R$_{18}$, or —C(O)OR$_{18}$, wherein $R_{18}$ is hydrogen, substituted or unsubstituted alkyl, substituted or unsubstituted aryl or substituted or unsubstituted arylalkyl; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl.

A more preferred compound of Formula (1) is where in any of the applicable foregoing preferred compounds at least one of $R_4$ and $R_5$ is of the formula Y-Z, wherein Z is of the formula —N(R$_{28}$)R$_{29}$, wherein $R_{28}$ and $R_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a five- or six-membered substituted or unsubstituted heterocyclic group.

A more preferred compound of Formula (I) is where in any of the applicable foregoing preferred compounds $R_5$ is Y-Z, wherein Z is of the formula N(R$_{30}$)R$_{31}$, wherein $R_{30}$ and $R_{31}$ are each, independently, hydrogen, alkyl, alkoxycarbonyl, alkoxyalkyl, hydroxyalkyl, aminocarbonyl, cyano, alkylcarbonyl or arylalkyl.

A more preferred compound of Formula (I) is where in any of the applicable foregoing preferred compounds $R_5$ is Y-Z, wherein Z is of the formula

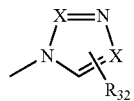

wherein each X is, independently, CH or N; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds $R_5$ is Y-Z, wherein Z is of the formula

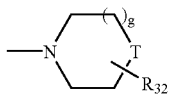

wherein
g is 0 or 1;
T is O, S, SO, SO$_2$, CH$_2$, CHOR$_{17}$ or NR$_{17}$, wherein R$_{17}$ is hydrogen, substituted or unsubstituted alkyl, substituted or unsubstituted aryl, substituted or unsubstituted arylalkyl, C(O)NH$_2$, —C(NH)NH$_2$, —C(O)R$_{17}$, or —C(O)OR$_{18}$, wherein R$_{18}$ is hydrogen, substituted or unsubstituted alkyl, substituted or unsubstituted aryl or substituted or unsubstituted arylalkyl; and
R$_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds R$_5$ is Y-Z, wherein Z is of the formula

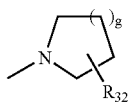

wherein
g is 0, 1 or 2; and
R$_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds R$_5$ is Y-Z, wherein Z is of the formula

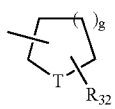

wherein
T is C(O), O, S, S O, SO$_2$, CH$_2$, CHOR$_{17}$ or NR$_{17}$, wherein R$_{17}$ is hydrogen, substituted or unsubstituted alkyl, aryl, arylalkyl, —C(NH)NH$_2$, —C(O)R$_{18}$, or —C(O)OR$_{18}$, wherein R$_{18}$ is hydrogen, substituted or unsubstituted alkyl, substituted or unsubstituted aryl or substituted or unsubstituted arylalkyl;
g is 0 or 1; and
R$_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds R$_5$ is Y-Z, wherein Z is of the formula

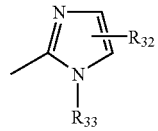

wherein
R$_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, alkylcarbonyl, substituted or unsubstituted thioalkoxy or substituted or unsubstituted arylalkyl; and
R$_{33}$ is hydrogen, substituted or unsubstituted alkyl, substituted or unsubstituted alkoxycarbonyl, substituted or unsubstituted alkoxyalkyl, substituted or unsubstituted aminocarbonyl, perhaloalkyl, substituted or unsubstituted alkenyl, substituted or unsubstituted alkylcarbonyl or substituted or unsubstituted arylalkyl.

A preferred compound of Formula (I) is where R$_3$ is H; R$_2$ is of the formula

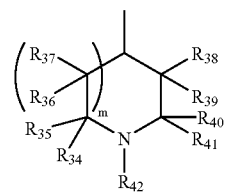

wherein
m is 0 or 1;
R$_{34}$, R$_{35}$, R$_{36}$, R$_{37}$, R$_{38}$, R$_{39}$, R$_{40}$ and R$_{41}$ are each, independently, methyl or hydrogen; or at least one pair of substituents R$_{34}$ and R$_{35}$; R$_{36}$ and R$_{37}$; R$_{39}$ and R$_{39}$; or R$_{40}$ and R$_4$ together are an oxygen atom; and
R$_{42}$ is H, substituted or unsubstituted azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl group; or
R$_{42}$ is of the formula

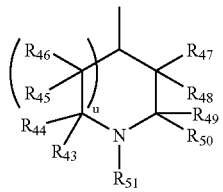

wherein u is 0 or 1;

$R_{43}$, $R_{44}$, $R_{45}$, $R_{46}$, $R_{47}$, $R_{48}$, $R_{49}$ and $R_{50}$ are each, independently, methyl or hydrogen; or at least one pair of substituents $R_{43}$ and $R_{44}$; $R_{45}$ and $R_{46}$; $R_{47}$ and $R_{48}$; or $R_{49}$ and $R_{50}$ together are an oxygen atom; and $R_{51}$ is H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl.

A preferred compound of Formula (I) is where $R_3$ is H; $R_2$ is of the formula

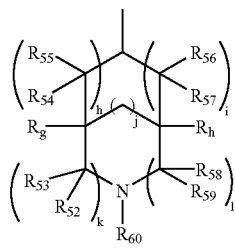

wherein h, i, j, k and l are independently 0 or 1;

$R_{52}$, $R_{53}$, $R_{54}$, $R_{55}$, $R_{56}$, $R_{57}$, $R_{58}$, $R_{59}$, $R_g$ and $R_h$ are each, independently, methyl or hydrogen; or at least one pair of substituents $R_{52}$ and $R_{53}$; $R_{54}$ and $R_{55}$; $R_{56}$ and $R_{57}$; or $R_{58}$ and $R_{59}$ together are an oxygen atom; and $R_{60}$ is H, substituted or unsubstituted azabicycloalkyl or Y-Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl; or $R_{60}$ is of the formula

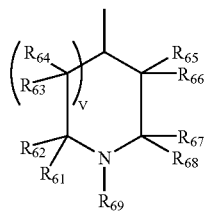

wherein v is 0 or 1;

$R_{61}$, $R_{62}$, $R_{63}$, $R_{64}$, $R_{65}$, $R_{66}$, $R_{67}$ and $R_{69}$ are each, independently, lower alkyl or hydrogen; or at least one pair of substituents $R_{61}$ and $R_{62}$; $R_{63}$ and $R_{64}$; $R_{65}$ and $R_{66}$; and $R_{67}$ and $R_{68}$ together are an oxygen atom; and $R_{69}$ is H, substituted or unsubstituted azabicycloalkyl or V-1, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl.

Another preferred compound of Formula (I) is where $R_3$ is H; $R_2$ is -$Z^{101}$-$Z^{102}$ where $Z^{101}$ is a covalent bond, —(C$_1$-C$_6$)—, —(C$_1$-C$_6$)—O—, —(C$_1$-C$_6$)—C(O)—, —(C$_1$-C$_6$)—C(O)O—, —(C$_1$-C$_6$)—C(O)—NH—, —(C$_1$-C$_6$)—C(O)—N((C$_1$-C$_6$))— or a substituted phenyl group; and $Z^{102}$ is hydrogen, a substituted or unsubstituted alkyl group or a substituted or unsubstituted, saturated or unsaturated heterocyclic group.

Another more preferred compound of Formula (I) is where in any of the applicable foregoing preferred compounds $Z^{101}$ is selected from the group consisting of —CH$_2$—C(O)O—, —CH$_2$—C(O)—, —CH$_2$—C(O)—NH—, —CH$_2$—C(O)—N(Me)—, —CH(Me)—C(O)O—, —(CH$_2$)$_3$—C(O)O—, —CH(Me)—C(O)—NH—, and —(CH$_2$)$_3$—C(O)—NH—; and $Z^{102}$ is selected from the group consisting of hydrogen, methyl, ethyl, N,N-dimethylaminoethyl, N,N-diethylaminoethyl, 2-phenyl-2-hydroxyethyl, morpholino, piperazinyl, N-methylpiperazinyl and 2-hydroxymethylpyrrolidinyl.

Another more preferred compound of Formula (I) is where in any of the applicable foregoing preferred compounds G is

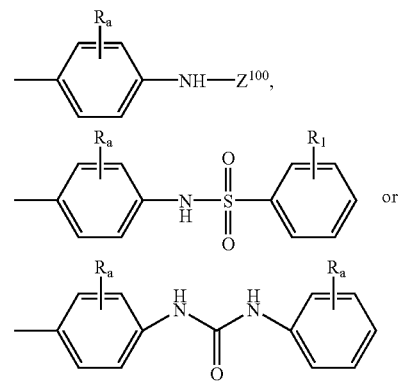

where $Z^{100}$ is a substituted or unsubstituted benzoxazolyl or a substituted or unsubstituted benzthiazolyl.

Another more preferred compound of Formula (I) is where in any of the applicable foregoing preferred compounds G is

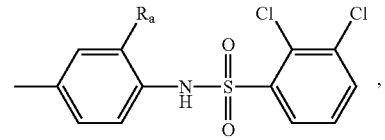

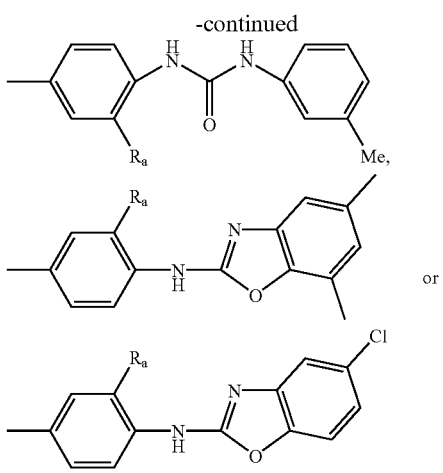

where there is only one $R_a$ and it is H or F.

Another more preferred compound of Formula (I) is where in any of the applicable foregoing preferred compounds $Z^{101}$ is a covalent bond; and $Z^{102}$ is an optionally substituted pyridyl.

Another more preferred compound of Formula (I) is where in any of the applicable foregoing preferred compounds G is

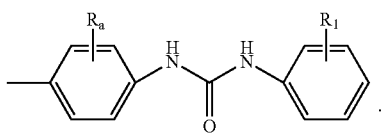

Another preferred compound of Formula (1) is where $R_3$ is H;
$R_2$ is cyclopentyl; and
G is

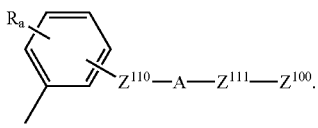

Another more preferred compound of Formula (I) is where in any of the applicable foregoing preferred compounds $Z^{110}$ is hydrogen; A is O; and $Z^{100}$ is optionally substituted phenyl, furanyl or thienyl, where $Z^{100}$ is optionally substituted with one or more substituents each independently selected from the group consisting of F, COOH, $NO_2$, OMe, —COOMe, $OCF_3$ and $CF_3$.

Another more preferred compound of Formula (a) is where in any of the applicable foregoing preferred compounds $Z^{110}$ is hydrogen; A is —O—, —O—$(CR_2)_n$—C(O)— or —O—$(CR_2)_n$—O—; n for each occurrence is 0 to 3;
$Z^{100}$ is an optionally substituted group selected from the group consisting of cyclohexyl, phenyl, tetrahydropyranyl, tetrahydrofuranyl, isoxazolyl and piperidinyl; where $Z^{100}$ is optionally substituted with one or more substituents selected from the group consisting of alkyl, alkoxy, halo, hydroxy and alkoxycarbonyl.

Another more preferred compound of Formula (I) is where in any of the applicable foregoing preferred compounds R is an optionally substituted group selected from the group consisting of cyclobutyl and cyclohexyl.

Another more preferred compound of Formula (I) is where in any of the applicable foregoing preferred compounds $R^2$ is optionally substituted with one or more substituents selected from the group consisting of hydroxy, alkyl, hydroxyalkyl, carboxyalkyl and phenylalkoxyalkyl.

Another more preferred compound of Formula (I) is where in any of the applicable foregoing preferred compounds G is 4-phenoxyphenyl.

Another more preferred compound of Formula (I) is where in any of the applicable foregoing preferred compounds m is 2; a is 0; $R_6$ is H; b is 1 or 2; and $R_4$ and $R_5$ are each hydrogen.

Another more preferred compound of Formula (I) is where in any of the applicable foregoing preferred compounds m is 0, 1 or 2; $R_6$ is hydrogen; $R_5$ is H or Y-Z; where Y is a covalent bond, —C(O)—, —$(CH_2)_qO$—, —$(CH_2)_q$—, —$(CH_2)_qC(O)$— or —$C(O)(CH_2)_q$—, where the alkyl portion of —$(CH_2)_qO$—, —$(CH_2)_p$—, —$(CH_2)_qC(O)$— and —$C(O)(CH_2)_q$— is optionally substituted by a halogen, hydroxy or an alkyl group; and
Z is hydrogen, alkyl, optionally substituted alkyl, alkoxyalkyl, optionally substituted heterocycloalkyl, optionally substituted heteroaryl, or optionally substituted amino.

Another more preferred compound of Formula (I) is where in any of the applicable foregoing preferred compounds Z is hydrogen, methyl, ethyl, hydroxymethyl, methoxyethyl, N-methyl-piperidinyl, (t-butoxycarbonyl)(hydroxy)-piperidinyl, hydroxypiperidinyl, (hydroxymethyl)piperdinyl, (hydroxy)(methyl)-piperidinyl, morpholino, (methoxyethyl)piperizinyl, methylpiperizinyl, 4-piperidinylpiperidinyl, imidazolyl, methylimidazolyl, N-methylamino, N,N-dimethylamino, N-isopropylamino, N,N-diethylamino, 2,3-dihydroxypropylamino, 2-hydroxyethylamino, 3-hydroxypropylamino, methoxyethylamino, ethoxycarbonylmethylamino, phenylmethylamino, N-methyl-N-methoxyamino,

furanylmethylamino, piperidinylethylamino, N-(2-N,N-dimethylaminoethyl)-N-methylamino, 2-N,N-dimethylaminoethylamino, N-methyl-N-(N-methylpiperidin-4-yl)amino, 2-morpholino-ethylamino, 3-morpholino-propylamino, 3-imidazolylpropylamino, or 3-(2-oxopyrrolidinyl)propylamino.

Another more preferred compound of Formula (I) is where in any of the applicable foregoing preferred compounds m is 2; $R_5$ is Y-Z; Y is —C(O)—; and Z is

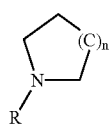

where n is 0, 1, 2 or 3.

Another more preferred compound of Formula (I) is where in any of the applicable foregoing preferred compounds $R_4$ is hydrogen or methyl;

G is 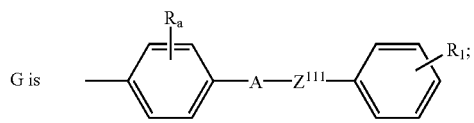

A is selected from the group consisting of O, —N(R)— and —N(R)C(O)—;

$Z^{111}$ is —(CH$_2$)$_n$-cycloalkyl-(CH$_2$)$_n$—; R is hydrogen or alkyl; n is 0 to 5;

$R_a$ is one or more substituents each independently selected from the group consisting of H, OH, F, Cl, methyl and methoxy;

$R_1$ is one or more substituents each independently selected from the group consisting of H, CN, F, CF$_3$, OCF$_3$, methyl, methoxy and an optionally substituted amino group; and where said amino group is optionally substituted with one or two groups each independently selected from the group consisting of alkyl, alkoxyalkyl, phenyl, substituted phenyl, and optionally substituted heteroaryl.

Another more preferred compound of Formula (I) is where in any of the applicable foregoing preferred compounds $R_1$ is 4-methylphenylthio or 2-pyridinylthio.

Another more preferred compound of Formula (I) is where in any of the applicable foregoing preferred compounds G is

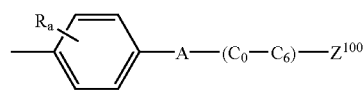

where $Z^{100}$ is selected from the group consisting of benzo[b]thiophene, furanyl and thiophene.

Another more preferred compound of Formula (I) is where in any of the applicable foregoing preferred compounds $R_a$ is alkoxy; A is —NH—C(O)—; and there is a covalent bond between A and $Z^{100}$.

Another more preferred compound of Formula (1) is where in any of the applicable foregoing preferred compounds G is

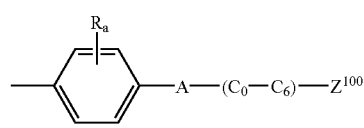

A is selected from the group consisting of —N(R)—C(O)—N(R)—, —(CH$_2$)—N(R)C(O)N(R)—, —N(R)— and —N(R)—SO$_2$—; R is hydrogen or alkyl;

$Z^{100}$ is

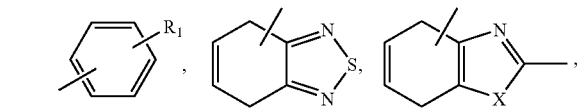

pyridinyl, thiazolyl, furanyl, benzofuranyl or oxazolyl;

X is S, O or NR$^1$ where R$^1$ for each occurrence is independently H or Me;

$R_a$ is one or more substituents each independently selected from the group consisting of H and F; and $R_1$ is one or more substituents each independently selected from the group consisting of H, F, Cl, Br, NO$_2$, CF$_3$, alkyl, alkoxy and alkoxycarbonyl.

Another more preferred compound of Formula (I) is where in any of the applicable foregoing preferred compounds $R_4$ is methyl; m is 1, 2 or 3; $R_5$ is Y-Z, where Y is —C(O)O—, —C(O)— or —C(O)—(CH$_2$)$_p$—; and Z is aminoalkyl, N-alkylamino, N,N-dialkylamino or hydroxyalkylaminoalkyl.

Another more preferred compound of Formula (I) is where in any of the applicable foregoing preferred compounds $R_4$ is methyl; G is

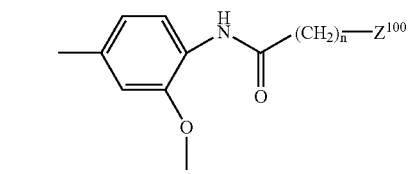

where n is 0 to 3; $Z^{100}$ is an optionally substituted group selected from the group consisting of indolyl, indenyl, methylindenyl, methylindolyl, dimethylaminophenyl, phenyl, cyclohexyl and benzofuranyl.

Another more preferred compound of Formula (I) is where in any of the applicable foregoing preferred compounds
G is

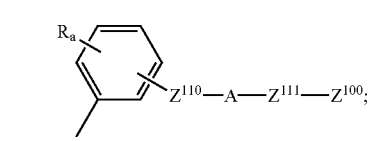

$Z^{100}$ is an optionally substituted group selected from the group consisting of phenyl, imidazolyl, indolyl, furanyl, benzofuranyl and 2,3-dihydrobenzofuranyl;

where $Z^{100}$ is optionally substituted with one or more substituents each independently selected from the group consisting of F, Cl, CN, optionally substituted alkyl, —O—(optionally substituted alkyl), —COOH, -$Z^{105}$-C(O)N(R)$_2$, -$Z^{105}$-N(R)—C(O)-$Z^{200}$, -$Z^{105}$-N(R)—S(O)$_2$-$Z^{200}$, and -$Z^{105}$-N(R)—C(O)—N(R)-$Z^{200}$;

$Z^{105}$ is a covalent bond or (C$_1$-C$_6$);

$Z^{200}$ is an optionally substituted group selected from group consisting of (C$_1$-C$_6$), phenyl and —(C$_1$-C$_6$)-phenyl;

$Z^{110}$ and $Z^{111}$ are each independently a covalent bond or (C$_1$-C$_3$) group optionally substituted with alkyl, hydroxy, COOH, CN or phenyl; and A is O, —N(R)—C(O)—N(R)—, —N(R)—C(O)—O—, —N(R)— or —N(R)—C(O)—, where R is H or alkyl.

Another more preferred compound of Formula (I) is where in any of the applicable foregoing preferred compounds R$_4$ is methyl.

Another more preferred compound of Formula (I) is where in any of the applicable foregoing preferred compounds G is 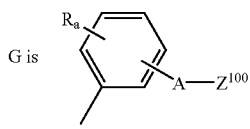

where Z$^{100}$ is an optionally substituted group selected from the group consisting of benzoxazolyl, benzothiazolyl and benzimidazolyl.

Another more preferred compound of Formula (I) is where in any of the applicable foregoing preferred compounds R$_4$ is methyl; A is —NH—; there is only one R$_a$ and it is H or F; and Z$^{100}$ is optionally substituted with one or more substituents each independently selected from the group consisting of alkyl, halo, CF$_3$, and alkoxy.

Another more preferred compound of Formula (I) is where in any of the applicable foregoing preferred compounds G is 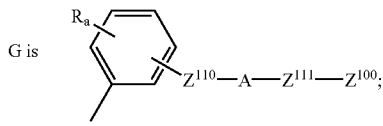

Z$^{100}$ is an optionally substituted group selected from the group consisting of phenyl, pyrrolyl, pyridyl, benzimidazolyl, naphthyl and

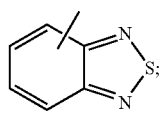

where Z$^{100}$ is optionally substituted with one or more substituents each independently selected from the group consisting of F, Cl, Br, NO$_2$, amino, N-alkylamino, N,N-dialkylamino, CN, optionally substituted alkyl, —O-(optionally substituted alkyl) and phenyl;

Z$^{110}$ and Z$^{111}$ for each occurrence is independently (C$_0$-C$_3$) optionally substituted with optionally substituted phenyl; and A is —N(R)—C(O)—N(R)—, —N(R)—S(O)$_2$—, —N(R)—C(O)—, —N(R)— or —N(R)—C(O)—O—.

Another more preferred compound of Formula (I) is where in any of the applicable foregoing preferred compounds R$_4$ is methyl and there is only one R$_a$ and it is F.

Another more preferred compound of Formula (I) is where in any of the applicable foregoing preferred compounds G is

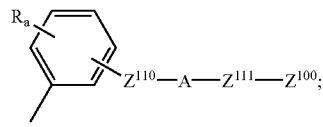

Z$^{100}$ is an optionally substituted group selected from the group consisting of phenyl, isoxazolyl, tetrahydronaphthyl, furanyl, benzofuranyl, pyridyl and indolyl; where Z$^{100}$ is optionally substituted with one or more substituents each independently selected from the group consisting of F, CN, NO$_2$, —C(O)H, —CONH$_2$, —NHSO$_2$CF$_3$, optionally substituted alkyl, optionally substituted heteroaryl and —O-(optionally substituted alkyl);

Z$^{110}$ and Z$^{111}$ are each independently optionally substituted (C$_0$-C$_3$); and A is O, —N(R)—C(O)—(CH$_2$)$_n$—N(R)—, —C(O)—N(R)—, —N(R)—C(O)—O—, —N(R)—C(O)— or —N(R)—.

Another more preferred compound of Formula (I) is where in any of the applicable foregoing preferred compounds R$_4$ is methyl; R$_a$ is H or methoxy; and Z$^{110}$ and Z$^{111}$ are each unsubstituted.

Another more preferred compound of Formula (I) is where in any of the applicable foregoing preferred compounds G is

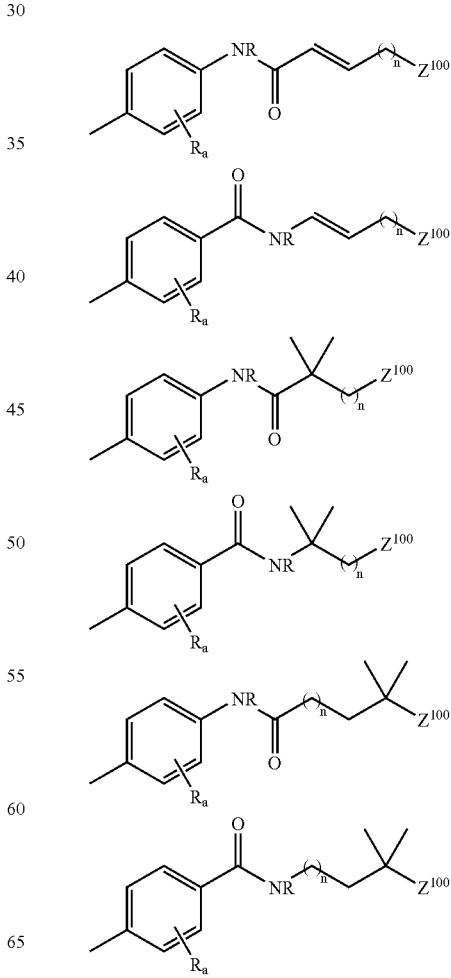

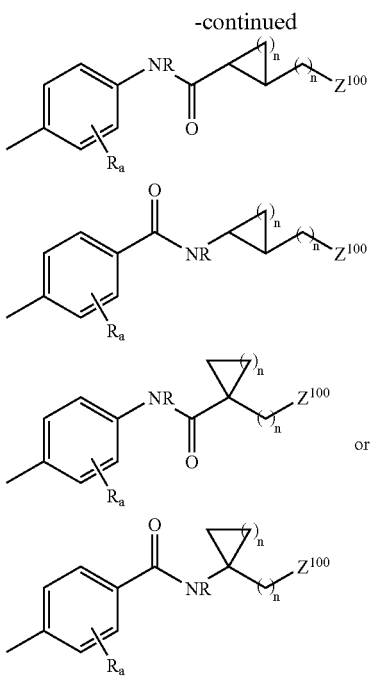

where R is H or lower alkyl and n is for each occurrence is independently 1 to 6.

Another more preferred compound of Formula (I) is where in any of the applicable foregoing preferred compounds G is

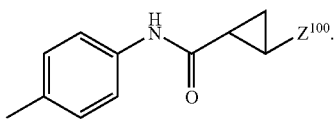

Another more preferred compound of Formula (I) is where in any of the applicable foregoing preferred compounds wherein $Z^{100}$ is substituted or unsubstituted phenyl.

Another more preferred compound of Formula (I) is where in any of the applicable foregoing preferred compounds G is

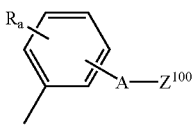

where $Z^{100}$ is an optionally substituted group selected from the group consisting of benzoxazolyl, benzothiazolyl and benzimidazolyl.

Another more preferred compound of Formula (I) is where in any of the applicable foregoing preferred compounds n is 2; $R_6$ is H; m is 1; r is 1; and $R_4$ and $R_5$ are each hydrogen.

Another more preferred compound of Formula (I) is where in any of the applicable foregoing preferred compounds wherein G is 4-phenoxyphenyl.

In another aspect the present invention is directed to a method of inhibiting one or more protein kinase activity in a patient comprising administering a therapeutically effective amount of a compound of Formula (I) or a physiologically acceptable salt, prodrug or biologically active metabolites thereof to said patient. A preferred method is where said protein kinase is selected from the group consisting of KDR, FGFR-1, PDGFRβ, PDGFRα, IGF-1R, c-Met, Flt-1, Flt-4, TIE-2, TIE-1, Lck, Src, fyn, Lyn, Blk, hck, fgr and yes. Another preferred method is where the protein kinase is a protein serine/threonine kinase or a protein tyrosine kinase. A more preferred method is where the protein kinase is TIE-2 and another more preferred method is where the protein kinase activity is involved in T cell activation, B cell activation, mast cell degranulation, monocyte activation, the potentiation of an inflammatory response or a combination thereof.

In another aspect the present invention is directed to a method of affecting hyperproliferative disorders in a patient comprising administering a therapeutically effective amount of a compound of Formula (I) or a physiologically acceptable salt, prodrug or biologically active metabolites thereof to said patient.

In another aspect the present invention is directed to a method of affecting angiogenesis in a patient comprising administering a therapeutically effective amount of a compound of Formula (I) or a physiologically acceptable salt, prodrug or biologically active metabolites thereof to said patient. A preferred method is where the compound or a physiologically acceptable salt, prodrug or biologically active metabolite thereof is administered in an amount effective to promote angiogenesis or vasculogenesis. A more preferred method is where the patient is suffering from anemia, ischemia, infarct, transplant rejection, a wound, gangrene or necrosis.

In another aspect the present invention is directed to a method of treating one or more ulcers in a patient comprising administering a therapeutically effective amount of a compound of Formula (I) or a physiologically acceptable salt, prodrug or biologically active metabolites thereof to said patient. A preferred method is where the ulcer or ulcers are caused by a bacterial or fungal infection; or the ulcer or ulcers are Mooren ulcers; or the ulcer or ulcers are a symptom of ulcerative colitis.

In another aspect the present invention is directed to a method of treating a condition in a patient comprising administering a therapeutically effective amount of a compound of Formula (I) or a physiologically acceptable salt, prodrug or biologically active metabolites thereof to said patient, wherein said condition is an ocular condition, a cardiovascular condition, a cancer, Crow-Fukase (POEMS) syndrome, a diabetic condition, sickle cell anaemia, chronic inflammation, systemic lupus, glomerulonephritis, synovitis, inflammatory bowel disease, Crohn's disease, glomerulonephritis, rheumatoid arthritis, osteoarthritis, multiple sclerosis, graft rejection, Lyme disease, sepsis, von Hippel Lindau disease, pemphigoid, psoriasis, Paget's disease, polycystic kidney disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, preeclampsia, menometrorrhagia, endometriosis, or infection by Herpes simplex, Herpes Zoster, human immunodeficiency virus, parapoxyirus, protozoa or toxoplasmosis.

A preferred method is where the ocular condition is:
ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy or macular degeneration;
the cardiovascular condition is:
atherosclerosis, restenosis, ischemia/reperfusion injury, vascular occlusion or carotid obstructive disease;
the cancer is:
a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, Kaposi's sarcoma, Hodgkin's disease, lymphoma, myeloma, leukemia or malignant ascites; and
the diabetic condition is:
insulin-dependent diabetes mellitus glaucoma, diabetic retinopathy or microangiopathy.

In another aspect the present invention is directed to a method of decreasing fertility in a patient, said method comprising the step of administering to the patient an effective amount of a compound of Formula (I) or a physiologically acceptable salt, prodrug or biologically active metabolite thereof.

In another aspect the present invention is directed to a method wherein the compound of Formula I, or physiologically acceptable salt, prodrug or biologically active metabolite thereof, is administered in combination with a pro-angiogenic growth factor. A preferred method is where the pro-angiogenic growth factor is selected from the group consisting of VEGF, VEGF-B, VEGF-C, VEGF-D, VEGF-E, HGF, FGF-1, FGF-2, derivatives thereof and antiiodotypic antibodies.

DETAILED DESCRIPTION OF THE INVENTION

In one embodiment, the present invention provides compounds of Formula I as described above. The values of substituents in preferred groups of compounds of Formula I are given below.

Preferably, $R_1$ is selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted and unsubstituted tetrazolyl, substituted and usubstituted styryl, substituted and unsubstituted arylthio, substituted or unsubstituted thioalkoxy, substituted and unsubstituted heteroarylthio; $CH_2OR_c$, wherein $R_c$ is hydrogen or substituted or unsubstituted alkyl or aryl; and —W—$(CH_2)_t$—$NR_dR_e$, wherein t is an integer from about 1 to about 6; W is a direct bond, O, S, S(O), $S(O)_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together form a five- or six-membered heterocyclic ring.

Preferably $R_a$ is selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, substituted or unsubstituted thioalkoxy, carboxyl, substituted and unsubstituted tetrazolyl, substituted and usubstituted styryl, substituted and unsubstituted arylthio, substituted and unsubstituted heteroarylthio; $CH_2OR_c$, wherein $R_c$ is hydrogen or substituted or unsubstituted alkyl or aryl; and —W—$(CH_2)_t$—$NR_dR_e$, wherein t is an integer from about 1 to about 6; W is a direct bond, O, S, S(O), $S(O)_2$, or $NR_f$, wherein $R_f$ is H or alkyl and $R_d$ and $R_e$ are independently H, alkyl, alkanoyl or $SO_2$-alkyl; or $R_d$, R, and the nitrogen atom to which they are attached together form a five- or six-membered heterocyclic ring.

Compounds of Formula (I) may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of Formula (I) which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centres, and exist in different optically active forms. When compounds of formula I contain one chiral centre, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of Formula (I) may exist in different tautomeric forms or as different geometric isomers, and the present invention includes each tautomer and/or geometric isomer of compounds of formula I and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

Heteroaromatic groups, as used herein, include heteroaryl ring systems (e.g., for purposes of exemplification, which should not be construed as limiting the scope of this invention: thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isothiazoles, oxazolyl or tetrazoles) and heteroaryl ring systems in which a carbocyclic aromatic ring, carbocyclic non-aromatic ring or heteroaryl ring is fused to one or more other heteroaryl rings (e.g., for purposes of exemplification, which should not be construed as limiting the scope of this invention: benzo(b)thienyl, benzimidazolyl, benzoxazolyl, benzothiazolyl, benzothiadiazolyl, benzoxadiazolyl, indole, tetrahydroindole, azaindole, indazole, quinoline, imidazopyridine, quinazoline purine, pyrrolo[2,3-d]pyrimidine, pyrazolo[3,4-d]pyrimidine) and their N-oxides. Substituted heteroaryl groups are preferably substituted with one or more substituents each independently selected from the group consisting of a halogen, hydroxy, alkyl, alkoxy, alkyl-O—C(O)—, alkoxyalkyl, a heterocycloalkyl group, optionally substituted phenyl, nitro, amino, mono-substituted amino or di-substituted amino.

A heterocyclic (heterocyclyl) group, as used herein, refers to both heteroaryl groups and heterocycloalkyl groups.

A heterobicyclic group, as used herein, refers to a bicyclic group having one or more heteroatoms, which is saturated, partially unsaturated or unsaturated.

An arylalkyl group, as used herein, is an aromatic substituent that is linked to a compound by an aliphatic group having from one to about six carbon atoms. A preferred arylalkyl group is a benzyl group An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur.

As used herein, aliphatic groups or notations such as "$(C_0\text{-}C_6)$" include straight chained, branched or cyclic hydrocarbons which are completely saturated or which contain one or more units of unsaturation. When the group is a Co it means that the moiety is not present or in other words is a bond.

As used herein, aromatic groups (or aryl groups) include aromatic carbocyclic ring systems (e.g. phenyl) and fused polycyclic aromatic ring systems (e.g. naphthyl and 1,2,3,4-tetrahydronaphthyl).

As used herein, acyloxy groups are —OC(O)R.

As used herein, the term "natural amino acid" refers to the twenty-three natural amino acids known in the art, which are as follows (denoted by their three letter acronym): Ala, Arg, Asn, Asp, Cys, Cys-Cys, Glu, Gln, Gly, His, Hyl, Hyp, Ile, Leu, Lys, Met, Phe, Pro, Ser, Thr, Trp, Tyr, and Val. The term non-natural amino acid refers to compounds of the formula $NH_2$—$(C(X)_2)_n$—COOH, which are alpha-(when n is 1) or beta-(when n is 2) amino acids where X for each occurrence is independently any side chain moiety recognized by those skilled in the art; examples of non-natural amino acids include, but are not limited to: hydroxyproline, homoproline, 4-amino-phenylalanine, β-(2-naphthyl)alanine, norleucine, cyclohexylalanine, β-(3-pyridinyl)alanine, β-(4-pyridinyl)alanine, α-aminoisobutyric acid, urocanic acid, N,N-tetramethylamidino-histidine, N-methyl-alanine, N-methyl-glycine, N-methyl-glutamic acid, tert-butylglycine, α-aminobutyric acid, tert-butylalanine, ornithine, α-aminoisobutyric acid, β-alanine, γ-aminobutyric acid, 5-aminovaleric acid, 12-aminododecanoic acid, 2-aminoindane-2-carboxylic acid, etc. and the derivatives thereof, especially where the amine nitrogen has been mono- or di-alkylated.

As used herein, many moieties or substituents are termed as being either "substituted or unsubstituted" or "optionally substituted". When a moiety is modified by one of these terms, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkyl groups (which itself can also be substituted, such as —$C_1$-$C_6$-alkyl-OR, —$C_1$-$C_6$-alkyl-N(R)$_2$, and —$CF_3$), alkoxy group (which itself can be substituted, such as —O—$C_1$-$C_6$-alkyl-OR, —O—$C_1$-$C_6$-alkyl-N(R)$_2$, and $OCF_3$), a halogen or halo group (F, Cl, Br, I), hydroxy, nitro, oxo, CN, COH, COOH, amino, N-alkylamino or N,N-dialkylamino (in which the alkyl groups can also be substituted), esters (—C(O)—OR, where R is groups such as alkyl, aryl, etc., which can be substituted), aryl (most preferred is phenyl, which can be substituted) and arylalkyl (which can be substituted).

Suitable synthetic routes to compounds of Formula I are outlined in Schemes I-XII. Scheme I shows the conversion of 3-halo-4-chloropyrazolopyrimidine, to an N1-substituted 3-aryl-4-aminopyrazolopyrimidine. Scheme II illustrates substitution at N-1 of a 3-halo-4-aminopyrazolopyrimidine, followed by replacement of halo with an aryl group. Scheme 1 ml illustrates substitution at N-1 of a 3-aryl-4-aminopyrazolopyrimidine. Scheme IV shows the conversion of 4-hydroxypyrazolopyrimidine to a 1-substituted 3-bromo-4-chloropyrazolopyrimidine. Scheme V illustrates the formation of the pyrazolopyrimidine core. Scheme VI shows the formation of a 3-aryl-4-aminopyrazolopyrimidine. Scheme VII shows further elaboration of the N-1 substituent. P represents a suitable amino protecting group. Scheme VIII illustrates the preparation of the aryl boronates utilized in Scheme I. Schemes IX and X show the modification of the N-1 substituent. Scheme XI illustrates functionalization of the 3-aryl group. In Schemes I-XI, certain reactions may require suitable protection/deprotection of non-participating functional groups, as is known in the art.

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, myocardial angiogenesis, coronary and cerebral collaterals, ischemic limb angiogenesis, ischemia/reperfusion injury, wound healing, peptic ulcer Helicobacter related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially GraveF☐s disease), and cysts (such as hypervascularity of ovarian stroma characteristic of polycystic ovarian syndrome (Stein-Leventhal syndrome) and polycystic kidney disease.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

Synthesis

The compounds of the invention can be prepared using the methods depicted in Schemes I-XI.

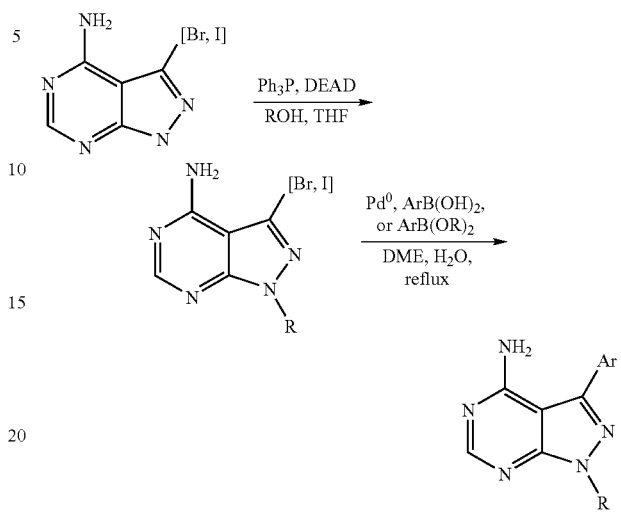

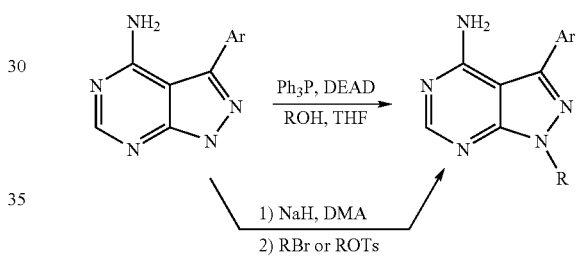

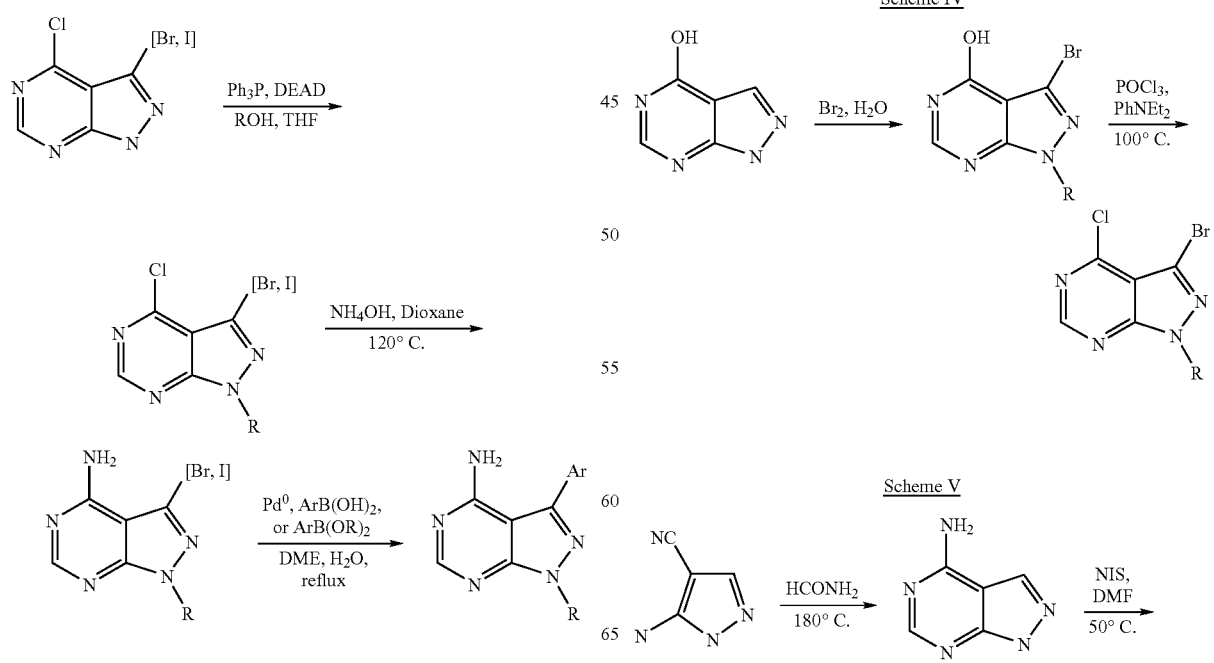

-continued
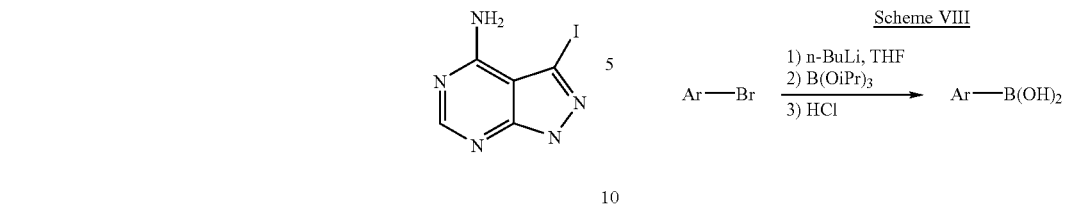
Scheme VIII
Scheme VI
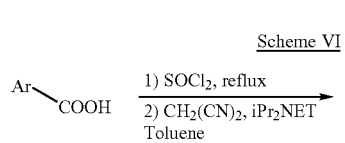
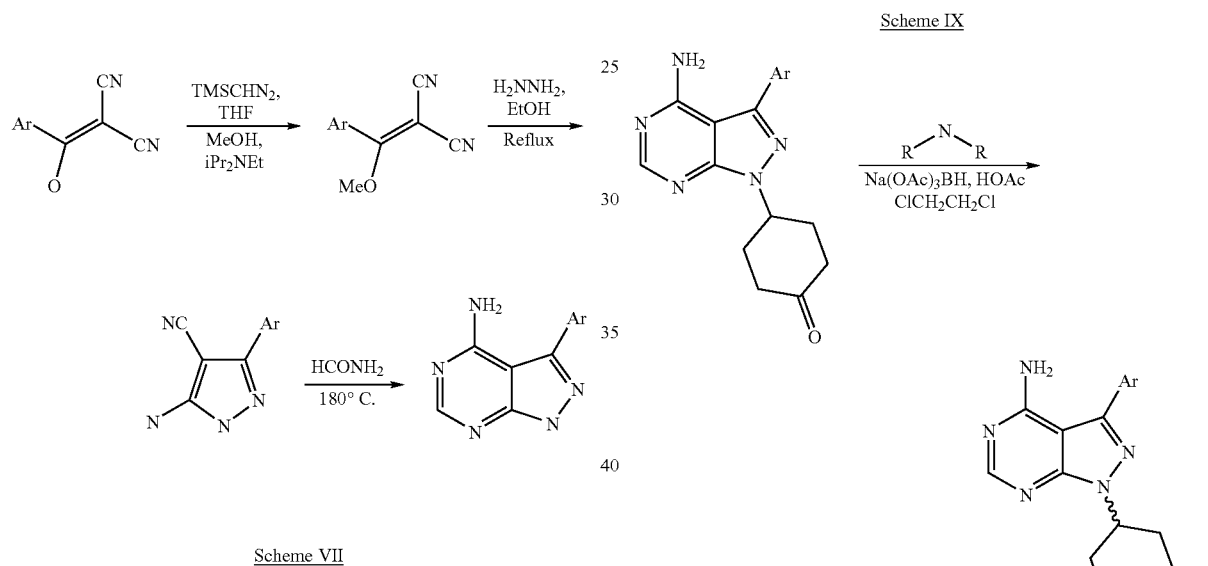
Scheme IX
Scheme VII
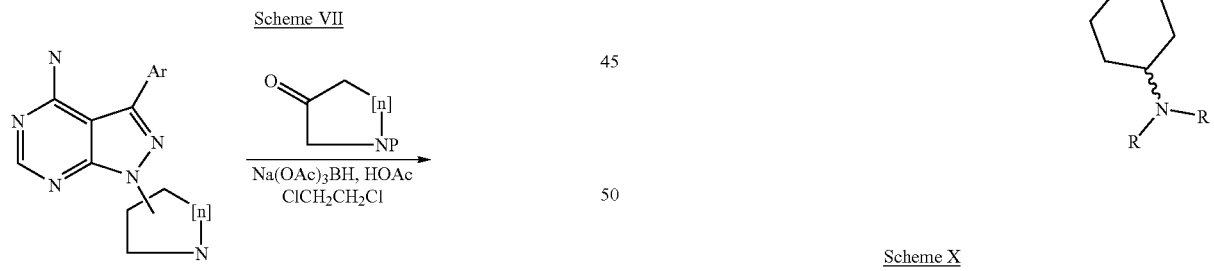
Scheme X
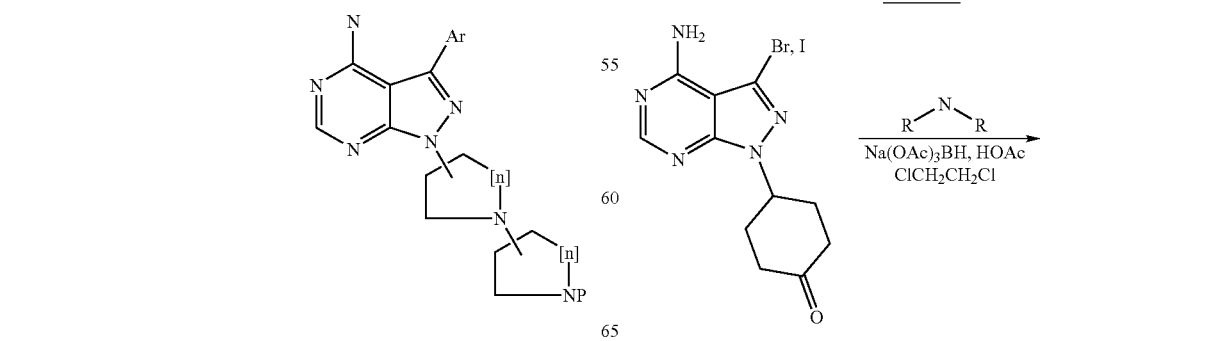

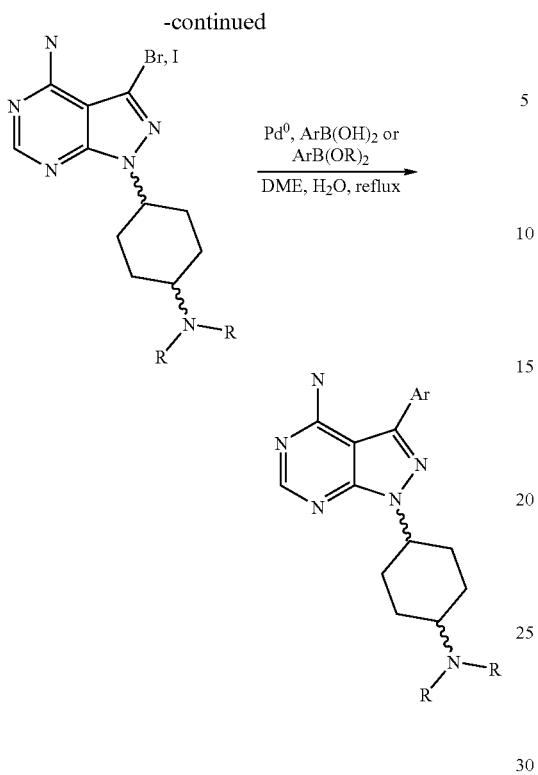

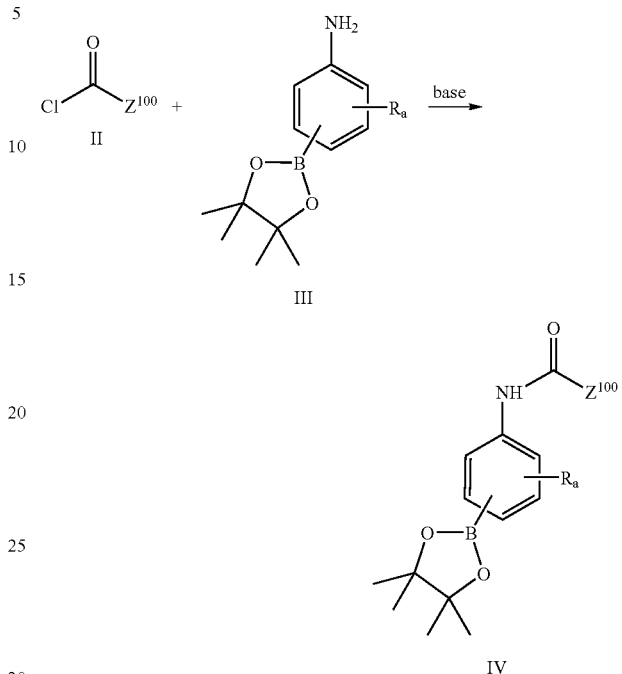

Scheme XII: Method of preparing a 4,4,5,5-tetramethyl-1,3,2-dioxaborolan-2-yl intermediate

Scheme XI

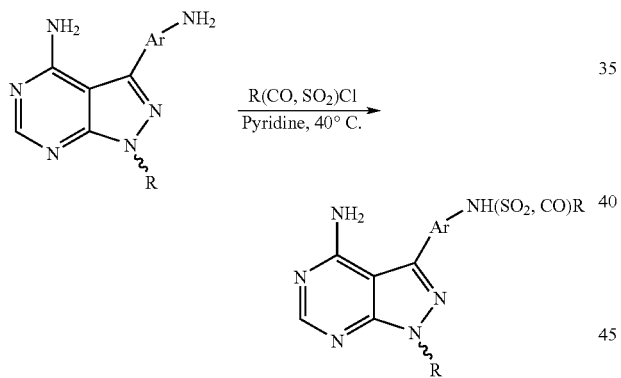

A preferred method of preparing the compounds of the invention involves preparing a 4,4,5,5-tetramethyl-1,3,2-dioxaborolan-2-yl intermediate (IV) (see Scheme XII). The method involves reacting an acid chloride (II) with a (4,4,5,5-tetramethyl-1,3,2-dioxaborolan-2-yl)aniline (III) in the presence of an aprotic base. Typically, the acid chloride (II) and (4,4,5,5-tetramethyl-1,3,2-dioxaborolan-2-yl)aniline (III) are dissolved in an organic solvent in approximately equal molar amounts. About 1 eq. to about 2 eq. of an aprotic base is added to the solution. Preferably, the solution is cooled to about −10° C. to about 10° C. before addition of the base and the base is added dropwise to the solution. After addition of the base, the solution is allowed to stir at ambient temperatures until the reaction is complete (as determined by thin layer chromatorgraphy, HPLC or other standard analytical techniques). Typically, the reaction is complete after about 10 h to about 26 h.

The 4,4,5,5-tetramethyl-1,3,2-dioxaborolan-2-yl intermediate (IV) can be used to prepare compounds of formula I by reacting it with a 3-iodo-1H-pyrazolo[3,4-d]pyrimidine (V) in the presence of tetrakis(triphenylphosphine)palladium(0) and sodium carbonate (see Scheme XIII). The 3-iodo-1H-pyrazolo[3,4-d]pyrimidine (V) in a polar organic solvent, such as an ether, is treated with an aqueous mixture of 4,4,5,5-tetramethyl-1,3,2-dioxaborolan-2-yl intermediate (IV), tetrakis(triphenylphosphine)palladium(0) and sodium carbonate. Typically, the 4,4,5,5-tetramethyl-1,3,2-dioxaborolan-2-yl intermediate (IV) is present in the solution in about 1 eq. to about 1.5 eq., the tetrakis(triphenylphosphine)palladium(0) is present in about 0.01 eq. to about 0.1 eq, and the sodium carbonate is present in about 1.5 eq. to about 3 eq. with respect to the 3-iodo-1H-pyrazolo[3,4-d]pyrimidine (V). The solution is heated to about 50° C. to about 100° C. The reaction is monitored by thin layer chromatorgraphy, HPLC or other standard analytical techniques to determine when the reaction is complete. Typically, the reaction is complete after about 16 h to about 30 h.

Scheme XIII: Method of preparing compounds of formula I in which $Z^{100}$—A—$Z^{111}$ is —NHC(O)—.

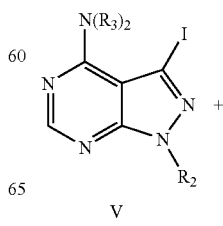

-continued

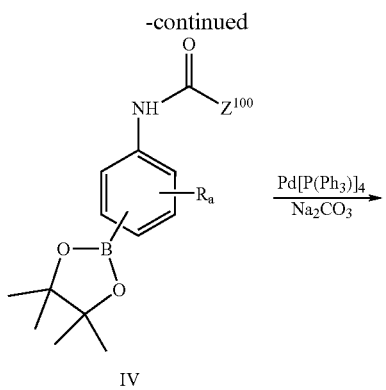

IV

Compounds of formula II can be prepared by reacting a carboxylic acid represented by formula VI with oxalyl chloride in the presence of an aprotic base.

VI

Ia

In a preferred embodiment, $Z^{100}$ is indolyl which is optionally substituted with R, in the methods of Schemes XII and XIII and in the method of preparing the acid chloride (II). In a more preferred embodiment, $Z^{100}$ is 1-methyl-indol-2-yl or 1-methyl-indol-3-yl in the methods of Schemes XII and XIII and in the method of preparing the acid chloride (II).

In another preferred embodiment, in the methods of Schemes XII and XIII and in the method of preparing the acid chloride (II), $Z^{100}$ is indolyl which is optionally substituted with $R_1$; the (4,4,5,5-tetramethyl-1,3,2-dioxaborolan-2-yl)aniline is represented by formula VII

VII and the 4,4,5,5-tetramethyl-1,3,2-dioxaborolan-2-yl intermediate is represented by formula VIII

VIII and the compounds of the invention prepared can be represented by formula IX

IX

In a more preferred embodiment, in the methods of Schemes XII and XIII and in the method of preparing the acid chloride (II), $Z^{100}$ is 1-methyl-indol-2-yl or 1-methyl-indol-3-yl; the (4,4,5,5-tetramethyl-1,3,2-dioxaborolan-2-yl)aniline is represented by formula VII; and the 4,4,5,5-tetramethyl-1,3,2-dioxaborolan-2-yl intermediate is represented by formula X

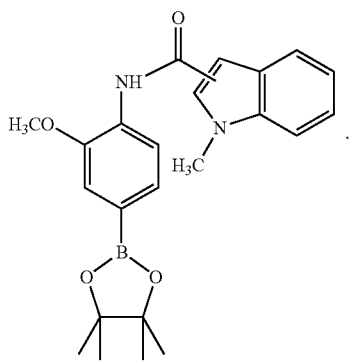

and the compounds of the invention prepared can be represented by formula XI

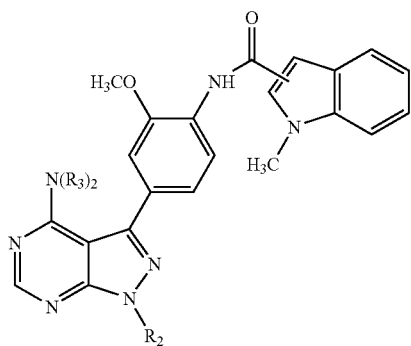

In a more preferred embodiment, $R_2$ is 4-(4-methylpiperazino)cyclohexyl in any of the above described methods.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemnia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention areuseful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or TIE-2 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Flt-4, Tie-1, Tie-2, FGFR, PDGFR, IGF-1R, c-Met, Src-subfamily kinases such as Lck, Src, hck, fgr, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, A and ring 1) and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278-1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising adiminstering to the patient a therapeutically or prophylactically effective amount of one or more compounds of Formula I.

A "protein kinase-mediated condition" or a "condition mediated by protein kinase activity" is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficincy virus, protozoa, toxoplasmosis or parapoxyirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

The Src, Tec, Jak, Map, Csk, NFKB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formula I may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the ltk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve FGF and/or PDGF—promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activities individually or in combination may be an efficacious strategy for inhibiting these phenomena. Thus compounds of formula I which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Flt-4, Tie-2/Tek and Tie) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. KDR/VEGFR-2 and/or Tie-2 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (*J. Clin. Investig.* 103: 1231-1236 (1999)). In some progenitors, Tie-2 may play a role in their recruitment, adhesion, regulation and differentiation (*Blood*, 4317-4326 (1997)). Certain agents according to formula I capable of blocking the kinase activity of endothelial cell specific kinases could therefore inhibit disease progression involving these situations.

Vascular destabilization of the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055-1066 (1999)). In an analogous manner a Tie-2 kinase inhibitor can be proangiogenic or antiangiogenic in the presence or absence of a VEGF-related stimulus, respectively. Hence, Tie-2 inhibitors can be employed with appropriate proangiogenic stimuli, such as VEGF, to promote therapeutic angiogenesis in situations such as wound healing, infarct and ischemia.

The compounds of formula I or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above for use as medicaments, particularly as inhibitors of protein kinase activity for example tyrosine kinase activity, serine kinase activity and threonine kinase activity. In yet another aspect the present invention provides the use of compounds of formula I as defined initially above in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

Phamaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 µl). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets
Tablets can be prepared from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-ILI agents, antihistamines, PAF-antagonists, COX-1 inhibitors, COX-2 inhibitors, NO synthase inhibitors, Akt/PTB inhibitors, IGF-1R inhibitors, PKC inhibitors and P13 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536-539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at $2\times10^6$/ml, and were infected at 0.5 plaque forming units per cell (MOI). Cells were harvested at 48 hours post infection.

Purification of KDR

SF-9 cells expressing $(His)_6$ KDR(aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1L of cell culture. The lysate was centrifuged at 19,000 rpm in a Sorval SS-34 rotor for 30 min at 4EC. The cell lysate was applied to a 5 ml $NiCl_2$ chelating sepharose column, equilibrated with 50 mM HEPES, pH 7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH 7.5, 25 mM NaCl, 5 mM DTT buffer and stored at −80EC.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 pI) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids $M(H)_6$ LVPRGS was placed 5' to the region encoding the entirety of ZAP70 (amino acids 1-619). The nucleotide sequence encoding the ZAP70 coding region was generated through PCR using cDNA libraries isolated from Jurkat immortalized T-cells. The histidine residues enabled affinity purification of the protein (vide infra). The LVPRGS bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 gg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g. from Upstate Biotechnology Inc. (Saranac Lake, N.Y.) and Santa Cruz Biotechnology Inc. (Santa Cruz, Ca.)) or purified from known natural or recombinant sources using conventional methods.

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359-371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000-50,000 MW) was employed together with ATP (typically 5 µM) at concentrations approximately twice the apparent Km in the assay.

The following procedure was used to assay the inhibitory effect of compounds of this invention on KDR, Flt-1, Flt-4/VEGFR-3, Tie-1, Tie-2, EGFR, FGFR, PDGFR, IGF-1-R, c-Met, Lck, Blk, Csk, Src, Lyn, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 µg/ml in Gibco PBS.

Reaction Buffer: 100 mM Hepes, 20 mM $MgCl_2$, 4 mM $MnCl_2$, 5 nM DTT, 0.02% BSA, 2001M $NaVO_4$, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1×with 250 µl washing buffer and dry for about 2 hrs in 37° C. dry incubator. Store coated plates in sealed bag at 4° C. until used.

2. Tyrosine Kinase Reaction:
Prepare inhibitor solutions at a 4×concentration in 20% DMSO in water.
Prepare reaction buffer
Prepare enzyme solution so that desired units are in 50 µl, e.g. for KDR make to 1 ng/µl for a total of 50 ng per well in the reactions. Store on ice.
Make 4×ATP solution to 20 µM from 100 mM stock in water. Store on ice
Add 50 µl of the enzyme solution per well (typically 5-50 ng enzyme/well depending on the specific activity of the kinase)
Add 25 µl 4×inhibitor
Add 25 µl 4×ATP for inhibitor assay
Incubate for 10 minutes at room temperature
Stop reaction by adding 50 µl 0.05N HCl per well
Wash plate

**Final Concentrations for Reaction: 5 µM ATP, 5% DMSO

3. Antibody Binding
Dilute 1 mg/ml aliquot of PY20—HRP (Pierce) antibody (a phosphotyrosine antibody)to 50 ng/ml in 0.1% BSA in PBS by a 2 step dilution (100×, then 200×)
Add 100 µl Ab per well. Incubate 1 hr at room temp. Incubate 1 hr at 4C.
Wash 4×plate 4. Color Reaction
Prepare TMB substrate and add 100 µl per well
Monitor OD at 650 nm until 0.6 is reached
Stop with 1M Phosphoric acid. Shake on plate reader.
Read OD immediately at 450 nm
Optimal incubation times and enzyme reaction conditions vary slightly with enzyme preparations and are determined empirically for each lot.

For Lck, the Reaction Buffer utilized was 100 mM MOPSO, pH 6.5, 4 mM MnCl$_2$, 20 mM MgCl$_2$, 5 mM DTT, 0.2% BSA, 200 mM NaVO$_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit either FGFR, PDGFR, KDR, Tie-2, Lck, Fyn, Blk, Lyn or Src at concentrations of 50 micromolar or below. Some compounds of this invention also significantly inhibit other tyrosine or serine/threonine kinases such as cdc2 (cdk1) at concentrations of 50 micromolar or below.

Cdc2 Source
The human recombinant enzyme and assay buffer may be obtained commercially (New England Biolabs, Beverly, Mass. USA) or purified from known natural or recombinant sources using conventional methods.

Cdc2 Assay
The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM MgCl$_2$ (commercial buffer) supplemented with fresh 300 µM ATP (31 µCi/ml) and 30 µg/ml histone type IIIss final concentrations. A reaction volume of 80 µL, containing units of enzyme, was run for 20 minutes at 25 degrees C. in the presence or absence of inhibitor. The reaction was terminated by the addition of 120 µL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 uM.

PKC Kinase Source
The catalytic subunit of PKC may be obtained commercially (Calbiochem).

PKC Kinase Assay
A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220-1227 (1990)). Briefly, all reactions were performed in a kinase buffer consisting of 50 mM Tris-HCl pH 7.5, 10 mM MgCl$_2$, 2 mM DTT, 1 mM EGTA, 100 µM ATP, 8 µM peptide, 5% DMSO and $^{33}$P ATP (8 Ci/mM). Compound and enzyme were mixed in the reaction vessel and the reaction initiated by addition of the ATP and substrate mixture. Following termination of the reaction by the addition of 10 µL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source
The recombinant murine enzyme and assay buffer may be obtained commercially (New England Biolabs, Beverly Mass. USA) or purified from known natural or recombinant sources using conventional methods.

Erk2 Enzyme Assay
In brief, the reaction was carried out in a buffer consisting of 50 mM Tris pH 7.5, 1 mM EGTA, 2 mM DTT, 0.01% Brij, 5% DMSO and 10 mM MgCl$_2$ (commercial buffer) supplemented with fresh 100 FM ATP (31 µCi/ml) and 30 µM myelin basic protein under conditions recommended by the supplier. Reaction volumes and method of assaying incorporated radioactivity were as described for the PKC assay (vide supra).

In vitro Models for T-Cell Activation
Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1-7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 III volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2mercaptoethanol and 0.5% DMSO, The cultures are pulsed with 0.5 µCi of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 µg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α (TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 µg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at 6×10$^6$ per ml in tissue culture medium (RPMI 1640 supplemented with heat inactivated fetal bovine serum (Hyclone Laboratories) 5×10$^{-5}$M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560-2566, 1991; murine model: Lab. Invest. 4(3):278, 1981; rodent model: J. Immunol 146(4): 1163-8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol: 142(7):2237-2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333-58, 1992; Transplantation: 57(12): 1701-17D6, 1994) or heart (Am.J.Anat.: 113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR$_2$. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3-8) were used for this assay. Cells were cultured in 100 mm dishes (Falcon for tissue culture; Becton Dickinson; Plymouth, England) using complete EBM media (Clonetics). 2. For evaluating a compound's inhibitory activity, cells were trypsinized and seeded at 0.5-1.0×10$^5$ cells/well in each well of 6-well cluster plates (Costar; Cambridge, Mass.).

3. 3-4 days after seeding, plates were 90-100% confluent. Medium was removed from all the wells, cells were rinsed with 5-10 ml of PBS and incubated 18-24 h with 5 ml of EBM base media with no supplements added (i.e., serum starvation).

4. Serial dilutions of inhibitors were added in 1 ml of EBM media (25 µM, 5 µM, or 1 µM final concentration to cells and incubated for one hour at 37° C. Human recombinant VEGF$_{165}$ (R & D Systems) was then added to all the wells in 2 ml of EBM medium at a final concentration of 50 ng/ml and incubated at 37° C. for 10 minutes. Control cells untreated or treated with VEGF only were used to assess background phosphorylation and phosphorylation induction by VEGF.

All wells were then rinsed with 5-10 ml of cold PBS containing 1 mM Sodium Orthovanadate (Sigma) and cells were lysed and scraped in 200 µl of RIPA buffer (50 mM Tris-HCl) pH 7, 150 mM NaCl, 1% NP-40, 0.25% sodium deoxycholate, 1 mM EDTA) containing protease inhibitors (PMSF 1 mM, aprotinin 1 µg/ml, pepstatin 1Φg/ml, leupeptin 1 µg/ml, Na vanadate 1 mM, Na fluoride 1 mM) and 1 µg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20° C.) Ethanol (2 volumes) for a minimum of 1 hour or a maximum of overnight. Pellets were reconstituted in Laemli sample buffer containing 5%-mercaptoethanol (BioRad; Hercules, Calif.) and boiled for 5min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated F(ab)$_2$ of goat anti-rabbit or goat-anti-mouse IgG the bands were visualized using the emission chemiluminescience (ECL) system (Amersham Life Sciences, Arlington Height, Ill.). Certain examples of the present invention significantly inhibit cellular VEGF-induced KDR tyrosine kinase phosphorylation at concentrations of less than 50 μM.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (La Jolla, Calif.) as lyophilized powders and prepared according to supplier instructions.

Vehicle components (DMSO, Cremaphor EL) were purchased from Sigma (St. Louis, Mo.).

Mice (Balb/c, 8-12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5-10. Test compounds were administered by i.p., i.v. or p.o. routes depending on solubility and vehicle at doses ranging from 1-100 mg/kg. Vehicle control group received vehicle only and two groups were left untreated.

Thirty minutes later, experimental, vehicle and 1 of the untreated groups were given an i.p. injection of 17-estradiol (500 g/kg). After 2-3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water. Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXAMPLES

Intermediate 1: 4-(4-amino-3-iodo-1H-pyrazolo[3,4-d]pyrimidin-1-yl)benzaldehyde

A mixture of 3-iodo-1H-pyrazolo[3,4-d]pyrimidin-4-amine (3.00 g, 11.5 mmol) and sodium hydride (60%, 0.506 g, 12.6 mmol) in DMF (50 mL) was stirred at ambient temperature for 1 h then 4-fluorobenzaldehyde (1.36 mL, 12.6 mmol) was added. The reaction mixture was heated at 100° C. for 21 h. The reaction mixture was cooled to ambient temperature and the precipitate was collected by filtration, washed with DMF (30 mL) and ether (30 mL), and dried to afford 4-(4-amino-3-iodo-1H-pyrazolo[3,4-d]pyrimidin-1-yl)benzaldehyde as a tan solid (2.80 g, 7.61 mmol): $^1$H NMR (d$_6$-DMSO, 400 MHz): δH 10.03 (1H, s), 8.46 (2H, d, J=8.4 Hz), 8.39 (1H, s), 8.09 (2H, d, J=8.8 Hz); RP-HPLC (Hypersil C18, 5 μm, 100 Å, 15 cm; 5%-100% acetonitrile—0.1 M ammonium acetate over 15 min, 1 mL/min). R$_t$ 9.71 min. MS: MH+365.8.

Intermediate 2: N1-{4-[4-amino-1-(4-formylphenyl)-1H-pyrazolo[3,4-d]pyrimidin-3-yl]-2-methoxyphenyl}-2-fluoro-4-(trifluoromethyl)benzamide A mixture of 4-(4-amino-3-iodo-1H-pyrazolo[3,4-d]pyrimidin-1-yl)benzaldehyde (0.400 g, 1.09 mmol), N1-[2-methoxy-4-(4,4,5,5-tetramethyl-1,3,2-dioxaborolan-2-yl)phenyl]-2-fluoro-4-(trifluoromethyl)benzamide (0.735 g, 1.20 mmol), palladium tetrakis(triphenylphosphine) (0.127 g, 0.110 mmol), and sodium carbonate (0.279 g, 2.63 mmol) in DME (10 mL) and water (10 mL) was heated at 85° C. for 1 h. Additional N1-[2-methoxy-4-(4,4,5,5-tetramethyl-1,3,2-dioxaborolan-2-yl)phenyl]-2-fluoro-4-(trifluoromethyl)benzamide (0.026 g, 0.059 mmol) was added and the reaction mixture was heated at 85° C. for 4 h. The reaction mixture was cooled to ambient temperature and filtered. The residual solid was washed with methanol (50 mL) and DMF (50 mL), and the combined filtrates were concentrated to afford N1-{4-[4-amino-1-(4-formylphenyl)-1H-pyrazolo[3,4-d]pyrimidin-3-yl]-2-methoxyphenyl}-2-fluoro-4-(trifluoromethyl)benzamide as a beige solid (0.402 g, 0.730 mmol): $^1$H NMR (d$_6$-DMSO, 400 MHz): δH 10.05 (1H, s), 9.96

(1H, d, J=4.0 Hz), 8.62 (1H, d, J=8.4 Hz), 8.46 (1H, s), 8.39 (1H, d, J=6.8 Hz), 8.12 (2H, d, J=8.8 Hz), 8.02-8.03 (1H, m), 7.84-8.00 (1H, m), 7.75-7.77 (1H, m), 7.51 (1H, s), 7.43 (1H, d, J=8.0 Hz), 3.97 (3H, s); RP-HPLC (Hypersil C18, 5 μm, 100 Å, 15 cm; 5%-100% acetonitrile—0.1 M ammonium acetate over 15 min, 1 mL/min). $R_t$ 12.46 min. MS: MH+551.2.

Intermediate 3: 2-(4-amino-3-iodo-1H-pyrazolo[3,4-d]pyrimidin-1-yl)-1-ethanol

To a solution of 3-iodo-1H-pyrazolo[3,4-d]pyrimidin-4-amine (5.00 g, 19.1 mmol) in DMF (40 mL) was added sodium hydride (60%, 1.53 g, 38.3 mmol) and the reaction mixture was stirred for 20 min. 2-Bromoethanol (1.50 mL, 21.1 mmol) was added and the reaction mixture was heated at 50° C. for 18 h. The reaction mixture was cooled to ambient temperature and concentrated to afford a brown sludge. Ice water (50 mL) was added and the resulting precipitate was collected by filtration, rinsed with water (50 mL) and ether (50 mL), and dried in vacuo to afford 2-(4-amino-3-iodo-1H-pyrazolo[3,4-d]pyrimidin-1-yl)-1-ethanol as a beige solid (4.30 g, 14.1 mmol): $^1$H NMR ($d_6$-DMSO, 400 MHz): δH 8.19 (1H, s), 4.84 (1H, t, J=5.8 Hz), 4.30 (1H, t, J=5.8 Hz), and 3.77 (2H, app q, J=5.6 Hz); RP-HPLC (Hypersil C18, 5 μm, 100 Å, 15 cm; 5%-100% acetonitrile—0.1 M ammonium acetate over 15 min, 1 mL/min). $R_t$ 7.35 min.

Intermediate 4: 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate To a 0° C. mixture of N2-{4-[4-amino-1-(2-hydroxyethyl)-1H-pyrazolo[3,4-d]pyrimidin-3-yl]-2-methoxyphenyl}-1-methyl-1H-2-indolecarboxamide (0.343 g, 0.750 mmol) and pyridine (7.5 mL) was added methanesulfonyl chloride (0.14 mL, 1.8 mmol) dropwise over 30 sec. The reaction mixture was stirred at 0° C. for 2 h then ice water (10 mL) was added. The precipitate was collected by filtration and dried in vacuo to afford 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate as a beige solid (0.268 g, 0.500 mmol): $^1$H NMR ($d_6$-DMSO, 400 MHz): δH 9.44 (1H, s), 8.30 (1H, s), 8.13 (1H, d, J=8.0 Hz), 7.70 (1H, d, J=8.0 Hz), 7.59 (1H, d, J=8.4 Hz), 7.31-7.38 (4H, m), 7.15 (1H, t, J=7.6 Hz), 4.70 (3H, s), 4.04 (3H, s), 3.96 (3H, s), 3.37 (2H, obscured by water peak), and 3.12 (2H, s); RP-HPLC (Hypersil C18, 5 μm, 100 Å, 15 cm; 5%-100% acetonitrile—0.1 M ammonium acetate over 15 min, 1 mL/min). $R_t$ 11.22 min. MS: M+ 536.2.

Example 1

N1-(4-{4-amino-1-[4-(morpholinomethyl)phenyl]-1H-pyrazolo[3,4-d]pyrimidin-3-yl}-2-methoxyphenyl)-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), morpholine (0.024 mL, 0.27 mmol), and sodium triacetoxyborohydride (0.087 g, 0.409 mmol) in dichloroethane (1.4 mL) was shaken at ambient temperature for 16 h. Additional portions of morpholine (0.012 mL, 0.14 mmol), sodium triacetoxyborohydride (0.043 g, 0.20 mmol), and acetic acid (0.016 mL) were added and the reaction mixture was stirred at ambient temperature for 24 h. 1 N NaOH (1 mL) was added and the reaction mixture was filtered to afford a gray solid which was purified by preparative RP-HPLC (Rainin C18, 8 μm, 300 A, 25 cm; 10-60% acetonitrile—0.05 M ammonium acetate over 25 min, 21 mL/min); the fraction eluting from 21-23 min was collected, concentrated, and lyophilized to afford N1-(4-{4-amino-1-[4-(morpholinomethyl)phenyl]-1H-pyrazolo[3,4-d]pyrimidin-3-yl}-2-methoxyphenyl)-2-fluoro-4-(trifluoromethyl)benzamide as a white solid (0.007 g, 0.011 mmol): $^1$H NMR ($d_6$-DMSO, 400 MHz): δH 9.93 (1H, s), 8.34-8.37 (2H, m), 8.14-8.18 (2H, m), 7.97-8.02 (1H, m), 7.87-7.91 (1H, m), 7.73-7.76 (1H, m), 7.45-7.51 (2H, m), 7.44 (1H, s), 7.38-7.43 (1H, m), 3.41-3.59 (8H, m), and 3.36 (2H, s); RP-HPLC (Hypersil C18, 5 μm, 100 Å, 15 cm; 5%-100% acetonitrile—0.1 M ammonium acetate over 15 min, 1 mL/min). $R_t$ 11.72 min. MS: MH+ 622.2.

Example 2

N1-[4-(4-amino-1-{4-[(4-hydroxypiperidino)methyl]phenyl}-1H-pyrazolo[3,4-d]pyrimidin-3-yl)-2-methoxyphenyl]-2-fluoro-4-(trifluoromethyl)benzamide monoacetate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), 4-hydroxypiperidine (0.028 g, 0.27 mmol), and sodium triacetoxyborohydride (0.087 g, 0.41 mmol) in dichloroethane (1.4 mL) was shaken at ambient temperature for 16 h. Additional portions of 4-hydroxypiperidine (0.028 g, 0.27 mmol) and acetic acid (0.016 mL) were added and the reaction mixture was shaken for 24 h. More 4-hydroxypiperidine (0.033 g, 0.33 mmol) and sodium triacetoxyborohydride (0.040 g, 0.19 mmol) were added and the reaction mixture was shaken for 72 h. 1N NaOH (1.5 mL) was added and the yellow-brown precipitate was collected by filtration and purified by preparative RP-HPLC (Rainin C18, 8 μm, 300 A, 25 cm; 10-60% acetonitrile—0.05 M ammonium acetate over 25 min, 21 mL/min); the fraction eluting from 21-23 min was collected, concentrated, and lyophilized to afford N1-[4-(4-amino-1-{4-[(4-hydroxypiperidino)methyl]phenyl}-1H-pyrazolo[3,4-d]pyrimidin-3-yl)-2-methoxyphenyl]-2-fluoro-4-(trifluoromethyl)benzamide monoacetate as a white solid (0.025 g, 0.039 mmol): $^1$H NMR ($d_6$-DMSO, 400 MHz): δH 9.95 (1H, s), 8.35-8.99 (2H, m), 8.14-8.19 (2H, m), 7.99-8.03 (1H, m), 7.89-7.93 (1H, m), 7.75-7.80 (1H, m), 7.39-7.51 (4H, m), 4.55 (1H, s), 3.96 (3H, s), 3.80 (2H, s), 2.68-2.71 (3H, m), 2.04-2.11 (2H, m), 1.85 (3H, s), 1.71-1.76 (2H, m), and 1.39-1.45 (2H, m); RP-HPLC (Hypersil C18, 5 μm, 100 Å, 15 cm; 5%-100% acetonitrile—0.1 M ammonium acetate over 15 min, 1 mL/min). $R_t$ 10.56 min. MS: MH+ 636.2.

Example 3

N1-{4-[4-amino-1-(4-{[4-(2-hydroxyethyl)piperazino]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), N-(2-hydroxyethyl)piperazine (0.035 g, 0.27 mmol), and sodium triacetoxyborohydride (0.087 g, 0.41 mmol) in dichloroethane (1.4 mL) was shaken at room temperature for 14 h. Additional portions of N-(2-hydroxyethyl)piperazine (0.010 g, 0.077 mmol) and sodium triacetoxyborohydride (0.020 g, 0.094 mmol) were added and the reaction mixture was shaken for 16 h. 1N NaOH (1.5 mL) was added and the precipitate was collected by filtration and purified by preparative RP-HPLC (Rainin C18, 8 μm, 300 A, 25 cm; 10-60% acetonitrile—0.05 M ammonium acetate over 25 min, 21 mL/min); the fraction eluting from 21.9-22.9 min was collected, concentrated, and lyopholized to afford N1-{4-[4-amino-1-(4-{[4-(2-hydroxyethyl)piperazino]methyl}phenyl)-1H-pyrazolo[3,4-d]pyrimidin-3-yl]-2-methoxyphenyl}-2-fluoro-4-(trifluoromethyl)benzamide as a white solid (0.034 g, 0.051 mmol): $^1$H NMR (d$_6$-DMSO, 400 MHz): δH 9.94 (1H, s), 8.35-8.37 (2H, m), 8.15 (2H, d, J=8.8 Hz), 8.00 (1H, t, J=8.0 Hz), 7.90 (1H, d, J=10.4 Hz), 7.75 (1H, d, J=8.0 Hz), 7.49 (1H, s), 7.46 (2H, d, J=7.2 Hz), 7.40 (1H, d, J=8.4 Hz), 3.96 (3H, s), 3.51 (2H, s), 3.46-3.49 (4H, m), and 2.35-2.44 (8H, m); RP-HPLC (Hypersil C18, 5 μm, 100 Å, 15 cm; 5%-100% acetonitrile—0.1 M ammonium acetate over 15 min, 1 mL/min). R$_t$ 10.92 min. MS: MH+ 664.7.

Example 4

N1-{4-[4-amino-1-(4-{[4-(2-hydroxyethyl)piperidino]methyl}phenyl)-1H-pyrazolo[3,4-d]pyrimidin-3-yl]-2-methoxyphenyl}-2-fluoro-4-(trifluoromethyl)benzamide diacetate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (0.075 g, 0.14 mmol), 4-piperidineethanol (0.035 g, 0.27 mmol), sodium triacetoxyborohydride (0.087 g, 0.41 mmol), and dichloroethane (1.4 mL) was shaken at room temperature for 16 h. Additional portions of 4-piperidineethanol (0.040 g, 0.31 mmol)) and sodium triacetoxyborohydride (0.053 g, 0.25 mmol) were added and the reaction mixture was shaken for 4 days. 1N NaOH (1 mL) was added and the precipitate was collected by filtration and purified by preparative RP-HPLC (Rainin C18, 8 μm, 300 A, 25 cm; 10-60% acetonitrile—0.05 M ammonium acetate over 25 min, 21 mL/min); the fraction eluting from 21.1-23.5 min was collected, concentrated, and lyopholized to afford N1-{4-[4-amino-1-(4-{[4-(2-hydroxyethyl)piperidino]methyl}phenyl)-1H-pyrazolo[3,4-d]pyrimidin-3-yl]-2-methoxyphenyl}-2-fluoro-4-(trifluoromethyl)benzamide diacetate as a white solid. (0.015 g, 0.023 mmol): $^1$H NMR (d$_6$-DMSO, 400 MHz): δH 9.94 (1H, s), 8.18-8.39 (2H, m), 8.14 (2H, d, J=8.4 Hz), 7.99-8.02 (1H, m), 7.90 (1H, d, J=10.4 Hz), 7.75 (1H, d, J=7.6 Hz), 7.39-7.48 (4H, m), 4.31-3.96 (3H, s), 3.37 (2H, s), 3.37-3.50 (3H, m), 2.80-2.83 (2H, m), 1.91 (6H, m), 1.61-1.64 (2H, m), 1.35-1.37 (3H, m), and 1.15-1.18 (2H, m); RP-HPLC (Hypersil C18, 5 μm, 100 Å, 15 cm; 5%-100% acetonitrile—0.1 M ammonium acetate over 15 min, 1 mL/min). R$_t$ 10.71 min. MS: MH+ 664.2.

Example 5

N1-{4-[4-amino-1-(4-{[3-(hydroxymethyl)piperidino]methyl}phenyl)-1H-pyrazolo[3,4-d]pyrimidin-3-yl]-2-methoxyphenyl}-2-fluoro-4-(trifluoromethyl)benzamide monoacetate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), 3-piperidinemethanol (0.031 g, 0.27 mmol), and sodium triacetoxyborohydride (0.087 g, 0.41 mmol) in dichloroethane (1.4 mL) was shaken at room temperature for 16 h. Additional 3-piperidinemethanol (0.045 g, 0.39 mmol) and sodium triacetoxyborohydride (0.090 g, 0.42 mmol) were added and the reaction mixture was shaken at ambient temperature for 16 h. 1N NaOH (1 mL) was added and the precipitate was collected by filtration and purified by preparative RP-HPLC (Rainin C18, 8 μm, 300 A, 25 cm; 10-60% acetonitrile—0.05 M ammonium acetate over 25 min, 21 mL/min); the fraction eluting from 21-23 min was collected, concentrated, and lyopholized to afford N1-{4-[4-amino-1-(4-{[3-(hydroxymethyl)piperidino]methyl}phenyl)-1H-pyrazolo[3,4-d]pyrimidin-3-yl]-2-methoxyphenyl}-2-fluoro-4-(trifluoromethyl)benzamide monoacetate as a white solid. (0.007 g, 0.11 mmol): $^1$H NMR (d$_6$-DMSO, 400 MHz): δH 9.95 (1H, s), 8.35-8.39 (2H, m), 8.14-8.17 (2H, m), 8.01-8.03 (1H, m), 7.89-7.93 (1H, m), 7.75-7.78 (1H, m), 7.40-7.50 (4H, m), 4.39-4.42 (1H, m), 3.97 (3H, s), 3.39-3.53 (3H, m), 3.01-3.21 (1H, m), 2.87-2.89 (1H, m), 2.75-2.77 (1H, m), 1.91 (3H, s), 1.61-1.65 (4H, m), 1.47-1.52 (1H, m), and 0.89-0.92 (1H,m); RP-HPLC (Hypersil C18, 5 μm, 100 Å, 15 cm; 5%-100% acetonitrile—0.1 M ammonium acetate over 15 min, 1 mL/min). R$_t$ 10.73 min. MS: MH+ 650.2.

Example 6

N1-{4-[4-amino-1-(4-{[2-(hydroxymethyl)piperidino]methyl}phenyl)-1H-pyrazolo[3,4-d]pyrimidin-3-yl]-2-methoxyphenyl}-2-fluoro-4-(trifluoromethyl)benzamide monoacetate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (0.075 g, 0.14 mmol), 2-piperidinemethanol (0.031 g, 0.27 mmol), and sodium triacetoxyborohydride (0.087 g, 0.41 mmol) in dichloroethane (1.4 mL) was shaken at room temperature for 16 h. Additional portions of 2-piperidinemethanol (0.031 g, 0.27 mmol) and sodium triacetoxyborohydride (0.087 g, 0.41 mmol) were added and the reaction mixture was shaken for 3 days. Again, 2-piperidinemethanol (0.030 g, 0.26 mmol) and sodium triacetoxyborohydride (0.073 g, 0.34 mmol) were added followed by acetic acid (0.11 mL). The reaction mixture was shaken for 5 days. 1N NaOH (1 mL) was added and the reaction mixture was concentrated in vacuo to remove the dichloroethane. The residue was dissolved in DMF (2 mL), filtered through an Acrodisc syringe-tip filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 14.6-17.0 min was collected, concentrated, and lyopholized to afford N1-{4-[4-amino-1-(4-{[2-(hydroxymethyl)piperidino]methyl}phenyl)-1H-pyrazolo[3,4-d]pyrimidin-3-yl]-2-methoxyphenyl}-2-fluoro-4-(trifluoromethyl)benzamide monoacetate as a white solid. (0.026 g, 0.040 mmol): $^1$H NMR (d$_6$-DMSO, 400 MHz): ΔH 9.91 (1H, s), 8.33-8.37 (2H, m), 8.09-8.14 (2H, m), 7.96-8.00 (1H, m), 7.86-7.89 (1H, m), 7.71-7.74 (1H, m), 7.37-7.52 (4H, m), 4.46 (1H, bs), 4.10-4.15 (1H, m), 3.94 (3H, s), 3.64-3.67 (1H, m), 3.44-3.48 (1H, m), 2.64-2.69 (2H, m), 2.00-2.07 (1H, m), 1.94 (3H, s), 1.60-1.89 (2H, m), and 1.20-1.40 (4H, m); RP-HPLC (Hypersil C18, 5 μm, 100 Å, 15 cm; 5%-100% acetonitrile—0.1 M ammonium acetate over 15 min, 1 mL/min). R$_t$ 10.59 min. MS: MH+ 649.7.

Example 7

N1-{4-[4-amino-1-(4-{[(2-morpholinoethyl)amino]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), N-(2-aminoethyl)morpholine (0.035 g, 0.27 mmol), and sodium triacetoxyborohydride (0.087 g, 0.41 mmol) in dichloroethane (1.4 mL) was shaken for 16 h at room temperature. Additiona portions of 1 N-(2-aminoethyl)morpholine (0.030 mL, 0.23 mmol) and sodium triacetoxyborohydride (0.087 g, 0.41 mmol) were added and the reaction mixture was shaken for 4 days. 1N NaOH (1 mL) was added and the precipitate was collected by filtration and purified by preparative RP-HPLC (Rainin C18, 8 μm, 300 Å, 25 cm; 20-80% acetonitrile—0.05 M ammonium acetate over 25 min, 21 mL/min); the fraction eluting from 16.6-19.0 min was collected, concentrated, and lyopholized to afford N1-{4-[4-amino-1-(4-{[(2-morpholinoethyl)amino]methyl}phenyl)-1H-pyrazolo[3,4-d]pyrimidin-3-yl]-2-methoxyphenyl}-2-fluoro-4-(trifluoromethyl)benzamide as a white solid. (0.014 g, 0.021 mmol): $^1$H NMR (d$_6$-DMSO, 400 MHz): δH 9.88 (1H, s), 8.29-8.93 (2H, m), 8.11-8.17 (2H, m), 7.92-7.97 (1H, m), 7.83-7.86 (1H, m), 7.68-7.72 (1H,m), 7.46-7.51 (2H, m), 7.39 (1H, s), 7.34-7.38 (1H, m), 3.90 (3H, s), 3.50-3.52 (4H, m), 2.61-2.62 (2H, m), 2.40-2.50 (2H, obscured by DMSO peak), and 2.27-2.40 (6H, m); RP-HPLC (Hypersil C18, 5 μm, 100 Å, 15 cm; 5%-100% acetonitrile—0.1 M ammonium acetate over 15 min, 1 mL/min). R$_t$ 10.96 min. MS: MH+ 665.2.

Example 8

N1-{4-[4-amino-1-(4-{[4-(hydroxymethyl)piperidino]methyl}phenyl)-1H-pyrazolo[3,4-d]pyrimidin-3-yl]-2-methoxyphenyl}-2-fluoro-4-(trifluoromethyl)benzamide diacetate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (0.075 g, 0.14 mmol), 4-piperidinemethanol (0.031 g, 0.27 mmol), and sodium triacetoxyborohydride (0.087 g, 0.41 mmol) in dichloroethane (1.4 mL) was shaken at room temperature for 3 days. Additional portions of 4-piperidinemethanol (0.096 g, 0.83 mmol) and sodium triacetoxyborohydride (0.085 g, 0.40 mmol) were added followed by acetic acid (0.1 mL). The reaction mixture was shaken for 5 days. 1N NaOH (1 mL) was added and the reaction mixture was concentrated, dissolved in DMF (2 mL), filtered through a syringe-tip Acrodisc filter, then purified by preparative RP-HPLC (Rainin C18, 8 μm, 300 Å, 25 cm; 20-80% acetonitrile—0.05 M ammonium acetate over 25 min, 21 mL/min); the fraction eluting from 17.2-18.3 min was collected, concentrated, and lyopholized to afford N1-{4-[4-amino-1-(4-{[4-(hydroxymethyl)piperidino]methyl}phenyl)-1H-pyrazolo[3,4-d]pyrimidin-3-yl]-2-methoxyphenyl}-2-fluoro-4-(trifluoromethyl)benzamide diacetate as a white solid (0.018 g, 0.028 mmol): $^1$H NMR (d$_6$-DMSO, 400 MHz): δH 9.94 (1H, s), 8.35-8.37 (2H, m), 8.14 (2H, d, J=8.4 Hz), 8.00 (1H, t, J=7.0 Hz), 7.90 (1H, d, J=10.4 Hz), 7.75 (1H, d, J=8.0 Hz), 7.39-7.64 (4H, m), 4.38-4.41 (1H, m), 3.96 (3H, s), 3.50 (2H, s), 2.83 (2H, d, J=10.8 Hz), 1.90 (6H, s), 1.63 (2H, d, J=11.6 Hz), 1.34-1.35 (2H, m), and 1.12-1.19 (2H, m); RP-HPLC (Hypersil C18, 5 μm, 100 Å, 15 cm; 5%-100% acetonitrile—0.1 M ammonium acetate over 15 min, 1 mL/min). R$_t$ 10.41 min. MS: MH+ 650.2.

Example 9

N1-{4-[4-amino-1-(4-{[4-(2-methoxyethyl)piperazino]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), 1-(2-methoxyethyl)-piperazine (0.039 g, 0.27 mmol), and sodium triacetoxyborohydride (0.087 g, 0.41 mmol) in dichloroethane (1.4 mL) was shaken at room temperature for 3 days. Additional portions of 1-(2-methoxyethyl)-piperazine (0.10 mL) and sodium triacetoxyborohydride (0.089 g, 0.41 mmol) were added and the reaction mixture was shaken for 16 h. 1N NaOH (1 mL) was added and the resulting solution was extracted with two portions of dichloromethane (2 mL each). The combined organic portions were concentrated to afford a brown solid which was purified by preparative RP-HPLC (Rainin C18, 8 μm, 300 Å, 25 cm; 20-80% acetonitrile—0.05 M ammonium acetate over 25 min, 21 mL/min); the fraction eluting from 16.9-20.2 min was collected, concentrated, and lyopholized to afford N1-{4-[4-amino-1-(4-{[4-(2-methoxyethyl)piperazino]methyl}phenyl)-1H-pyrazolo [3,4-d]pyrimidin-3-yl]-2-methoxyphenyl}-2-fluoro-4-(trifluoromethyl)benzamide as a white solid (0.021 g, 0.031 mmol): $^1$H NMR (d$_6$-DMSO, 400 MHz): δH 9.94 (1H, s), 8.34-8.37 (2H, m), 8.14-8.17 (1H, m), 7.98-8.02 (1H, m), 7.89 (1H, d, J=10.4 Hz), 7.74-7.76 (1H, m), 7.34-7.64 (6H, m), 3.96 (3H, s), 3.51 (2H, s), 3.31-3.43 (2H, m), 3.22 (3H, s), and 2.41-2.45 (10H, m); RP-HPLC (Hypersil C18, 5 μm, 100 Å, 15 cm; 5%-100% acetonitrile—0.1 M ammonium acetate over 15 min, 1 mL/min). R$_t$ 11.24 min. MS: MH+678.7.

Example 10

N1-{4-[4-amino-1-(4-{[(3R)-3-hydroxytetrahydro-1H-1-pyrrolyl]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (0.075 g, 0.14 mmol), (S)-3-hydroxypyrrolidine (0.024 g, 0.27 mmol), and sodium triacetoxyborohydride (0.087 g, 0.41 mmol) in dichloroethane (1.4 mL) was shaken at room temperature for 3 days. Additional portions of (S)-3-hydroxypyrrolidine (0.1 mL) and sodium triacetoxyborohydride (0.084 g, 0.40 mmol) were added and the reaction mixture was shaken for 3 days. Acetic acid (0.1 mL) was added and the reaction mixture was shaken for 4 days. 1N NaOH (1 mL) was added and the reaction mixture was concentrated in vacuo. The residue was dissolved in DMF (2 mL), filtered through a syringe-tip Acrodisc filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 16.5-18.4 min was collected, concentrated, and lyopholized to afford N1-{4-[4-amino-1-(4-{[(3R)-3-hydroxytetrahydro-1H-1-pyrrolyl]methyl}phenyl)-1H-pyrazolo[3,4-d]pyrimidin-3-yl]-2-methoxyphenyl}-2-fluoro-4-(trifluoromethyl)benzamide as a white solid (0.027 g, 0.043 mmol): $^1$H NMR (d$_6$-DMSO, 400 MHz): δH 9.89 (1H, s), 8.30-8.33 (2H, m), 8.13-8.14 (2H, m), 7.90-7.80 (1H, m), 7.84 (1H, d, J=10.8 Hz), 7.70 (1H, d, J=7.6 Hz), 7.35-7.59 (4H, m), 4.64 (1H, bs), 4.14-4.23 (1H, m), 3.91 (3H, s), 3.62 (2H, s), 2.61-2.62 (2H, m), 2.27-2.28 (2H, m), 2.27-2.28 (2H, m), 2.02 (1H, m), and 1.60 (1H, m); RP-HPLC (Hypersil C18, 5 μm, 100 Å, 15 cm; 5%-100% acetonitrile—0.1 M ammonium acetate over 15 min, 1 mL/min). R$_t$ 10.41 min. MS: MH+ 622.2.

Example 11

N1-{4-[4-amino-1-(4-{[(3R)-3-hydroxytetrahydro-1H-1-pyrrolyl]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), (R)-(+)-3-pyrrolidinol (0.024 g, 0.27 mmol), and sodium triacetoxyborohydride (0.087 g, 0.41 mmol) in dichloroethane (1.4 mL) was shaken at room temperature for 3 days. Additional portions of (R)-(+)-3-pyrrolidinol (0.1 mL), and sodium triacetoxyborohydride (0.084 g, 0.40 mmol) were added and the reaction mixture was shaken for 16 h. 1N NaOH (1 mL) was added and the precipitate was collected by filtration and combined with the residue obtained from extraction of the water layer with one portion of dichloromethane (20 mL). The crude mixture was purified by preparative RP-HPLC (Rainin C18, 8 μm, 300 Å, 25 cm; 20-80% acetonitrile—0.05 M ammonium acetate over 25 min, 21 mL/min). The appropriate fraction was collected, concentrated, and lyophilized to afford N1-{4-[4-amino-1-(4-{[(3R)-3-hydroxytetrahydro-1H-1-pyrrolyl]methyl}phenyl)-1H-pyrazolo[3,4-d]pyrimidin-3-yl]-2-methoxyphenyl}-2-fluoro-4-(trifluoromethyl)benzamide as a white solid (0.034 g, 0.055 mmol): $^1$H NMR (d$_6$-DMSO, 400 MHz): δH 9.93 (1H, s), 8.34-8.37 (2H, m), 8.15-8.19 (2H, m), 7.98-8.01 (1H, m), 7.85 (1H, d, J=10.4 Hz), 7.75 (1H, d, J=8.0 Hz), 7.48-7.54 (2H, m), 7.44 (1H, s), 7.40 (1H, d, J=8.4 Hz), 4.70 (1H, bs), 4.22 (1H, s), 3.96 (3H, s), 3.63 (2H, s), 2.49-2.72 (3H, m), 2.13-2.41 (1H, m), 1.91-2.06 (1H, m), and 1.53-1.61 (1H, m); RP-HPLC (Hypersil C18, 5 μm, 100 Å, 15 cm; 5%-100% acetonitrile—0.1 M ammonium acetate over 15 min, 1 mL/min). R$_t$ 10.53 min. MS: MH+ 622.2.

Example 12

N1-(4-{4-amino-1-[4-{([3-(1H-1-imidazolyl)propyl]amino}methyl)phenyl]-1H-pyrazolo[3,4-d]pyrimidin-3-yl}-2-methoxyphenyl)-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), 1-(3-aminopropyl)imidazole (0.034 g, 0.27 mmol), and sodium triacetoxyborohydride (0.087 g, 0.41 mmol) in dichloroethane (1.4 mL) was shaken at room temperature for 3 days. Additional portions of 1-(3-aminopropyl)imidazole (0.1 mL) and sodium triacetoxyborohydride (0.086 g, 0.40 mmol) were added and the reaction mixture was shaken for 3 days. Acetic acid (0.1 mL) was added and the reaction mixture was shaken for 4 days. 1N NaOH (1 mL) was added and the reaction mixture was concentrated, dissolved in DMF (2 mL), filtered through a syringe-tip Acrodisc filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 14.0-15.7 min was collected, concentrated, and lyopholyzed to afford N1-(4-{4-amino-1-[4-{([3-(1H-1-imidazolyl)propyl]amino}methyl)phenyl]-1H-pyrazolo [3,4-d]pyrimidin-3-yl}-2-methoxyphenyl)-2-fluoro-4-(trifluoromethyl)benzamide as a white solid (0.040 g, 0.061 mmol): $^1$H NMR (d$_6$-DMSO, 400 MHz): δH 9.94 (1H, s), 8.35-8.40 (2H, m), 8.16 (2H, d, J=7.6 Hz), 7.99 (1H, t, J=7.6 Hz), 7.89 (1H, d, J=10.0 Hz), 7.75 (1H, d, J=8.4 Hz), 7.59 (1H, s), 7.52 (2H, d, J=3.8 Hz), 6.45 (1H, s), 7.40 (1H, d, J=8.0 Hz), 7.16 (1H, s), 6.87 (1H, s), 4.04 (2H, t, J=7.0 Hz), 3.96 (3H, s), 3.77 (2H, S), 2.45-2.46 (2H, m), 1.91 (3H, s), and 1.86-1.90 (2H, m); RP-HPLC (Hypersil C18, 5 μm 100 Å, 15 cm; 5%-100% acetonitrile—0.1 M ammonium acetate over 15 min, 1 mL/min). R$_t$ 10.28 min. MS: MH+660.2.

Example 13

N1-{4-[4-amino-1-(4-{[(4-hydroxybutyl)amino]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), 4-amino-1-butanol (0.024 g, 0.27 mmol), and sodium triacetoxyborohydride (0.087 g, 0.41 mmol) in dichloroethane (1.4 mL) was shaken for 3 days. Additional portions of 4-amino-1-butanol (0.1 mL) and sodium triacetoxyborohydride (0.089 g, 0.42 mmol) were added and the reaction mixture was shaken for 3 days. Acetic acid (0.1 mL) was added and the reaction mixture was shaken for 7 days. An additional portion of sodium triacetoxyborohydride (0.098 g, 0.46 mmol) was added and the reaction mixture was shaken for 16 h. 1N NaOH (1 mL) was added and the reaction mixture was concentrated, dissolved in DMF (2 mL), filtered through a syringe-tip Acrodisc filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 12.5-14.8 min was collected, concentrated, and lyopholized to N1-{4-[4-amino-1-(4-{[(4-hydroxybutyl)amino]methyl}phenyl)-1H-pyrazolo[3,4-d]pyrimidin-3-yl]-2-methoxyphenyl}-2-fluoro-4-(trifluoromethyl)benzamide as a white solid. (0.030 g, 0.048 mmol): $^1$H NMR (d$_6$-DMSO, 400 MHz): δH 9.94 (1H, d, J=4.4 Hz), 8.35-8.40 (2H, m), 8.17 (2H, d, J=8.0 Hz), 8.00 (1H, t, J=7.4 Hz), 7.90 (1H, d, J=10.4 Hz), 7.75 (1H, d, J=7.2 Hz), 7.53-7.57 (2H, m), 7.45 (1H, s), 7.40 (1H, d, J=8.8 Hz), 3.96 (3H, s), 3.83 (2H, s), 3.39 (2H, t, J=6.2 Hz), 2.45-2.50 (2H, m), and 1.45-1.51 (4H, m); RP-HPLC (Hypersil C18, 5 μm, 100 Å, 15 cm; 5%-100% acetonitrile—0.1 M ammonium acetate over 15 min, 1 mL/min). R$_t$ 9.93 min. MS: MH+624.3.

Example 14

N1-{4-[4-amino-1-(4-{[(3-methoxypropyl)amino]methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2)

(0.075 g, 0.14 mmol), 3-methoxypropylamine (0.024 g, 0.27 mmol), and sodium triacetoxyborohydride (0.087 g, 0.41 mmol) in dichloroethane (1.4 mL) was shaken at room temperature for 3 days. Additional portions of 3-methoxypropylamine (0.1 mL, 1 mmol) and sodium triacetoxyborohydride (0.085 g, 0.40 mmol) were added and the mixture was shaken for 3 days. Acetic acid (0.1 mL) was added and the reaction mixture was shaken for 4 days. An additional portion of sodium triacetoxyborohydride (0.100 g, 0.470 mmol) was added and the reaction mixture was shaken for 16 h. 1N NaOH (1 mL) was added and the reaction mixture was concentrated, dissolved in DMF (2 mL), filtered through a syring-tip Acrodisc filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 18.0-19.7 min was collected, concentrated, and lyopholized to afford N1-{4-[4-amino-1-(4-{[(3-methoxypropyl)amino]methyl}phenyl)-1H-pyrazolo [3,4-d]pyrimidin-3-yl]-2-methoxyphenyl}-2-fluoro-4-(trifluoromethyl)benzamide as a white solid (0.009 g, 0.014 mmol): $^1$H NMR (d$_6$-DMSO, 400 MHz): δH 9.93 (1H, s), 8.33-8.38 (2H, m), 8.18-8.20 (2H, m), 7.97-8.01 (1H, m), 7.87-7.91 (1H, m), 7.73-7.76 (1H, m), 7.54-7.64 (5H, m), 7.31-7.45 (2H, m), 3.95 (3H, s), 3.85-3.89 (2H, m), 3.38 (2H, s), 2.55-2.68 (2H, m), and 1.70-1.74 (2H, m); RP-HPLC (Hypersil C18, 5 μm, 100 Å, 15 cm; 5%-100% acetonitrile—0.1 M ammonium acetate over 15 min, 1 mL/min). R$_t$ 10.58 min. MS: MH+624.2.

Example 15

N1-(4-{4-amino-1-[4-{([3-(dimethylamino)propyl] amino}methyl)phenyl]-1H-pyrazolo[3,4-d]pyrimidin-3-yl}2-methoxyphenyl)-2-fluoro-4-(trifluoromethyl)benzamide monoacetate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), N,N-dimethyl-1,3-propane diamine (0.028 g, 0.27 mmol), and sodium triacetoxyborohydride (0.087 g, 0.41 mmol) in dichloroethane (1.4 mL) was shaken at room temperature for 3 days. Additional portions of N,N-dimethyl-1,3-propane diamine (0.1 mL) and sodium triacetoxyborohydride (0.085 g, 0.40 mmol) were added and the mixture was shaken for 3 days. Acetic acid (0.1 mL) was added and the mixture was shaken for 4 days. Sodium triacetoxyborohydride (0.096 g, 0.45 mmol) was added and the mixture was shaken for 16 h. 1N NaOH (1 mL) was added and the reaction mixture was concentrated, dissolved in DMF (2 mL), filtered through a syringe-tip Acrodisc filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 14.3-14.9 min was collected, concentrated, and lyopholyzed to afford N1-(4-{4-amino-1-[4-{([3-(dimethylamino)propyl]amino}methyl)phenyl]-1H-pyrazolo[3,4-d]pyrimidin-3-yl}2-methoxyphenyl)-2-fluoro-4-(trifluoromethyl)benzamide monoacetate as a white solid (0.020 g, 0.031 mmol): $^1$H NMR (d$_6$-DMSO, 400 MHz): δH 9.93 (1H, s), 8.34-8.37 (2H, m), 8.13 (2H, d, J=8.4 Hz), 8.00 (1H, t, J=7.2 Hz), 7.89 (1H, d, J=10.0 Hz), 7.75 (1H, d, J=7.6 Hz), 7.49 (2H, d, J=8.0 Hz), 7.44 (1H, s), 7.39 (1H, d, J=8.0 Hz), 3.96 (3H, s), 3.74 (2H, s), 2.21-2.25 (2H, t, J=7.0 Hz), 2.09 (6H, s), 2.08 (3H, s), 1.86-1.87 (4H, m), and 1.54-1.58 (2H, t, J=7.2 Hz); RP-HPLC (Hypersil C18, 5 μm, 100 Å, 15 cm; 5%-100% acetonitrile—0.1 M ammonium acetate over 15 min, 1 mL/min). R$_t$ 10.85 min. MS: MH+637.3.

Example 16

Methyl (2S)-2-({4-[4-amino-3-(4-{[2-fluoro-4-(trifluoromethyl)benzoyl]amino}-3-methoxyphenyl)-1H-pyrazolo[3,4-d]pyrimidin-1-yl]benzyl}amino)-3-(4H-4-imidazolyl)propanoate A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), L-histidine methyl ester dihydrochloride (0.046 g, 0.27 mmol), and sodium triacetoxyborohydride (0.087 g, 0.41 mmol) in dichloroethane (1.4 mL) was shaken at room temperature for 3 days. Additional portions of ), L-histidine methyl ester dihydrochloride (0.100 g, 0.59 mmol) and sodium triacetoxyborohydride (0.085 g, 0.40 mmol) were added and the reaction mixture was shaken for 2 days. 1N NaOH (1 mL) was added and the brown precipitate was collected by filtration. The filtrate was extracted with dichloromethane (5 mL) and the organic extract was concentrated and combined with the aforementioned brown solid. The crude mixture was purified by preparative RP-HPLC (Rainin C18, 8 μm, 300 Å, 25 cm; 20-80% acetonitrile—0.05 M ammonium acetate over 25 min, 21 mL/min); the fraction eluting from 18.9-20.5 min was collected, concentrated, and lyopholized to afford methyl (2S)-2-({4-[4-amino-3-(4-{[2-fluoro-4-(trifluoromethyl)benzoyl]amino}-3-methoxyphenyl)-1H-pyrazolo[3,4-d]pyrimidin-1-yl]benzyl}amino)-3-(4H-4-imidazolyl)propanoate as a white solid. (0.029 g, 0.041 mmol): $^1$H NMR (d$_6$-DMSO, 400 MHz): δH 9.94 (1H, s), 8.35-8.38 (2H, m), 8.13 (2H, d, J=8.0 Hz), 7.99-8.02 (1H, m), 7.90 (1H, d, J=10.8 Hz), 7.75 (1H, d, J=8.4 Hz), 7.51 (1H, s), 7.39-7.45 (5H, m), 6.78 (1H, bs), 3.96 (3H, s), 3.82 (1H, d, J=14.0 Hz), 3.59 (3H, s), 3.47 (1H, t, J=6.4 Hz), 2.80-2.89 (2H, m), and 1.91 (3H, s); RP-HPLC (Hypersil C18, 5 μm, 100 Å, 15 cm; 5%-100% acetonitrile—0.1 M ammonium acetate over 15 min, 1 mL/min). R$_t$ 11.15 min. MS: MH+704.2.

Example 17

N1-{4-[4-amino-1-(4-{[(2-methoxyethyl)amino] methyl}phenyl)-1H-pyrazolo[3,4-d]pyrimidin-3-yl]-2-methoxyphenyl}-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.075 g, 0.14 mmol), 2-methoxyethylamine (0.018 g, 0.24 mmol), and sodium triacetoxyborohydride (0.106 g, 0.500 mmol) in dichloroethane (1.4 mL) was shaken at room temperature for 24 h. 1N NaOH (1 mL) was added and the reaction mixture was concentrated, dissolved in DMF (2 mL), filtered through a syringe-tip Acrodisc filter, and purified by preparative RP-HPLC (Rainin C18, 8 μm, 300 Å, 25 cm; 20-80% acetonitrile—0.05 M ammonium acetate over 25 min, 21 mL/min); the fraction eluting from 15.0-16.2 min was collected, concentrated, and lyopholized to afford N1-{4-[4-amino-1-(4-{[(2-methoxyethyl)amino]methyl}phenyl)-1H-pyrazolo[3,4-d]pyrimidin-3-yl]-2-methoxyphenyl}-2-fluoro-4-(trifluoromethyl)benzamide as a white solid (0.010 g, 0.016 mmol): $^1$H NMR (d$_6$-DMSO, 400 MHz): δH 9.94 (1H, d, J=4.0 Hz), 8.35-8.37 (2H, m), 8.16 (2H, d, J=8.0 Hz), 8.01 (1H, t, J=7.4 Hz), 7.90 (1H, d, J=10.0 Hz), 7.75 (1H, d, J=8.0 Hz), 7.52 (2H, d, J=8.0 Hz), 7.45 (1H, s), 7.40 (1H, d, J=8.8 Hz), 3.96 (3H, s), 3.80 (2H, s), 3.42-3.45 (2H, m), 3.25 (2H, m), and 2.70-2.71 (2H, m); RP-HPLC (Hypersil C18, 5 μm, 100 Å, 15 cm; 5%-100% acetonitrile—0.1 M ammonium acetate over 15 min, 1 mL/min). $R_t$ 10.23 min. MS: MH+610.2.

Example 18

N1-(4-{4-amino-1-[4-{([2-(dimethylamino)ethyl]amino}methyl)phenyl]-1H-pyrazolo[3,4-d]pyrimidin-3-yl}-2-methoxyphenyl)-2-fluoro-4-(trifluoromethyl)benzamide A mixture of N1-{4-[4-amino-1-(4-formylphenyl)-1H-pyrazolo[3,4-d]pyrimidin-3-yl]-2-methoxyphenyl}-2-fluoro-4-(trifluoromethyl)benzamide (Intermediate 2) (0.080 g, 0.14 mmol), N,N-dimethylaminoethylamine (0.03 mL), and sodium triacetoxyborohydride (0.100 g, 0.472 mmol) in dichloroethane (1.4 mL) was shaken at room temperature for 24 h. 1N NaOH (1 mL) was added and the reaction mixture was concentrated, dissolved in DMF (2 mL), filtered through a syringe-tip Acrodisc filter, and purified by RP-HPLC (Rainin C18, 8 μm, 300 Å, 25 cm; 20-80% acetonitrile—0.05 M ammonium acetate over 25 min, 21 mL/min); the fraction eluting from 16.5-17.8 min was collected, concentrated, and lyopholized to afford N1-(4-{4-amino-1-[4-{([2-(dimethylamino)ethyl]amino}methyl)phenyl]-1H-pyrazolo[3,4-d]pyrimidin-3-yl}-2-methoxyphenyl)-2-fluoro-4-(trifluoromethyl)benzamide as a white solid (0.020 g, 0.032 mmol): $^1$H NMR (d$_6$-DMSO, 400 MHz): δH 9.94 (1H, d, J=4.4 Hz), 8.35-8.37 (2H, m), 8.15 (2H, d, J=8.4 Hz), 8.01 (1H, t, J=7.8 Hz), 7.90 (1H, d, J=10.4 Hz), 7.75 (1H, d, J=7.6 Hz), 7.50 (2H, d, J=8.8 Hz), 7.45 (1H, s), 7.40 (H, d, J=8.0 Hz), 3.96 (3H, s), 3.77 (2H, s), 2.59 (2H, t, J=6.6 Hz), 2.35 (2H, t, J=6.6 Hz), and 2.12 (6H, s); RP-HPLC (Hypersil C18, 5 μm, 100 Å, 15 cm; 5%-100% acetonitrile—0.1 M ammonium acetate over 15 min, 1 mL/min). $R_t$ 10.85 min. MS: MH+623.2.

Example 19

N1-{4-[4-amino-1-(2-hydroxyethyl)-1H-pyrazolo[3,4-d]pyrimidin-3-yl]-2-methoxyphenyl}-2-fluoro-4-(trifluoromethyl)benzamide A mixture of 2-(4-amino-3-iodo-1H-pyrazolo[3,4-d]pyrimidin-1-yl)-1-ethanol (Intermediate 3) (0.120 g, 0.393 mmol), N1-[2-methoxy-4-(4,4,5,5-tetramethyl-1,3,2-dioxaborolan-2-yl)phenyl]-2-fluoro-4-(trifluoromethyl)benzamide (0.190 g, 0.433 mmol), palladium tetrakis(triphenylphosphine) (0.045 g, 0.039 mmol), and sodium carbonate (0.100 g, 0.943 mmol) in DME (3.9 mL) and water (3.9 mL) was heated at 85° C. for 3 h. The reaction mixture was cooled to ambient temperature and the organic solvent was removed in vacuo. The precipitate was collected by filtration, rinsed with water (20 mL) and ether (20 mL), and dried in vacuo to afford N1-{4-[4-amino-1-(2-hydroxyethyl)-1H-pyrazolo[3,4-d]pyrimidin-3-yl]-2-methoxyphenyl}-2-fluoro-4-(trifluoromethyl)benzamide as a brown solid (0.125 g, 0.254 mmol): $^1$H NMR (d$_6$-DMSO, 400 MHz): δH 9.89 (1H, d, J=4.0 Hz), 8.31 (1H, d, J=8.0 Hz), 8.25 (1H, s), 7.99 (1H, t, J=7.4 Hz), 7.89 (1H, d, J=10.4 Hz), 7.75 (1H, d, J=8.0 Hz), 7.34 (1H, s), 7.31 (1H, d, J=8.4 Hz), 4.89 (1H, s), 4.40 (2H, t, J=5.6 Hz), 3.94 (3H, s), and 3.86 (2H, t, J=5.6 Hz); RP-HPLC (Hypersil C18, 5 μm, 100 Å, 15 cm; 5%-100% acetonitrile—0.1 M ammonium acetate over 15 min, 1 mL/min). $R_t$ 9.85 min. MS: MH+491.

Example 20

N2-{4-[4-amino-1-(2-hydroxyethyl)-1H-pyrazolo[3,4-d]pyrimidin-3-yl]-2-methoxyphenyl}-1-methyl-1H-2-indolecarboxamide A mixture of 2-(4-amino-3-iodo-1H-pyrazolo[3,4-d]pyrimidin-1-yl)-1-ethanol (Intermediate 3) (0.364 g, 1.19 mol), N2-[2-methoxy-4-(4,4,5,5-tetramethyl-1,3,2-dioxaborolan-2-yl)phenyl]-1-methyl-1H-2-indolecarboxamide (0.485 g, 1.19 mmol), palladium tetrakis(triphenylphosphine) (0.138 g, 0.119 mmol), and sodium carbonate (0.303 g, 2.86 mmol) in DME (12 mL) and water (12 mL) was heated at 85° C. for 4 h then cooled to ambient temperature. The DME was removed in vacuo and the resulting precipitate was collected by filtration and rinsed with water (50 mL) and ether (50 mL) to afford N2-{4-[4-amino-1-(2-hydroxyethyl)-1H-pyrazolo[3,4-d]pyrimidin-3-yl]-2-methoxyphenyl}-1-methyl-1H-2-indolecarboxamide as a tan solid (0.459 g, 1.00 mmol): $^1$H NMR (d$_6$-DMSO, 400 MHz): δH 9.44 (1H, s), 8.26 (1H, s), 8.12 (1H, d, J=8.0 Hz), 7.70 (1H, d, J=8.0 Hz), 7.59 (1H, d, J=8.4 Hz), 7.29-7.41 (6H, m), 7.15 (1H, t, J=7.4 Hz), 4.90 (1H, t, J=5.8 Hz), 4.41 (2H, t, J=5.8 Hz), 4.04 (3H, s), 3.96 (3H, s), and 3.86 (2H, q, J=5.9 Hz); RP-HPLC (Hypersil C18, 5 μm, 100 Å, 15 cm; 5%-100% acetonitrile—0.1 M ammonium acetate over 15 min, 1 mL/min). $R_t$ 10.52 min. MS: MH+458.2.

Example 21

N2-(4-{4-amino-1-[2-(4-methylpiperazino)ethyl]-1H-pyrazolo[3,4-d]pyrimidin-3-yl}-2-methoxyphenyl)-1-methyl-1H-2-indolecarboxamide trimaleate A mixture of 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate (Intermediate 4) (0.265 g, 0.495 mmol), N-methylpiperazine (0.065 mL, 0.58 mmol), and triethylamine (0.10 mL, 0.74 mmol) in DMF (5 mL) was heated at 70° C. for 20 h. The reaction mixture was cooled to ambient temperature and the solvent removed in vacuo. Water (25 mL) was added and the resulting precipitate was collected by filtration, washed with water (25 mL) and ether (50 mL), and dried in vacuo to afford a brown solid which was purified by silica gel column chromatography. The appropriate fractions were combined and concentrated to afford N2-(4-{4-amino-1-[2-(4-methylpiperazino)ethyl]-1H-pyrazolo[3,4-d]pyrimidin-3-yl}-2-methoxyphenyl)-1-methyl-1H-2-indolecarboxamide as a beige solid (0.084 g, 0.16 mmol): $^1$H NMR (d$_6$-DMSO, 400 MHz): δH 9.44 (1H, s), 8.26 (1H, s), 8.11 (1H, d, J=8.4 Hz), 7.70 (1H, d, J=8.4 Hz), 7.29-7.35 (4H, m), 7.15 (1H, t, J=7.4 Hz), 4.46 (2H, t, J=6.8 Hz), 4.04 (3H, s), 3.96 (3H, s), 2.80 (2H, t, J=6.6 Hz), 2.49-2.50 (2H, obscured by DMSO peak), 2.23-2.26 (4H, m), 2.12 (3H, s), and 0.97-0.99 (2H, m); RP-HPLC (Hypersil C18, 5 μm, 100 Å, 15 cm; 5%-100% acetonitrile—0.1 M ammonium acetate over 15 min, 1 mL/min). $R_t$ 10.24. MS: MH+540.3.

To a mixture of N2-(4-{4-amino-1-[2-(4-methylpiperazino)ethyl]-1H-pyrazolo[3,4-d]pyrimidin-3-yl}-2-methoxyphenyl)-1-methyl-1H-2-indolecarboxamide (0.082 g, 0.15 mmol) in warm ethyl acetate (2 mL) was added a solution of maleic acid (0.053 g, 0.46 mmol) in warm ethyl acetate (1 mL). A precipitate formed immediately. The reaction mixture was allowed to cool to ambient temperature and the precipitate was collected by filtration, washed with ethyl acetate (5 mL), and dried in vacuo to afford N2-(4-{4-amino-1-[2-(4-methylpiperazino)ethyl]-1H-pyrazolo[3,4-d]pyrimidin-3-yl}-2-methoxyphenyl)-1-methyl-1H-indole-carboxamide trimaleate as a beige solid (0.090 g, 0.10 mmol): $^1$H NMR (d$_6$-DMSO, 400 MHz): δH 9.45 (1H, s), 8.27 (1H, s), 8.12 (1H, d, J=8.0 Hz), 7.71 (1H, d, J=8.0 Hz), 7.59 (1H, d, J=8.0 Hz), 7.29-7.36 (4H, m), 7.15 (1H, t, J=7.4 Hz), 6.17 (6H, s), 4.50 (2H, t, J=6.4 Hz), 4.04 (3H, s), 3.96 (3H, s), 3.10-3.20 (4H, m), 2.92-2.95 (4H, m), 2.74 (3H, s), and 2.32-2.37 (2H, m); RP-HPLC (Hypersil C18, 5 µm, 100 Å, 15 cm; 5%-100% acetonitrile—0.1 M ammonium acetate over 15 min, 1 mL/min). R$_t$ 10.48 min. MS: M+540.3.

Example 22

N2-{4-[4-amino-1-(2-morpholinoethyl)-1H-pyrazolo[3,4-d]pyrimidin-3-yl]-2-methoxyphenyl}-1-methyl-1H-2-indolecarboxamide Dimaleate To a mixture of 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate (Intermediate 4) (0.200 g, 0.373 mmol), triethylamine (0.052 mL, 0.37 mmol), and sodium iodide (0.056 g, 0.37 mmol) in DMF (5 mL) was added morpholine (0.039 mL, 0.45 mmol). The reaction mixture was heated at 60° C. for 60 h. Morpholine (0.100 mL, 1.15 mmol) was added and the reaction mixture was heated at 80° C. for 30 h. The reaction mixture was cooled to ambient temperature and concentrated in vacuo. Water (5 mL) was added and the resulting precipitate was collected by filtration, washed with water (5 mL) and ether (10 mL), and dried in vacuo to afford a tan solid which was purified twice by silica gel chromatography (elution with 20% MeOH—CH$_2$Cl$_2$); the appropriate fractions were combined and concentrated to afford a beige solid which was triturated from ether and dried in vacuo to afford N2-{4-[4-amino-1-(2-morpholinoethyl)-1H-pyrazolo[3,4-d]pyrimidin-3-yl]-2-methoxyphenyl}-1-methyl-1H-2-indolecarboxamide as a white solid (0.048 g, 0.054 mmol): $^1$H NMR (d$_6$-DMSO, 400 MHz): δH 9.44 (1H, s), 8.26 (1H, s), 8.11 (1H, d, J=8.0 Hz), 7.70 (1H, d, J=7.6 Hz), 7.58 (1H, d, J=7.6 Hz), 7.29-7.35 (4H, m), 7.15 (1H, t, J=7.6 Hz), 4.48 (2H, t, J=6.4 Hz), 4.04 (3H, s), 3.96 (3H, s), 3.50-3.53 (4H, m), 2.82 (2H, t, J=6.2 Hz), and 2.47-2.51 (4H, m);); RP-HPLC (Hypersil C18, 5 µm, 100 Å, 15 cm; 5%-100% acetonitrile—0.1 M ammonium acetate over 15 min, 1 mL/min). R$_t$ 10.02 min. MS: M+527.3.

To a mixture of N2-{4-[4-amino-1-(2-morpholinoethyl)-1H-pyrazolo[3,4-d]pyrimidin-3-yl]-2-methoxyphenyl}-1-methyl-1H-2-indolecarboxamide (0.048 g, 0.091 mmol) in warm ethyl acetate (2 mL) was added a solution of maleic acid (0.021 g, 0.18 mmol) in warm ethyl acetate (1 mL). A precipitate formed immediately. The reaction mixture was allowed to cool to ambient temperature and the precipitate was collected by filtration, washed with ethyl acetate (5 mL), and dried in vacuo to afford N2-{4-[4-amino-1-(2-morpholinoethyl)-1H-pyrazolo[3,4-d]pyrimidin-3-yl]-2-methoxyphenyl}-1-methyl-1H-2-indolecarboxamide dimaleate as a light brown solid (0.030 g, 0.039 mmol): $^1$H NMR (d$_6$-DMSO, 400 MHz): AH 9.45 (1H, s), 8.31 (1H, s), 8.15 (1H, d, J=8.0 Hz), 7.71 (1H, d, J=8.0 Hz), 7.59 (1H, d, J=8.4 Hz), 7.31-7.35 (4H, m), 7.16 (1H, t, J=7.4 Hz), 6.17 (4H, s), 4.72-4.73 (2H, m), 4.04 (3H, s), 3.96 (3H, s), 3.72-3.79 (4H, m), and 3.10-3.30 (6H, obscured by water peak); RP-HPLC (Hypersil C18, 5 µm, 100 Å, 15 cm; 5%-100% acetonitrile—0.1 M ammonium acetate over 15 min, 1 mL/min). R$_t$ 11.08 min.
MS: M+527.3.

Example 23

N2-[4-(4-amino-1-{2-[(2-hydroxyethyl)amino]ethyl}-1H-pyrazolo[3,4-d]pyrimidin-3-yl)-2-methoxyphenyl]-1-methyl-1H-2-indolecarboxamide monomaleate A mixture of 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate (Intermediate 4) (0.080 g, 0.15 mmol), ethanolamine (0.05 mL, 0.82 mmol), triethylamine (0.021 mL, 0.15 mmol), and sodium iodide (0.021 g, 0.15 mmol) in DMF (2.5 mL) was heated at 70° C. for 15 h. The reaction mixture was cooled to ambient temperature and concentrated; water (5 mL) was added and the resulting precipitate was collected by filtration and rinsed with water (5 mL). The crude solid was purified by silica gel column chromatography (elution with 20% MeOH—CH$_2$Cl$_2$). The appropriate fractions were combined and the solvent removed in vacuo to afford N2-[4-(4-amino-1-{2-[(2-hydroxyethyl)amino]ethyl}-1H-pyrazolo[3,4-d]pyrimidin-3-yl)-2-methoxyphenyl]-1-methyl-1H-2-indolecarboxamide as a white solid (0.009 g, 0.02 mmol). RP-HPLC (Hypersil C18, 5 µm, 100 Å, 15 cm; 5%-100% acetonitrile—0.1 M ammonium acetate over 15 min, 1 mL/min). R$_t$ 9.39 min. MS: M+501.3.

To a warm solution of N2-[4-(4-amino-1-{2-[(2-hydroxyethyl)amino]ethyl}-1H-pyrazolo[3,4-d]pyrimidin-3-yl)-2-methoxyphenyl]-1-methyl-1H-2-indolecarboxamide (0.009 g, 0.02 mmol) in ethyl acetate (2 mL) was added a solution of maleic acid (0.005 g, 0.04 mmol) in ethyl acetate (0.5 mL). The reaction mixture was allowed to cool to ambient temperature and the precipitate was collected by filtration and dried in vacuo to afford N2-[4-(4-amino-1-{2-[(2-hydroxyethyl)amino]ethyl}-1H-pyrazolo[3,4-d]pyrimidin-3-yl)-2-methoxyphenyl]-1-methyl-1H-2-indolecarboxamide monomaleate as a white solid (0.009 g, 0.014 mmol): $^1$H NMR (d$_6$-DMSO, 400 MHz): δH 9.45 (1H, s), 8.69-8.74 (2H, bs), 8.31 (1H, s), 8.14 (1H, d, J=8.0 Hz), 7.71 (1H, d, J=8.0 Hz), 7.59 (1H, d, J=8.4 Hz), 7.32-7.36 (4H, m), 7.15 (1H, t, J=7.4 Hz), 6.07 (2H, s), 5.28 (1H, t, J=4.2 Hz), 4.71 (2H, t, J=5.8 Hz), 4.04 (3H, s), 3.96 (3H, s), 3.65-3.67 (2H, m), 3.50-3.60 (2H, m), and 3.10-3.20 (2H, m); RP-HPLC (Hypersil C18, 5 µm, 100 Å, 15 cm; 5%-100% acetonitrile—0.1 M ammonium acetate over 15 min, 1 mL/min). R$_t$ 9.97 min.
MS: M+501.3.

Example 24

N2-(4-{4-amino-1-[2-(dimethylamino)ethyl]-1H-pyrazolo[3,4-d]pyrimidin-3-yl}-2-methoxyphenyl)-1-methyl-1H-2-indolecarboxamide Monomaleate A mixture of 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate (Intermediate 4) (0.080 g, 0.15 mmol), dimethylamine (2.0 M in THF, 0.07 mL, 0.15 mmol), triethylamine (0.021 mL, 0.15 mmol), and sodium iodide (0.021 g, 0.15 mmol) in DMF (2.5 mL) was heated in a resealable tube at 70° C. for 15 h. Additional dimethylamine solution (0.10 mL) was added and the reaction mixture was heated at 70° C. for 20 h. The reaction mixture was cooled to ambient temperature and concentrated in vacuo. Water (5 mL) was added and the resulting precipitate was collected by filtration and purified by silica gel column chromatography (elution with 20% MeOH/CH$_2$Cl$_2$ to 10:30:60 Et$_3$N:MeOH:CH$_2$Cl$_2$); the appropriate fractions were combined and concentrated to afford N2-(4-{4-amino-1-[2-(dimethylamino)ethyl]-1H-pyrazolo[3,4-d]pyrimidin-3-yl}-2-methoxyphenyl)-1-methyl-1H-2-indolecarboxamide as a white solid (0.009 g, 0.02 mmol). RP-HPLC (Hypersil C18, 5 µm, 100 Å, 15 cm; 5%-100% acetonitrile—0.1 M ammonium acetate over 15 min, 1 mL/min). R$_t$ 10.52. MS: M+485.2.

To a warm solution of N2-(4-{4-amino-1-[2-(dimethylamino)ethyl]-1H-pyrazolo [3,4-d]pyrimidin-3-yl}-2-methoxyphenyl)-1-methyl-1H-2-indolecarboxamide (0.009 g, 0.02 mmol) in ethyl acetate (2 mL) was added a solution of maleic acid (0.005 g, 0.04 mmol) in ethyl acetate (1 mL). The reaction mixture was allowed to cool to ambient temperature and the precipitate was collected by filtration and dried in vacuo to afford N2-(4-{4-amino-1-[2-(dimethylamino)ethyl]-1H-pyrazolo[3,4-d]pyrimidin-3-yl}-2-methoxyphenyl)-1-methyl-1H-2-indolecarboxamide monomaleate as a white solid (0.005 g, 0.008 mmol): $^1$H NMR (d$_6$-DMSO, 400 MHz): δ119.46 (1H, s), 8.32 (1H, s), 8.15 (1H, d, J=8.0 Hz), 7.71 (1H, d, J=7.6 Hz), 7.59 (1H, d, J=8.4 Hz), 7.32-7.35 (4H, m), 7.16 (1H, t, J=7.4 Hz), 6.06 (2H, s), 4.75 (2H, t, J=6.0 Hz), 4.04 (3H, s), 3.96 (3H, s), 3.65 (2H, t, J=5.6 Hz), and 2.88 (6H, s); RP-HPLC (Hypersil C18, 5 µm, 100 Å, 15 cm; 5%-100% acetonitrile—0.1 M ammonium acetate over 15 min, 1 mL/min). R$_t$ 10.08 min. MS: M+485.2.

Example 25

N2-(4-{4-amino-1-[2-(1H-1-imidazolyl)ethyl]-1H-pyrazolo[3,4-d]pyrimidin-3-yl}-2-methoxyphenyl)-1-methyl-1H-2-indolecarboxamide trimaleate A mixture of 2-[4-amino-3-(3-methoxy-4-{[(1-methyl-1H-2-indolyl)carbonyl]amino}phenyl)-1H-pyrazolo[3,4-d]pyrimidin-1-yl]ethyl methanesulfonate (Intermediate 4) (0.080 g, 0.15 mmol), imidazole (0.011 g, 0.15 mmol), triethylamine (0.021 mL, 0.15 mmol), and sodium iodide (0.021 g, 0.15 mmol) in DMF (2.5 mL) was heated at 70° C. for 15 h. Imidazole (0.011 g, 0.15 mmol) was added and the reaction mixture was heated at 70° C. for 60 h. The reaction mixture was cooled to ambient temperature and concentrated in vacuo. Water (5 mL) was added and the resulting precipitate was collected by filtration to afford a beige solid which was taken up in hot ethyl acetate then allowed to slowly cool to ambient temperature. The filtrate was concentrated to afford N2-(4-{4-amino-1-[2-(1H-1-imidazolyl)ethyl]-1H-pyrazolo[3,4-d]pyrimidin-3-yl}-2-methoxyphenyl)-1-methyl-1H-2-indolecarboxamide (0.034 g, 0.067 mmol): RP-HPLC (Hypersil C18, 5 µm, 100 Å, 15 cm; 5%-100% acetonitrile—0.1 M ammonium acetate over 15 min, 1 mL/min). R$_t$ 10.45 min. MS: M+508.2.

To a warm mixture of N2-(4-{4-amino-1-[2-(1H-1-imidazolyl)ethyl]-1H-pyrazolo[3,4-d]pyrimidin-3-yl}-2-methoxyphenyl)-1-methyl-1H-2-indolecarboxamide (0.034 g, 0.067 mmol) in ethyl acetate (2 mL) was added a solution of maleic acid (0.016 g, 0.13 mmol) in ethyl acetate (1 mL); a white precipitate formed immediately. The reaction mixture was allowed to cool to ambient temperature and the precipitate was collected by filtration and dried in vacuo to afford N2-(4-{4-amino-1-[2-(1H-1-imidazolyl)ethyl]-1H-pyrazolo[3,4-d]pyrimidin-3-yl}-2-methoxyphenyl)-1-methyl-1H-2-indolecarboxamide trimaleate as a yellow solid (0.011 g, 0.011 mmol): $^1$H NMR (d$_6$-DMSO, 400 MHz): δH 9.44 (1H, s), 8.90 (1H, s), 8.20 (1H, s), 8.12 (1H, d, J=8.0 Hz), 7.71 (1H, d, J=8.0 Hz), 7.58-7.63 (3H, m), 7.32-7.36 (2H, m), 7.24-7.26 (2H, m), 7.16 (1H, t, J=7.6 Hz), 6.18 (6H, s), 4.85 (2H, t, J=6.8 Hz), 4.71 (2H, t, J=5.2 Hz), 4.04 (3H, s), and 4.00 (3H, s); RP-HPLC (Hypersil C18, 5 µm, 100 Å, 15 cm; 5%-100% acetonitrile—0.1 M ammonium acetate over 15 min, 1 mL/min). R$_t$ 10.35 min. MS: M+508.2.

Example 26

N1-{4-[4-Amino-1-(4-oxocyclohexyl)-1H-pyrazolo[3,4-d]pyrimidin-3-yl]-2-methoxyphenyl}-2-fluoro-4-trifluoromethylbenzamide A solution of 2-fluoro-4-trifluoromethyl-1-benzenecarbonyl chloride (0.87 g, 3.83 mmol) in dichloromethane (5 mL) was added into a mixture of pyridine (15 mL) and 4-[4-amino-3-(4-amino-3-methoxyphenyl)-1H-pyrazolo[3,4-d]pyrimidin-1-yl]-1-cyclohexanone (1.00 g, 2.56 mmol) in dichloromethane (5 mL) at 0° C. over 5 minutes. The mixture was stirred at 0° C. for 10 minutes and at ambient temperature overnight. The solvent was removed under reduced pressure. The residue was partitioned between water and dichloromethane. The dichloromethane layer was washed with saturated aqueous ammonium chloride twice and saturated aqueous sodium chloride solution, dried over magnesium sulfate, filtered and evaporated under reduced pressure to give a crude product. The crude product was purified by flash column chromatography on silica using Isco system to provide N1-{4-[4-amino-1-(4-oxocyclohexyl)-1H-pyrazolo[3,4-d]pyrimidin-3-yl]-2-methoxyphenyl}-2-fluoro-4-trifluoromethylbenzamide (0.95 g, 1.76 mmol) as a white solid: $^1$H NMR (DMSO-d$_6$, 400 MHz) δ 9.90 (dd, 1H), 8.30(d, 1H), 8.28 (s, 1H), 7.99 (t, 1H), 7.89 (d, 1H), 7.75 (d, 1H), 7.34 (s, 1H), 7.30 (d, 1H), 6.90 (br, 2H), 5.27 (m, 1H), 3.94 (s, 3H), 2.70 (m, 2H), 2.47 (m, 4H), 2.17 (m, 2H); RP-HPLC (Hitachi HPLC, Hypersil C18, 5 µm, 100A, 250×4.6 mm; 25%-100% acetonitrile—0.05M ammonium acetate over 10 min, 1 mL/min) R$_t$ 9.23 min. MS: MH$^+$ 543.

Example 27

Cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide: and Example 28

Trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide Morpholine (0.08 mL, 0.93 mmol) was added into a mixture of N1-{4-[4-amino-1-(4-oxocyclohexyl)-1H-pyrazolo[3,4-d]pyrimidin-3-yl]-2-methoxyphenyl}-2-fluoro-4-trifluoromethylbenzamide (0.42 g, 0.78 mmol) and acetic acid (0.11 mL, 1.86 mmol) in dichloroethane (25 mL). The mixture was stirred at ambient temperature for 10 minutes. Sodium triacetoxyborohydride (0.23 g, 1.09 mmol) was added and the mixture was stirred at ambient temperature overnight. Water (6 mL) was added followed by sodium bicarbonate (0.38 g, 4.53 mmol). The mixture was stirred for 1 hour and the organic layer was separated. The aqueous layer was extracted with dichloromethane (20 mL). The combine organics were dried over magnesium sulfate, filtered and evaporated under reduced pressure to give a crude product. The crude product was purified by flash column chromatography on silica using Isco system to provide cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide (0.23 g, 0.37 mmol) and trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide (0.09 g, 0.14 mmol) as white solids.

Data for cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide: $^1$H NMR (DMSO-$d_6$, 400 MHz) δ 9.91 (dd, 1H), 8.30(d, 1H), 8.24 (s, 1H), 8.00 (t, 1H), 7.89 (d, 1H), 7.75 (d, 1H), 7.33 (s, 1H), 7.30 (d, 1H), 6.90 (br, 2H), 4.83 (m, 1H), 3.94 (s, 3H), 3.62 (br, 4H), 1.57-2.55 (m, 10H); MS: MH$^+$ 614.

Data for trans-N1-{4-[4-amino-1-(4-morpholinocyclohexyl)-1H-pyrazolo [3,4-d]pyrimidin-3-yl]-2-methoxyphenyl}-2-fluoro-4-trifluoromethylbenzamide: $^1$H NMR (DMSO-$d_6$, 400 MHz) δ 9.90 (dd, 1H), 8.30(d, 1H), 8.24 (s, 1H), 7.99 (t, 1H), 7.89 (d, 1H), 7.75 (d, 1H), 7.32 (s, 1H), 7.29 (s, 1H), 4.67 (m, 1H), 3.94 (s, 3H), 3.59 (br, 4H), 1.48-2.69 (m, 10H); MS: MH$^+$ 614.

Example 29

Cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino) propanoate; and Example 30

Trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino) propanoate A similar procedure to the preparation of cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide and trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide yielded cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate and trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate as white solids.

Data for cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate: $^1$H NMR (DMSO-$d_6$, 400 MHz) δ 9.90 (dd, 1H), 8.30(d, 1H), 8.23 (s, 1H), 8.00 (t, 1H), 7.89 (d, 1H), 7.75 (d, 1H), 7.33 (s, 1H), 7.30 (d, 1H), 6.90 (br, 2H), 4.37 (m, 1H), 4.08 (q, 2H), 3.94 (s, 3H), 2.76 (m, 2H), 2.32 (m, 2H), 1.88 (m, 2H), 1.67 (m, 4H), 1.16 (t, 3H); RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 7.92 min. MS: MH$^+$ 644.

Data for trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate: $^1$H NMR (DMSO-$d_6$, 400 MHz) δ 9.89 (dd, 1H), 8.30(d, 1H), 8.24 (s, 1H), 8.00 (t, 1H), 7.89 (d, 1H), 7.75 (d, 1H), 7.32 (s, 1H), 7.29 (d, 1H), 6.90 (br, 2H), 4.68 (m, 1H), 4.08 (q, 2H), 3.94 (s, 3H), 2.82 (m, 2H), 2.46 (m, 5H), 1.91-2.07 (m, 6H), 1.18 (t, 3H); RP-HPLC (Hitachi HPLC, Hypersil C18, 5 μm, 100A, 250×4.6 mm, 25%-100% acetonitrile—0.05M ammonium acetate over 10 min, 1 mL/min) R$_t$ 7.69 min. MS: MH$^+$ 644.

Example 31

Cis-3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoic Acid A mixture of cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate (0.23 g, 0.36 mmol), p-dioxane (15 mL), potassium hydroxide (0.10 g, 1.81 mmol) and water (1.5 mL) were heated at 80° C. for 3 hours. The solvents were evaporated and the residue was purified by preparative HPLC to yield cis-3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoic acid (0.11 g, 0.18 mmol) as a white solid: $^1$H NMR (DMSO-$d_6$, 400 MHz). 9.91 (dd, 1H), 8.31 (d, 1H), 8.25 (s, 1H), 8.00 (t, 1H), 7.89 (d, 1H), 7.75 (d, 1H), 7.35 (s, 1H), 7.32 (s, 1H), 6.89 (br, 2H), 4.79 (m, 1H), 3.95 (s, 3H), 2.46-3.00 (m, 7H), 2.29 (m, 2H), 1.91 (m, 2H), 1.80 (m, 2H); RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 6.06 min. MS: MH$^+$ 616.

Example 32

Trans-3-({4-[4-amino-3-(3-methoxy-4-{[2-methoxy-4-trifluoromethylbenzoyl]amino}phenyl)-1H-pyrazolo[3,4-d]pyrimidin-1-yl]cyclohexyl}amino)propanoic Acid A mixture of trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate (0.04 g, 0.06 mmol), p-dioxane (4 mL), potassium hydroxide (0.02 g, 0.31 mmol), a trace amount of methanol and water (0.4 mL) were heated at 80° C. for 1 hour. The mixture was stirred at ambient temperature overnight and at 80° C. for 4 hours. The solvents were evaporated and the residue was purified by preparative HPLC to yield trans-3-({4-[4-amino-3-(3-methoxy-4-{[2-methoxy-4-trifluoromethylbenzoyl]amino}phenyl)-1H-pyrazolo[3,4-d]pyrimidin-1-yl]cyclohexyl}amino)propanoic acid (0.04 g, 0.06 mmol) as a white solid: $^1$H NMR (DMSO-$d_6$, 400 MHz) δ 10.72 (s, 1H), 8.61(d, 1H), 8.28 (d, 1H), 8.24 (s, 1H), 7.61(s, 1H), 7.53 (d, 1H), 7.33 (s, 1H), 7.29 (d, 1H), 4.72 (m, 1H), 4.20 (s, 3H), 4.05 (s, 3H), 1.44-3.61 (m, 13H); RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 6.36 min. MS: MH$^+$ 628.

Example 33

N1-[4-(4-Amino-1H-pyrazolo[3,4-d]pyrimidin-3-yl)-2-methoxyphenyl]-2-fluoro-4-trifluoromethylbenzamide A. N1-[4-(4-Amino-1H-pyrazolo[3,4-d]pyrimidin-3-yl)-2-methoxyphenyl]-2-fluoro-4-trifluoromethylbenzamide A mixture of 3-iodo-1-trityl-1H-pyrazolo[3,4-d]pyrimidin-4-amine (0.10 g, 0.19 mmol), N1-[2-methoxy-4-(4,4,5,5-tetramethyl-1,3,2-dioxaborolan-2-yl)phenyl]-2-fluoro-4-trifluoromethylbenzamide (0.13 g, 0.29 mmol), tetrakis(triphenylphosphine)palladium(0) (0.01 g, 0.01 mmol) and sodium carbonate monohydrate (0.06 mg, 0.48 mmol) in water (2 mL) and ethylene glycol dimethyl ether (4 mL) was heated at 85° C. overnight. The solvents were removed under reduced pressure. Water was added into the residue and the mixture was extracted with ethyl acetate three times. The combined organics were washed with saturated aqueous sodium chloride solution, dried over magnesium sulfate, filtered and evaporated to yield a brown solid which was purified by flash column chromatography on silica using Isco system to provide N1-[4-(4-amino-1-trityl-1H-pyrazolo[3,4-d]pyrimidin-3-yl)-2-methoxyphenyl]-2-fluoro-4-trifluoromethylbenzamide (0.12 g, 0.17 mmol) as a white solid: $^1$H NMR (DMSO-$d_6$, 400 MHz) δ 9.89 (dd, 1H), 8.25(d, 1H), 8.28 (s, 1H), 8.00 (t, 1H), 7.94 (s, 1H), 7.88 (d, 1H), 7.73 (d, 1H), 7.24 (m, 15H), 3.90 (s, 3H); MS: MH$^+$ 689.

B. N1-[4-(4-Amino-1H-pyrazolo[3,4-d]pyrimidin-3-yl)-2-methoxyphenyl]-2-fluoro-4-trifluoromethylbenzamide A mixture of N1-[4-(4-amino-1-trityl-1H-pyrazolo[3,4-d]pyrimidin-3-yl)-2-methoxyphenyl]-2-fluoro-4-trifluoromethylbenzamide (2.10 g, 1.75 mmol), 6 N aqueous hydrochloric acid (10 mL), p-dioxane (10 mL) and ethanol (8 mL) was heated at 50° C. for 6 hours. The mixture was filtered and the solid was washed with ethanol, dried in a vacuum oven over the weekend, and purified by flash column chromatography on silica to provide N1-[4-(4-amino-1H-pyrazolo[3,4-d]pyrimidin-3-yl)-2-methoxyphenyl]-2-fluoro-4-trifluoromethylbenzamide (0.35 g, 0.78 mmol). The filtrate was concentrated and purified by flash column chromatography on silica and preparative HPLC to provide the same product N1-[4-(4-amino-1H-pyrazolo [3,4-d]pyrimidin-3-yl)-2-methoxyphenyl]-2-fluoro-4-trifluoromethylbenzamide (0.67 g, 1.51 mmol) as a white solid: $^1$H NMR (DMSO-$d_6$, 400 MHz) δ 13.58 (s, 1H), 9.90 (dd, 1H), 8.30(d, 1H), 8.23 (s, 1H), 8.05 (t, 1H), 7.90 (d, 1H), 7.75 (d, 1H), 7.36 (s, 1H), 7.24 (d, 1H), 3.94 (s, 3H); MS: MH$^+$ 447.

Example 34

N1-[4-(4-Amino-1-tetrahydro-2H-4-pyranyl-1H-pyrazolo[3,4-d]pyrimidin-3-yl)-2-methoxyphenyl]-2-fluoro-4-trifluoromethylbenzamide Diethyl azodicarboxylate (0.07 mL, 0.45 mmol) was added into a mixture of N1-[4-(4-amino-1H-pyrazolo[3,4-d]pyrimidin-3-yl)-2-methoxyphenyl]-2-fluoro-4-trifluoromethylbenzamide (0.10 g, 0.22 mmol), triphenylphosphine (0.12 g, 0.45 mmol) and tetrahydro-4H-pyran-4-ol (0.04 g, 0.34 mmol) in tetrahydrofuran (5 mL) and the mixture was stirred at ambient temperature overnight. Tetrahydro-4H-pyran-4-ol (0.01 g, 0.11 mmol), triphenylphosphine (0.04 g, 0.15 mmol) and diethyl azodicarboxylate (0.02 mL, 0.15 mmol) were added and the mixture was stirred at ambient temperature for 5 hours. The solvents were evaporated and the residue was purified by preparative HPLC to yield N1-[4-(4-amino-1-tetrahydro-2H-4-pyranyl-1H-pyrazolo[3,4-d]pyrimidin-3-yl)-2-methoxyphenyl]-2-fluoro-4-trifluoromethylbenzamide (0.03 g, 0.06 mmol) as a white solid: $^1$H NMR (DMSO-$d_6$, 400 MHz) δ 9.91 (dd, 1H), 8.30(d, 1H), 8.25 (s, 1H), 8.00 (t, 1H), 7.89 (d, 1H), 7.75 (d, 1H), 7.34 (s, 1H), 7.31 (d, 1H), 6.90 (br, 2H), 4.95 (m, 1H), 4.02 (m, 2H), 3.95 (s, 3H), 3.56 (t, 2H), 2.22 (m, 2H), 1.89 (m, 2H); MS: MH$^+$ 531.

Example 35

N1-{4-[4-Amino-1-(4-hydroxy-2-cyclopentenyl)-1H-pyrazolo[3,4-d]pyrimidin-3-yl]-2-methoxyphenyl}-2-fluoro-4-trifluoromethylbenzamide A. 4-(4-Amino-3-iodo-1H-pyrazolo[3,4-d]pyrimidin-1-yl)-2-cyclopenten-1-ol A mixture of tetrakis(triphenylphosphine)palladium(0) (0.04 g, 0.03 mmol), 3-iodo-1H-pyrazolo[3,4-d]pyrimidin-4-amine (0.30 g, 1.14 mmol) and dimethyl sulfoxide (3 mL) was stirred at ambient temperature in the dark for 2 minutes and cooled to 0° C. A solution of 2,4a-dihydro-1aH-cyclopenta[b]oxirene (0.14 g, 1.72 mmol) in tetrahydrofuran (3 mL) was added into the mixture at 0° C. and stirred at 0° C. for 3 hours. The mixture was stirred at ambient temperature overnight and purified by preparative HPLC to yield 4-(4-amino-3-iodo-1H-pyrazolo[3,4-d]pyrimidin-1-yl)-2-cyclopenten-1-ol (0.24 g, 0.70 mmol) as a white solid: RP-HPLC (Hitachi HPLC, Hypersil C18, 5 μm, 100A, 250×4.6 mm; 25%-100% acetonitrile—0.05M ammonium acetate over 10 min, 1 mL/min) $R_t$ 4.23 min. MS: MH$^+$ 344.

B. N1-{4-[4-Amino-1-(4-hydroxy-2-cyclopentenyl)-1H-pyrazolo[3,4-d]pyrimidin-3-yl]-2-methoxyphenyl}-2-fluoro-4-trifluoromethylbenzamide A mixture of 4-(4-amino-3-iodo-1H-pyrazolo[3,4-d]pyrimidin-1-yl)-2-cyclopenten-1-ol (0.12 g, 0.35 mmol), N1-[2-methoxy-4-(4,4,5,5-tetramethyl-1,3,2-dioxaborolan-2-yl)phenyl]-2-fluoro-4-trifluoromethylbenzamide (0.23 g, 0.53 mmol), tetrakis(triphenyl-phosphine)palladium(0) (0.02 g, 0.02 mmol) and sodium carbonate monohydrate (0.11 g, 0.88 mmol) was heated in a mixture of ethylene glycol dimethyl ether (6 mL) and water (3 mL) at 85° C. for 6 hours under an atmosphere of nitrogen. The mixture was allowed to cool to ambient temperature and solvents were removed under the reduced pressure. The residue was purified by preparative HPLC to yield N1-{4-[4-amino-1-(4-hydroxy-2-cyclopentenyl)-1H-pyrazolo[3,4-d]pyrimidin-3-yl]-2-methoxyphenyl}-2-fluoro-4-trifluoromethylbenzamide (0.18 g, 0.34 mmol) as a white solid: $^1$H NMR (DMSO-$d_6$, 400 MHz) δ 9.89 (dd, 1H), 8.31(d, 1H), 8.26 (s, 1H), 8.00 (t, 1H), 7.88 (d, 1H), 7.75 (d, 1H), 7.32 (s, 1H), 7.29 (d, 1H), 6.90 (br, 2H), 6.09 (d, 1H), 5.93 (d, 1H), 5.76 (m, 1H), 5.31 (m, 1H), 4.74 (m, 1H), 3.94 (s, 3H), 2.84 (m, 1H), 2.02 (m, 1H); RP-HPLC (Hitachi HPLC, Hypersil C18, 5 μm, 100A, 250×4.6 mm; 25%-100% acetonitrile—0.05M ammonium acetate over 10 min, 1 mL/min) $R_t$ 8.50 min. MS: MH$^+$ 529.

Example 36

N1-{4-[4-Amino-1-(3-hydroxycyclopentyl)-1H-pyrazolo[3,4-d]pyrimidin-3-yl]-2-methoxyphenyl}-2-fluoro-4-trifluoromethylbenzamide A mixture of N1-{4-[4-amino-1-(4-hydroxy-2-cyclopentenyl)-1H-pyrazolo[3,4-d]pyrimidin-3-yl]-2-methoxyphenyl}-2-fluoro-4-trifluoromethylbenzamide (0.10 g, 0.19 mmol) and 10% palladium on carbon (0.03 g) in ethanol (10 mL) was stirred at ambient temperature under one atmosphere of hydrogen overnight. The mixture was filtered and the filtrate was purified by preparative HPLC to yield N1-{4-[4-amino-1-(3-hydroxycyclopentyl)-1H-pyrazolo[3,4-d]pyrimidin-3-yl]-2-methoxyphenyl}-2-fluoro-4-trifluoromethylbenzamide (0.07 g, 0.13 mmol) as a white sold: $^1$H NMR (DMSO-d$_6$, 400 MHz) δ 9.91 (dd, 1H), 8.31(d, 1H), 8.24 (s, 1H), 8.00 (t, 1H), 7.89 (d, 1H), 7.75 (d, 1H), 7.34 (s, 1H), 7.30 (d, 1H), 6.90 (br, 2H), 5.17 (m, 1H), 4.97 (m, 1H), 4.22 (m, 1H), 3.94 (s, 3H), 1.79-2.41 (m, 6H); MS: MH$^+$ 531.

Example 37

4-(4-Amino-3-{4-[(1H-2-indolylcarbonyl)amino]-3-methoxyphenyl}-1H-pyrazolo[3,4-d]pyrimidin-1-yl) hexahydropyridinium acetate Oxalyl chloride (0.06 mL, 0.60 mmol) was added into a solution of indole-2-carboxylic acid (0.88 g, 0.546 mmol) in dichloromethane (5 mL) and tetrahydrofuran (5 mL) at 0° C. N,N-dimethylforamide (3 drops from 0.1 mL syringe) was added and the mixture was stirred at 0° C. for 10 minutes and at ambient temperature for 20 minutes. The solvents and excess of reagents were evaporated under reduced pressure. The residue was taken into dichloromethane (2 mL) and the resulting solution (1.25 mL) was added into a solution of tert-butyl 4-[4-amino-3-(4-amino-3-methoxyphenyl)-1H-pyrazolo[3,4-d]pyrimidin-1-yl]-1-piperidinecarboxylate (0.12 g, 0.27 mmol) and pyridine (0.4 mL) in dichloromethane (1 mL). The mixture was stirred at ambient temperature for 2 hours. Trifluoroacetic acid (1 mL) was added and the mixture was stirred at ambient temperature for 2 hours. The solvents were evaporated under reduced pressure and the residue was purified by preparative HPLC to yield 4-(4-amino-3-{4-[(1H-2-indolylcarbonyl)amino]-3-methoxyphenyl}-1H-pyrazolo[3,4-d]pyrimidin-1-yl) hexahydropyridinium acetate (0.07 g, 0.14 mmol) as a white solid: $^1$H NMR (DMSO-d$_6$, 400 MHz) δ 11.85 (br, 1H), 9.45 (s, 1H), 8.24 (d, 1H), 8.12 (d, 1H), 7.68(d, 1H), 7.48 (d, 1H), 7.40 (s, 1H), 7.35 (s, 1H), 7.30 (d, 1H), 7.24 (t, 1H), 7.09 (t, 1H), 4.77 (m, 1H), 3.97 (s, 3H), 3.11 (m, 2H), 2.68 (m, 2H), 2.09 (m, 2H), 1.89 (s, 3H), 1.84 (m, 2H); MS: MH$^+$ 483.

Example 38-53

Used the same protocol that was used to prepare 4-(4-amino-3-{4-[(1H-2-indolylcarbonyl)amino]-3-methoxyphenyl}-1H-pyrazolo[3,4-d]pyrimidin-1-yl)hexahydropyridinium acetate, the following compounds were made.

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 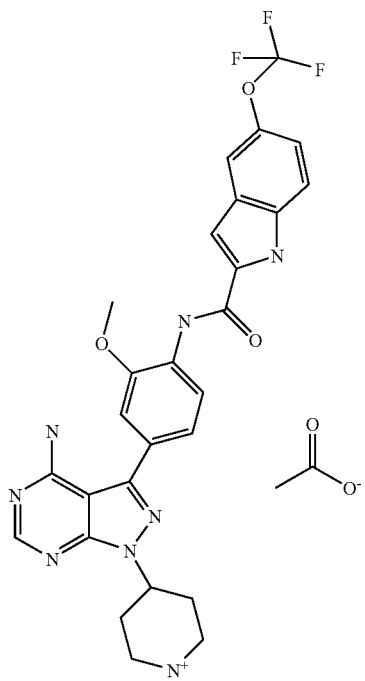 | 567 | 6.97 | 38 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 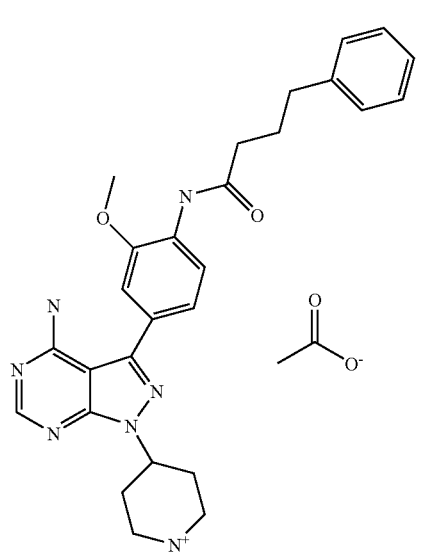 | 486 | 5.89 | 39 |
| 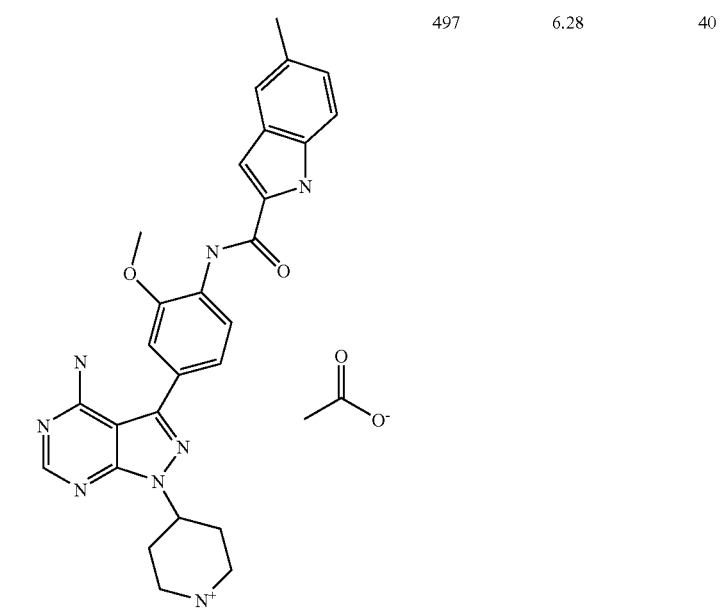 | 497 | 6.28 | 40 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 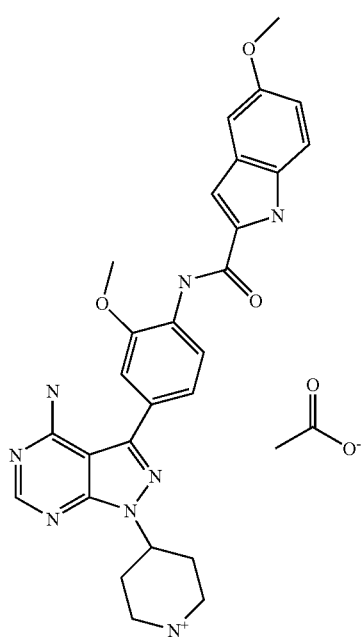 | 513 | 5.61 | 41 |
| 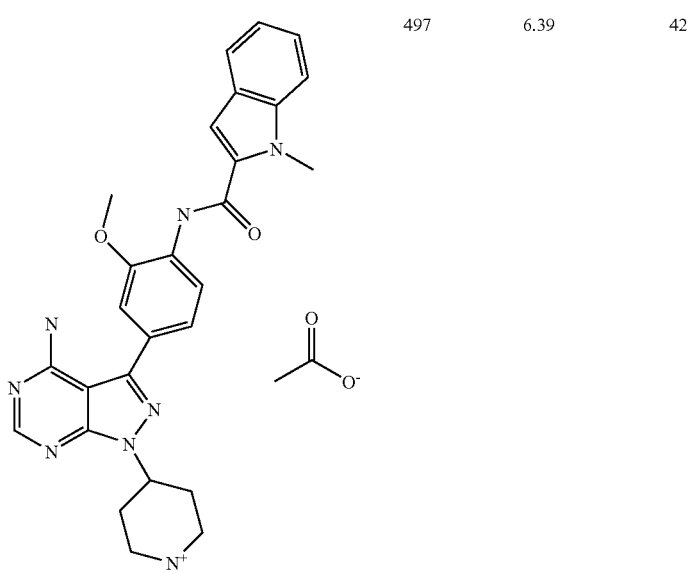 | 497 | 6.39 | 42 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 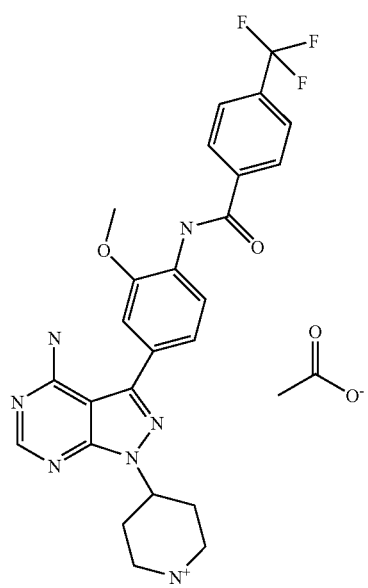 | 512 | 6.22 | 43 |
| 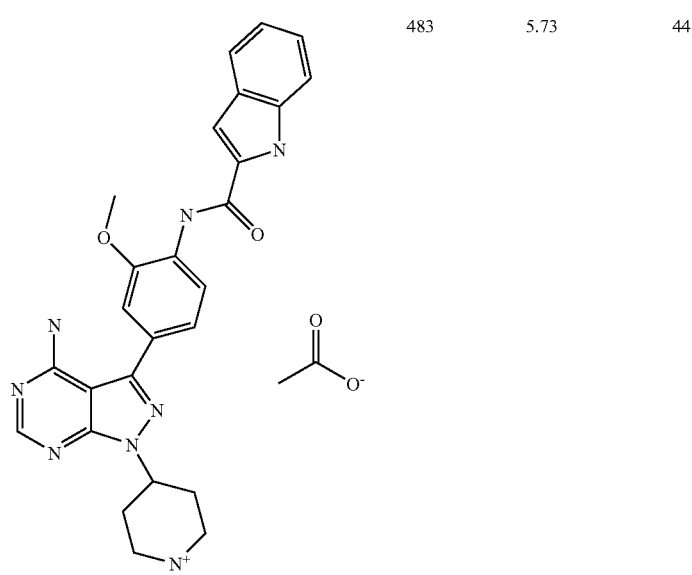 | 483 | 5.73 | 44 |

-continued

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 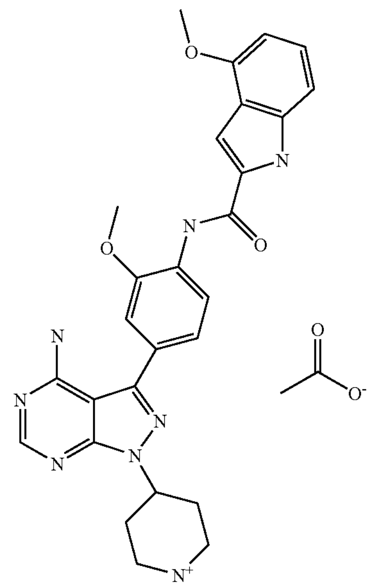 | 513 | 7.78 | 45 |
| 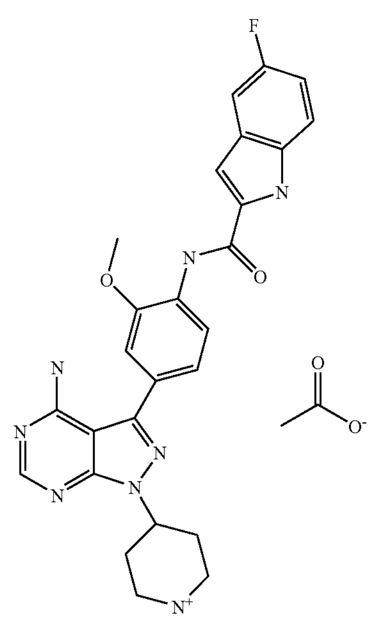 | 501 | 8.23 | 46 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 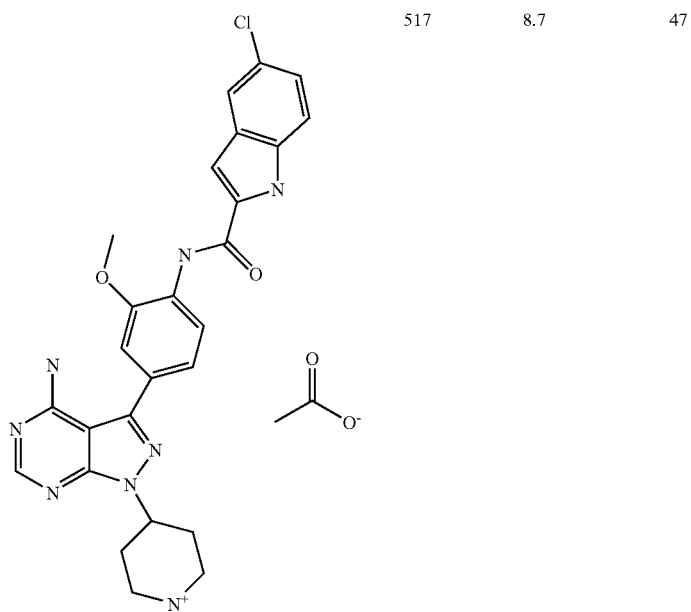 | 517 | 8.7 | 47 |
| 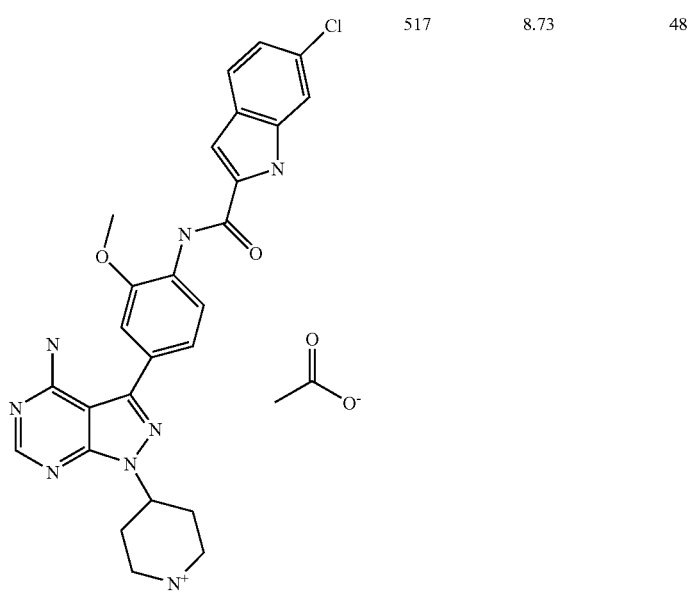 | 517 | 8.73 | 48 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 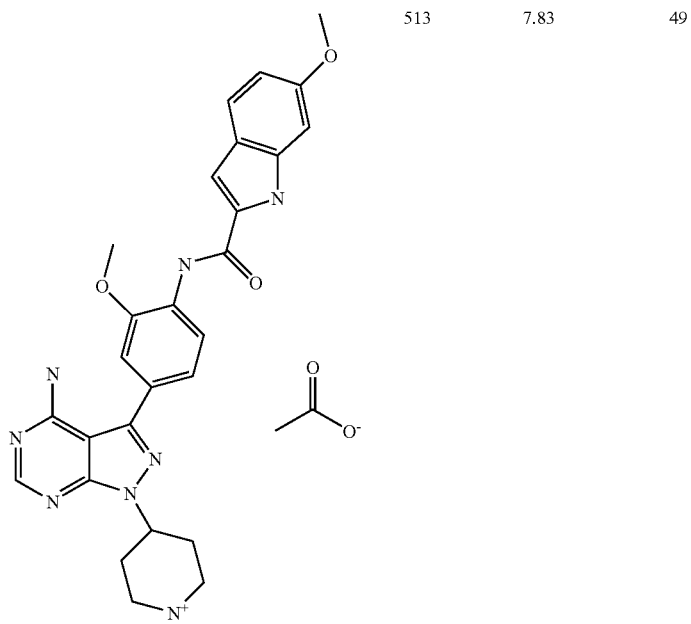 | 513 | 7.83 | 49 |
| 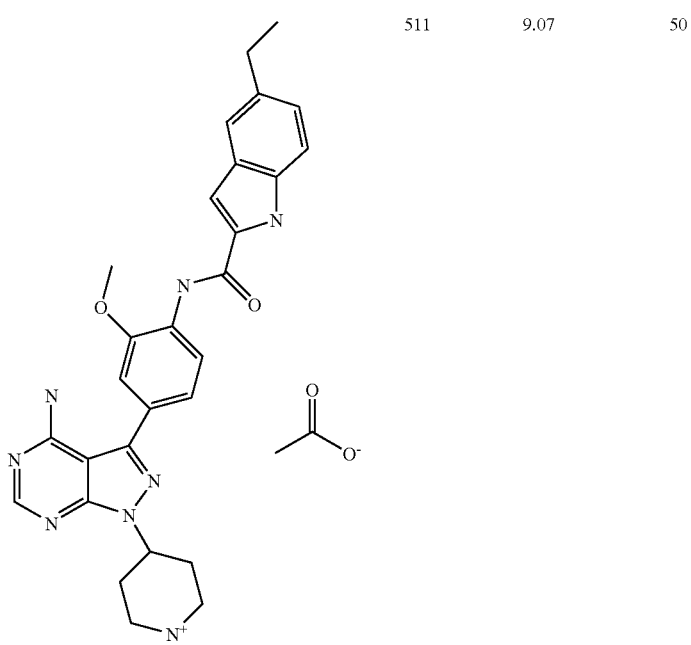 | 511 | 9.07 | 50 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 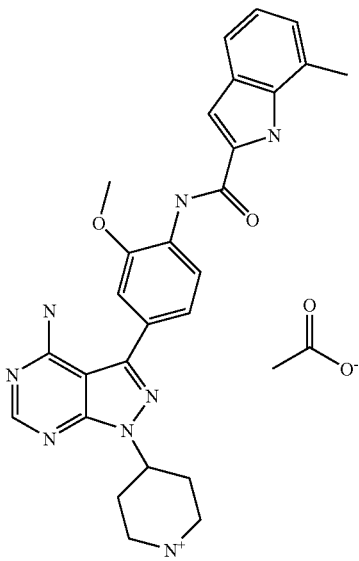 | 497 | 8.37 | 51 |
| 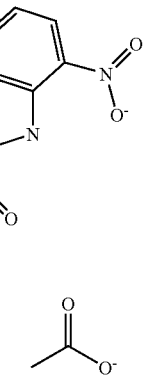 | 528 | 7.9 | 52 |

| Structure | MS: MH+ | HPLC Rt (min) (Hypersil C18, 5 µm, 100 A, 250 × 4.6 mm; 25%-100% acetonitrile - 0.05 M ammonium acetate over 10 min, 1 mL/min) | Example No. |
| --- | --- | --- | --- |
| 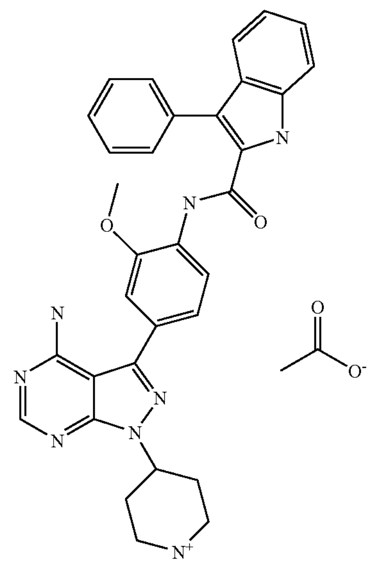 | 559 | 9.5 | 53 |

Example 54

4-[4-Amino-3-(4-{[(1-ethyl-1H-2-indolyl)carbonyl]amino}-3-methoxyphenyl)-1H-pyrazolo[3,4-d]pyrimidin-1-yl]hexahydropyridinium acetate Sodium hydride, 60% suspension in mineral oil (0.006 g, 0.15 mmol) was added into the solution of N2-{4-[4-amino-1-(4-piperidyl)-1H-pyrazolo[3,4-d]pyrimidin-3-yl]-2-methoxyphenyl}-1H-2-indolecarboxamide (0.08 g, 0.14 mmol) in N,N-dimethylforamide (1.0 mL) at 0° C. The mixture was stirred at 0° C. for 10 minutes and at ambient temperature for 20 minutes. A solution of ethyl iodide (0.02 g, 0.14 mmol) in N,N-dimethylforamide (0.5 mL) was added in and the mixture was stirred at ambient temperature overnight. Ethyl iodide (0.01 g, 0.07 mmol) was added in and the mixture was stirred at ambient temperature overnight. Trifluoroacetic acid (3 mL) was added and the mixture was stirred at ambient temperature for 24 hours. The solvents and excess reagents were evaporated under reduced pressure and the residue was purified by preparative HPLC to yield 4-[4-amino-3-(4-{[(1-ethyl-1H-2-indolyl)carbonyl]amino}-3-methoxyphenyl)-1H-pyrazolo[3,4-d]pyrimidin-1-yl] hexahydropyridinium acetate (0.05 g, 0.09 mmol) as a white solid: $^1$H NMR (DMSO-$d_6$, 400 MHz) δ 9.43 (s, 1H), 8.27 (s, 1H), 8.14 (d, 1H), 7.71(d, 1H), 7.61 (d, 1H), 7.34 (s, 2H), 7.31 (t, 2H), 7.15 (t, 1H), 4.96 (m, 1H), 4.62 (q, 2H), 3.96 (s, 3H), 3.00 (m, 2H), 2.28 (m, 2H), 2.03 (m, 2H), 1.91 (s, 3H), 1.33 (t, 3H); MS: MH$^+$ 511.

Example 55 and 56

Used the same protocol that was used to prepare 4-[4-amino-3-(4-{[(1-ethyl-1H-2-indolyl)carbonyl]amino}-3-methoxyphenyl)-1H-pyrazolo[3,4-d]pyrimidin-1-yl]hexahydropyridinium acetate, the following compounds were made.

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 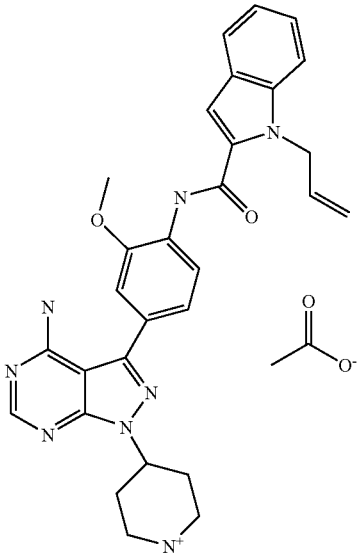 | 523 | 9.12 | 55 |
| 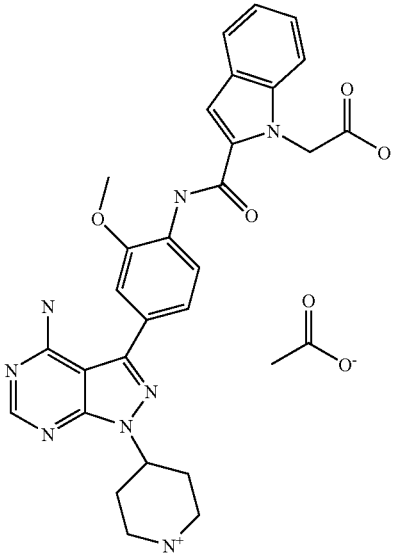 | 540 | 6.03 | 56 |

Example 57

1-(1-methyl-3-piperidyl)-3-(4-phenoxyphenyl)-1H-pyrazolo[3,4-d]pyrimidin-4-amine acetate A solution of racemic 3-iodo-1-(1-methyl-3-piperidyl)-1H-pyrazolo[3,4-d]pyrimidin-4-amine (0.050 g, 0.00014 mol) in dimethoxyethane (2.5 mL) and water (5 mL) was treated with 4-phenoxyphenylboronic acid (0.033 g, 0.00015 mol), sodium carbonate (0.037 g, 0.00037 mol) and tetrakis(triphenylphosphine) palladium (0) (0.016 g, 0.000014 mol) at 80° C. for 18 hours. The organic solvent was removed in vacuo, and the crude material was purified by preparative RP-HPLC (Rainin C18, 8 μm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give 1-(1-methyl-3-piperidyl)-3-(4-phenoxyphenyl)-1H-pyrazolo[3,4-d]pyrimidin-4-amine acetate as a white solid (0.040 g, 0.00009 mol).

$^1$H NMR (DMSO-d$_6$, 400 MHz). 8.24 (s, 1H), 7.65 (d, 2H), 7.43 (t, 2H), 7.10-7.22 (m, 5H), 4.74-4.84 (m, 1H), 2.94 (dd, 1H), 2.79 (d, 1H), 2.36 (t, 1H), 2.22 (s, 3H), 1.89 (s, 3H), 1.86-2.01 (m, 3H), 1.76-1.84 (m, 1H), 1.60-1.75 (m,

1H); RP-HPLC (Delta Pak C18, 5 μm, 300A, 15 cm; 5%-85% acetonitrile—0.1M ammonium acetate over 20 min, 1 mL/min) $R_t$ 13.74 min.; MS: MH$^+$ 401.

Example 58

1-[1-(2-methoxyethyl)-3-piperidyl]-3-(4-phenoxyphenyl)-1H-pyrazolo[3,4-d]pyrimidin-4-amine acetate BSF 4058532F.

A solution of racemic 3-iodo-1-[1-(2-methoxyethyl)-3-piperidyl]-1H-pyrazolo[3,4-d]pyrimidin-4-amine (0.050 g, 0.00012 mol) in dimethoxyethane (2.5 mL) and water (5 mL) was treated with 4-phenoxyphenylboronic acid (0.029 g, 0.00014 mol), sodium carbonate (0.033 g, 0.00031 mol) and tetrakis(triphenylphosphine) palladium (0) (0.014 g, 0.00001 mol) at 80° C. for 20 hours. The organic solvent was removed in vacuo, and the crude material was purified by preparative RP-HPLC (Rainin C18, 8 μm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give 1-[1-(2-methoxyethyl)-3-piperidyl]-3-(4-phenoxyphenyl)-1H-pyrazolo[3,4-d]pyrimidin-4-amine acetate as a white solid (0.038 g, 0.00007 mol).

$^1$H NMR (DMSO-d$_6$, 400 MHz) δ 8.24 (s, 1H), 7.65 (d, 2H), 7.43 (t, 2H), 7.09-7.22 (m, 5H), 4.71-4.82 (m, 1H), 3.44 (t, 2H), 3.21 (s, 3H), 3.04 (dd, 1H), 2.91 (d, 1H), 2.47-2.60 (m, 3H), 1.94-2.09 (m, 3H), 1.89 (s, 3H), 1.75-1.84 (m, 1H), 1.57-1.74 (m, 1H); RP-HPLC (Delta Pak C18, 5 μm, 300A, 15 cm; 5%-85% acetonitrile—0.1M ammonium acetate over 20 min, 1 mL/min) $R_t$ 14.26 min.; MS: MH$^+$ 445.

Example 59

Trans 1-{4-[4-amino-3-(3-chloro-4-{[4-(trifluoromethyl)benzoyl]amino}phenyl)-1H-pyrazolo[3,4-d]pyrimidin-1-yl]cyclohexyl}-4-methylhexahydropyrazinediium dimaleate A. Tert-butyl N-(4-bromo-2-chlorophenyl)carbamate A solution of 4-bromo-2-chloroaniline (5.00 g, 0.0242 mol) in tetrahydrofuran (50 mL) was reacted with a 1.0 M solution of sodium bis(trimethylsilyl)amide in tetrahydrofuran (53.2 mL, 0.0532 mol). The mixture was stirred 15 minutes at ambient temperature. Di-tert-butyl dicarbonate (6.34 g, 0.0290 mol) was added and the solution was stirred for 2 hours. The solvent was removed in vacuo, and the crude material was purified by flash column chromatography on silica using heptane/ethyl acetate (4:1). The solvent was removed in vacuo to give tert-butyl N-(4-bromo-2-chlorophenyl)carbamate as a white solid (4.214 g, 0.0137 mol).

$^1$H NMR (DMSO-d$_6$, 400 MHz) δ 8.75 (s, 1H), 7.71 (d, 1H), 7.54 (d, 1H), 7.50 (dd, 1H), 1.46 (s, 9H); TLC (heptane/ethylacetate 4:1) $R_f$ 0.54.

B. Tert-butyl N-[2-chloro-4-(4,4,5,5-tetramethyl-1,3,2-dioxaborolan-2-yl)phenyl]carbamate A mixture of tert-butyl N-(4-bromo-2-chlorophenyl)carbamate (2.10 g, 0.00685 mol), diboron pinacol ester (2.09 g, 0.00822 mol), [1,1'-bis(diphenylphosphino)ferro-cene] dichloropalladium(II) complex with dichloromethane (1:1) (0.17 g, 0.00021 mol) and potassium acetate (2.02 g, 0.02055 mol) in N,N-dimethylformamide (50 ml) was heated at 80° C. under a nitrogen atmosphere for 6 hours. The solvent was removed in vacuo. The residue was triturated with heptane (70 mL) and the resulting solids were removed by filtration through a pad of Celite® 521. The heptane was removed in vacuo to give tert-butyl N-[2-chloro-4-(4,4,5,5-tetramethyl-1,3,2-dioxaborolan-2-yl)phenyl]carbamate as a grey solid (1.93 g, 0.00546 mol): $^1$H NMR (DMSO-d$_6$, 400 MHz) δ 8.65 (s, 1H), 7.74 (d, 1H), 7.61 (d, 1H), 7.56 (dd, 1H), 1.47 (s,9H), 1.29 (s, 12H).

C. Trans tert-butyl N-(4-{4-amino-1-[4-(4-methylpiperazino)cyclohexyl]-1H-pyrazolo[3,4-d]pyrimidin-3-yl}-2-chlorophenyl)carbamate A mixture of trans 3-iodo-1-[4-(4-methylpiperazino)cyclohexyl]-1H-pyrazolo[3,4-d]pyrimidin-4-amine (2.20 g, 0.00498 mol), tert-butyl N-[2-chloro-4-(4,4,5,5-tetramethyl-1,3,2-dioxaborolan-2-yl)phenyl]carbamate (1.93 g, 0.00548 mol), sodium carbonate (1.32 g, 0.01245 mol) in 1,2-dimethoxyethane (50 mL) and water (100 mL) was stirred rapidly and tetrakis(triphenylphosphine)palladium(0) (0.345 g, 0.00030 mol) was added. The reaction mixture was stirred 6 hours at 80° C., after which time additional tetrakis (triphenylphosphine)palladium(0) (0.345 g, 0.00030 mol) was added. The reaction mixture was stirred an additional 16 hours at 80° C. The solvents were removed in vacuo and the residue was partitioned between ethyl acetate (100 mL) and saturated aqueous sodium bicarbonate (200 mL). The phases were separated and the aqueous phase was extracted with ethyl acetate (3×75 mL). The combined organic phases were dried over magnesium sulfate, and the solvent was removed in vacuo. The product was purified by flash column chromatography on silica using dichloromethane/methanol/ammonium hydroxide (90:10:0.5). The solvent was removed in vacuo to give trans tert-butyl N-(4-{4-amino-1-[4-(4-methylpiperazino)cyclohexyl]-1H-pyrazolo[3,4-d]pyrimidin-3-yl}-2-chlorophenyl)carbamate as a white solid (1.993 g, 0.00368 mol):

$^1$H NMR (DMSO-d$_6$, 400 MHz) δ 8.76 (s, 1H), 8.23 (s, 1H), 7.80 (d, 1H), 7.68 (d, 1H), 7.57 (dd, 1H), 4.58-4.71 (m, 1H), 2.15 (s, 3H), 1.89-2.61 (m, 15H), 1.49 (s, 9H), 1.40-1.48 (m, 2H); TLC (dichloromethane/methanol=90:10) $R_f$ 0.13, MS: MH$^+$ 541.

D. Trans 3-(4-amino-3-chlorophenyl)-1-[4-(4-methylpiperazino)cyclohexyl]-1H-pyrazolo[3,4-d]pyrimidin-4-amine Trans tert-butyl N-(4-{4-amino-1-[4-(4-methylpiperazino)cyclohexyl]-1H-pyrazolo[3,4-d]pyrimidin-3-yl}-2-chlorophenyl)carbamate (1.993 g, 0.00368 mol) was added to a solution of 20% trifluoracetic acid in dichloromethane. The mixture was stirred for 2 hours at ambient temperature. The solvent was removed in vacuo and the residue was dissolved in dichloromethane (50 mL) and washed with a 1.0 M aqueous solution of sodium hydroxide (2×25 mL). The organic layer was dried over magnesium sulfate and the solvent was removed in vacuo to give trans 3-(4-amino-3-chlorophenyl)-1-[4-(4-methylpiperazino)cyclohexyl]-1H-pyrazolo[3,4-d]pyrimidin-4-amine (1.564 g, 0.00355 mol) as a white solid.

$^1$H NMR (DMSO-d$_6$, 400 MHz) δ 8.20 (s, 1H), 7.45 (d, 1H), 7.31 (dd, 1H), 6.92 (d, 1H), 4.57-4.63 (m, 1H), 2.23-2.55 (m, 9H), 2.14 (s, 3H), 1.89-2.08 (m, 6H), 1.38-1.52 (m, 2H); TLC (dichloromethane/methanol=90:10) $R_f$ 0.08; MS: MH$^+$ 441.

E. Trans N1-(4-{4-amino-1-[4-(4-methylpiperazino)cyclohexyl]-1H-pyrazolo[3,4-d]pyrimidin-3-yl}-2-chlorophenyl)-4-(trifluoromethyl)benzamide dimaleate To a mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in pyridine (5 mL) at −10°

C. 4-(trifluoromethyl)-1-benzenecarbonyl chloride (0.188 g, 0.00090 mol) was added dropwise, keeping the temperature below −5° C. The mixture was stirred at −10° C. for 15 minutes, and then at ambient temperature for 18 hours. After addition of an 1N aqueous solution of sodium hydroxide (1.0 mL) the mixture was stirred one hour. The solvent was removed in vacuo, and the residue was partitioned between ethyl acetate (15 mL) and water (30 mL). The layers were separated and the aqueous phase was extracted with ethyl acetate (15 mL), and the combined organic layers were dried over magnesium sulfate. The solvent was removed in vacuo, and the residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give the purified free base (0.032 g, 0.000052 mol). The free base was dissolved in absolute ethanol (4 mL) and heated to reflux. After addition of a solution of maleic acid (0.018 g, 0.000156 mol) in absolute ethanol (1 mL) the solution was refluxed for further 15 minutes. The mixture was cooled to ambient temperature, and the resulting precipitate was filtered, washing with a minimal amount of absolute ethanol. The precipitate was dried in vacuo to give trans N1-(4-{4-amino-1-[4-(4-methylpiperazino)cyclohexyl]-1H-pyrazolo[3,4-d]pyrimidin-3-yl}-2-chlorophenyl)-4-(trifluoromethyl)benzamide dimaleate as a white solid (0.020 g, 0.00002 mol): $^1$H NMR (DMSO-$d_6$, 400 MHz) δ 10.42 (s, 1H), 8.26 (s, 1H), 8.20 (d, 2H), 7.96 (d, 2H), 7.80-7.83 (m, 2H), 7.46 (dd, 1H), 6.80-7.20 (b, 2H), 6.13 (s, 4H), 4.61-4.73 (m, 1H), 2.52-2.64 (m, 4H), 2.23-2.46 (m, 5H), 2.16 (s, 3H), 1.90-2.10 (m, 6H), 1.42-1.56 (m, 2H); RP-HPLC (Delta Pak C18, 5 µm, 300A, 15 cm; 5%-85% acetonitrile—0.1M ammonium acetate over 20 min, 1 mL/min) $R_t$ 14.97 min.; MS: MH$^+$ 613.

Example 60

Trans N1-(4-{4-amino-1-[4-(4-methylpiperazino) cyclohexyl]-1H-pyrazolo[3,4-d]pyrimidin-3-yl}-2-chlorophenyl)-4-(trifluoromethoxy)benzamide dimaleate To a mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in pyridine (5 mL) at −10° C. 4-(trifluoromethoxy)-1-benzenecarbonyl chloride (0.203 g, 0.00091 mol) was added dropwise, keeping the temperature less than −5° C. The mixture was stirred at −10° C. for 15 minutes and then at ambient temperature for 18 hours. After addition of an 1N aqueous solution of sodium hydroxide (1.0 mL) the mixture was stirred one hour. The solvent was removed in vacuo, and the residue was partitioned between ethyl acetate (15 mL) and water (30 mL). The layers were separated and the aqueous phase was extraxcted with ethyl acetate (15 mL), and the combined organic layers were dried over magnesium sulfate. The solvent was removed in vacuo, and the residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give the purified free base (0.034 g, 0.000054 mol). The free base was dissolved in absolute ethanol (4 mL) and heated to reflux. A solution of maleic acid (0.019 g, 0.000162 mol) in absolute ethanol (1 mL) was added and the solution was refluxed for 15 minutes. The mixture was cooled to ambient temperature, and the resulting precipitate was filtered, washing with a minimal amount of absolute ethanol. The precipitate was dried in vacuo to give trans N1-(4-{4-amino-1-[4-(4-methylpiperazino)cyclohexyl]-1H-pyrazolo[3,4-d]pyrimidin-3-yl}-2-chlorophenyl)-4-(trifluoromethoxy)benzamide dimaleate as a white solid (0.020 g, 0.00002 mol): $^1$H NMR (DMSO-$d_6$, 400 MHz) δ 10.29 (s, 1H), 8.26 (s, 1H), 8.14 (d, 2H), 7.78-7.87 (m, 2H), 7.68 (dd, 1H), 7.57 (d, 2H), 6.80-7.20 (b, 2H), 6.11 (s, 4H), 4.65-4.77 (m, 1H), 2.38-3.60 (m, 12H), 1.95-2.15 (m, 6H), 1.51-1.68 (m, 2H); RP-HPLC (Delta Pak C18, 5 µm, 300A, 15 cm; 5%-85% acetonitrile—0.1M ammonium acetate over 20 min, 1 mL/min) $R_t$ 15.41 min.; MS: MH$^+$ 629.

Example 61

Trans 3-(3-chloro-4-{[(5-methyl-2-furyl)methyl]amino}phenyl)-1-[4-(4-methylpiperazino)cyclohexyl]-1H-pyrazolo[3,4-d]pyrimidin-4-amineacetate A mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in 1,2-dichloroethane (20 mL) was reacted with 5-methyl-2-furfural (0.052 g, 0.00048 mol), acetic acid (0.095 g, 0.00159 mol) and sodium triacetoxyborohydride (0.336 g, 0.00159 mol) at ambient temperature. An additional two equivalents of sodium triacetoxyborohydride (0.672 g, 0.00318 mol) were added in two 24 hour intervals. The solvents were removed in vacuo and the residue was partitioned between chloroform (25 mL) and saturated aqueous sodium bicarbonate (50 mL). The phases were separated and the aqueous phase was extracted with chloroform (2×25 mL). The combined organic phases were dried over magnesium sulfate, and the solvent was removed in vacuo. The residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give trans 3-(3-chloro-4-{[(5-methyl-2-furyl)methyl]amino}phenyl)-1-[4-(4-methylpiperazino)cyclohexyl]-1H-pyrazolo[3,4-d]pyrimidin-4-amine acetate as a white solid (0.129 g, 0.00022 mol): $^1$H NMR (DMSO-$d_6$, 400 MHz) δ 8.20 (s, 1H), 7.51 (d, 1H), 7.39 (dd, 1H), 6.93 (d, 1H), 6.20 (d, 1H), 6.14 (t, 1H), 5.98 (d, 1H), 4.55-4.66 (m, 1H), 4.38 (d, 2H), 2.23 (s, 3H), 2.18-2.61 (m, 10H), 2.14 (s, 3H), 1.91 (s, 3H), 1.87-2.09 (m, 5H), 1.37-1.53 (m, 2H); RP-HPLC (Delta Pak C18, 5 µm, 300A, 15 cm; 5%-95% acetonitrile—0.1M ammonium acetate over 20 min, 1 mL/min) $R_t$ 14.48 min.; MS: MH$^+$ 535.

Example 62

Trans 3-{3-chloro-4-[(2-chloro-6-fluorobenzyl)amino]phenyl}-1-[4-(4-methylpiperazino)cyclohexyl]-1H-pyrazolo[3,4-d]pyrimidin-4-amine acetate A mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in 1,2-dichloroethane (20 mL) was reacted with 2-chloro-6-fluorobenzaldehyde (0.076 g, 0.00048 mol), acetic acid (0.095 g, 0.00159 mol) and sodium triacetoxyborohydride (0.336 g, 0.00159 mol) at ambient temperature. An additional three equivalents of sodium triacetoxyborohydride (1.008 g, 0.00477 mol) were added in three 24 hour intervals, after which time all the starting material had been consumed. The solvents were removed in vacuo and the residue was partitioned between chloroform (25 mL) and saturated aqueous sodium bicarbonate (50 mL). The phases were separated and the aqueous phase was extracted with chloroform (2×25 mL). The combined organic phases were dried over magnesium sulfate, and the solvent was removed in vacuo. The residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give to give trans 3-{3-chloro-4-[(2-chloro-6-fluorobenzyl)amino]phenyl}-1-[4-(4-methylpiperazino)cyclohexyl]-1H-pyrazolo[3,4-d]pyrimidin-4-amine acetate as a white solid (0.074 g, 0.00011 mol): $^1$H NMR (DMSO-$d_6$, 400 MHz) δ 8.20 (s, 1H), 7.52 (d, 1H), 7.35-7.47 (m, 4H), 6.99 (d, 1H), 5.75 (t, 1H), 4.55-4.66 (m, 1H), 4.57 (d, 2H), 2.25-2.61 (m, 11H), 2.16 (s, 3H), 1.91 (s, 3H), 1.87-2.09 (m, 4H), 1.37-1.53 (m, 2H);

RP-HPLC (Delta Pak C18, 5 µm, 300A, 15 cm; 5%-95% acetonitrile—0.1M ammonium acetate over 20 min, 1 mL/min) $R_t$ 15.97 min.; MS: MH$^+$ 583.

Example 63

Trans N1-(4-{4-amino-1-[1-(1H-2-imidazolylcarbonyl)-4-piperidyl]-1H-pyrazolo[3,4-d]pyrimidin-3-yl}-2-methoxyphenyl)-(trans)-2-phenyl-1-cyclopropanecarboxamide Maleate A mixture of N1-{4-[4-amino-1-(4-piperidyl)-1H-pyrazolo[3,4-d]pyrimidin-3-yl]-2-methoxyphenyl}-2-phenyl-1-cyclopropanecarboxamide (0.200 g, 0.00041 mol) in toluene (10 mL) was reacted with 5H,10H-diimidazo[1,5-a:1,5-d]pyrazine-5,10-dione (0.040 g, 0.00021 mol) at reflux for 18 hours. An additional equivalent of 5H,10H-diimidazo[1,5-a:1,5-d]pyrazine-5,10-dione was added and the mixture was refluxed an additional 6 hours. The solvent was removed in vacuo and the residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give the free base (0.103 g, 0.00017 mol). The free base was dissolved in absolute ethanol (10 mL) and heated to reflux. After addition of a solution of maleic acid (0.030 g, 0.00034 mol) in absolute ethanol (1 mL) the solution was refluxed for 15 minutes, after which time a precipitate formed. The mixture was cooled to ambient temperature, and the resulting precipitate was filtered, washing with a minimal amount of absolute ethanol. The precipitate was dried in vacuo to give trans N1-(4-{4-amino-1-[1-(1H-2-imidazolylcarbonyl)-4-piperidyl]-1H-pyrazolo[3,4-d]pyrimidin-3-yl}-2-methoxyphenyl)-(trans)-2-phenyl-1-cyclopropanecarboxamide maleate as a white solid (0.055 g, 0.00008 mol):

$^1$H NMR (DMSO-$d_6$, 400 MHz) δ 9.63 (s, 1H), 8.26 (s, 1H), 8.22 (d, 1H), 8.00 (b, 1H), 7.74 (b, 1H), 7.43-7.48 (m, 1H), 7.16-7.33(m, 7H), 6.21 (s, 2H), 4.97-5.13 (m, 1H), 2.91-3.47 (m, 4H), 2.53-2.65 (m, 1H), 2.30-2.45 (m, 1H), 2.07-2.26 (m, 2H), 1.95-2.07 (m, 2H), 1.45-1.50 (m, 1H), 1.28-1.32 (m, 1H); RP-HPLC (Delta Pak C18, 5 µm, 300A, 15 cm; 5%-95% acetonitrile—0.1M ammonium acetate over 20 min, 1 mL/min) $R_t$ 14.17 min.; MS: MH$^+$ 578.

Example 64

Cis N1-(4-{4-amino-1-[4-(2-aminoethyl)-4-hydroxycyclohexyl]-1H-pyrazolo[3,4-d]pyrimidin-3-yl}-2-methoxyphenyl)-(trans)$_2$-phenyl-1-cyclopropanecarboxamide acetate A. Cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropanecarboxamide A mixture of cis N1-{4-[4-amino-1-(1-oxaspiro[2.5]oct-6-yl)-1H-pyrazolo[3,4-d]pyrimidin-3-yl]-2-methoxyphenyl}-(trans)-2-phenylcyclopropane-1-carboxamide (0.605 g, 0.0012 mol), lithium perchlorate (0.189 g, 0.0018 mol) and potassium cyanide (0.116 g, 0.0018 mol) in acetonitrile (60 ml) was heated at 80° C. for two days. Cooled to ambient temperature, diluted with water (30 mL) and extracted with diethyl ether (3×30 mL). The combined organic phases were dried over magnesium sulfate. The solvent was removed in vacuo and the crude product was purified by flash column chromatography on silica using dichloromethane/methanol (95:5). The solvent was removed in vacuo to give cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropanecarboxamide as a white solid (0.602 g, 0.0011 mol): $^1$H NMR (DMSO-$d_6$, 400 MHz) δ 9.64 (s, 1H), 8.23 (t, 2H), 7.31 (t, 2H), 7.25 (s, 1H), 7.17-(m, 4H), 4.61-4.62 (m, 1H), 3.91 (s, 1H), 2.66 (s, 2H), 2.55-2.62 (m, 1H), 2.31-2.45 (m, 3H), 1.58-1.89 (m, 6H), 1.45-1.53 (m, 1H), 1.28-1.38 (m, 1H); RP-HPLC (Delta Pak C18, 5 µm, 300A, 15 cm; 5%-85% acetonitrile—0.1M ammonium acetate over 20 min, 1 mL/min) $R_t$ 15.21 min.; MS: MH$^+$ 538.

B. Cis N1-(4-{4-amino-1-[4-(2-aminoethyl)-4-hydroxycyclohexyl]-1H-pyrazolo[3,4-d]pyrimidin-3-yl}-2-methoxyphenyl)-(trans)$_2$-phenyl-1-cyclopropanecarboxamide acetate To a solution of cis N1-(4-{4-amino-1-[4-(cyanomethyl)-4-hydroxycyclohexyl]-1H-pyrazolo [3,4-d]pyrimidin-3-yl}-2-methoxyphenyl)-(trans)-2-phenyl-1-cyclopropane-carboxamide (0.200 g, 0.00037 mol) in methanol (20 ml) and ammonium hydroxide (1 mL) Raney nickel (0.5 mL) was added. The mixture was stirred 18 hours under a hydrogen atmosphere (1 atm). The reaction mixture was filtered through celite and the solvent was removed in vacuo. The residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give Cis N1-(4-{4-amino-1-[4-(2-aminoethyl)-4-hydroxycyclohexyl]-1H-pyrazolo[3,4-d]pyrimidin-3-yl}-2-methoxyphenyl)-(trans)$_2$-phenyl-1-cyclopropanecarboxamide acetate as a white solid (0.045 g, 0.000083 mol).: $^1$H NMR (DMSO-$d_6$, 400 MHz) δ 9.64 (s, 1H), 8.23 (d, 1H), 8.22-8.24 (m, 1H), 7.17-7.33 (m, 7H), 4.65-4.67 (m, 1H), 3.91 (s, 3H), 2.84-2.91 (m, 1H), 2.53-2.55 (m, 1H), 2.33-2.40 (m, 4H), 1.85 (s, 3H), 1.35-1.80 (m, 9H), 1.30-1.33 (m, 1H); RP-HPLC (Delta Pak C18, 5 µm, 300A, 15 cm; 5%-85% acetonitrile—0.1M ammonium acetate over 20 min, 1 mL/min) $R_t$ 13.29 min.; MS: MH$^+$ 444

Example 65

Cis N1-(4-{4-amino-1-[4-(2-amino-2-oxoethyl)-4-hydroxycyclohexyl]-1H-pyrazolo[3,4-d]pyrimidin-3-yl}-2-methoxyphenyl)-(trans)-2-phenyl-1-cyclopropanecarboxamide To a well-stirred solution of cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropanecarboxamide (0.200 g, 0.00037 mol) in dimethylsulfoxide (4 mL) potassium carbonate (0.216 g, 0.00156 mol) was added at ambient temperature. A 30% aqueous solution of hydrogen peroxide (0.6 mL) was added dropwise, keeping the temperature constant. The mixture was stirred at ambient temperature for 32 hours. Water (20 mL) was added to the mixture, and the precipitate which formed was filtered. The precipitate was washed with water and dried in vacuo. The solid was purified by preparative RP-HPLC (Rainin C18, 8 μm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give cis N1-(4-{4-amino-1-[4-(2-amino-2-oxoethyl)-4-hydroxycyclohexyl]-1H-pyrazolo[3,4-d]pyrimidin-3-yl}-2-methoxyphenyl)-(trans)-2-phenyl-1-cyclopropanecarboxamide as a white solid (0.117 g, 0.00021 mol): $^1$H NMR (DMSO-$d_6$, 400 MHz) δ 9.64 (s, 1H), 8.23 (d, 1H), 8.22 (s, 1H), 7.43-7.48 (m, 1H), 7.15-7.35 (m, 7H), 7.05-7.10 (m, 1H), 4.97 (s, 1H), 4.61-4.71 (m, 1H), 3.91 (s, 3H), 2.54-2.64 (m, 1H), 2.30-2.44 (m, 3H), 2.24 (s, 2H), 1.55-1.81 (m, 6H), 1.45-1.53 (m, 1H), 1.28-1.36 (m, 1H); RP-HPLC (Delta Pak C18, 5 μm, 300A, 15 cm; 5%-85% acetonitrile—0.1M ammonium acetate over 20 min, 1 mL/min) $R_t$ 14.05 min.; MS: MH$^+$ 556.

Example 66

Cis N1-[4-(4-amino-1-{4-[(dimethylamino)methyl]-4-hydroxycyclohexyl}-1H-pyrazolo[3,4-d]pyrimidin-3-yl)-2-methoxyphenyl]-(trans)-2-phenyl-1-cyclopropanecarboxamide acetate To a solution of cis N1-{4-[4-amino-1-(1-oxaspiro[2.5]oct-6-yl)-1H-pyrazolo[3,4-d]pyrimidin-3-yl]-2-methoxyphenyl}-(trans)-2-phenylcyclopropane-1-carboxamide (0.190 g, 0.000302 mol) in 2-propanol (10 mL) a 2 M solution of dimethylamine in methanol (0.91 mL) was added and the resulting mixture was heated at 65° C. in a pressure tube for 18 hours. The solvent was removed in vacuo, and the residue was purified by preparative RP-HPLC (Rainin C18, 8 μm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give Cis N1-[4-(4-amino-1-{4-[(dimethylamino)methyl]-4-hydroxycyclohexyl}-1H-pyrazolo [3,4-d]pyrimidin-3-yl)-2-methoxyphenyl]-(trans)-2-phenyl-1-cyclopropanecarboxamide acetate as a white solid (0.109 g, 0.000177 mol).:

$^1$H NMR (DMSO-$d_6$, 400 MHz) δ 9.64 (s, 1H), 8.23 (d, 1H), 8.22-8.24 (m, 1H), 7.17-7.33 (m, 7H), 4.56-4.68 (m, 1H), 3.91 (s, 3H), 2.54-2.64 (m, 1H), 2.30-2.44 (m, 3H), 2.28 (s, 6H), 2.24 (s, 2H), 1.91 (s, 3H), 1.63-1.78 (m, 4H), 1.44-1.58 (m, 3H), 1.28-1.36 (m, 1H); RP-HPLC (Delta Pak C18, 5 μm, 300A, 15 cm; 5%-85% acetonitrile—0.1M ammonium acetate over 20 min, 1 mL/min) $R_t$ 13.54 min.; MS: MH$^+$ 556.

Example 67

Trans N2-(4-{4-amino-1-[4-(4-methylpiperazino)cyclohexyl]-1H-pyrazolo[3,4-d]pyrimidin-3-yl}-2-methoxyphenyl)-(2R)tetrahydro-1H-2-pyrrolecarboxamide acetate A solution of trans 3-(4-amino-3-methoxyphenyl)-1-[4-(4-methylpiperazino)cyclohexyl]-1H-pyrazolo[3,4-d]pyrimidin-4-amine (0.200 g, 0.00046 mol) in N,N-dimethylformamide (10 mL) was reacted with 1-hydroxy-7-azabenzotriazole (0.068 g, 0.00050 mol), 1-(3-dimethylaminopropyl)-3-ethylcarbodiimide hydrochloride (0.132 g, 0.00069 mol), D-Boc-proline (0.108 g, 0.00050 mol) and N,N-diisopropylethylamine (0.184 g, 0.00142 mol) at ambient temperature for 24 hours. The solvent was removed in vacuo and the residue was partitioned between dichloromethane (10 mL) and a 5% aqueous citric acid solution (20 mL). The layers were separated and the aqueous layer was extracted with dichloromethane (2×10 mL). The combined organic phases were washed with saturated aqueous sodium bicarbonate (15 mL) and dried over magnesium sulfate. The solvent was removed in vacuo and the residue was stirred in 20% trifluoroacetic acid in dichloromethane for 6 hours at ambient temperature. The solvent was removed in vacuo and the residue was purified by preparative RP-HPLC (Rainin C18, 8 mm, 300 A, 25 cm; 5% isocratic for five minutes, then 5%-40% acetonitrile—0.1M ammonium acetate over 20 min, 21 mL/min). The acetonitrile was removed in vacuo and the aqueous mixture was lyopholyzed to give trans N2-(4-{4-amino-1-[4-(4-methylpiperazino)cyclohexyl]-1H-pyrazolo[3,4-d]pyrimidin-3-yl}-2-methoxyphenyl)-(2R)tetrahydro-1H-2-pyrrolecarboxamide acetate (0.096 g, 0.00016 mol) as a white solid.

$^1$H NMR (DMSO-$d_6$, 400 MHz) δ 10.33 (s, 1H), 8.45 (d, 1H), 8.22 (s, 1H), 7.25 (s, 1H), 7.21 (d, 1H), 4.58-4.69 (m, 1H), 3.93 (s, 3H), 3.77 (dd, 1H), 2.96-3.04 (m, 1H), 2.74-2.84 (m, 1H), 2.47-2.58 (m, 5H), 2.23-2.45 (m, 5H), 2.14 (s, 3H), 1.91 (s, 3H), 1.88-2.11 (m, 7H), 1.78-1.88 (m, 1H), 1.60-1.69 (m, 2H), 1.39-1.54 (m, 2H); RP-HPLC (Delta Pak C18, 5 μm, 300A, 15 cm; 5%-85% acetonitrile—0.1M ammonium acetate over 20 min, 1 mL/min) $R_t$ 8.47 min.; MS: MH$^+$ 534.

Example 68

4-[4-amino-3-(4-phenoxyphenyl)-1H-pyrazolo[3,4-d]pyrimidin-1-yl]-1-pyridiniumolate A. 4-(4-amino-3-iodo-1H-pyrazolo[3,4-d]pyrimidin-1-yl)-1-pyridiniumolate A solution of 3-iodo-1H-pyrazolo[3,4-d]pyrimidin-4-amine (5.00 g, 0.019 mol) in N,N-dimethylformamide (50 mL) was reacted with 60% sodium hydride in oil (0.92 g, 0.023 mol) at ambient temperature. The mixture was stirred for 15 minutes, and 4-nitropyridine-N-oxide (5.37 g, 0.038 mol) was added. The mixture was heated at 100° C. for 18 hours. The precipitate which formed was filtered, washing with N,N-dimethylformamide and ethyl acetate to give 4-(4-amino-3-iodo-1H-pyrazolo[3,4-d]pyrimidin-1-yl)-1-pyridiniumolate (3.79 g, 0.011 mol) as a tan solid:

$^1$H NMR (DMSO-$d_6$, 400 MHz) δ 8.38 (s, 1H), 8.34 (d, 2H), 8.24 (d, 2H); RP-HPLC (Delta Pak C18, 5 μm, 300A, 15 cm; 5%-95% acetonitrile—0.1M ammonium acetate over 10 min, 1 mL/min) $R_t$ 7.36 min.; MS: MH$^+$ 355.

B. 4-[4-amino-3-(4-phenoxyphenyl)-1H-pyrazolo[3,4-d]pyrimidin-1-yl]-1-pyridiniumolate A suspension of 4-(4-amino-3-iodo-1H-pyrazolo[3,4-d]pyrimidin-1-yl)-1-pyridiniumolate (0.140 g, 0.00040 mol) in dimethoxyethane (7 mL) and water (15 mL) was reacted with 4-phenoxyphenylboronic acid (0.093 g, 0.00043 mol), sodium carbonate (0.105 g, 0.00099 mol) and tetrakis(triphenylphosphine) palladium (0) (0.046 g, 0.00004 mol) at 80° C. for 18 hours. The solid was filtered to give 4-[4-amino-3-(4-phenoxyphenyl)-1H-pyrazolo[3,4-d]pyrimidin-1-yl]-1-pyridiniumolate (0.138 g, 0.00035 mol) as a brown solid. A portion (0.040 g, 0.00010 mol) was purified by preparative RP-HPLC (Rainin C18, 8 μm, 300 A, 25 cm; 40% isocratic for five minutes, then 40%-100% acetonitrile—0.1M ammonium acetate over 30 min, 21 mL/min). The acetonitrile was removed in vacuo and the aqueous mixture was lyopholyzed to give the product 4-[4-amino-3-(4-phenoxyphenyl)-1H-pyrazolo[3,4-d]pyrimidin-1-yl]-1-pyridiniumolate as a white solid (0.013 g, 0.00003 mol). $^1$H NMR (DMSO-$d_6$, 400 MHz) δ 8.44 (s, 1H), 8.34-8.41 (m, 4H), 7.77 (d, 2H), 7.45 (t, 2H), 7.13-7.24 (m, 5H);

RP-HPLC (Delta Pak C18, 5 μm, 300A, 15 cm; 5%-95% acetonitrile—0.1M ammonium acetate over 20 min, 1 mL/min) $R_t$ 14.66 min.; MS: MH$^+$ 397.

Example 69

3-(4-phenoxyphenyl)-1-(4-pyridyl)-1H-pyrazolo[3,4-d]pyrimidin-4-amine

A suspension of 4-[4-amino-3-(4-phenoxyphenyl)-1H-pyrazolo[3,4-d]pyrimidin-1-yl]-1-pyridiniumolate (0.100 g, 0.00025 mol) and 10% palladium on carbon (0.016 g, 0.00002 mol) in acetic acid (3 mL) was reacted with sodium hypophosphite monohydrate (0.033 g, 0.00038 mol) at 60° C. After 2 hours, an additional 10% palladium on carbon (0.016 g, 0.00002 mol) was added. The mixture was stirred 18 hours after which time additional 10% palladium on carbon (0.016 g, 0.00002 mol) and sodium hypophosphite monohydrate (0.033 g, 0.00038 mol) was added. The mixture was stirred for an additional 24 hours. The mixture was filtered through Celite® 521, washing with acetic acid. The solvent was removed in vacuo, and the residue was purified by preparative RP-HPLC (Rainin C18, 8 mm, 300 A, 25 cm; 40% isocratic for five minutes, then 40%-100% acetonitrile—0.1M ammonium acetate over 30 min, 21 mL/min). The acetonitrile was removed in vacuo and the aqueous mixture was lyopholyzed to give 3-(4-phenoxyphenyl)-1-(4-pyridyl)-1H-pyrazolo[3,4-d]pyrimidin-4-amine (0.020 g, 0.00005 mol) as a white solid:

$^1$H NMR (DMSO-$d_6$, 400 MHz) δ 8.71 (d, 2H), 8.46 (s, 1H), 8.39 (dd, 2H), 7.78 (d, 2H), 7.46 (t,2H), 7.13-7.25 (m, 5H); RP-HPLC (Delta Pak C18, 5 μm, 300A, 15 cm; 5%-95% acetonitrile—0.1M ammonium acetate over 20 min, 1 mL/min) $R_t$ 17.31 min.; MS: MH$^+$ 381.

Example 70

N2-{4-[4-amino-1-(4-pyridyl)-1H-pyrazolo [3,4-d]pyrimidin-3-yl]-2-methoxyphenyl}-1-methyl-1H-2-indolecarboxamide A. N2-{4-[4-amino-1-(4-pyridyl)-1H-pyrazolo[3,4-d]pyrimidin-3-yl]-2-methoxyphenyl}-1-methyl-1H-2-indolecarboxamide A suspension of 4-(4-amino-3-iodo-1H-pyrazolo [3,4-d]pyrimidin-1-yl)-1-pyridiniumolate (0.500 g, 0.0014 mol) in dimethoxyethane (15 mL) and water (30 mL) was reacted with N2-[2-methoxy-4-(4,4,5,5-tetramethyl-1,3,2-dioxaborolan-2-yl)phenyl]-1-methyl-1H-2-indolecarboxamide (0.631 g, 0.00155 mol), sodium carbonate (0.374 g, 0.0035 mol) and tetrakis(triphenylphosphine) palladium (0) (0.163 g, 0.00014 mol) at 80° C. for 18 hours. The solid was filtered and washed with water. The solid was slurried in ethyl acetate for 18 hours and filtered, washing with ethyl acetate. The solid was dried in vacuo to give crude 4-[4-amino-3-(3-methoxy-4-[(1-methyl-1H-2-indolyl)-carbonyl]aminophenyl)-1H-pyrazolo[3,4-d]pyrimidin-1-yl]-1-pyridiniumolate (0.523 g, 0.0010 mol) as a brown solid:

RP-HPLC (Delta Pak C18, 5 μm, 300A, 15 cm; 5%-95% acetonitrile—0.1M ammonium acetate over 10 min, 1 mL/min) $R_t$ 10.92 min.;

MS: MH$^+$ 507.

B. N2-{4-[4-amino-1-(4-pyridyl)-1H-pyrazolo[3,4-d]pyrimidin-3-yl]-2-methoxyphenyl}-1-methyl-1H-2-indolecarboxamide A suspension of 4-[4-amino-3-(3-methoxy-4-{[(1-methyl-1H-2-indolyl)carbonyl]amino}phenyl)-1H-pyrazolo[3,4-d]pyrimidin-1-yl]-1-pyridiniumolate (0.200 g, 0.00039 mol) and 10% palladium on carbon (0.042 g, 0.00004 mol) in acetic acid (3 mL) was reacted with sodium hypophosphite monohydrate (0.063 g, 0.00059 mol) at 60° C. for 2 hours. Additional 10% palladium on carbon (0.042 g, 0.00004 mol) and sodium hypophosphite (0.045 g, 0.00042 mol) was added and the mixture was stirred for 24 hours. The solvent was removed in vacuo and the residue was slurried in methanol for 4 hours. The mixture was filtered through Celite® 521, washing with methanol. The solvent was removed in vacuo and the residue was purified by preparative RP-HPLC (Rainin C18, 8 mm, 300 A, 25 cm; 50% isocratic for five minutes, then 50%-100% acetonitrile—0.1M ammonium acetate over 25 min, 21 mL/min). The acetonitrile was removed in vacuo and the aqueous mixture was lyopholyzed to give N2-{4-[4-amino-1-(4-pyridyl)-1H-pyrazolo[3,4-d]pyrimidin-3-yl]-2-methoxyphenyl}-1-methyl-1H-2-indolecarboxamide (0.020 g, 0.00004 mol) as a white solid: $^1$H NMR (DMSO-$d_6$, 400 MHz) δ 9.48 (s, 1H) 8.72 (d, 2H), 8.47 (s, 1H), 8.42 (d, 2H), 8.20 (d, 1H), 7.72 (d, 1H), 7.60 (d, 1H), 7.48 (s, 1H), 7.42 (d, 1H), 7.36 (s, 1H) 7.34 (t, 1H), 7.16 (t, 1H), 4.05 (s, 3H), 3.99 (s, 1H); RP-HPLC (Delta Pak C18, 5 μm, 300A, 15 cm; 5%-85% acetonitrile—0.1M ammonium acetate over 20 min, 1 mL/min) $R_t$ 19.50 min.;

MS: MH$^+$ 491.

Examples 71

1-(6-amino-3-pyridyl)-3-(4-phenoxyphenyl)-1H-pyrazolo[3,4-d]pyrimidin-4-amine; and

Example 72

3-(4-phenoxyphenyl)-1-(2-pyridyl)-1H-pyrazolo[3,4-d]pyrimidin-4-amine

A solution of 3-(4-phenoxyphenyl)-1H-pyrazolo[3,4-d]pyrimidin-4-amine (0.200 g, 0.00079 mol) in N-methylpyrrolidinone (10 mL) was reacted with 60% sodium hydride in oil (0.032 g, 0.00079 mol). After gas evolution ceased, the mixture was stirred at ambient temperature for 30 minutes, and 5-bromo-2-nitropyridine (0.161 g, 0.00079 mol) was added and heated at 40° C. for 18 hours. Additional 60% sodium hydride in oil (0.032 g, 0.00079 mol) was added and the mixture was stirred an additional 2 hours. The solvent was removed in vacuo and the residue was partitioned between dichloromethane (15 mL) and water (25 mL). The layers were separated and the aqueous layer was extracted with dichloromethane (2×15 mL). The combined organics were washed with brine and dried over magnesium sulfate. The solvent was removed in vacuo and the residue was purified by flash column chromatography on silica using heptane/ethyl acetate (1:2) as an eluent to give two products. The less polar compound, 1-(6-nitro-3-pyridyl)-3-(4-phenoxyphenyl)-1H-pyrazolo[3,4-d]pyrimidin-4-amine, was suspended in absolute ethanol (10 mL) and N,N-dimethylformamide (5 mL) and 10% palladium on carbon (0.007 g) was added. The mixture was stirred under a balloon atmosphere of hydrogen for 18 hours. The mixture was filtered through pad of Celite® 521, washing with absolute ethanol. The solvent was removed in vacuo to give 1-(6-amino-3-pyridyl)-3-(4-phenoxyphenyl)-1H-pyrazolo[3,4-d]pyrimidin-4-amine (0.007 g, 0.00002 mol) as a white solid. $^1$H NMR (DMSO-$d_6$, 400 MHz) δ 8.53 (d, 1H) 8.31 (s, 1H), 7.97 (dd, 1H), 7.73 (d, 2H), 7.44 (t, 2H), 7.12-23 (m, 5H), 6.60 (d, 1H), 6.20 (s, 2H); RP-HPLC (Delta Pak C18, 5 μm, 300A, 15 cm; 5%-85% acetonitrile—0.1M ammonium acetate over 20 min, 1 mL/min) $R_t$ 15.38 min.; MS: MH$^+$ 396.

The more polar compound, 3-(4-phenoxyphenyl)-1-(5-bromo-2-pyridyl)-1H-pyrazolo[3,4-d]pyrimidin-4-amine, was suspended in absolute ethanol (10 mL) and N,N-dimethylformamide (5 mL) and 10% palladium on carbon (0.007 g) was added. The mixture was stirred under a balloon atmosphere of hydrogen for 18 hours. The mixture was filtered through pad of Celite® 521, washing with absolute ethanol. The solvent was removed in vacuo to give 3-(4-phenoxyphenyl)-1-(2-pyridyl)-1H-pyrazolo[3,4-d]pyrimidin-4-amine (0.030 g, 0.00007 mol) as a white solid.

$^1$H NMR (DMSO-$d_6$, 400 MHz) δ 8.60-8.64 (m, 1H) 8.37 (s, 1H), 8.20 (d, 1H), 8.03-8.08 (m, 1H), 7.76 (d, 2H), 7.41-7.49 (m, 3H), 7.12-7.23 (m, 5H); RP-HPLC (Delta Pak C18, 5 μm, 300A, 15 cm; 5%-85% acetonitrile—0.1M ammonium acetate over 20 min, 1 mL/min) $R_t$ 16.32 min.; MS: MH$^+$ 381.

A general procedure for reductive amination using trans-3-(4-amino-phenyl)-1-[4-(4-methylpiperazino)cyclohexyl]-1H-pyrazolo[3,4-d]pyrimidin-4-amine as starting material and an aldehyde is described in Example 73. Various other aldehydes can be substituted for 2-methoxy-3-formyl-pyridine of Example 73 to attach other $Z^{100}$ groups.

Examples 73 trans-3-(4-[(2-methoxy-3-pyridyl)methyl]aminophenyl)-1-[4-(4-methyl-piperazino)cyclohexyl]-1H-pyrazolo[3,4-d]pyrimidin-4-amine diacetate A mixture of trans-3-(4-amino-phenyl)-1-[4-(4-methylpiperazino)cyclohexyl]-1H-pyrazolo[3,4-d]pyrimidin-4-amine (1 eq.), 2-methoxy-3-formyl-pyridine (1.05 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10-60% acetonitrile—0.1M ammonium acetate over 25 min, 21 mL/min) to yield the desired products. The following two compounds were prepared according to the procedure above: trans-3-(4-[(2-methoxy-3-pyridyl)methyl]aminophenyl)-1-[4-(4-methyl-piperazino)cyclohexyl]-1H-pyrazolo[3,4-d]pyrimidin-4-amine Diacetate $^1$H NMR (DMSO-$d_6$, 400 MHz) δ 8.18 (s, 1H), 8.06 (dd, 1H), 7.61 (d, 1H), 7.35 (d, 2H), 6.95 (dd, 1H), 6.69 (d, 2H), 6.51 (t, 1H), 4.60 (m, 1H), 4.26 (d, 2H), 3.94 (s, 3H), 2.64 (s, 3H), 2.6-2.2 (br, 9H), 2.13 (s, 3H), 2.05 (m, 6H), 1.91 (s, 6H), 1.46 (m, 2H);

RP-HPLC (Delta Pak C18, 5 μm, 300A, 15 cm; 5%-85% acetonitrile—0.1M ammonium acetate over 20 min, 1 mL/min) $R_t$ 12.07 min.

MS: MH$^+$ 528.

Example 74 trans-3-{4-[(1H-2-indolylmethyl)amino]phenyl}—[4-(4-methylpiperazino)-cyclohexyl]-1H-pyrazolo[3,4-d]pyrimidin-4-amine acetate Trans-3-{4-[(1H-2-indolylmethyl)amino]phenyl}-1-[4-(4-methylpiperazino)-cyclohexyl]-1H-pyrazolo[3,4-d]pyrimidin-4-amine acetate was prepared as in the method of Example 569 except that 2-formyl-indole was used instead of 2-methoxy-3-formyl-pyridine.

$^1$H NMR (DMSO-$d_6$, 400 MHz) δ 11.08 (s, 1H), 8.19 (s, 1H), 7.44 (d, 1H), 7.36 (d, 2H), 7.32 (d, 1H), 7.01 (t, 1H), 6.95 (t, 1H), 6.81 (d, 2H), 6.47 (t, 1H), 6.35 (s, 1H), 4.60 (m, 1H), 4.45 (d, 2H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 13.74 min. MS: MH$^+$ 536.

Example 75

Trans-3-[(4-{4-amino-1-[4-(4-methylpiperazino)cyclohexyl]-1H-pyrazolo[3,4-d]pyrimidin-3-yl}anilino)methyl]-1,2-dihydro-2-pyridinone diacetate Trans-3-(4-[(2-methoxy-3-pyridyl)methyl]aminophenyl)-1-[4-(4-methylpiperazino)cyclohexyl]-1H-pyrazolo[3,4-d]pyrimidin-4-amine diacetate (0.105 g, 0.000199 mol) was dissolved in 30% hydrogen bromide in acetic acid (4 mL) and the mixture was refluxed for 1.5 hours. The solvent was removed under reduced pressure and the residue was purified by preparative HPLC (Hypersil C18, 8 μm, 25 cm; 10-60% acetonitrile—0.1M ammonium acetate over 25 min, 21 mL/min) to yield trans-3-[(4-{4-amino-1-[4-(4-methylpiperazino)cyclohexyl]-1H-pyrazolo[3,4-d]pyrimidin-3-yl}anilino)methyl]-1,2-dihydro-2-pyridinone diacetate (0.0204 g, 0.0000324 mol) as a white solid.

$^1$H NMR (DMSO-$d_6$, 400 MHz), 8.18 (s, 1H), 7.29 (m, 4H), 6.68 (d, 2H), 6.40 (t, 1H), 6.15 (m, 1H), 4.60 (m, 1H), 4.09 (d, 2H), 2.64 (s, 3H), 2.6-2.2 (br, 9H), 2.13 (s, 3H), 2.05 (m, 6H), 1.91 (s, 6H), 1.46 (m, 2H); RP-HPLC Delta Pak C18, 5 μm, 300A, 15 cm; 5%-85% acetonitrile—0.1M ammonium acetate over 20 min, 1 mL/min) $R_t$ 9.40 min. MS: MH$^+$ 514.

A general procedure for reductive amination with trans-3-(4-amino-3-methoxyphenyl)-1-[4-(4-methylpiperazino)cyclohexyl]-1H-pyrazolo[3,4-d]pyrimidin-4-amine and an aldehyde as starting material is described in Example 76:

Example 76

Trans-5-[(4-{4-amino-1-[4-(4-methylpiperazino)cyclohexyl]-1H-pyrazolo[3,4-d]pyrimidin-3-yl}-2-methoxyanilino)methyl]-4-chloro-1,3-thiazol-2-amine diacetate A mixture of trans-3-(4-amino-3-methoxyphenyl)-1-[4-(4-methylpiperazino)cyclohexyl]-1H-pyrazolo[3,4-d]pyrimidin-4-amine (1 eq.), 2-amino-4-chloro-5-formyl-1,3-thiazole (1.05 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10-60% acetonitrile—0.1M ammonium acetate over 25 min, 21 mL/min) to yield the desired product.

$^1$H NMR (DMSO-$d_6$, 400 MHz). 8.19 (s, 1H), 7.19 (s, 2H), 7.06 (m, 3H), 6.68 (d, 1H), 5.76 (t, 1H), 4.60 (m, 1H), 4.30 (d, 2H), 3.85 (s, 3H), 2.6-2.2 (br, 9H), 2.17 (s, 3H), 2.05 (m, 6H), 1.91 (s, 6H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 11.59 min. MS: MH$^+$ 583.

Examples 77 and 78 were prepared according to the method of Example 76:

Example 77

Trans-3-(3-methoxy-4-[(5-methyl-3-isoxazolyl)methyl]aminophenyl)-1-[4-(4-methylpiperazino)cyclohexyl]-1H-pyrazolo[3,4-d]pyrimidin-4-amine acetate $^1$H NMR (DMSO-$d_6$, 400 MHz), 8.19 (s, 1H), 7.04 (m, 2H), 6.68 (d, 1H), 6.16 (s, 1H), 5.86 (t, 1H), 4.60 (m, 1H), 4.37 (d, 2H), 3.86 (s, 3H), 2.6-2.2 (br, 9H), 2.40 (s, 3H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 11.53 min. MS: MH$^+$ 532.

Example 78

Trans-3-{3-methoxy-4-[(1,3-thiazol-4-ylmethyl)amino]phenyl}-1-[4-(4-methylpiperazino)cyclohexyl]-1H-pyrazolo[3,4-d]pyrimidin-4-amine acetate $^1$H NMR (DMSO-$d_6$, 400 MHz) δ 9.08 (s, 1H), 8.19 (s, 1H), 7.47 (s, 1H), 7.06 (s, 1H), 7.03 (d, 1H), 6.68 (d, 1H), 5.76 (t, 1H), 4.60 (m, 1H), 4.52 (d, 2H), 3.88 (s, 3H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 11.17 min. MS: MH$^+$ 534.

A general procedure for the synthesis of benzotetrahydrofuran-derivatives with trans-3-(4-aminophenyl)-1-[4-(4-methylpiperazino)cyclohexyl]-1H-pyrazolo[3,4-d]pyrimidin-4-amine and a 2-hydroxybenzaldehyde as starting materials is given in Example 79.

Example 79

Trans-3-4-[(4,6-dichloro-2,3-dihydrobenzo[b]furan-3-yl)amino]phenyl-1-[4-(4-methylpiperazino)cyclohexyl]-1H-pyrazolo[3,4-d]pyrimidin-4-amine acetate Trans-3-(4-aminophenyl)-1-[4-(4-methylpiperazino)cyclohexyl]-1H-pyrazolo[3,4-d]pyrimidin-4-amine (1 equiv., 0.0001-0.0002 mol scale) and 2-hydroxy-4,6-dichlorobenzaldehdye (1 equiv.) were combined in absolute ethanol (5 mL) and stirred at ambient temperature for 48 hours. The reaction mixture was concentrated under reduced pressure and the residue dried overnight to yield the corresponding imine, which was used without further purification. Trimethylsulfoxonium iodide (2.5 equiv.) was dissolved in anhydrous dimethylsulfoxide (2 mL) and a 60% dispersion of sodium hydride in parafine (2.5 equiv.) was added at once. After 10 min., the solution of the imine in anhydrous dimethylsulfoxide (2 mL) was added and the resulting mixture was stirred at ambient temperature under an atmosphere of nitrogen for 2.5 hours. The solution was poured into ice-cold water (50 mL) and extracted with dichloromethane (2×40 mL). The combined organic extracts were dried with magnesium sulfate and concentrated under reduced pressure. The residue was purified by preparative HPLC (Hypersil C18, 8 μm, 25 cm; 10-60% acetonitrile—0.1M ammonium acetate over 25 min, 21 mL/min) to yield the final compound.

$^1$H NMR (DMSO-$d_6$, 400 MHz) δ 8.19 (s, 1H), 7.39 (d, 2H), 7.14 (s, 1H), 7.07 (s, 1H), 6.80 (d, 2H), 6.56 (d, 1H), 5.34 (m, 1H), 4.80 (dd, 1H), 4.60 (m, 1H), 4.42 (dd, 1H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 16.03 min. MS: MH$^+$ 593.

Example 80

Trans-3-{4-[(4-chloro-2,3-dihydrobenzo[b]furan-3-yl)amino]phenyl}-1-[4-(4-methylpiperazino)cyclohexyl]-1H-pyrazolo[3,4-d]pyrimidin-4-amine acetate Trans-3-{4-[(4-chloro-2,3-dihydrobenzo[b]furan-3-yl)amino]phenyl}-1-[4-(4-methylpiperazino)cyclohexyl]-1H-pyrazolo[3,4-d]pyrimidin-4-amine acetate was prepared using the method of Example 79 except 2-hydroxy-4,6-dichlorobenzaldehdye was replaced with 2-hydroxy-4-chlorobenzaldehdye.

$^1$H NMR (DMSO-$d_6$, 400 MHz) δ 8.20 (s, 1H), 7.39 (d, 2H), 7.28 (t, 1H), 6.99 (d, 1H), 6.89 (d, 1H), 6.81 (d, 2H), 6.53 (d, 1H), 5.34 (m, 1H), 4.74 (dd, 1H), 4.60 (m, 1H), 4.38 (dd, 1H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 14.42 min. MS: MH$^+$ 559.

Example 81

Trans-3-4-[(4,6-dichloro-2,3-dihydrobenzo[b]furan-3-yl)amino]-3-methoxyphenyl-1-[4-(4-methylpiperazino) cyclohexyl]-1H-pyrazolo[3,4-d]pyrimidin-4-amine acetate Trans-3-4-[(4,6-dichloro-2,3-dihydrobenzo[b]furan-3-yl)amino]-3-methoxyphenyl-1-[4-(4-methylpiperazino) cyclohexyl]-1H-pyrazolo[3,4-d]pyrimidin-4-amine acetate was prepared using the method of Example 79 except trans-3-(4-amino-3-methoxyphenyl)-1-[4-(4-methylpiperazino)cyclohexyl]-1H-pyrazolo[3,4-d]pyrimidin-4-amine was used instead of trans-3-(4-aminophenyl)-1-[4-(4-methylpiperazino)cyclohexyl]-1H-pyrazolo[3,4-d]pyrimidin-4-amine.

$^1$H NMR (DMSO-d$_6$, 400 MHz) δ 8.20 (s, 1H), 7.11 (m, 4H), 6.80 (d, 1H), 5.45(m, 2H), 4.84 (dd, 1H), 4.60 (m, 1H), 4.42 (dd, 1H), 3.82 (s, 3H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) R$_t$ 16.85 min. MS: MH$^+$ 623.

Intermediate 5: tert-butyl 4-[4-amino-3-(4-aminophenyl)-1H-pyrazolo[3,4-d]pyrimidin-1-yl]-1-piperidinecarboxylate A. Tert-butyl 4-[4-amino-3-(4-[(benzyloxy)carbonyl]aminophenyl)-1H-pyrazolo[3,4-d]pyrimidin-1-yl]-1-piperidinecarboxylate A mixture of benzyl N-[4-(4,4,5,5-tetramethyl-1,3,2-dioxaborolan-2-yl)phenyl]carbamate (9.54 g, 0.027 mol), tert-butyl 4-(4-amino-3-iodo-1H-pyrazolo[3,4-d]pyrimidin-1-yl)-1-piperidinecarboxylate (10.0 g, 0.0225 mol), tetrakis-(triphenylphosphine)palladium (1.56 g, 0.00135 mol) and sodium carbonate (5.97 g, 0.0563 mol) was heated in a mixture of ethylene glycol dimethyl ether (120 mL) and water (60 mL) at 80° C. for 16 hours under an atmosphere of nitrogen. The mixture was allowed to cool to ambient temperature and solvents were removed under the reduced pressure. The residue was partitioned between water (150 mL) and dichloromethane (150 mL); the organic phase was washed with brine, dried with magnesium sulfate and concentrated under reduced pressure. The residue was triturated in diethyl ether and the precipitate was collected by filtration and dried to yield tert-butyl 4-[4-amino-3-(4-[(benzyloxy)carbonyl]aminophenyl)-1H-pyrazolo[3,4-d]pyrimidin-1-yl]-1-piperidinecarboxylate (10.1 g, 0.0186 mol) as a white solid.

$^1$H NMR (DMSO-d$_6$, 400 MHz) δ 10.00 (s, 1H), 8.23 (s, 1H), 7.64 (d, 2H), 7.43 (d, 2H), 7.36 (m, 5H), 5.18 (s, 2H), 4.90 (m, 1H), 4.08 (br, 2H), 3.00 (br, 2H), 2.02 (m, 4H), 1.42 (s, 9H); RP-HPLC (Delta Pak C18, 5 μm, 300A, 15 cm; 5%-85% acetonitrile—0.1M ammonium acetate over 20 min, 1 mL/min) R$_t$ 18.58 min.

B. Tert-butyl 4-[4-amino-3-(4-aminophenyl)-1H-pyrazolo[3,4-d]pyrimidin-1-yl]-1-piperidinecarboxylate To a solution of tert-butyl 4-[4-amino-3-(4-[(benzyloxy)carbonyl]aminophenyl)-1H-pyrazolo[3,4-d]pyrimidin-1-yl]-1-piperidinecarboxylate (5.0 g, 0.0092 mol) in terahydrofuran (150 mL) 10% palladium on carbon (1.0 g) was added and the reaction mixture was hydrogenated on a Parr shaker over 96 hours. The catalyst was removed by filtration through a Celite pad and the filtrate was concentrated under reduced pressure. The residue was triturated in n-heptane and the precipitate was collected by filtration and dried to yield tert-butyl 4-[4-amino-3-(4-aminophenyl)-1H-pyrazolo[3,4-d]pyrimidin-1-yl]-1-piperidinecarboxylate (2.51 g, 0.0061 mol) as an off-white solid.

$^1$H NMR (DMSO-d$_6$, 400 MHz) δ 8.20 (s, 1H), 7.35 (d, 2H), 6.69 (d, 2H), 5.42 (s, 2H), 4.90 (m, 1H), 4.08 (m, 2H), 3.00 (br, 2H), 2.02 (m, 4H), 1.42 (s, 9H); RP-HPLC (Delta Pak C18, 5 μm, 300A, 15 cm; 5%-85% acetonitrile—0.1M ammonium acetate over 20 min, 1 mL/min) R$_t$ 14.18 min.

Example 82-94

A general procedure for reductive amination followed by BOC deprotection that was used to prepare Examples 82-94 is given below:

Protocol:

A mixture of tert-butyl 4-[4-amino-3-(4-aminophenyl)-1H-pyrazolo[3,4-d]pyrimidin-1-yl]-1-piperidinecarboxylate (Intermediate 5) (1 eq.), an aldehyde (1.2 eq.), sodium triacetoxyborohydride (3.4 eq.) and acetic acid (3.4 eq) was stirred in anhydrous 1,2-dichloroethane for 16 hours. The reaction mixture was concentrated under reduced pressure, triturated in ethyl acetate and treated with with a 4N aqueous solution of hydrochloric acid. The resulting mixture was stirred for 1 hour; aqueous phase was neutralized with saturated solution of sodium bicarbonate in water and the layers separated. Organic phase was concentrated under reduced pressure and the residue was purified by preparative HPLC (Hypersil C18, 8 μm, 25 cm; 10-60% acetonitrile—0.1M ammonium acetate over 25 min, 21 mL/min) to yield the desired products.

The following compounds were made using the above procedure:

Example 82

3-{4-[(benzo[b]furan-2-ylmethyl)amino]phenyl}-1-(4-piperidyl)-1H-pyrazolo[3,4-d]pyrimidin-4-amine diacetate $^1$H NMR (DMSO-d$_6$, 400 MHz) δ 8.19 (s, 1H), 7.57 (d, 1H), 7.53 (d, 1H), 7.39 (d, 2H), 7.23 (m, 2H), 6.85 (d, 2H), 6.80 (s, 1H), 6.66 (t, 1H), 4.70 (m, 1H), 4.51 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 13.37 min. MS: MH$^+$ 440.

Example 83

3-(4-[(2-methoxy-3-pyridyl)methyl]aminophenyl)-1-(4-piperidyl)-1H-pyrazolo[3,4-d]pyrimidin-4-amine diacetate $^1$H NMR (DMSO-d$_6$, 400 MHz) δ 8.19 (s, 1H), 8.06 (d, 1H), 7.61 (d, 1H), 7.36 (d, 2H), 6.96 (dd, 1H), 6.69 (d, 2H), 6.51 (t, 1H), 4.70 (m, 1H), 4.27 (d, 2H), 3.94 (s, 3H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 11.06 min. MS: MH$^+$ 431.

Example 84

3-(4-[(5-methyl-2-thienyl)methyl]aminophenyl)-1-(4-piperidyl)-1H-pyrazolo[3,4-d]pyrimidin-4-amine diacetate $^1$H NMR (DMSO-d$_6$, 400 MHz) δ 8.19 (s, 1H), 7.36 (d, 2H), 6.85 (d, 1H), 6.77 (d, 2H), 6.64 (d, 1H), 6.54 (t, 1H), 4.70 (m, 1H), 4.41 (d, 2H), 3.07 (m, 2H), 2.65 (m, 2H), 2.38 (s, 3H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.85 min. MS: MH$^+$ 420.

Example 85

3-{4-[(2-furylmethyl)amino]phenyl}-1-(4-piperidyl)-1H-pyrazolo[3,4-d]pyrimidin-4-amine diacetate $^1$H NMR (DMSO-d$_6$, 400 MHz) δ 8.19 (s, 1H), 7.59 (s, 1H), 7.36 (d, 2H), 6.77 (d, 2H), 6.46 (t, 1H), 6.39 (d, 1H), 6.34 (d, 1H), 4.70 (m, 1H), 4.31 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 10.96 min. MS: MH$^+$ 390.

Example 86

3-[4-(benzylamino)phenyl]-1-(4-piperidyl)-1H-pyrazolo[3,4-d]pyrimidin-4-amine diacetate $^1$H NMR (DMSO-d$_6$, 400 MHz) δ 8.19 (s, 1H), 7.34 (m, 6H), 7.24 (t, 1H), 6.73 (d, 2H), 6.60 (t, 1H), 4.70 (m, 1H), 4.33 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.32 min. MS: MH$^+$ 400.

Example 87

3-{4-[(2-methoxybenzyl)amino]phenyl}-1-(4-piperidyl)-1H-pyrazolo[3,4-d]pyrimidin-4-amine diacetate $^1$H NMR (DMSO-d$_6$, 400 MHz) δ 8.19 (s, 1H), 7.35 (d, 2H), 7.24 (m, 2H), 7.01 (d, 1H), 6.90 (t, 1H), 6.70 (d, 2H), 6.41 (t, 1H), 4.70 (m, 1H), 4.28 (d, 2H), 3.85 (s, 3H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.73 min. MS: MH$^+$ 430.

Example 88

3-{4-[(3-methoxybenzyl)amino]phenyl}-1-(4-piperidyl)-1H-pyrazolo[3,4-d]pyrimidin-4-amine diacetate $^1$H NMR (DMSO-d$_6$, 400 MHz) δ 8.19 (s, 1H), 7.35 (d, 2H), 7.25 (t, 1H), 6.96 (m, 2H), 6.81 (d, 1H), 6.72 (d, 2H), 6.59 (t, 1H), 4.70 (m, 1H), 4.30 (d, 2H), 3.74 (s, 3H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.38 min. MS: MH$^+$ 430.

Example 89

3-{4-[(4-methoxybenzyl)amino]phenyl}-1-(4-piperidyl)-1H-pyrazolo[3,4-d]pyrimidin-4-amine diacetate $^1$H NMR (DMSO-d$_6$, 400 MHz) δ 8.19 (s, 1H), 7.35 (m, 4H), 6.90 (d, 2H), 6.72 (d, 2H), 6.51 (t, 1H), 4.70 (m, 1H), 4.25 (d, 2H), 3.73 (s, 3H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.37 min. MS: MH$^+$ 430.

Example 90

1-(4-piperidyl)-3-(4-[3-(trifluoromethyl)benzyl]aminophenyl)-1H-pyrazolo[3,4-d]pyrimidin-4-amine diacetate $^1$H NMR (DMSO-d$_6$, 400 MHz), 8.19 (s, 1H), 7.71 (m, 2H), 7.58 (m, 2H), 7.36 (d, 2H), 6.72 (m, 3H), 4.70 (m, 1H), 4.44 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 14.08 min. MS: MH$^+$ 468.

Example 91

1-(4-piperidyl)-3-(4-[4-(trifluoromethyl)benzyl]aminophenyl)-1H-pyrazolo[3,4-d]pyrimidin-4-amine diacetate $^1$H NMR (DMSO-d$_6$, 400 MHz), 8.19 (s, 1H), 7.70 (d, 2H), 7.60 (d, 2H), 7.36 (d, 2H), 6.72 (m, 3H), 4.70 (m, 1H), 4.44 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 14.23 min. MS: MH$^+$ 468.

Example 92

3-(4-[(2-methyl-1,3-thiazol-4-yl)methyl]aminophenyl)-1-(4-piperidyl)-1H-pyrazolo[3,4-d]pyrimidin-4-amine diacetate $^1$H NMR (DMSO-d$_6$, 400 MHz), 8.19 (s, 1H), 7.41 (d, 2H), 7.26 (s, 1H), 6.73 (d, 2H), 6.51 (t, 1H), 4.70 (m, 1H), 4.36 (d, 2H), 3.07 (m, 2H), 2.70 (s, 3H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 10.13 min. MS: MH$^+$ 421.

Example 93

3-{4-[(2-chloro-6-fluorobenzyl)amino]phenyl}-1-(4-piperidyl)-1H-pyrazolo[3,4-d]pyrimidin-4-amine diacetate $^1$H NMR (DMSO-d$_6$, 400 MHz) δ 8.19 (s, 1H), 7.42 (m, 4H), 7.26 (t, 1H), 6.83 (d, 2H), 6.27 (t, 1H), 4.72 (m, 1H), 4.37 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.32 min. MS: MH$^+$ 452.

Example 94

3-(4-[2-fluoro-4-(trifluoromethyl)benzyl]aminophenyl)-1-(4-piperidyl)-1H-pyrazolo[3,4-d]pyrimidin-4-amine diacetate $^1$H NMR (DMSO-d$_6$, 400 MHz) δ 8.19 (s, 1H), 7.61 (m, 3H), 7.38 (d, 2H), 6.73 (d, 2H), 6.68 (t, 1H), 4.70 (m, 1H), 4.47 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.83 min. MS: MH$^+$ 486.

Example 95

3-{4-[(benzo[b]furan-2-ylmethyl)amino]-3-methoxyphenyl}-1-(4-piperidyl)-1H-pyrazolo[3,4-d]pyrimidin-4-amine diacetate A mixture of tert-butyl 4-[4-amino-3-(4-amino-3-methoxyphenyl)-1H-pyrazolo[3,4-d]pyrimidin-1-yl]-1-piperidinecarboxylate (g, mol), benzofuran-2-carbaldehyde (0.046 g, 0.000315 mol), sodium triacetoxyborohydride (0.089 g, 0.00042 mol.) and acetic acid (0.024 mL, 0.00042 mol) was stirred in anhydrous 1,2-dichloroethane for 16 hours. The reaction mixture was concentrated under reduced pressure, triturated in ethyl acetate (4 mL) and treated with a 4N aqueous solution of hydrochloric acid (1 mL). The resulting mixture was stirred for 1 hour; aqueous phase was neutralized with saturated solution of sodium bicarbonate in water and the layers separated. The organic phase was concentrated under reduced pressure and the residue was purified by preparative HPLC (Hypersil C18, 8 µm, 25 cm; 10-60% acetonitrile—0.1M ammonium acetate over 25 min, 21 mL/min) to yield 3-{4-[(benzo[b]furan-2-ylmethyl)amino]-3-methoxyphenyl}-1-(4-piperidyl)-1H-pyrazolo[3,4-d]pyrimidin-4-amine diacetate (0.027 g, 0.0000457 mol).

$^1$H NMR (DMSO-$d_6$, 400 MHz) δ 8.19 (s, 1H), 7.55 (m, 2H), 7.22 (m, 2H), 7.06 (m, 2H), 6.80 (d, 1H), 6.75 (s, 1H), 5.80 (t, 1H), 4.70 (m, 1H), 4.57 (d, 2H), 3.89 (s, 3H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 14.83 min. MS: MH$^+$ 470.

Example 96

3-[4-(2,3-dihydrobenzo[b]furan-3-ylamino)phenyl]-1-(4-piperidyl)-1H-pyrazolo[3,4-d]pyrimidin-4-amine acetate Salicylaldehyde (0.063 g, 0.000513 mol) and tert-butyl 4-[4-amino-3-(4-aminophenyl)-1H-pyrazolo[3,4-d]pyrimidin-1-yl]-1-piperidinecarboxylate (0.200 g, 0.000489 mol) were combined in absolute ethanol (5 mL) and stirred at ambient temperature for 48 hours. The reaction mixture was concentrated under reduced pressure and the residue dried overnight to yield tert-butyl 4-[4-amino-3-(4-{[-1-(2-hydroxyphenyl)methylidene]amino}phenyl)-1H-pyrazolo[3,4-d]pyrimidin-1-yl]-1-piperidinecarboxylate which was used without further purification. Trimethylsulfoxonium iodide (0.269 g, 0.00122 mol) was dissolved in anhydrous dimethylsulfoxide (2 mL) and a 60% dispersion of sodium hydride in parafine (0.049 g, 0.00122 mol) was added at once. After 10 min., the solution of tert-butyl 4-[4-amino-3-(4-{[-1-(2-hydroxyphenyl)methylidene]amino}phenyl)-1H-pyrazolo[3,4-d]pyrimidin-1-yl]-1-piperidinecarboxylate in anhydrous dimethylsulfoxide (2 mL) was added and the resulting mixture was stirred at ambient temperature under an atmosphere of nitrogen for 2.5 hours. The solution was poured into ice-cold water (70 mL) and extracted with dichloromethane (2×50 mL). The combined organic extracts were dried with magnesium sulfate and concentrated under reduced pressure to yield crude tert-butyl 4-{4-amino-3-[4-(2,3-dihydrobenzo[b]furan-3-ylamino)phenyl]-1H-pyrazolo[3,4-d]pyrimidin-1-yl}-1-piperidinecarboxylate which was used without further purification. The crude compound was dissolved in ethyl acetate (5 mL) and treated with a 4N aqueous solution of hydrochloric acid (1.5 mL). The resulting emulsion was vigorously stirred for 1 hour; the water layer was neutralized with saturated solution of sodium bicarbonate in water and the layers were separated. The organic phase was concentrated under reduced pressure and residue was purified by preparative HPLC (Hypersil C18, 8 µm, 25 cm; 10-60% acetonitrile—0.1M ammonium acetate over 25 min, 21 mL/min) to yield 3-[4-(2,3-dihydrobenzo[b]furan-3-ylamino)phenyl]-1-(4-piperidyl)-1H-pyrazolo[3,4-d]pyrimidin-4-amine acetate (0.038 g, 0.000078 mol) as a white solid $^1$H NMR (DMSO-$d_6$, 400 MHz) δ 8.19 (s, 1H), 7.41 (m, 3H), 7.25 (t, 1H), 6.89 (m, 4H), 6.51 (t, 1H), 5.35 (m, 1H), 4.79 (m, 2H), 4.27 (m, 1H), 3.07 (m, 2H), 2.65 (m, 2H), 2.04 (m, 2H), 1.90 (s, 3H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 11.38 min. MS: MH$^+$ 428.

Example 97

Trans-3-(4-{4-amino-1-[4-(4-methylpiperazino)cyclohexyl]-1H-pyrazolo[3,4-d]pyrimidin-3-yl}anilino)-1H-1$\lambda^6$-benzo[d]isothiazole-1,1-dione acetate A. 3-chloro-1H-1$\lambda^6$-benzo[d]isothiazole-1,1-dione Saccharin (10.0 g, 0.0546 mol) and phosphorus pentachloride (12.6 g, 0.060 mol) were heated at 170° C. for 1.5 hours. The reaction mixture was cooled to ambient temperature and suspended in diethyl ether (200 mL). The precipitate was collected by filtration, thoroughly washed with diethyl ether and dried to yield 3-chloro-1H-1$\lambda^6$-benzo[d]isothiazole-1,1-dione (3.7 g, 0.0184 mol) as a white solid which was used without further purification.

MS: MH$^+$ 202.

B. 3-(4-bromoanilino)-1H-1$\lambda^6$-benzo[d]isothiazole-1,1-dione

To a solution of 3-chloro-1H-1$\lambda^6$-benzo[d]isothiazole-1,1-dione (1.0 g, 0.00496 mol) in acetone (20 mL), 4-bromoaniline (1.71 g, 0.00992 mol) was added at once and the mixture was stirred for 15 min. The mixture was concentrated under reduced pressure and the residue was suspended in water (100 mL). The precipitate was collected by filtration, thoroughly washed with water and dried to yield 3-(4-bromoanilino)-1H-1$\lambda^6$-benzo[d]isothiazole-1,1-dione (1.57 g, 0.00467 mol) as a white solid.

$^1$H NMR (DMSO-$d_6$, 400 MHz) δ 10.93 (s, 1H), 8.47 (d, 1H), 8.09 (d, 1H), 7.93 (m, 4H), 7.69 (d, 2H);

C. 3-[4-(4,4,5,5-tetramethyl-1,3,2-dioxaborolan-2-yl)anilino]-1H-1$\lambda^6$-benzo[d]isothiazole-1,1-dione A mixture of 3-(4-bromoanilino)-1H-1$\lambda^6$-benzo[d]isothiazole-1,1-dione (1.57 g, 0.00467 mol), diboron pinacol ester (1.43 g, 0.00561 mol), [1.1'-bis(diphenylphosphino)ferrocene]-dichloropalladium (II) complex with dichloromethane (1:1) (0.114 g, 0.00014 mol) and potassium acetate (1.37 g, 0.014 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was triturated in diethyl ether to yield 3-[4-(4,4,5,5-tetramethyl-1,3,2-dioxaborolan-2-yl)anilino]-1H-1$\lambda^6$-benzo[d]isothiazole-1,1-dione (1.14 g, 0.00297 mol) as a white solid.

$^1$H NMR (DMSO-d$_6$, 400 MHz) δ 10.92 (br, 1H), 8.51 (d, 1H), 8.08 (d, 1H), 7.91 (m, 4H), 7.68 (d, 2H), 1.29 (s, 12H).

D. Trans-3-(4-{4-amino-1-[4-(4-methylpiperazino) cyclohexyl]-1H-pyrazolo[3,4-d]pyrimidin-3-yl}anilino)-1H-1λ$^6$-benzo[d]isothiazole-1,1-dione acetate A mixture of 3-[4-(4,4,5,5-tetramethyl-1,3,2-dioxaborolan-2-yl)anilino]-1H-1λ$^6$-benzo[d]isothiazole-1,1-dione (0.09 g, 0.000234 mol), trans-3-iodo-1-[4-(4-methylpiperazino)-cyclohexyl]-1H-pyrazolo[3,4-d]pyrimidin-4-amine (0.08 g, 0.00018 mol), tetrakis-(triphenylphosphine)palladium (0.013 g, 0.000011 mol) and sodium carbonate (0.048 g, 0.00045 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 µm, 25 cm; 10-60% acetonitrile—0.1M ammonium acetate over 25 min, 21 mL/min) to yield trans-3-(4-{4-amino-1-[4-(4-methylpiperazino)cyclohexyl]-1H-pyrazolo[3,4-d]pyrimidin-3-yl}anilino)-1H-1λ$^6$-benzo[d]isothiazole-1,1-dione acetate (0.075 g, 0.000119 mol) as a white solid.

$^1$H NMR (DMSO-d$_6$, 400 MHz) δ 8.29 (d, 1H), 8.23 (s, 1H), 7.91 (m, 3H), 7.79 (m, 2H), 7.66 (d, 2H), 4.65 (m, 1H), 2.6-2.2 (br, 9H), 2.13 (s, 3H), 2.05 (m, 6H), 1.91 (s, 3H), 1.46 (m, 2H); RP-HPLC (Delta Pak C18, 5 µm, 300A, 15 cm; 5%-85% acetonitrile—0.1M ammonium acetate over 20 min, 1 mL/min) R$_t$ 11.27 min.
MS: MH$^+$ 572.

Example 98

Cis-3-(4-{4-amino-1-[4-(4-methylpiperazino)cyclohexyl]-1H-pyrazolo[3,4-d]pyrimidin-3-yl}anilino)-1H-1λ$^6$-benzo[d]isothiazole-1,1-dione diacetate Cis-3-(4-{4-amino-1-[4-(4-methylpiperazino)cyclohexyl]-1H-pyrazolo[3,4-d]pyrimidin-3-yl}anilino)-1H-1λ$^6$-benzo[d]isothiazole-1,1-dione diacetate was prepared from 3-[4-(4,4,5,5-tetramethyl-1,3,2-dioxaborolan-2-yl)anilino]-1H-1λ$^6$-benzo[d]isothiazole-1,1-dione (0.09 g, 0.000234 mol) and cis-3-iodo-1-[4-(4-methylpiperazino)-cyclohexyl]-1H-pyrazolo[3,4-d]pyrimidin-4-amine by a similar protocol as described above.

$^1$H NMR (DMSO-d$_6$, 400 MHz) δ 8.42 (d, 1H), 8.23 (s, 11H), 7.91 (m, 3H), 7.84 (m, 2H), 7.62 (d, 2H), 4.80 (m, 1H), 2.6-2.2 (br, 9H), 2.13 (s, 3H), 2.07 (m, 4H), 1.91 (s, 6H), 1.65(m, 2H), 1.58 (m, 2H); RP-HPLC (Delta Pak C18, 5 µm, 300A, 15 cm; 5%-85% acetonitrile—0.1M ammonium acetate over 20 min, 1 mL/min) R$_t$ 11.59 min.
MS: MH$^+$ 572.

Example 99

Trans-N-3-(4-{4-amino-1-[4-(4-methylpiperazino) cyclohexyl]-1H-pyrazolo[3,4-d]pyrimidin-3-yl}phenyl)benzo[d]isoxazol-3-amine acetate A. N1-(4-bromophenyl)-2-fluorobenzamide A solution of 2-fluorobenzoyl chloride (5.82 g, 0.0367 mol) and 4-bromoaniline (6.31 g, 0.0367 mol) in anhydrous dichloromethane (150 mL) was cooled to 0° C. and N,N-diisopropylethylamine (5.21 g, 0.0407 mol) was added under nitrogen atmosphere dropwise. The resulting mixture was stirred at ambient temperature for 24 hours, concentrated and the residue partitioned between ethyl acetate (120 mL) and water (100 mL). The organic phase was washed with brine, dried with magnesium sulfate and concentrated. The residue was suspended in cold diethyl ether (50 mL) and the precipitate was collected by filtration and dried to yield N1-(4-bromophenyl)-2-fluorobenzamide (9.6 g, 0.0326 mol) as a white solid.

$^1$H NMR (DMSO-d$_6$, 400 MHz) δ 10.54 (s, 1H), 7.66 (m, 3H), 7.56 (m, 3H), 7.34 (m, 2H). TLC (ethyl acetate/heptane 1:2) R$_f$ 0.37

B. N1-(4-bromophenyl)-2-fluoro-1-benzenecarbothioamide

A mixture of N1-(4-bromophenyl)-2-fluorobenzamide (3.3 g, 0.0112 mol) and 2,4-bis-(4-methoxyphenyl)-1,3-dithia-2,4-diphosphetane-2,4-disulfide (2.27 g, 0.00561 mol) was heated in toluene at reflux under an atmosphere of nitrogen for 3 hours. The reaction mixture was cooled to ambient temperature, the solvent was removed under reduced pressure and the residue was purified by flash chromatography on silica using ethyl acetate/n-heptane (1:6) as mobile phase to yield N1-(4-bromophenyl)-2-fluoro-1-benzenecarbothioamide (3.1 g, 0.010 mol) as a yellow solid.

$^1$H NMR (DMSO-d$_6$, 400 MHz) δ 12.13 (s, 1H), 7.93 (d, 2H), 7.62 (m, 3H), 7.51 (m, 1H), 7.31 (m, 2H). TLC (ethyl acetate/heptane 1:4) R$_f$ 0.27

C.
N1-(4-bromophenyl)-2-fluoro-1-benzeneamidoxime

A mixture of N1-(4-bromophenyl)-2-fluoro-1-benzenecarbothioamide (1.56 g, 0.00505 mol), hydroxylamine hydrochloride (0.44 g, 0.00631 mol) and sodium bicarbonate (0.53 g, 0.00631 mol) was heated in absolute ethanol (25 mL) at reflux under nitrogen atmosphere for 14 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was suspended in cold diethyl ether and the precipitate was collected by filtration and dried to yield N1-(4-bromophenyl)-2-fluoro-1-benzeneamidoxime (1.21 g, 0.00392 mol) as an off-white solid.

TLC (ethyl acetate/heptane 1:4) R$_f$ 0.12

D.
N-benzo[d]isoxazol-3-yl-N-(4-bromophenyl)amine

To a solution of N1-(4-bromophenyl)-2-fluoro-1-benzeneamidoxime (1.51 g, 0.00489 mol) in N-methylpyrrolidinone (25 mL), potassium tert-butoxide (0.54 g, 0.00513 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was purified by flash chromatography on silica using ethyl acetate/n-heptane (1:5) as mobile phase to yield N-benzo[d]isoxazol-3-yl-N-(4-bromophenyl)amine (0.95 g, 0.00329 mol) as a white solid.

¹H NMR (DMSO-d₆, 400 MHz) δ 9.72 (s, 1H), 8.13 (d, 1H), 7.68 (d, 2H), 7.61 (m, 2H), 7.54 (d, 2H), 7.37 (dd, 1H). TLC (ethyl acetate/heptane 1:4) R$_f$ 0.26

E. N-benzo[d]isoxazol-3-yl-N-[4-(4,4,5,5-tetramethyl-1,3,2-dioxaborolan-2-yl)phenyl]amine A mixture of N-benzo[d]isoxazol-3-yl-N-(4-bromophenyl)amine (1.30 g, 0.0045 mol), diboron pinacol ester (1.37 g, 0.0054 mol), [1.1'-bis(diphenylphosphino) ferrocene]-dichloropalladium (II) complex with dichloromethane (1:1) (0.110 g, 0.000135 mol) and potassium acetate (1.32 g, 0.0135 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:5) as mobile phase to yield N-benzo[d]isoxazol-3-yl-N-[4-(4,4,5,5-tetramethyl-1,3,2-dioxaborolan-2-yl)phenyl]amine (0.40 g, 0.00119 mol) as a white solid.

¹H NMR (DMSO-d₆, 400 MHz) δ 9.74 (s, 1H), 8.16 (d, 1H), 7.70 (m, 4H), 7.61 (d, 2H), 7.37 (dd, 1H), 1.29 (s, 12H). TLC (ethyl acetate/heptane 1:4) R$_f$ 0.21

F. Trans-N-3-(4-{4-amino-1-[4-(4-methylpiperazino) cyclohexyl]-1H-pyrazolo[3,4-d]pyrimidin-3-yl}phenyl)benzo[d]isoxazol-3-amine acetate A mixture of N-benzo[d]isoxazol-3-yl-N-[4-(4,4,5,5-tetramethyl-1,3,2-dioxaborolan-2-yl)phenyl]amine (0.10 g, 0.000298 mol), trans-3-iodo-1-[4-(4-methylpiperazino)-cyclohexyl]-1H-pyrazolo[3,4-d]pyrimidin-4-amine (0.101 g, 0.000229 mol), tetrakis-(triphenylphosphine)palladium (0.016 g, 0.0000137 mol) and sodium carbonate (0.061 g, 0.000573 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10-60% acetonitrile—0.1M ammonium acetate over 25 min, 21 mL/min) to yield trans-N-3-(4-{4-amino-1-[4-(4-methylpiperazino)cyclohexyl]-1H-pyrazolo[3,4-d]pyrimidin-3-yl}phenyl)benzo[d]isoxazol-3-amine acetate (0.102 g, 0.000175 mol) as a white solid.

¹H NMR (DMSO-d₆, 400 MHz) δ 9.81 (s, 1H), 8.23 (s, 1H), 8.19 (d, 1H), 7.88 (d, 2H), 7.65 (m, 4H), 7.40 (m, 1H), 4.65 (m, 1H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) R$_t$ 13.66 min. MS: MH⁺ 524.

Example 100

Cis-N-3-(4-{4-amino-1-[4-(4-methylpiperazino) cyclohexyl]-1H-pyrazolo[3,4-d]pyrimidin-3-yl}phenyl)benzo[d]isoxazol-3-amine diacetate Cis-N-3-(4-{4-amino-1-[4-(4-methylpiperazino)cyclohexyl]-1H-pyrazolo[3,4-d]pyrimidin-3-yl}phenyl)benzo[d]isoxazol-3-amine diacetate was prepared from N-benzo[d]isoxazol-3-yl-N-[4-(4,4,5,5-tetramethyl-1,3,2-dioxaborolan-2-yl)phenyl]amine and cis-3-iodo-1-[4-(4-methylpiperazino)-cyclohexyl]-1H-pyrazolo[3,4-d]pyrimidin-4-amine by a similar protocol as described above.

¹H NMR (DMSO-d₆, 400 MHz) δ 9.86 (s, 1H), 8.26 (s, 1H), 8.24 (d, 1H), 7.93 (d, 2H), 7.67 (m, 4H), 7.43 (m, 114), 4.83 (m, 1H), 2.6-2.2 (br, 9H), 2.13 (s, 3H), 2.08 (m, 4H), 1.91 (s, 6H), 1.74 (m, 2H), 1.62 (m, 2H); RP-HPLC (Delta Pak C18, 5 μm, 300A, 15 cm; 5%-85% acetonitrile—0.1M ammonium acetate over 20 min, 1 mL/min) R$_t$ 13.77 min. MS: MH⁺ 524.

Example 101

N3-{4-[4-amino-1-(4-piperidyl)-1H-pyrazolo[3,4-d]pyrimidin-3-yl]phenyl}benzo[d]isoxazol-3-amine acetate A mixture of N-benzo[d]isoxazol-3-yl-N-[4-(4,4,5,5-tetramethyl-1,3,2-dioxaborolan-2-yl)phenyl]amine (0.087 g, 0.000258 mol), tert-butyl 4-(4-amino-3-iodo-1H-pyrazolo [3,4-d]pyrimidin-1-yl)-1-piperidinecarboxylate (0.088 g, 0.000198 mol), tetrakis-(triphenylphosphine)palladium (0.014 g, 0.000012 mol) and sodium carbonate (0.053 g, 0.000495 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure and the residue partitioned between water and dichloromethane. The organic phase was dried with magnesium sulfate and concentrated under reduced pressure to yield crude tert-butyl 4-{4-amino-3-[4-(benzo[d]isoxazol-3-ylamino)phenyl]-1H-pyrazolo[3,4-d]pyrimidin-1-yl}-1-piperidinecarboxylate which was used without further purification. It was dissolved in ethyl acetate (5 mL) and treated with a 4N aqueous solution of hydrochloric acid (1 mL). The resulting emulsion was vigorously stirred for 1 hour; the water layer was neutralized with saturated solution of sodium bicarbonate in water and the layers were separated. The organic phase was concentrated under reduced pressure and residue was purified by preparative HPLC (Hypersil C18, 8 μm, 25 cm; 10-60% acetonitrile—0.1M ammonium acetate over 25 min, 21 mL/min) to yield N3-{4-[4-amino-1-(4-piperidyl)-1H-pyrazolo[3,4-d]pyrimidin-3-yl]phenyl}benzo[d]isoxazol-3-amine acetate (0.009 g, 0.0000185 mol) as a white solid. ¹H NMR (DMSO-d₆, 400 MHz) δ 9.82 (s, 1H), 8.20 (m, 2H), 7.89 (d, 2H), 7.65 (m, 4H), 7.41 (t, 1H), 4.74 (m, 1H), 3.07 (m, 2H), 2.65 (m, 2H), 2.04 (m, 2H), 1.90 (s, 3H), 1.79 (m, 2H);

RP-HPLC (Delta Pak C18, 5 μm, 300A, 15 cm; 5%-85% acetonitrile—0.1M ammonium acetate over 20 min, 1 mL/min) R$_t$ 11.20 min. MS: MH⁺ 427.

Example 102

Trans-3-[4-(1H-3-indazolylamino)phenyl]-1-[4-(4-methylpiperazino) cyclohexyl]-1H-pyrazolo[3,4-d] pyrimidin-4-amine acetate A. N1-(4-bromophenyl)-2-fluoro-1-benzenecarbohydrazonamide N1-(4-bromophenyl)-2-fluoro-1-benzenecarbothioamide (1.50 g, 0.00485 mol) and a 1M solution of hydrazine in tetrahydrofuran (6.3 mL, 0.0063 mol) were heated in absolute ethanol (25 mL) at reflux under nitrogen atmosphere for 14 hours. Additional 3 mL of a 1M solution of hydrazine in tetrahydrofuran was added and the stirring at reflux was continued for another 6 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated to yield N1-(4-bromophenyl)-2-fluoro-1-benzenecarbohydrazonamide (1.54 g, 0.0050 mol) as a tan solid. TLC (ethyl acetate/heptane 1:3) $R_f$ 0.10

B. N-(4-bromophenyl)-N-(1H-3-indazolyl)amine

To a solution of N1-(4-bromophenyl)-2-fluoro-1-benzenecarbohydrazonamide (1.2 g, 0.00391 mol) in N-methylpyrrolidinone (25 mL), potassium tert-butoxide (0.50 g, 0.0041 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was purified by flash chromatography on silica using ethyl acetate/n-heptane (1:5) as mobile phase to yield N-(4-bromophenyl)-N-(1H-3-indazolyl)amine (0.29 g, 0.0010 mol) as a white solid. $^1$H NMR (DMSO-$d_6$, 400 MHz) δ 12.06 (s, 1H), 9.03 (s, 1H), 7.93 (d, 1H), 7.65 (d, 2H), 7.35 (m, 4H), 7.03 (dd, 1H). TLC (ethyl acetate/heptane 1:3) $R_f$ 0.26

C. N-(1H-3-indazolyl)-N-[4-(4,4,5,5-tetramethyl-1,3,2-dioxaborolan-2-yl)phenyl]amine A mixture of N-(4-bromophenyl)-N-(1H-3-indazolyl)amine (0.29 g, 0.00101 mol), diboron pinacol ester (0.31 g, 0.00121 mol), [1.1'-bis(diphenylphosphino) ferrocene]-dichloropalladium (II) complex with dichloromethane (1:1) (0.025 g, 0.00003 mol) and potassium acetate (0.294 g, 0.003 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:3) as mobile phase to yield N-(1H-3-indazolyl)-N-[4-(4,4,5,5-tetramethyl-1,3,2-dioxaborolan-2-yl)phenyl]amine (0.064 g, 0.000191 mol) as an off-white solid.

$^1$H NMR (DMSO-$d_6$, 400 MHz) δ 12.09 (s, 1H), 9.06 (s, 1H), 7.94 (d, 1H), 7.64 (d, 2H), 7.57 (d, 2H), 7.35 (m, 2H), 7.03 (dd, 1H), 1.28 (s, 12H). TLC (ethyl acetate/heptane 1:3) $R_f$ 0.21

D. Trans-3-[4-(1H-3-indazolylamino)phenyl]-1-[4-(4-methylpiperazino) cyclohexyl]-1H-pyrazolo[3,4-d]pyrimidin-4-amine acetate A mixture of N-(1H-3-indazolyl)-N-[4-(4,4,5,5-tetramethyl-1,3,2-dioxaborolan-2-yl)phenyl]amine (0.064 g, 0.000191 mol), trans-3-iodo-1-[4-(4-methylpiperazino)-cyclohexyl]-1H-pyrazolo[3,4-d]pyrimidin-4-amine (0.070 g, 0.000159 mol), tetrakis-(triphenylphosphine)palladium (0.011 g, 0.0000095 mol) and sodium carbonate (0.042 g, 0.000398 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10-60% acetonitrile—0.1M ammonium acetate over 25 min, 21 mL/min) to yield trans-3-[4-(1H-3-indazolylamino)phenyl]-1-[4-(4-methylpiperazino) cyclohexyl]-1H-pyrazolo[3,4-d]pyrimidin-4-amine acetate (0.035 g, 0.000060 mol) as a white solid.

$^1$H NMR (DMSO-$d_6$, 400 MHz) δ 12.09 (s, 1H), 9.14 (s, 1H), 8.21 (s, 1H), 7.99 (d, 1H), 7.83 (d, 2H), 7.55 (d, 2H), 7.37 (m, 2H), 7.06 (t, 1H), 4.64 (m, 1H), 2.6-2.2 (br, 9H), 2.13 (s, 3H), 2.05 (m, 6H), 1.91 (s, 3H), 1.49 (m, 2H); RP-HPLC (Delta Pak C18, 5 μm, 300A, 15 cm; 5%-85% acetonitrile—0.1M ammonium acetate over 20 min, 1 mL/min) $R_t$ 12.96 min.

MS: MH$^+$ 523.

Example 103

Trans-N-3-(4-{4-amino-1-[4-(4-methylpiperazino) cyclohexyl]-1H-pyrazolo[3,4-d]pyrimidin-3-yl}phenyl)-6-(trifluoromethyl)benzo[d]isoxazol-3-amine acetate A. N1-(4-bromophenyl)-2-fluoro-4-(trifluoromethyl) benzamide A solution of 2-fluoro-4-(trifluoromethyl)benzoyl chloride (5.05 g, 0.0223 mol) and 4-bromoaniline (3.83 g, 0.0223 mol) in anhydrous dichloromethane (150 mL) was cooled to 0° C. and N,N-diisopropylethylamine (4.26 mL, 0.0245 mol) was added under nitrogen atmosphere dropwise. The resulting mixture was stirred at ambient temperature for 24 hours, concentrated and the residue was partitioned between ethyl acetate (120 mL) and water (100 mL). The organic phase was washed with brine, dried with magnesium sulfate and concentrated. The residue was suspended in cold n-heptane (50 mL) and the precipitate was collected by filtration and dried to yield N1-(4-bromophenyl)-2-fluoro-4-(trifluoromethyl)benzamide (7.1 g, 0.0196 mol) as a white solid. $^1$H NMR (DMSO-$d_6$, 400 MHz) δ 10.74 (s, 1H), 7.90 (m, 2H), 7.74 (d, 1H), 7.68 (d, 2H), 7.56 (d, 2H).

B. N1-(4-bromophenyl)-2-fluoro-4-(trifluoromethyl)-1-benzenecarbothioamide

A mixture of N1-(4-bromophenyl)-2-fluoro-4-(trifluoromethyl)benzamide (7.1 g, 0.0196 mol) and 2,4-bis-(4-methoxyphenyl)-1,3-dithia-2,4-diphosphetane-2,4-disulfide (3.97 g, 0.0098 mol) was heated in toluene at reflux under an atmosphere of nitrogen for 3 hours. The reaction mixture was cooled to ambient temperature, the solvent was removed under reduced pressure and the residue was purified by flash chromatography on silica using ethyl acetate/n-heptane (1:8) as mobile phase to yield N1-(4-bromophenyl)-2-fluoro-4-(trifluoromethyl)-1-benzenecarbothioamide (6.0 g, 0.0159 mol) as a yellow solid.

$^1$H NMR (DMSO-$d_6$, 400 MHz) δ 12.33 (s, 1H), 7.94 (d, 2H), 7.81 (m, 2H), 7.65 (m, 3H). TLC (ethyl acetate/heptane 1:4) $R_f$ 0.61

C. N1-(4-bromophenyl)-2-fluoro-4-(trifluoromethyl)-1-benzeneamidoxime

A mixture of N1-(4-bromophenyl)-2-fluoro-4-(trifluoromethyl)-1-benzenecarbothioamide (2.50 g, 0.00663 mol), hydroxylamine hydrochloride (0.65 g, 0.00928 mol) and sodium bicarbonate (0.78 g, 0.00928 mol) was heated in absolute ethanol (25 mL) at reflux under nitrogen atmosphere for 14 hours: The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was suspended in cold n-heptane and the precipitate was collected by filtration and dried to yield N1-(4-bromophenyl)-2-fluoro-4-(trifluoromethyl)-1-benzeneamidoxime (2.35 g, 0.00625 mol) as an off-white solid.

TLC (ethyl acetate/heptane 1:4) $R_f$ 0.12

D. N-(4-bromophenyl)-N-[6-(trifluoromethyl)benzo[d]isoxazol-3-yl]amine

To a solution of N1-(4-bromophenyl)-2-fluoro-4-(trifluoromethyl)-1-benzeneamidoxime (2.25 g, 0.00598 mol) in N-methylpyrrolidinone (30 mL), potassium tert-butoxide (0.71 g, 0.00628 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was suspended in cold n-heptane and the precipitate was collected by filtration and dried to yield N-(4-bromophenyl)-N-[6-(trifluoromethyl)benzo[d]isoxazol-3-yl]amine (1.75 g, 0.0049 mol) as an off-white solid.

$^1$H NMR (DMSO-$d_6$, 400 MHz) δ 9.95 (s, 1H), 8.37 (d, 1H), 8.14 (s, 1H), 7.78 (d, 1H), 7.68 (d, 2H), 7.58 (d, 2H). TLC (ethyl acetate/heptane 1:5) $R_f$ 0.31

E. N-[4-(4,4,5,5-tetramethyl-1,3,2-dioxaborolan-2-yl)phenyl]-N-[6-(trifluoromethyl)benzo[d]isoxazol-3-yl]amine A mixture of N-(4-bromophenyl)-N-[6-(trifluoromethyl)benzo[d]isoxazol-3-yl]amine (1.75 g, 0.0049 mol), diboron pinacol ester (1.49 g, 0.0059 mol), [1.1'-bis(diphenylphosphino) ferrocene]-dichloropalladium (II) complex with dichloromethane (1:1) (0.120 g, 0.000147 mol) and potassium acetate (1.44 g, 0.0144 mol) in N,N-dimethylformamide (10 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:6) as mobile phase to yield N-[4-(4,4,5,5-tetramethyl-1,3,2-dioxaborolan-2-yl)phenyl]-N-[6-(trifluoromethyl)benzo[d]isoxazol-3-yl]amine (0.065 g, 0.000161 mol) as a white solid. $^1$H NMR (DMSO-$d_6$, 400 MHz), 9.97 (s, 1H), 8.39 (d, 1H), 8.14 (s, 1H), 7.77 (d, 1H), 7.71 (s, 4H), 1.29 (s, 12H).

F. Trans-N-3-(4-{4-amino-1-[4-(4-methylpiperazino)cyclohexyl]-1H-pyrazolo[3,4-d]pyrimidin-3-yl}phenyl)-6-(trifluoromethyl)benzo[d]isoxazol-3-amine acetate A mixture of N-[4-(4,4,5,5-tetramethyl-1,3,2-dioxaborolan-2-yl)phenyl]-N-[6-(trifluoromethyl)benzo[d]isoxazol-3-yl]amine (0.062 g, 0.000153 mol), trans-3-iodo-1-[4-(4-methylpiperazino)-cyclohexyl]-1H-pyrazolo[3,4-d]pyrimidin-4-amine (0.065 g, 0.000146 mol), tetrakis-(triphenylphosphine)palladium (0.010 g, 0.0000087 mol) and sodium carbonate (0.039 g, 0.000365 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10-70% acetonitrile—0.1M ammonium acetate over 30 min, 21 mL/min) to yield trans-N-3-(4-{4-amino-1-[4-(4-methylpiperazino)cyclohexyl]-1H-pyrazolo[3,4-d]pyrimidin-3-yl}phenyl)-6-(trifluoromethyl)benzo[d]isoxazol-3-amine acetate (0.026 g, 0.0000398 mol) as a white solid. $^1$H NMR (DMSO-$d_6$, 400 MHz) δ 10.05 (s, 1H), 8.44 (d, 1H), 8.23 (s, 1H), 8.16 (s, 1H), 7.88 (d, 2H), 7.79 (d, 1H), 7.69 (d, 2H), 4.67 (m, 1H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 16.18 min. MS: MH$^+$ 592.

Example 104

N2-(4-{4-amino-1-[1-(2-methoxyethyl)-4-piperidyl]-1H-pyrazolo[3,4-d]pyrimidin-3-yl}phenyl)-5,7-dimethyl-1,3-benzoxazol-2-amine

A. 3-iodo-1-[1-(2-methoxyethyl)-4-piperidyl]-1H-pyrazolo[3,4-d]pyrimidin-4-amine To a mixture of 3-iodo-1-(4-piperidyl)-1H-pyrazolo[3,4-d]pyrimidin-4-amine dihydrochloride (0.4 g, 0.00096 mol) and potassium carbonate (0.40 g, 0.0029 mol) in N,N-dimethylformamide (25 mL) was added 2-bromoethyl methyl ether (0.09 mL, 0.00096 mol) at room temperature. The heterogeneous mixture was stirred at 60° C. under an atmosphere of nitrogen for 7 hours. The reaction mixture was cooled to room temperature, and 2-bromoethyl methyl ether (0.045 mL, 0.00048 mol) was added. The mixture was stirred at 60° C. under an atmosphere of nitrogen for 16 hours. To the mixture to the room temperature, 2-bromoethyl methyl ether (0.019 mL, 0.00019 mol) and potassium iodide (0.008 g, 0.000048 mol) were added in order to complete the reaction. The mixture was stirred at 70° C. under an atmosphere of nitrogen for 7 hours. The solvent was removed under the reduced pressure. The residue was partitioned between water and dichloromethane. The aqueous layer was extracted with dichloromethane (4×50 mL). The combined organic extracts were washed with water, and brine, and dried over magnesium sulfate. The solvents were evaporated under the reduced pressure. The residue was purified by RP-HPLC (Hypersilprep HS C18, 8 μm, 250×21.1 mm; 5%-50% over 30 min with 0.1 M ammonium acetate, 21 mL/min) to yield 3-iodo-1-[1-(2-methoxyethyl)-4-piperidyl]-1H-pyrazolo[3,4-d]pyrimidin-4-amine (0.2 g, 0.0005 mol). RP-HPLC (Delta Pak C18, 5 μm, 300A, 15 cm; 5%-95% acetonitrile—0.1M ammonium acetate over 10 min, 1 mL/min) $R_t$ 6.4 min. MS: MH$^+$ 403

B. N2-(4-{4-amino-1-[1-(2-methoxyethyl)-4-piperidyl]-1H-pyrazolo[3,4-d]pyrimidin-3-yl}phenyl)-5,7-dimethyl-1,3-benzoxazol-2-amine A mixture of 3-iodo-1-[1-(2-methoxyethyl)-4-piperidyl]-1H-pyrazolo[3,4-d]pyrimidin-4-amine (0.2 g, 0.0005 mol), N-(5,7-dimethyl-1,3-benzoxazol-2-yl)-N-[4-(4,4,5,5-tetramethyl-1,3,2-dioxaborolan-2-yl)phenyl]amine (0.28 g, 0.00078 mol), tetrakis(triphenylphosphine)palladium (0.029 g, 0.000025 mol) and sodium carbonate (0.13 g, 0.00125 mol) in ethylene glycol dimethyl ether (25 mL) and water (5 mL) was heated at 80° C. for 5 hours under an atmosphere of nitrogen. Additional N-(5,7-dimethyl-1,3-benzoxazol-2-yl)-N-[4-(4,4,5,5-tetramethyl-1,3,2-dioxaborolan-2-yl)phenyl]amine (0.14 g, 0.00039 mol.) and tetrakis(triphenylphosphine)-palladium (0.015 g, 0.0000125 mol) were added, and the mixture was stirred at 80° C. for 16 hours. The mixture was allowed to cool to ambient temperature, and the solvent was removed under the reduced pressure. The residue was partitioned between water and dichloromethane. The aqueous layer was extracted with dichloromethane (2×50 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 5%-20% methanol/dichloromethane as a mobile phase to give N2-(4-{4-amino-1-[1-(2-methoxyethyl)-4-piperidyl]-1H-pyrazolo[3,4-d]pyrimidin-3-yl}phenyl)-5,7-dimethyl-1,3-benzoxazol-2-amine (0.14 g, 0.00027 mol). $^1$H NMR (TFA-d, 400 MHz) δ 8.53 (s, 1H), 7.88 (m, 2H), 7.81 (m, 2H), 7.14 (s, 2H), 5.40 (br, 1H), 4.05 (m, 2H), 3.98 (m, 2H), 3.66 (m, 2H), 3.56 (s, 3H), 3.47 (m, 2H), 2.96 (m, 2H), 2.54 (br, 2H), 2.50 (s, 3H), 2.43 (s, 3H). RP-HPLC (Delta Pak C18, 5 μm, 300A, 15 cm; 5%-95% acetonitrile—0.1M ammonium acetate over 10 min, 1 mL/min) $R_t$ 9.6 min. MS: MH$^+$ 513

Example 105

N2-{4-[4-amino-1-(1-methyl-4-piperidyl)-1H-pyrazolo[3,4-d]pyrimidin-3-yl]phenyl}-5,7-dimethyl-1,3-benzoxazol-2-amine A. 3-iodo-1-(1-methyl-4-piperidyl)-1H-pyrazolo[3,4-d]pyrimidin-4-amine To a mixture of 3-iodo-1-(4-piperidyl)-1H-pyrazolo[3,4-d]pyrimidin-4-amine dihydrochloride (0.5 g, 0.0012 mol) and sodium triacetoxyborohydride (0.36 g, 0.00168 mol) in dichloroethane (40 mL) was added formaldehyde solution (37% in water, 0.037 mL, 0.00132 mol) at room temperature. The mixture was stirred at room temperature under an atmosphere of nitrogen for 4 hours. A 5 N aqueous solution of sodium hydroxide (2 mL) was added to the mixture. The solvent was removed under the reduced pressure. The residue was partitioned between water and dichloromethane. The aqueous layer was extracted with dichloromethane (3×150 mL). The combined organic extracts were washed with water, and brine, and dried over magnesium sulfate. The solvents were evaporated under the reduced pressure to leave solid. The solid was resubjected to the same reaction and work-up conditions as above to yield 3-iodo-1-(1-methyl-4-piperidyl)-1H-pyrazolo[3,4-d]pyrimidin-4-amine (0.3 g, 0.00084 mol). TLC (methanol/dichloromethane=10:90) $R_f$ 0.63 MS: MH$^+$ 359

B. N2-{4-[4-amino-1-(1-methyl-4-piperidyl)-1H-pyrazolo[3,4-d]pyrimidin-3-yl]phenyl}-5,7-dimethyl-1,3-benzoxazol-2-amine A mixture of 3-iodo-1-(1-methyl-4-piperidyl)-1H-pyrazolo[3,4-d]pyrimidin-4-amine (0.2 g, 0.00056 mol), N-(5,7-dimethyl-1,3-benzoxazol-2-yl)-N-[4-(4,4,5,5-tetramethyl-1,3,2-dioxaborolan-2-yl)phenyl]amine (0.2 g, 0.00056 mol), tetrakis(triphenylphosphine)-palladium (0.032 g, 0.000028 mol) and sodium carbonate (0.15 g, 0.0014 mol) in ethylene glycol dimethyl ether (20 mL) and water (5 mL) was heated at 80° C. for 3 hours under an atmosphere of nitrogen. Additional N-(5,7-dimethyl-1,3-benzoxazol-2-yl)-N-[4-(4,4,5,5-tetramethyl-1,3,2-dioxaborolan-2-yl)phenyl]amine (0.2 g, 0.00056 mol) and tetrakis(triphenylphosphine)palladium (0.032 g, 0.000028 mol) were added, and the mixture was stirred at 80° C. for 16 hours. The mixture was allowed to cool to ambient temperature, and the solvent was removed under the reduced pressure. The residue was partitioned between water and dichloromethane. The aqueous layer was extracted with dichloromethane (2×50 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 5%-25% methanol/dichloromethane as a mobile phase to give N2-{4-[4-amino-1-(1-methyl-4-piperidyl)-1H-pyrazolo[3,4-d]pyrimidin-3-yl]phenyl}-5,7-dimethyl-1,3-benzoxazol-2-amine (0.16 g, 0.00034 mol). $^1$H NMR (TFA-d, 400 MHz) δ 8.50 (s, 1H), 7.85 (m, 2H), 7.80 (m, 2H), 7.10 (s, 2H), 5.45 (br, 1H), 3.95 (br, 2H), 3.75 (br, 1H), 3.45 (br, 1H), 3.10 (s, 3H), 2.85 (br, 1H), 2.65 (br, 1H), 2.49 (br, 2H), 2.40 (s, 3H), 2.42 (s, 3H). RP-HPLC (Delta Pak C18, 5 μm, 300A, 15 cm; 5%-85% acetonitrile—0.1M ammonium acetate over 20 min, 1 mL/min) Rt 10.7 min. MS: MH$^+$ 469

Example 106

N2-{4-[4-amino-1-(1-methyl-3-piperidyl)-1H-pyrazolo[3,4-d]pyrimidin-3-yl]phenyl}-5,7-dimethyl-1,3-benzoxazol-2-amine A. 3-Iodo-1-(3-piperidyl)-1H-pyrazolo[3,4-d]pyrimidin-4-ylamine Diethyl azodicarboxylate (12 mL, 0.08 mol) was added to a stirred suspension of 3-iodo-1H-pyrazolo[3,4-d]pyrimidin-4-amine (10.44 g, 0.04 mol), tert-butyl 3-hydroxy-1-piperidinecarboxylate (12.0 g, 0.0596 mol), and triphenylphosphine (20.98 g, 0.08 mol) in tetrahydrofuran (600 mL) at room temperature. After 19 h, additional diethyl azodicarboxylate (12 mL, 0.08 mol) was added and the reaction was continued for a further 2 h. Additional tert-butyl 3-hydroxy-1-piperidinecarboxylate (2.0 g) and triphenylphosphine (20.98 g, 0.08 mol) were added and the reaction continued for a further 72 h.

The reaction was concentrated in vacuo, acetone (200 mL) and an aqueous 5N solution of hydrogen chloride (100 mL) were added and the solution was heated at 40° C. for 2 h. The acetone was removed under reduced pressure and the aqueous layer was washed with dichloromethane (3×200 mL). The aqueous layer was then basified to pH 11 with aqueous solution of sodium hydroxide (1 N) and the product was extracted into dichloromethane (3×200 mL). The combined organic layers were dried over anhydrous sodium sulfate and concentrated to afford an orange solid. The solid was triturated with ethyl acetate to afford 3-iodo-1-(3-piperidyl)-1H-pyrazolo[3,4-d]pyrimidin-4-ylamine as a yellow solid (3.82 g, 25%); RP-HPLC Rt 4.792 min, 92% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column);

$^1$H NMR (400 MHz, d$_6$-DMSO) 1.54 (1H, m), 1.71 (1H, m), 2.01 (2H, m), 2.46 (1H, m), 2.81 (2H, m), 3.01 (1H, dd, J 11.8 and 3.4 Hz), 4.58 (1H, m), and 8.19 (1H, s).

B. 3-iodo-1-(1-methyl-3-piperidyl)-1H-pyrazolo[3,4-d]pyrimidin-4-amine

To a mixture of 3-iodo-1-(3-piperidyl)-1H-pyrazolo[3,4-d]pyrimidin-4-amine (0.4 g, 0.00116 mol) and sodium triacetoxyborohydride (0.34 g, 0.00162 mol) in dichloroethane (30 mL) was added formaldehyde solution (37% in water, 0.035 mL, 0.00128 mol, 1.1 eq.) at room temperature. The mixture was stirred at room temperature under an atmosphere of nitrogen for 18 hours. Additional formaldehyde solution (37% in water, 0.035 mL, 0.00128 mol, 1.1 eq.) was added, and the mixture was stirred at room temperature for 2 hours. A 5 N aqueous solution of sodium hydroxide (5 mL) was added to the mixture. The solvent was removed under the reduced pressure. The residue was partitioned between water and dichloromethane. The aqueous layer was extracted with dichloromethane (3×150 mL). The combined organic extracts were washed with water, and brine, and dried over magnesium sulfate. The solvents were evaporated under the reduced pressure, and the mixture was lyophilized to yield 3-iodo-1-(1-methyl-3-piperidyl)-1H-pyrazolo[3,4-d]pyrimidin-4-amine (0.41 g, 0.0011 mol). RP-HPLC (Delta Pak C18, 5 μm, 300A, 15 cm; 5%-95% acetonitrile—0.1M ammonium acetate over 10 min, 1 mL/min) Rt 6.0 min. MS: MH$^+$ 359

C. N2-{4-[4-amino-1-(1-methyl-3-piperidyl)-1H-pyrazolo[3,4-d]pyrimidin-3-yl]phenyl}-5,7-dimethyl-1,3-benzoxazol-2-amine A mixture of 3-iodo-1-(1-methyl-3-piperidyl)-1H-pyrazolo [3,4-d]pyrimidin-4-amine (0.35 g, 0.001 mol), N-(5,7-dimethyl-1,3-benzoxazol-2-yl)-N-[4-(4,4,5,5-tetramethyl-1,3,2-dioxaborolan-2-yl)phenyl]amine (0.44 g, 0.0012 mol), tetrakis(triphenylphosphine)-palladium (0.058 g, 0.00005 mol) and sodium carbonate (0.27 g, 0.0025 mol) in ethylene glycol dimethyl ether (30 mL) and water (6 mL) was heated at 80° C. for 16 hours under an atmosphere of nitrogen. The mixture was allowed to cool to ambient temperature, and the solvent was removed under the reduced pressure. The residue was partitioned between water and dichloromethane. The aqueous layer was extracted with dichloromethane (2×50 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 2%-10% methanol/dichloromethane as a mobile phase to give N2-{4-[4-amino-1-(1-methyl-3-piperidyl)-1H-pyrazolo[3,4-d]pyrimidin-3-yl]phenyl}-5,7-dimethyl-1,3-benzoxazol-2-amine (0.055 g, 0.00012 mol). $^1$H NMR (DMSO-d$_6$, 400 MHz) δ 10.80 (s, 1H), 8.22 (s, 1H), 7.95 (d, 2H), 7.65 (d, 2H), 7.15 (s, 1H), 6.80 (s, 1H), 4.80 (br, 1H), 2.95 (br, 1H), 2.85 (br, 1H), 2.45 (br, 1H), 2.40 (s, 3H), 2.35 (s, 3H), 2.25 (s, 3H), 2.00 (br, 3H), 1.80 (br, 1H), 1.70 (br, 1H). RP-HPLC (Delta Pak C18, 5 μm, 300A, 15 cm; 5%-95% acetonitrile—0.1M ammonium acetate over 10 min, 1 mL/min) Rt 9.7 min. MS: MH$^+$ 469

Example 107

N2-(4-{4-amino-1-[1-(2-methoxyethyl)-3-piperidyl]-1H-pyrazolo[3,4-d]pyrimidin-3-yl}phenyl)-5,7-dimethyl-1,3-benzoxazol-2-amine

A. 3-iodo-1-[1-(2-methoxyethyl)-3-piperidyl]-1H-pyrazolo[3,4-d]pyrimidin-4-amine To a mixture of 3-iodo-1-(3-piperidyl)-1H-pyrazolo[3,4-d]pyrimidin-4-amine (0.4 g, 0.00116 mol) and potassium carbonate (0.48 g, 0.00348 mol) in N,N-dimethylformamide (25 mL) were added 2-bromoethyl methyl ether (0.11 mL, 0.00116 mol) and potassium iodide (0.010 g, 0.000058 mol) at room temperature. The mixture was stirred at 65° C. under an atmosphere of nitrogen for 16 hours. The reaction mixture was cooled to room temperature, and additional 2-bromoethyl methyl ether (0.025 mL, 0.00027 mol) was added. The mixture was stirred at 65° C. under an atmosphere of nitrogen for 16 hours. The solvent was removed under the reduced pressure. The residue was partitioned between water and dichloromethane. The aqueous layer was extracted with dichloromethane (4×50 mL). The combined organic extracts were washed with water, and brine, and dried over magnesium sulfate. The solvents were evaporated under the reduced pressure. The residue was purified by RP-HPLC (Hypersilprep HS C18, 8 μm, 250×21.1 mm; 5%-50% over 30 min with 0.1 M ammonium acetate, 21 mL/min) to 3-iodo-1-[1-(2-methoxyethyl)-3-piperidyl]-1H-pyrazolo[3,4-d]pyrimidin-4-amine (0.2 g, 0.0005 mol). TLC (methanol/dichloromethane=10:90) R$_f$ 0.5 MS: MH$^+$ 403

B. N2-(4-{4-amino-1-[1-(2-methoxyethyl)-3-piperidyl]-1H-pyrazolo[3,4-d]pyrimidin-3-yl}phenyl)-5,7-dimethyl-1,3-benzoxazol-2-amine The mixture of 3-iodo-1-[1-(2-methoxyethyl)-3-piperidyl]-1H-pyrazolo[3,4-d]pyrimidin-4-amine (0.16 g, 0.0004 mol), N-(5,7-dimethyl-1,3-benzoxazol-2-yl)-N-[4-(4,4,5,5-tetramethyl-1,3,2-dioxaborolan-2-yl)phenyl]amine (0.17 g, 0.00048 mol), tetrakis(triphenylphosphine)palladium (0.023 g, 0.00002 mol) and sodium carbonate (0.11 g, 0.001 mol) in ethylene glycol dimethyl ether (25 mL) and water (5 mL) was heated at 80° C. for 16 hours under an atmosphere of nitrogen. The mixture was allowed to cool to ambient temperature, and the solvent was removed under the reduced pressure. The residue was partitioned between water and dichloromethane. The aqueous layer was extracted with dichloromethane (3×50 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 2%-10% methanol/dichloromethane as a mobile phase to give N2-(4-{4-amino-1-[1-(2-methoxyethyl)-3-piperidyl]-1H-pyrazolo[3,4-d]pyrimidin-3-yl}phenyl)-5,7-dimethyl-1,3-benzoxazol-2-amine (0.17 g, 0.00033 mol). $^1$H NMR (DMSO-d$_6$, 400 MHz) δ 10.85 (s, 1H), 8.22 (s, 1H), 7.95 (d, 2H), 7.65 (d, 2H), 7.14 (s, 1H), 6.80 (s, 1H), 4.79 (br, 1H), 3.50 (m, 2H), 3.25 (s, 3H), 3.10 (br, 1H), 2.90 (br, 1H), 2.55 (br, 2H), 2.54(br, 1H), 2.40 (s, 3H), 2.35 (s, 3H), 2.05 (br, 3H), 1.80 (br, 1H), 1.70 (br, 1H). RP-HPLC (Delta Pak C18, 5 µm, 300A, 15 cm; 5%-95% acetonitrile—0.1M ammonium acetate over 10 min, 1 mL/min) Rt 9.9 min. MS: MH⁺ 513

Example 108

N2-{4-[4-amino-1-(3-piperidyl)-1H-pyrazolo[3,4-d]pyrimidin-3-yl]phenyl}-5,7-dimethyl-1,3-benzoxazol-2-amine acetate A. tert-Butyl 3-(4-amino-3-iodo-1H-pyrazolo[3,4-d]pyrimidin-1-yl)-1-piperidinecarboxylate Di-tert-butyl dicarbonate (2.093 g, 0.00959 mol) was added to a solution of 3-iodo-1-(3-piperidyl)-1H-pyrazolo[3,4-d]pyrimidin-4-ylamine (3.00 g, 0.00872 mol) and sodium carbonate (3.23 g, 0.0305 mol) in 1,4-dioxane (50 mL) and water (50 mL). The mixture was stirred at room temperature for 2 h and the resulting white precipitate was collected by filtration. The solid was washed with water (10 mL) and dried in air to afford tert-butyl 3-(4-amino-3-iodo-1H-pyrazolo[3,4-d]pyrimidin-1-yl)-1-piperidinecarboxylate as a white solid (3.40 g, 88%); RP-HPLC Rt 12.532 min, 98% purity (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column);

$^1$H NMR (400 MHz, d$_6$-DMSO) 1.34 (9H, br s), 1.50 (2H, m), 2.02 (1H, m), 2.13 (1H, m), 2.97 (2H, m), 3.85 (2H, m), 4.59 (1H, m), and 8.21 (1H, s).

B. tert-Butyl 3-(4-amino-3-{4-[(5,7-dimethyl-1,3-benzoxazol-2-yl)amino]phenyl}-1H-pyrazolo[3,4-d]pyrimidin-1-yl)-1-piperidinecarboxylate The mixture of tert-butyl 3-(4-amino-3-iodo-1H-pyrazolo[3,4-d]pyrimidin-1-yl)-1-piperidinecarboxylate (0.6 g, 0.00135 mol), N-(5,7-dimethyl-1,3-benzoxazol-2-yl)-N-[4-(4,4,5,5-tetramethyl-1,3,2-dioxaborolan-2-yl)phenyl]amine (0.59 g, 0.00162 mol), tetrakis(triphenylphosphine)palladium (0.078 g, 0.000068 mol) and sodium carbonate (0.36 g, 0.00338 mol) in ethylene glycol dimethyl ether (50 mL) and water (10 mL) was heated at 80° C. for 16 hours under an atmosphere of nitrogen. After cooled the mixture to the room temperature, more N-(5,7-dimethyl-1,3-benzoxazol-2-yl)-N-[4-(4,4,5,5-tetramethyl-1,3,2-dioxaborolan-2-yl)phenyl]amine (0.24 g, 0.00066 mol), tetrakis(triphenylphosphine)palladium (0.078 g, 0.000068 mol) were added, and the mixture was stirred at 80° C. for 5 hours. The mixture was allowed to cool to ambient temperature, and the solvent was removed under the reduced pressure. The residue was partitioned between water and dichloromethane. The aqueous layer was extracted with dichloromethane (3×50 mL). The combined organic extracts were washed with water, saturated aqueous sodium bicarbonate solution, and brine, and dried over magnesium sulfate. The solvents were evaporated under the reduced pressure to leave a brownish oil which was purified by flash column chromatography on silica using 5%-25% isopropanol/dichloromethane as a mobile phase, and the product was triturated with N,N-dimethylformamide to give tert-butyl 3-(4-amino-3-{4-[(5,7-dimethyl-1,3-benzoxazol-2-yl)amino]phenyl}-1H-pyrazolo[3,4-d]pyrimidin-1-yl)-1-piperidinecarboxylate (0.28 g, 0.00051 mol). RP-HPLC (Delta Pak C18, 5 µm, 300A, 15 cm; 5%-95% acetonitrile—0.1M ammonium acetate over 10 min, 1 mL/min) Rt 11.9 min.
MS: MH⁺ 555

C. N2-{4-[4-amino-1-(3-piperidyl)-1H-pyrazolo[3,4-d]pyrimidin-3-yl]phenyl}-5,7-dimethyl-1,3-benzoxazol-2-amine acetate To a mixture of tert-butyl 3-(4-amino-3-{4-[(5,7-dimethyl-1,3-benzoxazol-2-yl)amino]phenyl}-1H-pyrazolo[3,4-d]pyrimidin-1-yl)-1-piperidinecarboxylate (0.28 g, 0.00051 mol) in acetone (10 mL) was added an 6N aqueous solution of hydrogen chloride (3 mL) at room temperature. The mixture was stirred at 45° C. for 1 hour. The solvent was removed, and the mixture was basified with an aqueous 5N sodium hydroxide solution. The aqueous layer was extracted with dichloromethane (3×80 mL). The solvent was removed under reduced pressure, and the residue was purified by RP-HPLC (Hypersilprep HS C18, 8 µm, 250×21.1 mm; 5%-100% over 20 min with 0.1 M ammonium acetate, 21 mL/min) to yield N2-{4-[4-amino-1-(3-piperidyl)-1H-pyrazolo[3,4-d]pyrimidin-3-yl]phenyl}-5,7-dimethyl-1,3-benzoxazol-2-amine acetate (0.06 g, 0.00012 mol). $^1$H NMR (DMSO-d$_6$, 400 MHz) δ 10.85 (s, 1H), 8.22 (s, 1H), 7.95 (d, 2H), 7.65 (d, 2H), 7.05 (s, 1H), 6.80 (s, 1H), 4.75 (br, 1H), 3.15 (br, 2H), 2.95 (m, 2H), 2.40 (s, 3H), 2.35 (s, 3H), 2.05 (br, 1H), 2.00 (br, 1H), 1.90 (s, 3H), 1.80 (br, 1H), 1.60 (br, 1H). RP-HPLC (Delta Pak C18, 5 µm, 300A, 15 cm; 5%-95% acetonitrile—0.1M ammonium acetate over 10 min, 1 mL/min) Rt 9.4 min.
MS: MH⁺ 455

Example 109

1-[3-(4-amino-3-{4-[(5,7-dimethyl-1,3-benzoxazol-2-yl)amino]phenyl}-1H-pyrazolo[3,4-d]pyrimidin-1-yl)piperidino]-2-(dimethylamino)-1-ethanone acetate A mixture of N2-{4-[4-amino-1-(3-piperidyl)-1H-pyrazolo[3,4-d]pyrimidin-3-yl]phenyl}-5,7-dimethyl-1,3-benzoxazol-2-amine acetate (0.04 g, 0.000078 mol), dimethylglycine (0.01 g, 0.000097 mol), 1-(3-dimethylaminopropyl)-3-ethylcarbodiimide hydrochloride (0.019 g, 0.000097 mol), N,N-diisopropylethylamine (0.033 g, 0.00026 mol) and 1-hydroxy-7-azabenzotriazole (0.011 g, 0.000078 mol) in anhydrous dichloromethane (5 mL) was stirred for 18 hours at room temperature. The solvent was removed under reduced pressure. The residue was partitioned between water and dichloromethane. The aqueous layer was extracted with dichloromethane, and the combined organic solvent was washed with brine. The solvent was removed under reduced pressure, and the residue was purified by RP-HPLC (Hypersilprep HS C18, 8 µm, 250×21.1 mm; 5%-100% over 35 min with 0.1 M ammonium acetate, 21 mL/min) to yield 1-[3-(4-amino-3-{4-[(5,7-dimethyl-1,3-benzoxazol-2-yl)amino]phenyl}-1H-pyrazolo[3,4-d]pyrimidin-1-yl)piperidino]-2-(dimethylamino)-1-ethanone acetate (0.015 g, 0.00003 mol). $^1$H NMR (DMSO-d$_6$, 400 MHz) δ 10.85 (s, 1H), 8.27 (d, 1H), 7.94 (d, 2H), 7.67 (d, 2H), 7.11 (s, 1H), 6.51 (s, 1H), 4.81-1.91 (br, 11H), 2.40 (s, 3H), 2.34 (s, 3H), 2.26 (s, 3H), 2.22 (s, 3H), 1.91 (s, 3H). RP-HPLC (Delta Pak C18, 5 µm, 300A, 15 cm; 5%-85% acetonitrile—0.1M ammonium acetate over 10 min, 1 mL/min) Rt 9.7 min.
MS: MH⁺ 540

Example 110

1-[3-(4-amino-3-{4-[(5,7-dimethyl-1,3-benzoxazol-2-yl)amino]phenyl}-1H-pyrazolo[3,4-d]pyrimidin-1-yl)piperidino]-2-methyl-2-(methylamino)-1-propanone

A. 3-iodo-1-(3-piperidyl)-1H-pyrazolo[3,4-d]pyrimidin-4-amine dihydrochloride To a mixture of tert-butyl 3-(4-amino-3-iodo-1H-pyrazolo[3,4-d]pyrimidin-1-yl)-1-piperidinecarboxylate (1.2 g, 0.0027 mol) in acetone (20 mL) was added an aqueous 6N solution of hydrogen chloride (8 mL) at room temperature. The mixture was stirred at 45° C. for 1.5 hours, and then room temperature for 16 hours. The precipitate was filtered and washed with acetone. The solid was dried to give 3-iodo-1-(3-piperidyl)-1H-pyrazolo[3,4-d]pyrimidin-4-amine dihydrochloride (1 g, 0.0024 mol). TLC (methanol/dichloromethane=5:95) $R_f$ 0.14 MS: MH$^+$ 345

B. 9H-9-fluorenylmethyl N-{2-[3-(4-amino-3-iodo-1H-pyrazolo[3,4-d]pyrimidin-1-yl)piperidino]-1,1-dimethyl-2-oxoethyl}-N-methylcarbamate A mixture of 3-iodo-1-(3-piperidyl)-1H-pyrazolo[3,4-d]pyrimidin-4-amine dihydrochloride (0.17 g, 0.00042 mol), 2-[[(9H-9-fluorenylmethoxy)carbonyl]-(methyl)amino]-2-methylpropanoic acid (0.175 g, 0.00052 mol), 1-(3-dimethylaminopropyl)-3-ethylcarbodiimide hydrochloride (0.1 g, 0.00052 mol), N,N-diisopropylethylamine (0.23 g, 0.0018 mol) and 1-hydroxy-7-azabenzotriazole (0.057 g, 0.00042 mol) in anhydrous dichloromethane (7 mL) was stirred for 18 hours at room temperature. Additional 2-[[(9H-9-fluorenylmethoxy)carbonyl](methyl)amino]-2-methylpropanoic acid (0.044 g, 0.00013 mol) and 1-(3-dimethylaminopropyl)-3-ethylcarbodiimide hydrochloride (0.025 g, 0.00013 mol) were added to the reaction and stirred for 16 hours. The solvent was removed under reduced pressure. The residue was partitioned between brine and ethyl acetate. The aqueous layer was extracted with ethyl acetate, and the combined organic solvent was removed under reduced pressure, and the residue was purified by RP-HPLC (Hypersilprep HS C18, 8 μm, 250×21.1 mm; 5%-100% over 20 min with 0.1 M ammonium acetate, 21 mL/min) to yield 9H-9-fluorenylmethyl N-{2-[3-(4-amino-3-iodo-1H-pyrazolo[3,4-d]pyrimidin-1-yl)piperidino]-1,1-dimethyl-2-oxoethyl}-N-methylcarbamate (0.030 g, 0.00005 mol). RP-HPLC (Delta Pak C18, 5 μm, 300A, 15 cm; 5%-85% acetonitrile—0.1M ammonium acetate over 10 min, 1 mL/min) Rt 11.2 min. MS: MH$^+$ 666

C. 9H-9-fluorenylmethyl N-2-[3-(4-amino-3-{4-[(5,7-dimethyl-1,3-benzoxazol-2-yl)amino]phenyl}-1H-pyrazolo[3,4-d]pyrimidin-1-yl)piperidino]-1,1-dimethyl-2-oxoethyl-N-methylcarbamate A mixture of 9H-9-fluorenylmethyl N-{2-[3-(4-amino-3-iodo-1H-pyrazolo[3,4-d]pyrimidin-1-yl)piperidino]-1,1-dimethyl-2-oxoethyl}-N-methylcarbamate (0.03 g, 0.000045 mol), N-(5,7-dimethyl-1,3-benzoxazol-2-yl)-N-[4-(4,4,5,5-tetramethyl-1,3,2-dioxaborolan-2-yl)phenyl]amine (0.02 g, 0.000054 mol), tetrakis(triphenylphosphine)-palladium (0.003 g, 0.000002 mol) and sodium carbonate (0.0126 g, 0.0001 mol) in ethylene glycol dimethyl ether (4 mL) and water (1 mL) was heated at 80° C. for 16 hours under an atmosphere of nitrogen. The mixture was allowed to cool to ambient temperature, and the solvent was removed under the reduced pressure. The residue was partitioned between water and ethyl acetate. The aqueous layer was extracted with ethyl acetate (3×30 mL). The combined organic extracts were washed with water, saturated aqueous sodium bicarbonate solution, and brine, and dried over magnesium sulfate. The solvents were evaporated under the reduced pressure to leave a brownish solid, which was carried to the next reaction. RP-HPLC (Delta Pak C18, 5 μm, 300A, 15 cm; 5%-85% acetonitrile—0.1M ammonium acetate over 10 min, 1 mL/min) Rt 10.4 min.

TLC (methanol/dichloromethane=5:95) $R_f$ 0.80

D. 1-[3-(4-amino-3-{4-[(5,7-dimethyl-1,3-benzoxazol-2-yl)amino]phenyl}-1H-pyrazolo[3,4-d]pyrimidin-1-yl)piperidino]-2-methyl-2-(methylamino)-1-propanone A crude mixture of 9H-9-fluorenylmethyl N-2-[3-(4-amino-3-{4-[(5,7-dimethyl-1,3-benzoxazol-2-yl)amino]phenyl}-1H-pyrazolo[3,4-d]pyrimidin-1-yl)piperidino]-1,1-dimethyl-2-oxoethyl-N-methylcarbamate (0.037 g, 0.00005 mol) in a 25% solution of piperidine in N,N-dimethylformamide (10 mL) was stirred for 16 hours at room temperature under an atmosphere of nitrogen. The solvent was removed, and the residue was partitioned between ethyl acetate and water. The combined organic layer was washed with brine and dried over magnesium sulfate. The solvent was removed, and the residue was purified by RP-HPLC (Hypersilprep HS C18, 8 μm, 250×21.1 mm; 5%-100% over 30 min with 0.1 M ammonium acetate, 21 mL/min) to yield 1-[3-(4-amino-3-{4-[(5,7-dimethyl-1,3-benzoxazol-2-yl)amino]phenyl}-1-H-pyrazolo[3,4-d]pyrimidin-1-yl)piperidino]-2-methyl-2-(methylamino)-1-propanone (0.011 g, 0.00002 mol). $^1$H NMR (Chloroform-d, 400 MHz) δ 8.35 (s, 1H), 7.75 (m, 2H), 7.40 (m, 2H), 7.10 (s, 1H), 6.78 (s, 1H), 4.98-1.70 (br, 9H), 2.49 (s, 3H), 2.48 (s, 3H), 2.40 (s, 3H), 2.10 (s, 6H). RP-HPLC (Delta Pak C18, 5 μm, 300A, 15 cm; 5%-85% acetonitrile—0.1M ammonium acetate over 10 min, 1 mL/min) Rt 10.0 min. MS: MH$^+$ 554

Example 111

N2-4-[4-amino-1-(3-azetanyl)-1H-pyrazolo[3,4-d]pyrimidin-3-yl]phenyl-5,7-dimethyl-1,3-benzoxazol-2-amine

A. tert-Butyl 3-(4-amino-3-iodo-1H-pyrazolo[3,4-d]pyrimidin-1-yl)-1-azetanecarboxylate A mixture of 3-iodo-1H-pyrazolo[3,4-d]pyrimidin-4-amine (0.73 g, 0.0028 mol), tert-butyl 3-[(methylsulfonyl)oxy]-1-azetanecarboxylate (1.05 g, 0.0042 mol) and cesium carbonate (1.4 g, 0.0042 mol) in N,N-dimethylformamide (25 mL) were stirred at 70° C. under an atmosphere of nitrogen for 16 hours. The mixture was cooled to room temperature. Additional tert-butyl 3-[(methylsulfonyl)oxy]-1-azetanecarboxylate (0.35 g, 0.0014 mol) and cesium carbonate (0.46 g, 0.0014 mol) were added to the mixture. The mixture was stirred at 70° C. under an atmosphere of nitrogen for 16 hours. The solvent was removed under the reduced pressure. The residue was partitioned between water and ethyl acetate. The aqueous layer was extracted with dichloromethane (3×70 mL). The combined organic extracts were washed with water, and brine, and dried over magnesium sulfate. The solvents were evaporated under the reduced pressure. The residue was triturated with dichloromethane (2×3 mL) to give tert-butyl 3-(4-amino-3-iodo-1H-pyrazolo[3,4-d]pyrimidin-1-yl)-1-azetanecarboxylate (0.57 g, 0.0014 mol). RP-HPLC (Delta Pak C18, 5 μm, 300A, 15 cm; 5%-95% acetonitrile—0.1M ammonium acetate over 10 min, 1 mL/min) Rt 9.4 min. MS: MH+ 417

B. tert-Butyl 3-(4-amino-3-{4-[(5,7-dimethyl-1,3-benzoxazol-2-yl)amino]phenyl}-1H-pyrazolo[3,4-d]pyrimidin-1-yl)-1-azetanecarboxylate A mixture of tert-butyl 3-(4-amino-3-iodo-1H-pyrazolo[3,4-d]pyrimidin-1-yl)-1-azetanecarboxylate (0.15 g, 0.00036 mol), N-(5,7-dimethyl-1,3-benzoxazol-2-yl)-N-[4-(4,4,5,5-tetramethyl-1,3,2-dioxaborolan-2-yl)phenyl]amine (0.16 g, 0.00045 mol), tetrakis(triphenylphosphine)palladium (0.021 g, 0.000018 mol) and sodium carbonate (0.095 g, 0.0009 mol) in ethylene glycol dimethyl ether (5 mL) and water (2 mL) was heated at 80° C. for 16 hours under an atmosphere of nitrogen. The reaction was cooled to room temperature. Additional tetrakis(triphenylphosphine)palladium (0.021 g, 0.000018 mol) was added to the mixture. The reaction was stirred at 80° C. for 3 hours. The mixture was allowed to cool to ambient temperature, and the solvent was removed under the reduced pressure. The residue was partitioned between water and dichloromethane. The aqueous layer was extracted with dichloromethane (3×50 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 5%-50% methanol/dichloromethane as a mobile phase to give tert-butyl 3-(4-amino-3-{4-[(5,7-dimethyl-1,3-benzoxazol-2-yl)amino]phenyl}-1H-pyrazolo[3,4-d]pyrimidin-1-yl)-1-azetanecarboxylate (0.033 g, 0.00006 mol). RP-HPLC (Delta Pak C18, 5 μm, 300A, 15 cm; 5%-95% acetonitrile—0.1M ammonium acetate over 10 min, 1 mL/min) Rt 11.6 min. MS: MH+ 527

C. N2-4-[4-amino-1-(3-azetanyl)-1H-pyrazolo[3,4-d]pyrimidin-3-yl]phenyl-5,7-dimethyl-1,3-benzoxazol-2-amine To a mixture of tert-butyl 3-(4-amino-3-{4-[(5,7-dimethyl-1,3-benzoxazol-2-yl)amino]phenyl}-1H-pyrazolo[3,4-d]pyrimidin-1-yl)-1-azetanecarboxylate (0.033 g, 0.000063 mol) in acetone (4 mL) was added an aqueous 6N solution of hydrogen chloride (0.3 mL) at room temperature. The mixture was stirred at 45° C. for 2 hour, and then at room temperature for 16 hours. The solid from the reaction was filtered and washed with acetone. In order to remove some impurities, the solid was partitioned between ethyl acetate and saturated aqueous sodium bicarbonate solution. The aqueous layer was extracted with ethyl acetate, and the organic layer was washed with brine. The solvent was removed to yield N2-4-[4-amino-1-(3-azetanyl)-1H-pyrazolo[3,4-d]pyrimidin-3-yl]phenyl-5,7-dimethyl-1,3-benzoxazol-2-amine (0.004 g, 0.00001 mol).

$^1$H NMR (DMSO-d$_6$, 400 MHz) δ 10.85 (s, 1H), 8.45 (s, 1H), 8.00 (d, 2H), 7.75(d, 2H), 7.09(s, 1H), 6.80(s, 1H), 5.90 (br, 1H), 5.20 (m, 4H), 2.40 (s, 3H), 2.20 (s, 3H). RP-HPLC (Delta Pak C18, 5 μm, 300A, 15 cm; 5%-95% acetonitrile—0.1M ammonium acetate over 10 min, 1 mL/min) Rt 9.1 min. MS: MH+ 427

Example 112

N2-{4-[4-amino-1-(1-methyl-3-azetanyl)-1H-pyrazolo[3,4-d]pyrimidin-3-yl]phenyl}-5,7-dimethyl-1,3-benzoxazol-2-amine A. 1-(3-azetanyl)-3-iodo-1H-pyrazolo[3,4-d]pyrimidin-4-amine diacetate A mixture of tert-butyl 3-(4-amino-3-iodo-1H-pyrazolo[3,4-d]pyrimidin-1-yl)-1-azetanecarboxylate (0.41 g, 0.00099 mol) in acetone (5 mL) was added an aqueous 6N solution of hydrogen chloride (1 mL) at room temperature. The mixture was stirred at 45° C. for 2 hour. The solvent was removed under reduced pressure, and the residue was basified with an aqueous 5N solution of sodium hydroxide at 0° C. The aqueous layer was extracted with dichloromethane (3×50 mL), and the organic layer was washed with brine and dried under magnesium sulfate. The solvent was removed under reduced pressure. The aqueous layer and the residue from organic layer were combined. The solvents were removed, and the residue was suspended in N,N-dimethylformamide, methanol, and acetic acid and purified by RP-HPLC (Hypersilprep HS C18, 8 μm, 250×21.1 mm; 5%-100% over 30 min with 0.1 M ammonium acetate, 21 mL/min) to 1-(3-azetanyl)-3-iodo-1H-pyrazolo[3,4-d]pyrimidin-4-amine diacetate (0.165 g, 0.0005 mol).

TLC (methanol/dichloromethane 5:95) R$_f$ 0.29. MS: MH+ 317

B. 3-iodo-1-(1-methyl-3-azetanyl)-1H-pyrazolo[3,4-d]pyrimidin-4-amine

To a mixture of to 1-(3-azetanyl)-3-iodo-1H-pyrazolo[3,4-d]pyrimidin-4-amine diacetate (0.165 g, 0.0005 mol) and sodium triacetoxyborohydride (0.15 g, 0.00073 mol) in dichloroethane (15 mL) was added a 37% solution of formaldehyde in 0.016 mL, 0.000572 mol) at room temperature. The mixture was stirred at room temperature under an atmosphere of nitrogen for 16 hours. Additonal formaldehyde (37% in water, 0.016 mL, 0.000572 mol) and sodium triacetoxyborohydride (0.15 g, 0.00073 mol) were added, and the mixture was stirred at room temperature for 2 days. An aqueous 5N solution of sodium hydroxide (1 mL) was added to the mixture. The solvent was removed under the reduced pressure. The residue was partitioned between water and ethyl acetate. The aqueous layer was extracted with ethyl acetate (2×50 mL). The combined organic extracts were washed with water, and brine, and dried over magnesium sulfate. The solvents were evaporated under the reduced pressure. Majority product was still in aqueous layer. The aqueous layer and the residue from organic layer were combined. The solvent was removed, and the residue was carried to the next step without purification. TLC (methanol/dichloromethane=10:90) R$_f$ 0.48 MS: MH+ 331

C. N2-{4-[4-amino-1-(1-methyl-3-azetanyl)-1H-pyrazolo[3,4-d]pyrimidin-3-yl]phenyl}-5,7-dimethyl-1,3-benzoxazol-2-amine A mixture of 3-iodo-1-(1-methyl-3-azetanyl)-1H-pyrazolo[3,4-d]pyrimidin-4-amine (0.17 g, 0.00052 mol), N-(5,7-dimethyl-1,3-benzoxazol-2-yl)-N-[4-(4,4,5,5-tetramethyl-1,3,2-dioxaborolan-2-yl)phenyl]amine (0.23 g, 0.000624 mol), tetrakis(triphenylphosphine)-palladium (0.030 g, 0.000026 mol) and sodium carbonate (0.14 g, 0.0013 mol) in ethylene glycol dimethyl ether (20 mL) and water (15 mL)

was heated at 80° C. for 16 hours under an atmosphere of nitrogen. The reaction was cooled to room temperature. The mixture was allowed to cool to ambient temperature, and the solvent was removed under the reduced pressure. The residue was partitioned between water and dichloromethane. The aqueous layer was extracted with dichloromethane (3×50 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 5%-50% methanol/dichloromethane as a mobile phase to give N2-{4-[4-amino-1-(1-methyl-3-azetanyl)-1H-pyrazolo[3,4-d]pyrimidin-3-yl]phenyl}-5,7-dimethyl-1,3-benzoxazol-2-amine (0.13 g, 0.0003 mol).

$^1$H NMR (DMSO-d$_6$, 400 MHz) δ 10.85 (s, 1H), 8.15 (s, 1H), 7.90(d, 2H), 7.70 (d, 2H), 7.09(s, 1H), 6.85(s, 1H), 5.40 (br, 1H), 3.90 (m, 2H), 3.70 (m, 2H), 2.40 (s, 3H), 2.39 (s, 3H), 2.30 (s, 3H). RP-HPLC (Delta Pak C18, 5 μm, 300A, 15 cm; 5%-95% acetonitrile—0.1M ammonium acetate over 10 min, 1 mL/min) Rt 9.5 min. MS: MH$^+$ 441

Example 113

Cis-2-(4-{4-amino-1-[4-(4-methylpiperazino)cyclohexyl]-1H-pyrazolo[3,4-d]pyrimidin-3-yl}anilino)-1,3-benzoxazole-5-carbonitrile A. 3-amino-4-hydroxybenzonitrile To a mixture of 4-hydroxy-3-nitrobenzonitrile (4 g, 0.0244 mol) in ethanol (180 mL) and water (90 mL) was added sodium thiosulfate (17 g, 0.0976 mol) at room temperature. The heterogeneous mixture was stirred at 80° C. under an atmosphere of nitrogen for 1 hour. The reaction mixture was cooled to room temperature, and ethanol was removed under reduced pressure. The yellow solid was filtered, washed with water, and dried under reduced pressure to yield 3-amino-4-hydroxybenzonitrile (1.46 g, 0.011 mol).

RP-HPLC (Delta Pak C18, 5 μm, 300A, 15 cm; 5%-95% acetonitrile—0.1M ammonium acetate over 10 min, 1 mL/min) Rt 4.5 min. MS: MH$^-$: 133

B. 2-(4-bromoanilino)-1,3-benzoxazole-5-carbonitrile

To a mixture of 3-amino-4-hydroxybenzonitrile (1.84 g, 0.0137 mol) in acetonitrile (140 mL) was added 4-bromophenyl isothiocyanate (2.93 g, 0.0137 mol) at room temperature. The mixture was stirred for 16 hours at room temperature. Cuprous chloride (1.36 g, 0.0137 mol) and triethylamine (1.9 mL, 0.0137 mol) were added to the reaction mixture. The mixture was stirred for 16 hours at room temperature. The solvent was removed under reduced pressure, and the solid was suspended in methanol. The mixture was filtered through celite pad using methanol. The brownish filtrate was left at 40 for three days. The precipitate was filtered and washed with methanol to yield 2-(4-bromoanilino)-1,3-benzoxazole-5-carbonitrile (2.4 g, 0.0076 mol). RP-HPLC (Delta Pak C18, 5 μm, 300A, 15 cm; 5%-95% acetonitrile—0.1M ammonium acetate over 10 min, 1 mL/min) Rt 11.1 min. MS: MH$^-$: 313

C. 2-[4-(4,4,5,5-tetramethyl-1,3,2-dioxaborolan-2-yl)anilino]-1,3-benzoxazole-5-carbonitrile A mixture of 2-(4-bromoanilino)-1,3-benzoxazole-5-carbonitrile (1.8 g, 0.0058 mol), diboron pinacol ester (1.8 g, 0.007 mol), [1.1'-bis(diphenylphosphino)ferrocene]-dichloropalladium (II) complex with dichloromethane (1:1) (0.47 g, 0.00058 mol) and potassium acetate (1.7 g, 0.0174 mol) in N,N-dimethylformamide (50 mL) was heated at 80° C. under an atmosphere of nitrogen for 16 hours. The mixture was allowed to cool to ambient temperature and the solvent removed under reduced pressure. The residue was purified by flash column chromatography on silica using 0%-40% ethyl acetate/n-heptane as a mobile phase to give 2-[4-(4,4,5,5-tetramethyl-1,3,2-dioxaborolan-2-yl)anilino]-1,3-benzoxazole-5-carbonitrile (0.80 g, 0.0022 mol). RP-HPLC (Delta Pak C18, 5 μm, 300A, 15 cm; 5%-95% acetonitrile—0.1M ammonium acetate over 20 min, 1 mL/min) Rt 16.9 min. MS: MH$^+$: 362

D. cis-2-(4-{4-amino-1-[4-(4-methylpiperazino)cyclohexyl]-1H-pyrazolo[3,4-d]pyrimidin-3-yl}anilino)-1,3-benzoxazole-5-carbonitrile A mixture of 3-iodo-1-[4-(4-methylpiperazino)cyclohexyl]-1H-pyrazolo[3,4-d]pyrimidin-4-amine (0.15 g, 0.00034 mol), 2-[4-(4,4,5,5-tetramethyl-1,3,2-dioxaborolan-2-yl)anilino]-1,3-benzoxazole-5-carbonitrile (0.153 g, 0.000425 mol), tetrakis(triphenylphosphine)palladium (0.028 g, 0.0000238 mol) and sodium carbonate (0.090 g, 0.00085 mol) in ethylene glycol dimethyl ether (3 mL) and water (1 mL) was heated at 80° C. for 16 hours. Additional 2-[4-(4,4,5,5-tetramethyl-1,3,2-dioxaborolan-2-yl)anilino]-1,3-benzoxazole-5-carbonitrile (0.072 g, 0.0002 mol), tetrakis(triphenylphosphine)palladium (0.012 g, 0.000010 mol, 0.03 eq.) were added, and the mixture was stirred at 80° C. for 16 hours under atmosphere of nitrogen. The mixture was allowed to cool to ambient temperature, and the solvent was removed under the reduced pressure. The residue was partitioned between water and ethyl acetate. The aqueous layer was extracted with ethyl acetate (2×50 mL). The combined organic extracts were washed with water, saturated aqueous sodium bicarbonate solution, and brine, and dried over magnesium sulfate. The solvents were evaporated under the reduced pressure, and the residue was purified by flash column chromatography on silica using 2% aqueous ammonium hydroxide solution/5%-20% methanol/dichloromethane as a mobile phase. The solvent was removed under reduced pressure, and the residue was purified by RP-HPLC (Hypersilprep HS C18, 8 μm, 250×21.1 mm; 5%-50% over 30 min with 0.1 M ammonium acetate, 21 mL/min) to give cis-2-(4-{4-amino-1-[4-(4-methylpiperazino)cyclohexyl]-1H-pyrazolo[3,4-d]pyrimidin-3-yl}anilino)-1,3-benzoxazole-5-carbonitrile (0.15 g, 0.00027 mol). $^1$H NMR (DMSO-d$_6$, 400 MHz) δ 11.25 (s, 1H), 8.53 (s, 1H), 8.00 (s, 1H), 7.95 (d, 2H), 7.70(m, 4H), 4.80 (br, 1H), 2.49 (s, 3H), 2.20 (br, 8H), 2.10 (br, 3H), 1.75 (br, 2H), 1.60 (br, 4H). RP-HPLC (Delta Pak C18, 5 μm, 300A, 15 cm; 5%-95% acetonitrile—0.1M ammonium acetate over 10 min, 1 mL/min) Rt 9.2 min. MS: MH$^+$ 549.

Example 114

Cis-N-2-(4-{4-amino-1-[4-(4-methylpiperazino)cyclohexyl]-1H-pyrazolo[3,4-d]pyrimidin-3-yl}phenyl)-5-(trifluoromethoxy)-1,3-benzoxazol-2-amine

A. 2-nitro-4-(trifluoromethoxy)phenol

To a mixture of 4-(trifluoromethoxy)phenol (4 g, 0.0225 mol) in ethylene glycol dimethyl ether (90 mL) was added a 0.5 M solution of nitronium tetrafluoroborate in sulfolane (46 mL, 0.0229 mol) at −50° C. The mixture was stirred at −50° C. under an atmosphere of nitrogen for 6 hours. The mixture was filtered through silica gel pad, and the pad was washed with 25% ethyl acetate/n-heptane. The solvent was removed under reduced pressure, and the residue was partitioned between ethyl acetate and water. The aqueous layer was extracted with ethyl acetate. The organic layer was washed with water and brine. The solvent was removed under reduced pressure, and the residue was purified by flash column chromatography on silica using 0%-50% ethyl acetate/n-heptane as a mobile phase to give 2-nitro-4-(trifluoromethoxy)phenol (2.5 g, 0.011 mol). TLC (ethyl acetate/n-heptane=25:75) $R_f$ 0.50 MS: MH$^-$: 222

B. 2-amino-4-(trifluoromethoxy)phenol

To a mixture of 2-nitro-4-(trifluoromethoxy)phenol (2 g, 0.0089 mol) in ethanol (50 mL) and water (25 mL) was added sodium thiosulfate (6.2 g, 0.0356 mol) at room temperature. The heterogeneous mixture was stirred at 80° C. under an atmosphere of nitrogen for 1 hour. The reaction mixture was cooled to room temperature, and ethanol was removed under reduced pressure. The aqueous layer was extracted with ethyl acetate (3×70 mL), and the organic layer was washed with brine and dried under sodium sulfate. The solvent was removed under reduced pressure to give yellow solid of 2-amino-4-(trifluoromethoxy)phenol (0.9 g, 0.005 mol). TLC (methanol/dichloromethane=5:95) $R_f$ 0.29 MS: MH$^+$: 194

C. N2-(4-bromophenyl)-5-(trifluoromethoxy)-1,3-benzoxazol-2-amine

To a mixture of 2-amino-4-(trifluoromethoxy)phenol (0.9 g, 0.0047 mol) in tetrahydrofuran (60 mL) was added 4-bromophenyl isothiocyanate (1 g, 0.0047 mol) at room temperature. The mixture was stirred for 16 hours at room temperature. Anhydrous copper sulfate (7.1 g, 0.0443 mol, 9.43 eq.), triethylamine (0.67 mL, 0.0047 mol, 1 eq.), and silica gel (8.5 g) were added to the reaction mixture. The mixture was stirred for 4 hours at room temperature. The solvent was removed under reduced pressure. The mixture was filtered through silica gel pad using 25% ethyl acetate/n-heptane as a mobile phase to give orange colored solid. The solid was purified by flash column chromatography on silica using 0%-25% ethyl acetate/n-heptane as a mobile phase. The solvent was removed, and the residue was triturated with n-heptane to give N2-(4-bromophenyl)-5-(trifluoromethoxy)-1,3-benzoxazol-2-amine (0.9 g, 0.0024 mol).

RP-HPLC (Delta Pak C18, 5 μm, 300A, 15 cm; 5%-95% acetonitrile—0.1M ammonium acetate over 10 min, 1 mL/min) Rt 12.2 min. MS: MH$^+$: 373

D. N2-[4-(4,4,5,5-tetramethyl-1,3,2-dioxaborolan-2-yl)phenyl]-5-(trifluoromethoxy)-1,3-benzoxazol-2-amine A mixture of N2-(4-bromophenyl)-5-(trifluoromethoxy)-1,3-benzoxazol-2-amine (0.9 g, 0.0024 mol), diboron pinacol ester (0.73 g, 0.0029 mol), [1.1'-bis(diphenylphosphino)ferrocene]dichloropalladium (II) complex with dichloromethane (1:1) (0.2 g, 0.00024 mol) and potassium acetate (0.71 g, 0.0072 mol) in N,N-dimethylformamide (25 mL) was heated at 80° C. under an atmosphere of nitrogen for 16 hours. The mixture was allowed to cool to ambient temperature and the solvent removed under reduced pressure. The residue was filtered through silica pad 25% ethyl acetate/n-heptane as a mobile phase. The solvent was removed, and the residue was triturated with n-heptane to give N2-[4-(4,4,5,5-tetramethyl-1,3,2-dioxaborolan-2-yl)phenyl]-5-(trifluoromethoxy)-1,3-benzoxazol-2-amine (0.68 g, 0.0016 mol). RP-HPLC (Delta Pak C18, 5 μm, 300A, 15 cm; 5%-95% acetonitrile—0.1M ammonium acetate over 20 min, 1 mL/min) Rt 18.8 min. MS: MH$^+$: 421

E. cis-N-2-(4-{4-amino-1-[4-(4-methylpiperazino)cyclohexyl]-1H-pyrazolo[3,4-d]pyrimidin-3-yl}phenyl)-5-(trifluoromethoxy)-1,3-benzoxazol-2-amine A mixture of 3-iodo-1-[4-(4-methylpiperazino)cyclohexyl]-1H-pyrazolo[3,4-d]pyrimidin-4-amine (0.06 g, 0.00014 mol), N2-[4-(4,4,5,5-tetramethyl-1,3,2-dioxaborolan-2-yl)phenyl]-5-(trifluoromethoxy)-1,3-benzoxazol-2-amine (0.071 g, 0.00017 mol), tetrakis(triphenylphosphine)palladium (0.011 g, 0.00001 mol) and sodium carbonate (0.037, 0.00035 mol) in ethylene glycol dimethyl ether (3 mL) and water (1 mL) was heated at 80° C. for 16 hours. Additional N2-[4-(4,4,5,5-tetramethyl-1,3,2-dioxaborolan-2-yl)phenyl]-5-(trifluoromethoxy)-1,3-benzoxazol-2-amine (0.030 g, 0.00007 mol) and tetrakis(triphenylphosphine)palladium (0.005 g, 0.000004 mol) were added, and the mixture was stirred at 80° C. for 5 hours under atmosphere of nitrogen. The mixture was allowed to cool to ambient temperature, and the solvent was removed under the reduced pressure. The residue was partitioned between water and ethyl acetate. The aqueous layer was extracted with ethyl acetate (2×50 mL). The combined organic extracts were washed with water, saturated aqueous sodium bicarbonate solution, and brine, and dried over magnesium sulfate. The solvents were evaporated under the reduced pressure, and the residue was purified by flash column chromatography on silica using 2% aqueous ammonium hydroxide solution/5%-25% methanol/dichloromethane as a mobile phase. The solvent was removed under reduced pressure to give cis-N-2-(4-{4-amino-1-[4-(4-methylpiperazino)cyclohexyl]-1H-pyrazolo[3,4-d]pyrimidin-3-yl}phenyl)-5-(trifluoromethoxy)-1,3-benzoxazol-2-amine (0.065 g, 0.00011 mol). $^1$H NMR (DMSO-d$_6$, 400 MHz) δ 11.25 (s, 1H), 8.20 (s, 1H), 7.95 (d, 2H), 7.65 (m, 3H), 7.50 (s, 1H), 7.15 (s, 1H), 4.80 (br, 1H), 2.60 (br, 9H), 2.49 (s, 3H), 2.20 (br, 3H), 2.10 (br, 1H), 1.75 (br, 2H), 1.60 (br, 2H). RP-HPLC (Delta Pak C18, 5 μm, 300A, 15 cm; 5%-95% acetonitrile—0.1M ammonium acetate over 10 min, 0.1 mL/min) Rt 10.7 min. MS: MH$^+$ 608

Example 115

Cis-N2-(4-{4-amino-1-[4-(4-methylpiperazino)cyclohexyl]-1H-pyrazolo[3,4-d]pyrimidin-3-yl}phenyl)-5-ethyl-1,3-benzoxazol-2-amine

A. 4-ethyl-2-nitrophenol

To a mixture of 4-ethylphenol (4 g, 0.0328 mol) in ethylene glycol dimethyl ether (100 mL) was added a 0.5 M solution of nitronium tetrafluoroborate in sulfolane (67 mL, 0.0335 mol) at −50° C. The mixture was stirred at −50° C. under the atmosphere of nitrogen for 6 hours. The mixture was filtered through silica gel pad, and the pad was washed with 25% ethyl acetate/n-heptane. The solvent was removed under reduced pressure, and the residue was partitioned between ethyl acetate and water. The aqueous layer was extracted with ethyl acetate. The organic layer was washed with water and brine. The solvent was removed under reduced pressure to give about 10 g of crude4-ethyl-2-nitrophenol. The crude material was used in the next step without purification.

$^1$H NMR (DMSO-$d_6$, 400 MHz) δ 10.68 (s, 1H), 7.71 (s, 1H), 7.40 (d, 1H), 7.07 (d, 1H), 2.60 (q, 2H), 1.20 (t, 3H). RP-HPLC (Delta Pak C18, 5 μm, 300A, 15 cm; 5%-95% acetonitrile—0.1M ammonium acetate over 10 min, 1 mL/min) Rt 10.2 min.

B. 2-amino-4-ethylphenol

To a mixture of 4-ethyl-2-nitrophenol (5.5 g, 0.032 mol) in ethanol (180 mL) and water (90 mL) was added sodium thiosulfate (23 g, 0.131 mol) at room temperature. The heterogeneous mixture was stirred at 80° C. under an atmosphere of nitrogen for 16 hour. The reaction mixture was cooled to room temperature, and ethanol was removed under reduced pressure. The aqueous layer was extracted with ethyl acetate (3×100 mL), and the organic layer was washed with brine and dried under sodium sulfate. The solvent was removed under reduced pressure, and the residue was purified by flash column chromatography on silica using 0%-25% methanol/dichloromethane as a mobile phase (×2). The solvent was removed under reduced pressure to give 2-amino-4-ethylphenol (0.89 g, 0.006 mol). $^1$H NMR (DMSO-$d_6$, 400 MHz) δ 8.61 (br, 2H), 6.47 (d, 1H), 6.37 (s, 1H), 6.18 (d, 1H), 2.17 (q, 2H), 1.08 (t, 3H). MS: MH$^-$: 137

C. N2-(4-bromophenyl)-5-ethyl-1,3-benzoxazol-2-amine

To a mixture of 2-amino-4-ethylphenol (0.89 g, 0.0065 mol) in tetrahydrofuran (80 mL) was added 4-bromophenyl isothiocyanate (1.4 g, 0.0065 mol) at room temperature. The mixture was stirred for 2 hours at room temperature. Anhydrous copper sulfate (6.2 g, 0.039 mol), triethylamine (0.9 mL, 0.0065 mol) and silica gel (11.7 g) were added to the reaction mixture. The mixture was stirred for 4 hours at room temperature. The solvent was removed under reduced pressure. The mixture was filtered through silica gel pad using 25% ethyl acetate/n-heptane as a mobile phase to give brown colored solid. The solid was purified by flash column chromatography on silica using 0%-25% ethyl acetate/n-heptane as a mobile phase. The solvent was removed, and the residue was triturated with n-heptane to give N2-(4-bromophenyl)-5-ethyl-1,3-benzoxazol-2-amine (0.96 g, 0.003 mol). RP-HPLC (Delta Pak C18, 5 μm, 300A, 15 cm; 5%-95% acetonitrile—0.1M ammonium acetate over 10 min, 1 mL/min) Rt 12.1 min. MS: MH$^+$: 318

D. N2-[4-(4,4,5,5-tetramethyl-1,3,2-dioxaborolan-2-yl)phenyl]-5-ethyl-1,3-benzoxazol-2-amine A mixture of N2-(4-bromophenyl)-5-ethyl-1,3-benzoxazol-2-amine (0.86 g, 0.0027 mol), diboron pinacol ester (0.84 g, 0.0033 mol), [1,1'-bis(diphenylphosphino)ferrocene]dichloropalladium (II) complex with dichloromethane (1:1) (0.22 g, 0.00027 mol) and potassium acetate (0.8 g, 0.0081 mol) in N,N-dimethylformamide (30 mL) was heated at 80° C. under an atmosphere of nitrogen for 16 hours. The mixture was allowed to cool to ambient temperature and the solvent removed under reduced pressure. The residue was partitioned between ethyl acetate and water. The aqueous layer was extracted with ethyl acetate (3×50 mL), and the organic layer was washed with brine. The solvent was removed under reduced pressure, and the crude material was purified by flash column chromatography on silica using 0%-25% ethyl acetate/n-heptane as a mobile phase to give N2-[4-(4,4,5,5-tetramethyl-1,3,2-dioxaborolan-2-yl)phenyl]-5-ethyl-1,3-benzoxazol-2-amine (0.82 g, 0.002 mol).

TLC (ethyl acetate/n-heptane=25:75) $R_f$ 0.30. MS: MH$^+$: 365

E. cis-N2-(4-{4-amino-1-[4-(4-methylpiperazino) cyclohexyl]-1H-pyrazolo[3,4-d]pyrimidin-3-yl}phenyl)-5-ethyl-1,3-benzoxazol-2-amine A mixture of 3-iodo-1-[4-(4-methylpiperazino)cyclohexyl]-1H-pyrazolo[3,4-d]pyrimidin-4-amine (0.06 g, 0.00014 mol), N2-[4-(4,4,5,5-tetramethyl-1,3,2-dioxaborolan-2-yl)phenyl]-5-ethyl-1,3-benzoxazol-2-amine (0.062 g, 0.00017 mol), tetrakis(triphenylphosphine)palladium (0.011 g, 0.00001 mol) and sodium carbonate (0.037, 0.00035 mol) in ethylene glycol dimethyl ether (3 mL) and water (1 mL) was heated at 80° C. for 16 hours. The mixture was allowed to cool to ambient temperature, and the solvent was removed under the reduced pressure. The residue was partitioned between water and ethyl acetate. The aqueous layer was extracted with ethyl acetate (2×25 mL). The combined organic extracts were washed with water, saturated aqueous sodium bicarbonate solution, and brine, and dried over magnesium sulfate. The solvents were evaporated under the reduced pressure, and the residue was purified by flash column chromatography on silica using 2% aqueous ammonium hydroxide solution/5%-25% methanol/dichloromethane as a mobile phase. The solvent was removed under reduced pressure to give cis-N2-(4-{4-amino-1-[4-(4-methylpiperazino)cyclohexyl]-1H-pyrazolo[3,4-d]pyrimidin-3-yl}phenyl)-5-ethyl-1,3-benzoxazol-2-amine (0.065 g, 0.00012 mol). $^1$H NMR (DMSO-$d_6$, 400 MHz) δ 11.25 (s, 1H), 8.65 (s, 1H), 8.37 (d, 2H), 8.09 (d, 2H), 7.84 (d, 1H), 7.76 (s, 1H), 7.42 (d, 1H), 5.22 (br, 1H), 3.13 (q, 2H), 2.52 (br, 7H), 2.69 (br, 4H), 2.64 (s, 3H), 2.49 (br, 21), 2.11 (br, 2H), 2.01 (br, 2H), 1.63 (t, 3H). RP-HPLC (Delta Pak C18, 5 μm, 300A, 15 cm; 5%-95% acetonitrile—0.1M ammonium acetate over 10 min, 1 mL/min) Rt 10.3 min. MS: MH$^+$ 552

Examples 116

Cis-N-2-(4-{4-amino-1-[4-(dimethylamino)cyclohexyl]-1H-pyrazolo[3,4-d]pyrimidin-3-yl}phenyl)-5,7-dimethyl-1,3-benzoxazol-2-amine; and

Example 117

Cis-N-2-(4-{4-amino-1-[4-(dimethylamino)cyclohexyl]-1H-pyrazolo[3,4-d]pyrimidin-3-yl}phenyl)-5,7-dimethyl-1,3-benzoxazol-2-amine A. Cis- and trans-1-[4-(dimethylamino)cyclohexyl]-3-iodo-1H-pyrazolo[3,4-d]pyrimidin-4-amine Sodium triacetoxyborohydride (1.40 g, 6.61 mmol) was added to a solution of 4-(4-amino-3-iodo-1H-pyrazolo[3,4-d]pyrimidin-1-yl)-1-cyclohexanone monohydrochloride (2.00 g, 5.08 mmol), dimethylamine solution (2 M in tetrahydrofuran, 7.62 mL, 15.24 mmol) and acetic acid (0.87 mL, 15.24 mmol) in 1,2-dichloroethane (200 mL) at room temperature. The reaction was stirred for 24 h and additional sodium triacetoxyborohydride (0.40 g) was added. After a further 24 h, saturated aqueous NaHCO$_3$ (50 mL) and CH$_2$Cl$_2$ (200 mL) were added and the organic layer was separated, dried over anhydrous Na$_2$SO$_4$, and concentrated in vacuo. The product was purified by column chromatography using a 1:5:94 aqueous ammonium hydroxide:MeOH:CH$_2$Cl$_2$ to 1:20:79 94 aqueous ammonium hydroxide: MeOH: CH$_2$Cl$_2$ gradient as the eluent to afford a mixture of cis- and trans-1-[4-(dimethylamino)cyclohexyl]-3-iodo-1H-pyrazolo[3,4-d]pyrimidin-4-amine as a white crystalline solid (0.87 g, 44%); RP-HPLC R$_t$ 5.458 min, 33% purity, trans-isomer; R$_t$ 5.621 min, 67% purity, cis-isomer (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 387 (MH$^+$) was observed for both the cis- and the trans-isomers.

B. Cis- and trans-N-2-(4-{4-amino-1-[4-(dimethylamino)cyclohexyl]-1H-pyrazolo[3,4-d]pyrimidin-3-yl}phenyl)-5,7-dimethyl-1,3-benzoxazol-2-amine A mixture of cis- and trans-1-[4-(dimethylamino)cyclohexyl]-3-iodo-1H-pyrazolo[3,4-d]pyrimidin-4-amine (0.50 g, 1.29 mmol), N2-[4-(4,4,5,5-tetramethyl-1,3,2-dioxaborolan-2-yl)phenyl]-5,7-dimethyl-1,3-benzoxazol-2-amine (0.565 g, 1.55 mmol), sodium carbonate (0.34 g, 3.24 mmol), and tetrakis(triphenylphosphine) palladium (0) (0.075 g, 0.06 mmol) in ethylene glycol dimethylether (150 mL) and water (25 mL) was heated at 80° C. for 16 h. Additional Pd catalyst (0.075 g) and N2-[4-(4,4,5,5-tetramethyl-1,3,2-dioxaborolan-2-yl)phenyl]-5,7-dimethyl-1,3-benzoxazol-2-amine (0.40 g) were added and the reaction was continued at 80° C. for a further 16 h. Further quantities of the Pd catalyst (0.020 g) and N2-[4-(4,4,5,5-tetramethyl-1,3,2-dioxaborolan-2-yl)phenyl]-5,7-dimethyl-1,3-benzoxazol-2-amine (0.12 g) were added and the reaction was continued at 80° C. for a further 16 h. The reaction was concentrated in vacuo and the residues were dissolved in dichloromethane (200 mL) and washed with water (50 mL). The organic layer was dried over anhydrous sodium sulfate and concentrated under reduced pressure. The residue was purified by column chromatography over silica gel using 1% aqueous ammonium hydroxide and 10% methanol in CH$_2$Cl$_2$ as the eluent to afford cis-N2-(4-{4-amino-1-[4-(dimethylamino)cyclohexyl]-1H-pyrazolo[3,4-d]pyrimidin-3-yl}phenyl)-5,7-dimethyl-1,3-benzoxazol-2-amine (0.08 g), a mixed fraction (0.24 g) and trans-N-2-(4-{4-amino-1-[4-(dimethylamino)cyclohexyl]-1H-pyrazolo[3,4-d]pyrimidin-3-yl}phenyl)-5,7-dimethyl-1,3-benzoxazol-2-amine (0.030 g); RP-HPLC R$_t$ 11.326 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 497 (MH$^+$); $^1$H NMR (400 MHz, d$_6$-DMSO) 1.49 (2H, m), 2.01 (6H, m), 2.33 (7H, m), 2.35 (3H, s), 2.40 (3H, s), 4.67 (1H, m), 6.80 (1H, s), 7.11 (1H, s), 7.65 (2H, d, J=8.5 Hz), 7.92 (2H, d, J=8.5 Hz), 8.23 (1H, s), and 10.85 (1H, s).

The cis-fraction required further purification by RP HPLC to afford cis-N-2-(4-{4-amino-1-[4-(dimethylamino)cyclohexyl]-1H-pyrazolo[3,4-d]pyrimidin-3-yl}phenyl)-5,7-dimethyl-1,3-benzoxazol-2-amine (0.050 g), RP-HPLC R$_t$ 11.337 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (400 MHz, d$_6$-DMSO) 1.61 (4H, m), 2.08 (2H, m), 2.27 (9H, m), 2.34 (3H, s), 2.40 (3H, s), 4.81 (1H, m), 6.80 (1H, s), 7.11 (1H, s), 7.65 (2H, d, J=8.5 Hz), 7.92 (2H, d, J=8.5 Hz), 8.23 (1H, s), and 10.85 (1H, s).

Exampls 614-620

The following is a general synthesis of analogs of cis-N-2-4-[4-amino-1-(4-aminocyclohexyl)-1H-pyrazolo[3,4-d]pyrimidin-3-yl]phenyl-1,3-benzoxazol-2-amine. Examples 118-124 were prepared using this method.

A. N2-(4-Bromophenyl)-5-chloro-1,3-benzoxazol-2-amine

4-Bromophenyl isothiocyanate (3.639 g, 17.00 mmol) was added to a solution of 2-amino-4-chlorophenol (2.441 g, 17.00 mmol) in acetonitrile (20 mL) and the reaction was stirred at room temperature for 2 h. The resulting brown solution was then added dropwise, via a dropping funnel, to a suspension of potassium superoxide (6.04 g, 85.0 mmol) in acetonitrile (20 mL) pre-cooled to 0° C. in an ice bath. After 20 minutes the initial exotherm had subsided and the reaction was allowed to warm to room temperature for 40 minutes. Water (120 mL) was added dropwise and the resulting off-white solid was collected by filtration, washed with additional water (60 mL) and dried overnight on a lyophilizer to afford N2-(4-bromophenyl)-5-chloro-1,3-benzoxazol-2-amine as an off-white solid (4.06 g, 74%); RP-HPLC Rt 17.229 min, 99% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 321 (M–H)— and 323 (M–H)$^-$; $^1$H NMR (400 MHz, d$_6$-DMSO) 7.17 (1H, dd, J 8.5 and 1.9 Hz), 7.53 (4H, m), 7.71 (2H, d, J=8.8 Hz), and 10.95 (1H, s).

B. N2-[4-(4,4,5,5-Tetramethyl-1,3,2-dioxaborolan-2-yl)phenyl]-5-chloro-1,3-benzoxazol-2-amine A mixture containing N2-(4-bromophenyl)-5-chloro-1,3-benzoxazol-2-amine (4.00 g, 12.36 mmol), bis(pinacolato)diboron (3.77 g, 14.83 mmol), potassium acetate (3.64 g, 37.09 mmol) and [1,1'-bis(diphenylphosphino)ferrocene]dichloropalladium (II) complexed with dichloromethane (1:1) (0.61 g, 0.74 mmol) in dimethylformamide (200 mL) was heated at 80° C. under nitrogen for 16 h. Additional Pd catalyst (0.61 g) was added and the reaction was continued for a further 6 h. Additional diboron (3.0 g) was then added and the reaction proceeded for a further 16 h. Silica gel (20 mL) was added to the reaction mixture and the solvent removed under reduced pressure. The resulting solid was then purified through a silica pad using a 10% to 20% ethyl acetate in heptane gradient as the eluent. The resulting solid was triturated with heptane to afford N2-[4-(4,4,5,5-tetramethyl-1,3,2-dioxaborolan-2-yl)phenyl]-5-chloro-1,3-benzoxazol-2-amine as a cream solid (2.40 g, 52%); RP-HPLC $R_t$ 18.164 min, 99% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (400 MHz, $d_6$-DMSO) 1.29 (12H, s), 7.17 (1H, dd, J 8.5 and 2.1 Hz), 7.56 (2H, m), 7.68 (2H, m), 7.75 (2H, m), and 10.96 (1H, s).

C. N2-(4-bromophenyl)-5-methyl-1,3-benzoxazol-2-amine

2-Amino-4-methylphenol (1.15 g, 9.34 mmol) was added to a solution of 4-bromophenyl isothiocyanate (2.00 g, 9.34 mmol) in tetrahydrofuran (35 mL) and the reaction was stirred at room temperature for 16 h. Anhydrous copper (II) sulfate (14.06 g, 88.10 mmol), silica gel (14.06 g), and triethylamine (1.3 mL, 9.34 mmol) were added, and the mixture was stirred at room temperature for 24 h. The reaction was concentrated under reduced pressure and then added to a silica pad and purified using 1:5 ethyl acetate: heptane (2 L) followed by diethyl ether as the eluent to afford N2-(4-bromophenyl)-5-methyl-1,3-benzoxazol-2-amine as a light brown solid (2.30 g, 81%); RP-HPLC $R_t$ 16.437 min, 94% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (400 MHz, $d_6$-DMSO) 2.37 (3H, s), 6.94 (1H, d, J=8.1 Hz), 7.27 (1H, s), 7.36 (1H, d, J=8.1 Hz), 7.54 (2H, d, J=8.4 Hz), 7.72 (2H, d, J=8.4 Hz), and 10.72 (1H, s).

D. N2-[4-(4,4,5,5-Tetramethyl-1,3,2-dioxaborolan-2-yl)phenyl]-5-methyl-1,3-benzoxazol-2-amine N2-[4-(4,4,5,5-Tetramethyl-1,3,2-dioxaborolan-2-yl)phenyl]-5-methyl-1,3-benzoxazol-2-amine was prepared from N2-(4-bromophenyl)-5-methyl-1,3-benzoxazol-2-amine (1.5 g, 4.95 mmol) using the method described for the preparation of N2-[4-(4,4,5,5-tetramethyl-1,3,2-dioxaborolan-2-yl)phenyl]-5-chloro-1,3-benzoxazol-2-amine. The product was formed as white floculent solid (0.79 g, 46%); RP-HPLC $R_t$ 17.382 min, 98% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (400 MHz, $d_6$-DMSO) 1.29 (121H, s), 2.38 (3H, s), 6.94 (1H, d, J=8.1 Hz), 7.30 (1H, s), 7.36 (1H, d, J=8.1 Hz), 7.67 (2H, d, J=8.5 Hz), 7.75 (2H, d, J=8.5 Hz), and 10.74 (1H, s).

E. General synthesis of cyclohexyl amine analogs of cis-1-(4-aminocyclohexyl)-3-iodo-1H-pyrazolo[3,4-d]pyrimidin-4-amine

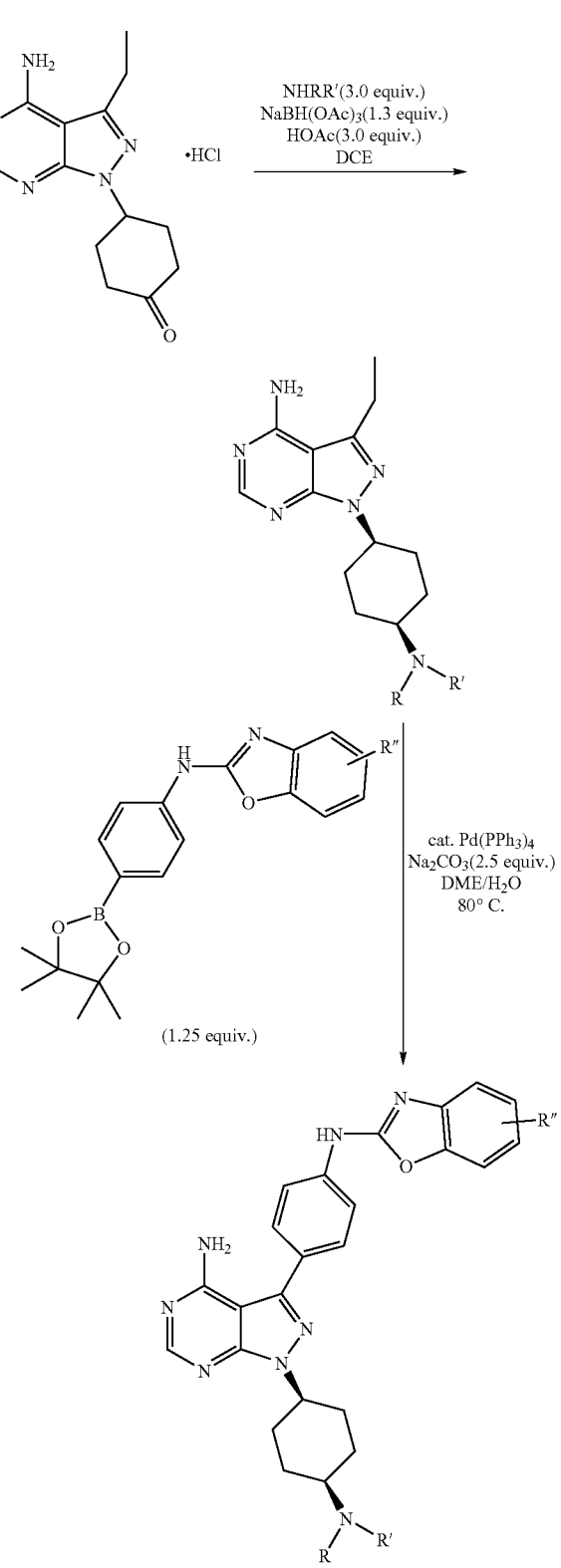

4-(4-Amino-3-iodo-1H-pyrazolo[3,4-d]pyrimidin-1-yl)-1-cyclohexanone monohydrochloride (5.08-7.62 mmol scale) was suspended in dichloroethane (200-300 mL) under a nitrogen atmosphere. The appropriate amine (3.0 equivalents), glacial acetic acid (3.0 equivalents) and sodium triacetoxyborohydride (1.3 equivalents) were added and the reaction was stirred at ambient temperature for 1-2 days. For the reactions which had not gone to completion, additional sodium triacetoxyborohydride (1.3 equivalents) was added and the reaction was continued for a further 1 or 2 days. The reactions were quenched with saturated sodium carbonate solution (50-75 mL) and extracted with dichloromethane (200-300 mL). The organic phase was separated, dried over anhydrous $Na_2SO_4$ and concentrated in vacuo to yield a mixture of cis- and trans-products as a white solid. The crude products were purified via flash column chromatography using a gradient of 2% methanol and 0.2% ammonium hydroxide in dichloromethane to 5% methanol and 0.5% ammonium hydroxide in dichloromethane as the eluent. The fractions containing the pure cis-products were combined, concentrated under reduced pressure and dried on a lyophilizer to afford the cyclohexyl amine analogs of cis-1-(4-aminocyclohexyl)-3-iodo-1H-pyrazolo[3,4-d]pyrimidin-4-amine as white solids (see Table 1 for analytical details and isolated yields).

TABLE 1

| Structure | Starting amine | Starting cyclohexanone scale (mmol) | m/z (MH+) | HPLC RT (min) | Purity | % Isolated yield of cis-isomer |
|---|---|---|---|---|---|---|
| | | 5.08 | 429.0 | 5.63 | 95% | 8 |
| | | 7.62 | 417.0 | 5.96 | 100% | 59 |
| | | 7.62 | 373.0 | 5.32 | 100% | 2 |

RP-HPLC analysis conditions: 5% to 85% acetonitrile/ 0.1M aqueous ammonium acetate, buffered to pH 4.5, over 20 min at 1 mL/min; λ=254 nm; Deltapak C18, 300 Å, 5 µm, 150×3.9 mm column.

F. General synthesis of analogs of cis-N-2-4-[4-amino-1-(4-aminocyclohexyl)-1H-pyrazolo[3,4-d]pyrimidin-3-yl]phenyl-1,3-benzoxazol-2-amine The cyclohexylamine analog of cis-1-(4-aminocyclohexyl)-3-iodo-1H-pyrazolo[3,4-d]pyrimidin-4-amine (0.10-0.52 mmol scale) was dissolved in ethylene glycol dimethylether (5-10 mL) and water (2.5-5 mL). The appropriate substituted or unsubstituted N-(1,3-benzoxazol-2-yl)-N-[4-(4,4,5,5-tetramethyl-1,3,2-dioxaborolan-2-yl)phenyl]amine (1.25 equivalents), tetrakis(triphenylphosphine) palladium (0) (0.05 equivalents) and sodium carbonate (2.5 equivalents) were added and the reaction was heated at 80° C. for 20 hours. For the reactions which had not reached completion, additional boronate (1.25 equivalents) and palladium catalyst (0.05 equivalents) were added. In addition, DME/H₂O 2:1 (5 mL) was added to the reactions where precipitation had occurred and the reactions were re-subjected to heating at 80° C. for a further 22-40 hours. Silica gel (5-8 mL) was added to the reaction and the mixture was concentrated under reduced pressure. Purification via flash column chromatography over silica gel using a gradient of 2% to 50% methanol containing 0.5M ammonium hydroxide in dichloromethane yielded analogs of cis-N-2-4-[4-amino-1-(4-aminocyclohexyl)-1H-pyrazolo[3,4-d]pyrimidin-3-yl]phenyl-1,3-benzoxazol-2-amine. For products with unsatisfactory purity, the samples were further purified via RP-HPLC (Waters PrepLC 4000, flow rate: 10 mL/min, λ=254 nm, gradient: 15% to 35% acetonitrile/0.1M aqueous ammonium acetate gradient over 40 minutes then 35% to 90% acetonitrile/0.1M aqueous ammonium acetate gradient over 150 minutes; Deltapak C18, 300A, 15 µm, 40×100 mm column). The fractions containing the desired products were combined and concentrated in vacuo then dried on a lyophilizer to afford the products as white or tan solids. (see Table 2 for analytical details and isolated yields).

TABLE 2

| Ex. | Structure | Starting cyclohexyl amine structure | scale (mmol) | Starting boronate | m/z (MH⁺) | HPLC RT (min) | Purity | % yield |
|---|---|---|---|---|---|---|---|---|
| 118 | 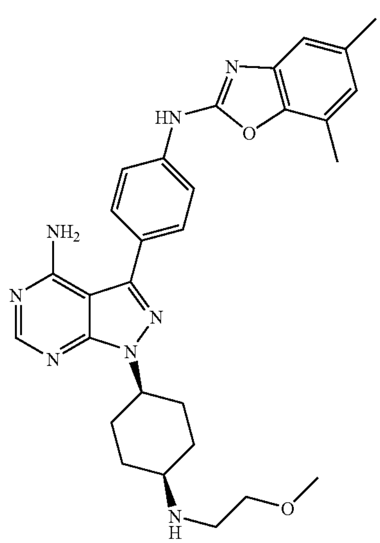 | | 0.24 | | 527.3 | 11.66 | 100% | 32 |

TABLE 2-continued
| Ex. | Structure | Starting cyclohexyl amine structure | scale (mmol) | Starting boronate | m/z (MH+) | RT (min) | Purity | % yield |
|---|---|---|---|---|---|---|---|---|
| 119 | 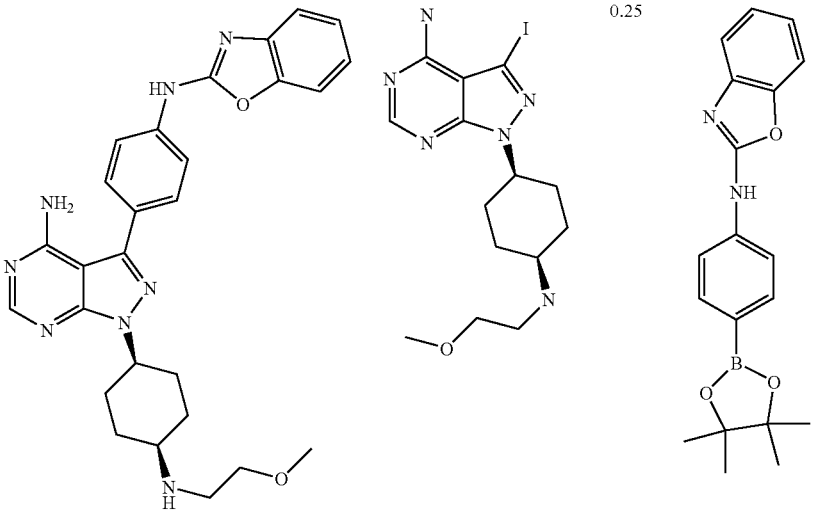 | 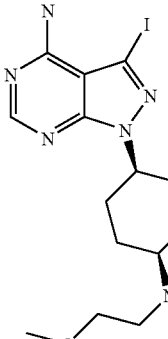 | 0.25 | 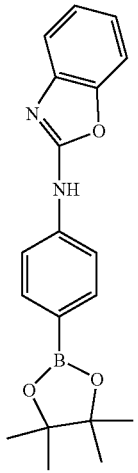 | 499.3 | 9.72 | 100% | 79 |
| 120 | 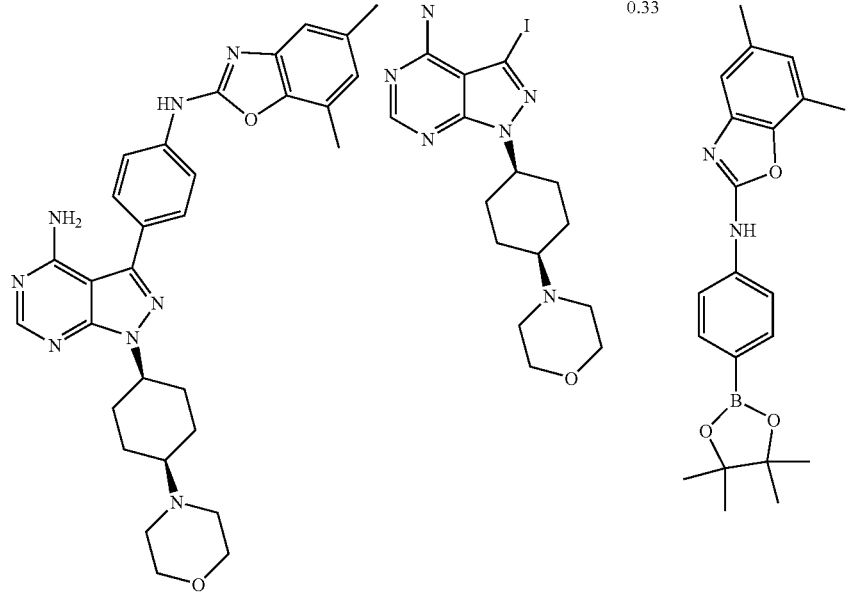 | 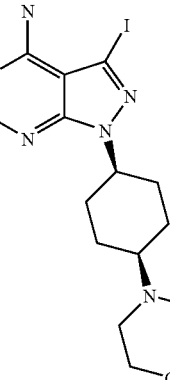 | 0.33 | 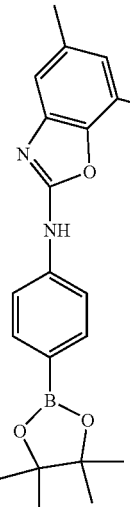 | 539.3 | 11.50 | 100% | 28 |

TABLE 2-continued

| Ex. | Structure | Starting cyclohexyl amine structure | scale (mmol) | Starting boronate | m/z (MH+) | RT (min) | Purity | % yield |
|---|---|---|---|---|---|---|---|---|
| 121 | | | 0.12 | | 511.3 | 9.77 | 100% | 60 |
| 122 | | | 0.10 | | 545.2 | 11.36 | 97% | 27 |

TABLE 2-continued

| Ex. | Structure | Starting cyclohexyl amine structure | scale (mmol) | Starting boronate | m/z (MH+) | RT (min) | Purity | % yield |
|---|---|---|---|---|---|---|---|---|
| 123 | | | 0.13 | | 455.2 | 9.48 | 100% | 61 |
| 124 | | | 0.52 | | | | | |

RP-HPLC analysis conditions: 5% to 85% acetonitrile/ 0.1M aqueous ammonium acetate, buffered to pH 4.5, over 20 min at 1 mL/min; λ=254 nm; Deltapak C18, 300 Å, 5 µm, 150×3.9 mm column.

Example 125 cis-N-2-(4-{4-Amino-1-[4-(4-methylpiperazino) cyclohexyl]-1H-pyrazolo[3,4-d]pyrimidin-3-yl}phenyl)-4-(2-nitrophenyl)-1,3-thiazol-2-amine The procedure described in the preparation of cis-N-2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine was employed with the exception that 2-bromo-2'nitroacetophenone (0.126 g, 0.516 mmol) was used as the alkylating agent. Purification of the product by preparative HPLC (25 to 100% acetonitrile in 0.1 M aqueous ammonium acetate over 20 min at 21 mL/min using an 8µ Hypersil HS C18, 250×21 mm column, $R_t$ 7.0-8.0 min) afforded cis-N-2-(4-{4-amino-1-[4-(4-methylpiperazino)cyclohexyl]-1H-pyrazolo[3,4-d]pyrimidin-3-yl}phenyl)-4-(2-nitrophenyl)-1,3-thiazol-2-amine as a yellow foam (0.088 g, 0.144 mmol); RP-HPLC (25 to 100% acetonitrile in 0.1 M aqueous ammonium acetate over 10 min at 1 mL/min using a 5μ Hypersil HS C18, 250×4.6 mm column) R$_t$ 7.72 min; MS (MH)$^+$ 611.

Example 126

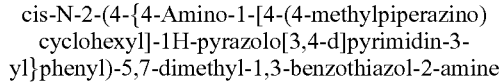
cis-N-2-(4-{4-Amino-1-[4-(4-methylpiperazino)cyclohexyl]-1H-pyrazolo[3,4-d]pyrimidin-3-yl}phenyl)-5,7-dimethyl-1,3-benzothiazol-2-amine Pyridinium tribromide (0.894 g, 2.80 mmol) and 3,5-dimethylcyclohexanone (0.180 mL, 1.27 mmol) were suspended in dichloromethane (5 mL). The reaction mixture was stirred at ambient temperature for 24 h, then diluted with dichloromethane (60 mL). The organic layer was extracted sequentially with water (10 mL) and sodium bicarbonate (10 mL), dried (magnesium sulfate), filtered, and concentrated. Purification of the product by flash column chromatography (7.5% ethyl acetate/heptane) afforded 2,6-dibromo-3,5-dimethyl-1-cyclohexanone as a mixture of diastereomers (0.243 g, 0.855 mmol): TLC R$_f$ (20% ethyl acetate/heptane): 0.35.

Alkylation of 2,6-dibromo-3,5-dimethyl-1-cyclohexanone (0.243 g, 0.855 mmol) was conducted using the alkylation procedure described in the preparation of cis-N-2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine, with the exception that the alkylation was conducted at 75° C., to afford N-(4-bromophenyl)-N-(5,7-dimethyl-1,3-benzothiazol-2-yl)amine (0.251 g, 0.754 mmol); RP-HPLC (25 to 100% acetonitrile in 0.1 M aqueous ammonium acetate over 10 min at 1 mL/min using a 5μ Hypersil HS C18, 250×4.6 mm column) R$_t$ 14.8 min.

N-(4-Bromophenyl)-N-(5,7-dimethyl-1,3-benzothiazol-2-yl)amine (0.251 g, 0.754 mmol) was converted to the title compound using the procedure described in the preparation of cis-N-2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine. Purification of the product by preparative HPLC (25 to 100% acetonitrile in 0.1 M aqueous ammonium acetate over 20 min at 21 mL/min using an 8μ Hypersil HS C18, 250×21 mm column, R$_t$ 8.8-10.5 min) afforded cis-N-2-(4-{4-amino-1-[4-(4-methylpiperazino)cyclohexyl]-1H-pyrazolo[3,4-d]pyrimidin-3-yl}phenyl)-5,7-dimethyl-1,3-benzothiazol-2-amine as a white powder (0.081 g, 0.143 mmol); RP-HPLC (25 to 100% acetonitrile in 0.1 M aqueous ammonium acetate over 10 min at 1 mL/min using a 5μ Hypersil HS C18, 250×4.6 mm column) R$_t$ 8.75 min; MS (MH)$^+$ 568.

Examples 127

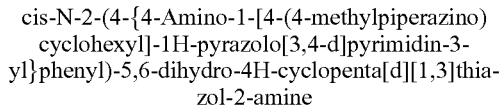
cis-N-2-(4-{4-Amino-1-[4-(4-methylpiperazino)cyclohexyl]-1H-pyrazolo[3,4-d]pyrimidin-3-yl}phenyl)-5,6-dihydro-4H-cyclopenta[d][1,3]thiazol-2-amine Cyclopentanone (200 μL, 2.26 mmol) and pyridinium tribromide (0.723 g, 2.26 mmol) were suspended in dichloromethane (5 mL). The reaction mixture was stirred at ambient temperature overnight, then was diluted with ether/petroleum ether (1:1, 60 mL). The organic phase was extracted sequentially with water (10 mL) and aqueous sodium bicarbonate (10 mL), then was dried (magnesium sulfate), filtered, and concentrated. Purification of the product by flash column chromatography (25% ether/petroleum ether) afforded 2-bromocyclopentanone (0.220 g, 1.35 mmol) as a colorless oil; TLC (25% ether/petroleum ether) R$_f$: 0.35.

2-Bromocyclopentanone (0.220 g, 1.35 mmol) was converted to the title compound using the procedure described for cis-N-2-(4-{4-amino-1-[4-(4-methylpiperazino)cyclohexyl]-1H-pyrazolo[3,4-d]pyrimidin-3-yl}phenyl)-4-(2-nitrophenyl)-1,3-thiazol-2-amine, except that the alkylation reaction was conducted at 60° C. Purification of the product by preparative HPLC (25 to 100% acetonitrile in 0.1 M aqueous ammonium acetate over 20 min at 21 mL/min using an 8μ Hypersil HS C18, 250×21 mm column, R$_t$ 7.8-8.8 min) afforded cis-N-2-(4-{4-amino-1-[4-(4-methylpiperazino)cyclohexyl]-1H-pyrazolo[3,4-d]pyrimidin-3-yl}phenyl)-5,6-dihydro-4H-cyclopenta[d][1,3]thiazol-2-amine as a tan powder (0.009 g, 0.017 mmol); RP-HPLC (25 to 100% acetonitrile in 0.1 M aqueous ammonium acetate over 10 min at 1 mL/min using a 5 U Hypersil HS C18, 250×4.6 mm column) R$_t$ 7.23 min; MS (MH)$^+$ 530.

Example 128

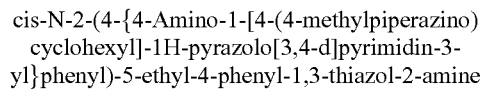
cis-N-2-(4-{4-Amino-1-[4-(4-methylpiperazino)cyclohexyl]-1H-pyrazolo[3,4-d]pyrimidin-3-yl}phenyl)-5-ethyl-4-phenyl-1,3-thiazol-2-amine The procedure for the preparation of cis-N-2-(4-{4-amino-1-[4-(4-methylpiperazino)cyclohexyl]-1H-pyrazolo[3,4-d]pyrimidin-3-yl}phenyl)-5,6-dihydro-4H-cyclopenta[d][1,3]thiazol-2-amine was used to convert butyrophenone (436 μL, 3.00 mmol) to the title compound. Purification of the product by preparative HPLC (25 to 100% acetonitrile in 0.1 M aqueous ammonium acetate over 20 min at 21 mL/min using an 8μ Hypersil HS C18, 250×21 mm column, R$_t$ 8.9-11.1 min) afforded cis-N-2-(4-{4-amino-1-[4-(4-methylpiperazino)cyclohexyl]-1H-pyrazolo[3,4-d]pyrimidin-3-yl}phenyl)-5-ethyl-4-phenyl-1,3-thiazol-2-amine as a white powder (0.022 g, 0.037 mmol); RP-HPLC (25 to 100% acetonitrile in 0.1 M aqueous ammonium acetate over 10 min at 1 mL/min using a 5μ Hypersil HS C18, 250×4.6 mm column) R$_t$ 9.27 min; MS (MH)$^+$ 594.

Example 129

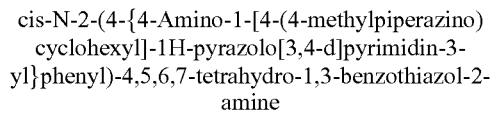
cis-N-2-(4-{4-Amino-1-[4-(4-methylpiperazino)cyclohexyl]-1H-pyrazolo[3,4-d]pyrimidin-3-yl}phenyl)-4,5,6,7-tetrahydro-1,3-benzothiazol-2-amine The procedure described for cis-N-2-(4-{4-amino-1-[4-(4-methylpiperazino)cyclohexyl]-1H-pyrazolo[3,4-d]pyrimidin-3-yl}phenyl)-5,6-dihydro-4H-cyclopenta[d][1,3]thiazol-2-amine was used to convert cyclohexanone (310 μL, 3.00 mmol) to the title compound. Purification of the product by preparative HPLC (25 to 100% acetonitrile in 0.1 M aqueous ammonium acetate over 20 min at 21 mL/min using an 8μ Hypersil HS C18, 250×21 mm column, R$_t$ 6.8-8.6 min) afforded cis-N-2-(4-{4-amino-1-[4-(4-methylpiperazino)cyclohexyl]-1H-pyrazolo[3,4-d]pyrimidin-3-yl}phenyl)-4,5,6,7-tetrahydro-1,3-benzothiazol-2-amine as an orange powder (0.022 g, 0.040 mmol); RP-HPLC (25 to 100% acetonitrile in 0.1 M aqueous ammonium acetate over 10 min at 1 mL/min using a 5μ Hypersil HS C18, 250×4.6 mm column) R$_t$ 7.62 min; MS (MH)$^+$ 544.

Example 130 cis-N-2-(4-{4-Amino-1-[4-(4-methylpiperazino)
cyclohexyl]-1H-pyrazolo[3,4-d]pyrimidin-3-
yl}phenyl)-5-isopropyl-4-phenyl-1,3-thiazol-2-
amine The procedure described for cis-N-2-(4-{4-amino-1-[4-(4-methylpiperazino)cyclohexyl]-1H-pyrazolo[3,4-d]pyrimidin-3-yl}phenyl)-5,6-dihydro-4H-cyclopenta[d][1,3]thiazol-2-amine was used to convert isovalerophenone (0.484 g, 2.98 mmol) to the title compound. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 9.5-11.7 min) afforded cis-N-2-(4-{4-amino-1-[4-(4-methylpiperazino)cyclohexyl]-1H-pyrazolo[3,4-d]pyrimidin-3-yl}phenyl)-5-isopropyl-4-phenyl-1,3-thiazol-2-amine as a pink powder (0.060 g, 0.099 mmol);

RP-HPLC (25 to 100% acetonitrile in 0.1 M aqueous ammonium acetate over 10 min at 1 mL/min using a 5μ Hypersil HS C18, 250×4.6 mm column) $R_t$ 9.82 min; MS (MH)$^+$ 608.

Example 131 cis-N-2-(4-{4-Amino-1-[4-(4-methylpiperazino)
cyclohexyl]-1H-pyrazolo[3,4-d]pyrimidin-3-
yl}phenyl)-4-phenyl-5-propyl-1,3-thiazol-2-amine The procedure described for cis-N-2-(4-{4-amino-1-[4-(4-methylpiperazino)cyclohexyl]-1H-pyrazolo[3,4-d]pyrimidin-3-yl}phenyl)-5,6-dihydro-4H-cyclopenta[d][1,3]thiazol-2-amine was used to convert valerophenone (0.488 g, 3.01 mmol) to the title compound. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 9.6-11.8 min) afforded cis-N-2-(4-{4-amino-1-[4-(4-methylpiperazino)cyclohexyl]-1H-pyrazolo[3,4-d]pyrimidin-3-yl}phenyl)-4-phenyl-5-propyl-1,3-thiazol-2-amine as a yellow powder (0.135 g, 0.222 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 10.08 min; MS (MH)$^+$ 608.

Example 132

3-[4-(1,3-Benzoxazol-2-ylmethyl)phenyl]-1-[4-(4-
methylpiperazino)cyclohexyl]-1H-pyrazolo[3,4-d]
pyrimidin-4-amine 2-Aminophenol (0.257 g, 2.36 mmol) and 4-bromophenylacetic acid (0.500 g, 2.36 mmol) were heated neat in a sealed tube at 200° C. After 4 h, the reaction mixture was cooled to ambient temperature and diluted with methanol/dichloromethane (5%, 60 mL). The organic phase was extracted with aqueous sodium carbonate (1 M, 10 mL), dried (magnesium sulfate), filtered, and concentrated. Purification of the residue by flash column chromatography (15% ethyl acetate/heptane) afforded N-(1,3-benzoxazol-2-yl)-N-[4-(4,4,5,5-tetramethyl-1,3,2-dioxaborolan-2-yl)phenyl]amine as a brown solid (0.347 g, 1.20 mmol); (MH)$^+$ 290.

N-(1,3-Benzoxazol-2-yl)-N-[4-(4,4,5,5-tetramethyl-1,3,2-dioxaborolan-2-yl)phenyl]amine was converted to 2-[4-(4,4,5,5-tetramethyl-1,3,2-dioxaborolan-2-yl)benzyl]-1,3-benzoxazole and then to the title compound using the procedure described in the preparation of cis-N-2-(4-{4-amino-1-[4-(4-methylpiperazino)cyclohexyl]-1H-pyrazolo[3,4-d]pyrimidin-3-yl}phenyl)-6-chloro-1,3-benzothiazol-2-amine. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 5.6-7.3 min) afforded 3-[4-(1,3-benzoxazol-2-ylmethyl)phenyl]-1-[4-(4-methylpiperazino)cyclohexyl]-1H-pyrazolo[3,4-d]pyrimidin-4-amine as a white powder (0.102 g, 0.195 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 6.83 min; MS (MH)$^+$ 523.

Example 133

N1-[2-(Dimethylamino)ethyl]-2-{4-amino-3-[4-(1,3-
benzoxazol-2-ylamino)phenyl]-1H-pyrazolo[3,4-d]
pyrimidin-1-yl}propanamide The procedure described in the preparation of N1-[2-(dimethylamino)ethyl]-2-(4-amino-3-{4-[(5,7-dimethyl-1,3-benzoxazol-2-yl)amino]phenyl}-1H-pyrazolo[3,4-d]pyrimidin-1-yl)propanamide was employed, except that the Suzuki coupling procedure employed N-(1,3-benzoxazol-2-yl)-N-[4-(4,4,5,5-tetramethyl-1,3,2-dioxaborolan-2-yl)phenyl]amine. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 5.5-7.0 min) afforded N1-[2-(dimethylamino)ethyl]-2-{4-amino-3-[4-(1,3-benzoxazol-2-ylamino)phenyl]-1H-pyrazolo[3,4-d]pyrimidin-1-yl}propanamide as an off-white solid (0.003 g, 0.006 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 6.70 min; MS (MH)$^+$ 486.

Example 134 cis-N-2-(4-{4-Amino-1-[4-(4-methylpiperazino)
cyclohexyl]-1H-pyrazolo[3,4-d]pyrimidin-3-
yl}phenyl)-5-ethyl-4-(4-methylphenyl)-1,3-thiazol-
2-amine p-Tolylboronic acid (0.150 g, 1.10 mmol), tetrakis(triphenylphosphine)palladium(0) (0.064 g, 0.055 mmol), and cesium carbonate (1.80 g, 5.52 mmol) were suspended in toluene (25 mL). The reaction mixture was purged under a vigorous flow of nitrogen for 15 minutes. Butyryl chloride (0.344 mL, 3.31 mmol) was added, and the reaction mixture was heated at 100° C. under an atmosphere of nitrogen for 24 h. The reaction mixture was cooled to ambient temperature and diluted with ether (100 mL). The organic layer was extracted sequentially with water (10 mL), aqueous sodium bicarbonate (10 mL), and aqueous sodium chloride (10 mL). The organic layer was dried (magnesium sulfate), filtered, and concentrated. Purification of the residue by flash column chromatography (7.5% ether/petroleum ether) afforded 1-(4-methylphenyl)-1-butanone as a colorless oil (0.134 g, 0.827 mmol); $^1$H NMR (CDCl$_3$, 400 MHz) δ 7.86 (d, 2H), 7.25 (d, 2H), 2.92 (t, 2H), 2.41 (s, 3H), 1.76 (sx, 2H), 1.00 (t, 3H).

1-(4-Methylphenyl)-1-butanone (0.134 g, 0.827 mmol) was converted to the title compound using the procedure described in the preparation of cis-N-2-(4-{4-amino-1-[4-

(4-methylpiperazino)cyclohexyl]-1H-pyrazolo[3,4-d]pyrimidin-3-yl}phenyl)-5,6-dihydro-4H-cyclopenta[d][1,3]thiazol-2-amine. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 10.0-12.0 min) afforded cis-N-2-(4-{4-amino-1-[4-(4-methylpiperazino)cyclohexyl]-1H-pyrazolo[3,4-d]pyrimidin-3-yl}phenyl)-5-ethyl-4-(4-methylphenyl)-1,3-thiazol-2-amine as an off-white solid (0.036 g, 0.059 mmol);

RP-HPLC (25 to 100% acetonitrile in 0.1 M aqueous ammonium acetate over 10 min at 1 mL/min using a 5μ Hypersil HS C18, 250×4.6 mm column) $R_t$ 10.13 min; MS (MH)$^+$ 608.

Example 135 cis-N-2-(4-{4-Amino-1-[4-(4-methylpiperazino)cyclohexyl]-1H-pyrazolo[3,4-d]pyrimidin-3-yl}phenyl)-5-ethyl-4-(2-methylphenyl)-1,3-thiazol-2-amine The procedure described for cis-N-2-(4-{4-amino-1-[4-(4-methylpiperazino)cyclohexyl]-1H-pyrazolo[3,4-d]pyrimidin-3-yl}phenyl)-5-ethyl-4-(4-methylphenyl)-1,3-thiazol-2-amine was used to convert o-tolylboronic acid (0.200 g, 1.47 mmol) to the title compound. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 9.8-11.7 min) afforded cis-N-2-(4-{4-amino-1-[4-(4-methylpiperazino)cyclohexyl]-1H-pyrazolo[3,4-d]pyrimidin-3-yl}phenyl)-5-ethyl-4-(2-methylphenyl)-1,3-thiazol-2-amine as an off-white solid (0.075 g, 0.123 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 9.83 min; MS (MH)$^+$ 608.

Example 138 cis-N-2-(4-{4-Amino-1-[4-(4-methylpiperazino)cyclohexyl]-1H-pyrazolo[3,4-d]pyrimidin-3-yl}phenyl)-5-ethyl-4-(3-methylphenyl)-1,3-thiazol-2-amine The procedure described for cis-N-2-(4-{4-amino-1-[4-(4-methylpiperazino)cyclohexyl]-1H-pyrazolo[3,4-d]pyrimidin-3-yl}phenyl)-5-ethyl-4-(4-methylphenyl)-1,3-thiazol-2-amine was used to convert m-tolylboronic acid (0.175 g, 1.29 mmol) to the title compound. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 10.0-12.0 min) afforded cis-N-2-(4-{4-amino-1-[4-(4-methylpiperazino)cyclohexyl]-1H-pyrazolo[3,4-d]pyrimidin-3-yl}phenyl)-5-ethyl-4-(3-methylphenyl)-1,3-thiazol-2-amine as an off-white solid (0.051 g, 0.084 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 10.13 min; MS (MH)$^+$ 608.

Example 139

Cis-N-2-{4-(4-amino-1-(4-(4-methylpiperazino)cyclohexyl)-1H-pyrazolo[3,4-d]pyrimidin-3-yl)-2-methoxyphenyl}-1H-2-indolecarboxamide bismaleate A mixture of cis-3-(4-amino-3-methoxyphenyl)-1-[4-(4-methylpiperazino)cyclohexyl-1H-pyrazolo[3,4-d]pyrimidin-4-amine (0.50 g, 1.15 mmol) in dichloromethane (4 mL) and pyridine (4 mL) was cooled to 0° C. then treated with 1H-2-indolecarbonyl chloride (0.27 g, 1.49 mmol) in dichloromethane (4 mL). The mixture was allowed to warm to ambient temperature and stirred for one hour. The solvents were evaporated under reduced pressure then the residue was partitioned between dichloromethane (50 mL) and 1 N aqueous sodium hydroxide. The layers were separated then the organic solution was dried over magnesium sulfate, filtered and the filtrate concentrated under reduced pressure to yield a residue which was purified by flash chromatography on silica using dichloromethane-methanol (7:3) as mobile phase. The solid (0.53 g) was dissolved in ethyl acetate (60 mL) and ethanol (35 mL) by warming to 60° C. Maleic acid (0.32 g, 2.75 mmol) in ethyl acetate (5 mL) was added then the mixture was cooled to 0° C. The solid which formed was collected by filtration to give (0.70 g, 0.86 mmol) Cis-N-2-{4-(4-amino-1-(4-(4-methylpiperazino)cyclohexyl)-1H-pyrazolo[3,4-d]pyrimidin-3-yl)-2-methoxyphenyl}-1H-2-indolecarboxamide bismaleate: $^1$H NMR (DMSO-d$_6$, 400 MHz) δ 11.82 (s, 1H), 9.46 (s, 1H), 8.26 (s, 1H), 8.10 (d, 1H), 7.68 (d, 1H), 7.48 (d, 1H), 7.40 (s, 1H), 7.33 (s, 1H), 7.30 (d, 1H), 7.24 (t, 1H), 7.09 (t, 1H), 6.14 (s, 4H), 4.88 (m, 1H), 3.97 (s, 3H), 2.3-3.3 (m, 14H), 2.09 (m, 2H), 1.7-1.8 (m, 4H);

RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.22 min;

MS: MH$^+$ 580.3.

Example 140

Cis-N-2-{4-4-amino-1-[4-(4-methylpiperazino)cyclohexyl]-1H-pyrazolo[3,4-d]pyrimidin-3-yl-2-methoxyphenyl}-1-methyl-1H-2-indolecarboxamide bismaleate The title compound was prepared from cis-3-(4-amino-3-methoxyphenyl)-1-[4-(4-methylpiperazino)cyclohexyl-1H-pyrazolo[3,4-d]pyrimidin-4-amine and 1-methyl-1H-2-indolecarbonyl chloride in a similar manner as described for the preparation of Cis-N-2-{4-(4-amino-1-(4-(4-methylpiperazino)cyclohexyl)-1H-pyrazolo[3,4-d]pyrimidin-3-yl)-2-methoxyphenyl}-1H-2-indolecarboxamide bismaleate: $^1$H NMR (DMSO-d$_6$, 400 MHz) δ 9.47 (s, 1H), 8.26 (s, 1H), 8.09 (d, 1H), 7.71 (d, 1H), 7.59 (d, 1H), 7.17-7.36 (m, 4H), 7.16 (t, 1H), 6.16 (s, 4H), 4.88 (m, 1H), 3.96 (s, 3H), 2.3-3.3 (m, 14H), 2.09 (m, 2H), 1.7-1.8 (m, 4H); RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.98 min;

MS: MH$^+$ 594.3.

Example 141

N1-{4-[4-amino-1-(4-piperidyl)-1H-pyrazolo[3,4-d]pyrimidin-3-yl]-2-methoxyphenyl}-2-fluoro-4-(trifluoromethyl)benzamide acetate A. 2-methoxy-4-(4,4,5,5-tetramethyl-1,3,2-dioxaborolan-2-yl)aniline A mixture of tert-butyl N-[2-methoxy-4-(4,4,5,5-tetramethyl-1,3,2-dioxaborolan-2-yl)phenyl]carbamate (45.0 g, 0.129 mol) was dissolved in dichloromethane (270 mL) then the solution was cooled to 5° C. in and ice bath. A mixture of 20% trifluoroacetic acid in dichloromethane was added dropwise over the course of one hour while maintaining the temperature of the mixture at <5° C. The reaction mixture was warmed to ambient temperature and stirred for 2 hours. The solvents were removed under reduced pressure then the resulting oil was dissolved in dichloromethane (250 mL) and cautiously extracted with 2.5 N aqueous sodium hydroxide (300 mL) then brine (100 mL). The organic solution was dried over magnesium sulfate, filtered and the fitrate concentrated under reduced pressure to give 2-methoxy-4-(4,4,5,5-tetramethyl-1,3,2-dioxaborolan-2-yl)aniline (21.7 g, 67.5%) as a light brown solid bismaleate: $^1$H NMR (DMSO-$d_6$, 400 MHz) δ 7.06 (d, 1H), 6.98 (s, 1H), 8.09 (d, 1H), 6.59 (d, 1H), 5.13 (bs, 2H), 3.76 (s, 3H), 1.26 (s, 12H); RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 10.85 min.

B. tert-butyl 4-[4-amino-3-(4-amino-3-methoxyphenyl)-1H-pyrazolo[3,4-d]pyrimidin-1-yl]-1-piperidinecarboxylate A mixture of tert-butyl 4-(4-amino-3-iodo-1H-pyrazolo[3,4-d]pyrimidin-1-yl)-1-piperidinecarboxylate (0.50 g, 11.26 mmol), 2-methoxy-4-(4,4,5,5-tetramethyl-1,3,2-dioxaborolan-2-yl)aniline (3.10 g, 12.39 mmol), sodium carbonate (2.90 g, 27.0 mmol) and tetrakis(triphenylphosphine)palladium (0.78 g, 0.67 mmol) in ethylene glycol dimethyl ether (90 mL) and water (45 mL) was heated at 85° C. for 18 hours. The mixture was cooled and evaporated under reduced pressure then partitioned between water (50 mL) and dichloromethane (150 mL). The aqueous layer was extracted further with dichloromethane (2×50 mL) then the combined organic solutions were dried over magnesium sulfate and then filtered. The filtrate was concentrated and purified by flash chromatography on silica gel using dichloromethane/methanol (96:4) as an eluent to provide the title compound (4.51 g, 91%) as a tan solid: $^1$H NMR (DMSO-$d_6$, 400 MHz) δ 8.20 (s, 1H), 7.04 (s, 1H), 6.98 (d, 1H), 6.76 (d, 1H), 5.06 (bs, 1H), 4.86 (m, 1H), 4.08 (m, 2H), 3.83 (s, 3H), 2.90 (m, 2H), 2.03 (m, 2H), 1.90 (m, 2H), 1.43 (s, 9H); RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 9.70 min.

C. N1-{4-[4-amino-1-(4-piperidyl)-1H-pyrazolo[3,4-d]pyrimidin-3-yl]-2-methoxyphenyl}-2-fluoro-4-(trifluoromethyl)benzamide acetate A mixture of tert-butyl 4-[4-amino-3-(4-amino-3-methoxyphenyl)-1H-pyrazolo[3,4-d]pyrimidin-1-yl]-1-piperidinecarboxylate (0.10 g, 0.228 mmol) in dichloromethane (2 mL) and pyridine (1 mL) was treated with 2-fluoro-4-trifluoromethylbenzoyl chloride (0.057 g, 0.251 mmol) then stirred for 1 hour. The solvents were evaporated then the residue was treated with trifluoroacetic acid (1 mL) in dichloromethane (2 mL). The mixture was stirred for 1 hour at ambient temperature then the solvents were evaporated under reduced pressure and the residue purified by RP preparative HPLC on a C18 column using acetonitrile-0.05 M ammonium acetate as a mobile phase. Lyophilization afforded the pure title compound: $^1$H NMR (DMSO-$d_6$, 400 MHz) δ 9.90 (d, 1H), 8.31 (d, 1H), 8.24 (s, 1H), 7.99 (t, 1H), 7.89 (d, 1H), 7.75 (d, 1H), 7.33 (s, 1H), 7.30 (d, 1H), 4.78 (m, 1H), 3.94 (s, 3H), 3.10 (m, 2H), 2.69 (m, 2H), 2.08 (m, 2H), 1.85-2.0 (m, 5H); RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 17.33 min;
MS: MH$^+$ 530.2.

Examples 142-216 were prepared from tert-butyl 4-[4-amino-3-(4-amino-3-methoxyphenyl)-1H-pyrazolo[3,4-d]pyrimidin-1-yl]-1-piperidinecarboxylate and the appropriate acid chloride in a manner similar to that described for the preparation of N1-{4-[4-amino-1-(4-piperidyl)-1H-pyrazolo[3,4-d]pyrimidin-3-yl]-2-methoxyphenyl}-2-fluoro-4-(trifluoromethyl)benzamide acetate. In several cases functional group manipulation using standard organic chemistry techniques was required to obtain the desired compound. Free bases were obtained by partitioning the material obtained after preparative HPLC purification between aqueous sodium hydroxide and dichloromethane. The organic layer was dried over magnesium sulfate then filtered and the filtrate concentrated to provide the desired product.

Example 143

N1-{4-[4-amino-1-(4-piperidyl)-1H-pyrazolo[3,4-d]pyrimidin-3-yl]-2-methoxyphenyl}-3-fluoro-4-(trifluoromethyl)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 17.12 min; MS: MH$^+$ 530.2.

Example 144

N1-{4-[4-amino-1-(4-piperidyl)-1H-pyrazolo[3,4-d]pyrimidin-3-yl]-2-methoxyphenyl}benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.20 min; MS: MH$^+$ 444.1.

Example 145

N1-{4-[4-amino-1-(4-piperidyl)-1H-pyrazolo[3,4-d]pyrimidin-3-yl]-2-methoxyphenyl}-3-phenylpropanamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.97 min; MS: MH$^+$ 472.2.

Example 146

N1-{4-[4-amino-1-(4-piperidyl)-1H-pyrazolo[3,4-d]pyrimidin-3-yl]-2-methoxyphenyl}-3-cyclopentylpropanamide bisacetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.95 min; MS: MH$^+$ 464.2.

Example 147

N5-{4-[4-amino-1-(4-piperidyl)-1H-pyrazolo[3,4-d]pyrimidin-3-yl]-2-methoxyphenyl}-1,3-dimethyl-1H-5-pyrazolecarboxamide bisacetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 11.62 min; MS: MH$^+$ 462.2.

Example 148

N1-{4-[4-amino-1-(4-piperidyl)-1H-pyrazolo[3,4-d]pyrimidin-3-yl]-2-methoxyphenyl}-2-(2-thienyl)acetamide bisacetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.17 min; MS: MH$^+$ 464.2.

Example 149

N1-{4-[4-amino-1-(4-piperidyl)-1H-pyrazolo[3,4-d]pyrimidin-3-yl]-2-methoxyphenyl}-2-phenylacetamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.63 min; MS: MH$^+$ 458.2.

Example 150

N1-{4-[4-amino-1-(4-piperidyl)-1H-pyrazolo[3,4-d]pyrimidin-3-yl]-2-methoxyphenyl}-2-(3,4-dimethoxyphenyl)acetamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.20 min; MS: MH$^+$ 518.3.

Example 151

N1-{-4-[4-amino-1-(4-piperidyl)-1H-pyrazolo[3,4-d]pyrimidin-3-yl]-2-methoxyphenyl}-2-phenoxypropanamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.43 min; MS: MH$^+$ 488.2.

Example 152

N5-{4-[4-amino-1-(4-piperidyl)-1H-pyrazolo[3,4-d]pyrimidin-3-yl]-2-methoxyphenyl}-5-isoxazolecarboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 10.93 min; MS: MH$^+$ 433.1.

Example 153

N2-{4-[4-amino-1-(4-piperidyl)-1H-pyrazolo[3,4-d]pyrimidin-3-yl]-2-methoxyphenyl}-2-pyridinecarboxamide triacetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.52 min; MS: MH$^+$ 445.2.

Example 154

N1-{4-[4-amino-1-(4-piperidyl)-1H-pyrazolo[3,4-d]pyrimidin-3-yl]-2-methoxyphenyl}-2,4-difluorobenzamide bisacetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.65 min; MS: MH$^+$ 480.1.

Example 155

N1-{4-[4-amino-1-(4-piperidyl)-1H-pyrazolo[3,4-d]pyrimidin-3-yl]-2-methoxyphenyl}-2,5-difluorobenzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.75 min; MS: MH$^+$ 480.2.

Example 156

N2-{4-[4-amino-1-(4-piperidyl)-1H-pyrazolo[3,4-d]pyrimidin-3-yl]-2-methoxyphenyl}-2-furamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) t, 13.40 min; MS: MH$^+$ 434.2.

Example 157

N1-{4-[4-amino-1-(4-piperidyl)-1H-pyrazolo[3,4-d]pyrimidin-3-yl]-2-methoxyphenyl}-2,2-dimethylpropanamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.53 min; MS: MH$^+$ 424.2.

Example 158

N1-{4-[4-amino-1-(4-piperidyl)-1H-pyrazolo[3,4-d]pyrimidin-3-yl]-2-methoxyphenyl}-4-cyanobenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.68 min; MS: MH$^+$ 469.2.

Example 159

N1-{4-[4-amino-1-(4-piperidyl)-1H-pyrazolo[3,4-d]pyrimidin-3-yl]-2-methoxyphenyl}-1-cyclopropanecarboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 11.05 min; MS: MH$^+$ 408.2.

Example 160

N3-{4-[4-amino-1-(4-piperidyl)-1H-pyrazolo[3,4-d]pyrimidin-3-yl]-2-methoxyphenyl}-2-methylnicotinamide acetate RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 11.53 min; MS: MH$^+$ 459.1.

Example 161

N1-{4-[4-amino-1-(4-piperidyl)-1H-pyrazolo[3,4-d]pyrimidin-3-yl]-2-methoxyphenyl}-4-fluoro-3-methylbenzamide RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 15.32 min; MS: MH$^+$ 476.2.

Example 162

N1-1-{4-[4-amino-1-(4-piperidyl)-1H-pyrazolo[3,4-d]pyrimidin-3-yl]-2-methoxyphenyl}-3-(dimethylamino)benzamide RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 14.63 min; MS: MH$^+$ 487.2.

Example 163

N1-{4-[4-amino-1-(4-piperidyl)-1H-pyrazolo[3,4-d]pyrimidin-3-yl]-2-methoxyphenyl}-2,3-difluoro-4-methylbenzamide RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 16.03 min; MS: MH$^+$ 494.2.

Example 164

N4-{4-[4-amino-1-(4-piperidyl)-1H-pyrazolo[3,4-d]pyrimidin-3-yl]-2-methoxyphenyl}isonicotinamide bisacetate RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 15.77 min; MS: MH$^+$ 445.1.

Example 165

N3-{4-[4-amino-1-(4-piperidyl)-1H-pyrazolo[3,4-d]pyrimidin-3-yl]-2-methoxyphenyl}nicotinamide acetate RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 17.50 min; MS: MH$^+$ 445.1.

Example 166

N2-{-[4-amino-1-(4-piperidyl)-1H-pyrazolo[3,4-d]pyrimidin-3-yl]-2-methoxyphenyl}-1-methyl-1H-2-pyrrolecarboxamide acetate RP-HPLC (Hypersil HS C18 Hypersil HS C18, 5 µm, 100A, 250×4.6 mm; 5%-50% acetonitrile-0.05 M ammonium acetate over 25 min, 1 mL/min) $t_r$ 22.20 min; MS: MH$^+$ 447.2.

Example 167

N3-{4-[4-amino-1-(4-piperidyl)-1H-pyrazolo[3,4-d]pyrimidin-3-yl]-2-methoxyphenyl}-6-methylnicotinamide acetate RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 17.97 min; MS: MH$^+$ 459.2.

Example 168

N2-{4-[4-amino-1-(4-piperidyl)-1H-pyrazolo[3,4-d]pyrimidin-3-yl]-2-methoxyphenyl}-2-pyrazinecarboxamide acetate RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 17.63 min; MS: MH$^+$ 446.1.

Example 169

N1-{4-[4-amino-1-(4-piperidyl)-1H-pyrazolo[3,4-d]pyrimidin-3-yl]-2-methoxyphenyl}-4-iodobenzamide bisacetate RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 16.08 min; MS: MH$^+$ 570.1.

Example 170

N1-{4-[4-amino-1-(4-piperidyl)-1H-pyrazolo[3,4-d]pyrimidin-3-yl]-2-methoxyphenyl}-4-bromobenzamide RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 15.42 min; MS: MH$^+$ 524.1.

Example 171

N1-{4-[4-amino-1-(4-piperidyl)-1H-pyrazolo[3,4-d]pyrimidin-3-yl]-2-methoxyphenyl}-4-phenoxybenzamide RP-HPLC (Hypersil HS C18 Hypersil HS C18, 5 µm, 100A, 250×4.6 mm; 5%-100% acetonitrile-0.05 M ammonium acetate over 25 min, 1 mL/min) $t_r$ 17.17 min; MS: MH$^+$ 536.2.

Example 172

N1-4-[4-amino-1-(4-piperidyl)-1H-pyrazolo[3,4-d]
pyrimidin-3-yl]-2-methoxyphenyl-4-fluorobenza-
mide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.65 min; MS: MH$^+$ 462.1.

Example 173

N1-{4-[4-amino-1-(4-piperidyl)-1H-pyrazolo[3,4-d]
pyrimidin-3-yl]-2-methoxyphenyl}-4-chlorobenza-
mide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.57 min; MS: MH$^+$ 478.2.

Example 174

N1-{4-[4-amino-1-(4-piperidyl)-1H-pyrazolo[3,4-d]
pyrimidin-3-yl]-2-methoxyphenyl}-4-methoxyben-
zamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.62 min; MS: MH$^+$ 474.2.

Example 175

N1-{4-[4-amino-1-(4-piperidyl)-1H-pyrazolo[3,4-d]
pyrimidin-3-yl]-2-methoxyphenyl}-4-(trifluo-
romethoxy)benzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.30 min; MS: MH$^+$ 528.2.

Example 176

N1-{4-[4-amino-1-(4-piperidyl)-1H-pyrazolo[3,4-d]
pyrimidin-3-yl]-2-methoxyphenyl}-4-nitrobenza-
mide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.77 min; MS: MH$^+$ 489.2.

Example 177

N2-{4-[4-amino-1-(4-piperidyl)-1H-pyrazolo[3,4-d]
pyrimidin-3-yl]-2-methoxyphenyl}benzo[b]
thiophene-2-carboxamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.12 min; MS: MH$^+$ 500.2.

Example 178

N2-{4-[4-amino-1-(4-piperidyl)-1H-pyrazolo[3,4-d]
pyrimidin-3-yl]-2-methoxyphenyl}benzo[b]furan-2-
carboxamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.70 min; MS: MH$^+$ 484.2.

Example 179

N1-{4-[4-amino-1-(4-piperidyl)-1H-pyrazolo[3,4-d]
pyrimidin-3-yl]-2-methoxyphenyl}-4-methylbenza-
mide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.47 min; MS: MH$^+$ 458.2.

Example 180

N1-{4-[4-amino-1-(4-piperidyl)-1H-pyrazolo[3,4-d]
pyrimidin-3-yl]-2-methoxyphenyl}-4-(tert-butyl)
benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 17.93 min; MS: MH$^+$ 500.2.

Example 181 methyl 4-{(4-[4-amino-1-(4-piperidyl)-1H-pyrazolo
[3,4-d]pyrimidin-3-yl]-2-methoxyanilino}carbonyl)
benzoate acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.70 min; MS: MH$^+$ 502.1.

Example 182

4-{(4-[4-amino-1-(4-piperidyl)-1H-pyrazolo[3,4-d]
pyrimidin-3-yl]-2-methoxyanilino}carbonyl)benzoic
acid RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 10.02 min; MS: MH$^+$ 478.1.

Example 183

N1-{4-[4-amino-1-(4-piperidyl)-1H-pyrazolo[3,4-d]
pyrimidin-3-yl]-2-methoxyphenyl}-2-chlorobenza-
mide acetate RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 7.28 min; MS: MH$^+$ 478.1.

Example 184

N1-{4-[4-amino-1-(4-piperidyl)-1H-pyrazolo [3,4-d]pyrimidin-3-yl]-2-methoxyphenyl}-2-bromobenzamide acetate RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 7.42 min; MS: $MH^+$ 524.1.

Example 185

N1-{4-[4-amino-1-(4-piperidyl)-1H-pyrazolo[3,4-d]pyrimidin-3-yl]-2-methoxyphenyl}-2-methoxybenzamide acetate RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 7.87 min; MS: $MH^+$ 474.2.

Example 186

N1-{4-[4-amino-1-(4-piperidyl)-1H-pyrazolo[3,4-d]pyrimidin-3-yl]-2-methoxyphenyl}-2-phenylbenzamide RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 8.27 min; MS: $MH^+$ 520.2.

Example 187

N1-{4-[4-amino-1-(4-piperidyl)-1H-pyrazolo[3,4-d]pyrimidin-3-yl]-2-methoxyphenyl}-2-(trifluoromethyl)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.07 min; MS: $MH^+$ 512.2.

Example 188

N1-{4-[4-amino-1-(4-piperidyl)-1H-pyrazolo[3,4-d]pyrimidin-3-yl]-2-methoxyphenyl}-2-(trifluoromethoxy)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.77 min; MS: $MH^+$ 528.2.

Example 189

N1-{4-[4-amino-1-(4-piperidyl)-1H-pyrazolo[3,4-d]pyrimidin-3-yl]-2-methoxyphenyl}-3-methoxybenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.43 min; MS: $MH^+$ 474.2.

Example 190

N1-{4-[4-amino-1-(4-piperidyl)-1H-pyrazolo[3,4-d]pyrimidin-3-yl]-2-methoxyphenyl}-3-(trifluoromethyl)benzamide RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 8.15 min; MS: $MH^+$ 512.2.

Example 191

N1-{4-[4-amino-1-(4-piperidyl)-1H-pyrazolo[3,4-d]pyrimidin-3-yl]-2-methoxyphenyl}-2-fluoro-3-(trifluoromethyl)benzamide acetate RP-HPLC (Hypersil HS C18 Hypersil HS C18, 5 μm, 100A, 250×4.6 mm; 25%-100% acetonitrile-0.05 M ammonium acetate over 10 min, 1 mL/min) $t_r$ 8.50 nm; MS: $MH^+$ 530.2.

Example 192

N1-{4-[4-amino-1-(4-piperidyl)-1H-pyrazolo[3,4-d]pyrimidin-3-yl]-2-methoxyphenyl}-2-fluoro-6-(trifluoromethyl)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.30 min; MS: $MH^+$ 530.2.

Example 193

N1-{4-[4-amino-1-(4-piperidyl)-1H-pyrazolo[3,4-d]pyrimidin-3-yl]-2-methoxyphenyl}-2-fluoro-5-(trifluoromethyl)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.68 min; MS: $MH^+$ 530.2.

Example 194

N1-{4-[4-amino-1-(4-piperidyl)-1H-pyrazolo[3,4-d]pyrimidin-3-yl]-2-methoxyphenyl}-2-fluoro-5-methylbenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.32 min; MS: $MH^+$ 476.2.

Example 195

N1-{4-[4-amino-1-(4-piperidyl)-1H-pyrazolo[3,4-d]pyrimidin-3-yl]-2-methoxyphenyl}-4-chloro-2-fluorobenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.50 min; MS: $MH^+$ 496.1.

Example 196

N1-{4-[4-amino-1-(4-piperidyl)-1H-pyrazolo[3,4-d]pyrimidin-3-yl]-2-methoxyphenyl}-4-benzoylbenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.33 min; MS: MH$^+$ 548.2.

Example 197

N1-{4-[4-amino-1-(4-piperidyl)-1H-pyrazolo[3,4-d]pyrimidin-3-yl]-2-methoxyphenyl}-4-acetylbenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.77 min; MS: MH$^+$ 486.2.

Example 198

N1-{4-[4-amino-1-(4-piperidyl)-1H-pyrazolo[3,4-d]pyrimidin-3-yl]-2-methoxyphenyl}-4-isopropylbenzamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 17.10 min; MS: MH$^+$ 486.2.

Example 199

N1-{4-[4-amino-1-(4-piperidyl)-1H-pyrazolo[3,4-d]pyrimidin-3-yl]-2-methoxyphenyl}-4-ethylbenzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.85 min; MS: MH$^+$ 472.2.

Example 200

N1-{4-[4-amino-1-(4-piperidyl)-1H-pyrazolo[3,4-d]pyrimidin-3-yl]-2-methoxyphenyl}-4-propylbenzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 17.02 min; MS: MH$^+$ 486.2.

Example 201

N1-{4-[4-amino-1-(4-piperidyl)-1H-pyrazolo[3,4-d]pyrimidin-3-yl]-2-methoxyphenyl}-4-cyclohexylbenzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 19.55 min; MS: MH$^+$ 526.2.

Example 202

N1-1-{4-[4-amino-1-(4-piperidyl)-1H-pyrazolo[3,4-d]pyrimidin-3-yl]-2-methoxyphenyl}-4-ethoxybenzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.28 min; MS: MH$^+$ 488.2.

Example 203

N1-{4-[4-amino-1-(4-piperidyl)-1H-pyrazolo [3,4-d]pyrimidin-3-yl]-2-methoxyphenyl}-4-(methylsulfonyl)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.01 min; MS: MH$^+$ 527.2.

Example 204

N1-{4-[4-amino-1-(4-piperidyl)-1H-pyrazolo[3,4-d]pyrimidin-3-yl]-2-methoxyphenyl}-4-sopropoxybenzamide bisacetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.20 min; MS: MH$^+$ 502.2.

Example 205

N1-{4-[4-amino-1-(4-piperidyl)-1H-pyrazolo[3,4-d]pyrimidin-3-yl]-2-methoxyphenyl}-4-(1H-1-imidazolyl)benzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.02 min; MS: MH$^+$ 510.2.

Example 206

N1-{4-[4-amino-1-(4-piperidyl)-1H-pyrazolo[3,4-d]pyrimidin-3-yl]-2-methoxyphenyl}-2-fluorobenzamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.60 min; MS: MH$^+$ 462.3.

Example 207

N2-1-{4-[4-amino-1-(4-piperidyl)-1H-pyrazolo[3,4-d]pyrimidin-3-yl]-2-methoxyphenyl}-5-methoxybenzo[b]furan-2-carboxamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.38 min; MS: MH$^+$ 514.3.

Example 208

N2-1-{4-[4-amino-1-(4-piperidyl)-1H-pyrazolo[3,4-d]pyrimidin-3-yl]-2-methoxyphenyl}-5-bromobenzo[b]furan-2-carboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 17.03 min; MS: MH$^+$ 564.1.

Example 209

N2-1-{4-[4-amino-1-(4-piperidyl)-1H-pyrazolo[3,4-d]pyrimidin-3-yl]-2-methoxyphenyl}-5-methylbenzo[b]furan-2-carboxamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.27 min; MS: MH$^+$ 498.3.

Example 210

N2-{4-[4-amino-1-(4-piperidyl)-1H-pyrazolo[3,4-d]pyrimidin-3-yl]-2-methoxyphenyl}-3-methylbenzo[b]furan-2-carboxamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 16.67 min; MS: MH$^+$ 498.3.

Example 211

N2-{4-[4-amino-1-(4-piperidyl)-1H-pyrazolo[3,4-d]pyrimidin-3-yl]-2-methoxyphenyl}-5-nitrobenzo[b]furan-2-carboxamide RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 15.33 min; MS: MH$^+$ 529.2.

Example 212

N2-{4-[4-amino-1-(4-piperidyl)-1H-pyrazolo[3,4-d]pyrimidin-3-yl]-2-methoxyphenyl}-5-aminobenzo[b]furan-2-carboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 11.93 min; MS: MH$^+$ 499.3.

Example 213

N2-{4-[4-(acetylamino)-1-(4-piperidyl)-1H-pyrazolo[3,4-d]pyrimidin-3-yl]-2-methoxyphenyl}-5-(acetylamino)benzo[b]furan-2-carboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 12.47 min; MS: MH$^+$ 583.2.

Example 214

N2-{4-[4-amino-1-(4-piperidyl)-1H-pyrazolo[3,4-d]pyrimidin-3-yl]-2-methoxyphenyl}-5-(acetylamino)benzo[b]furan-2-carboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 11.95 min; MS: MH$^+$ 541.2.

Example 215

N2-{4-[4-amino-1-(4-piperidyl)-1H-pyrazolo[3,4-d]pyrimidin-3-yl]-2-methoxyphenyl}-7-methylbenzo[b]furan-2-carboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 14.23 min; MS: MH$^+$ 498.3.

Example 216

N2-{4-[4-amino-1-(4-piperidyl)-1H-pyrazolo[3,4-d]pyrimidin-3-yl]-2-methoxyphenyl}-7-methoxybenzo[b]furan-2-carboxamide acetate RP-HPLC (Hypersil HS C18 Hypersil HS C18, 5 μm, 100A, 250×4.6 mm; 5%-100% acetonitrile-0.05 M ammonium acetate over 25 min, 1 mL/min) $t_r$ 13.03 min; MS: MH$^+$ 514.3.

Example 217 rac-N-2-{4-[4-Amino-1-(1-methyltetrahydro-1H-3-pyrrolyl)-1H-pyrazolo[3,4-d]pyrimidin-3-yl]phenyl}-5,7-dimethyl-1,3-benzoxazol-2-amine

A. rac-tert-butyl 3-hydroxy-1-pyrrolidinecarboxylate

To a solution of 3-pyrrolidinol (3.144 g, 3.00 mL, 36.09 mmol) in 1,4-dioxane (50 mL) and water (50 mL) was added di-tert-butyl dicarbonate (8.664 g, 39.70 mmol) and sodium bicarbonate (10.612 g, 126.3 mmol). The mixture was stirred at room temperature for 18 h to afford a white suspension in a yellow solution. The reaction mixture was filtered and the filtrate was extracted with ethyl acetate (2×50 mL). The combined organic phases were washed with brine, dried over anhydrous magnesium sulfate, filtered, and concentrated to afford rac-tert-butyl 3-hydroxy-1-pyrrolidinecarboxylate as a pale yellow oil (6.039 g, 89%). $^1$H NMR (DMSO-d$_6$, 400 MHz) δ 1.51 (s, 9H), 1.84-2.05 (m, 2H), 2.28 (d, 1H), 3.33-3.48 (m, 4H), 4.43 (s, 1H).

B. rac-3-Iodo-1-tetrahydro-1H-3-pyrrolyl-1H-pyrazolo[3,4-d]pyrimidin-4-amine monohydrochloride To a solution of 3-iodo-1H-pyrazolo[3,4-d]pyrimidin-4-amine (5.610 g, 21.49 mmol) in tetrahydrofuran (200 mL) was added rac-tert-butyl 3-hydroxy-1-pyrrolidinecarboxylate (6.039 g, 32.25 mmol), triphenylphosphine (11.273 g, 42.98 mmol), and diethyl azodicarboxylate (7.485 g, 6.77 mL, 42.98 mmol). The reaction mixture was stirred at room temperature for 6 days and then concentrated to afford an orange-brown oil. Acetone (100 mL) and 5 N hydrochloric acid (50 mL) were added and the solution was heated at 40° C. for 18 h and then cooled to room temperature. The resulting yellow precipitate was filtered, and the filter cake was washed with diethyl ether and dried to afford rac-3-iodo-1-tetrahydro-1H-3-pyrrolyl-1H-pyrazolo[3,4-d]pyrimidin-4-amine monohydrochloride as an off-white solid (5.153 g, 65%). RP-HPLC $R_t$ 4.079 min, 99% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 331 (MH$^+$).

C. rac-3-Iodo-1-(1-methyltetrahydro-1H-3-pyrrolyl)-1H-pyrazolo[3,4-d]pyrimidin-4-amine To a solution of rac-3-iodo-1-tetrahydro-1H-3-pyrrolyl-1H-pyrazolo[3,4-d]pyrimidin-4-amine monohydrochloride (0.400 g, 1.09 mmol) in dichloroethane (10 mL) was added formaldehyde (37% in water, 0.12 mL, 1.63 mmol), sodium triacetoxyborohydride (0.578 g, 2.73 mmol), and acetic acid (0.37 mL, 6.55 mmol). The reaction mixture was stirred at room temperature for 3 days and then additional formaldehyde (37% in water, 0.12 mL, 1.63 mmol), sodium triacetoxyborohydride (0.578 g, 2.73 mmol), and acetic acid (0.37 mL, 6.55 mmol) were added. The reaction mixture stirred for an additional 3 h and was then concentrated to afford rac-3-iodo-1-(1-methyltetrahydro-1H-3-pyrrolyl)-1H-pyrazolo[3,4-d]pyrimidin-4-amine as a pale yellow solid (0.639 g) which was used in subsequent reactions without further purification. RP-HPLC $R_t$ 4.226 min, 96% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 345 (MH$^+$).

D. N2-(4-Bromophenyl)-5,7-dimethyl-1,3-benzoxazol-2-amine 1,1'-Thiocarbonyldi-2(1H)-pyridone (1.418 g, 6.104 mmol) was added to a solution of 4-bromoaniline (1.000 g, 5.813 mmol) in dichloromethane (50 mL). The purple solution was stirred at room temperature for 30 min and then washed with water (50 mL) and 0.5 N hydrochloric acid (50 mL), dried over anhydrous magnesium sulfate, filtered, and concentrated to afford a purple solid. 6-Amino-2,4-xylenol (0.837 g, 6.104 mmol) and toluene (50 mL) were added and the mixture was heated at 80° C. for 30 min. 1,3-Dicyclohexylcarbodiimide (1.799 g, 8.720 mmol) was added, and the solution was heated at 80° C. for 48 h and then cooled to room temperature. The resulting precipitate was filtered, and the filter cake was washed with dichloromethane (50 mL) to afford N2-(4-bromophenyl)-5,7-dimethyl-1,3-benzoxazol-2-amine as a pale orange solid (1.215 g, 66%). RP-HPLC Rt 17.643 min, 86% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 317 (MH$^+$).

E. N2-[4-(4,4,5,5-Tetramethyl-1,3,2-dioxaborolan-2-yl)phenyl]-5,7-dimethyl-1,3-benzoxazol-2-amine N2-[4-(4,4,5,5-tetramethyl-1,3,2-dioxaborolan-2-yl)phenyl]-5,7-dimethyl-1,3-benzoxazol-2-amine was prepared from N2-(4-bromophenyl)-5,7-dimethyl-1,3-benzoxazol-2-amine (1.215 g, 3.831 mmol) in a manner similar to that used for the preparation of N2-[2-fluoro-4-(4,4,5,5-tetramethyl-1,3,2-dioxaborolan-2-yl)phenyl]-1,3-benzoxazol-2-amine. The compound was formed as a tan powder (0.880 g, 63%). RP-HPLC (25 to 100% CR$_3$CN in 0.1 N aqueous ammonium acetate over 10 min at 1 mL/min using a Hypersil HS C18, 250×4.6 mm column) Rt=14.48 min, 81%; m/z 365 (MH$^+$).

F. rac-N-2-{4-[4-Amino-1-(1-methyltetrahydro-1H-3-pyrrolyl)-1H-pyrazolo[3;4-d]pyrimidin-3-yl]phenyl}-5,7-dimethyl-1,3-benzoxazol-2-amine rac-N-2-{4-[4-Amino-1-(1-methyltetrahydro-1H-3-pyrrolyl)-1H-pyrazolo[3,4-d]pyrimidin-3-yl]phenyl}-5,7-dimethyl-1,3-benzoxazol-2-amine was prepared from rac-3-iodo-1-(1-methyltetrahydro-1H-3-pyrrolyl)-1H-pyrazolo[3,4-d]pyrimidin-4-amine (0.200 g, 0.581 mmol) and N2-[4-(4,4,5,5-tetramethyl-1,3,2-dioxaborolan-2-yl)phenyl]-5,7-dimethyl-1,3-benzoxazol-2-amine (0.265 g, 0.726 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as a white powder (0.062 g, 23%). $^1$H NMR (DMSO-d$_6$, 400 MHz) 2.39 (s, 3H), 2.32-2.40 (m, 3H), 2.40 (s, 3H), 2.75-2.80 (m, 2H), 3.08 (t, 1H), 3.26 (s, 3H), 5.40 (m, 1H), 6.80 (s, 1H), 7.11 (s, 1H), 7.66 (d, 2H), 7.93 (d, 2H), 8.24 (s, 1H), 10.85 (s, 1H);
RP-HPLC Rt 10.905 min, 96% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 455 (MH$^+$).

Example 218 rac-N-2-(4-{4-Amino-1-[1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine

A. rac-3-Iodo-1-[1-(2-methoxyethyl)tetrahydro-1H-3-pyrrolyl]-1H-pyrazolo[3,4-d]pyrimidin-4-amine To a solution of rac-3-iodo-1-tetrahydro-1H-3-pyrrolyl-1H-pyrazolo[3,4-d]pyrimidin-4-amine mono hydrochloride (0.350 g, 1.09 mmol) in N,N-dimethylformamide (10 mL) was added 2-bromoethylmethyl ether (0.159 g, 0.11 mL, 1.15 mmol), potassium carbonate (0.462 g, 3.34 mmol), and potassium iodide (0.008 g, 0.05 mmol). The reaction mixture was stirred at 65° C. for 18 h and then additional 2-bromoethylmethyl ether (0.066 g, 0.040 mL, 0.48 mmol), potassium carbonate (0.130 g, 0.940 mmol), and potassium iodide (0.008 g, 0.05 mmol) were added. The reaction mixture was stirred for an additional 18 h and was then concentrated. The residue was partitioned between dichloromethane (10 mL) and water (10 mL). The organic phase was separated, washed with brine, dried over anhydrous magnesium sulfate, filtered, and concentrated to afford rac-3-iodo-1-[1-(2-methoxyethyl)tetrahydro-1H-3-pyrrolyl]-1H-pyrazolo[3,4-d]pyrimidin-4-amine as a yellow solid (0.313 g, 84%) which was used in subsequent reactions without further purification. RP-HPLC Rt 5.089 min, 80% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 389 (MH$^+$).

B. rac-N-2-(4-{4-Amino-1-[1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine rac-N-2-(4-{4-Amino-1-[1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine was prepared from rac-3-iodo-1-[1-(2-methoxyethyl)tetrahydro-1H-3-pyrrolyl]-1H-pyrazolo[3,4-d]pyrimidin-4-amine (0.250 g, 0.515 mmol) and N2-[4-(4,4,5,5-tetramethyl-1,3,2-dioxaborolan-2-yl)phenyl]-5,7-dimethyl-1,3-benzoxazol-2-amine (0.235 g, 0.644 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as a yellow powder (0.185 g, 72%). $^1$H NMR (DMSO-$d_6$, 400 MHz) 2.30-2.49 (m, 2H), 2.41 (s, 3H), 2.49 (s, 3H), 2.66 (m, 2H), 2.78 (m, 2H), 3.17 (m. 2H), 3.24 (s, 3H), 3.45 (t, 2H), 5.40 (m, 1H), 6.80 (s, 1H), 7.11 (s, 1H), 7.66 (d, 2H), 7.93 (d, 2H), 8.24 (s, 1H), 10.85 (s, 1H); RP-HPLC Rt 11.477 min, 96% purity (5% to 85% acetonitrile/0.1M aqueous ammonium acetate, buffered to pH 4.5, over 20 min at 1 mL/min; 254 nm; Deltapak C18, 300 Å, 5 μm, 150×3.9 mm column); m/z 499 (MH$^+$).

Example 219

Cis-N-2-(4-{4-amino-1-[4-(4-methylpiperazino)cyclohexyl]-1H-pyrazolo[3,4-d]pyrimidin-3-yl}-2-fluorophenyl)-5,7-dimethyl-1,3-benzoxazol-2-amine A. N2-(4-Bromo-2-fluorophenyl)-5,7-dimethyl-1,3-benzoxazol-2-amine N2-(4-Bromo-2-fluorophenyl)-5,7-dimethyl-1,3-benzoxazol-2-amine was prepared from 4-bromo-2-fluoroaniline (2.000 g, 10.53 mmol) in a manner similar to that used for the preparation of N2-(4-bromophenyl)-5,7-dimethyl-1,3-benzoxazol-2-amine. The compound was formed as a pink solid (1.916 g, 54%). RP-HPLC Rt 17.96 min, 95% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 337 (MH$^+$).

B. N2-[2-Fluoro-4-(4,4,5,5-tetramethyl-1,3,2-dioxaborolan-2-yl)phenyl]-5,7-dimethyl-1,3-benzoxazol-2-amine N2-[2-Fluoro-4-(4,4,5,5-tetramethyl-1,3,2-dioxaborolan-2-yl)phenyl]-5,7-dimethyl-1,3-benzoxazol-2-amine was prepared from N2-(4-bromo-2-fluorophenyl)-5,7-dimethyl-1,3-benzoxazol-2-amine (6.500 g, 19.39 mmol) in a manner similar to that used for the preparation of N2-[2-fluoro-4-(4,4,5,5-tetramethyl-1,3,2-dioxaborolan-2-yl)phenyl]-1,3-benzoxazol-2-amine. The compound was formed as a pink solid (3.549 g, 48%). RP-HPLC (25 to 100% CH$_3$CN in 0.1 N aqueous ammonium acetate over 10 min at 1 mL/min using a Hypersil HS C18, 250×4.6 mm column) Rt=15.50 min, 78%; m/z 383 (MH$^+$).

C. Cis-N-2-(4-{4-amino-1-[4-(4-methylpiperazino)cyclohexyl]-1H-pyrazolo[3,4-d]pyrimidin-3-yl}-2-fluorophenyl)-5,7-dimethyl-1,3-benzoxazol-2-amine Cis-N-2-(4-{4-amino-1-[4-(4-methylpiperazino)cyclohexyl]-1H-pyrazolo[3,4-d]pyrimidin-3-yl}-2-fluorophenyl)-5,7-dimethyl-1,3-benzoxazol-2-amine was prepared from cis-3-iodo-1-[4-(4-methylpiperazino)cyclohexyl]-1H-pyrazolo[3,4-d]pyrimidin-4-amine (0.200 g, 0.453 mmol) and N2-[2-fluoro-4-(4,4,5,5-tetramethyl-1,3,2-dioxaborolan-2-yl)phenyl]-5,7-dimethyl-1,3-benzoxazol-2-amine (0.216 g, 0.566 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as a pale yellow powder (0.111 g, 43%). $^1$H NMR (DMSO-$d_6$, 400 MHz) 1.56-1.83 (m, 4H), 2.15 (s, 3H), 2.22-2.55 (m, 12H), 2.34 (s, 3H), 2.41 (s, 3H), 3.22-3.53 (m, 1H), 4.78-4.83 (m, 1H), 6.81 (s, 1H), 7.10 (s, 1H), 7.45-7.53 (m, 2H), 8.23 (s, 1H), 8.49 (t, 1H), 10.59 (s, 1H); RP-HPLC Rt 11.873 min, 95% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 570 (MH$^+$).

Example 220

Cis-3-(4-imidazo[1,2-a]pyridin-2-ylphenyl)-1-[4-(4-methylpiperazino)cyclohexyl]-1H-pyrazolo[3,4-d]pyrimidin-4-amine A. 2-[4-(4,4,5,5-Tetramethyl-1,3,2-dioxaborolan-2-yl)phenyl]imidazo[1,2-a]pyridine 2-[4-(4,4,5,5-tetramethyl-1,3,2-dioxaborolan-2-yl)phenyl]imidazo[1,2-a]pyridine was prepared from 2-(4-bromophenyl)imidazo[1,2-a]pyridine (0.273 g, 1.00 mmol) in a manner similar to that used for the preparation of N2-[2-fluoro-4-(4,4,5,5-tetramethyl-1,3,2-dioxaborolan-2-yl)phenyl]-1,3-benzoxazol-2-amine. The compound was formed as a white solid (0.250 g, 78%). RP-HPLC (25 to 100% CH$_3$CN in 0.1 N aqueous ammonium acetate over 10 min at 1 mL/min using a Hypersil HS C18, 250×4.6 mm column) Rt=11.35 min, 87%; m/z 321 (MH$^+$).

B. Cis-3-(4-imidazo[1,2-a]pyridin-2-ylphenyl)-1-[4-(4-methylpiperazino)cyclohexyl]-1H-pyrazolo[3,4-d]pyrimidin-4-amine Cis-3-(4-imidazo[1,2-a]pyridin-2-ylphenyl)-1-[4-(4-methylpiperazino)cyclohexyl]-1H-pyrazolo[3,4-d]pyrimidin-4-amine was prepared from cis-3-iodo-1-[4-(4-methylpiperazino)cyclohexyl]-1H-pyrazolo[3,4-d]pyrimidin-4-amine (0.200 g, 0.453 mmol) and 2-[4-(4,4,5,5-tetramethyl-1,3,2-dioxaborolan-2-yl)phenyl]imidazo[1,2-a]pyridine (0.250 g, 0.679 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as a white powder (0.021 g, 9%). $^1$H NMR (DMSO-$d_6$, 400 MHz) 1.57-1.73 (m, 4H), 2.08-2.50 (m, 12H), 2.16 (s, 3H), 3.37 (m, 1H), 4.82 (m, 1H), 6.92 (t, 1H), 7.27 (t, 1H), 7.61 (d, 1H), 7.74 (d, 2H), 8.15 (d, 2H), 8.24 (s, 1H), 8.56 (d, 1H); RP-HPLC Rt 8.16 min, 97% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 508 (MH$^+$).

Example 221 rac-1-[3-(4-Amino-3-{4-[(5,7-dimethyl-1,3-benzoxazol-2-yl)amino]phenyl}-1H-pyrazolo[3,4-d]pyrimidin-1-yl)tetrahydro-1H-1-pyrrolyl]-2-(dimethylamino)-1-ethanone A. rac-1-[3-(4-Amino-3-iodo-1H-pyrazolo[3,4-d]pyrimidin-1-yl)tetrahydro-1H-1-pyrrolyl]-2-(dimethylamino)-1-ethanone To a solution of rac-3-iodo-1-tetrahydro-1H-3-pyrrolyl-1H-pyrazolo[3,4-d]pyrimidin-4-amine monohydrochloride (0.367 g, 1.00 mmol) in dichloromethane (10 mL) was added 2-(dimethylamino)acetic acid (0.134 g, 1.30 mmol), 1-hydroxy-7-azabenzotriazole (0.150 g, 1.10 mmol), 1-(3- dimethylaminopropyl)-3-ethylcarbodiimide hydrochloride (0.249 g, 1.30 mmol), and diisopropylethyl amine (0.65 g, 0.87 mL, 5.0 mmol). The reaction mixture stirred at room temperature for 18 h and was then poured into water (10 mL). The organic phase was separated and washed with brine (10 mL), dried over anhydrous magnesium sulfate, filtered, and concentrated to afford rac-1-[3-(4-amino-3-iodo-1H-pyrazolo[3,4-d]pyrimidin-1-yl)tetrahydro-1H-1-pyrrolyl]-2-(dimethylamino)-1-ethanone as a yellow-orange solid (0.278 g, 67%) which was used in subsequent reactions without further purification.

RP-HPLC Rt 4.881 min, 80% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 416 (MH$^+$).

B. rac-1-[3-(4-Amino-3-{4-[(5,7-dimethyl-1,3-benzoxazol-2-yl)amino]phenyl}-1H-pyrazolo[3,4-d]pyrimidin-1-yl)tetrahydro-1H-1-pyrrolyl]-2-(dimethylamino)-1-ethanone rac-1-[3-(4-Amino-3-{4-[(5,7-dimethyl-1,3-benzoxazol-2-yl)amino]phenyl}-1H-pyrazolo[3,4-d]pyrimidin-1-yl)tetrahydro-1H-1-pyrrolyl]-2-(dimethylamino)-1-ethanone was prepared from rac-1-[3-(4-amino-3-iodo-1H-pyrazolo[3,4-d]pyrimidin-1-yl)tetrahydro-1H-1-pyrrolyl]-2-(dimethylamino)-1-ethanone (0.278 g, 0.669 mmol) and N2-[4-(4,4,5,5-tetramethyl-1,3,2-dioxaborolan-2-yl)phenyl]-5,7-dimethyl-1,3-benzoxazol-2-amine (0.305 g, 0.837 mmol) in a manner similar to that used for the preparation of cis-N-2-(4-{4-amino-1-[4-(4-methylpiperazino)cyclohexyl]-1H-pyrazolo [3,4-d]pyrimidin-3-yl}-2-fluorophenyl)-1,3-benzoxazol-2-amine. The compound was formed as a white powder (0.219 g, 62%). $^1$H NMR (DMSO-d$_6$, 400 MHz) 2.17 (s, 3H), 2.23 (s, 3H), 2.3-2.50 (m, 4H), 2.34 (s, 3H), 2.40 (s, 3H), 2.99-4.26 (m, 4H), 5.44-5.49 (m, 1H), 6.80 (s, 1H), 7.11 (s, 1H), 7.65 (d, 2H), 7.92 (d, 2H), 8.26 (s, 1H), 10.86 (s, 1H); RP-HPLC Rt 10.765 min, 96% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 526 (MH$^+$).

Example 222 rac-1-[3-(4-Amino-3-{4-[(5,7-dimethyl-1,3-benzoxazol-2-yl)amino]phenyl}-1H-pyrazolo[3,4-d]pyrimidin-1-yl)tetrahydro-1H-1-pyrrolyl]-2-methyl-2-(methylamino)-1-propanone A. rac-9H-9-Fluorenylmethyl N-{2-[3-(4-amino-3-iodo-1H-pyrazolo[3,4-d]pyrimidin-1-yl)tetrahydro-1H-1-pyrrolyl]-1,1-dimethyl-2-oxoethyl}-N-methylcarbamate To a solution of rac-3-iodo-1-tetrahydro-1H-3-pyrrolyl-1H-pyrazolo[3,4-d]pyrimidin-4-amine monohydrochloride (0.100 g, 0.273 mmol) in dichloromethane (5 mL) was added 2-[[(9H-9-fluorenylmethoxy)carbonyl](methyl)amino]-2-methylpropanoic acid (0.120 g, 0.354 mmol), 1-hydroxy-7-azabenzotriazole (0.041 g, 0.30 mmol), 1-(3-dimethylaminopropyl)-3-ethylcarbodiimide hydrochloride (0.068 g, 0.35 mmol), and diisopropylethyl amine (0.18 g, 0.24 mL, 1.4 mmol). The reaction mixture was stirred at room temperature for 5 h and then poured into water (10 mL). The organic phase was separated and washed with brine (10 mL), dried over anhydrous magnesium sulfate, filtered, and concentrated to afford rac-9H-9-fluorenylm-ethyl N-{2-[3-(4-amino-3-iodo-1H-pyrazolo[3,4-d]pyrimidin-1-yl)tetrahydro-1H-1-pyrrolyl]-1,1-dimethyl-2-oxoethyl}-N-methylcarbamate as a yellow solid (0.223 g) which was used in subsequent reactions without further purification. RP-HPLC Rt 13.688 min, 63% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 652 (MH$^+$).

B. rac-1-[3-(4-Amino-3-{4-[(5,7-dimethyl-1,3-benzoxazol-2-yl)amino]phenyl}-1H-pyrazolo[3,4-d]pyrimidin-1-yl)tetrahydro-1H-1-pyrrolyl]-2-methyl-2-(methylamino)-1-propanone To a solution of rac-9H-9-fluorenylmethyl N-{2-[3-(4-amino-3-iodo-1H-pyrazolo[3,4-d]pyrimidin-1-yl)tetrahydro-1H-1-pyrrolyl]-1,1-dimethyl-2-oxoethyl}-N-methylcarbamate (0.178 g, 0.273 mmol) in ethylene glycol dimethyl ether (6 mL) and water (3 mL) was added N2-[4-(4,4,5,5-tetramethyl-1,3,2-dioxaborolan-2-yl)phenyl]-5,7-dimethyl-1,3-benzoxazol-2-amine (0.124 g, 0.341 mmol), tetrakis(triphenylphosphine) palladium (0) (0.016 g, 0.014 mmol), and sodium carbonate (0.072 g, 0.683 mmol). The solution was heated at 80° C. for 18 h, and then cooled to room temperature. The reaction mixture was partitioned between ethyl acetate (10 mL) and water (10 mL). The organic layer was separated and washed with brine (10 mL), dried over anhydrous magnesium sulfate, filtered, and concentrated to afford rac-9H-9-fluorenylmethyl N-2-[3-(4-amino-3-4-[(5,7-dimethyl-1,3-benzoxazol-2-yl)amino]phenyl-1H-pyrazolo[3,4-d]pyrimidin-1-yl)tetrahydro-1H-1-pyrrolyl]-1,1-dimethyl-2-oxoethyl-N-methylcarbamate as a pale brown oil (0.223 g), which was used in the next step without further purification.

A solution of rac-9H-9-fluorenylmethyl N-2-[3-(4-amino-3-4-[(5,7-dimethyl-1,3-benzoxazol-2-yl)amino]phenyl-1H-pyrazolo[3,4-d]pyrimidin-1-yl)tetrahydro-1H-1-pyrrolyl]-1,1-dimethyl-2-oxoethyl-N-methylcarbamate (0.223 g) in N,N-dimethylformamide (4 mL) was treated with piperidine (0.8 mL), and the reaction mixture stirred at room temperature for 18 h. The green solution was partitioned between dichloromethane (10 mL) and water (10 mL). The organic phase was separated and washed with brine, dried over anhydrous magnesium sulfate, filtered, and concentrated to afford a dark green oil. Purification by preparative RP-HPLC (25 to 100% CH$_3$CN in 0.1 N aqueous ammonium acetate over 20 min at 21 mL/min using a 8 μm Hypersil HS C18, 250×21 mm column, Rt=6.7-8.1 min) afforded rac-1-[3-(4-amino-3-{4-[(5,7-dimethyl-1,3-benzoxazol-2-yl)amino]phenyl}-1H-pyrazolo[3,4-d]pyrimidin-1-yl)tetrahydro-1H-1-pyrrolyl]-2-methyl-2-(methylamino)-1-propanone as an off-white solid (0.085 g, 58%). $^1$H NMR (DMSO-d$_6$, 400 MHz) Major rotamer: 1.20 (s, 6H), 1.96 (s, 3H), 2.3-2.50 (m, 3H), 2.34 (s, 3H), 2.40 (s, 3H), 3.17-4.44 (m, 4H), 5.42 (s, 1H), 6.80 (s, 1H), 7.11 (s, 1H), 7.63 (d, 2H), 7.91 (d, 2H), 8.26 (s, 1H), 10.85 (s, 1H); Minor rotamer: 1.15 (s, 6H), 2.15 (s, 3H), 2.3-2.50 (m, 3H), 2.34 (s, 3H), 2.40 (s, 3H), 3.17-4.44 (m, 4H), 5.42 (s, 1H), 6.80 (s, 1H), 7.11 (s, 1H), 7.63 (d, 2H), 7.91 (d, 2H), 8.26 (s, 1H), 10.85 (s, 1H); RP-HPLC Rt 10.994 min, 95% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 540 (MH$^+$).

Example 223 rac-N-2-[4-(4-Amino-1-tetrahydro-1H-3-pyrrolyl-1H-pyrazolo[3,4-d]pyrimidin-3-yl)phenyl]-5,7-dimethyl-1,3-benzoxazol-2-amine

A. rac-tert-Butyl 3-(4-amino-3-iodo-1H-pyrazolo[3,4-d]pyrimidin-1-yl)-1-pyrrolidinecarboxylate A solution of rac-3-iodo-1-tetrahydro-1H-3-pyrrolyl-1H-pyrazolo[3,4-d]pyrimidin-4-amine monohydrochloride (0.500 g, 1.36 mmol), sodium bicarbonate (0.401 g, 4.77 mmol), and di-tert-butyl dicarbonate (0.327 g, 1.50 mmol) in 1,4-dioxane (8 mL) and water (8 mL) was stirred at room temperature for 3 h. The resulting off-white suspension was filtered, and the filter cake was washed with water (10 mL) and dried to afford rac-tert-butyl 3-(4-amino-3-iodo-1H-pyrazolo[3,4-d]pyrimidin-1-yl)-1-pyrrolidinecarboxylate as an off-white solid (0.412 g, 70%). RP-HPLC Rt 11.540 min, 100% purity (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column); m/z 431 (MH$^+$).

B. rac-N-2-[4-(4-Amino-1-tetrahydro-1H-3-pyrrolyl-1H-pyrazolo[3,4-d]pyrimidin-3-yl)phenyl]-5,7-dimethyl-1,3-benzoxazol-2-amine To a solution of rac-tert-butyl 3-(4-amino-3-iodo-1H-pyrazolo[3,4-d]pyrimidin-1-yl)-1-pyrrolidinecarboxylate (0.412 g, 0.958 mmol) in ethylene glycol dimethyl ether (6 mL) and water (3 mL) was added N2-[4-(4,4,5,5-tetramethyl-1,3,2-dioxaborolan-2-yl)phenyl]-5,7-dimethyl-1,3-benzoxazol-2-amine (0.436 g, 1.20 mmol), tetrakis(triphenylphosphine) palladium (0) (0.055 g, 0.048 mmol), and sodium carbonate (0.254 g, 2.39 mmol). The solution was heated at 80° C. for 18 h, and then cooled to room temperature. The reaction mixture was partitioned between ethyl acetate (10 mL) and water (10 mL). The organic layer was separated and washed with brine (10 mL), dried over anhydrous magnesium sulfate, filtered, and concentrated to afford rac-tert-butyl 3-(4-amino-3-{4-[(5,7-dimethyl-1,3-benzoxazol-2-yl)amino]phenyl}-1H-pyrazolo[3,4-d]pyrimidin-1-yl)-1-pyrrolidinecarboxylate as an orange solid (1.029 g), which was used in the next step without further purification.

6 N Hydrochloric acid (10 mL) was added to a solution of rac-tert-butyl 3-(4-amino-3-{4-[(5,7-dimethyl-1,3-benzoxazol-2-yl)amino]phenyl}-1H-pyrazolo[3,4-d]pyrimidin-1-yl)-1-pyrrolidinecarboxylate (1.029 g) in acetone (10 mL) and the reaction mixture was stirred at 45° C. for 5 h. The reaction mixture was filtered, and the resulting opaque filtrate was concentrated to afford an orange solid. Purification by preparative RP-HPLC (25 to 100% CH$_3$CN in 0.1 N aqueous ammonium acetate over 20 min at 21 mL/min using a 8 µm Hypersil HS C18, 250×21 mm column, tr=6.2-7.5 min) afforded rac-N-2-[4-(4-amino-1-tetrahydro-1H-3-pyrrolyl-1H-pyrazolo[3,4-d]pyrimidin-3-yl)phenyl]-5,7-dimethyl-1,3-benzoxazol-2-amine as an off-white solid (0.148 g, 35%). $^1$H NMR (DMSO-d$_6$, 400 MHz) 2.15-2.22 (m, 2H), 2.40 (s, 3H), 2.50 (s, 3H), 2.93-4.04 (m, 5H), 5.31 (m, 1H), 6.79 (s, 1H), 7.11 (s, 1H), 7.66 (d, 2H), 7.93 (d, 2H), 8.24 (s, 1H), 10.85 (s, 1H); RP-HPLC Rt 10.603 min, 99% purity (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column); m/z 441 (MH$^+$).

Example 224

Cis-N-2-(4-{4-amino-1-[4-(4-methylpiperazino)cyclohexyl]-1H-pyrazolo[3,4-d]pyrimidin-3-yl}phenyl)-7-isopropyl-1,3-benzoxazol-2-amine diacetate

A. 2-Amino-6-isopropylphenol

A solution of 6-isopropyl-2-nitrophenol (3.000 g, 16.56 mmol) and sodium hydrosulfite (11.53 g, 66.23 mmol) in ethanol (180 mL) and water (90 mL) was stirred at 80° C. for 20 h and then cooled to room temperature. The resulting orange solution was concentrated and then partitioned between dichloromethane (50 mL) and water (50 mL). The organic phase was separated and washed with brine (25 mL), dried over anhydrous magnesium sulfate, filtered, and concentrated to afford 2-amino-6-isopropylphenol as an orange solid (1.792 g, 72%). RP-HPLC Rt 8.171 min, 92% purity (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column); m/z 150 (M–H)$^-$.

c1. N2-(4-Bromophenyl)-7-isopropyl-1,3-benzoxazol-2-amine

A solution of 2-amino-6-isopropylphenol (0.354 g, 2.34 mmol) and 4-bromophenylisothiocyanate (0.500 g, 2.34 mmol) in tetrahydrofuran (35 mL) was stirred at room temperature for 3 h. Anhydrous copper (II) sulfate (3.361 g, 21.06 mmol), silica gel (3.361 g), and triethylamine (0.236 g, 0.33 mL, 2.34 mmol) were added, and the mixture stirred at room temperature for 18 h. The reaction mixture was filtered through a pad of Celite and the washed with diethyl ether (3×50 mL). The filtrate was concentrated to afford a brown solid. The solid material was applied to silica gel and passed through a pad a silica gel along with ethyl acetate (3×50 mL). The filtrate was concentrated to afford N2-(4-bromophenyl)-7-isopropyl-1,3-benzoxazol-2-amine (0.702 g, 91%). RP-HPLC Rt 18.066 min, 86% purity (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column); m/z 333 (MH$^+$).

C. N2-[4-(4,4,5,5-Tetramethyl-1,3,2-dioxaborolan-2-yl)phenyl]-7-isopropyl-1,3-benzoxazol-2-amine N2-[4-(4,4,5,5-Tetramethyl-1,3,2-dioxaborolan-2-yl)phenyl]-7-isopropyl-1,3-benzoxazol-2-amine was prepared from N2-(4-bromophenyl)-7-isopropyl-1,3-benzoxazol-2-amine (0.412 g, 1.24 mmol) in a manner similar to that used for the preparation of N2-[2-fluoro-4-(4,4,5,5-tetramethyl-1,3,2-dioxaborolan-2-yl)phenyl]-1,3-benzoxazol-2-amine. The compound was formed as an off-white solid (0.346 g, 74%). RP-HPLC Rt 18.964 min, 79% purity (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column); m/z 379 (MH$^+$).

D. Cis-N-2-(4-{4-amino-1-[4-(4-methylpiperazino)cyclohexyl]-1H-pyrazolo[3,4-d]pyrimidin-3-yl}phenyl)-7-isopropyl-1,3-benzoxazol-2-amine diacetate Cis-N-2-(4-{4-amino-1-[4-(4-methylpiperazino)cyclohexyl]-1H-pyrazolo[3,4-d]pyrimidin-3-yl}phenyl)-7-isopropyl-1,3-benzoxazol-2-amine diacetate was prepared from cis-3-iodo-1-[4-(4-methylpiperazino)cyclohexyl]-1H- pyrazolo[3,4-d]pyrimidin-4-amine (0.250 g, 0.566 mmol) and N2-[4-(4,4,5,5-tetramethyl-1,3,2-dioxaborolan-2-yl) phenyl]-7-isopropyl-1,3-benzoxazol-2-amine (0.339 g, 0.708 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white solid (0.205 g, 64%). $^1$H NMR (DMSO-$d_6$, 400 MHz) 1.36 (d, 6H), 1.56-2.50 (m, 16H), 1.90 (6H), 2.15 (s, 3H), 3.23-3.28 (m, 2H), 4.80 (m, 1H), 7.04 (d, 1H), 7.18 (t, 1H), 7.34 (d, 1H), 7.66 (d, 2H), 7.96 (d, 2H), 8.24 (s, 1H); RP-HPLC Rt 12.508 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 566 (MH$^+$).

Example 225

N2-(4-{4-Amino-1-[(3S)-1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine monoacetate N2-(4-{4-Amino-1-[(3S)-1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine monoacetate was prepared from (R)-(+)-3-pyrrolidinol in a manner analogous to that used for the preparation of rac-N-2-(4-{4-amino-1-[1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine. The compound was formed as a pink solid (0.103 g, 53%). $^1$H NMR (DMSO-$d_6$, 400 MHz) 1.89 (s, 3H), 2.28-2.31 (m, 2H), 2.35 (s, 3H), 2.40 (s, 3H), 2.65 (t, 2H), 2.73-2.87 (m, 2H), 3.17 (t, 2H), 3.24 (s, 3H), 3.45 (t, 2H), 5.37 (m, 1H), 6.79 (s, 1H), 7.11 (s, 1H), 7.66 (d, 2H), 7.93 (d, 2H), 8.24 (s, 1H), 10.59 (s, 2H); RP-HPLC Rt 11.607 min, 95% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 499 (MH$^+$).

Example 226 rac-N-2-(4-{4-Amino-1-[1-(2-methoxyethyl)tetrahydro-1H-3-pyrrolyl]-1H-pyrazolo[3,4-d]pyrimidin-3-yl}phenyl)-5-ethyl-1,3-benzoxazol-2-amine monoacetate rac-N-2-(4-{4-Amino-1-[1-(2-methoxyethyl)tetrahydro-1H-3-pyrrolyl]-1H-pyrazolo[3,4-d]pyrimidin-3-yl}phenyl)-5-ethyl-1,3-benzoxazol-2-amine monoacetate was prepared from rac-3-iodo-1-[1-(2-methoxyethyl)tetrahydro-1H-3-pyrrolyl]-1H-pyrazolo[3,4-d]pyrimidin-4-amine (0.200 g, 0.319 mmol) and N2-[4-(4,4,5,5-tetramethyl-1,3,2-dioxaborolan-2-yl)phenyl]-5-ethyl-1,3-benzoxazol-2-amine (0.145 g, 0.399 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as a white solid (0.082 g, 52%). $^1$H NMR (DMSO-$d_6$, 400 MHz) 1.23 (t, 3H), 1.90 (s, 3H), 2.33-3.47 (m, 10H), 2.66 (q, 2H), 3.25 (s, 3H), 5.40 (m, 1H), 6.99 (d, 1H), 7.33 (s, 1H), 7.40 (d, 1H), 7.66 (d, 2H), 7.93 (d, 2H), 8.25 (s, 1H), 10.81 (s, 1H); RP-HPLC Rt 11.781 min, 93% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 499 (MH$^+$).

Example 228 rac-N-2-(4-{4-Amino-1-[1-(2-methoxyethyl)tetrahydro-1H-3-pyrrolyl]-1H-pyrazolo [3,4-d]pyrimidin-3-yl}phenyl)-5-methyl-1,3-benzoxazol-2-amine monoacetate rac-N-2-(4-{4-Amino-1-[1-(2-methoxyethyl)tetrahydro-1H-3-pyrrolyl]-1H-pyrazolo[3,4-d]pyrimidin-3-yl}phenyl)-5-ethyl-1,3-benzoxazol-2-amine monoacetate was prepared from rac-3-iodo-1-[1-(2-methoxyethyl)tetrahydro-1H-3-pyrrolyl]-1H-pyrazolo[3,4-d]pyrimidin-4-amine (0.200 g, 0.319 mmol) and N2-[4-(4,4,5,5-tetramethyl-1,3,2-dioxaborolan-2-yl)phenyl]-5-methyl-1,3-benzoxazol-2-amine (0.145 g, 0.399 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white solid (0.038 g, 16%). $^1$H NMR (DMSO-$d_6$, 400 MHz) 1.91 (s, 3H), 2.33 (m, 2H), 2.39 (s, 3H), 2.66 (m, 2H), 2.75-2.83 (m, 3H), 3.17 (t, 1H), 3.29 (s, 3H), 3.45 (t, 2H), 5.37 (m, 1H), 6.96 (d, 1H), 7.30 (s, 1H), 7.38 (d, 1H), 7.67 (d, 2H), 7.93 (d, 2H), 8.24 (s, 1H), 10.80 (s, 1H); RP-HPLC Rt 10.756 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 485 (MH$^+$).

Example 229

N2-(4-{4-Amino-1-[(3R)-1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine diacetate N2-(4-{4-Amino-1-[(3R)-1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine diacetate was prepared from (S)-(−)-3-pyrrolidinol in a manner analogous to that used for the preparation of rac-N-2-(4-{4-amino-1-[1-(2-methoxyethyl)tetrahydro-1H-3-pyrrolyl]-1H-pyrazolo[3,4-d]pyrimidin-3-yl}phenyl)-5,7-dimethyl-1,3-benzoxazol-2-amine. The compound was formed as an off-white solid (0.214 g, 39%). $^1$H NMR (DMSO-$d_6$, 400 MHz) 1.89 (s, 6H), 2.28-2.31 (m, 2H), 2.35 (s, 3H), 2.40 (s, 3H), 2.65 (t, 2H), 2.73-2.87 (m, 2H), 3.17 (t, 2H), 3.24 (s, 3H), 3.45 (t, 2H), 5.37 (m, 1H), 6.79 (s, 1H), 7.11 (s, 1H), 7.66 (d, 2H), 7.93 (d, 2H), 8.24 (s, 1H); RP-HPLC Rt 11.674 min, 97% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 499 (MH$^+$).

Example 230

Rac-N-2-(4-{4-Amino-1-[1-(2-methoxyethyl)tetrahydro-1H-3-pyrrolyl]-1H-pyrazolo[3,4-d]pyrimidin-3-yl}phenyl)-5-chloro-1,3-benzoxazol-2-amine monoacetate rac-N-2-(4-{4-Amino-1-[1-(2-methoxyethyl)tetrahydro-1H-3-pyrrolyl]-1H-pyrazolo[3,4-d]pyrimidin-3-yl}phenyl)-5-chloro-1,3-benzoxazol-2-amine monoacetate was prepared from rac-3-iodo-1-[1-(2-methoxyethyl)tetrahydro-1H-3-pyrrolyl]-1H-pyrazolo[3,4-d]pyrimidin-4-amine (0.200 g, 0.319 mmol) and N2-[4-(4,4,5,5-tetramethyl-1,3, 2-dioxaborolan-2-yl)phenyl]-5-chloro-1,3-benzoxazol-2- amine (0.148 g, 0.399 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white solid (0.080 g, 50%). $^1$H NMR (DMSO-$d_6$, 400 MHz) 1.91 (s, 3H), 2.33 (m, 2H), 2.66 (m, 2H), 2.75-2.85 (m, 3H), 3.17 (t, 1H), 3.24 (s, 3H), 3.45 (t, 2H), 5.37 (m, 1H), 7.18 (d, 1H), 7.55 (d, 2H), 7.68 (d, 2H), 7.92 (d, 2H), 8.24 (s, 1H), 9.80 (s, 1H); RP-HPLC Rt 11.337 min, 97% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 505 (MH$^+$).

Example 231 trans-N1-(4-{4-amino-1-[4-(4-methylpiperazino)cyclohexyl]-1H-pyrazolo[3,4-d]pyrimidin-3-yl}-2-methoxyphenyl)-3-phenylpropanamide A solution of trans-3-(4-amino-3-methoxyphenyl)-1-[4-(4-methylpiperazino)cyclohexyl]-1H-pyrazolo[3,4-d]pyrimidin-4-amine (0.700 g, 1.6 mmol) in pyridine (11 mL) at 0° C. was treated with hydrocinnamoyl chloride (0.324 g, 1.92 mmol). The reaction mixture was stirred at 0° C. for 20 min and the ice bath was removed to stir at room temperature. The reaction was complete after 5.5 hours. Sodium hydroxide solution (1 N, 20 mL) was added and stirred for 30 minutes. The organic layer was removed under reduced pressure. Dichloromethane (20 mL) was added, and the layers were partitioned. The aqueous layer was extracted with dichloromethane (80 mL). The combined organic layers were washed with water, dried over magnesium sulfate, filtered and evaporated under reduced pressure. The crude material was purified by flash chromatography on silica gel using a gradient of 5% methanol in dichloromethane to 50% methanol in dichloromethane on a 35 g ISCO silica gel column to give 0.569 g (63%) of trans-N1-(4-{4-amino-1-[4-(4-methylpiperazino)cyclohexyl]-1H-pyrazolo[3,4-d]pyrimidin-3-yl}-2-methoxyphenyl)-3-phenylpropanamide. trans-N1-(4-{4-amino-1-[4-(4-methylpiperazino)cyclohexyl]-1H-pyrazolo[3,4-d]pyrimidin-3-yl}-2-methoxyphenyl)-3-phenylpropanamide (0.569 g, 1 mmol) in warmed ethyl acetate was treated with a warmed solution of maleic acid (0.384 g, 3 mmol) in ethyl acetate. The formed precipitate was filtered under a nitrogen atmosphere and dried under high vacuum to give the tri maleate salt. $^1$H NMR ($d_6$-DMSO) δ 9.238 (s, 1H), 8.2216 (s, 1H), 8.1991-8.1786 (d, 1H, J=8.2 Hz), 7.3147-7.2664 (m, 4H), 2.2366-7.2330 (m, 1H), 7.2026-7.1732 (dd, 2H), 6.171 (s, 6H), 4.6649-4.6083 (m, 1H), 4.0948-4.0697 (m, 1H), 3.8916 (s, 3H), 3.1750-3.1632 (d, 2H, J=4.72 Hz), 2.9364-2.8984 (m, 2H), 2.7885-2.7506 (m, 2H), 2.5290 (s, 2H), 2.3905-2.3231 (m, 4H), 2.1489 (s, 3H), 2.0549-1.9243 (m, 6H), 1.4821-1.4457 (m, 2H); LCMS (Thermoquest AQA single-quad MS, Genesis C18 column, 3 μm particle size, 33×4.6 mm; 70% 50 mM ammonium Acetate in Water to 95% Acetonitrile over 6 min, 0.8 to 0.5 mL/min) R$_t$ 1.75 min (100%), MH$^+$ 569.4.

Example 232 trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide A suspension of trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide di-maleate (0.200 g, 0.242 mmol) in dichloromethane (15 mL) was treated with 1N sodium hydroxide solution. The reaction mixture was stirred for 1 h at room temperature. The layers were partitioned using an Empore extraction cartridge. The organic layer was removed by blowing nitrogen over the top of the solvent to give 0.072 g (50%) of trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide. $^1$H NMR (d-DMSO) δ 9.4355 (s, 1H), 8.2464 (s, 1H), 8.1241-8.1037 (d, 1H, J=8.16 Hz), 7.7186-7.6987 (d, 1H, J=7.96 Hz), 7.6005-7.5795 (d, 1H, J=8.4 Hz), 7.3532-7.2795 (m, 4H), 7.1717-7.1343 (t, 1H), 4.6833 (m, 1H), 4.0560 (s, 3H), 3.9573 (s, 3H), 2.6704 (m, 6H), 2.4404 (m, 2H), 2.2953 (s, 6H), 2.1282-1.9889 (m, 5H), 1.5124 (m, 2H). The compound was directly used in the subsequent reaction without purificaction.

Example 233 trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide di-mesylate A warmed solution of trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide (0.072 g, 0.12 mmol) in ethyl acetate (20 mL) was treated with methane sulfonic acid (0.012 g, 0.12 mmol). A precipitate slowly formed and was filtered under a nitrogen atmosphere to give 0.051 g of trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide di-mesylate. The melting range was determined to be 345.5 to 348.1° C. $^1$H NMR ($d_6$-DMSO) δ 9.4353 (s, 1H), 8.2461 (s, 1H), 8.1239-8.1035 (d, 1H, J=8.16 Hz), 7.7182-7.6985 (d, 1H, J=7.88 Hz), 7.6004-7.5792 (d, 1H, J=8.48 Hz), 7.3442-7.2794 (m, 4H), 7.1718-7.1349 (t, 1H), 4.6829 (m, 1H), 4.0396 (s, 3H), 3.9570 (s, 3H), 2.6703 (m, 6H), 2.5 (s, 3H), 2.2949 (s, 6H), 2.0891-2.9086 (m, 7H), 1.5179 (m, 2H).

Example 234

3-(4-Amino-3-methoxyphenyl)-1-(1-methyl-4-piperidyl)-1H-pyrazolo[3,4-d]pyrimidin-4-amine A. 3-Iodo-1-(1-methyl-4-piperidyl)-1H-pyrazolo[3,4-d]pyrimidin-4-amine 3-Iodo-1-(4-piperidyl)-1H-pyrazolo[3,4-d]pyrimidin-4-amine (500 mg, 1.45 mmol), formaldehyde (30% solution in water, 0.16 mL, 1.60 mmol) and sodium triacetoxyborohydride (430 mg, 2.03 mmol) were mixed in 1,2-dichloroethane (5 mL). The reaction mixture was stirred at room temperature for 4 hours. Saturated sodium bicarbonate solution was added to adjust the pH to about 8. The layers were separated and the aqueous layer was extracted with dichloromethane. The combined organic layer was washed with brine, dried over MgSO$_4$, filtered and evaporated to give 3-iodo-1-(1-methyl-4-piperidyl)-1H-pyrazolo[3,4-d]pyrimidin-4-amine (275 mg, 53%). $^1$H NMR (DMSO-$d_6$) δ 1.85 (m, 2H), 2.09 (m, 4H), 2.22 (s, 3H), 2.88 (m, 2H), 4.75 (m, 1H), 8.19 (s, 1H), 8.32 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min.

(B: acetonitrile, A: 50 mM ammonia acetate buffer, pH 4.5), 0.8 mL/min.): MH+ 359.0, $R_t$ 0.46 min.

B. tert-Butyl N-{4-[4-amino-1-(1-methyl-4-piperidyl)-1H-pyrazolo[3,4-d]pyrimidin-3-yl]-2-methoxyphenyl}carbamate 3-Iodo-1-(1-methyl-4-piperidyl)-1H-pyrazolo[3,4-d]pyrimidin-4-amine (270 mg, 0.754 mmol), tert-butyl N-[2-methoxy-4-(4,4,5,5-tetramethyl-1,3,2-dioxaborolan-2-yl)phenyl]carbamate (290 mg, 0.829 mmol), palladium tetrakistriphenyphosphine (52 mg, 0.045 mmol) and sodium carbonate (192 mg, 1.81 mmol) were mixed in ethylene glycol dimethyl ether (8 mL) and water (4 mL). The reaction mixture was heated at reflux overnight under nitrogen. Organic solvent was removed under reduced pressure and the aqueous layer was extracted with dichloromethane. The combined organic layer was washed with water then brine, dried over MgSO₄, filtered and evaporated. The residue was purified by flash column chromatography using dichloromethane/methanol (90:10 to 70:30) as mobile phase to give tert-butyl N-{4-[4-amino-1-(1-methyl-4-piperidyl)-1H-pyrazolo[3,4-d]pyrimidin-3-yl]-2-methoxyphenyl}carbamate (250 mg, 73%). ¹H NMR (DMSO-d₆) δ 1.48 (s, 9H), 1.88 (m, 2H), 2.10 (m, 2H), 2.24 (m, 5H), 2.92 (m, 2H), 3.69 (s, 3H), 4.64 (m, 1H), 7.21 (m, 2H), 7.91 (d, J=8.16 Hz, 1H), 8.04 (s, 1H), 8.23 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH+=454.2, $R_t$=1.67 min.

C. 3-(4-Amino-3-methoxyphenyl)-1-(1-methyl-4-piperidyl)-1H-pyrazolo[3,4-d]pyrimidin-4-amine A mixture of trifluoroacetic acid/dichloromethane (20:80, 7 mL) was added to a solution of tert-butyl N-{4-[4-amino-1-(1-methyl-4-piperidyl)-1H-pyrazolo[3,4-d]pyrimidin-3-yl]-2-methoxyphenyl}carbamate (240 mg, 0.529 mmol) in dichloromethane (4 mL) at 0° C. 15 minutes later, the ice-bath was removed and the reaction mixture was stirred at room temperature for 4 hours. The solvents were evaporated and the residue was dissolved in dichloromethane. Sodium hydroxide (1.0N) was added to adjust the pH to about 10. The layers were separated and the aqueous layer was extracted with dichloromethane four times. The combined organic layer was washed with brine, dried over MgSO₄, filtered and evaporated to give 3-(4-amino-3-methoxyphenyl)-1-(1-methyl-4-piperidyl)-1H-pyrazolo[3,4-d]pyrimidin-4-amine (178 mg, 95%). HPLC (Waters 486-Column: delta pak, C18, 5 um, 300 Å, 150×3.9 mm. Eluents: 5% B/A to 95% B/A in 10 min. (B: acetonitrile, A: 50 mM ammonia acetate buffer, pH 4.5), 1.0 mL/min.) R=6.45 min.

Example 235

N1-{4-[4-Amino-1-(1-methyl-4-piperidyl)-1H-pyrazolo[3,4-d]pyrimidin-3-yl]-2-methoxyphenyl}-trans-2-phenyl-1-cyclopropanecarboxamide trans-2-Phenyl-1-cyclopropanecarbonyl chloride (31 mg, 0.170 mmol) in dichloromethane (0.3 mL) was added to a solution of 3-(4-amino-3-methoxyphenyl)-1-(1-methyl-4-piperidyl)-1H-pyrazolo[3,4-d]pyrimidin-4-amine (60 mg, 0.17 mmol) in pyridine (1.2 mL) at 0° C. After 5 minutes, the ice-water bath was removed and the reaction mixture was stirred at room temperature for 1 hours then, more trans-2-Phenyl-1-cyclopropanecarbonyl chloride (15 mg, 0.083 mmol) was added. After 2 hours, the solvent was evaporated and the residue was purified by flash column chromatography using dichloromethane/methanol (95:5 to 70:30) as mobile phase to give N1-{4-[4-Amino-1-(1-methyl-4-piperidyl)-1H-pyrazolo[3,4-d]pyrimidin-3-yl]-2-methoxyphenyl}-trans-2-phenyl-1-cyclopropanecarboxamide (75 mg, 89%). ¹H NMR (CDCl₃) δ 1.42 (m, 1H), 1.77 (m, 1H), 1.85 (m, 1H), 2.03 (m, 1H), 2.24 (m, 2H), 2.37 (s, 3H), 2.46 (m, 2H), 2.62 (m, 1H), 3.05 (m, 2H), 3.96 (s, 3H), 4.77 (m, 1H), 5.69 (s, 2H), 7.24 (m, 7H), 8.11 (s, 1H), 8.35 (m, 1H), 8.45 (d, J=8.38 Hz, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH+=498.3, $R_t$=1.84 min.

Example 236

N1-{4-[4-amino-1-(1-methyl-4-piperidyl)-1H-pyrazolo[3,4-d]pyrimidin-3-yl]-2-methoxyphenyl}-4-(trifluoromethyl)benzamide 4-(Trifluoromethyl)-1-benzenecarbonyl chloride (35 mg, 0.170 mmol) in dichloromethane (0.3 mL) was added to a solution of 3-(4-amino-3-methoxyphenyl)-1-(1-methyl-4-piperidyl)-1H-pyrazolo[3,4-d]pyrimidin-4-amine (60 mg, 0.17 mmol) in pyridine (1.2 mL) at 0° C. After 5 minutes, the ice-water bath was removed and the reaction mixture was stirred at room temperature for 1 hours then, more 4-(trifluoromethyl)-1-benzenecarbonyl chloride (18 mg, 0.086 mmol) was added. 2 hours later, the solvent was evaporated and the residue was purified by flash column chromatography using dichloromethane/methanol (95:5 to 70:30) as mobile phase to give N1-{4-[4-amino-1-(1-methyl-4-piperidyl)-1H-pyrazolo[3,4-d]pyrimidin-3-yl]-2-methoxyphenyl}-4-(trifluoromethyl)benzamide (85 mg, 95%). ¹H NMR (CDCl₃) δ 2.10 (m, 2H), 2.37-2.59 (m, 7H), 3.15 (m, 2H), 4.02 (s, 3H), 4.83 (m, 1H), 5.68 (s, 2H), 7.34 (m, 2H), 7.80 (d, J=8.21 Hz, 2H), 8.04 (d, J=8.10 Hz, 2H), 8.38 (s, 1H), 8.67 (m, 2H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH+=526.3, $R_t$=1.93 min.

Example 237

N1-{4-[4-amino-1-(1-methyl-4-piperidyl)-1H-pyrazolo[3,4-d]pyrimidin-3-yl]-2-methoxyphenyl}-4-(trifluoromethoxy)benzamide 4-(Trifluoromethoxy)-1-benzenecarbonyl chloride (38 mg, 0.170 mmol) in dichloromethane (0.3 mL) was added to a solution of 3-(4-amino-3-methoxyphenyl)-1-(1-methyl-4-piperidyl)-1H-pyrazolo[3,4-d]pyrimidin-4-amine (60 mg, 0.17 mmol) in pyridine (1.2 mL) at 0° C. After 5 minutes, the ice-water bath was removed and the reaction mixture was stirred at room temperature for 1 hours then, more 4-(trifluoromethyl)-1-benzenecarbonyl chloride (19 mg, 0.085 mmol) was added. After 2 hours, the solvent was evaporated and the residue was purified by flash column chromatography using dichloromethane/methanol (95:5 to 70:30) as mobile phase to give N1-{4-[4-amino-1-(1-methyl-4-piperidyl)-1H-pyrazolo[3,4-d]pyrimidin-3-yl]-2-methoxyphenyl}-4-(trifluoromethoxy)benzamide (70 mg, 76%).

¹H NMR (CDCl₃) δ 2.06 (d, J=11.79 Hz, 2H), 2.28 (m, 2H), 2.40 (s, 3H), 2.50 (m, 2H), 3.07 (d, J=10.8 Hz, 2H), 4.02 (s, 3H), 4.80 (m, 1H), 5.71 (s, 2H), 7.27 (m, 2H), 7.36 (d, J=8.20 Hz, 2H), 7.98 (d, J=6.20 Hz, 2H), 8.37 (s, 1H), 8.59 (s, 1), 8.67 (d, J=8.55 Hz, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH⁺=542.3, $R_t$=1.98 min.

Example 238 cis-1-[4-(4-Methylpiperazino)cyclohexyl]-3-[4-(1,3-oxazol-5-yl)phenyl]-1H-pyrazolo[3,4-d]pyrimidin-4-amine A. 4-{4-Amino-1-[4-(4-methylpiperazino)cyclohexyl]-1H-pyrazolo[3,4-d]pyrimidin-3-yl}benzaldehyde cis-3-Methyl-1-[4-(4-methylpiperazino)cyclohexyl]-1H-pyrazolo[3,4-d]pyrimidin-4-amine (3.0 g, 6.80 mmol), 4-formylphenylboronic acid (1.22 g, 8.16 mmol), palladium tetrakistriphenyphosphine (0.47 g, 0.41 mmol) and sodium carbonate (1.73 g, 16.31 mmol) were mixed with ethylene glycol dimethyl ether (70 mL) and water (35 mL). The reaction mixture was heated at reflux overnight under nitrogen. Organic solvent was removed under reduced pressure and the aqueous layer was filtered and washed with water. After drying on the lyophilizer, the residue was purified by flash column chromatography using dichloromethane/methanol (90:10 to 70:30) as mobile phase to give 4-{4-amino-1-[4-(4-methylpiperazino)cyclohexyl]-1H-pyrazolo[3,4-d]pyrimidin-3-yl}benzaldehyde (1.55 g, 54%). ¹H NMR (DMSO-d₆) δ 1.60 (m, 2H), 1.72 (m, 2H). 2.07 (m, 2H), 2.15 (s, 3H), 2.22-2.46 (m, 1H), 4.83 (m, 1H), 7.88 (d, J=8.13 Hz, 2H), 8.07 (d, J=8.10 Hz, 2H), 8.21 (s, 1H), 10.11 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH⁺=420.2, $R_t$=0.70 min.

B. cis-1-[4-(4-Methylpiperazino)cyclohexyl]-3-[4-(1,3-oxazol-5-yl)phenyl]-1H-pyrazolo[3,4-d]pyrimidin-4-amine Sodium methoxide (130 mg, 2.41 mmol) was added in portions to a mixture of 4-{4-amino-1-[4-(4-methylpiperazino)cyclohexyl]-1H-pyrazolo[3,4-d]pyrimidin-3-yl}benzaldehyde (300 mg, 0.715 mmol) in methanol (20 mL). After 5 minutes, (p-tolylsulfonyl)methyl isocyanide (tosmic) (167 mg, 0.858 mmol) was added in portions. The solution was heated at reflux for 5 hours. Water (10 mL) was added while it was still hot. After cooling on ice for 5 minutes, the solid was filtered and washed with a mixture of methanol/water (50/50, 2 mL) then dried. The filtrate was evaporated to remove organic solvent and the solid was collected and washed with water. The combined solid was first purified by flash column chromatography using dichloromethane/methanol (90:10 to 70:30) as mobile phase then re-crystallized twice from DMF to give cis-1-[4-(4-methylpiperazino)cyclohexyl]-3-[4-(1,3-oxazol-5-yl)phenyl]-1H-pyrazolo[3,4-d]pyrimidin-4-amine (90 mg, 27%). ¹H NMR (DMSO-d₆) δ 1.61 (m, 2H), 1.71 (m, 2H), 2.10 (m, 2H), 2.15 (s, 3H), 2.44 (m, 1H), 4.82 (m, 1H), 7.78 (m, 3H), 7.79 (m, 2H), 8.24 (s, 1H), 8.51 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH⁺=459.2, $R_t$ 0.72 nm.

Example 239 trans-N-(4-{4-amino-1-[4-(4-methylpiperazino)cyclohexyl]-1H-pyrazolo[3,4-d]pyrimidin-3-yl}-5-fluoro-2-methoxyphenyl)-2,2-dimethyl-3-phenylpropanamide 2,2-Dimethyl-3-phenylpropanoyl chloride (52 mg, 0.264 mmol) was added to a solution of trans-3-(4-amino-2-fluoro-5-methoxyphenyl)-1-[4-(4-methylpiperazino) cyclohexyl]-1H-pyrazolo[3,4-d]pyrimidin-4-amine (80 mg, 0.176 mmol) in pyridine (1.5 mL). After 5 hours, the solvent was evaporated and the residue was first purified by flash column chromatography chromatography using dichloromethane/methanol (95:5 to 85:15) as mobile phase then by preparatory LC/MS to give trans-N1-(4-{4-amino-1-[4-(4-methylpiperazino) cyclohexyl]-1H-pyrazolo [3,4-d]pyrimidin-3-yl}-5-fluoro-2-methoxyphenyl)-2,2-dimethyl-3-phenylpropanamide (22 mg, 19%). ¹H NMR (CDCl₃-d) δ 1.33 (s, 6H), 1.57 (m, 2H), 1.92 (m, 2H), 2.15 (m, 6H), 2.30 (s, 3H), 2.49 (m, 4H), 2.66 (m, 3H), 2.95 (s, 2H), 3.84 (s, 3H), 4.76 (m, 1H), 5.51 (bs, 2H), 6.98 (d, J=6.86 Hz, 1H), 7.15 (m, 2H), 7.23 (m, 3H), 8.01 (s, 1H), 8.35 (s, 1H), 8.47 (d, J=11.88, 1H). LCMS LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH⁺=615.3, $R_t$=2.18 min.

Example 240 cis-(4-{4-Amino-1-[4-(4-methylpiperazino)cyclohexyl]-1H-pyrazolo[3,4-d]pyrimidin-3-yl}phenyl)(1H-benzo[d]imidazol-2-yl)methanol A. 1H-Benzo[d]imidazol-1-ylmethanol Formaldehyde (37% in water, 1 mL, 13.3 mmol) was added to a solution of 1H-benzo[d]imidazole (1.57 g, 13.3 mmol) in THF (60 ml). After 10 minutes, the solvent was removed and dried to give 1H-benzo[d]imidazol-1-ylmethanol as a brown solid which was used without any further purification. ¹H NMR (DMSO-d₆) δ 5.60 (d, J=7.09 Hz, 2H), 6.70 (m, 1H), 7.25 (m, 2H), 7.65 (d, J=9.13 Hz, 2H), 8.26 (s, 1H).

B. cis-(4-{4-Amino-1-[4-(4-methylpiperazino)cyclohexyl]-1H-pyrazolo[3,4-d]pyrimidin-3-yl}phenyl)(1H-benzo[d]imidazol-2-yl)methanol n-Butylithum (1.34M, 3.0 mL, 4 mmol) was added slowly to a mixture of 1H-benzo[d]imidazol-1-ylmethanol (296 mg, 2.0 mmol) in THF (9.0 mL) at −78° C. The reaction mixture was allowed to warm up to −20° C. and kept at −20° C. for 30 minutes then cooled back to −78° C. cis-4-{4-amino-1-[4-(4-methylpiperazino)cyclohexyl]-1H-pyrazolo[3,4-d]pyrimidin-3-yl}benzaldehyde (420 mg, 1 mmol) in THF (5 mL) was added slowly. After 20 minutes, the dry ice bath was removed and the reaction mixture was stirred at room temperature overnight. Saturated ammonium chloride solution was added followed by ether. The layers were separated and the aqueous layer was neutralized with sodium hydroxide (1.0N) and extracted with dichloromethane. The organic layer was washed with brine, dried over MgSO$_4$, filtered and evaporated. The residue was first purified by flash column chromatography using dichloromethane/methanol (95:5 to 85:15) as mobile phase then by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give cis-(4-{4-amino-1-[4-(4-methylpiperazino)cyclohexyl]-1H-pyrazolo[3,4-d]pyrimidin-3-yl}phenyl)(1H-benzo[d]imidazol-2-yl)methanol (2 mg, 0.4%). $^1$H NMR (CDCl$_3$) δ 1.68 (m, 2H), 1.81 (m, 2H), 2.01 (m, 2H), 2.13 (m, 2H), 2.33 (s, 3H), 2.42 (m, 2H), 2.64 (m, 7H), 4.68 (bs, 3H), 4.93 (m, 1H), 5.77 (bs, 2H), 6.06 (s, 1H), 7.20 (m, 2H), 7.52 (m, 2H), 7.58 (m, 4H), 8.32 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$=538.3, R$_t$=3.80 min.

Examples 241-252

Examples 241-252 were prepared from 4-[4-amino-3-(4-phenoxyphenyl)-1H-pyrazolo[3,4-d]pyrimidin-1-yl]benzaldehyde using the following method:

4-[4-Amino-3-(4-phenoxyphenyl)-1H-pyrazolo [3,4-d] pyrimidin-1-yl]benzaldehyde (50 mg, 0.123 mmol), the appropriate amine (0.246 mmol), sodium triacetoxyborohydride (78 mg, 0.368 mmol) and glacial acetic acid (32 mg, 0.540 mmol) were mixed in THF (3 mL). After shaking at room temperature overnight on a J-Kem shaker, further amount of the amine (0.246 mmol), sodium triacetoxyborohydride (78 mg, 0.368 mmol) and glacial acetic acid (32 mg, 0.540 mmol) were added again and the reaction mixtures were shaken at room temperature overnight. The solvent was evaporated and dichloromethane was added followed by sodium hydroxide (1.0N). The layers were separated with the aid of Empore Cartridge. The organic layer was evaporated and the residue was purified by reverse phase preparative LC/MS (Micromass-Column: Hypersil BDS, C18, 5 um, 100×21.2 mm. Eluents: 15% B/A to 100% B/A in 7 min.(B: acetonitrile, A: 50 mM ammonia acetate buffer, PH 4.5), 25 mL/min.). After removing solvent, the resulting solid was dissolved in dichloromethane/sodium hydroxide (1.0N) mixture and the layers were separated. The organic layer was evaporated to give the corresponding product, detailed on the following table.

| Entry | Structure | Compound name | MH$^+$ | R$_t$ (mins) | Qty (mg) |
|---|---|---|---|---|---|
| 241 | 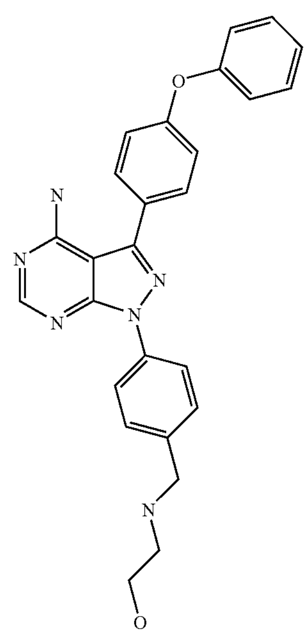 | 2-({4-[4-amino-3-(4-phenoxyphenyl)-1H-pyrazolo[3,4-d]pyrimidin-1-yl]benzyl}amino-1-ethanol | 453.2 | 2.05 | 10 |

-continued

| Entry | Structure | Compound name | MH+ | R$_t$ (mins) | Qty (mg) |
|---|---|---|---|---|---|
| 242 | 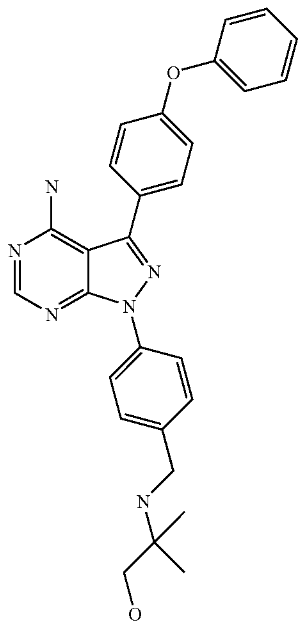 | 2-({4-[4-amino-3-(4-phenoxy-phenyl)-1H-pyrazolo[3,4-d]pyrimidin-1-yl]benzyl}amino)-2-methyl-1-propanol | 481.2 | 2.12 | 12 |
| 243 | 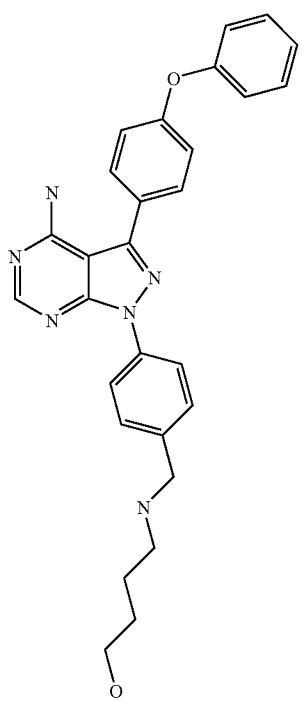 | 4-({4-[4-amino-3-(4-phenoxy-phenyl)-1H-pyrazolo[3,4-d]pyrimidin-1-yl]benzyl}amino)-1-butanol | 481.2 | 2.05 | 10 |

-continued

| Entry | Structure | Compound name | MH+ | R$_t$ (mins) | Qty (mg) |
|---|---|---|---|---|---|
| 244 | 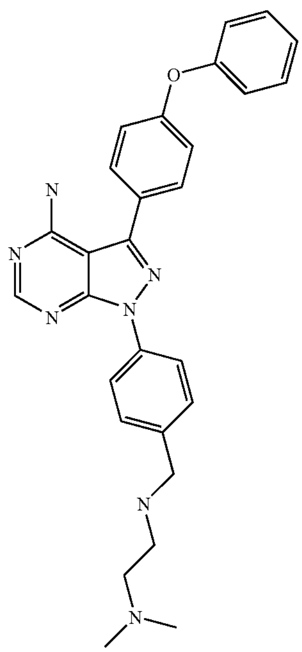 | N1-{4-[4-amino-3-(4-phenoxy-phenyl)-1H-pyrazolo[3,4-d]pyrimidin-1-yl]benzyl}-N2,N2-dimethyl-1,2-ethanediamine | 480.2 | 2.03 | 2 |
| 245 | 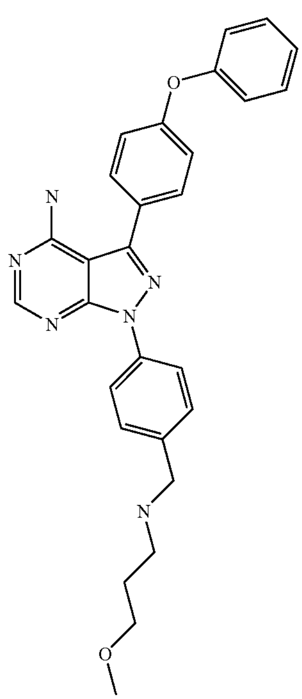 | 1-(4-{[(3-methoxy-propyl)amino]methyl}phenyl)-3-(4-phenoxy-phenyl)-1H-pyrazolo[3,4-d]pyrimidin-4-amine | 481.2 | 2.3 | 2 |

-continued

| Entry | Structure | Compound name | MH+ | R$_t$ (mins) | Qty (mg) |
|---|---|---|---|---|---|
| 246 | 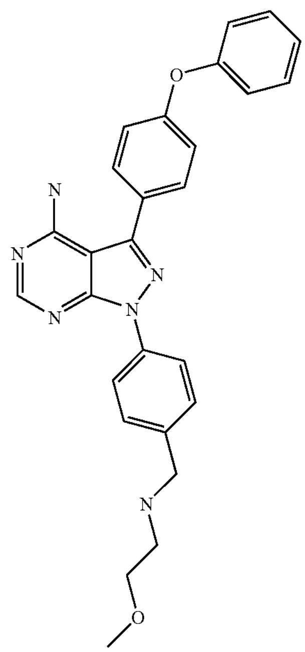 | 1-(4-{[(2-methoxy-ethyl)amino]methyl}phenyl)-3-(4-phenoxy-phenyl)-1H-pyra-zolo[3,4-d]pyrimidin-4-amine | 467.2 | 2.22 | 10 |
| 247 | 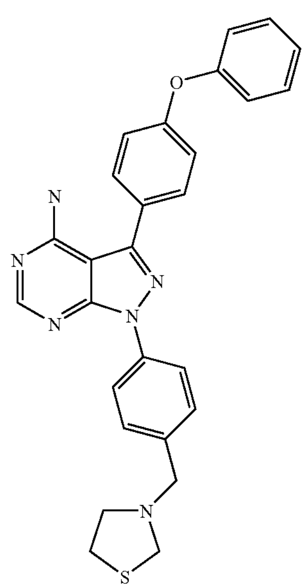 | 3-(4-phenoxyphenyl)-1-[4-(1,3-thia-zolan-3-ylmethyl)phenyl]-1H-py-razolo[3,4-d]pyrimidin-4-amine | 481.2 | 4.2 | 3 |

-continued

| Entry | Structure | Compound name | MH+ | R_t (mins) | Qty (mg) |
|---|---|---|---|---|---|
| 248 | 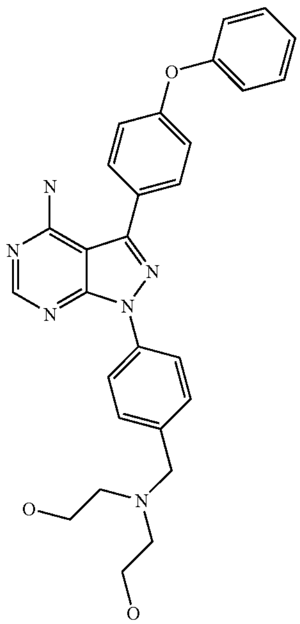 | 2-[{4-[4-amino-3-(4-phenoxy-phenyl)-1H-pyrazolo[3,4-d]py-rimidin-1-yl]benzyl}(2-hydroxy-ethyl)amino]-1-ethanol | 497.2 | 2.02 | 2 |
| 249 | 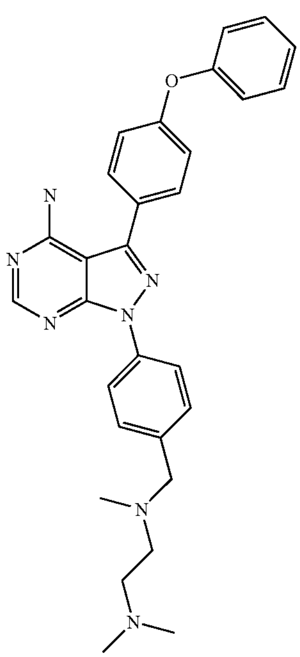 | N1-{4-[4-amino-3-(4-phenoxy-phenyl)-1H-pyrazolo[3,4-d]py-rimidin-1-yl]benzyl}-N1,N2,N2-tri-methyl-1,2-ethanediamine | 494.3 | 2.47 | 8 |

| Entry | Structure | Compound name | MH+ | R$_t$ (mins) | Qty (mg) |
|---|---|---|---|---|---|
| 250 | 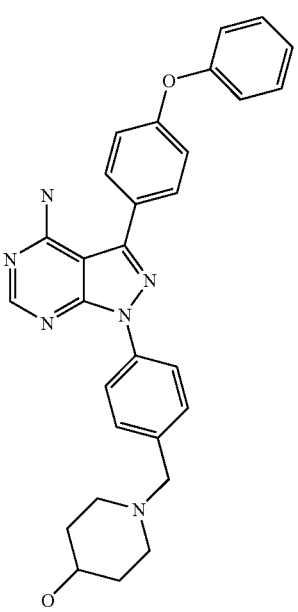 | 1-{4-[4-amino-3-(4-phenoxyphenyl)-1H-pyrazolo[3,4-d]pyrimidin-1-yl]benzyl}-4-piperidinol | 493.3 | 2.13 | 2 |
| 251 | 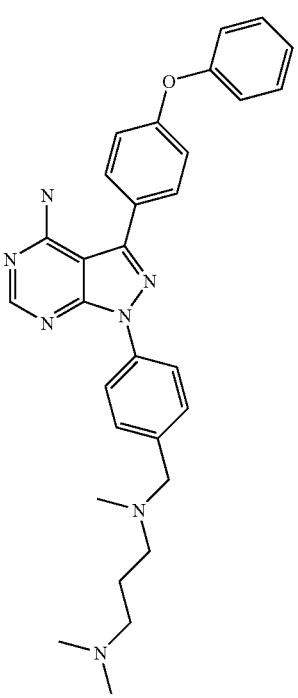 | N1-{4-[4-amino-3-(4-phenoxyphenyl)-1H-pyrazolo[3,4-d]pyrimidin-1-yl]benzyl}-N1,N3,N3-trimethyl-1,3-propanediamine | 508.3 | 1.78 | 9 |

-continued

| Entry | Structure | Compound name | MH+ | R_t (mins) | Qty (mg) |
|---|---|---|---|---|---|
| 252 | 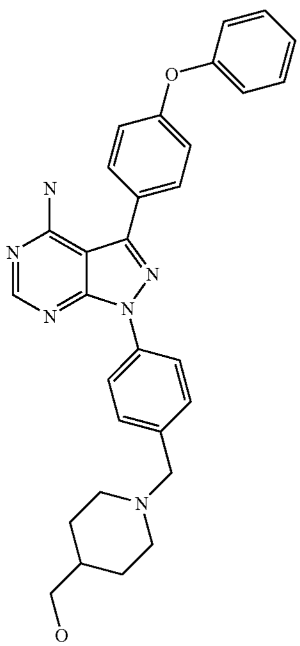 | (1-{4-[4-amino-3-(4-phenoxyphenyl)-1H-pyrazolo[3,4-d]pyrimidin-1-yl]benzyl}-4-piperidyl)methanol | 507.3 | 2.12 | 9 |

Example 253

N1-{4-[4-amino-1-(4-piperidyl)-1H-pyrazolo[3,4-d]pyrimidin-3-yl]-2-methoxyphenyl}-2-fluoro-4-(trifluoromethyl)benzamide, Dimaleate salt N1-{4-[4-amino-1-(4-piperidyl)-1H-pyrazolo[3,4-d]pyrimidin-3-yl]-2-methoxyphenyl}-2-fluoro-4-(trifluoromethyl)benzamide (380 mg, 0.717 mmol) was dissolved in hot ethyl acetate (70 mL) and maleic acid (167 mg, 1.435 mmol) in hot ethyl acetate (3 mL) was added. The reaction mixture was stirred at room temperature for 3 hours. The solid was collected by filtration to give N1-{4-[4-amino-1-(4-piperidyl)-1H-pyrazolo[3,4-d]pyrimidin-3-yl]-2-methoxyphenyl}-2-fluoro-4-(trifluoromethyl) benzamide, dimaleate salt (489 mg, 90%). $^1$H NMR (DMSO-$d_6$) δ 2.15 (m, 2H), 2.41 (m, 2H), 3.23 (m, 2H), 3.94 (s, 3H), 5.09 (m, 1H), 6.14 (m, s, 4H), 7.33 (m, 2H), 7.76 (m, 1H), 7.88 (m, 1H), 7.99 (m, 1H), 8.28 (s, 1H), 8.33 (m, 2H), 8.70 (bs, 1H), 9.92 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH+=530.2, $R_t$=2.03 min.

Intermediate 6: N1-4-[4-amino-1-(4-piperidyl)-1H-pyrazolo[3,4-d]pyrimidin-3-yl]-2-methoxyphenyl-2-fluoro-4-(trifluoromethyl)benzamide A. tert-Butyl 4-[4-amino-3-(4-[2-fluoro-4-(trifluoromethyl)benzoyl]amino-3-methoxyphenyl)-1H-pyrazolo[3,4-d]pyrimidin-1-yl]-1-piperidinecarboxylate 2-Fluoro-4-(trifluoromethyl)-1-benzenecarbonyl chloride (3.05 mL, 20.2 mmol) in dichloromethane (25 mL) was added to a solution of tert-butyl 4-[4-amino-3-(4-amino-3-methoxyphenyl)-1H-pyrazolo[3,4-d]pyrimidin-1-yl]-1-piperidinecarboxylate (8.77 g, 20.0 mmol) in pyridine (50 mL) at 0° C. After 5 minutes, the ice water bath was removed and the reaction mixture stirred at room temperature for 1 hours. 2-Fluoro-4-(trifluoromethyl)-1-benzenecarbonyl chloride (0.5 mL, 3.31 mmol) was added and the reaction mixture was stirred for addition 30 minutes. The solvent was evaporated and the residue was dissolved in dichloromethane. The organic layer was washed with water, brine then dried over MgSO$_4$. The solvent was evaporated and the residue was purified by flash column chromatography using ethyl acetate/dichloromethane (80:20 to 100:0) as mobile phase to give tert-Butyl 4-[4-amino-3-(4-[2-fluoro-4-(trifluoromethyl)benzoyl]amino-3-methoxyphenyl)-1H-pyrazolo[3,4-d]pyrimidin-1-yl]-1-piperidinecarboxylate (11.2 g, 89%). $^1$H NMR (CDCl$_3$-d) δ 1.48 (s, 9H), 2.04 (m, 2H), 2.30 (m, 2H), 2.98 (m, 2H), 4.05 (s, 3H), 4.32 (m, 2H), 4.95 (m, 1H), 5.89 (bs, 2H), 7.33 (m, 2H), 7.51 (d, J=11.62 Hz, 1H), 7.61 (d, J=8.21 Hz, 1H), 8.36 (m, 2H), 8.72 (d, J=8.18 Hz, 1H), 9.32 (d, J=14.39 Hz, 1H).

B. N1-4-[4-amino-1-(4-piperidyl)-1H-pyrazolo[3,4-d]pyrimidin-3-yl]-2-methoxyphenyl-2-fluoro-4-(trifluoromethyl)benzamide A mixture of trifluoroacetic acid/dichloromethane (20:80, 100 mL) was added to a solution of tert-Butyl 4-[4-amino-3-(4-[2-fluoro-4-(trifluoromethyl)benzoyl]amino-3-methoxyphenyl)-1H-pyrazolo [3,4-d]pyrimidin-1-yl]-1-piperidinecarboxylate (11.2, 17.79 mmol) in dichloromethane (50 mL) at 0° C. 15 minutes later, the ice-bath was removed and the reaction mixture was stirred at room temperature for 3 hours. The solvents were evaporated and the residue was dissolved in dichloromethane. Saturated sodium bicarbonate solution was added to adjust the pH to about 8. The suspension was lyophilized. Water (100 ml) was added and the aqueous was extracted with dichloromethane repetitively to give N1-4-[4-amino-1-(4-piperidyl)-1H-pyrazolo[3,4-d]pyrimidin-3-yl]-2-methoxyphenyl-2-fluoro-4-(trifluoromethyl)benzamide (9.12 g, 97%). $^1$H NMR (DMSO-d$_6$) δ 1.85 (m, 2H), 2.12 (m, 2H), 2.70 (m, 2H), 3.14 (m, 2H), 3.94 (s, 3H), 4.77 (m, 1H), 7.32 (m, 2H), 7.75 (d, J=8.02 Hz, 1H), 7.89 (d, J=10.31 Hz, 1H), 8.00 (m, 1H), 8.24 (s, 1H), 8.31 (d, J=8.16 Hz, 1H), 9.90 (s, 1H).

Examples 254-293

Examples 254-293 were derived from N1-4-[4-amino-1-(4-piperidyl)-1H-pyrazolo [3,4-d]pyrimidin-3-yl]-2-methoxyphenyl-2-fluoro-4-(trifluoromethyl)benzamide (Intermediate 6) using method A or method B: Method A: N1-{4-[4-amino-1-(4-piperidyl)-1H-pyrazolo[3,4-d]pyrimidin-3-yl]-2-methoxyphenyl}-2-fluoro-4-(trifluoromethyl) benzamide (100 mg, 0.189 mmol), the appropriate aldehyde (0.378 mmol), sodium triacetoxyborohydride (120 mg, 0.567 mmol) and glacial acetic acid (48 mg, 0.378 mmol) were mixed in 1,2-dichloroethane (4 mL). After shacking at room temperature overnight, further amount of the aldehyde (0.378 mmol), sodium triacetoxyborohydride (120 mg, 0.567) and glacial acetic acid (48 mg, 0.378 mmol) were added again and the reaction mixtures were shaken at room temperature overnight. The solvent was evaporated and the residue was purified either by flash column chromatography using dichloromethane/methanol (95:5 to 70:30) or by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give the corresponding product, detailed on the following table.

Method B: N1-{4-[4-amino-1-(4-piperidyl)-1H-pyrazolo[3,4-d]pyrimidin-3-yl]-2-methoxyphenyl}-2-fluoro-4-(trifluoromethyl)benzamide (100 mg, 0.189 mmol), the appropriate ketone or some less reactive aldehyde (0.378 mmol), sodium triacetoxyborohydride (120 mg, 0.567 mmol) and glacial acetic acid (48 mg, 0.378 mmol) were mixed in 1,2-dichloroethane (4 mL). The reaction mixture was shaken at 70° C. for 4 hours. The solvent was evaporated and the residue was purified ether by flash column chromatography using dichloromethane/methanol (95:5 to 70:30) or by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give the corresponding product, detailed on the following table.

| | Structure | Compound name | MH$^+$ | R$_t$ (mins) | Qty (mg) | Method |
|---|---|---|---|---|---|---|
| 254 | 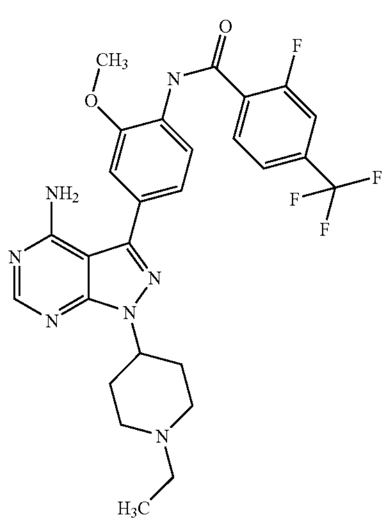 | N1-{4-[4-amino-1-(1-ethyl-4-piperidyl)-1H-pyrazolo[3,4-d]pyrimidin-3-yl]-2-methoxyphenyl}-2-fluoro-4-(trifluoromethyl)benzamide | MH$^-$ 556.1 | 2.07 | 56 | A |

-continued

| | Structure | Compound name | MH+ | R_t (mins) | Qty (mg) | Method |
|---|---|---|---|---|---|---|
| 255 | 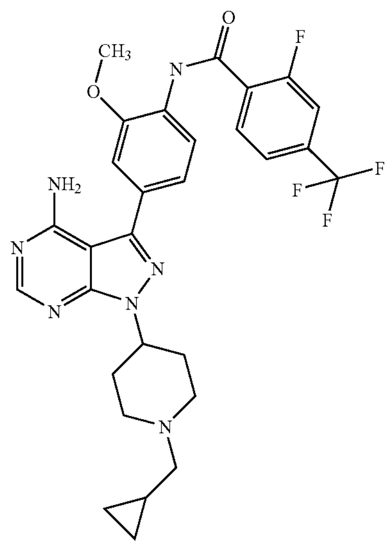 | N1-(4-{4-amino-1-[1-(cyclo-propylmethyl)-4-piperidyl]-1H-pyrazolo[3,4-d]pyrimidin-3-yl}-2-methoxyphenyl)-2-fluoro-4-(trifluoromethyl)benzamide | MH⁻ 582.1 | 2.22 | 80 | A |
| 256 | 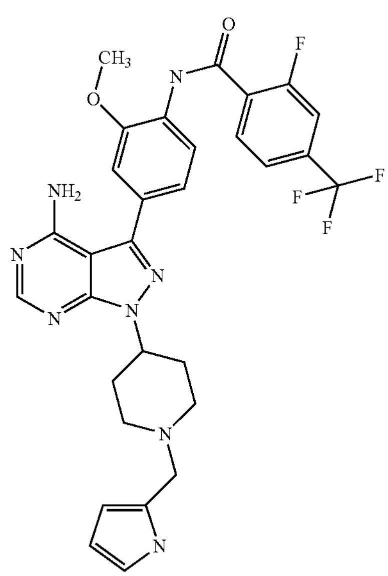 | N1-(4-{4-amino-1-[1-(1H-2-pyrrolylmethyl)-4-piperidyl]-1H-pyrazolo[3,4-d]pyrimidin-3-yl}-2-methoxyphenyl)-2-fluoro-4-(trifluoromethyl)benzamide, acetate salt | MH⁻ 607.0 | 2.45 | 60 | A |

-continued

| | Structure | Compound name | MH+ | R$_t$ (mins) | Qty (mg) | Method |
|---|---|---|---|---|---|---|
| 257 | 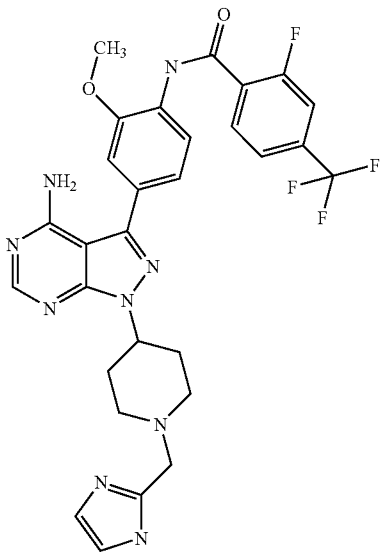 | N1-(4-{4-amino-1-[1-(1H-2-imidazolylmethyl)-4-piperidyl]-1H-pyrazolo[3,4-d]pyrimidin-3-yl}-2-methoxyphenyl)-2-fluoro-4-(trifluoromethyl)benzamide | MH+ 610.2 | 2.17 | 68 | B |
| 258 | 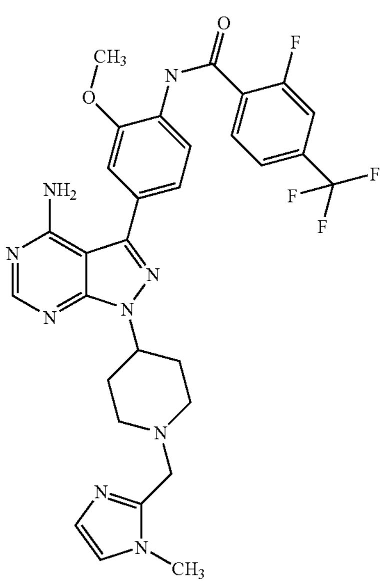 | N1-[4-(4-amino-1-{1-[(1-methyl-1H-2-imidazolyl)methyl]-4-piperidyl}-1H-pyrazolo[3,4-d]pyrimidin-3-yl)-2-methoxyphenyl]-2-fluoro-4-(trifluoromethyl)benzamide, acetate salt | MH− 622.0 | 2.23 | 56 | A |

|  | Structure | Compound name | MH+ | R<sub>t</sub> (mins) | Qty (mg) | Method |
|---|---|---|---|---|---|---|
| 259 | 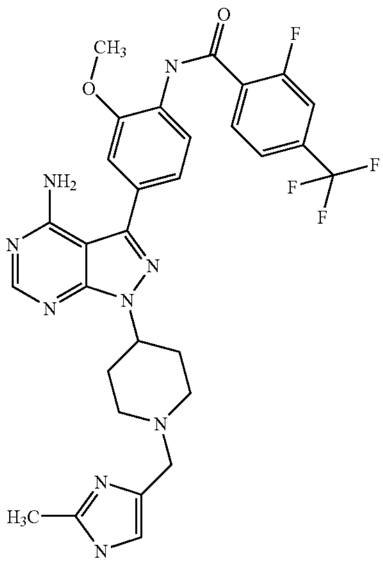 | N1-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-2-fluoro-4-(trifluoromethyl)benzamide, acetate salt | MH⁻ 622.0 | 2.05 | 32 | A |
| 260 | 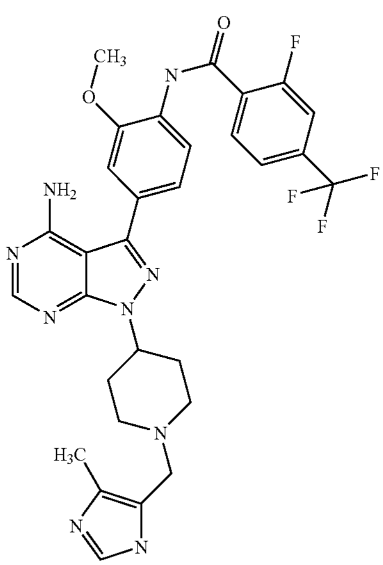 | N1-[4-(4-amino-1-{1-[(4-methyl-1H-5-imidazolyl)methyl]-4-piperidyl}-1H-pyrazolo[3,4-d]pyrimidin-3-yl)-2-methoxyphenyl]-2-fluoro-4-(trifluoromethyl)benzamide, acetate salt | MH⁻ 622.0 | 2.08 | 84 | A |

-continued

| | Structure | Compound name | MH+ | R$_t$ (mins) | Qty (mg) | Method |
|---|---|---|---|---|---|---|
| 261 | 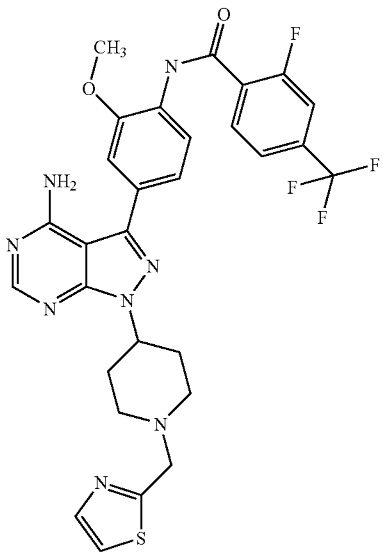 | N1-(4-{4-amino-1-[1-(1,3-thiazol-2-ylmethyl)-4-piperidyl]-1H-pyrazolo[3,4-d]pyrimidin-3-yl}-2-methoxyphenyl)-2-fluoro-4-(trifluoromethyl)benzamide | MH⁻ 625.1 | 3.15 | 73 | A |
| 262 | 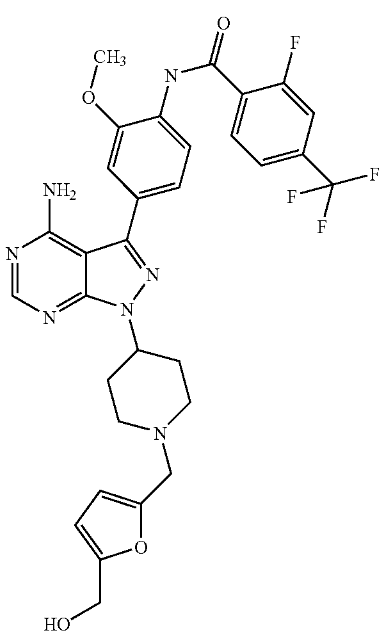 | N1-{4-[4-amino-1-(1-{[5-hydroxymethyl)-2-furyl]methyl}-4-piperidyl)-1H-pyrazolo[3,4-d]pyrimidin-3-yl]-2-methoxyphenyl}-2-fluoro-4-(trifluoromethyl)benzamide | MH⁻ 638.1 | 2.20 | 36 | A |

-continued

| | Structure | Compound name | MH+ | R$_t$ (mins) | Qty (mg) | Method |
|---|---|---|---|---|---|---|
| 263 | 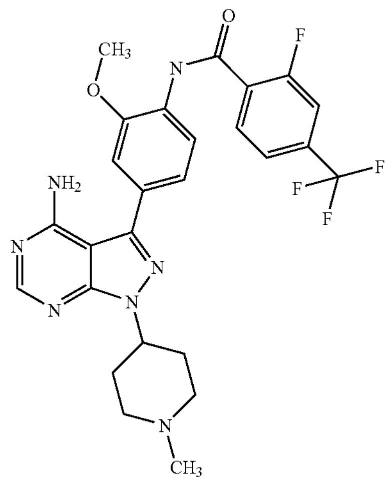 | N1-{4-[4-amino-1-(1-methyl-4-piperidyl)-1H-pyrazolo[3,4-d]pyrimidin-3-yl]-2-methoxyphenyl}-2-fluoro-4-(trifluoromethyl)benzamide | MH⁻ 542.2 | 2.03 | 67 | A |
| 264 | 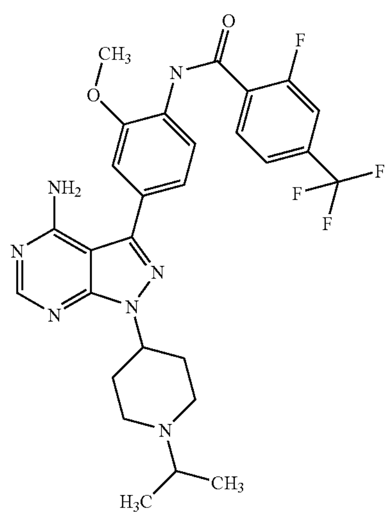 | N1-{4-[4-amino-1-(1-isopropyl-4-piperidyl)-1H-pyrazolo[3,4-d]pyrimidin-3-yl]-2-methoxyphenyl}-2-fluoro-4-(trifluoromethyl)benzamide | MH⁻ 570.1 | 2.08 | 58 | B |
| 265 | 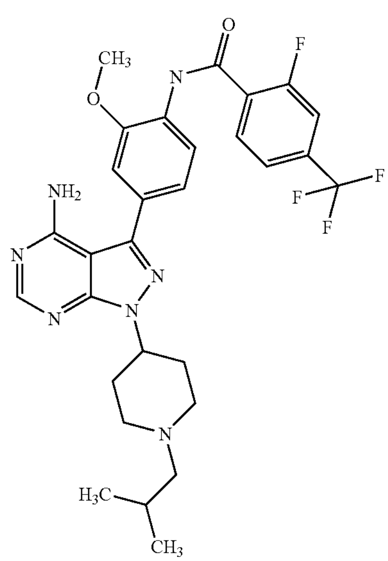 | N1-{4-[4-amino-1-(1-isobutyl-4-piperidyl)-1H-pyrazolo[3,4-d]pyrimidin-3-yl]-2-methoxyphenyl}-2-fluoro-4-(trifluoromethyl)benzamide, acetate salt | MH⁻ 584.0 | 2.43 | 54 | A |

| | Structure | Compound name | MH+ | R_t (mins) | Qty (mg) | Method |
|---|---|---|---|---|---|---|
| 266 | 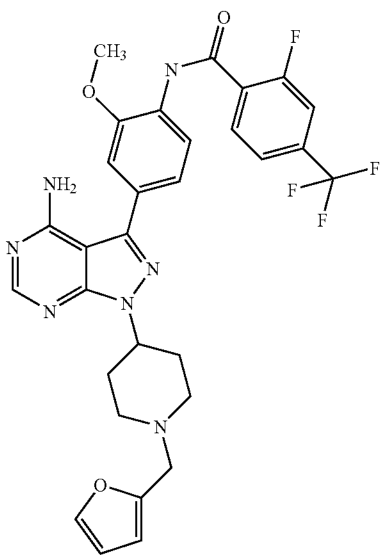 | N1-(4-{4-amino-1-[1-(2-furyl-methyl)-4-piperidyl]-1H-pyrazolo[3,4-d]pyrimidin-3-yl}-2-methoxyphenyl)-2-fluoro-4-(trifluoromethyl)benzamide | MH⁻ 608.1 | 2.63 | 82 | A |
| 267 | 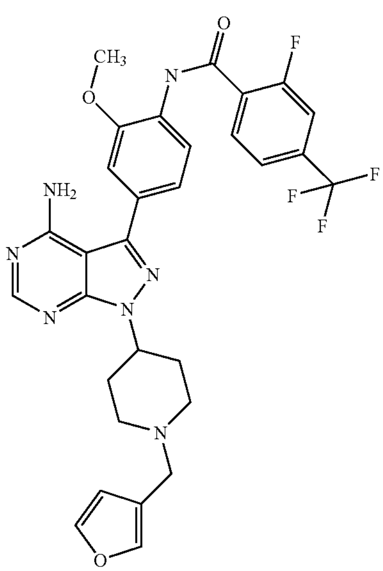 | N1-(4-{4-amino-1-[1-(3-furyl-methyl)-4-piperidyl]-1H-pyrazolo[3,4-d]pyrimidin-3-yl}-2-methoxyphenyl)-2-fluoro-4-(trifluoromethyl)benzamide | MH+ 610.2 | 2.43 | 54 | A |

-continued
| | Structure | Compound name | MH+ | R_t (mins) | Qty (mg) | Method |
|---|---|---|---|---|---|---|
| 268 | 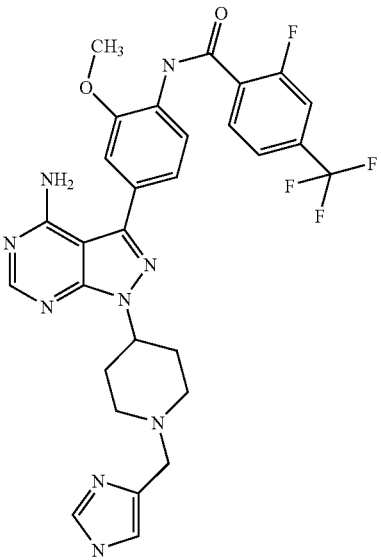 | N1-(4-{4-amino-1-[1-(1H-4-imidazolylmethyl)-4-piperidyl]-1H-pyrazolo[3,4-d]pyrimidin-3-yl}-2-methoxyphenyl)-2-fluoro-4-(trifluoromethyl)benzamide, acetate salt | MH⁻ 608.0 | 1.90 | 55 | A |
| 269 | 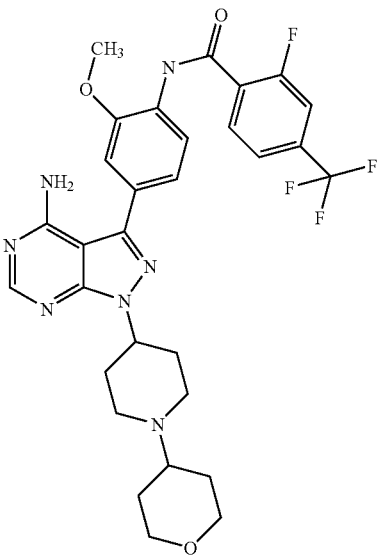 | N1-{4-[4-amino-1-(1-tetrahydro-2H-4-pyranyl-4-piperidyl)-1H-pyrazolo[3,4-d]pyrimidin-3-yl]-2-methoxyphenyl}-2-fluoro-4-(trifluoromethyl)benzamide | MH+ 614.2 | 2.13 | 91 | B |

| | Structure | Compound name | MH+ | R_t (mins) | Qty (mg) | Method |
|---|---|---|---|---|---|---|
| 270 | 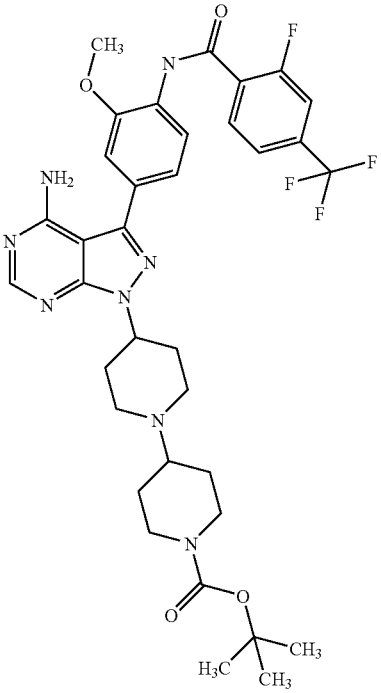 | tert-butyl 4-{4-[4-amino-3-(4-{[2-fluoro-4-(tri-fluoromethyl)benzoyl]amino}-3-methoxy-phenyl)-1H-pyrazolo[3,4-d]py-rimidin-1-yl]-1-piperidyl}-1-piperidine-carboxylate | MH+ 713.3 | 2.57 | 74 | B |
| 271 | 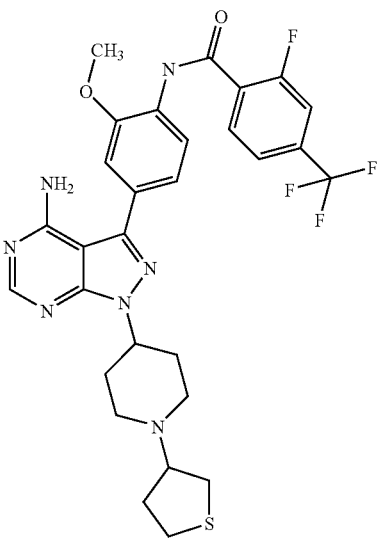 | N1-{4-[4-amino-1-(1-tetrahydro-3-thio-phenyl-4-piperidyl)-1H-py-razolo[3,4-d]pyrimidin-3-yl]-2-methoxy-phenyl}-2-fluoro-4-(tri-methyl)benzamide | MH+ 616.2 | 2.53 | 102 | B |

-continued
| | Structure | Compound name | MH+ | R_t (mins) | Qty (mg) | Method |
|---|---|---|---|---|---|---|
| 272 | 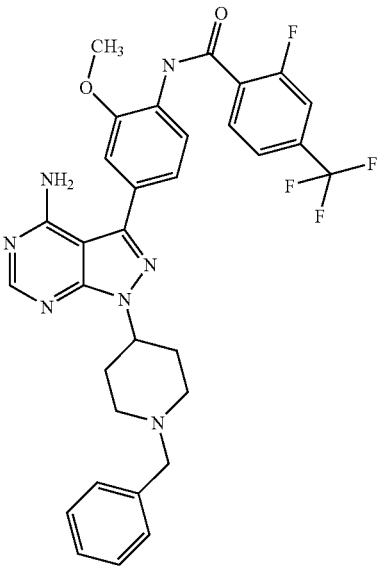 | N1-{4-[4-amino-1-(1-benzyl-4-piperidyl)-1H-pyrazolo[3,4-d]pyrimidin-3-yl]-2-methoxyphenyl}-2-fluoro-4-(trifluoromethyl)benzamide | MH− 618.0 | 2.67 | 69 | A |
| 273 | 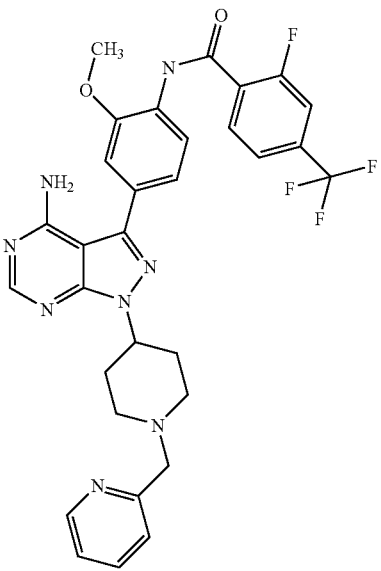 | N1-(4-{4-amino-1-[1-(2-pyridylmethyl)-4-piperidyl]-1H-pyrazolo[3,4-d]pyrimidin-3-yl}-2-methoxyphenyl)-2-fluoro-4-(trifluoromethyl)benzamide, acetate salt | MH− 619.1 | 2.32 | 84 | A |

| | Structure | Compound name | MH+ | R_t (mins) | Qty (mg) | Method |
|---|---|---|---|---|---|---|
| 274 | 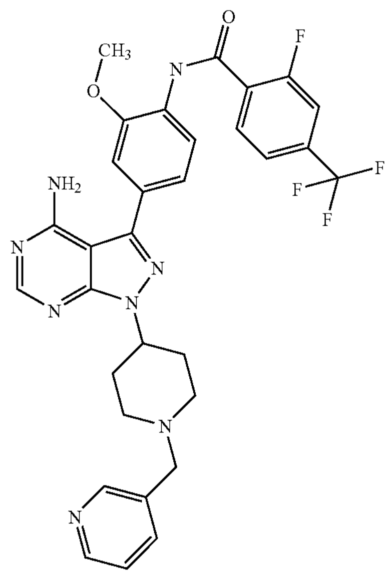 | N1-(4-{4-amino-1-[1-(3-pyridyl-methyl)-4-piperidyl]-1H-pyrazolo[3,4-d]pyrimidin-3-yl}-2-methoxyphenyl)-2-fluoro-4-(trifluoromethyl)benzamide | MH⁻ 619.1 | 2.32 | 77 | A |
| 275 | 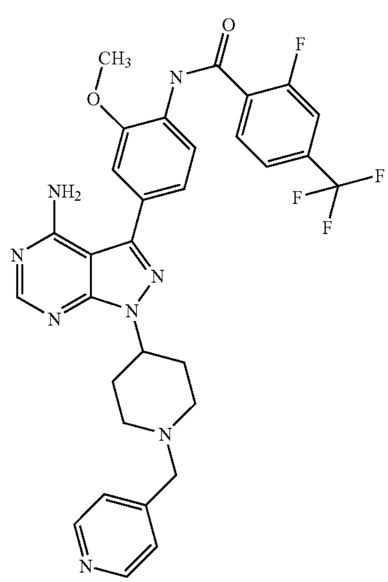 | N1-(4-{4-amino-1-[1-(4-pyridyl-methyl)-4-piperidyl]-1H-pyrazolo[3,4-d]pyrimidin-3-yl}-2-methoxyphenyl)-2-fluoro-4-(trifluoromethyl)benzamide | MH⁻ 619.1 | 2.63 | 81 | A |

-continued

| | Structure | Compound name | MH+ | R_t (mins) | Qty (mg) | Method |
|---|---|---|---|---|---|---|
| 276 | 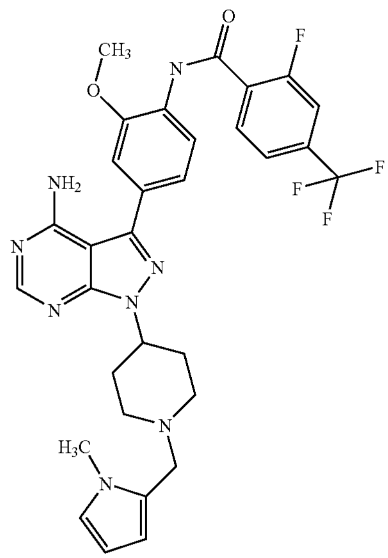 | N1-[4-(4-amino-1-{1-[(1-methyl-1H-2-pyr-rolyl)methyl]-4-piperidyl}-1H-py-razolo[3,4-d]pyrimidin-3-yl)-2-methoxy-phenyl]-2-fluoro-4-(tri-fluoromethyl)benzamide, acetate salt | MH⁻ 621.2 | 2.52 | 35 | B |
| 277 | 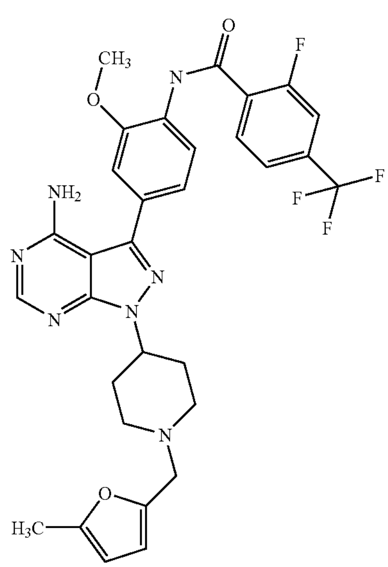 | N1-[4-(4-amino-1-{1-[(5-methyl-2-furyl)meth-yl]-4-piperidyl}-1H-py-razolo[3,4-d]pyrimidin-3-yl)-2-methoxy-phenyl]-2-fluoro-4-(tri-fluoromethyl)benzamide, acetate salt | MH⁻ 622.1 | 2.65 | 78 | A |

-continued

| | Structure | Compound name | MH+ | R$_t$ (mins) | Qty (mg) | Method |
|---|---|---|---|---|---|---|
| 278 | 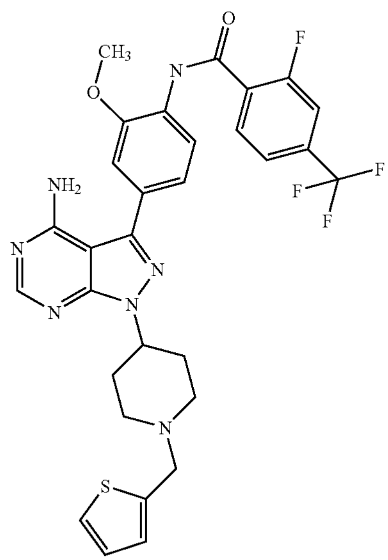 | N1-(4-{4-amino-1-[1-(2-thienyl-methyl)-4-piperidyl]-1H-pyrazolo[3,4-d]pyrimidin-3-yl}-2-methoxy-phenyl)-2-fluoro-4-(trifluoromethyl)benzamide | MH⁻ 624.0 | 3.00 | 57 | B |
| 279 | 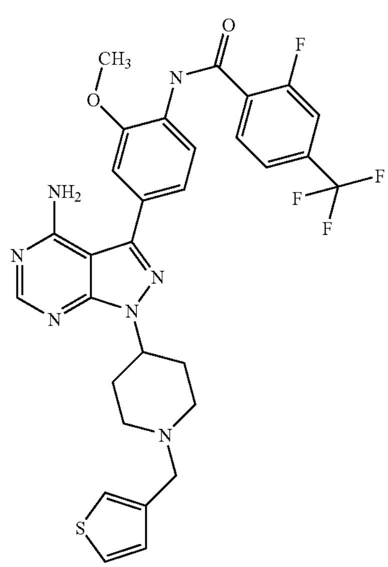 | N1-(4-{4-amino-1-[1-(3-thienyl-methyl)-4-piperidyl]-1H-pyrazolo[3,4-d]pyrimidin-3-yl}-2-methoxy-phenyl)-2-fluoro-4-(trifluoromethyl)benzamide, acetate salt | MH+ 626.2 | 2.55 | 87 | A |

| | Structure | Compound name | MH+ | R$_t$ (mins) | Qty (mg) | Method |
|---|---|---|---|---|---|---|
| 280 | 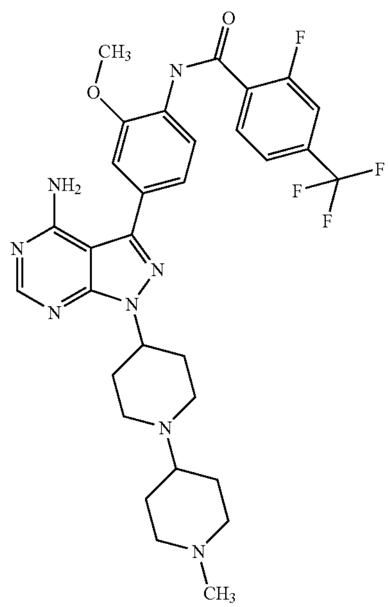 | N1-[4-(4-amino-1-{1-[(1-methyl-piperidin-4-yl]-4-piperidyl}-1H-pyrazolo[3,4-d]pyrimidin-3-yl)-2-methoxy-phenyl]-2-fluoro-4-(trifluoromethyl)benzamide, diacetate salt | MH+ 627.2 | 1.80 | 72 | B |
| 281 | 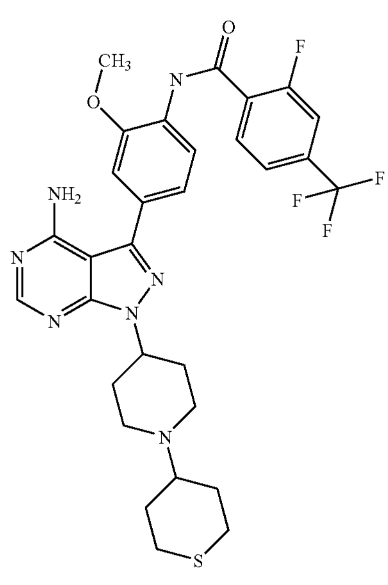 | N1-{4-[4-amino-1-(1-tetrahydro-2H-4-thiopyranyl-4-piperidyl)-1H-pyrazolo[3,4-d]pyrimidin-3-yl]-2-methoxy-phenyl}-2-fluoro-4-(trifluoromethyl)benzamide | MH+ 630.2 | 2.37 | 20 | B |

-continued

| | Structure | Compound name | MH+ | R_t (mins) | Qty (mg) | Method |
|---|---|---|---|---|---|---|
| 282 | 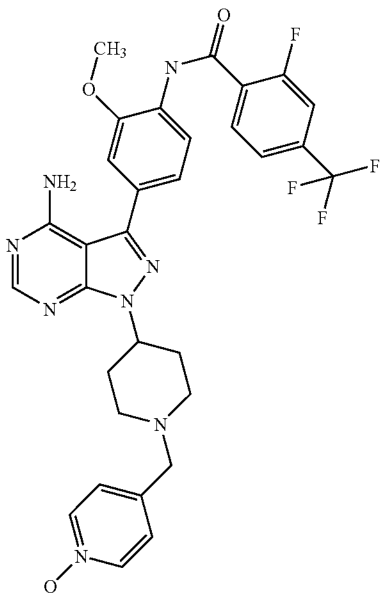 | 4-({4-[4-amino-3-(4-{[2-fluoro-4-(tri-fluoromethyl)benzoyl]amino}-3-methoxy-phenyl)-1H-pyrazolo[3,4-d]pyrimidin-1-yl]piperidino}methyl)-1-pyridine-N-oxide | MH+ 637.2 | 2.13 | 93 | A |
| 283 | 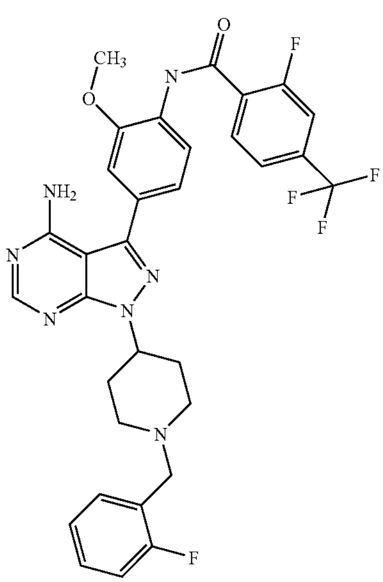 | N1-(4-{4-amino-1-[1-(2-fluoro-benzyl)-4-piperidyl]-1H-pyrazolo[3,4-d]pyrimidin-3-yl}-2-methoxy-phenyl)-2-fluoro-4-(tri-fluoromethyl)benzamide | MH+ 638.2 | 3.13 | 84 | A |

-continued

| | Structure | Compound name | MH+ | R$_t$ (mins) | Qty (mg) | Method |
|---|---|---|---|---|---|---|
| 284 | 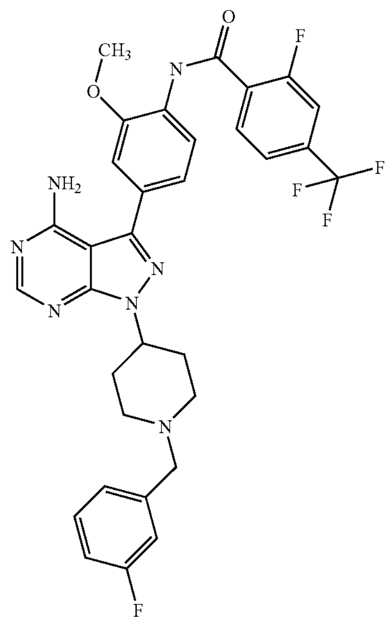 | N1-(4-{4-amino-1-[1-(3-fluoro-benzyl)-4-piperidyl]-1H-pyrazolo[3,4-d]pyrimidin-3-yl}-2-methoxy-phenyl)-2-fluoro-4-(trifluoromethyl)benzamide | MH+ 638.2 | 3.25 | 77 | A |
| 285 | 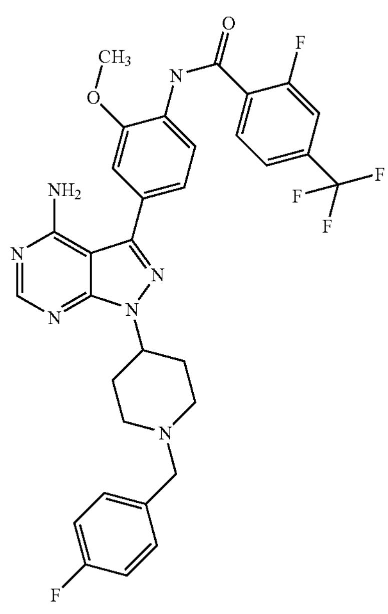 | N1-(4-{4-amino-1-[1-(4-fluoro-benzyl)-4-piperidyl]-1H-pyrazolo[3,4-d]pyrimidin-3-yl}-2-methoxy-phenyl)-2-fluoro-4-(trifluoromethyl)benzamide | MH+ 638.2 | 2.87 | 88 | A |

-continued

| | Structure | Compound name | MH+ | R_t (mins) | Qty (mg) | Method |
|---|---|---|---|---|---|---|
| 286 | 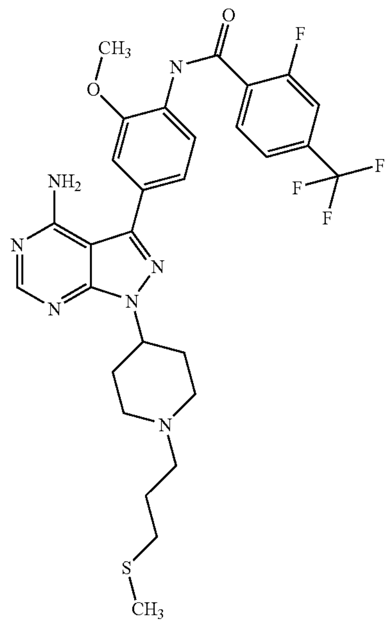 | N1-[4-(4-amino-1-{1-[3-(methyl-sulfanyl)propyl]-4-piperidyl}-1H-pyrazolo[3,4-d]pyrimidin-3-yl)-2-methoxyphenyl]-2-fluoro-4-(trifluoromethyl)benzamide | MH+ 618.2 | 2.42 | 76 | A |
| 287 | 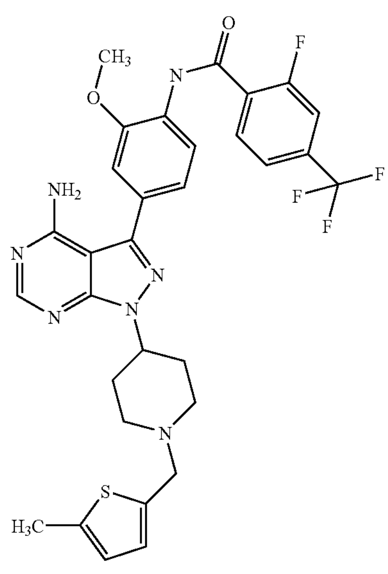 | N1-[4-(4-amino-1-{1-[(5-methyl-2-thienyl)methyl]-4-piperidyl}-1H-pyrazolo[3,4-d]pyrimidin-3-yl)-2-methoxyphenyl]-2-fluoro-4-(trifluoromethyl)benzamide | MH+ 640.2 | 3.23 | 73 | A |

| Structure | Compound name | MH+ | R$_t$ (mins) | Qty (mg) | Method |
|---|---|---|---|---|---|
| 288 | N1-(4-{4-amino-1-[1-(3-cyano-benzyl)-4-piperidyl]-1H-pyrazolo[3,4-d]pyrimidin-3-yl}-2-methoxyphenyl)-2-fluoro-4-(trifluoromethyl)benzamide | MH+ 645.2 | 3.28 | 57 | A |
| 289 | N1-(4-{4-amino-1-[1-(4-cyano-benzyl)-4-piperidyl]-1H-pyrazolo[3,4-d]pyrimidin-3-yl}-2-methoxyphenyl)-2-fluoro-4-(trifluoromethyl)benzamide | MH+ 645.2 | 3.32 | 62 | A |

-continued

| | Structure | Compound name | MH+ | R$_t$ (mins) | Qty (mg) | Method |
|---|---|---|---|---|---|---|
| 290 | 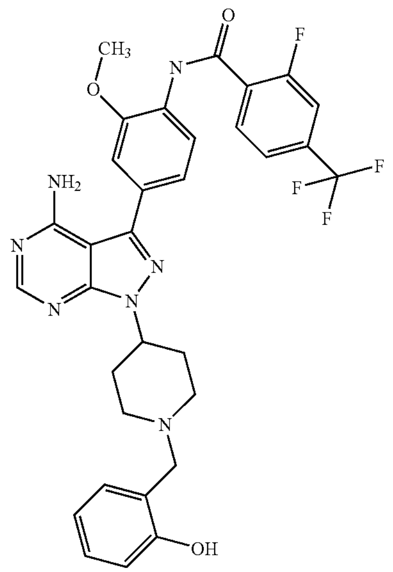 | N1-(4-{4-amino-1-[1-(2-cyano-benzyl)-4-piperidyl]-1H-pyrazolo[3,4-d]pyrimidin-3-yl}-2-methoxyphenyl)-2-fluoro-4-(trifluoromethyl)benzamide | MH+ 645.2 | 3.78 | 62 | A |
| 291 | 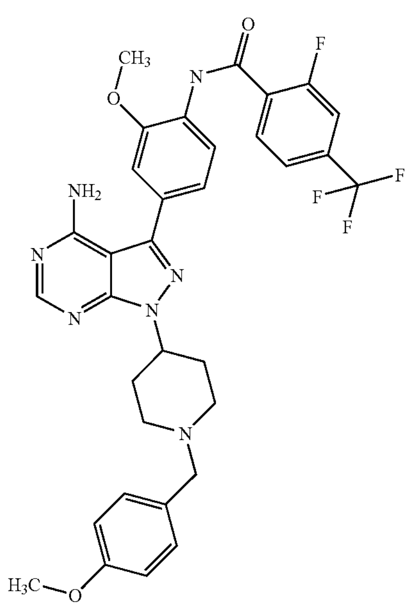 | N1-(4-{4-amino-1-[1-(4-methoxy-benzyl)-4-piperidyl]-1H-pyrazolo[3,4-d]pyrimidin-3-yl}-2-methoxyphenyl)-2-fluoro-4-(trifluoromethyl)benzamide | MH+ 650.2 | 2.63 | 45 | A |

-continued

| | Structure | Compound name | MH+ | R_t (mins) | Qty (mg) | Method |
|---|---|---|---|---|---|---|
| 292 | 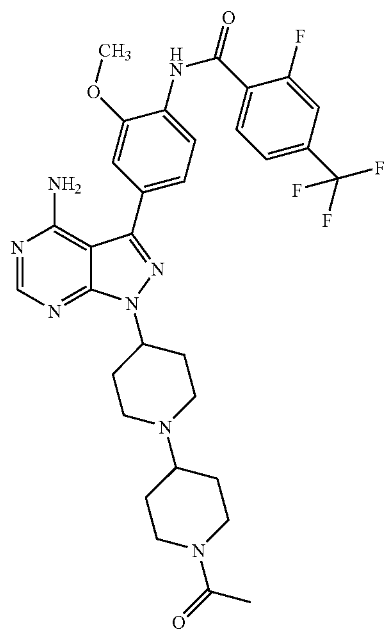 | N1-[4-(4-amino-1-{1-[(1-acetyl-piperidin-4-yl]-4-piperidyl}-1H-pyrazolo[3,4-d]pyrimidin-3-yl)-2-methoxyphenyl]-2-fluoro-4-(trifluoromethyl)benzamide | MH+ 655.2 | 2.02 | 71 | B |
| 293 | 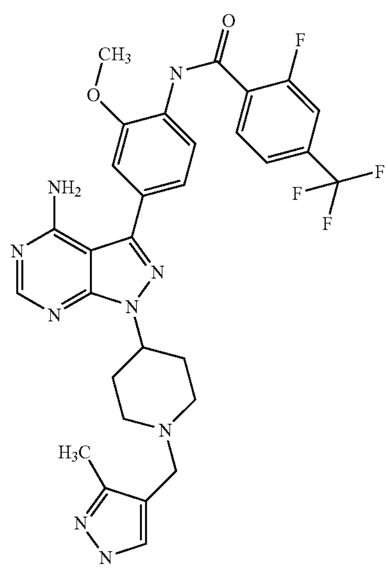 | N1-[4-(4-amino-1-{1-[(3-methyl-1H-4-pyrazolyl)methyl]-4-piperidyl}-1H-pyrazolo[3,4-d]pyrimidin-3-yl)-2-methoxy-phenyl]-2-fluoro-4-(trifluoromethyl)benzamide, acetate salt | MH+ 624.2 | 2.07 | 109 | A |

Example 294

Methyl 2-4-[4-amino-3-(4-[2-fluoro-4-(trifluoromethyl)benzoyl]amino-3-methoxyphenyl)-1H-pyrazolo[3,4-d]pyrimidin-1-yl]piperidinoacetate N1-{4-[4-amino-1-(4-piperidyl)-1H-pyrazolo[3,4-d]pyrimidin-3-yl]-2-methoxyphenyl}-2-fluoro-4-(trifluoromethyl)benzamide (122 g, 0.230 mmol), methyl 2-bromoacetate (33 uL, 0.346 mmol) and cesium carbonate (150 mg, 0.461 mmol) was mixted with DMF (2 mL). The mixture was heated to 85° C. for 2 hours. LC/MS showed formation of two new peaks, one of them was bis-alkylated one and the other the desired product. The crude mixture was purified by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give methyl 2-4-[4-amino-3-(4-[2-fluoro-4-(trifluoromethyl)benzoyl]amino-3-methoxyphenyl)-1-pyrazolo[3,4-d]pyrimidin-1-yl]piperidinoacetate (60 mg, 43%). $^1$H NMR (DMSO-d$_6$) δ 1.91 (m, 2H), 2.27 (m, 2H), 2.42 (m, 2H), 2.98 (m, 2H), 3.32 (s, 2H), 3.64 (s, 3H), 3.95 (s, 3H), 4.67 (m, 1H), 7.32 (m, 2H), 7.75 (d, J=7.96 Hz, 1H), 7.89 (d, J=10.35 Hz, 1H), 8.00 (s, 1H), 8.24 (s, 1H), 8.30 (d, J=8.13 Hz, 1H), 9.89 (s, 1H). LCMS (Thermoquest AQA single Quad MS, Finnigan HPLC-Column: Genesis, C18, 3 um, 33×4.6 mm.

Eluents: 30% B/A to 95% B/A in 4.5 min. (B: acetonitrile, A: 50 mM ammonia acetate buffer, pH 4.5), 0.8 mL/min.): MH$^+$=602.2, R$_t$=2.80 min.

Example 295 trans-3-[4-(1H-benzo[d]imidazol-1-ylmethyl)-3-methoxyphenyl]-1-[4-(4-methylpiperazino)cyclohexyl]-1H-pyrazolo[3,4-d]pyrimidin-4-amine A. 1-(4-Bromobenzyl)-1H-benzo[d]imidazole 1-Bromo-4-(bromomethyl)benzene (2.50 g, 10 mmol), 1H-benzo[d]imidazole (1.181 g, 10.0 mmol), potassium hydroxide (0.561 g, 10.0 mmol), potassium carbonate (1.382 g, 10.0 mmol) and tetrabutylammonium bromide (0.161 g, 0.5 mmol) was mixed in xylenes (60 mL). The reaction mixture was heated at 139° C. overnight. The hot reaction mixture was filtered and washed with hot xylenes. The solvent was evaporated and the residue was purified by flash column chromatography using dichloromethane/methanol (95:5 to 80:20) as mobile phase to give 1-(4-Bromobenzyl)-1H-benzo[d]imidazole (1.193 g, 42%). $^1$H NMR (CDCl$_3$) δ 5.31 (s, 2H), 7.05 (m, 2H), 7.28 (m, 3H), 7.46 (m, 2H), 7.82 (m, 1H), 7.95 (s, 1H).

B. 1-[4-(4,4,5,5-tetramethyl-1,3,2-dioxaborolan-2-yl)benzyl]-1H-benzo[d]imidazole A mixture of 1-(4-Bromobenzyl)-1H-benzo[d]imidazole (1.193 mg, 4.15 mmol), diboron pinacol ester (1.27 g, 4.98 mmol), [1.1'-bis(diphenylphosphino)ferrocene]dichloropalladium (II) complex with dichloromethane (1:1) (0.10 g, 0.12 mol) and potassium acetate (1.22 g, 12.46 mol) in N,N-dimethylformamide (25 mL) was heated at 85° C. under an atmosphere of nitrogen for 16 hours. The mixture was allowed to cool to ambient temperature and the solvent removed under reduced pressure. Dichloromethane (20 mL) was added to the residue and the resulting solid was removed by filtration through a pad of celite. The filtrate was concentrated and the residue was purified by flash chromatography on silica using dichloromethane/methanol (98:2 to 95:5) as mobile phase to give 1-[4-(4,4,5,5-tetramethyl-1,3,2-dioxaborolan-2-yl)benzyl]-1H-benzo[d]imidazole (1.38 g, 100%): $^1$H NMR (CDCl$_3$) δ 1.27 (s, 12H), 5.33 (s, 2H), 7.06 (d, J=8.24 Hz, 2H), 7.28 (d, J=8.34 Hz, 2H), 7.84 (d, J=7.70 Hz, 1H), 8.01 (s, 1H).

C. trans-3-[4-(1H-benzo[d]imidazol-1-ylmethyl)-3-methoxyphenyl]-1-[4-(4-methylpiperazino)cyclohexyl]-1H-pyrazolo[3,4-d]pyrimidin-4-amine trans-3-Iodo-1-[4-(4-methylpiperazino)cyclohexyl]-1H-pyrazolo[3,4-d]pyrimidin-4-amine (200 mg, 0.453 mmol), 1-[4-(4,4,5,5-tetramethyl-1,3,2-dioxaborolan-2-yl)benzyl]-1H-benzo[d]imidazole (303 mg, 0.906 mmol), palladium tetrakistriphenyphosphine (0.31 mg, 0.027 mmol) and sodium carbonate (155 mg, 1.09 mmol) were mixed with ethylene glycol dimethyl ether (5 mL) and water (2.5 mL). The reaction mixture was heated at reflux overnight under nitrogen. The solvent was removed and the residue was purified by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give trans-3-[4-(1H-benzo[d]imidazol-1-ylmethyl)-3-methoxyphenyl]-1-[4-(4-methylpiperazino)cyclohexyl]-1H-pyrazolo[3,4-d]pyrimidin-4-amine (35 mg, 15%).
$^1$H NMR (DMSO-d$_6$) δ 1.46 (m, 2H), 1.95 (m, 10H), 2.13 (s, (3H), 2.32 (m, 5H), 4.62 (m, 1H), 5.78 (s, 2H), 7.22 (m, 2H), 7.49 (m, 2H), 7.62 (m, 4H), 8.22 (s, 1H), 8.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$=522.3, R$_t$=0.82 min.

Example 296

N1-(4-{4-amino-1-[1-(2-methoxyethyl)-4-piperidyl]-1H-pyrazolo[3,4-d]pyrimidin-3-yl}-2-methoxyphenyl)-2-fluoro-4-(trifluoromethyl)benzamide, acetate salt N1-{4-[4-amino-1-(4-piperidyl)-1H-pyrazolo[3,4-d]pyrimidin-3-yl]-2-methoxyphenyl}-2-fluoro-4-(trifluoromethyl)benzamide (10 g, 0.189 mmol), 2-bromoethyl methyl ether (20 uL, 0.208 mmol) and potassium carbonate (52 mg, 0.378 mmol) was mixed in DMF (2 mL). The mixture was heated at 65° C. overnight. The crude mixture was purified by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give N1-(4-{4-amino-1-[1-(2-methoxyethyl)-4-piperidyl]-1H-pyrazolo[3,4-d]pyrimidin-3-yl}-2-methoxyphenyl)-2-fluoro-4-(trifluoromethyl)benzamide, acetate salt (75 mg, 68%). $^1$H NMR (DMSO-d$_6$) δ 1.90 (m, 2H), 2.22 (m, 4H), 2.54 (m, 2H), 3.02 (m, 2H), 3.26 (s, 3H), 3.46 (m, 2H), 3.94 (m, s, 3H), 4.66 (m, 1H), 7.30 (d, J=8.19 Hz, 1H), 7.34 (s, 1H), 7.74 (d, J=7.84 Hz, 1H), 7.90 (d, J=10.33 Hz, 1H), 7.99 (m, 1H), 8.24 (s, 1H), 8.30 (d, J=8.23 Hz, 1H), 9.89 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$=587.2, R$_t$=2.17 min.

Example 297

N1-(4-{4-amino-1-[1-(cyanomethyl)-4-piperidyl]-1H-pyrazolo[3,4-d]pyrimidin-3-yl}-2-methoxyphenyl)-2-fluoro-4-(trifluoromethyl)benzamide N1-{4-[4-amino-1-(4-piperidyl)-1H-pyrazolo[3,4-d]pyrimidin-3-yl]-2-methoxyphenyl}-2-fluoro-4-(trifluoromethyl)benzamide (100 g, 0.189 mmol), 2-bromoacetonitrile (14 uL, 0.208 mmol) and cesium carbonate (52 mg, 0.378 mmol) was mixed in DMF (2 mL). The mixture was stirred at room temperature overnight. The crude mixture was purified by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give, N1-(4-{4-amino-1-[1-(cyanomethyl)-4-piperidyl]-1H-pyrazolo[3,4-d]pyrimidin-3-yl}-2-methoxyphenyl)-2-fluoro-4-(trifluoromethyl) benzamide (68 mg, 64%). $^1$H NMR (DMSO-d$_6$) δ 1.99 (m, 2H), 2.27 (m, 2H), 2.45 (m, 2H), 2.99 (m, 2H), 3.80 (s, 2H), 3.94 (s, 3H), 4.68 (m, 1H), 7.30 (d, J=8.21 Hz, 1H), 7.34 (s, 1H), 7.75 (d, J=8.26 Hz, 1H), 7.90 (d, J=10.51 Hz, 1H), 7.99 (m, 1H), 8.25 (s, 1H), 8.30 (d, J=8.18 Hz, 1H), 9.90 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH+=569.2, $R_t$=3.03 min.

Example 298

N1-(4-{4-amino-1-[1-(2-amino-2-oxoethyl)-4-piperidyl]-1H-pyrazolo[3,4-d]pyrimidin-3-yl}-2-methoxyphenyl)-2-fluoro-4-(trifluoromethyl)benzamide, acetate salt N1-{4-[4-amino-1-(4-piperidyl)-1H-pyrazolo[3,4-d]pyrimidin-3-yl]-2-methoxyphenyl}-2-fluoro-4-(trifluoromethyl)benzamide (100 g, 0.189 mmol), 2-bromoacetamide (28 mg, 0.208 mmol) and cesium carbonate (123 mg, 0.378 mmol) was mixed in DMF (2 mL). The mixture was stirred at room temperature overnight. The crude mixture was purified by reverse phase preparative HPLC (Rainin HPLC, Column: Thermoquest, hyperprep HS C18, 8 um, 250×21.2 mm. Eluents: 5% B/A to 100% B/A in 25 min. (B: acetonitrile, A: 50 mM ammonia acetate buffer, pH 4.5), 21 mL/min.) to give N1-(4-{4-amino-1-[1-(2-amino-2-oxoethyl)-4-piperidyl]-1H-pyrazolo[3,4-d]pyrimidin-3-yl}-2-methoxyphenyl)-2-fluoro-4-(trifluoromethyl)benzamide, acetate salt (70 mg, 63%). $^1$H NMR (DMSO-$d_6$) δ 1.90 (m, 5H), 2.34 (m, 4H), 2.93 (s, 2H), 2.99 (m, 2H), 3.94 (s, 3H), 4.69 (m, 1H), 7.12 (s, 1H), 7.25 (s, 1H), 7.30 (d, J=8.15 Hz, 1H), 7.34 (s, 1H), 7.75 (d, J=8.15 Hz, 1H), 7.87 (d, J=10.30 Hz, 1H), 7.99 (m, 1H), 8.25 (s, 1H), 8.31 (d, J=8.14 Hz, 1H), 9.90 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH+=587.2, $R_t$=2.17 min.

Example 299

1-(1-methyl-3-piperidyl)-3-(4-phenoxyphenyl)-1H-pyrazolo[3,4-d]pyrimidin-4-amine acetate A solution of racemic 3-iodo-1-(1-methyl-3-piperidyl)-1H-pyrazolo[3,4-d]pyrimidin-4-amine (0.050 g, 0.00014 mol) in dimethoxyethane (2.5 mL) and water (5 mL) was treated with 4-phenoxyphenylboronic acid (0.033 g, 0.00015 mol), sodium carbonate (0.037 g, 0.00037 mol) and tetrakis (triphenylphosphine) palladium (0) (0.016 g, 0.000014 mol) at 80° C. for 18 hours. The organic solvent was removed in vacuo, and the crude material was purified by preparative RP-HPLC (Rainin C18, 8 μm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give 1-(1-methyl-3-piperidyl)-3-(4-phenoxyphenyl)-1H-pyrazolo[3,4-d]pyrimidin-4-amine acetate as a white solid (0.040 g, 0.00009 mol).

$^1$H NMR (DMSO-$d_6$, 400 MHz) δ 8.24 (s, 1H), 7.65 (d, 2H), 7.43 (t, 2H), 7.10-7.22 (m, 5H), 4.74-4.84 (m, 1H), 2.94 (dd, 1H), 2.79 (d, 1H), 2.36 (t, 1H), 2.22 (s, 3H), 1.89 (s, 3H), 1.86-2.01 (m, 3H), 1.76-1.84 (m, 1H), 1.60-1.75 (m, 1H);

RP-HPLC (Delta Pak C18, 5 μm, 300A, 15 cm; 5%-85% acetonitrile—0.1M ammonium acetate over 20 min, 1 mL/min) $R_t$ 13.74 min.;

MS: MH+ 401.

Example 300

1-[1-(2-methoxyethyl)-3-piperidyl]-3-(4-phenoxyphenyl)-1H-pyrazolo[3,4-d]pyrimidin-4-amine acetate A solution of racemic 3-iodo-1-[1-(2-methoxyethyl)-3-piperidyl]-1H-pyrazolo[3,4-d]pyrimidin-4-amine (0.050 g, 0.00012 mol) in dimethoxyethane (2.5 mL) and water (5 mL) was treated with 4-phenoxyphenylboronic acid (0.029 g, 0.00014 mol), sodium carbonate (0.033 g, 0.00031 mol) and tetrakis(triphenylphosphine) palladium (0) (0.014 g, 0.00001 mol) at 80° C. for 20 hours. The organic solvent was removed in vacuo, and the crude material was purified by preparative RP-HPLC (Rainin C18, 8 μm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give 1-[1-(2-methoxyethyl)-3-piperidyl]-3-(4-phenoxyphenyl)-1H-pyrazolo[3,4-d]pyrimidin-4-amine acetate as a white solid (0.038 g, 0.00007 mol).

$^1$H NMR (DMSO-$d_6$, 400 MHz) δ 8.24 (s, 1H), 7.65 (d, 2H), 7.43 (t, 2H), 7.09-7.22 (m, 5H), 4.714.82 (m, 1H), 3.44 (t, 2H), 3.21 (s, 3H), 3.04 (dd, 1H), 2.91 (d, 1H), 2.47-2.60 (m, 3H), 1.94-2.09 (m, 3H), 1.89 (s, 3H), 1.75-1.84 (m, 1H), 1.57-1.74 (m, 1H); RP-HPLC (Delta Pak C18, 5 μm, 300A, 15 cm; 5%-85% acetonitrile—0.1M ammonium acetate over 20 min, 1 mL/min) $R_t$ 14.26 min.; MS: MH+ 445.

Example 301

Trans 1-{4-[4-amino-3-(3-chloro-4-{[4-(trifluoromethyl)benzoyl]amino}phenyl)-1H-pyrazolo[3,4-d]pyrimidin-1-yl]cyclohexyl}-4-methylhexahydropyrazinediium dimaleate A. Tert-butyl N-(4-bromo-2-chlorophenyl)carbamate A solution of 4-bromo-2-chloroaniline (5.00 g, 0.0242 mol) in tetrahydrofuran (50 mL) was reacted with a 1.0 M solution of sodium bis(trimethylsilyl)amide in tetrahydrofuran (53.2 mL, 0.0532 mol). The mixture was stirred 15 minutes at ambient temperature. Di-tert-butyl dicarbonate (6.34 g, 0.0290 mol) was added and the solution was stirred for 2 hours. The solvent was removed in vacuo, and the crude material was purified by flash column chromatography on silica using heptane/ethyl acetate (4:1). The solvent was removed in vacuo to give tert-butyl N-(4-bromo-2-chlorophenyl)carbamate as a white solid (4.214 g, 0.0137 mol).

$^1$H NMR (DMSO-$d_6$, 400 MHz) δ 8.75 (s, 1H), 7.71 (d, 1H), 7.54 (d, 1H), 7.50 (dd, 1H), 1.46 (s, 9H); TLC (heptane/ethylacetate 4:1) $R_f$ 0.54.

B. Tert-butyl N-[2-chloro-4-(4,4,5,5-tetramethyl-1,3,2-dioxaborolan-2-yl)phenyl]carbamate A mixture of tert-butyl N-(4-bromo-2-chlorophenyl)carbamate (2.10 g, 0.00685 mol), diboron pinacol ester (2.09 g, 0.00822 mol), [1,1'-bis(diphenylphosphino)ferro-cene] dichloropalladium(I) complex with dichloromethane (1:1) (0.17 g, 0.00021 mol) and potassium acetate (2.02 g, 0.02055 mol) in N,N-dimethylformamide (50 ml) was heated at 80° C. under a nitrogen atmosphere for 6 hours. The solvent was removed in vacuo. The residue was triturated with heptane (70 mL) and the resulting solids were removed by filtration through a pad of Celite® 521. The heptane was removed in vacuo to give tert-butyl N-[2- chloro-4-(4,4,5,5-tetramethyl-1,3,2-dioxaborolan-2-yl)phenyl]carbamate as a grey solid (1.93 g, 0.00546 mol):

$^1$H NMR (DMSO-d$_6$, 400 MHz) δ 8.65 (s, 1H), 7.74 (d, 1H), 7.61 (d, 1H), 7.56 (dd, 1H), 1.47 (s,9H), 1.29 (s, 12H).

C. Trans tert-butyl N-(4-{4-amino-1-[4-(4-methylpiperazino)cyclohexyl]-1H-pyrazolo[3,4-d]pyrimidin-3-yl}-2-chlorophenyl)carbamate A mixture of trans 3-iodo-1-[4-(4-methylpiperazino)cyclohexyl]-1H-pyrazolo[3,4-d]pyrimidin-4-amine (2.20 g, 0.00498 mol), tert-butyl N-[2-chloro-4-(4,4,5,5-tetramethyl-1,3,2-dioxaborolan-2-yl)phenyl]carbamate (1.93 g, 0.00548 mol), sodium carbonate (1.32 g, 0.01245 mol) in 1,2-dimethoxyethane (50 mL) and water (100 mL) was stirred rapidly and tetrakis(triphenylphosphine)palladium(0) (0.345 g, 0.00030 mol) was added. The reaction mixture was stirred 6 hours at 80° C., after which time additional tetrakis (triphenylphosphine)palladium(0) (0.345 g, 0.00030 mol) was added. The reaction mixture was stirred an additional 16 hours at 80° C. The solvents were removed in vacuo and the residue was partitioned between ethyl acetate (100 mL) and saturated aqueous sodium bicarbonate (200 mL). The phases were separated and the aqueous phase was extracted with ethyl acetate (3×75 ml). The combined organic phases were dried over magnesium sulfate, and the solvent was removed in vacuo. The product was purified by flash column chromatography on silica using dichloromethane/methano/ammonium hydroxide (90:10:0.5). The solvent was removed in vacuo to give trans tert-butyl N-(4-{4-amino-1-[4-(4-methylpiperazino)cyclohexyl]-1H-pyrazolo[3,4-d]pyrimidin-3-yl}-2-chlorophenyl)carbamate as a white solid (1.993 g, 0.00368 mol):

$^1$H NMR (DMSO-t$_6$, 400 MHz) δ 8.76 (s, 1H), 8.23 (s, 1H), 7.80 (d, 1H), 7.68 (d, 1H), 7.57 (dd, 1H), 4.58-4.71 (m, 1H), 2.15 (s, 3H), 1.89-2.61 (m, 15H), 1.49 (s, 9H), 1.40-1.48 (m, 2H); TLC (dichloromethane/methanol=90:10) R$_f$ 0.13, MS: MH$^+$ 541.

D. Trans 3-(4-amino-3-chlorophenyl)-1-[4-(4-methylpiperazino)cyclohexyl]-1H-pyrazolo[3,4-d]pyrimidin-4-amine Trans tert-butyl N-(4-{4-amino-1-[4-(4-methylpiperazino)cyclohexyl]-1H-pyrazolo[3,4-d]pyrimidin-3-yl}-2-chlorophenyl)carbamate (1.993 g, 0.00368 mol) was added to a solution of 20% trifluoracetic acid in dichloromethane. The mixture was stirred for 2 hours at ambient temperature. The solvent was removed in vacuo and the residue was dissolved in dichloromethane (50 mL) and washed with a 1.0 M aqueous solution of sodium hydroxide (2×25 mL). The organic layer was dried over magnesium sulfate and the solvent was removed in vacuo to give trans 3-(4-amino-3-chlorophenyl)-1-[4-(4-methylpiperazino)cyclohexyl]-1H-pyrazolo[3,4-d]pyrimidin-4-amine (1.564 g, 0.00355 mol) as a white solid.

$^1$H NMR (DMSO-d$_6$, 400 MHz) δ 8.20 (s, 1H), 7.45 (d, 1H), 7.31 (dd, 1H), 6.92 (d, 1H), 4.57-4.63 (m, 1H), 2.23-2.55 (m, 9H), 2.14 (s, 3H), 1.89-2.08 (m, 6H), 1.38-1.52 (m, 2H); TLC (dichloromethane/methanol=90:10) R$_f$ 0.08; MS: MH$^+$ 441.

E. Trans N1-(4-{4-amino-1-[4-(4-methylpiperazino) cyclohexyl]-1H-pyrazolo [3,4-d]pyrimidin-3-yl}-2-chlorophenyl)-4-(trifluoromethyl)benzamide dimaleate To a mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in pyridine (5 µL) at −10° C. 4-(trifluoromethyl)-1-benzenecarbonyl chloride (0.188 g, 0.00090 mol) was added dropwise, keeping the temperature below −5° C. The mixture was stirred at −10° C. for 15 minutes, and then at ambient temperature for 18 hours. After addition of an 1N aqueous solution of sodium hydroxide (1.0 mL) the mixture was stirred one hour. The solvent was removed in vacuo, and the residue was partitioned between ethyl acetate (15 mL) and water (30 mL). The layers were separated and the aqueous phase was extracted with ethyl acetate (15 mL), and the combined organic layers were dried over magnesium sulfate. The solvent was removed in vacuo, and the residue was purified by preparative RP-HPLC (Rainin C18, 8 µm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give the purified free base (0.032 g, 0.000052 mol). The free base was dissolved in absolute ethanol (4 mL) and heated to reflux. After addition of a solution of maleic acid (0.018 g, 0.000156 mol) in absolute ethanol (1 mL) the solution was refluxed for further 15 minutes. The mixture was cooled to ambient temperature, and the resulting precipitate was filtered, washing with a minimal amount of absolute ethanol. The precipitate was dried in vacuo to give trans N1-(4-{4-amino-1-[4-(4-methylpiperazino)cyclohexyl]-1H-pyrazolo[3,4-d]pyrimidin-3-yl}-2-chlorophenyl)-4-(trifluoromethyl)benzamide dimaleate as a white solid (0.020 g, 0.00002 mol):

$^1$H NMR (DMSO-d$_6$, 400 MHz) δ 10.42 (s, 1H), 8.26 (s, 1H), 8.20 (d, 2H), 7.96 (d, 2H), 7.80-7.83 (m, 2H), 7.46 (dd, 1H), 6.80-7.20 (b, 2H), 6.13 (s, 4H), 4.61-4.73 (m, 1H), 2.52-2.64 (m, 4H), 2.23-2.46 (m, 5H), 2.16 (s, 3H), 1.90-2.10 (m, 6H), 1.42-1.56 (m, 2H); RP-HPLC (Delta Pak C18, 5 µm, 300A, 15 cm; 5%-85% acetonitrile—0.1M ammonium acetate over 20 min, 1 mL/min) R$_t$ 14.97 min.; MS: MH$^+$ 613.

Example 302

Trans N1-(4-{4-amino-1-[4-(4-methylpiperazino) cyclohexyl]-1H-pyrazolo [3,4-d]pyrimidin-3-yl}-2-chlorophenyl)-4-(trifluoromethoxy)benzamide Dimaleate To a mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in pyridine (5 µL) at −10° C. 4-(trifluoromethoxy)-1-benzenecarbonyl chloride (0.203 g, 0.00091 mol) was added dropwise, keeping the temperature less than −5° C. The mixture was stirred at −10° C. for 15 minutes and then at ambient temperature for 18 hours. After addition of an 1N aqueous solution of sodium hydroxide (1.0 mL) the mixture was stirred one hour. The solvent was removed in vacuo, and the residue was partitioned between ethyl acetate (15 mL) and water (30 mL). The layers were separated and the aqueous phase was extraxcted with ethyl acetate (15 mL), and the combined organic layers were dried over magnesium sulfate. The solvent was removed in vacuo, and the residue was purified by preparative RP-HPLC (Rainin C18, 8 µm, 300 A, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give the purified free base (0.034 g, 0.000054 mol). The free base was dissolved in absolute ethanol (4 mL) and heated to reflux. A solution of maleic acid (0.019 g, 0.000162 mol) in absolute ethanol (1 mL) was added and the solution was refluxed for 15 minutes. The mixture was cooled to ambient temperature, and the resulting precipitate was filtered, washing with a minimal amount of absolute ethanol. The precipitate was dried in vacuo to give trans N1-(4-{4-amino-1-[4-(4-methylpiperazino)cyclohexyl]-1H-pyrazolo[3,4-d]pyrimidin-3-yl}-2-chlorophenyl)-4-(trifluoromethoxy)benzamide dimaleate as a white solid (0.020 g, 0.00002 mol):

$^1$H NMR (DMSO-$d_6$, 400 MHz) δ 10.29 (s, 1H), 8.26 (s, 1H), 8.14 (d, 2H), 7.78-7.87 (m, 2H), 7.68 (dd, 1H), 7.57 (d, 2H), 6.80-7.20 (b, 2H), 6.11 (s, 4H), 4.65-4.77 (m, 1H), 2.38-3.60 (m, 12H), 1.95-2.15 (m, 6H), 1.51-1.68 (m, 2H); RP-HPLC (Delta Pak C18, 5 μm, 300A, 15 cm; 5%-85% acetonitrile—0.1M ammonium acetate over 20 min, 1 mL/min) $R_t$ 15.41 min.; MS: MH$^+$ 629.

Example 303

Trans 3-(3-chloro-4-{[(5-methyl-2-furyl)methyl] amino}phenyl)-1-[4-(4-methylpiperazino)cyclohexyl]-1H-pyrazolo[3,4-d]pyrimidin-4-amine acetate A mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in 1,2-dichloroethane (20 mL) was reacted with 5-methyl-2-furfural (0.052 g, 0.00048 mol), acetic acid (0.095 g, 0.00159 mol) and sodium triacetoxyborohydride (0.336 g, 0.00159 mol) at ambient temperature. An additional two equivalents of sodium triacetoxyborohydride (0.672 g, 0.00318 mol) were added in two 24 hour intervals. The solvents were removed in vacuo and the residue was partitioned between chloroform (25 mL) and saturated aqueous sodium bicarbonate (50 mL). The phases were separated and the aqueous phase was extracted with chloroform (2×25 mL). The combined organic phases were dried over magnesium sulfate, and the solvent was removed in vacuo. The residue was purified by preparative RP-HPLC (Rainin C18, 8 μm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give trans 3-(3-chloro-4-{[(5-methyl-2-furyl)methyl] amino}phenyl)-1-[4-(4-methylpiperazino)cyclohexyl]-1H-pyrazolo[3,4-d]pyrimidin-4-amine acetate as a white solid (0.129 g, 0.00022 mol):

$^1$H NMR (DMSO-$d_6$, 400 MHz) δ 8.20 (s, 1H), 7.51 (d, 1H), 7.39 (dd, 1H), 6.93 (d, 1H), 6.20 (d, 1H), 6.14 (t, 1H), 5.98 (d, 1H), 4.55-4.66 (m, 1H), 4.38 (d, 2H), 2.23 (s, 3H), 2.18-2.61 (m, 10H), 2.14 (s, 3H), 1.91 (s, 3H), 1.87-2.09 (m, 5H), 1.37-1.53 (m, 2H); RP-HPLC (Delta Pak C18, 5 μm, 300A, 15 cm; 5%-95% acetonitrile—0.1M ammonium acetate over 20 min, 1 mL/min) $R_t$ 14.48 min.; MS: MH$^+$ 535.

Example 304

Trans 3-{3-chloro-4-[(2-chloro-6-fluorobenzyl) amino]phenyl}-1-[4-(4-methylpiperazino)cyclohexyl]-1H-pyrazolo[3,4-d]pyrimidin-4-amine acetate A mixture of 3-(4-amino-3-chlorophenyl)-1-[4-(4-methylpiperazino)cyclohexyl]-1H-pyrazolo[3,4-d]pyrimidin-4-amine (0.200 g, 0.00045 mol) in 1,2-dichloroethane (20 mL) was reacted with 2-chloro-6-fluorobenzaldehyde (0.076 g, 0.00048 mol), acetic acid (0.095 g, 0.00159 mol) and sodium triacetoxyborohydride (0.336 g, 0.00159 mol) at ambient temperature. An additional three equivalents of sodium triacetoxyborohydride (1.008 g, 0.00477 mol) were added in three 24 hour intervals, after which time all the starting material had been consumed. The solvents were removed in vacuo and the residue was partitioned between chloroform (25 mL) and saturated aqueous sodium bicarbonate (50 mL). The phases were separated and the aqueous phase was extracted with chloroform (2×25 mL). The combined organic phases were dried over magnesium sulfate, and the solvent was removed in vacuo. The residue was purified by preparative RP-HPLC (Rainin C18, 8 μm, 300 Å, 25 cm; 30% isocratic for five minutes, then 30%-60% acetonitrile—0.1M ammonium acetate over 15 min, 21 ml/min). The acetonitrile was removed in vacuo and the aqueous mixture was lyopholyzed to give to give trans 3-{3-chloro-4-[(2-chloro-6-fluorobenzyl)amino]phenyl}-1-[4-(4-methylpiperazino)cyclohexyl]-1H-pyrazolo[3,4-d]pyrimidin-4-amine acetate as a white solid (0.074 g, 0.00011 mol):

$^1$H NMR (DMSO-$d_6$, 400 MHz) δ 8.20 (s, 1H), 7.52 (d, 1H), 7.35-7.47 (m, 4H), 6.99 (d, 1H), 5.75 (t, 1H), 4.55-4.66 (m, 1H), 4.57 (d, 2H), 2.25-2.61 (m, 11H), 2.16 (s, 3H), 1.91 (s, 3H), 1.87-2.09 (m, 4H), 1.37-1.53 (m, 2H); RP-HPLC (Delta Pak C18, 5 μm, 300A, 15 cm; 5%-95% acetonitrile—0.1M ammonium acetate over 20 min, 1 mL/min) $R_t$ 15.97 min.; MS: MH$^+$ 583.

Example 305

Trans N1-(4-{4-amino-1-[1-(1H-2-imidazolylcarbonyl)-4-piperidyl]-1H-pyrazolo[3,4-d]pyrimidin-3-yl}-2-methoxyphenyl)-(trans)-2-phenyl-1-cyclopropanecarboxamide maleate A mixture of N1-{4-[4-amino-1-(4-piperidyl)-1H-pyrazolo[3,4-d]pyrimidin-3-yl]-2-methoxyphenyl}-2-phenyl-1-cyclopropanecarboxamide (0.200 g, 0.00041 mol) in toluene (10 mL) was reacted with 5H,10H-diimidazo[1,5-a:1,5-d] pyrazine-5,10-dione (0.040 g, 0.00021 mol) at reflux for 18 hours. An additional equivalent of 5H,10H-diimidazo[1,5-a:1,5-d]pyrazine-5,10-dione was added and the mixture was refluxed an additional 6 hours. The solvent was removed in vacuo and the residue was purified by preparative RP-HPLC (Rainin C18, 8 μm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give the free base (0.103 g, 0.00017 mol). The free base was dissolved in absolute ethanol (10 mL) and heated to reflux. After addition of a solution of maleic acid (0.030 g, 0.00034 mol) in absolute ethanol (1 mL) the solution was refluxed for 15 minutes, after which time a precipitate formed. The mixture was cooled to ambient temperature, and the resulting precipitate was filtered, washing with a minimal amount of absolute ethanol. The precipitate was dried in vacuo to give trans N1-(4-{4-amino-1-[1-(1H-2-imidazolylcarbonyl)-4-piperidyl]-1H-pyrazolo[3,4-d]pyrimidin-3-yl}-2-methoxyphenyl)-(trans)-2-phenyl-1-cyclopropanecarboxamide maleate as a white solid (0.055 g, 0.00008 mol):

$^1$H NMR (DMSO-$d_6$, 400 MHz) δ 9.63 (s, 1H), 8.26 (s, 1H), 8.22 (d, 1H), 8.00 (b, 1H), 7.74 (b, 1H), 7.43-7.48 (m, 1H), 7.16-7.33(m, 7H), 6.21 (s, 2H), 4.97-5.13 (m, 1H), 2.91-3.47 (m, 4H), 2.53-2.65 (m, 1H), 2.30-2.45 (m, 1H), 2.07-2.26 (m, 2H), 1.95-2.07 (m, 2H), 1.45-1.50 (m, 1H), 1.28-1.32 (m, 1H); RP-HPLC (Delta Pak C18, 5 μm, 300A,

Example 306

Cis N1-(4-{4-amino-1-[4-(2-aminoethyl)-4-hydroxycyclohexyl]-1H-pyrazolo [3,4-d]pyrimidin-3-yl}-2-methoxyphenyl)-(trans)₂-phenyl-1-cyclopropanecarboxamide acetate

A. Cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropanecarboxamide A mixture of cis N1-{4-[4-amino-1-(1-oxaspiro[2.5]oct-6-yl)-1H-pyrazolo[3,4-d]pyrimidin-3-yl]-2-methoxyphenyl}-(trans)-2-phenylcyclopropane-1-carboxamide (0.605 g, 0.0012 mol), lithium perchlorate (0.189 g, 0.0018 mol) and potassium cyanide (0.116 g, 0.0018 mol) in acetonitrile (60 ml) was heated at 80° C. for two days. Cooled to ambient temperature, diluted with water (30 mL) and extracted with diethyl ether (3×30 mL). The combined organic phases were dried over magnesium sulfate. The solvent was removed in vacuo and the crude product was purified by flash column chromatography on silica using dichloromethane/methanol (95:5). The solvent was removed in vacuo to give cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropanecarboxamide as a white solid (0.602 g, 0.0011 mol):
$^1$H NMR (DMSO-d$_6$, 400 MHz) δ 9.64 (s, 1H), 8.23 (t, 2H), 7.31 (t, 2H), 7.25 (s, 1H), 7.17-(m, 4H), 4.61-4.62 (m, 1H), 3.91 (s, 1H), 2.66 (s, 2H), 2.55-2.62 (m, 1H), 2.31-2.45 (m, 3H), 1.58-1.89 (m, 6H), 1.45-1.53 (m, 1H), 1.28-1.38 (m, 1H); RP-HPLC (Delta Pak C18, 5 μm, 300A, 15 cm; 5%-85% acetonitrile—0.1M ammonium acetate over 20 min, 1 mL/min) R$_t$ 15.21 min.; MS: MH⁺ 538.

B. Cis N1-(4-{4-amino-1-[4-(2-aminoethyl)-4-hydroxycyclohexyl]-1H-pyrazolo[3,4-d]pyrimidin-3-yl}-2-methoxyphenyl)-(trans)₂-phenyl-1-cyclopropanecarboxamide acetate To a solution of cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropane-carboxamide (0.200 g, 0.00037 mol) in methanol (20 ml) and ammonium hydroxide (1 mL) Raney nickel (0.5 mL) was added. The mixture was stirred 18 hours under a hydrogen atmosphere (1 atm). The reaction mixture was filtered through celite and the solvent was removed in vacuo. The residue was purified by preparative RP-HPLC (Rainin C18, 8 μm, 300 Å, 25 cm; 30% isocratic for five minutes, then 30%-60% acetonitrile—0.1M ammonium acetate over 15 min, 21 ml/min). The acetonitrile was removed in vacuo and the aqueous mixture was lyopholyzed to give Cis N1-(4-{4-amino-1-[4-(2-aminoethyl)-4-hydroxycyclohexyl]-1H-pyrazolo[3,4-d]pyrimidin-3-yl}-2-methoxyphenyl)-(trans)₂-phenyl-1-cyclopropanecarboxamide acetate as a white solid (0.045 g, 0.000083 mol).:
$^1$H NMR (DMSO-d$_6$, 400 MHz) δ 9.64 (s, 1H), 8.23 (d, 1H), 8.22-8.24 (m, 1H), 7.17-7.33 (m, 7H), 4.65-4.67 (m, 1H), 3.91 (s, 3H), 2.84-2.91 (m, 2H), 2.53-2.55 (m, 1H), 2.33-2.40 (m, 4H), 1.85 (s, 3H), 1.35-1.80 (m, 9H), 1.30-1.33 (m, 1H); RP-HPLC (Delta Pak C18, 5 μm, 300A, 15 cm; 5%-85% acetonitrile—0.1M ammonium acetate over 20 min, 1 mL/min) R$_t$ 13.29 min.; MS: MH⁺ 444

Example 308

Cis N1-(4-{4-amino-1-[4-(2-amino-2-oxoethyl)-4-hydroxycyclohexyl]-1H-pyrazolo[3,4-d]pyrimidin-3-yl}-2-methoxyphenyl)-(trans)-2-phenyl-1-cyclopropanecarboxamide To a well-stirred solution of cis N1-(4-{4-amino-1-[4-(cyanomethyl)-4-hydroxycyclohexyl]-1H-pyrazolo[3,4-d]pyrimidin-3-yl}-2-methoxyphenyl)-(trans)-2-phenyl-1-cyclopropanecarboxamide (0.200 g, 0.00037 mol) in dimethylsulfoxide (4 mL) potassium carbonate (0.216 g, 0.00156 mol) was added at ambient temperature. A 30% aqueous solution of hydrogen peroxide (0.6 mL) was added dropwise, keeping the temperature constant. The mixture was stirred at ambient temperature for 32 hours. Water (20 mL) was added to the mixture, and the precipitate which formed was filtered. The precipitate was washed with water and dried in vacuo. The solid was purified by preparative RP-HPLC (Rainin C18, 8 μm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give cis N1-(4-{4-amino-1-[4-(2-amino-2-oxoethyl)-4-hydroxycyclohexyl]-1H-pyrazolo[3,4-d]pyrimidin-3-yl}-2-methoxyphenyl)-(trans)-2-phenyl-1-cyclopropanecarboxamide as a white solid (0.117 g, 0.00021 mol):
$^1$H NMR (DMSO-d$_6$, 400 MHz) δ 9.64 (s, 1H), 8.23 (d, 1H), 8.22 (s, 1H), 7.43-7.48 (m, 1H), 7.15-7.35 (m, 7H), 7.05-7.10 (m, 1H), 4.97 (s, 1H), 4.61-4.71 (m, 1H), 3.91 (s, 3H), 2.54-2.64 (m, 1H), 2.30-2.44 (m, 3H), 2.24 (s, 2H), 1.55-1.81 (m, 6H), 1.45-1.53 (m, 1H), 1.28-1.36 (m, 1H); RP-HPLC (Delta Pak C18, 5 μm, 300A, 15 cm; 5%-85% acetonitrile—0.1M ammonium acetate over 20 min, 1 mL/min) R$_t$ 14.05 min.; MS: MH⁺ 556.

Example 308

Cis N1-[4-(4-amino-1-{4-[(dimethylamino)methyl]-4-hydroxycyclohexyl}-1H-pyrazolo[3,4-d]pyrimidin-3-yl)-2-methoxyphenyl]-(trans)-2-phenyl-1-cyclopropanecarboxamide acetate To a solution of cis N1-{4-[4-amino-1-(1-oxaspiro[2.5]oct-6-yl)-1H-pyrazolo[3,4-d]pyrimidin-3-yl]-2-methoxyphenyl}-(trans)-2-phenylcyclopropane-1-carboxamide (0.190 g, 0.000302 mol) in 2-propanol (10 mL) a 2 M solution of dimethylamine in methanol (0.91 mL) was added and the resulting mixture was heated at 65° C. in a pressure tube for 18 hours. The solvent was removed in vacuo, and the residue was purified by preparative RP-HPLC (Rainin C18, 8 μm, 300 Å, 25 cm; 30% isocratic for five minutes, then 30%-60% acetonitrile—0.1M ammonium acetate over 15 min, 21 mL/min). The acetonitrile was removed in vacuo and the aqueous mixture was lyopholyzed to give Cis N1-[4-(4-amino-1-{4-[(dimethylamino)methyl]-4-hydroxycyclohexyl}-1H-pyrazolo[3,4-d]pyrimidin-3-yl)-2-methoxyphenyl]-(trans)-2-phenyl-1-cyclopropanecarboxamide acetate as a white solid (0.109 g, 0.000177 mol).:
$^1$H NMR (DMSO-d$_6$, 400 MHz), 9.64 (s, 1H), 8.23 (d, 1H), 8.22-8.24 (m, 1H), 7.17-7.33 (m, 7H), 4.56-4.68 (m, 1H), 3.91 (s, 3H), 2.54-2.64 (m, 1H), 2.30-2.44 (m, 3H), 2.28 (s, 6H), 2.24 (s, 2H), 1.91 (s, 3H), 1.63-1.78 (m, 4H), 1.44-1.58 (m, 3H), 1.28-1.36 (m, 1H); RP-HPLC (Delta Pak C18, 5 μm, 300A, 15 cm; 5%-85% acetonitrile—0.1M ammonium acetate over 20 min, 1 mL/min) $R_t$ 13.54 min.; MS: MH$^+$ 556.

Example 310

Trans N2-(4-{4-amino-1-[4-(4-methylpiperazino) cyclohexyl]-1H-pyrazolo[3,4-d]pyrimidin-3-yl}-2-methoxyphenyl)-(2R)tetrahydro-1H-2-pyrrolecarboxamide acetate A solution of trans 3-(4-amino-3-methoxyphenyl)-1-[4-(4-methylpiperazino)cyclohexyl]-1H-pyrazolo[3,4-d]pyrimidin-4-amine (0.200 g, 0.00046 mol) in N,N-dimethylformamide (10 mL) was reacted with 1-hydroxy-7-azabenzotriazole (0.068 g, 0.00050 mol), 1-(3-dimethylaminopropyl)-3-ethylcarbodiimide hydrochloride (0.132 g, 0.00069 mol), D-Boc-proline (0.108 g, 0.00050 mol) and N,N-diisopropylethylamine (0.184 g, 0.00142 mol) at ambient temperature for 24 hours. The solvent was removed in vacuo and the residue was partitioned between dichloromethane (10 mL) and a 5% aqueous citric acid solution (20 mL). The layers were separated and the aqueous layer was extracted with dichloromethane (2×10 mL). The combined organic phases were washed with saturated aqueous sodium bicarbonate (15 mL) and dried over magnesium sulfate. The solvent was removed in vacuo and the residue was stirred in 20% trifluoroacetic acid in dichloromethane for 6 hours at ambient temperature. The solvent was removed in vacuo and the residue was purified by preparative RP-HPLC (Rainin C18, 8 mm, 300 Å, 25 cm; 5% isocratic for five minutes, then 5%-40% acetonitrile—0.1M ammonium acetate over 20 min, 21 mL/min). The acetonitrile was removed in vacuo and the aqueous mixture was lyopholyzed to give trans N2-(4-{4-amino-1-[4-(4-methylpiperazino)cyclohexyl]-1H-pyrazolo[3,4-d]pyrimidin-3-yl}-2-methoxyphenyl)-(2R)tetrahydro-1H-2-pyrrolecarboxamide acetate (0.096 g, 0.00016 mol) as a white solid.

$^1$H NMR (DMSO-d$_6$, 400 MHz) δ 10.33 (s, 1H), 8.45 (d, 1H), 8.22 (s, 1H), 7.25 (s, 1H), 7.21 (d, 1H), 4.58-4.69 (m, 1H), 3.93 (s, 3H), 3.77 (dd, 1H), 2.96-3.04 (m, 1H), 2.74-2.84 (m, 1H), 2.47-2.58 (m, 5H), 2.23-2.45 (m, 5H), 2.14 (s, 3H), 1.91 (s, 3H), 1.88-2.11 (m, 7H), 1.78-1.88 (m, 1H), 1.60-1.69 (m, 2H), 1.39-1.54 (m, 2H); RP-HPLC (Delta Pak C18, 5 μm, 300A, 15 cm; 5%-85% acetonitrile—0.1M ammonium acetate over 20 min, 1 mL/min) $R_t$ 8.47 min.; MS: MH$^+$ 534.

Example 311

4-[4-amino-3-(4-phenoxyphenyl)-1H-pyrazolo[3,4-d]pyrimidin-1-yl]-1-pyridiniumolate A. 4-(4-amino-3-iodo-1H-pyrazolo[3,4-d]pyrimidin-1-yl)-1-pyridiniumolate A solution of 3-iodo-1H-pyrazolo[3,4-d]pyrimidin-4-amine (5.00 g, 0.019 mol) in N,N-dimethylformamide (50 mL) was reacted with 60% sodium hydride in oil (0.92 g, 0.023 mol) at ambient temperature. The mixture was stirred for 15 minutes, and 4-nitropyridine-N-oxide (5.37 g, 0.038 mol) was added. The mixture was heated at 100° C. for 18 hours. The precipitate which formed was filtered, washing with N,N-dimethylformamide and ethyl acetate to give 4-(4-amino-3-iodo-1H-pyrazolo[3,4-d]pyrimidin-1-yl)-1-pyridiniumolate (3.79 g, 0.011 mol) as a tan solid:

$^1$H NMR (DMSO-d$_6$, 400 MHz) δ 8.38 (s, 1H), 8.34 (d, 2H), 8.24 (d, 2H); RP-HPLC (Delta Pak C18, 5 μm, 300A, 15 cm; 5%-95% acetonitrile—0.1M ammonium acetate over 10 min, 1 mL/min) $R_t$ 7.36 min.; MS: MH$^+$ 355.

B. 4-[4-amino-3-(4-phenoxyphenyl)-1H-pyrazolo[3,4-d]pyrimidin-1-yl]-1-pyridiniumolate A suspension of 4-(4-amino-3-iodo-1H-pyrazolo[3,4-d]pyrimidin-1-yl)-1-pyridiniumolate (0.140 g, 0.00040 mol) in dimethoxyethane (7 mL) and water (15 mL) was reacted with 4-phenoxyphenylboronic acid (0.093 g, 0.00043 mol), sodium carbonate (0.105 g, 0.00099 mol) and tetrakis(triphenylphosphine) palladium (0) (0.046 g, 0.00004 mol) at 80° C. for 18 hours. The solid was filtered to give 4-[4-amino-3-(4-phenoxyphenyl)-1H-pyrazolo[3,4-d]pyrimidin-1-yl]-1-pyridiniumolate (0.138 g, 0.00035 mol) as a brown solid. A portion (0.040 g, 0.00010 mol) was purified by preparative RP-HPLC (Rainin C18, 8 μm, 300 A, 25 cm; 40% isocratic for five minutes, then 40%-100% acetonitrile—0.1M ammonium acetate over 30 min, 21 mL/min). The acetonitrile was removed in vacuo and the aqueous mixture was lyopholyzed to give the product 4-[4-amino-3-(4-phenoxyphenyl)-1H-pyrazolo[3,4-d]pyrimidin-1-yl]-1-pyridiniumolate as a white solid (0.013 g, 0.00003 mol).

$^1$H NMR (DMSO-d$_6$, 400 MHz) δ 8.44 (s, 1H), 8.34-8.41 (m, 4H), 7.77 (d, 2H), 7.45 (t, 2H), 7.13-7.24 (m, 5H); RP-HPLC (Delta Pak C18, 5 μm, 300A, 15 cm; 5%-95% acetonitrile—0.1M ammonium acetate over 20 min, 1 mL/min) $R_t$ 14.66 min.; MS: MH$^+$ 397.

Example 312

3-(4-phenoxyphenyl)-1-(4-pyridyl)-1H-pyrazolo[3,4-d]pyrimidin-4-amine

A suspension of 4-[4-amino-3-(4-phenoxyphenyl)-1H-pyrazolo[3,4-d]pyrimidin-1-yl]-1-pyridiniumolate (0.100 g, 0.00025 mol) and 10% palladium on carbon (0.016 g, 0.00002 mol) in acetic acid (3 mL) was reacted with sodium hypophosphite monohydrate (0.033 g, 0.00038 mol) at 60° C. After 2 hours, an additional 10% palladium on carbon (0.016 g, 0.00002 mol) was added. The mixture was stirred 18 hours after which time additional 10% palladium on carbon (0.016 g, 0.00002 mol) and sodium hypophosphite monohydrate (0.033 g, 0.00038 mol) was added. The mixture was stirred for an additional 24 hours. The mixture was filtered through Celite® 521, washing with acetic acid. The solvent was removed in vacuo, and the residue was purified by preparative RP-HPLC (Rainin C18, 8 mm, 300 Å, 25 cm; 40% isocratic for five minutes, then 40%-100% acetonitrile—0.1M ammonium acetate over 30 min, 21 mL/min). The acetonitrile was removed in vacuo and the aqueous mixture was lyopholyzed to give 3-(4-phenoxyphenyl)-1-(4-pyridyl)-1H-pyrazolo[3,4-d]pyrimidin-4-amine (0.020 g, 0.00005 mol) as a white solid:

$^1$H NMR (DMSO-d$_6$, 400 MHz), 8.71 (d, 2H), 8.46 (s, 1H), 8.39 (dd, 2H), 7.78 (d, 2H), 7.46 (t,2H), 7.13-7.25 (m, 5H); RP-HPLC (Delta Pak C18, 5 μm, 300A, 15 cm; 5%-95% acetonitrile—0.1M ammonium acetate over 20 min, 1 mL/min) $R_t$ 17.31 min.; MS: MH$^+$ 381.

Example 313

N2-{4-[4-amino-1-(4-pyridyl)-1H-pyrazolo[3,4-d]pyrimidin-3-yl]-2-methoxyphenyl}-1-methyl-1H-2-indolecarboxamide A. N2-{4-[4-amino-1-(4-pyridyl)-1H-pyrazolo[3,4-d]pyrimidin-3-yl]-2-methoxyphenyl}-1-methyl-1H-2-indolecarboxamide A suspension of 4-(4-amino-3-iodo-1H-pyrazolo[3,4-d]pyrimidin-1-yl)-1-pyridiniumolate (0.500 g, 0.0014 mol) in dimethoxyethane (15 mL) and water (30 mL) was reacted with N2-[2-methoxy-4-(4,4,5,5-tetramethyl-1,3,2-dioxaborolan-2-yl)phenyl]-1-methyl-1H-2-indolecarboxamide (0.631 g, 0.00155 mol), sodium carbonate (0.374 g, 0.0035 mol) and tetrakis(triphenylphosphine) palladium (0) (0.163 g, 0.00014 mol) at 80° C. for 18 hours. The solid was filtered and washed with water. The solid was slurried in ethyl acetate for 18 hours and filtered, washing with ethyl acetate. The solid was dried in vacuo to give crude 4-[4-amino-3-(3-methoxy-4-[(1-methyl-1H-2-indolyl)-carbonyl]aminophenyl)-1H-pyrazolo[3,4-d]pyrimidin-1-yl]-1-pyridiniumolate (0.523 g, 0.0010 mol) as a brown solid:

RP-HPLC (Delta Pak C18, 5 μm, 300A, 15 cm; 5%-95% acetonitrile—0.1M ammonium acetate over 10 min, 1 mL/min) $R_t$ 10.92 min.; MS: $MH^+$ 507.

B. N2-{4-[4-amino-1-(4-pyridyl)-1H-pyrazolo[3,4-d]pyrimidin-3-yl]-2-methoxyphenyl}-1-methyl-1H-2-indolecarboxamide A suspension of 4-[4-amino-3-(3-methoxy-4-{[(1-methyl-1H-2-indolyl)carbonyl]amino}phenyl)-1H-pyrazolo[3,4-d]pyrimidin-1-yl]-1-pyridiniumolate (0.200 g, 0.00039 mol) and 10% palladium on carbon (0.042 g, 0.00004 mol) in acetic acid (3 mL) was reacted with sodium hypophosphite monohydrate (0.063 g, 0.00059 mol) at 60° C. for 2 hours. Additional 10% palladium on carbon (0.042 g, 0.00004 mol) and sodium hypophosphite (0.045 g, 0.00042 mol) was added and the mixture was stirred for 24 hours. The solvent was removed in vacuo and the residue was slurried in methanol for 4 hours. The mixture was filtered through Celite® 521, washing with methanol. The solvent was removed in vacuo and the residue was purified by preparative RP-HPLC (Rainin C18, 8 mm, 300 Å, 25 cm; 50% isocratic for five minutes, then 50%-100% acetonitrile—0.1M ammonium acetate over 25 min, 21 mL/min). The acetonitrile was removed in vacuo and the aqueous mixture was lyopholyzed to give N2-{4-[4-amino-1-(4-pyridyl)-1H-pyrazolo[3,4-d]pyrimidin-3-yl]-2-methoxyphenyl}-1-methyl-1H-2-indolecarboxamide (0.020 g, 0.00004 mol) as a white solid:

$^1$H NMR (DMSO-$d_6$, 400 MHz) δ 9.48 (s, 1H) 8.72 (d, 2H), 8.47 (s, 1H), 8.42 (d, 2H), 8.20 (d, 1H), 7.72 (d, 1H), 7.60 (d, 1H), 7.48 (s, 1H), 7.42 (d, 1H), 7.36 (s, 1H) 7.34 (t, 1H), 7.16 (t, 1H), 4.05 (s, 3H), 3.99 (s, 1H); RP-HPLC (Delta Pak C18, 5 μm, 300A, 15 cm; 5%-85% acetonitrile—0.1M ammonium acetate over 20 min, 1 mL/min) $R_t$ 19.50 min.; MS: $MH^+$ 491.

Example 314

1-(6-amino-3-pyridyl)-3-(4-phenoxyphenyl)-1H-pyrazolo[3,4-d]pyrimidin-4-amine; and Example 315

3-(4-phenoxyphenyl)-1-(2-pyridyl)-1H-pyrazolo[3,4-d]pyrimidin-4-amine

A solution of 3-(4-phenoxyphenyl)-1H-pyrazolo[3,4-d]pyrimidin-4-amine (0.200 g, 0.00079 mol) in N-methylpyrrolidinone (10 mL) was reacted with 60% sodium hydride in oil (0.032 g, 0.00079 mol). After gas evolution ceased, the mixture was stirred at ambient temperature for 30 minutes, and 5-bromo-2-nitropyridine (0.161 g, 0.00079 mol) was added and heated at 40° C. for 18 hours. Additional 60% sodium hydride in oil (0.032 g, 0.00079 mol) was added and the mixture was stirred an additional 2 hours. The solvent was removed in vacuo and the residue was partitioned between dichloromethane (15 mL) and water (25 mL). The layers were separated and the aqueous layer was extracted with dichloromethane (2×15 mL). The combined organics were washed with brine and dried over magnesium sulfate. The solvent was removed in vacuo and the residue was purified by flash column chromatography on silica using heptane/ethyl acetate (1:2) as an eluent to give two products. The less polar compound, 1-(6-nitro-3-pyridyl)-3-(4-phenoxyphenyl)-1H-pyrazolo[3,4-d]pyrimidin-4-amine, was suspended in absolute ethanol (10 mL) and N,N-dimethylformamide (5 mL) and 10% palladium on carbon (0.007 g) was added. The mixture was stirred under a balloon atmosphere of hydrogen for 18 hours. The mixture was filtered through pad of Celite® 521, washing with absolute ethanol. The solvent was removed in vacuo to give 1-(6-amino-3-pyridyl)-3-(4-phenoxyphenyl)-1H-pyrazolo[3,4-d]pyrimidin-4-amine (0.007 g, 0.00002 mol) as a white solid.

$^1$H NMR (DMSO-$d_6$, 400 MHz) δ 8.53 (d, 1H) 8.31 (s, 1H), 7.97 (dd, 1H), 7.73 (d, 21), 7.44 (t, 2H), 7.12-23 (m, 5H), 6.60 (d, 1H), 6.20 (s, 2H); RP-HPLC (Delta Pak C18, 5 μm, 300A, 15 cm; 5%-85% acetonitrile—0.1M ammonium acetate over 20 min, 1 mL/min) $R_t$ 15.38 min.; MS: $MH^+$ 396.

The more polar compound, 3-(4-phenoxyphenyl)-1-(5-bromo-2-pyridyl)-1H-pyrazolo[3,4-d]pyrimidin-4-amine, was suspended in absolute ethanol (10 mL) and N,N-dimethylformamide (5 mL) and 10% palladium on carbon (0.007 g) was added. The mixture was stirred under a balloon atmosphere of hydrogen for 18 hours. The mixture was filtered through pad of Celite® 521, washing with absolute ethanol. The solvent was removed in vacuo to give 3-(4-phenoxyphenyl)-1-(2-pyridyl)-1H-pyrazolo[3,4-d]pyrimidin-4-amine (0.030 g, 0.00007 mol) as a white solid.

$^1$H NMR (DMSO-$d_6$, 400 MHz) δ 8.60-8.64 (m, 1H) 8.37 (s, 1H), 8.20 (d, 1H), 8.03-8.08 (m, 1H), 7.76 (d, 2H), 7.41-7.49 (m, 3H), 7.12-7.23 (m, 5H); RP-HPLC (Delta Pak C18, 5 μm, 300A, 15 cm; 5%-85% acetonitrile—0.1M ammonium acetate over 20 min, 1 mL/min) $R_t$ 16.32 min.; MS: $MH^+$ 381.

A general procedure for reductive amination with trans-3-(4-amino-phenyl)-1-[4-(4-methylpiperazino)cyclohexyl]-1H-pyrazolo[3,4-d]pyrimidin-4-amine and an aldehyde as starting materials is given below. Examples 316 and 317 were prepared using this method.

Protocol:

A mixture of trans-3-(4-amino-phenyl)-1-[4-(4-methylpiperazino)cyclohexyl]-1H-pyrazolo[3,4-d]pyrimidin-4-amine (1 eq.), the corresponding aldehyde (1.05 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10-60% acetonitrile—0.1M ammonium acetate over 25 min, 21 mL/min) to yield the desired products. Example 316 was prepare according to this method using the aldehyde 2-methoxy-3-formyl-pyridine and Example 317 was prepared using the aldehyde 2-formy-indole.

Example 316 trans-3-(4-[(2-methoxy-3-pyridyl)methyl]aminophenyl)-1-[4-(4-methyl-piperazino)cyclohexyl]-1H-pyrazolo[3,4-d]pyrimidin-4-amine diacetate $^1$H NMR (DMSO-$d_6$, 400 MHz) δ 8.18 (s, 1H), 8.06 (dd, 1H), 7.61 (d, 1H), 7.35 (d, 2H), 6.95 (dd, 1H), 6.69 (d, 2H), 6.51 (t, 1H), 4.60 (m, 1H), 4.26 (d, 2H), 3.94 (s, 3H), 2.64 (s, 3H), 2.6-2.2 (br, 9H), 2.13 (s, 3H), 2.05 (m, 6H), 1.91 (s, 6H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 12.07 min. MS: 528.

Example 317 trans-3-{4-[(1H-2-indolylmethyl)amino]phenyl}-1-[4-(4-methylpiperazino)-cyclohexyl]-1H-pyrazolo[3,4-d]pyrimidin-4-amine acetate $^1$H NMR (DMSO-d$_6$, 400 MHz) δ 11.08 (s, 1H), 8.19 (s, 1H), 7.44 (d, 1H), 7.36 (d, 2H), 7.32 (d, 1H), 7.01 (t, 1H), 6.95 (t, 1H), 6.81 (d, 2H), 6.47 (t, 1H), 6.35 (s, 1H), 4.60 (m, 1H), 4.45 (d, 2H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 13.74 min. MS: MH$^+$ 536.

Example 318

Trans-3-[(4-{4-amino-1-[4-(4-methylpiperazino)cyclohexyl]-1H-pyrazolo[3,4-d]pyrimidin-3-yl}anilino)methyl]-1,2-dihydro-2-pyridinone diacetate Trans-3-(4-[(2-methoxy-3-pyridyl)methyl]aminophenyl)-1-[4-(4-methylpiperazino)cyclohexyl]-1H-pyrazolo[3,4-d]pyrimidin-4-amine diacetate (0.105 g, 0.000199 mol) was dissolved in 30% hydrogen bromide in acetic acid (4 mL) and the mixture was refluxed for 1.5 hours. The solvent was removed under reduced pressure and the residue was purified by preparative HPLC (Hypersil C18, 8 μm, 25 cm; 10-60% acetonitrile—0.1M ammonium acetate over 25 min, 21 mL/min) to yield trans-3-[(4-{4-amino-1-[4-(4-methylpiperazino)cyclohexyl]-1H-pyrazolo[3,4-d]pyrimidin-3-yl}anilino)methyl]-1,2-dihydro-2-pyridinone diacetate (0.0204 g, 0.0000324 mol) as a white solid.

$^1$H NMR (DMSO-d$_6$, 400 MHz) δ 8.18 (s, 1H), 7.29 (m, 4H), 6.68 (d, 2H), 6.40 (t, 1H), 6.15 (m, 1H), 4.60 (m, 1H), 4.09 (d, 2H), 2.64 (s, 3H), 2.6-2.2 (br, 9H), 2.13 (s, 3H), 2.05 (m, 6H), 1.91 (s, 6H), 1.46 (m, 2H);

RP-HPLC (Delta Pak C18, 5 μm, 300A, 15 cm; 5%-85% acetonitrile—0.1M ammonium acetate over 20 min, 1 mL/min) $R_t$ 9.40 min. MS: MH$^+$ 514.

A general procedure for reductive amination with trans-3-(4-amino-3-methoxyphenyl)-1-[4-(4-methylpiperazino)cyclohexyl]-1H-pyrazolo[3,4-d]pyrimidin-4-amine and an aldehyde as starting materials is given below. Examples 319-321 were prepared using this method.

Protocol:

A mixture of trans-3-(4-amino-3-methoxyphenyl)-1-[4-(4-methylpiperazino)cyclohexyl]-1H-pyrazolo[3,4-d]pyrimidin-4-(1 eq.), the corresponding aldehyde (1.05 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10-60% acetonitrile—0.1M ammonium acetate over 25 min, 21 mL/min) to yield the desired products.

Example 319 was prepared using the aldehyde 2-amino-4-chloro-5-formyl-1,3-thiazole. Example 320 was prepared using the aldehyde 5-methyl-3-formyl-isoxazole. Example 321 was prepared using the aldehyde 4-formy-1,3-thiazole.

Example 319

Trans-5-[(4-{4-amino-1-[4-(4-methylpiperazino)cyclohexyl]-1H-pyrazolo[3,4-d]pyrimidin-3-yl}-2-methoxyanilino)methyl]-4-chloro-1,3-thiazol-2-amine diacetate $^1$H NMR (DMSO-d$_6$, 400 MHz) δ 8.19 (s, 1), 7.19 (s, 2H), 7.06 (m, 3H), 6.68 (d, 1H), 5.76 (t, 1H), 4.60 (m, 1H), 4.30 (d, 2H), 3.85 (s, 3H), 2.6-2.2 (br, 9H), 2.17 (s, 3H), 2.05 (m, 6H), 1.91 (s, 6H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 11.59 min. MS: MH$^+$ 583.

Example 320

Trans-3-(3-methoxy-4-[(5-methyl-3-isoxazolyl)methyl]aminophenyl)-1-[4-(4-methylpiperazino)cyclohexyl]-1H-pyrazolo[3,4-d]pyrimidin-4-amine acetate $^1$H NMR (DMSO-d$_6$, 400 MHz) δ 8.19 (s, 1H), 7.04 (m, 2H), 6.68 (d, 1H), 6.16 (s, 1H), 5.86 (t, 1H), 4.60 (m, 1H), 4.37 (d, 2H), 3.86 (s, 3H), 2.6-2.2 (br, 9H), 2.40 (s, 3H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 11.53 min. MS: MH$^+$ 532.

Example 321

Trans-3-{3-methoxy-4-[(1,3-thiazol-4-ylmethyl)amino]phenyl}—[4-(4-methylpiperazino)cyclohexyl]-1H-pyrazolo[3,4-d]pyrimidin-4-amine acetate $^1$H NMR (DMSO-d$_6$, 400 MHz) δ 9.08 (s, 1H), 8.19 (s, 1H), 7.47 (s, 1H), 7.06 (s, 1H), 7.03 (d, 1H), 6.68 (d, 1H), 5.76 (t, 1H), 4.60 (m, 1H), 4.52 (d, 2H), 3.88 (s, 3H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 11.17 min. MS: MH$^+$ 534.

A general procedure for the synthesis of benzotetrahydrofuran-derivatives with trans-3-(4-aminophenyl)-1-[4-(4-methylpiperazino)cyclohexyl]-1H-pyrazolo[3,4-d]pyrimidin-4-amine and the appropriate 2-hydroxy-benzaldehyde as starting material is given below. Examples 322 and 323 were prepared using this method.

Protocol:

Trans-3-(4-aminophenyl)-1-[4-(4-methylpiperazino)cyclohexyl]-1H-pyrazolo[3,4-d]pyrimidin-4-amine (1 equiv., 0.0001-0.0002 mol scale) and the corresponding 2-hydroxy-benzaldehyde (1 equiv.) were combined in absolute ethanol (5 mL) and stirred at ambient temperature for 48 hours. The reaction mixture was concentrated under reduced pressure and the residue dried overnight to yield the corresponding imine, which was used without further purification. Trimethylsulfoxonium iodide (2.5 equiv.) was dissolved in anhydrous dimethylsulfoxide (2 mL) and a 60% dispersion of sodium hydride in parafine (2.5 equiv.) was added at once. After 10 min., the solution of the imine in anhydrous dimethylsulfoxide (2 mL) was added and the resulting mixture was stirred at ambient temperature under an atmosphere of nitrogen for 2.5 hours. The solution was poured into ice-cold water (50 mL) and extracted with dichloromethane (2×40 mL). The combined organic extracts were dried with magnesium sulfate and concentrated under reduced pressure. The residue was purified by preparative HPLC (Hypersil C18, 8 µm, 25 cm; 10-60% acetonitrile—0.1M ammonium acetate over 25 min, 21 mL/min) to yield the final compound.

Example 322 was prepared using 2-hydroxy-4,6-dichlorobenzaldehyde and Example 323 was prepared using 2-hydroxy-4-chlorobenzaldehyde.

Example 322

Trans-3-4-[(4,6-dichloro-2,3-dihydrobenzo[b]furan-3-yl)amino]phenyl-1-[4-(4-methylpiperazino)cyclohexyl]-1H-pyrazolo[3,4-d]pyrimidin-4-amine acetate $^1$H NMR (DMSO-$d_6$, 400 MHz) δ 8.19 (s, 1H), 7.39 (d, 2H), 7.14 (s, 1H), 7.07 (s, 1H), 6.80 (d, 2H), 6.56 (d, 1H), 5.34 (m, 1H), 4.80 (dd, 1H), 4.60 (m, 1H), 4.42 (dd, 1H), 2.6-2.2 (br, 9H), 2.13 (s, 3H), 2.05 (m, 6H), 1.91 (s, 3H), 1.46 (m, 2H); RP-HPLC (Delta Pak C18, 5 µm, 300A, 15 cm; 5%-85% acetonitrile—0.1M ammonium acetate over 20 min, 1 mL/min) R$_t$ 16.03 min. MS: MH$^+$ 593.

Example 323

Trans-3-{4-[(4-chloro-2,3-dihydrobenzo[b]furan-3-yl)amino]phenyl}-1-[4-(4-methylpiperazino)cyclohexyl]-1H-pyrazolo[3,4-d]pyrimidin-4-amine acetate $^1$H NMR (DMSO-$d_6$, 400 MHz) δ 8.20 (s, 1H), 7.39 (d, 2H), 7.28 (t, 1H), 6.99 (d, 1H), 6.89 (d, 1H), 6.81 (d, 2H), 6.53 (d, 1H), 5.34 (m, 1H), 4.74 (dd, 1H), 4.60 (m, 1H), 4.38 (dd, 1H), 2.6-2.2 (br, 9H), 2.13 (s, 3H), 2.05 (m, 6H), 1.91 (s, 3H), 1.46 (m, 2H); RP-HPLC (Delta Pak C18, 5 µm, 300A, 15 cm; 5%-85% acetonitrile—0.1M ammonium acetate over 20 min, 1 mL/min) R$_t$ 14.42 min. MS: MH$^+$ 559.

Example 324

Trans-3-4-[(4,6-dichloro-2,3-dihydrobenzo[b]furan-3-yl)amino]-3-methoxyphenyl-1-[4-(4-methylpiperazino) cyclohexyl]-1H-pyrazolo[3,4-d]pyrimidin-4-amine acetate Trans-3-4-[(4,6-dichloro-2,3-dihydrobenzo[b]furan-3-yl)amino]-3-methoxyphenyl-1-[4-(4-methylpiperazino) cyclohexyl]-1H-pyrazolo[3,4-d]pyrimidin-4-amine acetate was prepared using the method of Examples 322 and 323 using trans-3-(4-amino-3-methoxyphenyl)-1-[4-(4-methylpiperazino)cyclohexyl]-1H-pyrazolo[3,4-d]pyrimidin-4-amine and 2-hydroxy-4,6-dichlorobenzaldehyde as the starting materials.

$^1$H NMR (DMSO-$d_6$, 400 MHz) δ 8.20 (s, 1H), 7.11 (m, 4H), 6.80 (d, 1H), 5.45(m, 2H), 4.84 (dd, 1H), 4.60 (m, 1H), 4.42 (dd, 1H), 3.82 (s, 3H), 2.6-2.2 (br, 9H), 2.13 (s, 3H), 2.05 (m, 6H), 1.91 (s, 3H), 1.46 (m, 2H); RP-HPLC (Delta Pak C18, 5 µm, 300A, 15 cm; 5%-85% acetonitrile—0.1M ammonium acetate over 20 min, 1 mL/min) R$_t$ 16.85 min. MS: MH$^+$ 623.

Intermediate 7: tert-butyl 4-[4-amino-3-(4-aminophenyl)-1H-pyrazolo[3,4-d]pyrimidin-1-yl]-1-piperidinecarboxylate A. tert-butyl 4-[4-amino-3-(4-[(benzyloxy)carbonyl] aminophenyl)-1H-pyrazolo[3,4-d]pyrimidin-1-yl]-1-piperidinecarboxylate A mixture of benzyl N-[4-(4,4,5,5-tetramethyl-1,3,2-dioxaborolan-2-yl)phenyl]carbamate (9.54 g, 0.027 mol), tert-butyl 4-(4-amino-3-iodo-1H-pyrazolo[3,4-d]pyrimidin-1-yl)-1-piperidinecarboxylate (10.0 g, 0.0225 mol), tetrakis-(triphenylphosphine)palladium (1.56 g, 0.00135 mol) and sodium carbonate (5.97 g, 0.0563 mol) was heated in a mixture of ethylene glycol dimethyl ether (120 mL) and water (60 mL) at 80° C. for 16 hours under an atmosphere of nitrogen. The mixture was allowed to cool to ambient temperature and solvents were removed under the reduced pressure. The residue was partitioned between water (150 mL) and dichloromethane (150 mL); the organic phase was washed with brine, dried with magnesium sulfate and concentrated under reduced pressure. The residue was triturated in diethyl ether and the precipitate was collected by filtration and dried to yield tert-butyl 4-[4-amino-3-(4-[(benzyloxy)carbonyl]aminophenyl)-1H-pyrazolo[3,4-d]pyrimidin-1-yl]-1-piperidinecarboxylate (10.1 g, 0.0186 mol) as a white solid.

$^1$H NMR (DMSO-$d_6$, 400 MHz) δ 10.00 (s, 1H), 8.23 (s, 1H), 7.64 (d, 2H), 7.43 (d, 2H), 7.36 (m, 5H), 5.18 (s, 2H), 4.90 (m, 1H), 4.08 (br, 2H), 3.00 (br, 2H), 2.02 (m, 4H), 1.42 (s, 9H); RP-HPLC (Delta Pak C18, 5 µm, 300A, 15 cm; 5%-85% acetonitrile—0.1M ammonium acetate over 20 min, 1 mL/min) R$_t$ 18.58 min.

B. tert-butyl 4-[4-amino-3-(4-aminophenyl)-1H-pyrazolo[3,4-d]pyrimidin-1-yl]-1-piperidinecarboxylate To a solution of tert-butyl 4-[4-amino-3-(4-[(benzyloxy) carbonyl]aminophenyl)-1H-pyrazolo[3,4-d]pyrimidin-1-yl]-1-piperidinecarboxylate (5.0 g, 0.0092 mol) in terahydrofuran (150 mL) 10% palladium on carbon (1.0 g) was added and the reaction mixture was hydrogenated on a Parr shaker over 96 hours. The catalyst was removed by filtration through a Celite pad and the filtrate was concentrated under reduced pressure. The residue was triturated in n-heptane and the precipitate was collected by filtration and dried to yield tert-butyl 4-[4-amino-3-(4-aminophenyl)-1H-pyrazolo [3,4-d]pyrimidin-1-yl]-1-piperidinecarboxylate (2.51 g, 0.0061 mol) as an off-white solid.

$^1$H NMR (DMSO-$d_6$, 400 MHz) δ 8.20 (s, 1H), 7.35 (d, 2H), 6.69 (d, 2H), 5.42 (s, 2H), 4.90 (m, 1H), 4.08 (br, 2H), 3.00 (br, 2H), 2.02 (m, 4H), 1.42 (s, 9H);

RP-HPLC (Delta Pak C18, 5 µm, 300A, 15 cm; 5%-85% acetonitrile—0.1M ammonium acetate over 20 min, 1 mL/min) R$_t$ 14.18 min.

Examples 325-337 were prepared with the following general procedure for reductive amination followed by BOC deprotection. Tert-butyl 4-[4-amino-3-(4-aminophenyl)-1H-pyrazolo[3,4-d]pyrimidin-1-yl]-1-piperidinecarboxylate and the appropriate aldehyde were used as starting materials.

Protocol:

A mixture of tert-butyl 4-[4-amino-3-(4-aminophenyl)-1H-pyrazolo[3,4-d]pyrimidin-1-yl]-1-piperidinecarboxylate (1 eq.), aldehyde (1.2 eq.), sodium triacetoxyborohydride (3.4 eq.) and acetic acid (3.4 eq) was stirred in anhydrous 1,2-dichloroethane for 16 hours. The reaction mixture was concentrated under reduced pressure, triturated in ethyl acetate and treated with with a 4N aqueous solution of hydrochloric acid. The resulting mixture was stirred for 1 hour; aqueous phase was neutralized with saturated solution of sodium bicarbonate in water and the layers separated. Organic phase was concentrated under reduced pressure and the residue was purified by preparative HPLC (Hypersil C18, 8 µm, 25 cm; 10-60% acetonitrile -0.1M ammonium acetate over 25 min, 21 mL/min) to yield the desired products. The following compounds were made using the above procedure:

Example 325

3-{4-[(benzo[b]furan-2-ylmethyl)amino]phenyl}-1-(4-piperidyl)-1H-pyrazolo[3,4-d]pyrimidin-4-amine diacetate $^1$H NMR (DMSO-$d_6$, 400 MHz), 8.19 (s, 1H), 7.57 (d, 1H), 7.53 (d, 1H), 7.39 (d, 2H), 7.23 (m, 2H), 6.85 (d, 2H), 6.80 (s, 1H), 6.66 (t, 1H), 4.70 (m, 1H), 4.51 (d, 2H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 13.37 min. MS: MH$^+$ 440.

Example 326

3-(4-[(2-methoxy-3-pyridyl)methyl]aminophenyl)-1-(4-piperidyl)-1H-pyrazolo[3,4-d]pyrimidin-4-amine diacetate $^1$H NMR (DMSO-$d_6$, 400 MHz) δ 8.19 (s, 1H), 8.06 (d, 1H), 7.61 (d, 1H), 7.36 (d, 2H), 6.96 (dd, 1H), 6.69 (d, 2H), 6.51 (t, 1H), 4.70 (m, 1H), 4.27 (d, 2H), 3.94 (s, 3H), 3.07 (m, 2H), 2.65 (m, 2H), 2.04 (m, 2H), 1.90 (s, 6H), 1.79 (m, 2H);

RP-HPLC (Delta Pak C18, 5 µm, 300A, 15 cm; 5%-85% acetonitrile—0.1M ammonium acetate over 20 min, 1 mL/min) $R_t$ 11.06 min. MS: MH$^+$ 431.

Example 327

3-(4-[(5-methyl-2-thienyl)methyl]aminophenyl)-1-(4-piperidyl)-1H-pyrazolo[3,4-d]pyrimidin-4-amine diacetate $^1$H NMR (DMSO-$d_6$, 400 MHz) δ 8.19 (s, 1H), 7.36 (d, 2H), 6.85 (d, 1H), 6.77 (d, 2H), 6.64 (d, 1H), 6.54 (t, 1H), 4.70 (m, 1H), 4.41 (d, 2H), 3.07 (m, 2H), 2.65 (m, 2H), 2.38 (s, 3H), 2.04 (m, 2H), 1.90 (s, 6H), 1.79 (m, 2H);

RP-HPLC (Delta Pak C18, 5 µm, 300A, 15 cm; 5%-85% acetonitrile—0.1M ammonium acetate over 20 min, 1 mL/min) $R_t$ 12.85 min. MS: MH$^+$ 420.

Example 328

3-{4-[(2-furylmethyl)amino]phenyl}-1-(4-piperidyl)-1H-pyrazolo[3,4-d]pyrimidin-4-amine diacetate $^1$H NMR (DMSO-$d_6$, 400 MHz) δ 8.19 (s, 1H), 7.59 (s, 1H), 7.36 (d, 2H), 6.77 (d, 2H), 6.46 (t, 1H), 6.39 (d, 1H), 6.34 (d, 1H), 4.70 (m, 1H), 4.31 (d, 2H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 10.96 min. MS: MH$^+$ 390.

Example 329

3-[4-(benzylamino)phenyl]-1-(4-piperidyl)-1H-pyrazolo[3,4-d]pyrimidin-4-amine diacetate $^1$H NMR (DMSO-$d_6$, 400 MHz) δ 8.19 (s, 1H), 7.34 (m, 6H), 7.24 (t, 1H), 6.73 (d, 2H), 6.60 (t, 1H), 4.70 (m, 1H), 4.33 (d, 2H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 12.32 min. MS: MH$^+$ 400.

Example 330

3-{4-[(2-methoxybenzyl)amino]phenyl}-1-(4-piperidyl)-1H-pyrazolo[3,4-d]pyrimidin-4-amine diacetate $^1$H NMR (DMSO-$d_6$, 400 MHz) δ 8.19 (s, 1H), 7.35 (d, 2H), 7.24 (m, 2H), 7.01 (d, 1H), 6.90 (t, 1H), 6.70 (d, 2H), 6.41 (t, 1H), 4.70 (m, 1H), 4.28 (d, 2H), 3.85 (s, 3H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 12.73 min. MS: MH$^+$ 430.

Example 331

3-{4-[(3-methoxybenzyl)amino]phenyl}-1-(4-piperidyl)-1H-pyrazolo[3,4-d]pyrimidin-4-amine diacetate $^1$H NMR (DMSO-$d_6$, 400 MHz), 8.19 (s, 1H), 7.35 (d, 2H), 7.25 (t, 1H), 6.96 (m, 2H), 6.81 (d, 1H), 6.72 (d, 2H), 6.59 (t, 1H), 4.70 (m, 1H), 4.30 (d, 2H), 3.74 (s, 3H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 12.38 min. MS: MH$^+$ 430.

Example 332

3-{4-[(4-methoxybenzyl)amino]phenyl}-1-(4-piperidyl)-1H-pyrazolo[3,4-d]pyrimidin-4-amine diacetate $^1$H NMR (DMSO-$d_6$, 400 MHz), 8.19 (s, 1H), 7.35 (m, 4H), 6.90 (d, 2H), 6.72 (d, 2H), 6.51 (t, 1H), 4.70 (m, 1H), 4.25 (d, 2H), 3.73 (s, 3H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 12.37 min. MS: MH$^+$ 430.

Example 333

1-(4-piperidyl)-3-(4-[3-(trifluoromethyl)benzyl]aminophenyl)-1H-pyrazolo[3,4-d]pyrimidin-4-amine diacetate $^1$H NMR (DMSO-$d_6$, 400 MHz) δ 8.19 (s, 1H), 7.71 (m, 2H), 7.58 (m, 2H), 7.36 (d, 2H), 6.72 (m, 3H), 4.70 (m, 1H), 4.44 (d, 2H), 3.07 (m, 2H), 2.65 (m, 2H), 2.04 (m, 2H), 1.90 (s, 6H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 14.08 min. MS: MH$^+$ 468.

Example 334

1-(4-piperidyl)-3-(4-[4-(trifluoromethyl)benzyl]aminophenyl)-1H-pyrazolo[3,4-d]pyrimidin-4-amine diacetate $^1$H NMR (DMSO-d$_6$, 400 MHz) δ 8.19 (s, 1H), 7.70 (d, 2H), 7.60 (d, 2H), 7.36 (d, 2H), 6.72 (m, 3H), 4.70 (m, 1H), 4.44 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 14.23 min. MS: MH$^+$ 468.

Example 335

3-(4-[(2-methyl-1,3-thiazol-4-yl)methyl]aminophenyl)-1-(4-piperidyl)-1H-pyrazolo[3,4-d]pyrimidin-4-amine diacetate $^1$H NMR (DMSO-d$_6$, 400 MHz), 8.19 (s, 1H), 7.41 (d, 2H), 7.26 (s, 1H), 6.73 (d, 2H), 6.51 (t, 1H), 4.70 (m, 1H), 4.36 (d, 2H), 3.07 (m, 2H), 2.70 (s, 3H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 10.13 min. MS: MH$^+$ 421.

Example 336

3-{4-[(2-chloro-6-fluorobenzyl)amino]phenyl}-1-(4-piperidyl)-1H-pyrazolo[3,4-d]pyrimidin-4-amine diacetate $^1$H NMR (DMSO-d$_6$, 400 MHz). 8.19 (s, 1H), 7.42 (m, 4H), 7.26 (t, 1H), 6.83 (d, 2H), 6.27 (t, 1H), 4.72 (m, 1H), 4.37 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.32 min. MS: MH$^+$ 452.

Example 337

3-(4-[2-fluoro-4-(trifluoromethyl)benzyl]aminophenyl)-1-(4-piperidyl)-1H-pyrazolo[3,4-d]pyrimidin-4-amine diacetate $^1$H NMR (DMSO-d$_6$, 400 MHz) δ 8.19 (s, 1H), 7.61 (m, 3H), 7.38 (d, 2H), 6.73 (d, 2H), 6.68 (t, 1H), 4.70 (m, 1H), 4.47 (d, 2H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 12.83 min. MS: MH$^+$ 486.

Example 338

3-{4-[(benzo[b]furan-2-ylmethyl)amino]-3-methoxyphenyl}-1-(4-piperidyl)-1H-pyrazolo[3,4-d]pyrimidin-4-amine diacetate A mixture of tert-butyl 4-[4-amino-3-(4-amino-3-methoxyphenyl)-1H-pyrazolo[3,4-d]pyrimidin-1-yl]-1-piperidinecarboxylate (g, mol), benzofuran-2-carbaldehyde (0.046 g, 0.000315 mol), sodium triacetoxyborohydride (0.089 g, 0.00042 mol.) and acetic acid (0.024 mL, 0.00042 mol) was stirred in anhydrous 1,2-dichloroethane for 16 hours. The reaction mixture was concentrated under reduced pressure, triturated in ethyl acetate (4 mL) and treated with a 4N aqueous solution of hydrochloric acid (1 mL). The resulting mixture was stirred for 1 hour; aqueous phase was neutralized with saturated solution of sodium bicarbonate in water and the layers separated. The organic phase was concentrated under reduced pressure and the residue was purified by preparative HPLC (Hypersil C18, 8 μm, 25 cm; 10-60% acetonitrile—0.1M ammonium acetate over 25 min, 21 mL/min) to yield 3-{4-[(benzo[b]furan-2-ylmethyl)amino]-3-methoxyphenyl}-1-(4-piperidyl)-1H-pyrazolo[3,4-d]pyrimidin-4-amine diacetate (0.027 g, 0.0000457 mol).

$^1$H NMR (DMSO-d$_6$, 400 MHz) δ 8.19 (s, 1H), 7.55 (m, 2H), 7.22 (m, 2H), 7.06 (m, 2H), 6.80 (d, 1H), 6.75 (s, 1H), 5.80 (t, 1H), 4.70 (m, 1H), 4.57 (d, 2H), 3.89 (s, 3H), 3.07 (m, 2H), 2.65 (m, 2H), 2.04 (m, 2H), 1.90 (s, 6H), 1.79 (m, 2H); RP-HPLC (Delta Pak C18, 5 μm, 300A, 15 cm; 5%-85% acetonitrile—0.1M ammonium acetate over 20 min, 1 mL/min) R$_t$ 14.83 min. MS: MH$^+$ 470.

Example 339

3-[4-(2,3-dihydrobenzo[b]furan-3-ylamino)phenyl]-1-(4-piperidyl)-1H-pyrazolo[3,4-d]pyrimidin-4-amine acetate Salicylaldehyde (0.063 g, 0.000513 mol) and tert-butyl 4-[4-amino-3-(4-aminophenyl)-1H-pyrazolo[3,4-d]pyrimidin-1-yl]-1-piperidinecarboxylate (0.200 g, 0.000489 mol) were combined in absolute ethanol (5 mL) and stirred at ambient temperature for 48 hours. The reaction mixture was concentrated under reduced pressure and the residue dried overnight to yield tert-butyl 4-[4-amino-3-(4-{[-1-(2-hydroxyphenyl)methylidene]amino}phenyl)-1H-pyrazolo[3,4-d]pyrimidin-1-yl]-1-piperidinecarboxylate which was used without further purification. Trimethylsulfoxonium iodide (0.269 g, 0.00122 mol) was dissolved in anhydrous dimethylsulfoxide (2 mL) and a 60% dispersion of sodium hydride in parafine (0.049 g, 0.00122 mol) was added at once. After 10 min., the solution of tert-butyl 4-[4-amino-3-(4-{[-1-(2-hydroxyphenyl)methylidene]amino}phenyl)-1H-pyrazolo [3,4-d]pyrimidin-1-yl]-1-piperidinecarboxylate in anhydrous dimethylsulfoxide (2 mL) was added and the resulting mixture was stirred at ambient temperature under an atmosphere of nitrogen for 2.5 hours. The solution was poured into ice-cold water (70 mL) and extracted with dichloromethane (2×50 mL). The combined organic extracts were dried with magnesium sulfate and concentrated under reduced pressure to yield crude tert-butyl 4-{4-amino-3-[4-(2,3-dihydrobenzo[b]furan-3-ylamino)phenyl]-1H-pyrazolo [3,4-d]pyrimidin-1-yl}-1-piperidinecarboxylate which was used without further purification. The crude compound was dissolved in ethyl acetate (5 mL) and treated with a 4N aqueous solution of hydrochloric acid (1.5 mL). The resulting emulsion was vigorously stirred for 1 hour; the water layer was neutralized with saturated solution of sodium bicarbonate in water and the layers were separated. The organic phase was concentrated under reduced pressure and residue was purified by preparative HPLC (Hypersil C18, 8 μm, 25 cm; 10-60% acetonitrile—0.1M ammonium acetate over 25 min, 21 mL/min) to yield 3-[4-(2,3-dihydrobenzo [b]furan-3-ylamino)phenyl]-1-(4-piperidyl)-1H-pyrazolo[3,4-d]pyrimidin-4-amine acetate (0.038 g, 0.000078 mol) as a white solid $^1$H NMR (DMSO-d$_6$, 400 MHz) δ 8.19 (s, 1H), 7.41 (m, 3H), 7.25 (t, 1H), 6.89 (m, 4H), 6.51 (t, 1H), 5.35 (m, 1H), 4.79 (m, 2H), 4.27 (m, 1H), 3.07 (m, 2H), 2.65 (m, 2H), 2.04 (m, 2H), 1.90 (s, 3H), 1.79 (m, 2H); RP-HPLC (Delta Pak C18, 5 µm, 300A, 15 cm; 5%-85% acetonitrile—0.1M ammonium acetate over 20 min, 1 mL/min) $R_t$ 11.38 min. MS: MH+ 428.

Example 340

Trans-3-(4-{4-amino-1-[4-(4-methylpiperazino)cyclohexyl]-1H-pyrazolo[3,4-d]pyrimidin-3-yl}anilino)-1H-1$\lambda^6$-benzo[d]isothiazole-1,1-dione acetate A. 3-chloro-1H-1$\lambda^6$-benzo[d]isothiazole-1,1-dione Saccharin (10.0 g, 0.0546 mol) and phosphorus pentachloride (12.6 g, 0.060 mol) were heated at 170° C. for 1.5 hours. The reaction mixture was cooled to ambient temperature and suspended in diethyl ether (200 mL). The precipitate was collected by filtration, thoroughly washed with diethyl ether and dried to yield 3-chloro-1H-1$\lambda^6$-benzo[d]isothiazole-1,1-dione (3.7 g, 0.0184 mol) as a white solid which was used without further purification.
MS: MH+ 202.

B. 3-(4-bromoanilino)-1H-1$\lambda^6$-benzo[d]isothiazole-1,1-dione

To a solution of 3-chloro-1H-1$\lambda^6$-benzo[d]isothiazole-1,1-dione (1.0 g, 0.00496 mol) in acetone (20 mL), 4-bromoaniline (1.71 g, 0.00992 mol) was added at once and the mixture was stirred for 15 min. The mixture was concentrated under reduced pressure and the residue was suspended in water (100 mL). The precipitate was collected by filtration, thoroughly washed with water and dried to yield 3-(4-bromoanilino)-H-1$\lambda^6$-benzo[d]isothiazole-1,1-dione (1.57 g, 0.00467 mol) as a white solid.
$^1$H NMR (DMSO-$d_6$, 400 MHz) δ 10.93 (s, 1H), 8.47 (d, 1H), 8.09 (d, 1H), 7.93 (m, 4H), 7.69 (d, 2H);

C. 3-[4-(4,4,5,5-tetramethyl-1,3,2-dioxaborolan-2-yl)anilino]-1H-1$\lambda^6$-benzo[d]isothiazole-1,1-dione A mixture of 3-(4-bromoanilino)-1H-1$\lambda^6$-benzo[d]isothiazole-1,1-dione (1.57 g, 0.00467 mol), diboron pinacol ester (1.43 g, 0.00561 mol), [1.1'-bis(diphenylphosphino)ferrocene]-dichloropalladium (11) complex with dichloromethane (1:1) (0.114 g, 0.00014 mol) and potassium acetate (1.37 g, 0.014 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was triturated in diethyl ether to yield 3-[4-(4,4,5,5-tetramethyl-1,3,2-dioxaborolan-2-yl)anilino]-1H-1$\lambda^6$-benzo[d]isothiazole-1,1-dione (1.14 g, 0.00297 mol) as a white solid.
$^1$H NMR (DMSO-$d_6$, 400 MHz) δ 10.92 (br, 1H), 8.51 (d, 1H), 8.08 (d, 1H), 7.91 (m, 4H), 7.68 (d, 2H), 1.29 (s, 12H).

D. Trans-3-(4-{4-amino-1-[4-(4-methylpiperazino)cyclohexyl]-1H-pyrazolo[3,4-d]pyrimidin-3-yl}anilino)-1H-1$\lambda^6$-benzo[d]isothiazole-1,1-dione acetate A mixture of 3-[4-(4,4,5,5-tetramethyl-1,3,2-dioxaborolan-2-yl)anilino]-1H-1$\lambda^6$-benzo[d]isothiazole-1,1-dione (0.09 g, 0.000234 mol), trans-3-iodo-1-[4-(4-methylpiperazino)-cyclohexyl]-1H-pyrazolo[3,4-d]pyrimidin-4-amine (0.08 g, 0.00018 mol), tetrakis-(triphenylphosphine)palladium (0.013 g, 0.000011 mol) and sodium carbonate (0.048 g, 0.00045 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 µm, 25 cm; 10-60% acetonitrile—0.1M ammonium acetate over 25 min, 21 mL/min) to yield trans-3-(4-{4-amino-1-[4-(4-methylpiperazino)cyclohexyl]-1H-pyrazolo[3,4-d]pyrimidin-3-yl}anilino)-1H-1$\lambda^6$-benzo[d]isothiazole-1,1-dione acetate (0.075 g, 0.000119 mol) as a white solid.
$^1$H NMR (DMSO-$d_6$, 400 MHz) δ 8.29 (d, 1H), 8.23 (s, 1H), 7.91 (m, 3H), 7.79 (m, 2H), 7.66 (d, 2H), 4.65 (m, 1H), 2.6-2.2 (br, 9H), 2.13 (s, 3H), 2.05 (m, 6H), 1.91 (s, 3H), 1.46 (m, 2H); RP-HPLC (Delta Pak C18, 5 µm, 300A, 15 cm; 5%-85% acetonitrile—0.1M ammonium acetate over 20 min, 1 mL/min) $R_t$ 11.27 min. MS: MH+ 572.

Example 341

Cis-3-(4-{4-amino-1-[4-(4-methylpiperazino)cyclohexyl]-1H-pyrazolo[3,4-d]pyrimidin-3-yl}anilino)-1H-1$\lambda^6$-benzo[d]isothiazole-1,1-dione diacetate Cis-3-(4-{4-amino-1-[4-(4-methylpiperazino)cyclohexyl]-1H-pyrazolo[3,4-d]pyrimidin-3-yl}anilino)-1H-1$\lambda^6$-benzo[d]isothiazole-1,1-dione diacetate was prepared from 3-[4-(4,4,5,5-tetramethyl-1,3,2-dioxaborolan-2-yl)anilino]-1H-1$\lambda^6$-benzo[d]isothiazole-1,1-dione (0.09 g, 0.000234 mol) and cis-3-iodo-1-[4-(4-methylpiperazino)-cyclohexyl]-1H-pyrazolo[3,4-d]pyrimidin-4-amine by a similar protocol as described above.
$^1$H NMR (DMSO-$d_6$, 400 MHz) δ 8.42 (d, 1H), 8.23 (s, 1H), 7.91 (m, 3H), 7.84 (m, 2H), 7.62 (d, 2H), 4.80 (m, 1H), 2.6-2.2 (br, 9H), 2.13 (s, 3H), 2.07 (m, 4H), 1.91 (s, 6H), 1.65 (m, 2H), 1.58 (m, 2H); RP-HPLC (Delta Pak C18, 5 µm, 300A, 15 cm; 5%-85% acetonitrile—0.1M ammonium acetate over 20 min, 1 mL/min) $R_t$ 11.59 min. MS: MH+ 572.

Example 342

Trans-N-3-(4-{4-amino-1-[4-(4-methylpiperazino)cyclohexyl]-1H-pyrazolo[3,4-d]pyrimidin-3-yl}phenyl)benzo[d]isoxazol-3-amine acetate A. N1-(4-bromophenyl)-2-fluorobenzamide A solution of 2-fluorobenzoyl chloride (5.82 g, 0.0367 mol) and 4-bromoaniline (6.31 g, 0.0367 mol) in anhydrous dichloromethane (150 mL) was cooled to 0° C. and N,N-diisopropylethylamine (5.21 g, 0.0407 mol) was added under nitrogen atmosphere dropwise. The resulting mixture was stirred at ambient temperature for 24 hours, concentrated and the residue partitioned between ethyl acetate (120 mL) and water (100 mL). The organic phase was washed with brine, dried with magnesium sulfate and concentrated. The residue was suspended in cold diethyl ether (50 mL) and the precipitate was collected by filtration and dried to yield N1-(4-bromophenyl)-2-fluorobenzamide (9.6 g, 0.0326 mol) as a white solid.
$^1$H NMR (DMSO-$d_6$, 400 MHz), 10.54 (s, 1H), 7.66 (m, 3H), 7.56 (m, 3H), 7.34 (m, 2H). TLC (ethyl acetate/heptane 1:2) $R_f$ 0.37

B. N1-(4-bromophenyl)-2-fluoro-1-benzenecarbothioamide

A mixture of N1-(4-bromophenyl)-2-fluorobenzamide (3.3 g, 0.0112 mol) and 2,4-bis-(4-methoxyphenyl)-1,3-dithia-2,4-diphosphetane-2,4-disulfide (2.27 g, 0.00561 mol) was heated in toluene at reflux under an atmosphere of nitrogen for 3 hours. The reaction mixture was cooled to ambient temperature, the solvent was removed under reduced pressure and the residue was purified by flash chromatography on silica using ethyl acetate/n-heptane (1:6) as mobile phase to yield N1-(4-bromophenyl)-2-fluoro-1-benzenecarbothioamide (3.1 g, 0.010 mol) as a yellow solid.

$^1$H NMR (DMSO-$d_6$, 400 MHz) δ 12.13 (s, 1H), 7.93 (d, 2H), 7.62 (m, 3H), 7.51 (m, 1H), 7.31 (m, 2H). TLC (ethyl acetate/heptane 1:4) $R_f$ 0.27

C. N1-(4-bromophenyl)-2-fluoro-1-benzeneamidoxime

A mixture of N1-(4-bromophenyl)-2-fluoro-1-benzenecarbothioamide (1.56 g, 0.00505 mol), hydroxylamine hydrochloride (0.44 g, 0.00631 mol) and sodium bicarbonate (0.53 g, 0.00631 mol) was heated in absolute ethanol (25 mL) at reflux under nitrogen atmosphere for 14 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was suspended in cold diethyl ether and the precipitate was collected by filtration and dried to yield N1-(4-bromophenyl)-2-fluoro-1-benzeneamidoxime (1.21 g, 0.00392 mol) as an off-white solid.

TLC (ethyl acetate/heptane 1:4) $R_f$ 0.12

D. N-benzo[d]isoxazol-3-yl-N-(4-bromophenyl)amine

To a solution of N1-(4-bromophenyl)-2-fluoro-1-benzeneamidoxime (1.51 g, 0.00489 mol) in N-methylpyrrolidinone (25 mL), potassium tert-butoxide (0.54 g, 0.00513 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was purified by flash chromatography on silica using ethyl acetate/n-heptane (1:5) as mobile phase to yield N-benzo[d]isoxazol-3-yl-N-(4-bromophenyl)amine (0.95 g, 0.00329 mol) as a white solid.

$^1$H NMR (DMSO-$d_6$, 400 MHz) δ 9.72 (s, 1H), 8.13 (d, 1H), 7.68 (d, 2H), 7.61 (m, 21), 7.54 (d, 2H), 7.37 (dd, 1H). TLC (ethyl acetate/heptane 1:4) $R_f$ 0.26

E. N-benzo[d]isoxazol-3-yl-N-[4-(4,4,5,5-tetramethyl-1,3,2-dioxaborolan-2-yl)phenyl]amine A mixture of N-benzo[d]isoxazol-3-yl-N-(4-bromophenyl)amine (1.30 g, 0.0045 mol), diboron pinacol ester (1.37 g, 0.0054 mol), [1,1'-bis(diphenylphosphino) ferrocene]-dichloropalladium (II) complex with dichloromethane (1:1) (0.110 g, 0.000135 mol) and potassium acetate (1.32 g, 0.0135 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:5) as mobile phase to yield N-benzo[d]isoxazol-3-yl-N-[4-(4,4,5,5-tetramethyl-1,3,2-dioxaborolan-2-yl)phenyl]amine (0.40 g, 0.00119 mol) as a white solid.

$^1$H NMR (DMSO-$d_6$, 400 MHz) δ 9.74 (s, 1H), 8.16 (d, 1H), 7.70 (m, 4H), 7.61 (d, 2H), 7.37 (dd, 1H), 1.29 (s, 12H). TLC (ethyl acetate/heptane 1:4) $R_f$ 0.21

F. Trans-N-3-(4-{4-amino-1-[4-(4-methylpiperazino)cyclohexyl]-1H-pyrazolo[3,4-d]pyrimidin-3-yl}phenyl)benzo[d]isoxazol-3-amine acetate A mixture of N-benzo[d]isoxazol-3-yl-N-[4-(4,4,5,5-tetramethyl-1,3,2-dioxaborolan-2-yl)phenyl]amine (0.10 g, 0.000298 mol), trans-3-iodo-1-[4-(4-methylpiperazino)-cyclohexyl]-1H-pyrazolo[3,4-d]pyrimidin-4-amine (0.101 g, 0.000229 mol), tetrakis-(triphenylphosphine)palladium (0.016 g, 0.0000137 mol) and sodium carbonate (0.061 g, 0.000573 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 µm, 25 cm; 10-60% acetonitrile—0.1M ammonium acetate over 25 min, 21 mL/min) to yield trans-N-3-(4-{4-amino-1-[4-(4-methylpiperazino)cyclohexyl]-1H-pyrazolo[3,4-d]pyrimidin-3-yl}phenyl)benzo[d]isoxazol-3-amine acetate (0.102 g, 0.000175 mol) as a white solid.

$^1$H NMR (DMSO-$d_6$, 400 MHz) δ 9.81 (s, 1H), 8.23 (s, 1H), 8.19 (d, 1H), 7.88 (d, 2H), 7.65 (m, 4H), 7.40 (m, 1H), 4.65 (m, 1H), 2.6-2.2 (br, 9H), 2.13 (s, 3H), 2.05 (m, 6H), 1.91 (s, 3H), 1.46 (m, 2H); RP-HPLC (Delta Pak C18, 5 µm, 300A, 15 cm; 5%-85% acetonitrile—0.1M ammonium acetate over 20 min, 1 mL/min) $R_t$ 13.66 min. MS: MH$^+$ 524.

Example 343

Cis-N-3-(4-{4-amino-1-[4-(4-methylpiperazino)cyclohexyl]-1H-pyrazolo[3,4-d]pyrimidin-3-yl}phenyl)benzo[d]isoxazol-3-amine diacetate Cis-N-3-(4-{4-amino-1-[4-(4-methylpiperazino)cyclohexyl]-1H-pyrazolo[3,4-d]pyrimidin-3-yl}phenyl)benzo[d]isoxazol-3-amine diacetate was prepared from N-benzo[d]isoxazol-3-yl-N-[4-(4,4,5,5-tetramethyl-1,3,2-dioxaborolan-2-yl)phenyl]amine and cis-3-iodo-1-[4-(4-methylpiperazino)-cyclohexyl]-1H-pyrazolo[3,4-d]pyrimidin-4-amine by a similar protocol as described above.

$^1$H NMR (DMSO-$d_6$, 400 MHz) δ 9.86 (s, 1H), 8.26 (s, 1H), 8.24 (d, 1H), 7.93 (d, 2H), 7.67 (m, 4H), 7.43 (m, 1H), 4.83 (m, 1H), 2.6-2.2 (br, 9H), 2.13 (s, 3H), 2.08 (m, 4H), 1.91 (s, 6H), 1.74 (m, 2H), 1.62 (m, 2H); RP-HPLC (Delta Pak C18, 5 µm, 300A, 15 cm; 5%-85% acetonitrile—0.1M ammonium acetate over 20 min, 1 mL/min) $R_t$ 13.77 min. MS: MH$^+$ 524.

Example 344

N3-{4-[4-amino-1-(4-piperidyl)-1H-pyrazolo[3,4-d]pyrimidin-3-yl]phenyl}benzo[d]isoxazol-3-amine acetate A mixture of N-benzo[d]isoxazol-3-yl-N-[4-(4,4,5,5-tetramethyl-1,3,2-dioxaborolan-2-yl)phenyl]amine (0.087 g, 0.000258 mol), tert-butyl 4-(4-amino-3-iodo-1H-pyrazolo

[3,4-d]pyrimidin-1-yl)-1-piperidinecarboxylate (0.088 g, 0.000198 mol), tetrakis-(triphenylphosphine)palladium (0.014 g, 0.000012 mol) and sodium carbonate (0.053 g, 0.000495 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure and the residue partitioned between water and dichloromethane. The organic phase was dried with magnesium sulfate and concentrated under reduced pressure to yield crude tert-butyl 4-{4-amino-3-[4-(benzo[d]isoxazol-3-ylamino)phenyl]-1H-pyrazolo[3,4-d]pyrimidin-1-yl}-1-piperidinecarboxylate which was used without further purification. It was dissolved in ethyl acetate (5 mL) and treated with a 4N aqueous solution of hydrochloric acid (1 mL). The resulting emulsion was vigorously stirred for 1 hour; the water layer was neutralized with saturated solution of sodium bicarbonate in water and the layers were separated. The organic phase was concentrated under reduced pressure and residue was purified by preparative HPLC (Hypersil C18, 8 μm, 25 cm; 10-60% acetonitrile—0.1M ammonium acetate over 25 min, 2 mL/min) to yield N3-{4-[4-amino-1-(4-piperidyl)-1H-pyrazolo[3,4-d]pyrimidin-3-yl]phenyl}benzo[d]isoxazol-3-amine acetate (0.009 g, 0.0000185 mol) as a white solid.

$^1$H NMR (DMSO-$d_6$, 400 MHz) δ 9.82 (s, 1H), 8.20 (m, 2H), 7.89 (d, 2H), 7.65 (m, 4H), 7.41 (t, 1H), 4.74 (m, 1H), 3.07 (m, 2H), 2.65 (m, 2H), 2.04 (m, 2H), 1.90 (s, 3H), 1.79 (m, 2H); RP-HPLC (Delta Pak C18, 5 μm, 300A, 15 cm; 5%-85% acetonitrile—0.1M ammonium acetate over 20 min, 1 mL/min) $R_t$ 11.20 min. MS: MH$^+$ 427.

Example 345

Trans-3-[4-(1H-3-indazolylamino)phenyl]-1-[4-(4-methylpiperazino) cyclohexyl]-1H-pyrazolo[3,4-d]pyrimidin-4-amine acetate A. N1-(4-bromophenyl)-2-fluoro-1-benzenecarbohydrazonamide N1-(4-bromophenyl)-2-fluoro-1-benzenecarbothioamide (1.50 g, 0.00485 mol) and a 1M solution of hydrazine in tetrahydrofuran (6.3 mL, 0.0063 mol) were heated in absolute ethanol (25 mL) at reflux under nitrogen atmosphere for 14 hours. Additional 3 mL of a 1M solution of hydrazine in tetrahydrofuran was added and the stirring at reflux was continued for another 6 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated to yield N1-(4-bromophenyl)-2-fluoro-1-benzenecarbohydrazonamide (1.54 g, 0.0050 mol) as a tan solid.

TLC (ethyl acetate/heptane 1:3) $R_f$ 0.10

B. N-(4-bromophenyl)-N-(1H-3-indazolyl)amine

To a solution of N1-(4-bromophenyl)-2-fluoro-1-benzenecarbohydrazonamide (1.2 g, 0.00391 mol) in N-methylpyrrolidinone (25 mL), potassium tert-butoxide (0.50 g, 0.0041 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was purified by flash chromatography on silica using ethyl acetate/n-heptane (1:5) as mobile phase to yield N-(4-bromophenyl)-N-(1H-3-indazolyl)amine (0.29 g, 0.0010 mol) as a white solid.

$^1$H NMR (DMSO-$d_6$, 400 MHz) δ 12.06 (s, 1H), 9.03 (s, 1H), 7.93 (d, 1H), 7.65 (d, 2H), 7.35 (m, 4H), 7.03 (dd, 1H). TLC (ethyl acetate/heptane 1:3) $R_f$ 0.26

C. N-(1H-3-indazolyl)-N-[4-(4,4,5,5-tetramethyl-1,3,2-dioxaborolan-2-yl)phenyl]amine A mixture of N-(4-bromophenyl)-N-(1H-3-indazolyl)amine (0.29 g, 0.00101 mol), diboron pinacol ester (0.31 g, 0.00121 mol), [1.1'-bis(diphenylphosphino) ferrocene]-dichloropalladium (11) complex with dichloromethane (1:1) (0.025 g, 0.00003 mol) and potassium acetate (0.294 g, 0.003 mol) in N,N-dimethylformamide (35 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:3) as mobile phase to yield N-(1H-3-indazolyl)-N-[4-(4,4,5,5-tetramethyl-1,3,2-dioxaborolan-2-yl)phenyl]amine (0.064 g, 0.000191 mol) as an off-white solid.

$^1$H NMR (DMSO-$d_6$, 400 MHz) δ 12.09 (s, 1H), 9.06 (s, 1H), 7.94 (d, 1H), 7.64 (d, 2H), 7.57 (d, 2H), 7.35 (m, 2H), 7.03 (dd, 1H), 1.28 (s, 12H). TLC (ethyl acetate/heptane 1:3) $R_f$ 0.21

D. Trans-3-[4-(1H-3-indazolylamino)phenyl]-1-[4-(4-methylpiperazino) cyclohexyl]-1H-pyrazolo[3,4-d]pyrimidin-4-amine acetate A mixture of N-(1H-3-indazolyl)-N-[4-(4,4,5,5-tetramethyl-1,3,2-dioxaborolan-2-yl)phenyl]amine (0.064 g, 0.000191 mol), trans-3-iodo-1-[4-(4-methylpiperazino)-cyclohexyl]-1H-pyrazolo[3,4-d]pyrimidin-4-amine (0.070 g, 0.000159 mol), tetrakis-(triphenylphosphine)palladium (0.011 g, 0.0000095 mol) and sodium carbonate (0.042 g, 0.000398 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10-60% acetonitrile—0.1M ammonium acetate over 25 min, 21 mL/min) to yield trans-3-[4-(1H-3-indazolylamino)phenyl]-1-[4-(4-methylpiperazino) cyclohexyl]-1H-pyrazolo[3,4-d]pyrimidin-4-amine acetate (0.035 g, 0.000060 mol) as a white solid.

$^1$H NMR (DMSO-$d_6$, 400 MHz) δ 12.09 (s, 1H), 9.14 (s, 1H), 8.21 (s, 1H), 7.99 (d, 1H), 7.83 (d, 2H), 7.55 (d, 2H), 7.37 (m, 2H), 7.06 (t, 1H), 4.64 (m, 1H), 2.6-2.2 (br, 9H), 2.13 (s, 3H), 2.05 (m, 6H), 1.91 (s, 3H), 1.49 (m, 2H); RP-HPLC (Delta Pak C18, 5 μm, 300A, 15 cm; 5%-85% acetonitrile—0.1M ammonium acetate over 20 min, 1 mL/min) $R_t$ 12.96 min. MS: MH$^+$ 523.

Example 346

Trans-N-3-(4-{4-amino-1-[4-(4-methylpiperazino)cyclohexyl]-1H-pyrazolo [3,4-d]pyrimidin-3-yl}phenyl)-6-(trifluoromethyl)benzo[d]isoxazol-3-amine acetate

A. N1-(4-bromophenyl)-2-fluoro-4-(trifluoromethyl)benzamide

A solution of 2-fluoro-4-(trifluoromethyl)benzoyl chloride (5.05 g, 0.0223 mol) and 4-bromoaniline (3.83 g, 0.0223 mol) in anhydrous dichloromethane (150 mL) was cooled to 0° C. and N,N-diisopropylethylamine (4.26 mL, 0.0245 mol) was added under nitrogen atmosphere dropwise. The resulting mixture was stirred at ambient temperature for 24 hours, concentrated and the residue was partitioned between ethyl acetate (120 mL) and water (100 mL). The organic phase was washed with brine, dried with magnesium sulfate and concentrated. The residue was suspended in cold n-heptane (50 mL) and the precipitate was collected by filtration and dried to yield N1-(4-bromophenyl)-2-fluoro-4-(trifluoromethyl)benzamide (7.1 g, 0.0196 mol) as a white solid.

$^1$H NMR (DMSO-$d_6$, 400 MHz) δ 10.74 (s, 1H), 7.90 (m, 2H), 7.74 (d, 1H), 7.68 (d, 2H), 7.56 (d, 2H).

B. N1-(4-bromophenyl)-2-fluoro-4-(trifluoromethyl)-1-benzenecarbothioamide

A mixture of N1-(4-bromophenyl)-2-fluoro-4-(trifluoromethyl)benzamide (7.1 g, 0.0196 mol) and 2,4-bis-(4-methoxyphenyl)-1,3-dithia-2,4-diphosphetane-2,4-disulfide (3.97 g, 0.0098 mol) was heated in toluene at reflux under an atmosphere of nitrogen for 3 hours. The reaction mixture was cooled to ambient temperature, the solvent was removed under reduced pressure and the residue was purified by flash chromatography on silica using ethyl acetate/n-heptane (1:8) as mobile phase to yield N1-(4-bromophenyl)-2-fluoro-4-(trifluoromethyl)-1-benzenecarbothioamide (6.0 g, 0.0159 mol) as a yellow solid.

$^1$H NMR (DMSO-$d_6$, 400 MHz) δ 12.33 (d, 2H), 7.94 (d, 2H), 7.81 (m, 2H), 7.65 (m, 3H).

TLC (ethyl acetate/heptane 1:4) $R_f$ 0.61

C. N1-(4-bromophenyl)-2-fluoro-4-(trifluoromethyl)-1-benzeneamidoxime

A mixture of N1-(4-bromophenyl)-2-fluoro-4-(trifluoromethyl)-1-benzenecarbothioamide (2.50 g, 0.00663 mol), hydroxylamine hydrochloride (0.65 g, 0.00928 mol) and sodium bicarbonate (0.78 g, 0.00928 mol) was heated in absolute ethanol (25 mL) at reflux under nitrogen atmosphere for 14 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was suspended in cold n-heptane and the precipitate was collected by filtration and dried to yield N1-(4-bromophenyl)-2-fluoro-4-(trifluoromethyl)-1-benzeneamidoxime (2.35 g, 0.00625 mol) as an off-white solid.

TLC (ethyl acetate/heptane 1:4) $R_f$ 0.12

D. N-(4-bromophenyl)-N-[6-(trifluoromethyl)benzo[d]isoxazol-3-yl]amine

To a solution of N1-(4-bromophenyl)-2-fluoro-4-(trifluoromethyl)-1-benzeneamidoxime (2.25 g, 0.00598 mol) in N-methylpyrrolidinone (30 mL), potassium tert-butoxide (0.71 g, 0.00628 mol) was added and the resulting solution was heated at 100° C. under an atmosphere of nitrogen for 3 hours. The reaction mixture was cooled to ambient temperature, the solvent was removed under reduced pressure and the residue partitioned between saturated solution of sodium bicarbonate in water (50 mL) and ethyl acetate (50 mL). The organic phase was washed with brine, dried with magnesium sulfate and concentrated. The residue was suspended in cold n-heptane and the precipitate was collected by filtration and dried to yield N-(4-bromophenyl)-N-[6-(trifluoromethyl)benzo[d]isoxazol-3-yl]amine (1.75 g, 0.0049 mol) as an off-white solid.

$^1$H NMR (DMSO-$d_6$, 400 MHz) δ 9.95 (s, 1H), 8.37 (d, 1H), 8.14 (s, 1H), 7.78 (d, 1H), 7.68 (d, 2H), 7.58 (d, 2H).

TLC (ethyl acetate/heptane 1:5) $R_f$ 0.31

E. N-[4-(4,4,5,5-tetramethyl-1,3,2-dioxaborolan-2-yl)phenyl]-N-[6-(trifluoromethyl)benzo[d]isoxazol-3-yl]amine A mixture of N-(4-bromophenyl)-N-[6-(trifluoromethyl)benzo[d]isoxazol-3-yl]amine (1.75 g, 0.0049 mol), diboron pinacol ester (1.49 g, 0.0059 mol), [1.1'-bis(diphenylphosphino) ferrocene]-dichloropalladium (II) complex with dichloromethane (1:1) (0.120 g, 0.000147 mol) and potassium acetate (1.44 g, 0.0144 mol) in N,N-dimethylformamide (10 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil that was purified by flash chromatography on silica using ethyl acetate/n-heptane (1:6) as mobile phase to yield N-[4-(4,4,5,5-tetramethyl-1,3,2-dioxaborolan-2-yl)phenyl]-N-[6-(trifluoromethyl)benzo[d]isoxazol-3-yl]amine (0.065 g, 0.000161 mol) as a white solid.

$^1$H NMR (DMSO-$d_6$, 400 MHz) δ 9.97 (s, 1H), 8.39 (d, 1H), 8.14 (s, 1H), 7.77 (d, 1H), 7.71 (s, 4H), 1.29 (s, 12H).

F. Trans-N-3-(4-{4-amino-1-[4-(4-methylpiperazino)cyclohexyl]-1H-pyrazolo[3,4-d]pyrimidin-3-yl}phenyl)-6-(trifluoromethyl)benzo[d]isoxazol-3-amine acetate A mixture of N-[4-(4,4,5,5-tetramethyl-1,3,2-dioxaborolan-2-yl)phenyl]-N-[6-(trifluoromethyl)benzo[d]isoxazol-3-yl]amine (0.062 g, 0.000153 mol), trans-3-iodo-1-[4-(4-methylpiperazino)-cyclohexyl]-1H-pyrazolo[3,4-d]pyrimidin-4-amine (0.065 g, 0.000146 mol), tetrakis-(triphenylphosphine)palladium (0.010 g, 0.0000087 mol) and sodium carbonate (0.039 g, 0.000365 mol) was heated in a mixture of ethylene glycol dimethyl ether (4 mL) and water (2 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 µm, 25 cm; 10-70% acetonitrile—0.1M ammonium acetate over 30 min, 21 mL/min) to yield trans-N-3-(4-{4-amino-1-[4-(4-methylpiperazino)cyclohexyl]-1H-pyrazolo[3,4-d]pyrimidin-3-yl}phenyl)-6-(trifluoromethyl)benzo[d]isoxazol-3-amine acetate (0.026 g, 0.0000398 mol) as a white solid.

$^1$H NMR (DMSO-$d_6$, 400 MHz) δ 10.05 (s, 1H), 8.44 (d, 1H), 8.23 (s, 1H), 8.16 (s, 1H), 7.88 (d, 2H), 7.79 (d, 1H), 7.69 (d, 2H), 4.67 (m, 1H), 2.6-2.2 (br, 9H), 2.13 (s, 3H), 2.05 (m, 6H), 1.91 (s, 3H), 1.46 (m, 2H); RP-HPLC (Delta Pak C18, 5 μm, 300A, 15 cm; 5%-85% acetonitrile—0.1M ammonium acetate over 20 min, 1 mL/min) $R_t$ 16.18 min. MS: MH$^+$ 592.

Example 347

N2-[4-(4-amino-1-{1-[(2-methyl-1H-4-imidazolyl) methyl]-4-piperidyl}-1H-pyrazolo[3,4-d]pyrimidin-3-yl)-2-methoxyphenyl]-1-methyl-1H-2-indolecarboxamide, dimaleate salt A. N2-{4-[4-amino-1-(4-piperidyl)-1H-pyrazolo[3,4-d]pyrimidin-3-yl]-2-methoxyphenyl}-1-methyl-1H-2-indolecarboxamide 3-Iodo-1-(4-piperidyl)-1H-pyrazolo[3,4-d]pyrimidin-4-amine, HCl salt (6.75 g, 17.73 mmol), N2-[2-methoxy-4-(4,4,5,5-tetramethyl-1,3,2-dioxaborolan-2-yl)phenyl]-1-methyl-1H-2-indolecarboxamide (7.571 g, 18.63 mmol), palladium tetrakistriphenyphosphine (1.23 g, 1.06 mmol) and sodium carbonate (8.27 g, 78.03 mmol) were mixed with ethylene glycol dimethyl ether (180 mL) and water (90 mL). The reaction mixture was heated at reflux overnight. Organic solvent was removed under reduced pressure and the aqueous suspension was extracted with copious dichloromethane. The combined organic layer was washed with water then brine, dried over MgSO$_4$, filtered and evaporated. The residue was purified by flash column chromatography using dichloromethane/methanol/ammonium hydroxide (90:10:0.5 to 60:40:0.5) as mobile phase to give N2-{4-[4-amino-1-(4-piperidyl)-1H-pyrazolo[3,4-d]pyrimidin-3-yl]-2-methoxyphenyl}-1-methyl-1H-2-indolecarboxamide (4.38 g). The aqueous suspension was filtered, washed with water and dried to give N2-{4-[4-amino-1-(4-piperidyl)-1H-pyrazolo[3,4-d]pyrimidin-3-yl]-2-methoxyphenyl}-1-methyl-1H-2-indolecarboxamide (2.77 g). Combined the solids (7.15 g, 81%). $^1$H NMR (DMSO-$d_6$) δ 1.85 (m, 2H), 2.08 (m, 2H), 2.64 (m, 2H), 3.10 (m, 2H), 3.96 (s, 3H), 4.04 (s, 3H), 4.77 (m, 1H), 7.13 (m, 1H), 7.33 (m, 4H), 7.58 (d, J=8.45 Hz, 1H), 7.71 (d, J=7.94 Hz, 1H), 8.12 (d, J=8.15 Hz, 1H), 8.25 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): $R_T$=1.97 min. MH$^+$=497.3.

B. N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-2-indolecarboxamide N2-{4-[4-amino-1-(4-piperidyl)-1H-pyrazolo[3,4-d]pyrimidin-3-yl]-2-methoxyphenyl}-1-methyl-1H-2-indolecarboxamide (250 mg, 0.503 mmol), 2-methyl-1H-4-imidazolecarbaldehyde (83 mg, 0.755 mmol), sodium triacetoxyborohydride (159 mg, 0.755 mmol) and glacial acetic acid (30 mg, 0.554 mmol) were mixed in 1,2-dichloroethane (6 mL). The reaction mixture was stirred at room temperature overnight. Saturated sodium bicarbonate solution was added to adjust the pH to about 8. The layers were separated and the aqueous layer was extracted with dichloromethane. The combined organic layer was washed with brine, dried over MgSO$_4$, filtered and evaporated. The residue was purified by flash column chromatography using dichloromethane/methanol/ammonium hydroxide (95:5:0.5 to 80:20:05) as mobile phase to give N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-2-indolecarboxamide (215 mg, 72%). $^1$H NMR (DMSO-$d_6$) δ 1.91 (m, 2H), 2.23 (m, 7H), 3.00 (m, 2H), 3.41 (s, 2H), 3.96 (s, 3H), 4.04 (s, 3H), 4.78 (m, 1H), 6.72 (s, 1H), 7.15 (m, 1H), 7.32 (m, 4H), 7.78 (d, J=8.43 Hz, 1H), 7.70 (d, J=7.92 Hz, 1H), 8.11 (d, J=7.92 Hz, 1H), 8.24 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): $R_T$=2.00 min. MH$^+$=591.3.

C. N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-2-indolecarboxamide, dimaleate salt N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-2-indolecarboxamide (210 mg, 0.355 mmol) was dissolved in hot ethyl acetate (25 mL) and a few drops of ethanol. Maleic acid (83 mg, 0.711 mmol) in hot ethyl acetate (3 mL) was added. The reaction mixture was stirred at room temperature for 3 hours. The solid was collected by filtration to give N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-2-indolecarboxamide, dimaleate salt (255 mg, 87%).

$^1$H NMR (DMSO-$d_6$) δ 2.12 (m, 2H), 2.43 (m, 5H), 2.92 (m, 2H), 3.38 (m, 2H), 3.96 (s, 3H), 3.99 (s, 2H), 4.04 (s, 3H), 4.93 (m, 1H), 6.13 (s, 4H), 7.16 (m, 1H), 7.34 (m, 5H), 7.60 (d, J=8.43 Hz, 1H), 7.70 (d, J=7.92 Hz, 1H), 7.72 (d, J=8.15 Hz, 1H), 8.27 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): $R_T$=1.98 min. MH$^+$=591.3.

Example 348

N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-2-indolecarboxamide, dimaleate salt A. N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-2-indolecarboxamide, diacetate salt N2-{4-[4-amino-1-(4-piperidyl)-1H-pyrazolo[3,4-d]pyrimidin-3-yl]-2-methoxyphenyl}-1-methyl-1H-2-indolecarboxamide (250 mg, 0.503 mmol), 1H-4-imidazolecarbaldehyde (73 mg, 0.755 mmol), sodium triacetoxyborohydride (159 mg, 0.755 mmol) and glacial acetic acid (30 mg, 0.554 mmol) were mixed in 1,2-dichloroethane (6 mL). The reaction mixture was stirred at room temperature overnight. Saturated sodium bicarbonate solution was added to adjust the pH to about 8. The layers were separated and the aqueous layer was extracted with dichloromethane. The combined organic layer was washed with brine, dried over MgSO$_4$, filtered and evaporated. The residue was first purified by flash column chromatography using dichloromethane/methanol/ammonium hydroxide (95:5:0.5 to 80:20:05) as mobile phase then purified again by reverse phase preparative HPLC using acetonitrile/water (50 mM ammonium acetate buffer) as mobile phase to give N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-2-indolecarboxamide, diacetate salt (170 mg, 49%). $^1$H NMR (DMSO-d$_6$) δ 1.90 (m, 8H), 2.20 (m, 4H), 2.99 (m, 2H), 3.47(s, 2H), 3.96 (s, 3H), 4.04 (s, 3H), 4.67 (m, 1H), 7.15 (m, 1H), 7.31 (m, 5H), 7.54 (s, 1H), 7.58 (d, J=8.43 Hz, 1H), 7.70 (d, J=7.95 Hz, 1H), 8.10 (d, J=8.14 Hz, 1H), 8.24 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=1.97 min. MH$^+$=577.3.

B. N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-2-indolecarboxamide, dimaleate salt N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-2-indolecarboxamide, diacetate salt (170 mg, 0.244 mmol) was dissolved in hot ethyl acetate (25 mL) and a few drops of ethanol. Maleic acid (103 mg, 0.884 mmol) in hot ethyl acetate (3 mL) was added. The reaction mixture was stirred at room temperature for 3 hours. The solid was collected by filtration to give N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-2-indolecarboxamide, dimaleate salt (153 mg, 76%). $^1$H NMR (DMSO-d$_6$) δ 2.19 (m, 2H), 2.49 (m, 2H), 3.19 (m, 2H), 3.52 (m, 2H), 3.96 (s, 3H), 4.04 (s, 3H), 4.21 (s, 2H), 5.02 (m, 1H), 6.15 (s, 4H), 7.16 (m, 1H), 7.32 (m, 5H), 7.40 (s, 1H), 7.59 (d, J=8.45 Hz, 1H), 7.71 (d, J=7.95 Hz, 1H), 7.98 (bs, 1H), 8.13 (d, J=8.16 Hz, 1H), 8.27 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=1.98 min. MH$^+$=577.3.

Example 349

N2-(4-{4-amino-1-[1-(2-fluoroethyl)-4-piperidyl]-1H-pyrazolo[3,4-d]pyrimidin-3-yl}-2-methoxyphenyl)-1-methyl-1H-2-indolecarboxamide, dimaleate salt A. N2-(4-{4-amino-1-[1-(2-fluoroethyl)-4-piperidyl]-1H-pyrazolo[3,4-d]pyrimidin-3-yl}-2-methoxyphenyl)-1-methyl-1H-2-indolecarboxamide N2-{4-[4-amino-1-(4-piperidyl)-1H-pyrazolo[3,4-d]pyrimidin-3-yl]-2-methoxyphenyl}-methyl-1H-2-indolecarboxamide (250 mg, 0.503 mmol), 1-bromo-2-fluoroethane (47 ul, 0.629 mmol), Potassium carbonate (87 mg, 0.629 mmol) and Sodium iodide (10 mg, 0.066 mmol) were mixed in DMF (3 mL). The reaction mixture was heated at 80° C. overnight. The crude reaction mixture was purified by reverse phase preparative HPLC using acetonitrile/water (50 mM ammonium acetate buffer) as mobile phase to give N2-(4-{4-amino-1-[1-(2-fluoroethyl)-4-piperidyl]-1H-pyrazolo[3,4-d]pyrimidin-3-yl}-2-methoxyphenyl)-1-methyl-1H-2-indolecarboxamide (221 mg, 81%). $^1$H NMR (DMSO-d$_6$) δ 1.91 (m, 2H), 2.26 (m, 4H), 2.66 (m, 1H), 2.73 (m, 1H), 3.05 (m, 2H), 3.97 (s, 3H), 4.04 (s, 3H), 4.61 (m, 1H), 4.61 (m, 1H), 4.64 (m, 1H), 7.15 (m, 1H), 7.33 (m, 4H), 7.58 (d, J=8.46 Hz, 1H), 7.70 (d, J=7.95 Hz, 1H), 8.11 (d, J=8.14 Hz, 1H), 8.25 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.17 min. MH$^+$=543.3.

B. N2-(4-{4-amino-1-[1-(2-fluoroethyl)-4-piperidyl]-1H-pyrazolo[3,4-d]pyrimidin-3-yl}-2-methoxyphenyl)-1-methyl-1H-2-indolecarboxamide, dimaleate salt N2-(4-{4-amino-1-[1-(2-fluoroethyl)-4-piperidyl]-1H-pyrazolo[3,4-d]pyrimidin-3-yl}-2-methoxyphenyl)-1-methyl-1H-2-indolecarboxamide (221 mg, 0.407 mmol) was dissolved in hot ethyl acetate (25 mL) and a few drops of ethanol. Maleic acid (94 mg, 0.814 mmol) in hot ethyl acetate (3 mL) was added. The reaction mixture was stirred at room temperature overnight. No precipitate was formed. The organic solvent was removed and the solid was triturated with ethyl acetate. The solid was collected by filtration to give N2-(4-{4-amino-1-[1-(2-fluoroethyl)-4-piperidyl]-1H-pyrazolo[3,4-d]pyrimidin-3-yl}-2-methoxyphenyl)-1-methyl-1H-2-indolecarboxamide, dimaleate salt (252 mg, 80%). $^1$H NMR (DMSO-d$_6$) δ 2.34 (m, 2H), 2.54 (m, 2H), 3.49-3.67(m, 6H), 3.96 (s, 3H), 4.04 (s, 3H), 4.81 (m, 1H), 4.92 (m, 1H), 5.06 (m, 1H), 6.14 (s, 4H), 7.16 (m, 1H), 7.34 (m, 4H), 7.60 (d, J=8.32 Hz, 1H), 7.70 (d, J=7.95 Hz, 1H), 8.14 (d, J=8.15 Hz, 1H), 8.29 (s, 1H), 9.45 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.17 min. MH$^+$=543.3.

Example 350

N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide, dimaleate salt A. N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide N2-{4-[4-amino-1-(4-piperidyl)-1H-pyrazolo[3,4-d]pyrimidin-3-yl]-2-methoxyphenyl}-1-methyl-1H-2-indolecarboxamide (250 mg, 0.503 mmol), 2-bromo-1,1-difluoroethane (91 mg, 0.629 mmol), Potassium carbonate (87 mg, 0.629 mmol) and Sodium iodide (10 mg, 0.066 mmol) were mixed in DMF (3 mL). The reaction mixture was heated at 80° C. overnight. HPLC showed only about fifty percent conversion. The bath temperature was lowered to 55° C. and more 2-bromo-1,1-difluoroethane (0.1 mL) was added. After stirring at 55° C. overnight, more 2-bromo-1,1-difluoroethane (0.1 mL) was added and the reaction mixture was stirred at 55° C. overnight. HPLC showed most of starting material was converted to product. The crude reaction mixture was purified by reverse phase preparative HPLC using acetonitrile/water (50 mM ammonium acetate buffer)

as mobile phase to give N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide (227 mg, 81%). $^1$H NMR (DMSO-d$_6$) δ 1.89 (m, 2H), 2.27 (m, 2H), 2.42 (m, 2H), 2.80 (m, 1H), 3.05 (m, 2H), 3.96 (s, 3H), 4.04 (s, 3H), 4.69 (m, 1H), 6.17 (t t, J=55.81 Hz, J=4.35 Hz, 1H), 7.15 (m, 1H), 7.33 (m, 4H), 7.78 (d, J=7.94 Hz, 1H), 7.70 (d, J=7.94 Hz, 1H), 8.11 (d, J=8.19 Hz, 1H), 8.25 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=3.32 min. MH$^+$=561.3.

B. N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide, dimaleate salt N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide (227 mg, 0.405 mmol) was dissolved in hot ethyl acetate (25 mL). Maleic acid (94 mg, 0.810 mmol) in hot ethyl acetate (3 mL) was added. The reaction mixture was stirred at room temperature overnight. No precipitate was formed. After stirring at room temperature for 4 days, precipitate was formed at bottom of the flask. The solvent was decanted. The solid was washed with ethyl acetate and dried to give N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide, dimaleate salt (220 mg, 68%).

$^1$H NMR (DMSO-d$_6$) δ 2.05 (m, 2H), 2.40 (m, 2H), 2.84-3.32 (bm, 6H), 3.96 (s, 3H), 4.04 (s, 3H), 4.85 (m, 1H), 6.22 (s, 4H), 6.34 (t, J=56.07 Hz, 1H), 7.15 (m, 1H), 7.33 (m, 4H), 7.59 (d, J=8.45 Hz, 1H), 7.70 (d, J=7.94 Hz, 1H), 8.12 (d, J=8.19 Hz, 1H), 8.28 (s, 1H), 9.45 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=3.32 min. MH$^+$=561.3.

Example 351

N2-{4-[4-amino-1-(1-ethyl-4-piperidyl)-1H-pyrazolo[3,4-d]pyrimidin-3-yl]-2-methoxyphenyl}-1-methyl-1H-2-indolecarboxamide N2-{4-[4-amino-1-(4-piperidyl)-1H-pyrazolo[3,4-d]pyrimidin-3-yl]-2-methoxyphenyl}-1-methyl-1H-2-indolecarboxamide (250 mg, 0.503 mmol), acetaldehyde (44 mg, 1.007 mmol) and sodium triacetoxyborohydride (212 mg, 1.007 mmol) were mixed in 1,2-dichloroethane (6 mL). The reaction mixture was stirred at room temperature overnight. The solvent was removed and the residue was purified by reverse phase preparative HPLC using acetonitrile/water (50 mM ammonium acetate buffer) as mobile phase to give N2-{4-[4-amino-1-(1-ethyl-4-piperidyl)-1H-pyrazolo[3,4-d]pyrimidin-3-yl]-2-methoxyphenyl}-1-methyl-1H-2-indolecarboxamide (247 mg, 93%). $^1$H NMR (DMSO-d$_6$) δ 1.04 ((t, J=7.15 Hz, 3H), 1.92 (m, 2H), 2.08 (m, 2H), 2.25 (m, 2H), 2.40 (q, J=7.15 Hz, 2H), 3.03 (m, 2H), 3.96 (s, 3H), 4.04 (s, 3H), 4.68 (m, 1H), 7.13 (m, 1H), 7.33 (m, 4H), 7.58 (d, J=8.00 Hz, 1H), 7.70 (d, J=7.95 Hz, 1H), 8.11 (d, J=8.15 Hz, 1H), 8.25 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.08 min. MH$^+$=525.3.

Examples 352-356 were made using the methods described in Example 351.

Example 352

N2-[4-(4-amino-1-{1-[(3-methyl-1H-4-pyrazolyl)methyl]-4-piperidyl}-1H-pyrazolo[3,4-d]pyrimidin-3-yl)-2-methoxyphenyl]-1-methyl-1H-2-indolecarboxamide, acetate salt Yield: 187 mg, 63% $^1$H NMR (DMSO-d$_6$) δ 1.91 (m, 2H), 2.09 (m, 2H), 2.19 (m, 5H), 2.96 (m, 2H), 3.35 (s, 2H), 3.96 (s, 3H), 4.04 (s, 3H), 4.67 (m, 1H), 7.17 (m, 1H), 7.31 (m, 5H), 7.58 (d, J=8.46 Hz, 1H), 7.70 (d, J=7.94 Hz, 1H), 8.10 (d, J=8.15 Hz, 1H), 8.24 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.03 min. MH$^+$=591.3.

Example 353

N2-(4-{4-amino-1-[1-(3-furylmethyl)-4-piperidyl]-1H-pyrazolo[3,4-d]pyrimidin-3-yl}-2-methoxyphenyl)-1-methyl-1H-2-indolecarboxamide Yield 233 mg, 80%

$^1$H NMR (DMSO-d$_6$) δ 1.91 (m, 2H), 2.13-2.23 (m, 4H), 3.00 (m, 2H), 3.39 (s, 2H), 3.96 (s, 3H), 4.04 (s, 3H), 4.68 (m, 1H), 6.47 (s, 1H), 7.31 (m, 4H), 7.60 (m, 3H), 7.70 (d, J=7.94 Hz, 1H), 8.11 (d, J=8.05 Hz, 1H), 8.24 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.37 min. MH$^+$=577.3.

Example 354

N2-{4-[4-amino-1-(1-tetrahydro-2H-4-pyranyl-4-piperidyl)-1H-pyrazolo[3,4-d]pyrimidin-3-yl]-2-methoxyphenyl}-1-methyl-1H-2-indolecarboxamide The reaction was carried out at 70° C. overnight instead of room temperature overnight as described in the example 351.

Yield 176 mg, 71%. $^1$H NMR (DMSO-d$_6$) δ 1.46 (m, 2H), 1.71 (m, 2H), 1.91 (m, 2H), 2.20 (m, 2H), 2.30 (m, 2H), 3.07 (m, 3H), 3.27 (m, 2H), 3.91(m, 2H), 3.96 (s, 3H), 4.04 (s, 3H), 4.67 (m, 1H), 7.15 (m, 1H), 7.33 (m, 4H), 7.58 (d, J=8.44 Hz, 1H), 7.70 (d, J=7.94 Hz, 1H), 8.10 (d, J=8.04 Hz, 1H), 8.24 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.08 min. MH$^+$=581.3.

Example 355

N2-(4-{4-amino-1-[(1-acetylpiperidin-4-yl)-piperidin-4-yl]-1H-pyrazolo [3,4-d]pyrimidin-3-yl}-2-methoxyphenyl)-1-methyl-1H-2-indolecarboxamide The reaction was carried out at 70° C. overnight instead of room temperature overnight as described in the Example 351.

Yield 223 mg, 71%. $^1$H NMR (DMSO-d$_6$) δ 1.28 (m, 1H), 1.43 (m, 1H), 1.75 (m, 2H), 1.91 (m, 2H), 1.99 (s, 3H), 2.19 (m, 2H), 2.34 (m, 2H), 2.54 (m, 2H), 3.01 (m, 3H), 3.83 (m, 1H), 3.96 (s, 3H), 4.04 (s, 3H), 4.38 (m, 1H), 4.66 (m, 1H), 7.15 (m, 1H), 7.31 (m, 4H), 7.78 (d, J=7.94 Hz, 1H), 7.70 (d, J=7.94 Hz, 1H), 8.11 (d, J=8.15 Hz, 1H), 8.24 (s, 1H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=1.97 min. MH$^+$=622.3.

Example 356

N2-(4-{4-amino-1-[1-(4-pyridylmethyl)-4-piperidyl]-1H-pyrazolo[3,4-d]pyrimidin-3-yl}-2-methoxyphenyl)-1-methyl-1H-2-indolecarboxamide Yield 57 mg, 18%. $^1$H NMR (DMSO-d$_6$) δ 1.91 (m, 2H), 2.28 (m, 4H), 3.95 (m, 2H), 3.59 (s, 2H), 3.96 (s, 3H), 4.04 (s, 3H), 4.71 (m, 1H), 7.17 (m, 1H), 7.34 (m, 6H), 7.59 (d, J=8.03 Hz, 1H), 7.71 (d, J=7.94 Hz, 1H), 8.11 (d, J=8.14 Hz, 1H), 8.25 (s, 1H), 8.52 (d, J=5.78 Hz, 2H), 9.44 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, PH 4.5), 0.8 mL/min.): R$_T$=2.50 min. MH$^+$=588.3.

Example 357

N2-(4-{4-amino-1-[3-(4-methylpiperazino)propyl]-1H-pyrazolo[3,4-d]pyrimidin-3-yl}-2-methoxyphenyl)-1-methyl-1H-2-indolecarboxamide

A. 1-(3-bromopropyl)-3-iodo-1H-pyrazolo[3,4-d]pyrimidin-4-amine

A suspension of 3-iodo-1H-pyrazolo[3,4-d]pyrimidin-4-amine (10.00 g, 38.31 mmol) in tetrahydrofuran (150 mL) was treated with 3-bromo-1-propanol (15.98 g, 114.93 mmol) and triphenylphosphine (20.1 g, 76.62 mmol). Diethylazodicarboxyate (13.34 g, 76.62 mmol) was slowly added to the reaction mixture. The reaction mixture was stirred at 0° C. for 30 min, after which the ice bath was removed and was stirred for 30 minutes at room temperature. The reaction mixture was partially concentrated and ethyl acetate (200 mL) was added. The precipitate was filtered and the filtrate was concentrated to dryness. The crude compound was purified by flash chromatography on silica gel using 100% ethyl acetate as the eluent. The afforded 7.8 g (53%) of 1-(3-bromopropyl)-3-iodo-1H-pyrazolo[3,4-d]pyrimidin-4-amine. $^1$H NMR (DMSO-d$_6$, 400 MHz) δ 8.230 (s, 1H), 4.419-4.385 (t, 2H), 3.530-3.498 (t, 2H), 2.370-2.304 (q, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_t$ 2.05 min (100%), MH$^+$ 422.9.

B. 3-iodo-1-[3-(4-methylpiperazino)propyl]-1H-pyrazolo[3,4-d]pyrimidin-4-amine A suspension of 1-(3-bromopropyl)-3-iodo-1H-pyrazolo [3,4-d]pyrimidin-4-amine (0.500 g, 1.31 mmol) in dimethylformamide (10 mL) was treated with 1-methylpiperazine (0.157 g, 1.572 mmol) and triethylamine (0.133 g, 1.31 mmol). The reaction mixture was stirred at 70° C. for 66.25 h. Solvent was removed under reduced pressure. Dichloromethane (15 mL) and 1 N hydrochloric acid (20 mL) were added. The layers were partitioned and the aqueous layer was washed with dichloromethane (100 mL). The aqueous layer was neutralized to pH 13 and then extracted with dichloromethane (250 mL). The organic layer was dried over magnesium sulfate, filtered and evaporated under reduced pressure. The crude material was purified by flash chromatography on silica gel using a step-wise gradient; 20% methanol in dichloromethane to 50% methanol in dichloromethane over 55 minutes on a 35 g ISCO column. The column afforded 0.238 g (45%) of pure 3-iodo-1-[3-(4-methylpiperazino)propyl]-1H-pyrazolo[3,4-d]pyrimidin-4-amine. $^1$H NMR (DMSO-d$_6$, 400 MHz) δ 8.191 (s, 1H), 4.308-4.273 (t, 2H), 2.262-2.228 (m, 10H), 1.944-1.877(m, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_t$ 0.75 min (100%), MH$^+$ 402.1.

C. N2-(4-{4-amino-1-[3-(4-methylpiperazino)propyl]-1H-pyrazolo[3,4-d]pyrimidin-3-yl}-2-methoxyphenyl)-1-methyl-1H-2-indolecarboxamide A solution of 3-iodo-1-[3-(4-methylpiperazino)propyl]-1H-pyrazolo[3,4-d]pyrimidin-4-amine (0.188 g, 0.469 mmol) in ethylene glycol dimethyl ether (16 mL) was treated with N2-[2-methoxy-4-(4,4,5,5-tetramethyl-1,3,2-dioxaborolan-2-yl)phenyl]-1-methyl-1H-2-indolecarboxamide (0.209 g, 0.516 mmol), tetrakis(triphenylphosphine) palladium (0.033 g, 0.028 mmol), and a solution of sodium carbonate (0.119 g, 1.13 mmol) in water (8 mL). The reaction mixture was stirred for 4.5 h at 80° C. The organic solvent was removed under reduced pressure and ethyl acetate (200 mL) was added. The layers were partitioned and the aqueous layer was extracted with ethyl acetate (400 mL). The combined organic layers were dried over magnesium sulfate, filtered and evaporated under reduced pressure. The crude material was purified by flash chromatography on silica gel using a step-wise gradient of 20% methanol in dichloromethane to 50% methanol in dichloromethane. The column afforded 0.078 g (30%) of pure N2-(4-{4-amino-1-[3-(4-methylpiperazino)propyl]-1H-pyrazolo[3,4-d]pyrimidin-3-yl}-2-methoxyphenyl)-1-methyl-1H-2-indolecarboxamide. $^1$H NMR (DMSO-d$_6$, 400 MHz) δ 9.442 (s, 1H), 8.258 (s, 1H), 8.122-8.1076 (d, 1H, J=8.16 Hz), 7.719-7.6991 (d, 1H, J=7.96 Hz), 7.6005-7.5793 (d, 1H, J=8.48 Hz), 7.349-7.294 (m, 4H), 7.172-7.135 (t, 1H), 4.405-4.371 (m, 2H), 4.04 (s, 3H), 3.958 (s, 3H), 3.291 (m, 2H), 2.5 (m, 3H), 2.45-2.337 (m, 5H), 2.30-2.10 (m, 3H), 2.022-2.005 (m, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_t$ 2.05 min (100%), MH$^+$ 554.3.

Example 358

N2-{4-[4-amino-1-(3-morpholinopropyl)-1H-pyrazolo[3,4-d]pyrimidin-3-yl]-2-methoxyphenyl}-1-methyl-1H-2-indolecarboxamide

A. 3-iodo-1-(3-morpholinopropyl)-1H-pyrazolo[3,4-d]pyrimidin-4-amine

A suspension of 1-(3-bromopropyl)-3-iodo-1H-pyrazolo[3,4-d]pyrimidin-4-amine (0.500 g, 1.31 mmol) in dimethylformamide (10 mL) was treated with morpholine (0.137 g, 1.572 mmol) and triethylamine (0.133 g, 1.31 mmol). The reaction mixture was stirred at 70° C. for 66.25 h. Solvent was removed under reduced pressure. Dichloromethane (15 mL) and 1 N hydrochloric acid (20 mL) were added. The layers were partitioned and the aqueous layer was washed with dichloromethane (100 mL). The aqueous layer was neutralized to pH 14 and then extracted with dichloromethane (250 mL). The organic layer was dried over magnesium sulfate, filtered and evaporated under reduced pressure. The crude material was purified by flash chromatography on silica gel using a step-wise gradient of 10% methanol in dichloromethane to 50% methanol in dichloromethane over 58 minutes on a 35 g ISCO column. The column afforded 0.244 g (48%) of pure 3-iodo-1-(3-morpholinopropyl)-1H-pyrazolo[3,4-d]pyrimidin-4-amine. $^1$H NMR (DMSO-d$_6$, 400 MHz) δ 8.194 (s, 1H), 4.327-4.293 (t, 2H), 3.485-3.364 (m, 4H), 2.253-2.238 (m, 6H), 1.963-1.895(m, 2H); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) R, 0.71 min (100%), MH$^+$ 389.0.

B. N2-{4-[4-amino-1-(3-morpholinopropyl)-1H-pyrazolo[3,4-d]pyrimidin-3-yl]-2-methoxyphenyl}-1-methyl-1H-2-indolecarboxamide A solution of 3-iodo-1-(3-morpholinopropyl)-1H-pyrazolo[3,4-d]pyrimidin-4-amine (0.244 g, 0.629 mmol) in ethylene glycol dimethyl ether (16 mL) was treated with N2-[2-methoxy-4-(4,4,5,5-tetramethyl-1,3,2-dioxaborolan-2-yl)phenyl]-1-methyl-1H-2-indolecarboxamide (0.281 g, 0.692 mmol), tetrakis(triphenylphosphine)palladium (0.044 g, 0.038 mmol), and a solution of sodium carbonate (0.160 g, 1.51 mmol) in water (8 mL). The reaction mixture was stirred for 4.5 h at 80° C. The organic solvent was removed under reduced pressure and ethyl acetate (200 mL) was added. The layers were partitioned and the aqueous layer was extracted with ethyl acetate (400 mL). The combined organic layers were dried over magnesium sulfate, filtered and evaporated under reduced pressure. The crude material was purified by flash chromatography on silica gel using a step-wise gradient of 10% methanol in dichloromethane to 50% methanol in dichloromethane as the eluent. The column afforded 0.191 g (56%) of pure N2-{4-[4-amino-1-(3-morpholinopropyl)-1H-pyrazolo[3,4-d]pyrimidin-3-yl]-2-methoxyphenyl}-1-methyl-1H-2-indolecarboxamide. $^1$H NMR (DMSO-d$_6$, 400 MHz) δ 9.440 (s, 1H), 8.260 (s, 1H), 8.1229-8.1026 (d, 1H, J=8.12 Hz), 7.7184-7.6986 (d, 1H, J=7.92 Hz), 7.5983-7.578 (d, 1H, J=8.08 Hz), 7.345-7.290 (m, 4H), 7.172-7.133 (m, 1H), 4.421-4386 (m, 2H), 4.04 (s, 3H), 3.958 (s, 3H), 3.521-3.500 (m, 4H), 2.349-2.314 (m, 6H), 2.035-2.001 (m, 2H); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) R, 2.05 min (100%), MH$^+$ 541.3.

Example 359

N2-(4-{4-amino-1-[3-(1H-1-imidazolyl)propyl]-1H-pyrazolo[3,4-d]pyrimidin-3-yl}-2-methoxyphenyl)-1-methyl-1H-2-indolecarboxamide

A. 1-[3-(1H-1-imidazolyl)propyl]-3-iodo-1H-pyrazolo[3,4-d]pyrimidin-4-amine

A suspension of 1-(3-bromopropyl)-3-iodo-1H-pyrazolo[3,4-d]pyrimidin-4-amine (0.500 g, 1.31 mmol) in dimethylformamide (10 mL) was treated with imidazole (0.107 g, 1.572 mmol) and triethylamine (0.133 g, 1.31 mmol). The reaction mixture was stirred at 70° C. for 25.5 h. Solvent was removed under reduced pressure. Dichloromethane (15 mL) and 1 N hydrochloric acid (20 mL) were added. The layers were partitioned and the aqueous layer was washed with dichloromethane (100 mL). The aqueous layer was neutralized to pH 14 and then extracted with dichloromethane (250 mL). The organic layer was dried over magnesium sulfate, filtered and evaporated under reduced pressure. The crude material was purified by flash chromatography on silica gel using 10% methanol in dichloromethane as the eluent. The column afforded 0.086 g (18%) of pure 1-[3-(1H-1-imidazolyl)propyl]-3-iodo-1H-pyrazolo[3,4-d]pyrimidin-4-amine. $^1$H NMR (DMSO-d$_6$, 400 MHz) δ 8.211 (s, 1H), 7.896 (s, 1H), 7.264 (s, 1H), 6.96 (s, 1H), 4.32-4.227 (m, 2H), 4.011-3.977 (m, 2H), 2.329-2.215 (m, 2H); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) R, 0.46 min (100%), MH$^+$ 370.0.

B. N2-(4-{4-amino-1-[3-(1H-1-imidazolyl)propyl]-1H-pyrazolo[3,4-d]pyrimidin-3-yl}-2-methoxyphenyl)-1-methyl-1H-2-indolecarboxamide A suspension of 1-[3-(1H-1-imidazolyl)propyl]-3-iodo-1H-pyrazolo[3,4-d]pyrimidin-4-amine (0.086 g, 0.233 mmol) in ethylene glycol dimethyl ether (4 mL) was treated with N2-[2-methoxy-4-(4,4,5,5-tetramethyl-1,3,2-dioxaborolan-2-yl)phenyl]-1-methyl-1H-2-indolecarboxamide (0.104 g, 0.256 mmol), tetrakis(triphenylphosphine)palladium (0.016 g, 0.014 mmol), and a solution of sodium carbonate (0.059 g, 0.56 mmol) in water (2 mL). The reaction mixture was stirred for 24 h at 80° C. The organic solvent was removed under reduced pressure and dichloromethane (25 mL) was added. The layers were partitioned and the aqueous layer was extracted with dichloromethane (100 mL). The combined organic layers were dried over magnesium sulfate, filtered and evaporated under reduced pressure. The crude material was purified by flash chromatography on silica gel using a step-wise gradient of 5% methanol in dichloromethane to 50% methanol in dichloromethane on a 10 g ISCO column. The column afforded 0.06 g (49%) of pure N2-(4-{4-amino-1-[3-(1H-1-imidazolyl)propyl]-1H-pyrazolo[3,4-d]pyrimidin-3-yl}-2-methoxyphenyl)-1-methyl-1H-2-indolecarboxamide. $^1$H NMR (DMSO-d$_6$, 400 MHz) δ 9.443 (s, 1H), 8.278 (s, 1H), 8.1324-8.1121 (d, 1H, J=8.12 Hz), 7.744-7.699 (m, 2H), 7.6-7.579 (d, 1H, J=8.4 Hz), 7.365-7.283 (m, 5H), 7.172-7.135 (m, 1H), 6.939 (s, 1H), 4.36-4.326 (m, 2H), 4.079-4.019 (m, 5H), 3.964 (s, 3H), 2.324-2.309 (m, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$ 2.25 min (100%), MH$^+$ 522.3.

Example 360

N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide

A. tert-butyl 3-(4-amino-3-iodo-1H-pyrazolo[3,4-d]pyrimidin-1-yl)-1-pyrrolidinecarboxylate A suspension of 3-iodo-1H-pyrazolo[3,4-d]pyrimidin-4-amine (5.0 g, 19.15 mmol) in tetrahydrofuran (100 mL) was treated with tert-butyl 3-hydroxy-1-pyrrolidinecarboxylate (5.38 g, 28.73 mmol) and triphenylphosphine (7.53 g, 28.73 mmol). The reaction mixture was cooled to 0° C. on an ice bath. Diethylazodicarboxyate (5.0 g, 28.73 mmol) was slowly added to the reaction mixture. The solvent was removed under reduced pressure after 6 days. The crude oil was used directly in the subsequent reaction without further analysis.

B. 3-iodo-1-tetrahydro-1H-3-pyrrolyl-1H-pyrazolo[3,4-d]pyrimidin-4-amine hydrochloride A suspension of the crude tert-butyl 3-(4-amino-3-iodo-1H-pyrazolo[3,4-d]pyrimidin-1-yl)-1-pyrrolidinecarboxylate in acetone (100 mL) was treated with 6 N hydrochloric acid (50 mL). The reaction mixture was stirred at 40° C. for 15 hours. The initial precipitate was filtered and confirmed by LCMS to be impurities. The reaction mixture was allowed to sit at room temperature and a precipitate formed over night. The precipitate was filtered and washed with diethyl ether. The filtration afforded 2.186 g (31%) of pure 3-iodo-1-tetrahydro-1H-3-pyrrolyl-1H-pyrazolo[3,4-d]pyrimidin-4-amine hydrochloride. $^1$H NMR (DMSO-d$_6$, 400 MHz) δ 9.8815 (s, 1H), 8.9923 (br.s, 1H), 8.4803 (s, 1H), 7.82 (br.s, 1H), 5.5908-5.5295 (m, 1H), 3.7131-3.6706 (m, 1H), 3.5590-3.5003 (m, 1H), 3.4466-3.4174 (m, 2H), 2.4592-2.4255 (m, 1H), 2.4064-2.3146 (m, 1H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$ 1.09 min (100%), MH$^+$ 331.0.

C. N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide A suspension of 3-iodo-1-tetrahydro-1H-3-pyrrolyl-1H-pyrazolo[3,4-d]pyrimidin-4-amine hydrochloride (2.186 g, 5.96 mmol) in ethylene glycol dimethyl ether (50 mL) was treated with N2-[2-methoxy-4-(4,4,5,5-tetramethyl-1,3,2-dioxaborolan-2-yl)phenyl]-1-methyl-1H-2-indolecarboxamide (2.66 g, 6.56 mmol), tetrakis(triphenylphosphine)palladium (0.413 g, 0.358 mmol), and a solution of sodium carbonate (2.65 g, 25.03 mmol) in water (25 mL). The reaction mixture was stirred for 24 h at 80° C. The organic solvent was removed under reduced pressure. Dichloromethane (100 mL) and 1N sodium hydroxide (50 mL) were added. The product precipitated out of the aqueous layer. The aqueous layer was evaporated under reduced pressure. The resulting solid was washed with copious amounts of dichloromethane and ethyl acetate. The organic solvent was removed under reduced pressure to give 2.218 g (77%) of pure N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide. $^1$H NMR (DMSO-d$_6$, 400 MHz) δ 9.443 (s, 1H), 8.256 (s, 1H), 8.1168-8.0965 (d, 1H, J=8.12 Hz), 7.7181-7.6983 (d, 1H, J=7.92 Hz), 7.598-7.5778 (d, 1H, J=8.08 Hz), 7.349-7.291 (m, 4H), 7.171-7.132 (m, 1H), 5.332-5.313 (m, 1H), 4.041 (s, 3H), 3.96 (s, 3H), 3.224-3.058 (m, 3H), 2.926-2.910 (m, 1H), 2.213-2.158 (m, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$ 2.09 min (100%), MH$^+$ 483.3.

Example 361

N2-[4-(4-amino-1-{1-[(1-methyl-1H-2-imidazolyl)methyl]tetrahydro-1H-3-pyrrolyl}-1H-pyrazolo[3,4-d]pyrimidin-3-yl)-2-methoxyphenyl]-1-methyl-1H-2-indolecarboxamide A suspension of N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide (0.250 g, 0.518 mmol) in dichloroethane (5 mL) was treated with 1-methyl-2-imidazolecarboxaldehyde (0.115 g, 1.04 mmol) and sodium triacetoxy borohydride (0.220 g, 1.04 mmol). The reaction mixture was stirred at room temperature for 18 h under a nitrogen atmosphere. Sodium hydroxide (1N, 15 mL) was added to the reaction mixture and was stirred for 1 h. The organic layer was removed under reduced pressure and dichloromethane was added. The layers were partitioned and the aqueous layer was extracted with dichloromethane (200 mL). The combined organic layers were dried over magnesium sulfate, filtered and evaporated under reduced pressure. The crude material was purified by flash chromatography on silica gel using 10% methanol in dichloromethane (15 min), 15% methanol in dichloromethane (15 min), 20% methanol in dichloromethane (20 min) and 50% methanol in dichloromethane (5 min) as the eluent. The column afforded 0.060 g (20%) of pure N2-[4-(4-amino-1-{1-[(1-methyl-1H-2-imidazolyl)methyl]tetrahydro-1H-3-pyrrolyl})—H-pyrazolo[3,4-d]pyrimidin-3-yl)-2-methoxyphenyl]-1-methyl-1H-2-indolecarboxamide. $^1$H NMR (DMSO-d$_6$, 400 MHz) δ 9.446 (s, 1H), 8.249 (s, 1H), 8.1312-8.1108 (d, 1H, J=8.16 Hz), 7.7207-7.7008 (d, 1H, J=7.96 Hz), 7.6023-7.5812 (d, 1H, J=8.44 Hz), 7.356-7.293 (m, 4H), 7.174-7.120 (m, 2H), 6.822 (s, 1H), 5.425-5.391 (m, 1H), 4.044 (s, 3H), 3.962 (s, 3H), 3.693 (m, 2H), 3.651 (s, 3H), 2.86-2.797 (m, 3H), 2.368-2.323 (m, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$ 2.34 min (100%), MH$^+$ 577.3.

Example 362

N2-{4-[4-amino-1-(1-isopropyltetrahydro-1H-3-pyrrolyl)-1H-pyrazolo[3,4-d]pyrimidin-3-yl]-2-methoxyphenyl}-1-methyl-1H-2-indolecarboxamide A suspension of N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide (0.250 g, 0.518 mmol) in dichloroethane (5 mL) was treated with acetone (1.96 g, 33.15 mmol) and sodium triacetoxy borohydride (0.220 g, 1.04 mmol). The reaction mixture was stirred at room temperature for 18 h under a nitrogen atmosphere. Sodium hydroxide (1N, 15 mL) was added to the reaction mixture and was stirred for 1 h. The organic layer was removed under reduced pressure and dichloromethane was added. The layers were partitioned and the aqueous layer was extracted with dichloromethane (200 mL). The combined organic layers were dried over magnesium sulfate, filtered and evaporated under reduced pressure. The crude material was purified by flash chromatography on silica gel using 10% methanol in dichloromethane (15 min), 15% methanol in dichloromethane (15 min), 20% methanol in dichloromethane (20 min) and 50% methanol in dichloromethane (5 min) as the eluent. The column afforded 0.123 g (44%) of pure N2-{4-[4-amino-1-(1-isopropyltetrahydro-1H-3-pyrrolyl)-1H-pyrazolo[3,4-d]pyrimidin-3-yl]-2-methoxyphenyl}-1-methyl-1H-2-indolecarboxamide. $^1$H NMR (DMSO-$d_6$, 400 MHz) δ 9.449 (s, 1H), 8.265 (s, 1H), 8.127-8.1068 (d, 1H, J=8.08 Hz), 7.7196-7.6999 (d, 1H, J=7.88 Hz), 7.6013-7.5803 (d, 1H, J=8.4 Hz), 7.351-7.299 (m, 4H), 7.173-7.135 (m, 1H), 5.394 (m, 1H), 4.042 (s, 3H), 3.961 (s, 3H), 2.793 (m, 3H), 2.337 (m, 3H), 1.068 (br.s, 6H); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) $R_t$ 2.38 min (100%), MH$^+$ 525.3.

Example 363

N2-(4-{4-amino-1-[1-(2-methoxyethyl)tetrahydro-1H-3-pyrrolyl]-1H-pyrazolo[3,4-d]pyrimidin-3-yl}-2-methoxyphenyl)-1-methyl-1H-2-indolecarboxamide A suspension of N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide (0.250 g, 0.518 mmol) in dimethylformamide (5 mL) was treated with 2-bromoethyl methyl ether (0.079 g, 0.569 mmol) and potassium carbonate (0.143 g, 1.04 mmol). The reaction mixture was stirred at 65° C. for 18 h under a nitrogen atmosphere. Water (25 mL) was added to the reaction mixture. The precipitate formed was filtered and dried on the lyophilizer. The crude material was purified by flash chromatography on silica gel using 10% methanol in dichloromethane (15 min), 15% methanol in dichloromethane (15 min), 20% methanol in dichloromethane (20 min) and 50% methanol in dichloromethane (5 min) as the eluent. The column afforded 0.082 g (29%) of pure N2-(4-{4-amino-1-[1-(2-methoxyethyl)tetrahydro-1H-3-pyrrolyl]-1H-pyrazolo[3,4-d]pyrimidin-3-yl}-2-methoxyphenyl)-1-methyl-1H-2-indolecarboxamide. $^1$H NMR (DMSO-$d_6$, 400 MHz) δ 9.447 (s, 1H), 8.265 (s, 1H), 8.1278-8.1075 (d, 1H, J=8.12 Hz), 7.7192-7.6993 (d, 1H, J=7.96 Hz), 7.5996-7.5799 (d, 1H, J=7.88 Hz), 7.349-7.295 (m, 4H), 7.172-7.133 (m, 1H), 5.42 (m, 1H), 4.042 (s, 3H), 3.96 (s, 3H), 3.479 (m, 2H), 3.266-3.258 (m, 3H), 2.95-2.60 (m, 4H), 2.332 (m, 2H); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) $R_t$ 2.34 min (100%), MH$^+$ 541.3.

Example 364

N2-(4-{4-amino-1-[1-(1H-4-imidazolylmethyl)tetrahydro-1H-3-pyrrolyl]-1H-pyrazolo[3,4-d]pyrimidin-3-yl}-2-methoxyphenyl)-1-methyl-1H-2-indolecarboxamide A suspension of N2-[4-(4-amino-1-tetrahydro-1H-3-pyrrolyl-1H-pyrazolo [3,4-d]pyrimidin-3-yl)-2-methoxyphenyl]-1-methyl-1H-2-indolecarboxamide (0.200 g, 0.415 mmol) in dichloroethane (5 mL) was treated with 4-formylimidazole (0.08 g, 0.83 mmol) and sodium triacetoxy borohydride (0.176 g, 0.83 mmol). The reaction mixture was stirred at room temperature for 24 h under a nitrogen atmosphere. Sodium hydroxide (1N, 15 mL) was added to the reaction mixture and was stirred for 1 h. The organic layer was removed under reduced pressure and dichloromethane was added. The layers were partitioned and the aqueous layer was extracted with dichloromethane (200 mL). The combined organic layers were dried over magnesium sulfate, filtered and evaporated under reduced pressure. The crude material was purified by flash chromatography on silica gel using 10% methanol in dichloromethane (20 min), 15% methanol in dichloromethane (10 min), 20% methanol in dichloromethane (10 min) and 50% methanol in dichloromethane (8 min) as the eluent. The column afforded 0.074 g (25%) of pure N2-(4-{4-amino-1-[1-(1H-4-imidazolylmethyl)tetrahydro-1H-3-pyrrolyl]-1H-pyrazolo[3,4-d]pyrimidin-3-yl}-2-methoxyphenyl)-1-methyl-1H-2-indolecarboxamide. $^1$H NMR (DMSO-$d_6$, 400 MHz) 69.446 (s, 1H), 8.252 (s, 1H), 8.126-8.1082 (d, 1H, J=8.16 Hz), 7.7198-7.7 (d, 1H, J=7.92 Hz), 7.6-7.569 (m, 2H), 7.35-7.298 (m, 4H), 7.171-7.134 (m, 1H), 6.946 (s, 1H), 5.422-5.385 (m, 1H), 4.043 (s, 3H), 3.961 (s, 3H), 3.691 (s, 2H), 3.175-3.162 (m, 2H), 2.9-2.883 (m, 3H), 2.385-2.332 (m, 2H); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) $R_t$ 2.13 min (100%), MH$^+$ 563.3.

Example 365

N2-[4-(4-amino-1-{1-[(3-methyl-1H-4-pyrazolyl)methyl]tetrahydro-1H-3-pyrrolyl}-1H-pyrazolo[3,4-d]pyrimidin-3-yl)-2-methoxyphenyl]-1-methyl-1H-2-indolecarboxamide A suspension of N2-[4-(4-amino-1-tetrahydro-1H-3-pyrrolyl-1H-pyrazolo[3,4-d]pyrimidin-3-yl)-2-methoxyphenyl]-1-methyl-1H-2-indolecarboxamide (0.200 g, 0.415 mmol) in dichloroethane (5 mL) was treated with 3-methyl-1H-pyrazol-4-carboxaldehyde (0.091 g, 0.83 mmol) and sodium triacetoxy borohydride (0.176 g, 0.83 mmol). The reaction mixture was stirred at room temperature for 24 h under a nitrogen atmosphere. Sodium hydroxide (1N, 15 mL) was added to the reaction mixture and was stirred for 1 h. The organic layer was removed under reduced pressure and dichloromethane was added. The layers were partitioned and the aqueous layer was extracted with dichloromethane (100 mL) and ethyl acetate (100 mL). The combined organic layers were dried over magnesium sulfate, filtered and evaporated under reduced pressure. The crude material was purified by flash chromatography on silica gel using 10% methanol in dichloromethane (15 min), 15% methanol in dichloromethane (10 min), 20% methanol in dichloromethane (10 min) and 50% methanol in dichloromethane (8 min) as the eluent. The column afforded 0.106 g (44%) of pure N2-[4-(4-amino-1-{1-[(3-methyl-1H-4-pyrazolyl)methyl]tetrahydro-1H-3-pyrrolyl}-1H-pyrazolo[3,4-d]pyrimidin-3-yl)-2-methoxyphenyl]-1-methyl-1H-2-indolecarboxamide. $^1$H NMR (DMSO-$d_6$, 400 MHz) δ 9.446 (s, 1H), 8.247 (s, 1H), 8.1275-8.1071 (d, 1H, J=8.16 Hz), 7.72-7.7003 (d, 1H, J=7.96 Hz), 7.6004-7.5793 (d, 1H, J=8.44 Hz), 7.398-7.286 (m, 5H), 7.172-7.134 (m, 1H), 5.379 (m, 1H), 4.0443 (s, 3H), 3.962 (s, 3H), 3.492 (m, 2H), 3.1 (m, 1H), 2.75 (m, 3H), 2.352-2.335 (m, 2H), 1.909 (s, 3l); LCMS (Thermoquest AQA single-quad MS, Genesis C18 column, 3 µm particle size, 33×4.6 mm; 70% 50 mM ammonium acetate in water to 95% acetonitrile over 6 min, 0.8 to 0.5 mL/min) $R_t$ 2.17 min (100%), MH$^+$ 577.3.

Example 366

N2-(4-{4-amino-1-[(3R)-1-methyltetrahydro-1H-3-pyrrolyl]-1H-pyrazolo [3,4-d]pyrimidin-3-yl}phenyl)-5,7-dimethyl-1,3-benzoxazol-2-amine N2-(4-{4-amino-1-[(3R)-1-methyltetrahydro-1H-3-pyrrolyl]-1H-pyrazolo[3,4-d]pyrimidin-3-yl}phenyl)-5,7-dimethyl-1,3-benzoxazol-2-amine was prepared from (S)-(−)-3-pyrrolidinol in a manner analogous to that used for the preparation of rac-N-2-{4-[4-Amino-1-(1-methyltetrahydro-1H-3-pyrrolyl)-1H-pyrazolo[3,4-d]pyrimidin-3-yl]phenyl}-5,7-dimethyl-1,3-benzoxazol-2-amine. The compound was formed as a white solid (0.195 g, 53%). $^1$H NMR (DMSO-$d_6$, 400 MHz) $^1$H NMR (DMSO-$d_6$, 400 MHz) 2.31-2.35 (m, 2H), 2.32 (s, 3H), 2.35 (s, 3H), 2.40 (s, 3H), 2.70-2.77 (m, 3), 3.05 (t, 1H), 5.40 (m, 1H), 6.80 (s, 1H), 7.11 (s, 1H), 7.66 (d, 2H), 7.93 (d, 2H), 8.24 (s, 1H), 10.85 (s, 1H); RP-HPLC $R_t$ 11.090 min, 99% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 455 (MH$^+$).

Example 367

N2-(4-{4-amino-1-[(3S)-1-methyltetrahydro-1H-3-pyrrolyl]-1H-pyrazolo[3,4-d]pyrimidin-3-yl}phenyl)-5,7-dimethyl-1,3-benzoxazol-2-amine N2-(4-{4-amino-1-[(3S)-1-methyltetrahydro-1H-3-pyrrolyl]-1H-pyrazolo[3,4-d]pyrimidin-3-yl}phenyl)-5,7-dimethyl-1,3-benzoxazol-2-amine was prepared from (R)-(−)-3-pyrrolidinol in a manner analogous to that used for the preparation of rac-N-2-{4-[4-Amino-1-(1-methyltetrahydro-1H-3-pyrrolyl)-1H-pyrazolo[3,4-d]pyrimidin-3-yl]phenyl}-5,7-dimethyl-1,3-benzoxazol-2-amine. The compound was formed as a white solid (0.126 g, 20%). $^1$H NMR (DMSO-$d_6$, 400 MHz) $^1$H NMR (DMSO-$d_6$, 400 MHz) 2.31-2.35 (m, 2H), 2.31 (s, 3H), 2.35 (s, 3H), 2.40 (s, 3H), 2.67-2.76 (m, 3H), 3.05 (t, 1H), 5.40 (m, 1H), 6.80 (s, 1H), 7.11 (s, 1H), 7.66 (d, 2H), 7.93 (d, 2H), 8.24 (s, 1H), 10.84 (s, 1H); RP-HPLC $R_t$ 11.129 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 455 (MH$^+$).

Example 368 rac-N-2-(4-{4-amino-1-[1-(2-methoxyethyl)tetrahydro-1H-3-pyrrolyl]-1H-pyrazolo[3,4-d]pyrimidin-3-yl}phenyl)-7-isopropyl-5-methyl-1,3-benzoxazol-2-amine rac-N-2-(4-{4-Amino-1-[1-(2-methoxyethyl)tetrahydro-1H-3-pyrrolyl]-1H-pyrazolo[3,4-d]pyrimidin-3-yl}phenyl)-7-isopropyl-1,3-benzoxazol-2-amine was prepared from rac-3-iodo-1-[1-(2-methoxyethyl)tetrahydro-1H-3-pyrrolyl]-1H-pyrazolo[3,4-d]pyrimidin-4-amine (0.200 g, 0.515 mmol) and N2-[4-(4,4,5,5-tetramethyl-1,3,2-dioxaborolan-2-yl)phenyl]-7-isopropyl-1,3-benzoxazol-2-amine (0.244 g, 0.644 mmol) in a manner similar to that used for the preparation of cis-N-2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white solid (0.067 g, 25%). $^1$H NMR (DMSO-$d_6$, 400 MHz) 1.361 (d, 6H), 2.30 (m, 2H), 2.66 (m, 2H), 2.76-2.83 (m, 3H), 3.17 (t, 1H), 3.24 (s, 3H), 3.38 (m, 1H), 3.45 (t, 2H), 5.37 (m, 1H), 7.04 (d, 1H), 7.18 (t, 1H), 7.32 (d, 2H), 7.67 (d, 2H), 7.95 (d, 2H), 8.24 (s, 1H), 10.88 (s, 1H); RP-HPLC $R_t$ 12.337 min, 94% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z 513 (MH$^+$).

Example 369 cis-Ethyl 4-(4-amino-3-{4-[(5,7-dimethyl-1,3-benzoxazol-2-yl)amino]phenyl}-1H-pyrazolo[3,4-d]pyrimidin-1-yl)-1-cyclohexanecarboxylate 3-Iodo-1H-pyrazolo[3,4-d]pyrimidin-4-amine (0.52 g, 2.0 mmol), ethyl 4-hydroxycyclohexanecarboxylate (0.806 mL, 5.0 mmol, triphenylphosphine (1.05 g, 4.0 mmol), diethyl azodicarboxylate (0.628 mL, 4.0 mmol) were suspended in tetrahydrofuran (15 mL), and the mixture was stirred at ambient temperature under a gentle flow of nitrogen for 48 h. The mixture was diluted with water (50 mL), and extracted with ethyl acetate (3×50 mL). The organic fractions were combined, dried over magnesium sulfate, filtered, and concentrated. The residue was partially purified by flash column chromatography (100% ethyl acetate) to afford ethyl 4-(4-amino-5-iodo-7H-pyrrolo[3,4-d]pyrimidin-7-yl)-1-cyclohexanecarboxylate as a mixture of cis- and trans-diastereomers, along with triphenylphosphine oxide. Repurification of the mixture by flash column chromatography on silica gel deactivated with triethylamine (0.5% methanol/dichloromethane as eluant) afforded the desired cis-ethyl 4-(4-amino-5-iodo-7H-pyrrolo[3,4-d]pyrimidin-7-yl)-1-cyclohexanecarboxylate as a yellow solid (0.260 g, 0.625 mmol): RP-HPLC (25 to 100% acetonitrile in 0.1 M aqueous ammonium acetate over 10 min at 1 mL/min using a 5μ Hypersil HS C18, 250×4.6 mm column) $R_t$ 9.55 min; MS (MH)$^+$ 416.

cis-Ethyl 4-(4-amino-5-iodo-7H-pyrrolo[3,4-d]pyrimidin-7-yl)-1-cyclohexanecarboxylate (0.10 g, 0.24 mmol) was combined with N-(5,7-dimethyl-1,3-benzoxazol-2-yl)-N-[4-(4,4,5,5-tetramethyl-1,3,2-dioxaborolan-2-yl)phenyl]amine (0.088 g, 0.24 mmol), sodium carbonate (0.064 g, 0.60 mmol), tetrakis(triphenylphosphine)-palladium (0) (0.014 g, 0.012 mmol), ethylene glycol dimethyl ether (2 mL) and water (1 mL), and the mixture was heated at 85° C. in a resealable Schlenk tube for 14 h. The reaction mixture was cooled to ambient temperature, diluted with water (10 mL), and extracted with 10% methanol dichloromethane (3×20 mL). The organic fractions were combined, dried over magnesium sulfate, filtered, and concentrated. Purification of the product by flash column chromatography on silica gel deactivated with triethylamine (2.5% methanol/dichloromethane as eluant) afforded cis-ethyl 4-(4-amino-3-{4-[(5,7-dimethyl-1,3-benzoxazol-2-yl)amino]phenyl}-1H-pyrazolo[3,4-d]pyrimidin-1-yl)-1-cyclohexanecarboxylate as a white solid (0.040 g, 0.076 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 12.63 min; $^1$H NMR (DMSO-$d_6$, 400 MHz) δ 10.85 (s, 1H), 8.23 (s, 1H), 7.92 (d, 2H), 7.64 (d, 2H), 7.11 (s, 1H), 6.80 (s, 1H), 4.66 (m, 1H), 4.10 (qt, 2H), 3.27 (m, 1H), 2.40 (s, 3H), 2.35 (s, 3H), 2.08 (m, 6H), 1.61 (m, 2H), 1.20 (t, 3H).

Example 370 cis-Methyl 4-(4-amino-3-{4-[(5,7-dimethyl-1,3-benzoxazol-2-yl)amino]phenyl}-1H-pyrazolo[3,4-d]pyrimidin-1-yl)-1-cyclohexanecarboxylate cis-Ethyl 4-(4-amino-3-{4-[(5,7-dimethyl-1,3-benzoxazol-2-yl)amino]phenyl}-1H-pyrazolo[3,4-d]pyrimidin-1-yl)-1-cyclohexanecarboxylate (0.030 g, 0.057 mmol), sodium methoxide (0.0033 g, 0.063 mmol) and methanol (2 mL) were combined and heated in a resealable Schlenk tube for 48 h at 75° C. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 15.6-16.5 min) afforded cis-methyl 4-(4-amino-3-{4-[(5,7-dimethyl-1,3-benzoxazol-2-yl)amino]phenyl}-1H-pyrazolo[3,4-d]pyrimidin-1-yl)-1-cyclohexanecarboxylate as a white powder (0.010 g, 0.020 mmol): RP-HPLC (25 to 100% acetonitrile in 0.1 M aqueous ammonium acetate over 10 min at 1 mL/min using a 5μ Hypersil HS C18, 250×4.6 mm column) $R_t$ 11.82 min; $^1$H NMR (DMSO-d$_6$, 400 MHz) δ 10.85 (s, 1H), 8.23 (s, 1H), 7.92 (d, 2H), 7.65 (d, 2H), 7.12 (s, 1H), 6.80 (s, 1H), 4.67 (m, 1H), 3.63 (s, 3H), 3.27 (m, 1H), 2.40 (s, 3H), 2.35 (s, 3H), 2.07 (m, 6H), 1.61 (m, 2H).

Example 371 cis-4-(4-Amino-3-{4-[(5,7-dimethyl-1,3-benzoxazol-2-yl)amino]phenyl}-1H-pyrazolo[3,4-d]pyrimidin-1-yl)-1-cyclohexanecarboxylic acid cis-Ethyl 4-(4-amino-3-{4-[(5,7-dimethyl-1,3-benzoxazol-2-yl)amino]phenyl}-1H-pyrazolo[3,4-d]pyrimidin-1-yl)-1-cyclohexanecarboxylate (0.10 g, 0.19 mmol), aqueous sodium hydroxide (1 M, 2 mL, 2 mmol), and methanol (2 mL) were combined and heated under an air condenser at 70° C. for 14 h. The residue was acidified with aqueous hydrochloric acid (3 M, 2 mL, 6 mmol), and extracted with 10% methanol/dichloromethane (3×20 mL). The combined organic fractions were dried over magnesium sulfate, filtered, and concentrated. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 8.8-10.9 min) afforded cis-4-(4-Amino-3-{4-[(5,7-dimethyl-1,3-benzoxazol-2-yl)amino]phenyl}-1H-pyrazolo[3,4-d]pyrimidin-1-yl)-1-cyclohexanecarboxylic acid as a cream-colored powder (0.026 g, 0.052 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 9.03 min; MS (MH)$^+$ 498.

Example 372 cis-1-[4-(4-Methylpiperazino)cyclohexyl]-3-[4-(2-pyrimidinylamino)phenyl]-1H-pyrazolo[3,4-d]pyrimidin-4-amine 4-Bromoaniline (0.300 g, 1.74 mmol) and 2-chloropyrimidine (0.200 g, 1.74 mmol) were heated neat at 150° C. in a 25 mL flask for 2 h. The reaction mixture was cooled to ambient temperature, and purification of the residue by preparative HPLC (25 to 100% acetonitrile in 0.1 M aqueous ammonium acetate over 20 min at 21 mL/min using an 8μ Hypersil HS C18, 250×21 mm column, $R_t$ 13.8-15.9 min) afforded N-(4-bromophenyl)-N-(2-pyrimidinyl)amine as a yellow solid (0.135 g, 0.54 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 11.08 min; $^1$H NMR (DMSO-d$_6$, 400 MHz) δ 9.78 (s, 1H), 8.50 (d, 2H), 7.76 (d, 2H), 7.45 (d, 2H), 6.87 (t, 1H).

N-(4-Bromophenyl)-N-(2-pyrimidinyl)amine was converted to the title compound using a procedure similar to the one described in the preparation of cis-N2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 4.0-5.0 min) afforded cis-1-[4-(4-methylpiperazino)cyclohexyl]-3-[4-(2-pyrimidinylamino)phenyl]-1H-pyrazolo[3,4-d]pyrimidin-4-amine as a white powder (0.095 g, 0.196 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 5.38 min; MS (MH)$^+$ 485.

Example 373

N2-(4-{4-amino-1-[2-(4-methylpiperazino)-4-pyridyl]-1H-pyrazolo[3,4-d]pyrimidin-3-yl}-2-methoxyphenyl)-1H-2-indolecarboxamide acetate A. 1-(2-chloro-4-pyridyl)-3-iodo-1H-pyrazolo[3,4-d]pyrimidin-4-amine A solution of 3-iodo-1H-pyrazolo[3,4-d]pyrimidin-4-amine (4.12 g, 0.016 mol) in N,N-dimethylformamide (50 mL) was reacted with 60% sodium hydride in oil (0.75 g, 0.019 mol) at ambient temperature. The mixture was stirred for 15 minutes, and 2-chloro-4-nitropyridine (3.00 g, 0.019 mol) was added. The mixture was heated at 100° C. for 18 hours. The mixture was cooled to room temperature and the precipitate was filtered, washing with N,N-dimethylformamide (20 mL), and then slurried in ethyl acetate (50 mL) for four hours. The solid was filtered and dried in vacuo to give 1-(2-chloro-4-pyridyl)-3-iodo-1H-pyrazolo[3,4-d]pyrimidin-4-amine (2.39 g, 0.009 mol) as a tan solid:

$^1$H NMR (DMSO-d$_6$, 400 MHz) δ 8.52 (d, 1H), 8.43 (s, 1H), 8.40 (d, 1H), 8.25 (dd, 1H); RP-HPLC (Delta Pak C18, 5 μm, 300A, 15 cm; 5%-95% acetonitrile—0.1M ammonium acetate over 10 min, 1 mL/min) $R_t$ 10.29 min.;

MS: MH$^+$ 373.

B. N2-{4-[4-amino-1-(2-chloro-4-pyridyl)-1H-pyrazolo[3,4-d]pyrimidin-3-yl]-2-methoxyphenyl}-1-methyl-1H-2-indolecarboxamide A suspension of 1-(2-chloro-4-pyridyl)-3-iodo-1H-pyrazolo[3,4-d]pyrimidin-4-amine (0.95 g, 0.00256 mol) in dimethoxyethane (30 mL) and water (60 mL) was reacted with N2-[2-methoxy-4-(4,4,5,5-tetramethyl-1,3,2-dioxaborolan-2-yl)phenyl]-1-methyl-1H-2-indolecarboxamide (1.14 g, 0.00281 mol), sodium carbonate (0.68 g, 0.00640 mol) and tetrakis (triphenylphosphine)palladium (0) (0.30 g, 0.00026 mol) at 80° C. for 3 days. The solid was filtered and washed with water. The solid was triturated with ethyl acetate (75 mL) for 6 hours and filtered, washing with ethyl acetate (20 mL). The solid was then triturated with methanol (75 mL) for 6 hours and filtered, washing with methanol (20 mL). The solid was dried in vacuo to give crude N2-{4-[4-amino-1-(2-chloro-4-pyridyl)-1H-pyrazolo[3,4-d]pyrimidin-3-yl]-2-methoxyphenyl}-1-methyl-1H-2-indolecarboxamide (0.672 g, 0.00128 mol) as a tan solid:

$^1$H NMR (DMSO-d$_6$, 400 MHz) δ 9.48 (s, 1H) 8.55-8.58 (m, 2H), 8.50 (s, 1H), 8.44 (dd, 1), 8.21 (d, 1H), 7.72 (d, 1H), 7.60 (d, 1H), 7.49 (d, 1H), 7.43 (dd, 1H), 7.31-7.38 (m, 2H), 7.16 (t, 1H), 4.05 (s, 3H), 4.00 (s, 1H); RP-HPLC (Delta Pak C18, 5 μm, 300A, 15 cm; 5%-95% acetonitrile—0.1M ammonium acetate over 10 min, isocratic at 95% for 3 min., 1 mL/min) $R_t$ 12.70 min.; MS: MH$^+$ 525.

C. N2-(4-{4-amino-1-[2-(4-methylpiperazino)-4-pyridyl]-1H-pyrazolo[3,4-d]pyrimidin-3-yl}-2-methoxyphenyl)-1H-2-indolecarboxamide acetate A suspension of N2-{4-[4-amino-1-(2-chloro-4-pyridyl)-1H-pyrazolo[3,4-d]pyrimidin-3-yl]-2-methoxyphenyl}-1-methyl-1H-2-indolecarboxamide (0.120 g, 0.00023 mol) in 1-methylpiperazine (5 mL) heated at 120° C. for 5 days. The solvent was removed in vacuo and the residue was slurried in diethyl ether (25 mL) for 4 hours. The mixture was filtered, washing with diethyl ether (105 mL) and dried in vacuo. The crude material was purified by preparative RP-HPLC (Rainin C18, 8 mm, 300 Å, 25 cm; 40% isocratic for five minutes, then 40%-100% acetonitrile—0.1M ammonium acetate over 30 min, 21 mL/min). The acetonitrile was removed in vacuo and the aqueous mixture was lyopholyzed to give N2-(4-{4-amino-1-[2-(4-methylpiperazino)-4-pyridyl]-1H-pyrazolo[3,4-d]pyrimidin-3-yl}-2-methoxyphenyl)-1H-2-indolecarboxamide acetate (0.030 g, 0.00005 mol) as a white solid.

$^1$H NMR (DMSO-$d_6$, 400 MHz) δ 9.47 (s, 1H), 8.44 (s, 1H), 8.12 (d, 1H), 7.77 (s, 1H), 7.72 (d, 1H), 7.68 (d, 1H), 7.60 (d, 1H), 7.30-7.37 (m, 3H), 7.26 (d, 1H), 7.15 (t, 1H), 4.06 (s, 3H), 3.50-3.58 (m, 4H), 2.38-2.46 (m, 4H), 2.24 (s, 3H), 1.91 (s, 3H); RP-HPLC (Delta Pak C18, 5 μm, 300A, 15 cm; 5%-95% acetonitrile—0.1M ammonium acetate over 20 min, 1 mL/min) R$_t$ 15.33 min.; MS: MH$^+$ 575.

Example 374

N2-{4-[4-amino-1-(2-morpholino-4-pyridyl)-1H-pyrazolo[3,4-d]pyrimidin-3-yl]-2-methoxyphenyl}-1-methyl-1H-2-indolecarboxamide A suspension of N2-{4-[4-amino-1-(2-chloro-4-pyridyl)-1H-pyrazolo[3,4-d]pyrimidin-3-yl]-2-methoxyphenyl}-1-methyl-1H-2-indolecarboxamide (0.120 g, 0.00023 mol) and morpholine (10 mL) was heated at 100° C. for 6 days. The solvent was removed in vacuo and the residue was slurried in water (25 mL) for 4 hours. The mixture was filtered and the crude solid was purified by preparative RP-HPLC (Rainin C18, 8 mm, 300 Å, 25 cm; 35%-80% acetonitrile—0.050 M ammonium acetate over 20 min, 21 mL/min). The acetonitrile was removed in vacuo and the aqueous mixture was lyopholyzed to give N2-{4-[4-amino-1-(2-morpholino-4-pyridyl)-1H-pyrazolo[3,4-d]pyrimidin-3-yl]-2-methoxyphenyl}-1-methyl-1H-2-indolecarboxamide (0.048 g, 0.00008 mol) as a white solid.

$^1$H NMR (DMSO-$d_6$, 400 MHz) δ 9.48 (s, 1H), 8.44 (s, 1H), 8.27 (d, 1H), 8.18 (d, 1H), 7.82 (d, 1H), 7.74 (dd, 1H), 7.72 (d, 1H), 7.60 (d, 1H), 7.46 (d, 1H), 7.41 (dd, 1H), 7.36 (s,1H), 7.34 (t, 1H), 7.16 (t, 1H), 4.05 (s, 3H), 3.99 (s, 3H), 3.72-3.78 (m, 4H), 3.49-3.56 (m, 4H); RP-HPLC (Delta Pak C18, 5 μm, 300A, 15 cm; 5%-95% acetonitrile—0.1M ammonium acetate over 20 min, 1 mL/min) R$_t$ 17.89 min.; MS: MH$^+$ 576.

Example 375

(S)-N-2-(4-{4-amino-1-[1-(2-methoxyethyl)-3-piperidyl]-1H-pyrazolo[3,4-d]pyrimidin-3-yl}phenyl)-5,7-dimethyl-1,3-benzoxazol-2-amine

A. (R)-tert-butyl 3-hydroxy-1-piperidinecarboxylate

A mixture of (R)-3-hydroxy piperidine hydrochloride (10 g, 0.073 mol), di-tert-butyl dicarbonate (20 g, 0.091 mol) and sodium carbonate (19 g, 0.182 mol) in dioxane (80 mL) and water (80 mL) was stirred at room temperature under an atmosphere of nitrogen for 18 hours. The organic solvent was removed under the reduced pressure. The aqueous layer was extracted with diethyl ether (2×200 mL). The organic layer was washed with brine and dried over magnesium sulfate. The solvent was removed under the reduced pressure to yield clear oil of (R)-tert-butyl 3-hydroxy-1-piperidinecarboxylate (17.6 g, 0.087 mol). The crude product was carried to the next reaction.

$^1$H NMR (Chloroform-d, 400 MHz) δ 3.76 (m, 1H), 3.67 (br, 1H), 3.55 (br, 1H), 2.92 (m, 2H), 2.75 (s, 1H), 1.85 (br, 1H), 1.72 (br, 1H), 1.46 (br, 11H) GC-MS: MH$^+$ 202

B. (S)-Tert-butyl 3-(4-amino-3-iodo-1H-pyrazolo[3,4-d]pyrimidin-1-yl)-1-piperidinecarboxylate To a mixture of 3-iodo-1H-pyrazolo[3,4-d]pyrimidin-4-amine (2 g, 0.0077 mol), (R)-tert-butyl 3-hydroxy-1-piperidinecarboxylate (2.3 g, 0.012 mol), and triphenylphosphine (3 g, 0.012 mol) in tetrahydrofuran (70 mL), diethyl azodicarboxylate (2 g, 0.012 mol) was added at 0° C. The mixture was stirred at room temperature under an atmosphere of nitrogen for 2 days. In order to complete the reaction, additional (R)-tert-butyl 3-hydroxy-1-piperidinecarboxylate (0.62 g, 0.003 mol), and triphenylphosphine (0.81 g, 0.012 mol), and diethyl azodicarboxylate (0.6 g, 0.003 mol) were added to the mixture. The mixture was stirred at room temperature under an atmosphere of nitrogen for additional 18 hours. The solvent was removed under the reduced pressure to yield crude (S)-tert-butyl 3-(4-amino-3-iodo-1H-pyrazolo[3,4-d]pyrimidin-1-yl)-1-piperidinecarboxylate, which was used crude for the next reaction.

RP-HPLC (Delta Pak C18, 5 μm, 300A, 15 cm; 5%-85% acetonitrile—0.1M ammonium acetate over 10 min, 1 mL/min) Rt 10.0 min. MS: MH$^+$ 445

C. (S)-3-iodo-1-(3-piperidyl)-1H-pyrazolo[3,4-d]pyrimidin-4-amine acetate

To a mixture of (S)-tert-butyl 3-(amino-3-iodo-1H-pyrazolo[3,4-d]pyrimidin-1-yl)-1-piperidinecarboxylate (3.4 g, 0.0077 mol) in acetone (80 mL) was added an aqueous 6N solution of hydrogen chloride (20 mL) at room temperature. The mixture was stirred at 45° C. for 4 hours, then at room temperature for 18 hours. Acetone was removed under reduced pressure, and the aqueous layer was washed with toluene (2×20 mL) and dichloromethane (2×20 mL). The aqueous layer was basified with an aqueous 5N solution of sodium hydroxide (25 mL) at 0° C. The aqueous layers were concentrated to dryness, and the residue was purified by RP-HPLC (Hypersilprep HS C18, 8 μm, 250× 21.1 mm; 2%-30% over 15 min with 0.1 M ammonium acetate, 21 mL/min) to yield (S)-3-iodo-1-(3-piperidyl)-1H-pyrazolo[3,4-d]pyrimidin-4-amine acetate (0.75 g, 0.0019 mol).

RP-HPLC (Hypersil C18, 5 μm, 250×4.6 mm; 5%-85% acetonitrile—0.1M ammonium acetate over 10 min, 1 mL/min) Rt 8.2 min. MS: MH$^+$ 345

D. (S)-3-iodo-1-[1-(2-methoxyethyl)-3-piperidyl]-1H-pyrazolo[3,4-d]pyrimidin-4-amine To a mixture of (S)-3-iodo-1-(3-piperidyl)-1H-pyrazolo[3,4-d]pyrimidin-4-amine acetate (0.75 g, 0.0019 mol) and potassium carbonate (0.77 g, 0.00568 mol) in N,N-dimethylformamide (30 mL) were added 2-bromoethyl methyl ether (0.27 g, 0.0019 mol) and potassium iodide (0.0016 g, 0.000095 mol) at room temperature. The mixture was stirred at 65° C. under an atmosphere of nitrogen for 16 hours. The reaction mixture was cooled to room temperature, and 2-bromoethyl methyl ether (0.27 g, 0.0019 mol) and potassium iodide (0.0016 g, 0.000095 mol) were added. The mixture was stirred at 65° C. under an atmosphere of nitrogen for 4 hours. The solvent was removed under the reduced pressure. The residue was partitioned between saturated sodium bicarbonate solution (25 mL) and dichloromethane (50 mL). The aqueous layer was extracted with dichloromethane (4×50 mL). The solvents were evaporated under the reduced pressure, and the residue was purified by RP-HPLC (Hypersilprep HS C18, 8 μm, 250×21.1 mm; 2%-30% over 15 min with 0.1 M ammonium acetate, 21 mL/min) to (S)-3-iodo-1-[1-(2-methoxyethyl)-3-piperidyl]-1H-pyrazolo[3,4-d]pyrimidin-4-amine acetate (0.64 g, 0.0014 mol).

RP-HPLC (Hypersil C18, 5 μm, 250×4.6 mm; 5%-85% acetonitrile—0.1M ammonium acetate over 10 min, 1 mL/min) Rt 8.9 min. MS: MH+ 403

E. (S)-N-2-(4-f{4-amino-1-[1-(2-methoxyethyl)-3-piperidyl]-1H-pyrazolo[3,4-d]pyrimidin-3-yl}phenyl)-5,7-dimethyl-1,3-benzoxazol-2-amine A mixture of (S)-3-iodo-1-[1-(2-methoxyethyl)-3-piperidyl]-1H-pyrazolo[3,4-d]pyrimidin-4-amine acetate (0.64 g, 0.0014 mol), N-(5,7-dimethyl-1,3-benzoxazol-2-yl)-N-[4-(4,4,5,5-tetramethyl-1,3,2-dioxaborolan-2-yl)phenyl] amine (0.64 g, 0.00175 mol, 1.2 eq.), tetrakis(triphenylphosphine)palladium (0.081 g, 0.00007 mol) and sodium carbonate (0.37 g, 0.0035 mol) in N,N-dimethylformamide (15 mL) and water (7 mL) was heated at 80° C. for 16 hours under an atmosphere of nitrogen. The mixture was allowed to cool to ambient temperature, and the solvent was removed under the reduced pressure. The residue was partitioned between water (25 mL) and dichloromethane (50 mL). The aqueous layer was extracted with dichloromethane (3×50 mL). The combined organic extracts were washed with brine and dried over magnesium sulfate. The solvents were evaporated under the reduced pressure to leave a brownish oil, which was purified by flash column chromatography on silica using 2%-10% methanol/dichloromethane as a mobile phase to give (S)-N-2-(4-{4-amino-1-[1-(2-methoxyethyl)-3-piperidyl]-1H-pyrazolo[3,4-d]pyrimidin-3-yl}phenyl)-5,7-dimethyl-1,3-benzoxazol-2-amine (0.60 g, 0.0012 mol).

$^1$H NMR (DMSO-d$_6$, 400 MHz) δ 10.85 (s, 1H), 8.25 (s, 1H), 7.93 (d, 2H), 7.65 (d, 2H), 7.11 (s, 1H), 6.80 (s, 1H), 4.77 (br, 1H), 3.36 (m, 2H), 3.25 (s, 3H), 3.04 (br, 1H), 2.90 (br, 1H), 2.55 (br, 2H), 2.54 (br, 1H), 2.40 (s, 3H), 2.35 (s, 3H), 2.02 (br, 3H), 1.80 (br, 1H), 1.70 (br, 1H).

RP-HPLC (Delta Pak C18, 5 μm, 300A, 15 cm; 5%-95% acetonitrile—0.1M ammonium acetate over 10 min, 1 mL/min) Rt 11.9 min. MS: MH+ 513

Example 376

Cis-2-(4-{4-amino-1-[4-(4-methylpiperazino)cyclohexyl]-1H-pyrazolo[3,4-d]pyrimidin-3-yl}anilino)-1,3-benzoxazole-5-carboxamide triacetate To a mixture of cis-2-(4-{4-amino-1-[4-(4-methylpiperazino)cyclohexyl]-1H-pyrazolo[3,4-d]pyrimidin-3-yl}anilino)-1,3-benzoxazole-5-carbonitrile triacetate (0.18 g, 0.00025 mol) in dioxane (2 mL) were added a 2N aqueous solution of sodium hydroxide (1.25 mL, 0.0025 mol) and water (0.75 mL). The mixture was stirred at room temperature for 2 minutes under the atmosphere of nitrogen before adding 30% hydrogen peroxide solution (0.2 mL). The mixture was refluxed for 5 hours, then stirred at room temperature for 18 hours. More 30% hydrogen peroxide solution (0.2 mL) was added to the mixture before refluxing for additional 6 hours, then stirred at room temperature for 2 days. The organic solvent was removed under reduced pressure, and 5% citric acid solution was added to maintain pH 7. The aqueous layer was removed under reduced pressure, and the crude was purified by RP-HPLC (Hypersilprep HS C18, 8 μm, 250×21.1 mm; 5%-100% over 25 min with 0.1 M ammonium acetate, 21 mL/min) to give cis-2-(4-{4-amino-1-[4-(4-methylpiperazino)cyclohexyl]-1H-pyrazolo[3,4-d]pyrimidin-3-yl}anilino)-1,3-benzoxazole-5-carboxamide triacetate (0.11 g, 0.00015 mol).

$^1$H NMR (DMSO-d$_6$, 400 MHz), 8.30 (s, 1H), 8.15 (s, 1H), 8.00 (m, 3H), 7.75 (m, 1H), 7.70(m, 2H), 7.60 (d, 1H), 7.35 (br, 1H), 4.80 (br, 1H), 2.50 (br, 2H), 2.40 (br, 4H), 2.25 (br, 4H), 2.15 (s, 3H), 2.10 (br, 3H), 1.90 (s, 9H), 1.70 (br, 2H), 1.60 (br, 2H). RP-HPLC (Delta Pak C18, 5 μm, 300A, 15 cm; 5%-95% acetonitrile—0.1M ammonium acetate over 10 min, 1 mL/min) Rt 8.2 min. MS: MH+ 567

Example 377

N1-{4-[4-Amino-1-(4-oxocyclohexyl)-1H-pyrazolo[3,4-d]pyrimidin-3-yl]-2-methoxyphenyl}-2-fluoro-4-trifluoromethylbenzamide

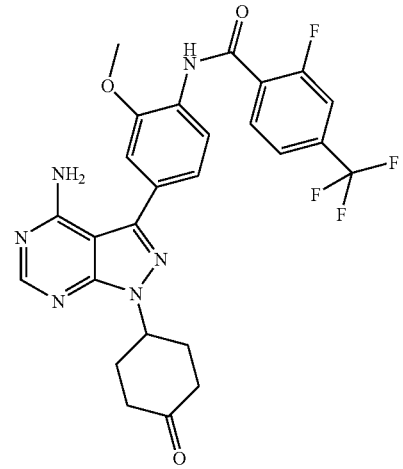

A solution of 2-fluoro-4-trifluoromethyl-1-benzenecarbonyl chloride (0.87 g, 3.83 mmol) in dichloromethane (5 mL) was added into a mixture of pyridine (15 mL) and 4-[4-amino-3-(4-amino-3-methoxyphenyl)-1H-pyrazolo[3,4-d]pyrimidin-1-yl]-1-cyclohexanone (1.00 g, 2.56 mmol) in dichloromethane (5 mL) at 0° C. over 5 minutes. The mixture was stirred at 0° C. for 10 minutes and at ambient temperature overnight. The solvent was removed under reduced pressure. The residue was partitioned between water and dichloromethane. The dichloromethane layer was washed with saturated aqueous ammonium chloride twice and saturated aqueous sodium chloride solution, dried over magnesium sulfate, filtered and evaporated under reduced pressure to give a crude product. The crude product was purified by flash column chromatography on silica using Isco system to provide N1-{4-[4-amino-1-(4-oxocyclohexyl)-1H-pyrazolo [3,4-d]pyrimidin-3-yl]-2-methoxyphenyl}-2-fluoro-4-trifluoromethylbenzamide (0.95 g, 1.76 mmol) as a white solid: $^1$H NMR (DMSO-d$_6$, 400 MHz) δ 9.90 (dd, 1H), 8.30(d, 1H), 8.28 (s, 1H), 7.99 (t, 1H), 7.89 (d, 1H), 7.75 (d, 1H), 7.34 (s, 1H), 7.30 (d, 1H), 6.90 (br, 2H), 5.27 (m, 1H), 3.94 (s, 3H), 2.70 (m, 2H), 2.47 (m, 4H), 2.17 (m, 2H); RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 9.23 min. MS: MH$^+$ 543.

Example 378

Cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide; and

Example 379

Trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide

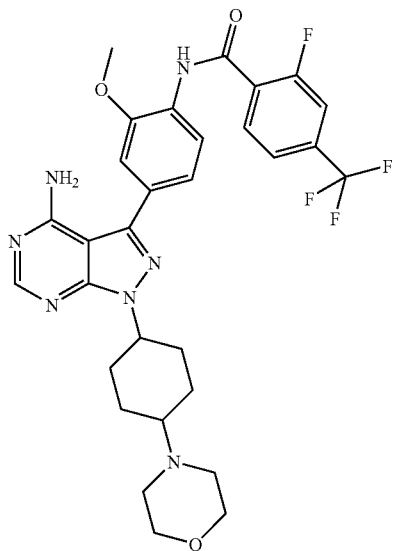

Morpholine (0.08 mL, 0.93 mmol) was added into a mixture of N-{4-[4-amino-1-(4-oxocyclohexyl)-1H-pyrazolo[3,4-d]pyrimidin-3-yl]-2-methoxyphenyl}-2-fluoro-4-trifluoromethylbenzamide (0.42 g, 0.78 mmol) and acetic acid (0.11 mL, 1.86 mmol) in dichloroethane (25 mL). The mixture was stirred at ambient temperature for 10 minutes. Sodium triacetoxyborohydride (0.23 g, 1.09 mmol) was added and the mixture was stirred at ambient temperature overnight. Water (6 mL) was added followed by sodium bicarbonate (0.38 g, 4.53 mmol). The mixture was stirred for 1 hour and the organic layer was separated. The aqueous layer was extracted with dichloromethane (20 mL). The combine organics were dried over magnesium sulfate, filtered and evaporated under reduced pressure to give a crude product. The crude product was purified by flash column chromatography on silica using Isco system to provide cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide (0.23 g, 0.37 mmol) and trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide (0.09 g, 0.14 mmol) as white solids.

Data for cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide: $^1$H NMR (DMSO-d$_6$, 400 MHz), 9.91 (dd, 1H), 8.30(d, 1H), 8.24 (s, 1H), 8.00 (t, 1H), 7.89 (d, 1H), 7.75 (d, 1H), 7.33 (s, 1H), 7.30 (d, 1H), 6.90 (br, 2H), 4.83 (m, 1H), 3.94 (s, 3H), 3.62 (br, 4H), 1.57-2.55 (m, 10H); MS: MH$^+$ 614.

Data for trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide: $^1$H NMR (DMSO-d$_6$, 400 MHz) δ 9.90 (dd, 1H), 8.30(d, 1H), 8.24 (s, 1H), 7.99 (t, 1H), 7.89 (d, 1H), 7.75 (d, 1H), 7.32 (s, 1H), 7.29 (s, 1H), 4.67 (m, 1H), 3.94 (s, 3H), 3.59 (br, 4H), 1.48-2.69 (m, 10H); MS: MH$^+$ 614.

Example 380

Cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino) propanoate; and

Example 381

Trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino) propanoate

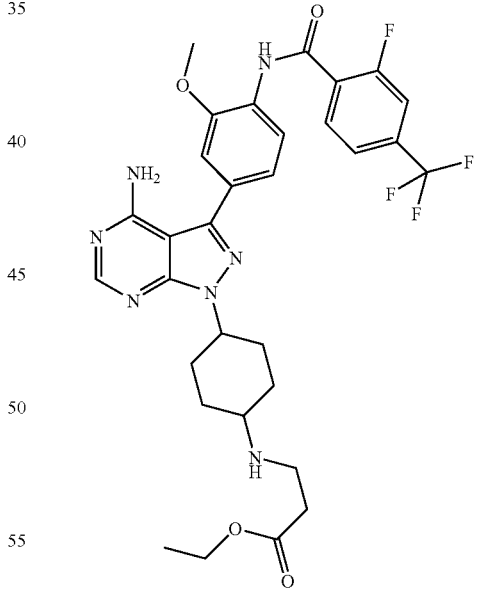

A similar procedure to the preparation of cis-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide and trans-N1-{4-[4-amino-1-(4-morpholinocyclohexyl)-1H-pyrazolo[3,4-d]pyrimidin-3-yl]-2-methoxyphenyl}-2-fluoro-4-trifluoromethylbenzamide yielded cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]

cyclohexyl}amino)propanoate and trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate as white solids.

Data for cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate:
$^1$H NMR (DMSO-$d_6$, 400 MHz), 9.90 (dd, 1H), 8.30(d, 1H), 8.23 (s, 1H), 8.00 (t, 1H), 7.89 (d, 1H), 7.75 (d, 1H), 7.33 (s, 1H), 7.30 (d, 1H), 6.90 (br, 2H), 4.37 (m, 1H), 4.08 (q, 2H), 3.94 (s, 3H), 2.76 (m, 2H), 2.32 (m, 2H), 1.88 (m, 2H), 1.67 (m, 4H), 1.16 (t, 3H); RP-HPLC (Hitachi HPLC, Hypersil C18, 5 μm, 100A, 250×4.6 mm; 25%-100% acetonitrile—0.05M ammonium acetate over 10 min, 1 mL/min) $R_t$ 7.92 min. MS: MH$^+$ 644.

Data for trans-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate:
$^1$H NMR (DMSO-$d_6$, 400 MHz), 9.89 (dd, 1H), 8.30(d, 1H), 8.24 (s, 1H), 8.00 (t, 1H), 7.89 (d, 1H), 7.75 (d, 1H), 7.32 (s, 1H), 7.29 (d, 1H), 6.90 (br, 2H), 4.68 (m, 1H), 4.08 (q, 2H), 3.94 (s, 3H), 2.82 (m, 2H), 2.46 (m, 5H), 1.91-2.07 (m, 6H), 1.18 (t, 3H); RP-HPLC (Hitachi HPLC, Hypersil C18, 5 μm, 100A, 250×4.6 mm, 25%-100% acetonitrile—0.05M ammonium acetate over 10 min, 1 mL/min) $R_t$ 7.69 min. MS: MH$^+$ 644.

Example 382

N1-[4-(4-Amino-1-trityl-1H-pyrazolo[3,4-d]pyrimidin-3-yl)-2-methoxyphenyl]-2-fluoro-4-trifluoromethylbenzamide

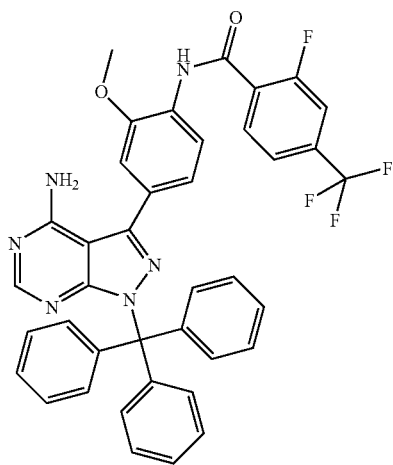

A mixture of 3-iodo-1-trityl-1H-pyrazolo[3,4-d]pyrimidin-4-amine (0.10 g, 0.19 mmol), N1-[2-methoxy-4-(4,4,5,5-tetramethyl-1,3,2-dioxaborolan-2-yl)phenyl]-2-fluoro-4-trifluoromethylbenzamide (0.13 g, 0.29 mmol), tetrakis(triphenylphosphine)palladium(0) (0.01 g, 0.01 mmol) and sodium carbonate monohydrate (0.06 mg, 0.48 mmol) in water (2 mL) and ethylene glycol dimethyl ether (4 mL) was heated at 85° C. overnight. The solvents were removed under reduced pressure. Water was added into the residue and the mixture was extracted with ethyl acetate three times. The combined organics were washed with saturated aqueous sodium chloride solution, dried over magnesium sulfate, filtered and evaporated to yield a brown solid which was purified by flash column chromatography on silica using Isco system to provide N1-[4-(4-amino-1-trityl-1H-pyrazolo[3,4-d]pyrimidin-3-yl)-2-methoxyphenyl]-2-fluoro-4-trifluoromethylbenzamide (0.12 g, 0.17 mmol) as a white solid: $^1$H NMR (DMSO-$d_6$, 400 MHz) δ 9.89 (dd, 1H), 8.25(d, 1H), 8.28 (s, 1H), 8.00 (t, 1H), 7.94 (s, 1H), 7.88 (d, 1H), 7.73 (d, 1H), 7.24 (m, 15H), 3.90 (s, 3H); MS: MH$^+$ 689.

Example 383

Cis-3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoic acid

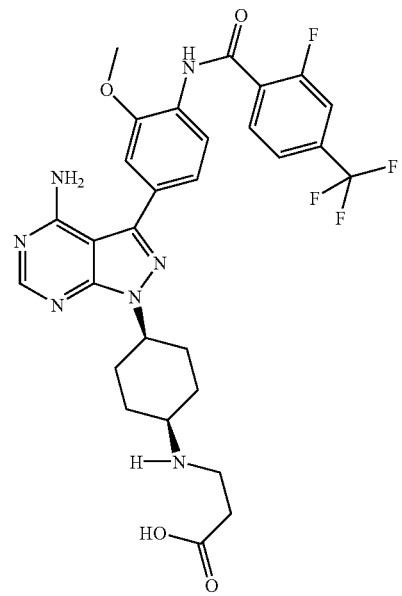

A mixture of cis-ethyl 3-({4-[4-amino-3-(4-{[2-fluoro-4-trifluoromethylbenzoyl]amino}-3-methoxyphenyl)-1H-pyrazolo[3,4-d]pyrimidin-1-yl]cyclohexyl}amino)propanoate (0.23 g, 0.36 mmol), p-dioxane (15 mL), potassium hydroxide (0.10 g, 1.81 mmol) and water (1.5 mL) were heated at 80° C. for 3 hours. The solvents were evaporated and the residue was purified by preparative HPLC to yield cis-3-({4-[4-amino-3-(4-{[2-fluoro-4-trifluoromethylbenzoyl]amino)}-3-methoxyphenyl)-1H-pyrazolo[3,4-d]pyrimidin-1-yl]cyclohexyl}amino)propanoic acid (0.11 g, 0.18 mmol) as a white solid: $^1$H NMR (DMSO-$d_6$, 400 MHz:) δ 9.91 (dd, 1H), 8.31 (d, 1H), 8.25 (s, 1H), 8.00 (t, 1H), 7.89 (d, 1H), 7.75 (d, 1H), 7.35 (s, 1H), 7.32 (s, 1H), 6.89 (br, 2H), 4.79 (m, 1H), 3.95 (s, 3H), 2.46-3.00 (m, 7H), 2.29 (m, 2H), 1.91 (m, 2H), 1.80 (m, 2H); RP-HPLC (Hitachi HPLC, Hypersil C18, 5 μm, 100A, 250×4.6 mm; 25%-100% acetonitrile—0.05M ammonium acetate over 10 min, 1 mL/min) $R_t$ 6.06 min. MS: MH$^+$ 616.

Example 384

Trans-3-({4-[4-amino-3-(3-methoxy-4-{[2-methoxy-4-trifluoromethylbenzoyl]amino}phenyl)-1H-pyrazolo[3,4-d]pyrimidin-1-yl]cyclohexyl}amino)propanoic acid

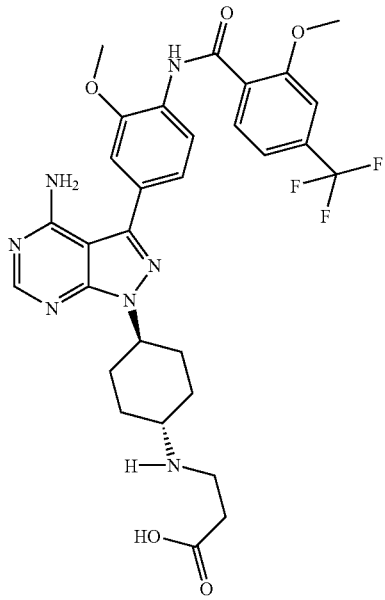

A mixture of trans-ethyl 3-({4-[4-amino-3-(4-{[2-fluoro-4-trifluoromethylbenzoyl]amino}-3-methoxyphenyl)-1H-pyrazolo [3,4-d]pyrimidin-1-yl]cyclohexyl}amino)propanoate (0.04 g, 0.06 mmol), p-dioxane (4 mL), potassium hydroxide (0.02 g, 0.31 mmol), a trace amount of methanol and water (0.4 mL) were heated at 80° C. for 1 hour. The mixture was stirred at ambient temperature overnight and at 80° C. for 4 hours. The solvents were evaporated and the residue was purified by preparative HPLC to yield trans-3-({4-[4-amino-3-(3-methoxy-4-{[2-methoxy-4-trifluoromethylbenzoyl]amino}phenyl)-1H-pyrazolo[3,4-d]pyrimidin-1-yl]cyclohexyl}amino)propanoic acid (0.04 g, 0.06 mmol) as a white solid: $^1$H NMR (DMSO-d$_6$, 400 MHz) δ 10.72 (s, 1H), 8.61(d, 1H), 8.28 (d, 1H), 8.24 (s, 1H), 7.61(s, 1H), 7.53 (d, 1H), 7.33 (s, 1H), 7.29 (d, 1H), 4.72 (m, 1H), 4.20 (s, 3H), 4.05 (s, 3H), 1.44-3.61 (m, 13H); RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 6.36 min. MS: MH$^+$ 628.

Example 385

N1-[4-(4-Amino-1H-pyrazolo[3,4-d]pyrimidin-3-yl)-2-methoxyphenyl]-2-fluoro-4-trifluoromethylbenzamide

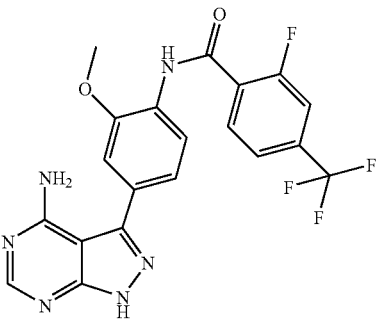

A mixture of N1-[4-(4-amino-1-trityl-1H-pyrazolo[3,4-d]pyrimidin-3-yl)-2-methoxyphenyl]-2-fluoro-4-trifluoromethylbenzamide (2.10 g, 1.75 mmol), 6 N aqueous hydrochloric acid (10 mL), p-dioxane (10 mL) and ethanol (8 mL) was heated at 50° C. for 6 hours. The mixture was filtered and the solid was washed with ethanol, dried in a vacuum oven over the weekend, and purified by flash column chromatography on silica to provide N1-[4-(4-amino-1H-pyrazolo[3,4-d]pyrimidin-3-yl)-2-methoxyphenyl]-2-fluoro-4-trifluoromethylbenzamide (0.35 g, 0.78 mmol). The filtrate was concentrated and purified by flash column chromatography on silica and preparative HPLC to provide the same product N1-[4-(4-amino-1H-pyrazolo[3,4-d]pyrimidin-3-yl)-2-methoxyphenyl]-2-fluoro-4-trifluoromethylbenzamide (0.67 g, 1.51 mmol) as a white solid: $^1$H NMR (DMSO-d$_6$, 400 MHz) δ 13.58 (s, 1H), 9.90 (dd, 1H), 8.30(d, 1H), 8.23 (s, 1H), 8.05 (t, 1H), 7.90 (d, 1H), 7.75 (d, 1H), 7.36 (s, 1H), 7.24 (d, 1H), 3.94 (s, 3H); MS: MH$^+$ 447.

Example 386

N1-[4-(4-Amino-1-tetrahydro-2H-4-pyranyl-1H-pyrazolo[3,4-d]pyrimidin-3-yl)-2-methoxyphenyl]-2-fluoro-4-trifluoromethylbenzamide

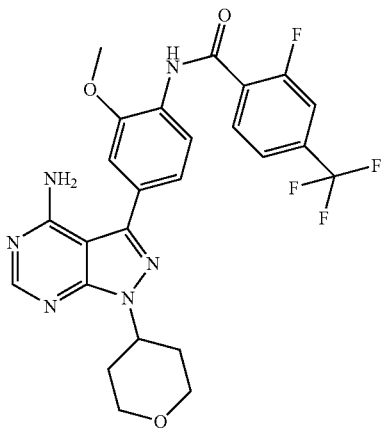

Diethyl azodicarboxylate (0.07 mL, 0.45 mmol) was added into a mixture of N1-[4-(4-amino-1H-pyrazolo[3,4-d]pyrimidin-3-yl)-2-methoxyphenyl]-2-fluoro-4-trifluoromethylbenzamide (0.10 g, 0.22 mmol), triphenylphosphine (0.12 g, 0.45 mmol) and tetrahydro-4H-pyran-4-ol (0.04 g, 0.34 mmol) in tetrahydrofuran (5 mL) and the mixture was stirred at ambient temperature overnight. Tetrahydro-4H-pyran-4-ol (0.01 g, 0.11 mmol), triphenylphosphine (0.04 g, 0.15 mmol) and diethyl azodicarboxylate (0.02 mL, 0.15 mmol) were added and the mixture was stirred at ambient temperature for 5 hours. The solvents were evaporated and the residue was purified by preparative HPLC to yield N1-[4-(4-amino-1-tetrahydro-2H-4-pyranyl-1H-pyrazolo[3,4-d]pyrimidin-3-yl)-2-methoxyphenyl]-2-fluoro-4-trifluoromethylbenzamide (0.03 g, 0.06 mmol) as a white solid: $^1$H NMR (DMSO-d$_6$, 400 MHz) δ 9.91 (dd, 1H), 8.30(d, 1H), 8.25 (s, 1H), 8.00 (t, 1H), 7.89 (d, 1H), 7.75 (d, 1H), 7.34 (s, 1H), 7.31 (d, 1H), 6.90 (br, 2H), 4.95 (m, 1H), 4.02 (m, 2H), 3.95 (s, 3H), 3.56 (t, 2H), 2.22 (m, 2H), 1.89 (m, 2H); MS: MH$^+$ 531.

Example 387

N1-{4-[4-Amino-1-(4-hydroxy-2-cyclopentenyl)-1H-pyrazolo[3,4-d]pyrimidin-3-yl]-2-methoxyphenyl}-2-fluoro-4-trifluoromethylbenzamide

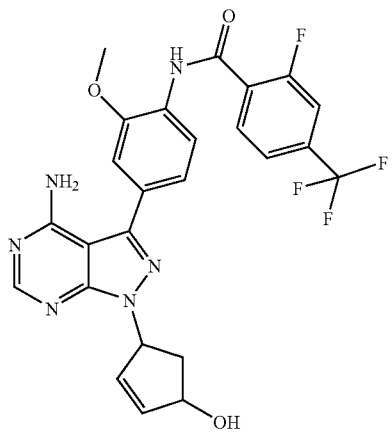

A. 4-(4-Amino-3-iodo-1H-pyrazolo[3,4-d]pyrimidin-1-yl)-2-cyclopenten-1-ol

A mixture of tetrakis(triphenylphosphine)palladium(0) (0.04 g, 0.03 mmol), 3-iodo-1H-pyrazolo[3,4-d]pyrimidin-4-amine (0.30 g, 1.14 mmol) and dimethyl sulfoxide (3 mL) was stirred at ambient temperature in the dark for 2 minutes and cooled to 0° C. A solution of 2,4a-dihydro-1aH-cyclopenta[b]oxirene (0.14 g, 1.72 mmol) in tetrahydrofuran (3 mL) was added into the mixture at 0° C. and stirred at 0° C. for 3 hours. The mixture was stirred at ambient temperature overnight and purified by preparative HPLC to yield 4-(4-amino-3-iodo-1H-pyrazolo[3,4-d]pyrimidin-1-yl)-2-cyclopenten-1-ol (0.24 g, 0.70 mmol) as a white solid: RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 4.23 min. MS: MH$^+$ 344.

B. N1-{4-[4-Amino-1-(4-hydroxy-2-cyclopentenyl)-1H-pyrazolo[3,4-d]pyrimidin-3-yl]-2-methoxyphenyl}-2-fluoro-4-trifluoromethylbenzamide A mixture of 4-(4-amino-3-iodo-1H-pyrazolo[3,4-d]pyrimidin-1-yl)-2-cyclopenten-1-ol (0.12 g, 0.35 mmol), N1-[2-methoxy-4-(4,4,5,5-tetramethyl-1,3,2-dioxaborolan-2-yl)phenyl]-2-fluoro-4-trifluoromethylbenzamide (0.23 g, 0.53 mmol), tetrakis(triphenyl-phosphine)palladium(0) (0.02 g, 0.02 mmol) and sodium carbonate monohydrate (0.11 g, 0.88 mmol) was heated in a mixture of ethylene glycol dimethyl ether (6 mL) and water (3 mL) at 85° C. for 6 hours under an atmosphere of nitrogen. The mixture was allowed to cool to ambient temperature and solvents were removed under the reduced pressure. The residue was purified by preparative HPLC to yield N1-{4-[4-amino-1-(4-hydroxy-2-cyclopentenyl)-1H-pyrazolo[3,4-d]pyrimidin-3-yl]-2-methoxyphenyl}-2-fluoro-4-trifluoromethylbenzamide (0.18 g, 0.34 mmol) as a white solid: $^1$H NMR (DMSO-d$_6$, 400 MHz) δ 9.89 (dd, 1H), 8.31(d, 1H), 8.26 (s, 1H), 8.00 (t, 1H), 7.88 (d, 1H), 7.75 (d, 1H), 7.32 (s, 1H), 7.29 (d, 1H), 6.90 (br, 2H), 6.09 (d, 1H), 5.93 (d, 1H), 5.76 (m, 1H), 5.31 (m, 1H), 4.74 (m, 1H), 3.94 (s, 3H), 2.84 (m, 1H), 2.02 (m, 1H); RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 8.50 min. MS: MH$^+$ 529.

Example 388

N1-{4-[4-Amino-1-(3-hydroxycyclopentyl)-1H-pyrazolo[3,4-d]pyrimidin-3-yl]-2-methoxyphenyl}-2-fluoro-4-trifluoromethylbenzamide

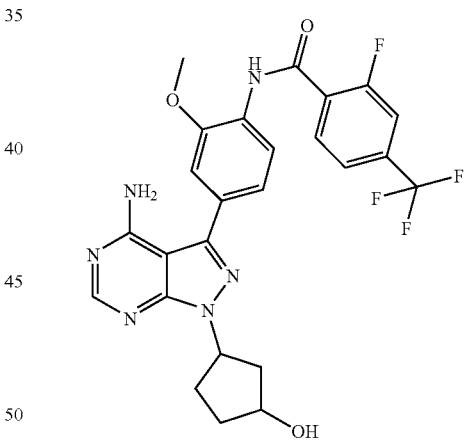

A mixture of N1-{4-[4-amino-1-(4-hydroxy-2-cyclopentenyl)-1H-pyrazolo[3,4-d]pyrimidin-3-yl]-2-methoxyphenyl}-2-fluoro-4-trifluoromethylbenzamide (0.10 g, 0.19 mmol) and 10% palladium on carbon (0.03 g) in ethanol (10 mL) was stirred at ambient temperature under one atmosphere of hydrogen overnight. The mixture was filtered and the filtrate was purified by preparative HPLC to yield N1-{4-[4-amino-1-(3-hydroxycyclopentyl)-1H-pyrazolo[3,4-d]pyrimidin-3-yl]-2-methoxyphenyl}-2-fluoro-4-trifluoromethylbenzamide (0.07 g, 0.13 mmol) as a white solid: $^1$H NMR (DMSO-d$_6$, 400 MHz) δ 9.91 (dd, 1H), 8.31(d, 1H), 8.24 (s, 1H), 8.00 (t, 1H), 7.89 (d, 1H), 7.75 (d, 1H), 7.34 (s, 1H), 7.30 (d, 1H), 6.90 (br, 2H), 5.17 (m, 1H), 4.97 (m, 1H), 4.22 (m, 1H), 3.94 (s, 3H), 1.79-2.41 (m, 6H); MS: MH$^+$ 531.

Example 389

4-(4-Amino-3-{4-[(1H-2-indolylcarbonyl)amino]-3-methoxyphenyl}-1H-pyrazolo[3,4-d]pyrimidin-1-yl)hexahydropyridinium acetate

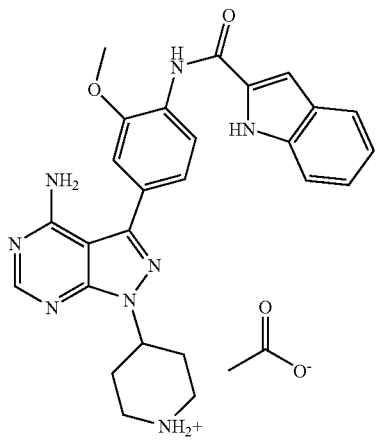

Oxalyl chloride (0.06 mL, 0.60 mmol) was added into a solution of indole-2-carboxylic acid (0.88 g, 0.546 mmol) in dichloromethane (5 mL) and tetrahydrofuran (5 mL) at 0° C. N,N-dimethylforamide (3 drops from 0.11 mL syringe) was added and the mixture was stirred at 0° C. for 10 minutes and at ambient temperature for 20 minutes. The solvents and excess of reagents were evaporated under reduced pressure. The residue was taken into dichloromethane (2 mL) and the resulting solution (1.25 mL) was added into a solution of tert-butyl 4-[4-amino-3-(4-amino-3-methoxyphenyl)-1H-pyrazolo[3,4-d]pyrimidin-1-yl]-1-piperidinecarboxylate (0.12 g, 0.27 mmol) and pyridine (0.4 mL) in dichloromethane (1 mL). The mixture was stirred at ambient temperature for 2 hours. Trifluoroacetic acid (1 mL) was added and the mixture was stirred at ambient temperature for 2 hours. The solvents were evaporated under reduced pressure and the residue was purified by preparative HPLC to yield 4-(4-amino-3-{4-[(1H-2-indolylcarbonyl)amino]-3-methoxyphenyl}-1H-pyrazolo[3,4-d]pyrimidin-1-yl)hexahydropyridinium acetate (0.07 g, 0.14 mmol) as a white solid: $^1$H NMR (DMSO-$d_6$, 400 MHz) δ 11.85 (br, 1H), 9.45 (s, 1H), 8.24 (d, 1H), 8.12 (d, 1H), 7.68(d, 1H), 7.48 (d, 1H), 7.40 (s, 1H), 7.35 (s, 1H), 7.30 (d, 1H), 7.24 (t, 1H), 7.09 (t, 1H), 4.77 (m, 1H), 3.97 (s, 3H), 3.11 (m, 2H), 2.68 (m, 2H), 2.09 (m, 2H), 1.89 (s, 3H), 1.84 (m, 2H); MS: MH$^+$ 483.

Example 390-410

The same protocol as was used to prepare 4-(4-amino-3-{4-[(1H-2-indolylcarbonyl)amino]-3-methoxyphenyl}-1H-pyrazolo[3,4-d]pyrimidin-1-yl)hexahydropyridinium acetate (Example 881) was used to prepare Examples 390-410.

| Structure | MS: MH+ | HPLC Rt (min) (Hypersil C18, 5 µm, 100 A, 250 × 4.6 mm; 25%-100% acetonitrile - 0.05 M ammonium acetate over 10 min, 1 mL/min) | Example No. |
|---|---|---|---|
| 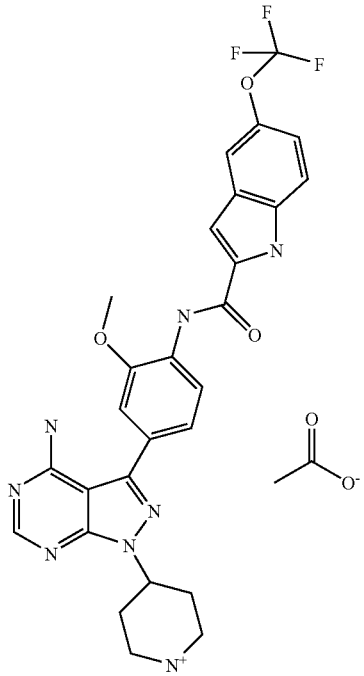 | 567 | 6.97 | 390 |

-continued

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 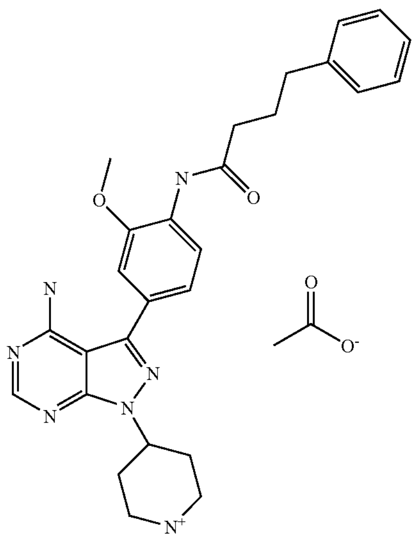 | 486 | 5.89 | 391 |
| 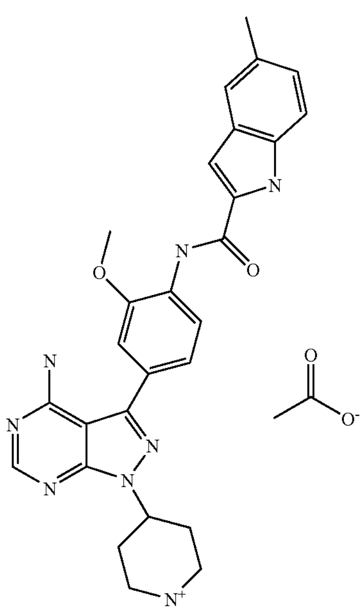 | 497 | 6.28 | 392 |

-continued

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 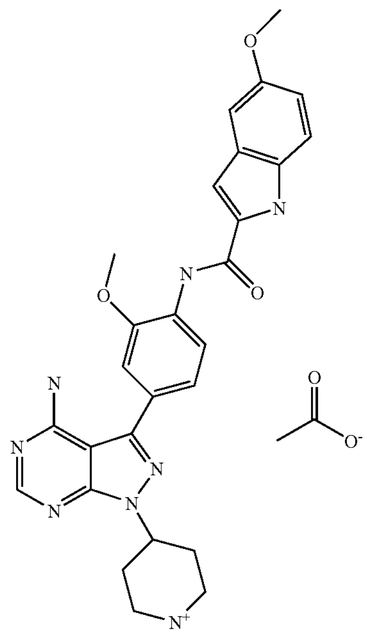 | 513 | 5.61 | 393 |
| 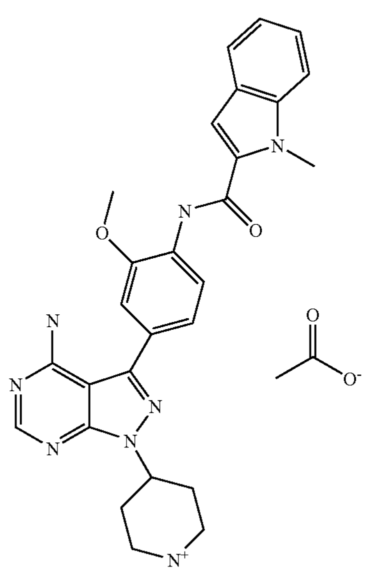 | 497 | 6.39 | 394 |

-continued

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 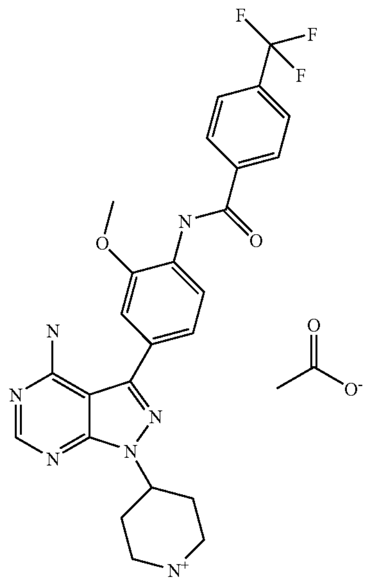 | 512 | 6.22 | 395 |
| 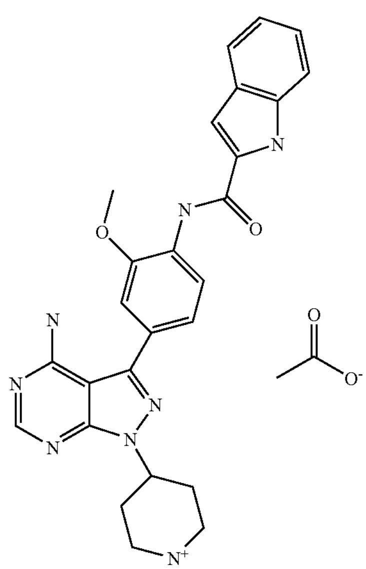 | 483 | 5.73 | 396 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 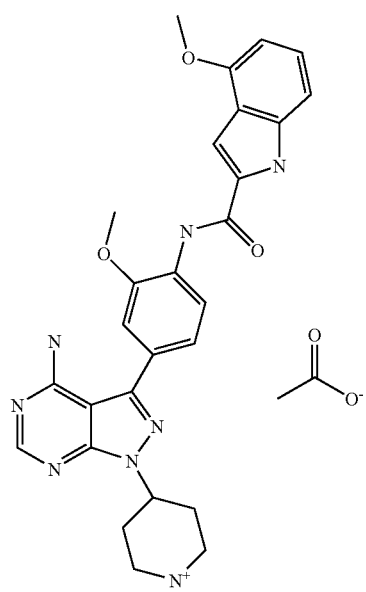 | 513 | 7.78 | 397 |
| 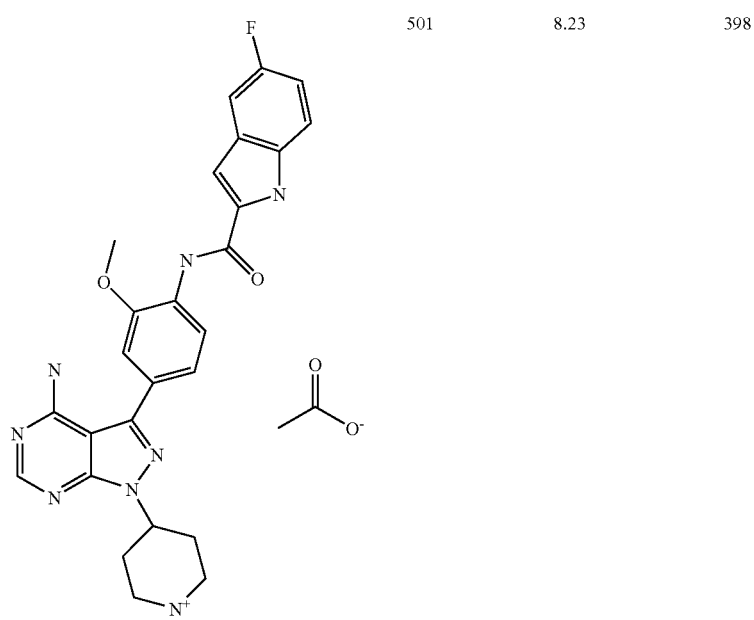 | 501 | 8.23 | 398 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 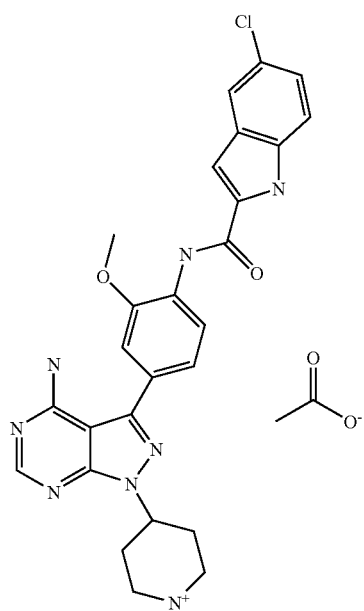 | 517 | 8.7 | 399 |
| 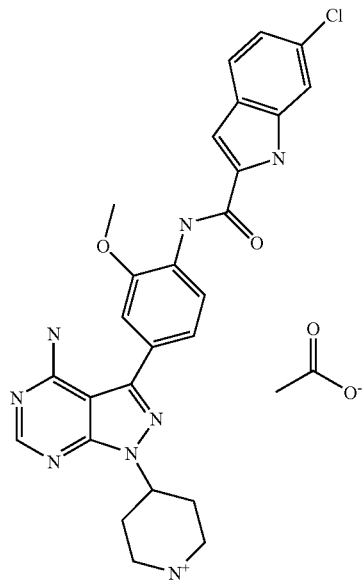 | 517 | 8.73 | 400 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 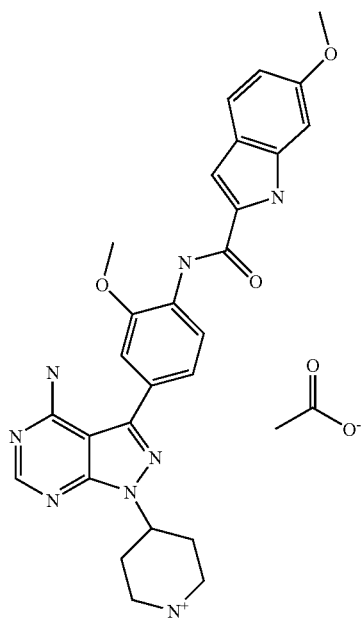 | 513 | 7.83 | 401 |
| 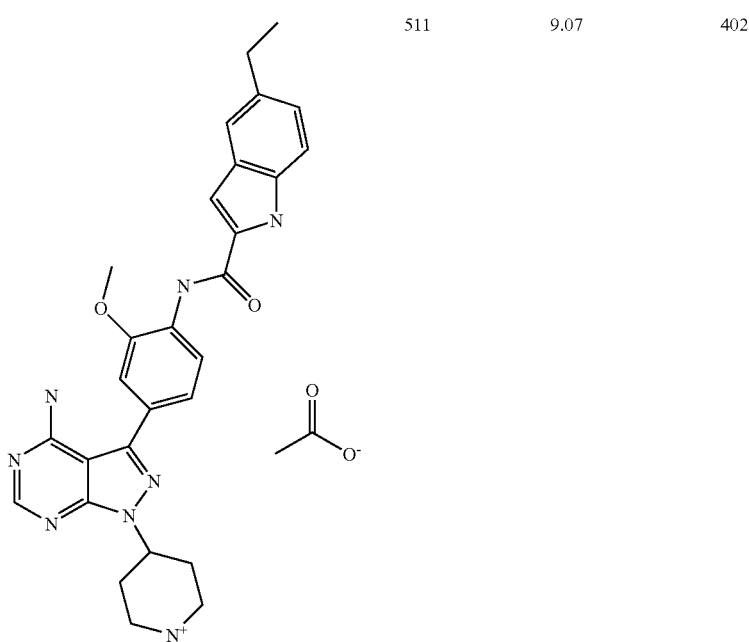 | 511 | 9.07 | 402 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 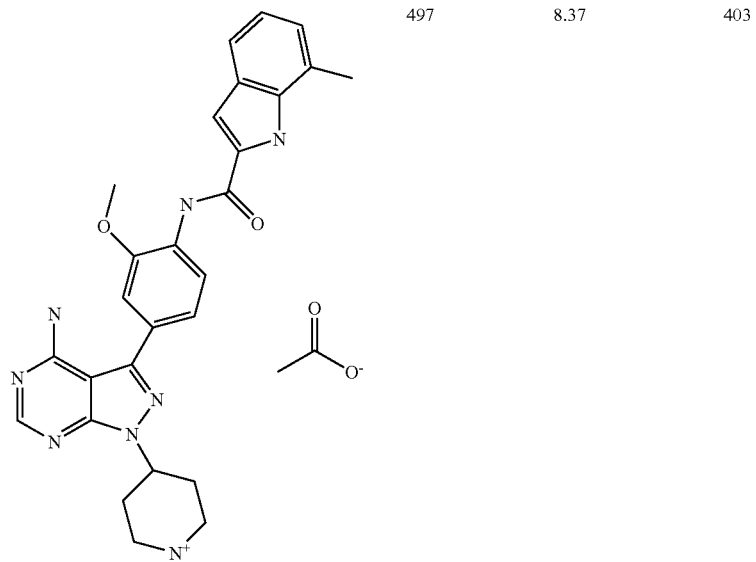 | 497 | 8.37 | 403 |
| 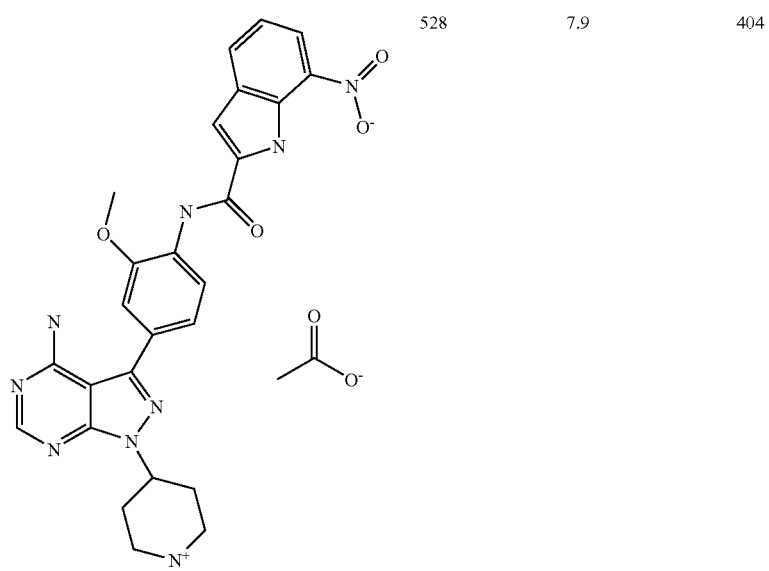 | 528 | 7.9 | 404 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 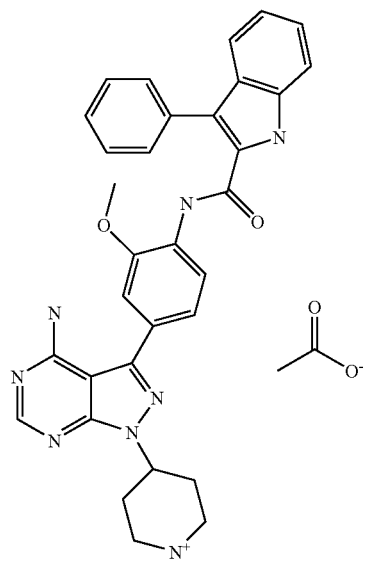 | 559 | 9.5 | 405 |
| 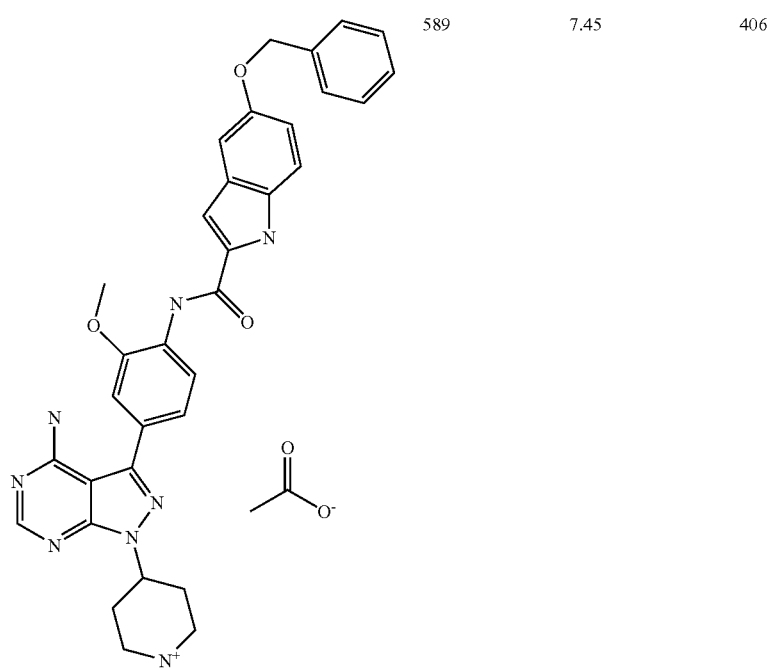 | 589 | 7.45 | 406 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 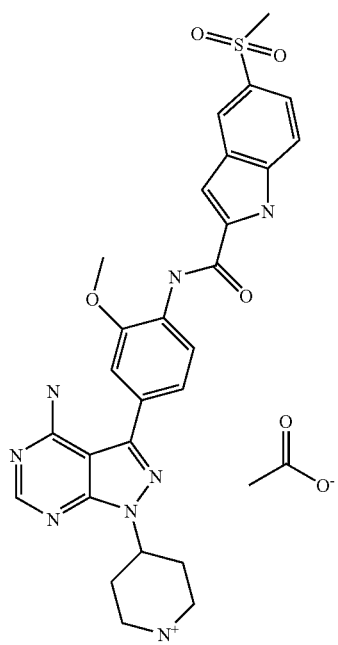 | 561 | 4.52 | 407 |
| 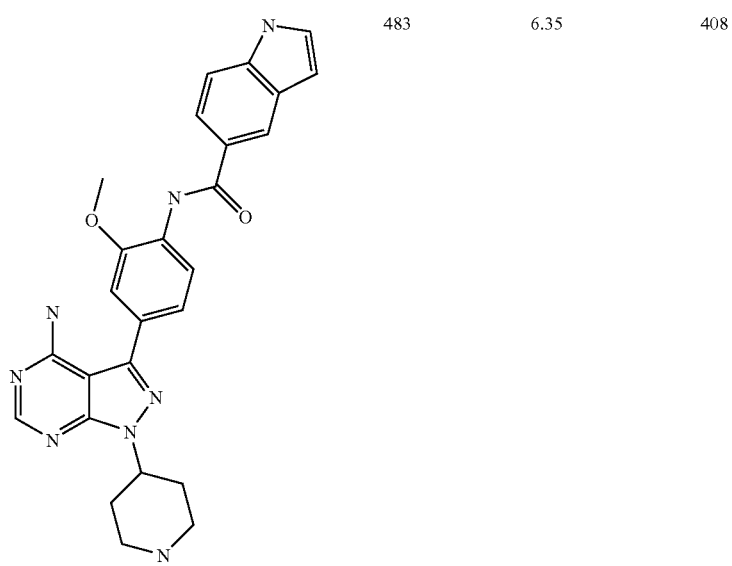 | 483 | 6.35 | 408 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 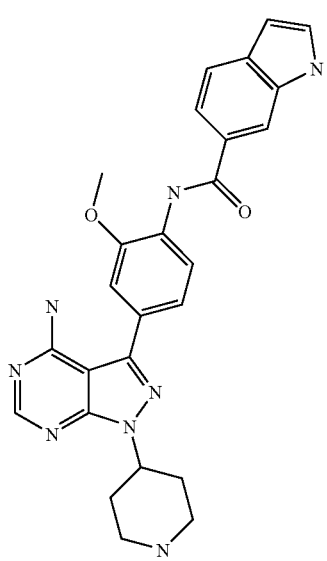 | 483 | 7.05 | 409 |
| 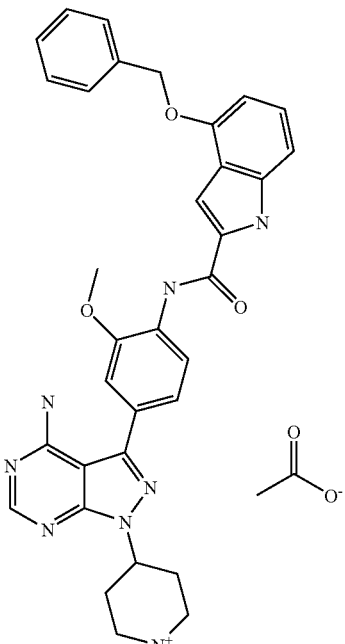 | 589 | 6.63 | 410 |

Example 411

4-[4-Amino-3-(4-{[(1-ethyl-1H-2-indolyl)carbonyl]amino}-3-methoxyphenyl)-1H-pyrazolo [3,4-d]pyrimidin-1-yl]hexahydropyridinium acetate

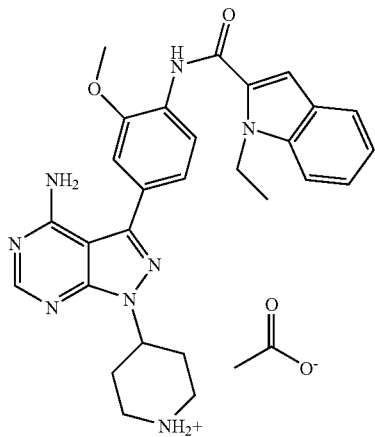

Sodium hydride, 60% suspension in mineral oil (0.006 g, 0.15 mmol) was added into the solution of N2-{4-[4-amino-1-(4-piperidyl)-1H-pyrazolo[3,4-d]pyrimidin-3-yl]-2-methoxyphenyl}-1H-2-indolecarboxamide (0.08 g, 0.14 mmol) in N,N-dimethylforamide (1.0 mL) at 0° C. The mixture was stirred at 0° C. for 10 minutes and at ambient temperature for 20 minutes. A solution of ethyl iodide (0.02 g, 0.14 mmol) in N,N-dimethylforamide (0.5 mL) was added in and the mixture was stirred at ambient temperature overnight. Ethyl iodide (0.01 g, 0.07 mmol) was added in and the mixture was stirred at ambient temperature overnight. Trifluoroacetic acid (3 mL) was added and the mixture was stirred at ambient temperature for 24 hours. The solvents and excess reagents were evaporated under reduced pressure and the residue was purified by preparative HPLC to yield 4-[4-amino-3-(4-{[(1-ethyl-1H-2-indolyl)carbonyl]amino}-3-methoxyphenyl)-1H-pyrazolo[3,4-d]pyrimidin-1-yl]hexahydropyridinium acetate (0.05 g, 0.09 mmol) as a white solid: $^1$H NMR (DMSO-$d_6$, 400 MHz) δ 9.43 (s, 1H), 8.27 (s, 1H), 8.14 (d, 1H), 7.71(d, 1H), 7.61 (d, 1H), 7.34 (s, 2H), 7.31 (t, 2H), 7.15 (t, 1H), 4.96 (m, 1H), 4.62 (q, 2H), 3.96 (s, 3H), 3.00 (m, 2H), 2.28 (m, 2H), 2.03 (m, 2H), 1.91 (s, 3H), 1.33 (t, 3H); MS: MH$^+$ 511.

Example 412 to 416

The same protocol that was used to prepare 4-[4-amino-3-(4-{[(1-ethyl-1H-2-indolyl)carbonyl]amino}-3-methoxyphenyl)-1H-pyrazolo[3,4-d]pyrimidin-1-yl]hexahydropyridinium acetate (Example 903) was used to prepare Examples 412-416.

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 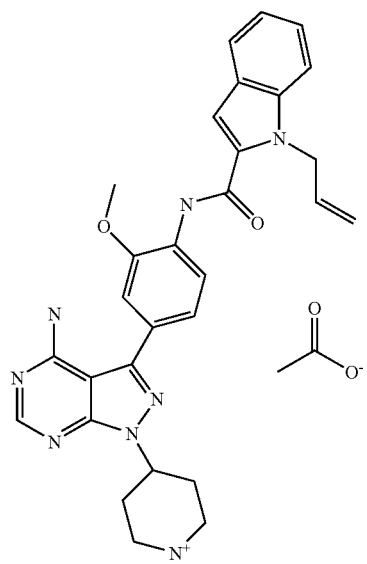 | 523 | 9.12 | 412 |

-continued
| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
| --- | --- | --- | --- |
| 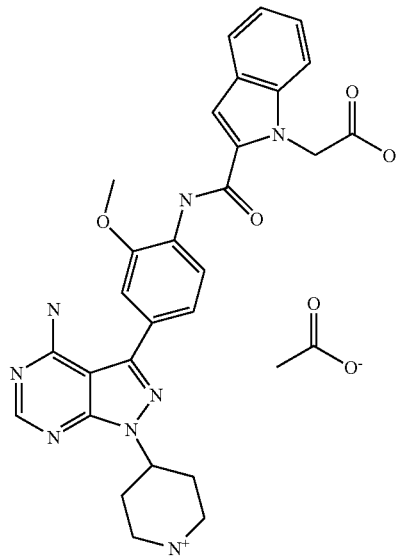 | 540 | 6.03 | 413 |
| 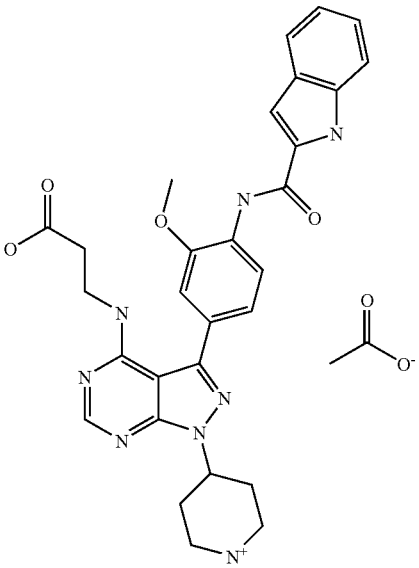 | 555 | 5.30 | 414 |

| Structure | MS: MH+ | HPLC Rt (min) (Hypersil C18, 5 μm, 100 A, 250 × 4.6 mm; 25%-100% acetonitrile - 0.05 M ammonium acetate over 10 min, 1 mL/min) | Example No. |
|---|---|---|---|
| 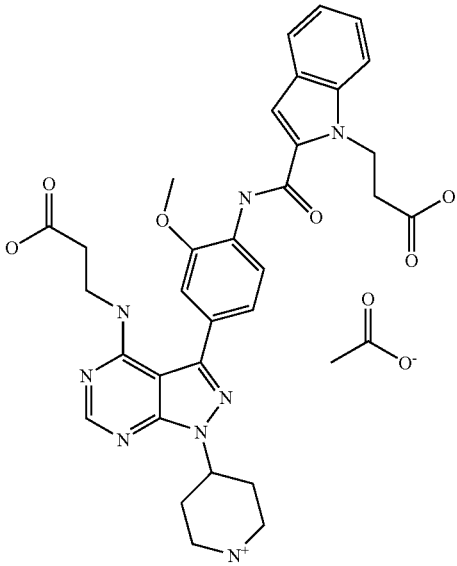 | 627 | 6.55 | 415 |
| 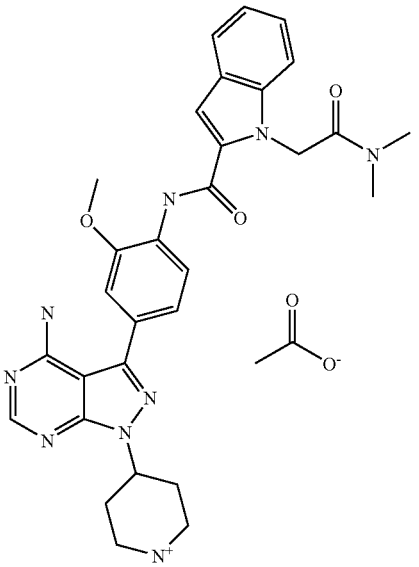 | 568 | 7.33 | 416 |

Example 417

N2-4-[4-Amino-1-(4-piperidyl)-1H-pyrazolo[3,4-d]pyrimidin-3-yl]-2-methoxyphenyl-5-hydroxy-1H-2-indolecarboxamide acetate salt

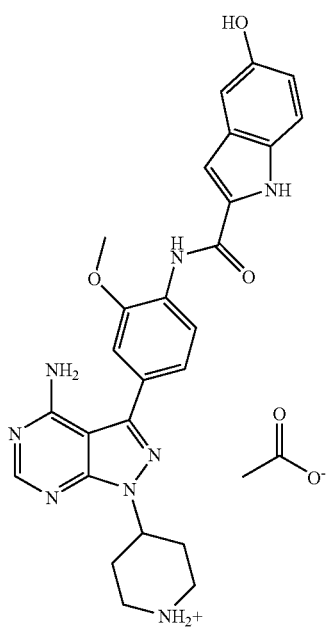

A mixture of N2-4-[4-amino-1-(4-piperidyl)-1H-pyrazolo[3,4-d]pyrimidin-3-yl]-2-methoxyphenyl-5-(benzyloxy)-1H-2-indolecarboxamide (0.08 g, 0.14 mmol), 10% palladium on carbon (0.03 g) and trifluroacetic acid (a drop) in ethanol (12 mL) and tetrahydrofuran (12 mL) was hydrogenated under one atmosphere of hydrogen overnight. The mixture was filtered and the filtrate was purified by preparative HPLC to yield N2-4-[4-amino-1-(4-piperidyl)-1H-pyrazolo[3,4-d]pyrimidin-3-yl]-2-methoxyphenyl-5-hydroxy-1H-2-indolecarboxamide acetate salt (0.02 g, 0.03 mmol) as a white solid:

$^1$H NMR (DMSO-$d_6$, 400 MHz) δ 11.55 (s, 1H), 9.29 (s, 1H), 8.88 (s, 1H), 8.28 (s, 1H), 8.18(d, 1H), 7.31 (m, 3H), 7.18 (s, 1H), 6.94 (s, 1H), 6.78 (dd, 1H), 5.06 (m, 1H), 3.97 (s, 3H), 3.44 (m, 2H), 3.17 (m, 2H), 2.39 (m, 2H), 2.11 (m, 2H), 1.91 (s, 3H); MS: MH$^+$ 499.

Example 418

N2-4-[4-Amino-1-(4-piperidyl)-1H-pyrazolo[3,4-d]pyrimidin-3-yl]-2-methoxyphenyl-4-hydroxy-1H-2-indolecarboxamide acetate salt

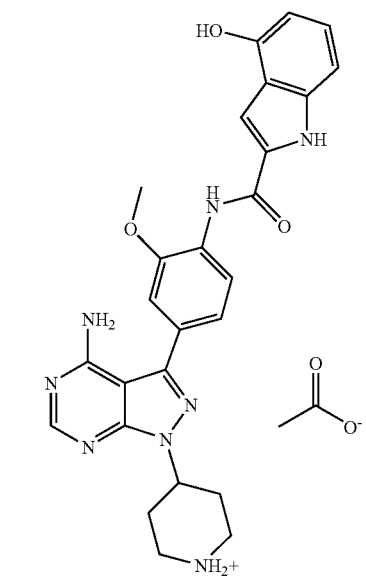

The same protocol that was used to prepare N2-4-[4-amino-1-(4-piperidyl)-1H-pyrazolo[3,4-d]pyrimidin-3-yl]-2-methoxyphenyl-5-hydroxy-1H-2-indolecarboxamide acetate salt was used to prepare N2-4-[4-amino-1-(4-piperidyl)-1H-pyrazolo[3,4-d]pyrimidin-3-yl]-2-methoxyphenyl-4-hydroxy-1H-2-indolecarboxamide acetate salt. RP-HPLC (Hitachi HPLC, Hypersil C18, 5 μm, 100A, 250×4.6 mm; 25%-100% acetonitrile—0.05M ammonium acetate over 10 min, 1 mL/min) R$_t$ 4.60 min. MS: MH$^+$ 499.

Example 419

N2-4-[4-Amino-1-(4-piperidyl)-1H-pyrazolo[3,4-d]pyrimidin-3-yl]-2-methoxyphenyl-7-amino-1H-2-indolecarboxamide acetate salt

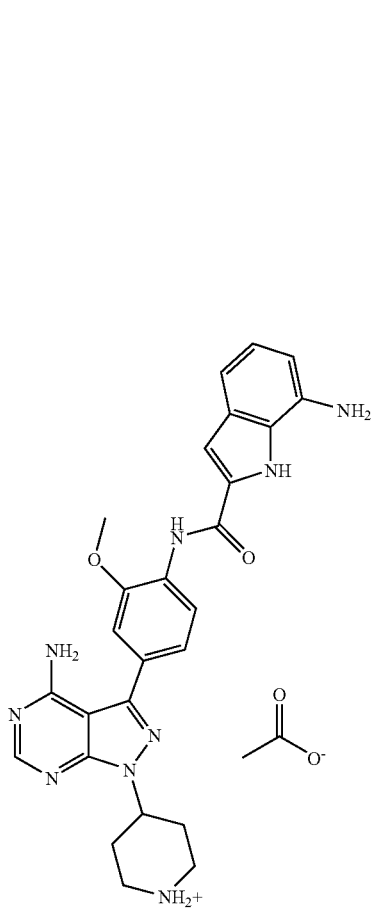

Sodium dithionite (0.07 g, 0.41 mmol) was added into a hot solution of N2-4-[4-amino-1-(4-piperidyl)-1H-pyrazolo[3,4-d]pyrimidin-3-yl]-2-methoxyphenyl-7-nitro-1H-2-indolecarboxamide acetate salt (0.04 g, 0.07 mmol) in water (2 mL) and ethanol (2 mL). The mixture was allowed to cool to ambient temperature. One drop of concentrated hydrochloric acid was added and the mixture was purified by preparative HPLC to yield N2-4-[4-amino-1-(4-piperidyl)-1H-pyrazolo[3,4-d]pyrimidin-3-yl]-2-methoxyphenyl-7-amino-1H-2-indolecarboxamide acetate salt (0.004 g, 0.01 mmol) as a white solid: RP-HPLC (Hitachi HPLC, Hypersil C18, 5 μm, 100A, 250×4.6 mm; 25%-100% acetonitrile—0.05M ammonium acetate over 10 min, 1 mL/min) $R_t$ 6.60 min. MS: MH$^+$ 498.

Example 420

N3-4-[4-Amino-1-(4-piperidyl)-1H-pyrazolo[3,4-d]pyrimidin-3-yl]-2-methoxyphenyl-1H-3-indolecarboxamide acetate salt

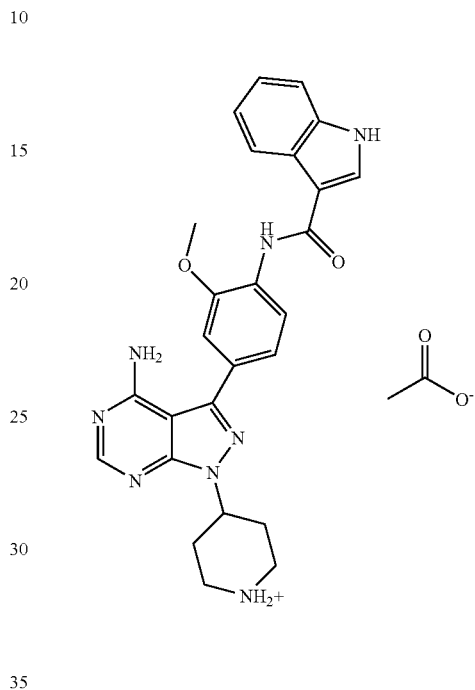

A. N3-[2-methoxy-4-(4,4,5,5-tetramethyl-1,3,2-dioxaborolan-2-yl)phenyl]-1H-3-indolecarboxamide Oxalyl chloride (0.07 mL, 0.79 mmol) was added into a solution of indole-3-carboxylic acid (0.12 g, 0.72 mmol) in dichloromethane (4 mL) and tetrahydrofuran (3 mL) at 0° C. N,N-dimethylforamide (3 drops from 0.1 mL syringe) was added and the mixture was stirred at 0° C. for 10 minutes and at ambient temperature for 20 minutes. The solvents and excess of reagents were evaporated under reduced pressure. The residue was taken into dichloromethane (2 mL) and the resulting solution (1.5 mL) was added into a solution of 2-methoxy-4-(4,4,5,5-tetramethyl-1,3,2-dioxaborolan-2-yl) aniline (0.09 g, 0.36 mmol) and pyridine (1 mL) in dichloromethane (2 mL). The mixture was stirred at ambient temperature overnight. The acid chloride solution in dichloromethane (0.3 mL) was added in and the mixture was stirred overnight. Water (a drop) was added in. The volatile components were evaporated under reduced pressure. The residue was partitioned between water and ethyl acetate. The aqueous layer was separated and extracted with ethyl acetate. The organic extracts were combined and washed with saturated aqueous sodium chloride solution and dried over magnesium sulfate. The mixture was filtered and the solvent of the filtrate was evaporated to yield the crude which was purified by flash column chromatography on silica using n-heptane: ethyl acetate (2/1) as a mobile phase to yield N3-[2-methoxy-4-(4,4,5,5-tetramethyl-1,3,2-dioxaborolan-2-yl)phenyl]-1H-3-indolecarboxamide (0.11 g, 0.28 mmol) as a white solid: $^1$H NMR (CDCl$_3$, 400 MHz)

δ 8.65 (m, 3H), 8.13 (d, 1H), 7.95 (s, 1H), 7.50 (m, 2H), 7.33(m, 3H), 4.02 (s, 3H), 1.36 (s, 12H); MS: MH+ 393.

B. N3-4-[4-Amino-1-(4-piperidyl)-1H-pyrazolo [3,4-d]pyrimidin-3-yl]-2-methoxyphenyl-1H-3-indolecarboxamide acetate salt A mixture of N3-[2-methoxy-4-(4,4,5,5-tetramethyl-1,3,2-dioxaborolan-2-yl)phenyl]-1H-3-indolecarboxamide (0.11 g, 0.28 mmol), 3-iodo-1-(4-piperidyl)-1H-pyrazolo[3,4-d]pyrimidin-4-amine hydrochloric salt (0.10 g, 0.27 mmol), tetrakis(triphenyl-phosphine)palladium(0) (0.02 g, 0.02 mmol) and sodium carbonate monohydrate (0.13 g, 1.07 mmol) was heated in a mixture of ethylene glycol dimethyl ether (4 mL) and water (2 mL) at 85° C. overnight under an atmosphere of nitrogen. The mixture was allowed to cool to ambient temperature and solvents were removed under the reduced pressure. The residue was purified by preparative HPLC to yield N3-4-[4-amino-1-(4-piperidyl)-1H-pyrazolo[3,4-d]pyrimidin-3-yl]-2-methoxyphenyl-1H-3-indolecarboxamide acetate salt (0.09 g, 0.16 mmol) as a white solid: $^1$H NMR (DMSO-$d_6$, 400 MHz) δ 11.83 (br, 1H), 8.92 (s, 1H), 8.31 (m, 3H), 8.14 (dd, 1H), 7.50 (dd, 1H), 7.31 (m, 2H), 7.20 (m, 2H), 4.82 (m, 1H), 3.99 (s, 3H), 3.16 (m, 2H), 2.73 (m, 2H), 2.15 (m, 2H), 1.91 (s, 3H), 1.88 (m, 2H); MS: MH+ 483.

Example 421

N4-4-[4-Amino-1-(4-piperidyl)-1H-pyrazolo [3,4-d] pyrimidin-3-yl]-2-methoxyphenyl-1H-4-indolecarboxamide acetate salt

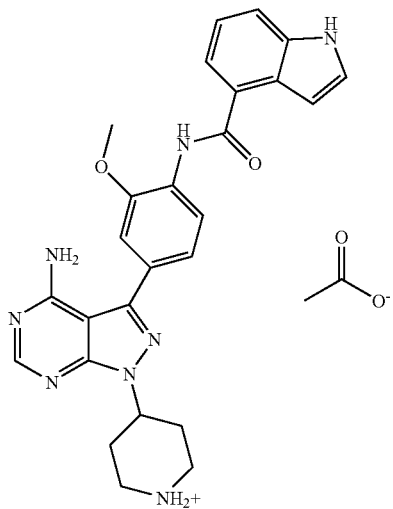

The same protocol that prepare N3-4-[4-amino-1-(4-piperidyl)-1H-pyrazolo[3,4-d]pyrimidin-3-yl]-2-methoxyphenyl-1H-3-indolecarboxamide acetate salt was used to N4-4-[4-amino-1-(4-piperidyl)-1H-pyrazolo[3,4-d]pyrimidin-3-yl]-2-methoxyphenyl-1H-4-indolecarboxamide acetate salt. RP-HPLC (Hitachi HPLC, Hypersil C18, 5 μm, 100A, 250×4.6 mm; 25%-100% acetonitrile—0.05M ammonium acetate over 10 min, 1 mL/min) $R_t$ 4.80 min. MS: MH+ 483.

Example 422 trans-N-2-(4-{4-amino-1-[4-(4-methylpiperazino) cyclohexyl]-1H-pyrazolo[3,4-d]pyrimidin-3-yl}-2-methoxyphenyl)-1-methyl-1H-2-indolecarboxamide A. 1-methyl-1H-2-indolecarbonyl chloride A suspension of 1-methylindole-2-carboxylic acid (9.87 g, 56.4 mmol) in dichloro-methane (150 mL) was reacted with oxalyl chloride (8.58 g, 67.63 mmol). DMF was added (0.2 mL), upon which a vigorous reaction transpired. The mixture was stirred at ambient temperature for four hours. The solvent was removed in vacuo to give 1-methyl-1H-2-indolecarbonyl chloride (10.69 g, 98%) as a light yellow solid.
$^1$H NMR (CDCl$_3$, 400 MHz) δ 7.70 (d, 1H), 7.66 (s, 1H), 7.44 (t, 1H), 7.35 (d, 1H), 7.18 (t, 1H), 3.98 (s, 3H).

B. N2-[2-methoxy-4-(4,4,5,5-tetramethyl-1,3,2-dioxaborolan-2-yl)phenyl]-1-methyl-1H-2-indolecarboxamide To a solution containing 1-methyl-1H-2-indolecarbonyl chloride (5.44 g, 0.0281 mol) and 2-methoxy-4-(4,4,5,5-tetramethyl-1,3,2-dioxaborolan-2-yl)aniline (7.00 g, 0.0281 mol) in anhydrous dichloromethane (150 mL), N-ethyl-N,N-diisopropylamine (4.9 mL, 0.0309 mol) was added dropwise at 0° C. and the resulting solution was stirred at ambient temperature under an atmosphere of nitrogen for 18 hours. The reaction mixture was concentrated under reduced pressure and the residue was partitioned between water (150 mL) and ethyl acetate (150 mL), The organic phase was washed with brine, dried with magnesium sulfate and concentrated under reduced pressure. The residue was purified by flash chromatography on silica using ethyl acetate/n-heptane (1:6)) as mobile phase to yield N2-[2-methoxy-4-(4,4,5,5-tetramethyl-1,3,2-dioxaborolan-2-yl)phenyl]-1-methyl-1H-2-indolecarboxamide (8.0 g, 0.0197 mol) as a white solid.
$^1$H NMR (DMSO-$d_6$, 400 MHz) δ 9.35 (s, 1H), 8.03 (d, 1H), 7.69 (d, 1H), 7.57 (d, 1H), 7.33 (m, 3H), 7.29 (s, 1H), 7.14 (t, 1H), 4.02 (s, 3H), 3.91 (s, 3H), 1.31 (s, 12H).
TLC (ethyl acetate/heptane 1:3) $R_f$ 0.44

C. trans-N-2-(4-{4-amino-1-[4-(4-methylpiperazino) cyclohexyl]-1H-pyrazolo[3,4-d]pyrimidin-3-yl}-2-methoxyphenyl)-1-methyl-1H-2-indolecarboxamide A suspension of trans-3-iodo-1-[4-(4-methylpiperazino)cyclohexyl]-1H-pyrazolo[3,4-d]pyrimidin-4-amine (0.100 g, 0.227 mmol) in ethylene glycol dimethyl ether (8 mL) was treated with N2-[2-methoxy-4-(4,4,5,5-tetramethyl-1,3,2-dioxaborolan-2-yl)phenyl]-1-methyl-1H-2-indolecarboxamide (0.097 g, 0.238 mmol), tetrakis(triphenylphosphine) palladium (0.016 g, 0.014 mmol), and a solution of sodium carbonate (0.057 g, 0.538 mmol) in water (4 mL). The reaction mixture was stirred for 21.5 h at 80° C. The precipitate was filtered, and the organic layer was evaporated under reduced pressure. Dichloromethane (15 mL) was added and the layers were partitioned. The aqueous layer was extracted with dichloromethane (200 mL). The combined organic layers were dried over magnesium sulfate, filtered, and evaporated under reduced pressure. The crude material was purified by flash chromatography on silica gel using a 10% methanol in dichloromethane to 50% methanol in dichloromethane step gradient on Sq 16×ISCO Combi- Flash. The column afforded 0.083 g (68%) of trans-N-2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide. $^1$H NMR (d$_6$-DMSO) δ 9.4316 (s, 1H), 8.2427 (s, 1H), 8.1207-8.1003 (d, 1H, J=8.16 Hz), 7.7173-7.6974 (d, 1H, J=7.96 Hz), 7.5979-7.5769 (d, 1H, J=8.4 Hz), 7.3507-7.2758 (m, 4H), 7.1695-7.1321 (t, 1H), 4.6893-4.6324 (m, 1H), 4.0400 (s, 3H), 3.9571 (s, 3H), 2.5 (m, 3H), 2.4055-2.3279 (m, 5H), 2.1606 (s, 3H), 2.1094-1.9367 (m, 6H), 1.5214-1.4624 (m, 2H); LCMS (Thermoquest AQA single-quad MS, Genesis C18 column, 3 μm particle size, 33×4.6 mm; 70% 50 mM ammonium Acetate in Water to 95% Acetonitrile over 6 min, 0.8 to 0.5 mL/min) R$_t$ 2.12 min (100%), MH$^+$ 594.3.

Example 423

N2-{4-[4-amino-1-(2-amino-4-pyridyl)-1H-pyrazolo[3,4-d]pyrimidin-3-yl]-2-methoxyphenyl-}1-methyl-1H-2-indolecarboxamide

Example 424

N2-(4-{4-amino-1-[2-(methylamino)-4-pyridyl]-1H-pyrazolo[3,4-d]pyrimidin-3-yl}-2-methoxyphenyl)-1-methyl-1H-2-indolecarboxamide

Example 425

N2-(4-{4-amino-1-[2-(dimethylamino)-4-pyridyl]-1H-pyrazolo[3,4-d]pyrimidin-3-yl}-2-methoxyphenyl)-1-methyl-1H-2-indolecarboxamide

Example 426

N2-(4-{4-amino-1-[2-(4-methylpiperazino)-4-pyridyl]-1H-pyrazolo[3,4-d]pyrimidin-3-yl}-2-methoxyphenyl)-1H-2-indolecarboxamide

Example 427

N2-(4-{4-amino-1-[2-(4-methylpiperazino)-4-pyridyl]-1H-pyrazolo[3,4-d]pyrimidin-3-yl}-2-methoxyphenyl)-1H-2-indolecarboxamide

Example 428

N2-{4-[4-amino-1-(2-morpholino-4-pyridyl)-1H-pyrazolo[3,4-d]pyrimidin-3-yl]-2-methoxyphenyl}-1-methyl-1H-2-indolecarboxamide

Example 429

N2-[4-(4-amino-1-{2-[(2-hydroxyethyl)amino]-4-pyridyl}-1H-pyrazolo[3,4-d]pyrimidin-3-yl)-2-methoxyphenyl]-1-methyl-1H-2-indolecarboxamide

Example 430

N2-(4-{4-amino-1-[2-(aminomethyl)-4-pyridyl]-1H-pyrazolo[3,4-d]pyrimidin-3-yl}-2-methoxyphenyl)-1-methyl-1H-2-indolecarboxamide

Example 431

N2-(4-{4-amino-1-[2-(aminocarbonyl)-4-pyridyl]-1H-pyrazolo[3,4-d]pyrimidin-3-yl}-2-methoxyphenyl)-1-methyl-1H-2-indolecarboxamide

Example 432

3-morpholino-1-(2-morpholino-4-pyridyl)-1H-pyrazolo[3,4-d]pyrimidin-4-amine

Example 433

N2-{4-[4-amino-1-(4-amino-2-pyridyl)-1H-pyrazolo[3,4-d]pyrimidin-3-yl]-2-methoxyphenyl}-1-methyl-1H-2-indolecarboxamide

Example 434

N2-{4-[4-amino-1-(2-oxo-1,2-dihydro-4-pyridinyl)-1H-pyrazolo[3,4-d]pyrimidin-3-yl]-2-methoxyphenyl}-1-methyl-1H-2-indolecarboxamide

Example 435

N2-{4-[4-amino-1-(4-morpholino-2-pyridyl)-1H-pyrazolo[3,4-d]pyrimidin-3-yl]-2-methoxyphenyl}-1-methyl-1H-2-indolecarboxamide

Example 436

N2-(4-{4-amino-1-[4-(4-methylpiperazino)-2-pyridyl]-1H-pyrazolo[3,4-d]pyrimidin-3-yl}-2-methoxyphenyl)-1-methyl-1H-2-indolecarboxamide

Example 437

N2-[4-(4-amino-1-{4-[(2-hydroxyethyl)amino]-2-pyridyl}-1H-pyrazolo[3,4-d]pyrimidin-3-yl)-2-methoxyphenyl]-1-methyl-1H-2-indolecarboxamide

Example 438

N2-{4-[4-amino-1-(6-amino-3-pyridyl)-1H-pyrazolo[3,4-d]pyrimidin-3-yl]-2-methoxyphenyl}-1-methyl-1H-2-indolecarboxamide

Example 439

N2-{4-[4-amino-1-(6-morpholino-3-pyridyl)-1H-pyrazolo[3,4-d]pyrimidin-3-yl]-2-methoxyphenyl}-1-methyl-1H-2-indolecarboxamide

Example 440

N2-(4-{4-amino-1-[6-(4-methylpiperazino)-3-pyridyl]-1H-pyrazolo[3,4-d]pyrimidin-3-yl}-2-methoxyphenyl)-1-methyl-1H-2-indolecarboxamide

Example 441

Cis-4-[4-(4-amino-3-{3-fluoro-4-[(5-methyl-1,3-benzoxazol-2-yl)amino]phenyl}-1H-pyrazolo[3,4-d]pyrimidin-1-yl)cyclohexyl]-2-piperazinone

Example 442

Trans-4-[4-(4-amino-3-{3-fluoro-4-[(5-methyl-1,3-benzoxazol-2-yl)amino]phenyl}-1H-pyrazolo[3,4-d]pyrimidin-1-yl)cyclohexyl]-2-piperazinone

Example 443

Cis-4-[4-(4-amino-3-{4-[(5-methyl-1,3-benzoxazol-2-yl)amino]phenyl}-1H-pyrazolo [3,4-d]pyrimidin-1-yl)cyclohexyl]-2-piperazinone

Example 444

Trans-4-[4-(4-amino-3-{4-[(5-methyl-1,3-benzoxazol-2-yl)amino]phenyl}-1H-pyrazolo[3,4-d]pyrimidin-1-yl)cyclohexyl]-2-piperazinone

Example 445

R-N-2-(4-{4-amino-1-[1-(1-methoxy-1-methylethyl)-3-piperidyl]-1H-pyrazolo[3,4-d]pyrimidin-3-yl}phenyl)-5,7-dimethyl-1,3-benzoxazol-2-amine

Example 446

S-N-2-(4-{4-amino-1-[1-(1-methoxy-1-methylethyl)-3-piperidyl]-1H-pyrazolo[3,4-d]pyrimidin-3-yl}phenyl)-5,7-dimethyl-1,3-benzoxazol-2-amine

Example 447

R/S-N-2-(4-{4-amino-1-[1-(1-methoxy-1-methylethyl)-3-piperidyl]-1H-pyrazolo[3,4-d]pyrimidin-3-yl}phenyl)-5,7-dimethyl-1,3-benzoxazol-2-amine

Example 448

R-N-2-(4-{4-amino-1-[1-(3-methoxypropyl)-3-piperidyl]-1H-pyrazolo[3,4-d]pyrimidin-3-yl}phenyl)-5,7-dimethyl-1,3-benzoxazol-2-amine

Example 449

S-N-2-(4-{4-amino-1-[1-(3-methoxypropyl)-3-piperidyl]-1H-pyrazolo[3,4-d]pyrimidin-3-yl}phenyl)-5,7-dimethyl-1,3-benzoxazol-2-amine

Example 450

R/S-N-2-(4-{4-amino-1-[1-(3-methoxypropyl)-3-piperidyl]-1H-pyrazolo[3,4-d]pyrimidin-3-yl}phenyl)-5,7-dimethyl-1,3-benzoxazol-2-amine

Example 451

R-N-2-(4-{4-amino-1-[1-(2-hydroxyethyl)-3-piperidyl]-1H-pyrazolo[3,4-d]pyrimidin-3-yl}phenyl)-5,7-dimethyl-1,3-benzoxazol-2-amine

Example 452

S-N-2-(4-{4-amino-1-[1-(2-hydroxyethyl)-3-piperidyl]-1H-pyrazolo[3,4-d]pyrimidin-3-yl}phenyl)-5,7-dimethyl-1,3-benzoxazol-2-amine

Example 453

R/S-N-2-(4-{4-amino-1-[1-(2-hydroxyethyl)-3-piperidyl]-1H-pyrazolo[3,4-d]pyrimidin-3-yl}phenyl)-5,7-dimethyl-1,3-benzoxazol-2-amine

Example 454

R-N-2-(4-{4-amino-1-[1-(2-{1,3-dihydroxypropyl})-3-piperidyl]-1H-pyrazolo[3,4-d]pyrimidin-3-yl}phenyl)-5,7-dimethyl-1,3-benzoxazol-2-amine

Example 455

S-N-2-(4-{4-amino-1-[1-(2-{1,3-dihydroxypropyl})-3-piperidyl]-1H-pyrazolo[3,4-d]pyrimidin-3-yl}phenyl)-5,7-dimethyl-1,3-benzoxazol-2-amine

Example 456

R/S-N-2-(4-{4-amino-1-[1-(2-{1,3-dihydroxypropyl})-3-piperidyl]-1H-pyrazolo[3,4-d]pyrimidin-3-yl}phenyl)-5,7-dimethyl-1,3-benzoxazol-2-amine

Example 457

R-2-[3-(4-amino-3-{4-[(5,7-dimethyl-1,3-benzoxazol-2-yl)amino]phenyl}-1H-pyrazolo[3,4-d]pyrimidin-1-yl)piperidino]acetonitrile

Example 458

S-2-[3-(4-amino-3-{4-[(5,7-dimethyl-1,3-benzoxazol-2-yl)amino]phenyl}-1H-pyrazolo[3,4-d]pyrimidin-1-yl)piperidino]acetonitrile

Example 459

R/S-2-[3-(4-amino-3-{4-[(5,7-dimethyl-1,3-benzoxazol-2-yl)amino]phenyl}-1H-pyrazolo[3,4-d]pyrimidin-1-yl)piperidino]acetonitrile

Example 460

R-N-2-(4-{4-amino-1-[1-(2-(methylsulfanyl)ethyl)-3-piperidyl]-1H-pyrazolo[3,4-d]pyrimidin-3-yl}phenyl)-5,7-dimethyl-1,3-benzoxazol-2-amine

Example 461

S-N-2-(4-{4-amino-1-[1-(2-(methylsulfanyl)ethyl)-3-piperidyl]-1H-pyrazolo[3,4-d]pyrimidin-3-yl}phenyl)-5,7-dimethyl-1,3-benzoxazol-2-amine

Example 462

R/S-N-2-(4-{4-amino-1-[1-(2-(methylsulfanyl)ethyl)-3-piperidyl]-1H-pyrazolo[3,4-d]pyrimidin-3-yl}phenyl)-5,7-dimethyl-1,3-benzoxazol-2-amine

Example 463

R-N-methoxy-3-(4-amino-3-{4-[(5,7-dimethyl-1,3-benzoxazol-2-yl)amino]phenyl}-1H-pyrazolo[3,4-d]pyrimidin-1-yl)-1-piperidinecarboximidamide

Example 464

S-N-methoxy-3-(4-amino-3-{4-[(5,7-dimethyl-1,3-benzoxazol-2-yl)amino]phenyl}-1H-pyrazolo[3,4-d]pyrimidin-1-yl)-11-pipeannecarboximidamide

Example 465

R/S-N-methoxy-3-(4-amino-3-1-{4-[(5,7-dimethyl-1,3-benzoxazol-2-yl)amino]phenyl}-1H-pyrazolo[3,4-d]pyrimidin-1-yl)-1-piperidinecarboximidamide

Example 466

R-N-2-(4-4-amino-1-[1-(1-2,2,2-trifluoroethyl)-3-piperidyl]-1H-pyrazolo[3,4-d]pyrimidin-3-ylphenyl)-5,7-dimethyl-1,3-benzoxazol-2-amine

Example 467

S-N-2-(4-4-amino-1-[1-(1-2,2,2-trifluoroethyl)-3-piperidyl]-1H-pyrazolo[3,4-d]pyrimidin-3-ylphenyl)-5,7-dimethyl-1,3-benzoxazol-2-amine

Example 960

R/S-N-2-(4-4-amino-1-[1-(1-2,2,2-trifluoroethyl)-3-piperidyl]-1H-pyrazolo [3,4-d]pyrimidin-3-ylphenyl)-5,7-dimethyl-1,3-benzoxazol-2-amine

Example 468

N2-{4-[4-amino-1-(1H-4-imidazolylmethyl)-1H-pyrazolo[3,4-d]pyrimidin-3-yl]phenyl}-5,7-dimethyl-1,3-benzoxazol-2-amine

Example 469

N2-(4-{4-amino-1-[1H-4-(2-methyl-imidazolyl)methyl]-1H-pyrazolo[3,4-d]pyrimidin-3-yl}phenyl)-5,7-dimethyl-1,3-benzoxazol-2-amine

Example 470

N2-(4-{4-amino-1-[1H-4-(2-amino-imidazolyl)methyl]-1H-pyrazolo[3,4-d]pyrimidin-3-yl}phenyl)-5,7-dimethyl-1,3-benzoxazol-2-amine

Example 471

N2-4-[4-amino-1-(1H-4-imidazolyl)-1H-pyrazolo[3,4-d]pyrimidin-3-yl]phenyl-5,7-dimethyl-1,3-benzoxazol-2-amine

Example 472

N2-(4-{4-amino-1-[1H-4-(2-amino-imidazolyl)]-1H-pyrazolo[3,4-d]pyrimidin-3-yl}phenyl)-5,7-dimethyl-1,3-benzoxazol-2-amine

Example 473

N2-(4-{4-amino-1-[1H-4-(2-methyl-imidazolyl)]-1H-pyrazolo[3,4-d]pyrimidin-3-yl}phenyl)-5,7-dimethyl-1,3-benzoxazol-2-amine

Example 474

1-(4-{4-amino-3-[4-(1,3-benzoxazol-2-ylamino)phenyl]-1H-pyrazolo[3,4-d]pyrimidin-1-yl}piperidino)-2-methyl-2-(methylamino)-1-propanone

Example 475

1-[4-(4-amino-3-{4-[(5-methyl-1,3-benzoxazol-2-yl)amino]phenyl}-1H-pyrazolo[3,4-d]pyrimidin-1-yl)piperidino]-2-methyl-2-(methylamino)-1-propanone

Example 476

1-[4-(4-amino-3-{4-[(5-ethyl-1,3-benzoxazol-2-yl)amino]phenyl}-1H-pyrazolo[3,4-d]pyrimidin-1-yl)piperidino]-2-methyl-2-(methylamino)-1-propanone

Example 477

1-[4-(4-amino-3-{4-[(5-chloro-1,3-benzoxazol-2-yl)amino]phenyl}-1H-pyrazolo[3,4-d]pyrimidin-1-yl)piperidino]-2-methyl-2-(methylamino)-1-propanone

Example 478

{4-[4-amino-1-(4-piperidyl)-1H-pyrazolo[3,4-d]pyrimidin-3-yl]phenyl}(1H-4-pyrazolyl)methanone

Example 479

1-(4-{4-[4-amino-1-(4-piperidyl)-1H-pyrazolo[3,4-d]pyrimidin-3-yl]benzoyl}-1H-1-pyrazolyl)-1-ethanone

Example 480

{4-[4-amino-1-(4-piperidyl)-1H-pyrazolo[3,4-d]pyrimidin-3-yl]phenyl}(1-methyl-1H-4-pyrazolyl)methanone

Example 481

1-{4-[4-amino-1-(4-piperidyl)-1H-pyrazolo [3,4-d]pyrimidin-3-yl]phenyl}(1-benzyl-1H-4-pyrazolyl)methanone

Example 482

{4-[4-amino-1-(4-piperidyl)-1H-pyrazolo[3,4-d]pyrimidin-3-yl]phenyl}(1-benzoyl-1H-4-pyrazolyl)methanone

Example 482

{4-[4-amino-1-(4-piperidyl)-1H-pyrazolo[3,4-d]pyrimidin-3-yl]phenyl}(5-isoxazolyl)methanone

Example 484

{4-[4-amino-1-(4-piperidyl)-1H-pyrazolo[3,4-d]pyrimidin-3-yl]phenyl}(3-methyl-5-isoxazolyl)methanone

Example 485

{4-[4-amino-1-(4-piperidyl)-1H-pyrazolo[3,4-d]pyrimidin-3-yl]phenyl}(3-phenyl-5-isoxazolyl)methanone

Example 486
N5-{4-[4-amino-1-(4-piperidyl)-1H-pyrazolo[3,4-d]pyrimidin-3-yl]phenyl}-3-phenyl-5-isoxazolamine
Example 487
N5-{4-[4-amino-1-(4-piperidyl)-1H-pyrazolo[3,4-d]pyrimidin-3-yl]phenyl}-3-(trifluoromethyl)-5-isoxazolamine
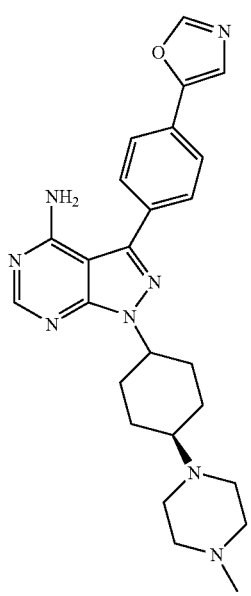
Example 488
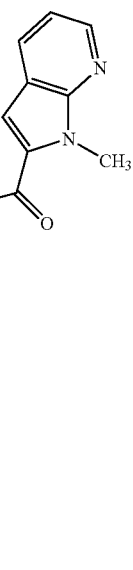
Example 489
Other Examples include the following compounds:
| Structure | Name |
|---|---|
| 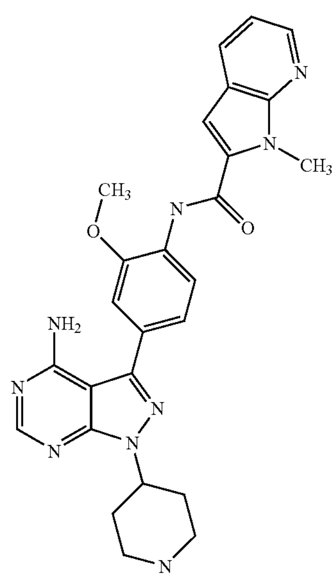 | N2-{4-[4-amino-1-(4-piperidyl)-1H-pyrazolo[3,4-d]pyrimidin-3-yl]-2-methoxyphenyl}-1-methyl-1H-pyrrolo[2,3-b]pyridine-2-carboxamide |

-continued

| Structure | Name |
|---|---|
| 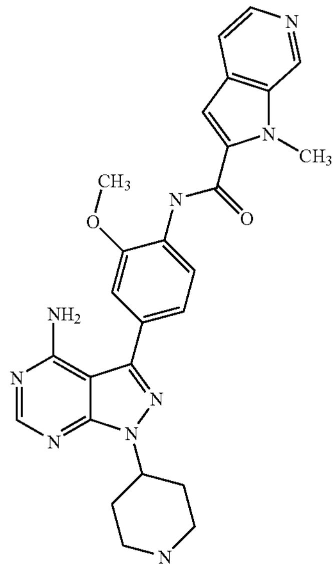 | N2-{4-[4-amino-1-(4-piperidyl)-1H-pyrazolo[3,4-d]pyrimidin-3-yl]-2-methoxyphenyl}-1-methyl-1H-pyrrolo[2,3-c]pyridine-2-carboxamide |
| 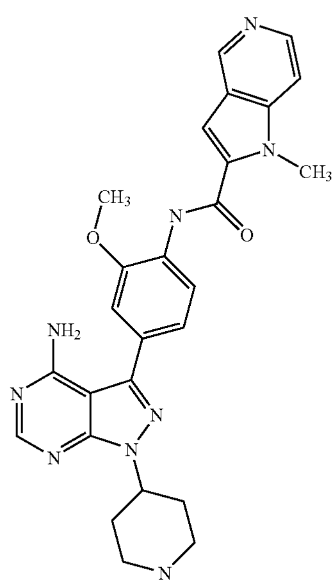 | N2-{4-[4-amino-1-(4-piperidyl)-1H-pyrazolo[3,4-d]pyrimidin-3-yl]-2-methoxyphenyl}-1-methyl-1H-pyrrolo[3,2-c]pyridine-2-carboxamide |

-continued
| Structure | Name |
|---|---|
| 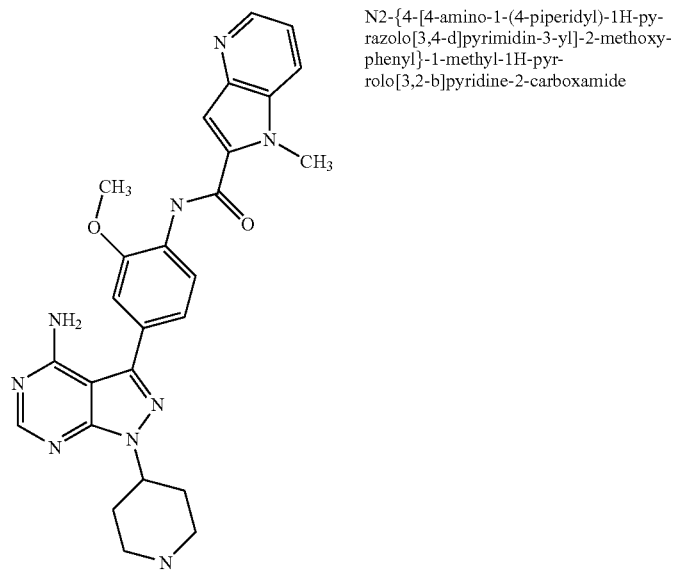 | N2-{4-[4-amino-1-(4-piperidyl)-1H-pyrazolo[3,4-d]pyrimidin-3-yl]-2-methoxyphenyl}-1-methyl-1H-pyrrolo[3,2-b]pyridine-2-carboxamide |
| 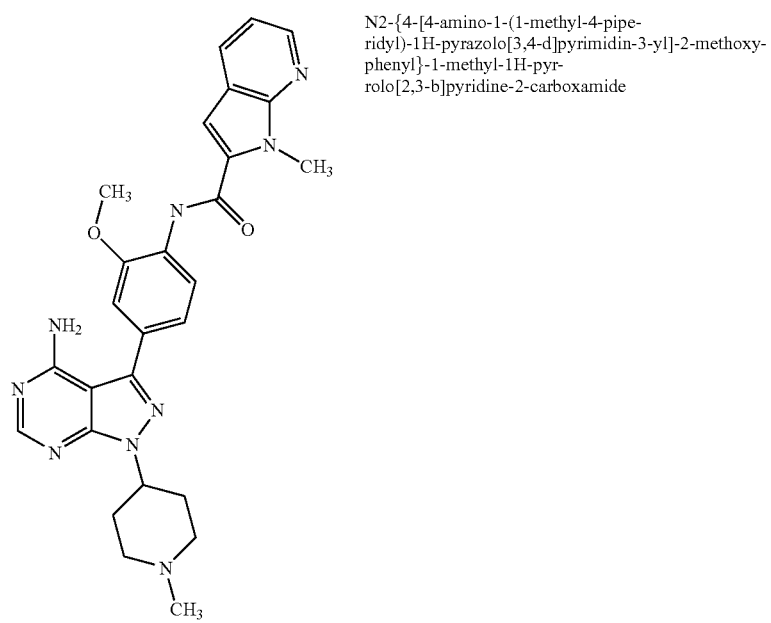 | N2-{4-[4-amino-1-(1-methyl-4-piperidyl)-1H-pyrazolo[3,4-d]pyrimidin-3-yl]-2-methoxyphenyl}-1-methyl-1H-pyrrolo[2,3-b]pyridine-2-carboxamide |

| Structure | Name |
|---|---|
| 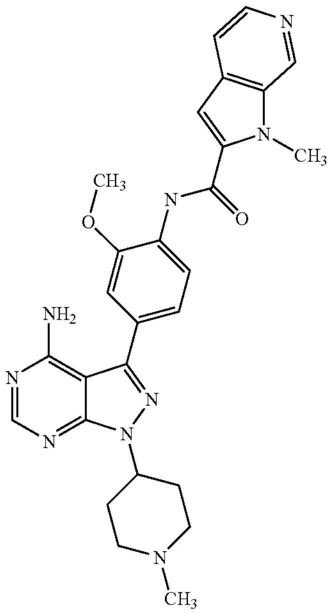 | N2-{4-[4-amino-1-(1-methyl-4-piperidyl)-1H-pyrazolo[3,4-d]pyrimidin-3-yl]-2-methoxyphenyl}-1-methyl-1H-pyrrolo[2,3-c]pyridine-2-carboxamide |
| 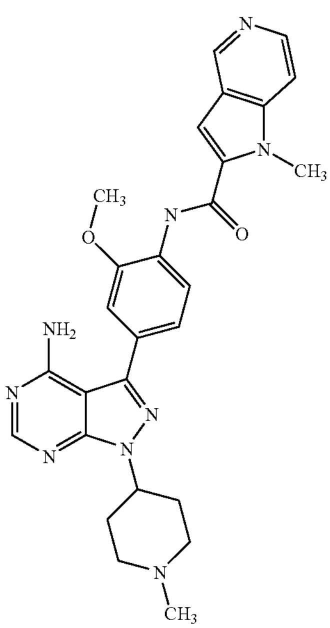 | N2-{4-[4-amino-1-(1-methyl-4-piperidyl)-1H-pyrazolo[3,4-d]pyrimidin-3-yl]-2-methoxyphenyl}-1-methyl-1H-pyrrolo[3,2-c]pyridine-2-carboxamide |

| Structure | Name |
|---|---|
| 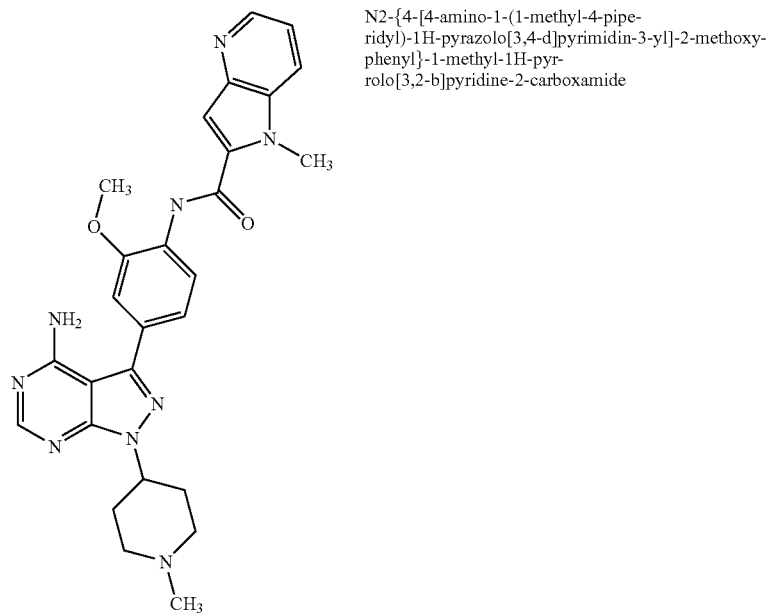 | N2-{4-[4-amino-1-(1-methyl-4-piperidyl)-1H-pyrazolo[3,4-d]pyrimidin-3-yl]-2-methoxyphenyl}-1-methyl-1H-pyrrolo[3,2-b]pyridine-2-carboxamide |
| 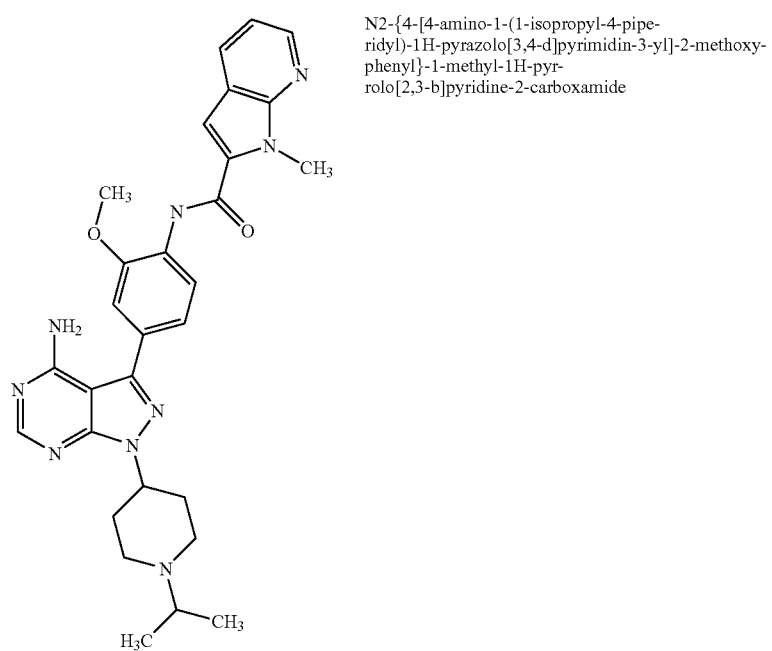 | N2-{4-[4-amino-1-(1-isopropyl-4-piperidyl)-1H-pyrazolo[3,4-d]pyrimidin-3-yl]-2-methoxyphenyl}-1-methyl-1H-pyrrolo[2,3-b]pyridine-2-carboxamide |

-continued

| Structure | Name |
|---|---|
| 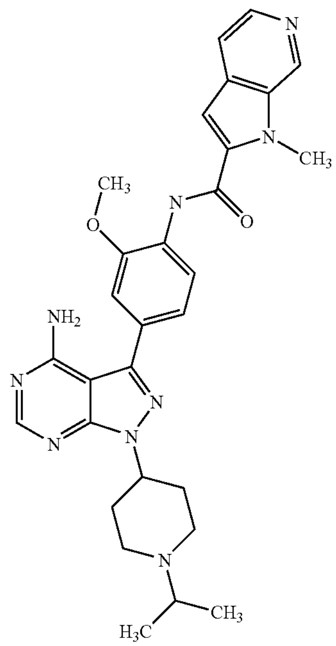 | N2-{4-[4-amino-1-(1-isopropyl-4-piperidyl)-1H-pyrazolo[3,4-d]pyrimidin-3-yl]-2-methoxyphenyl}-1-methyl-1H-pyrrolo[2,3-c]pyridine-2-carboxamide |
| 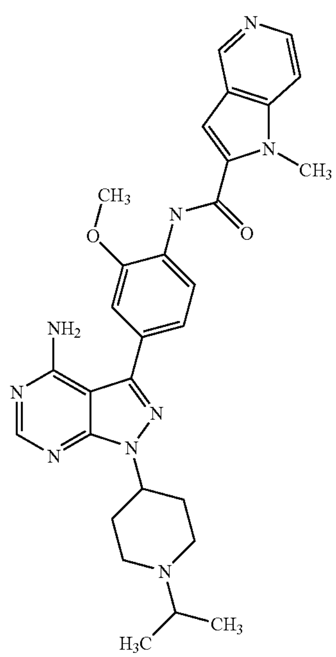 | N2-{4-[4-amino-1-(1-isopropyl-4-piperidyl)-1H-pyrazolo[3,4-d]pyrimidin-3-yl]-2-methoxyphenyl}-1-methyl-1H-pyrrolo[3,2-c]pyridine-2-carboxamide |

-continued

| Structure | Name |
|---|---|
| 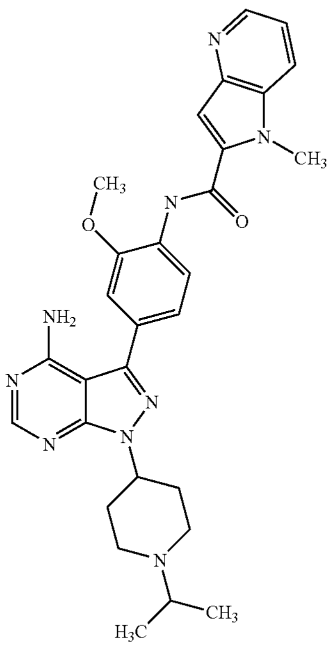 | N2-{4-[4-amino-1-(1-isopropyl-4-piperidyl)-1H-pyrazolo[3,4-d]pyrimidin-3-yl]-2-methoxyphenyl}-1-methyl-1H-pyrrolo[3,2-b]pyridine-2-carboxamide |
| 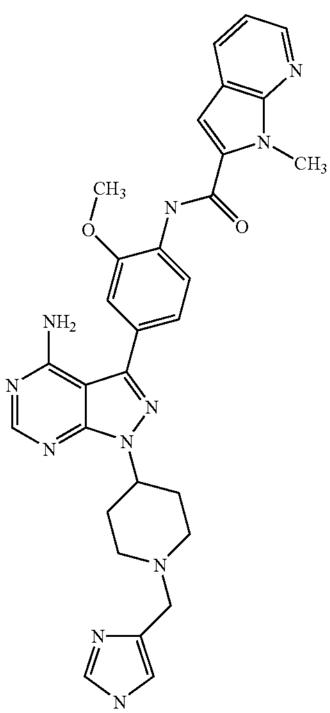 | N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-pyrrolo[2,3-b]pyridine-2-carboxamide |

-continued
| Structure | Name |
|---|---|
| 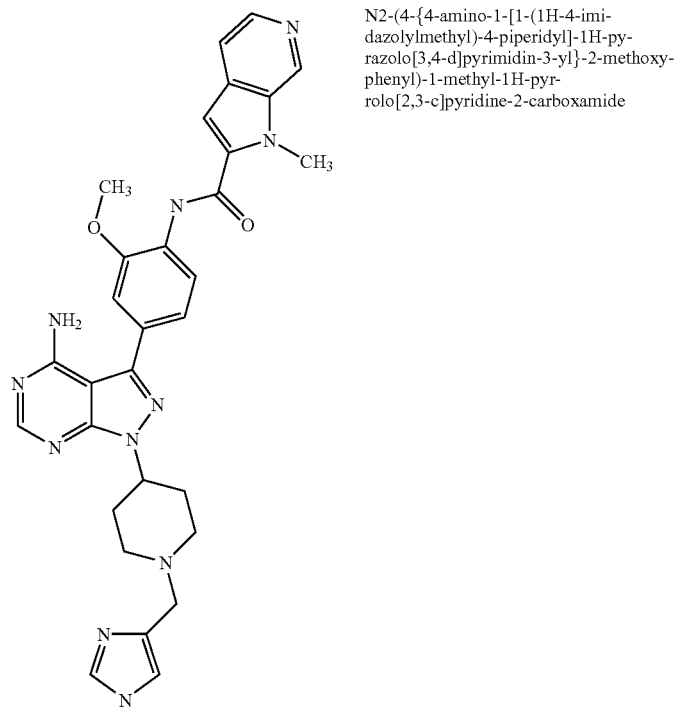 | N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-pyrrolo[2,3-c]pyridine-2-carboxamide |
| 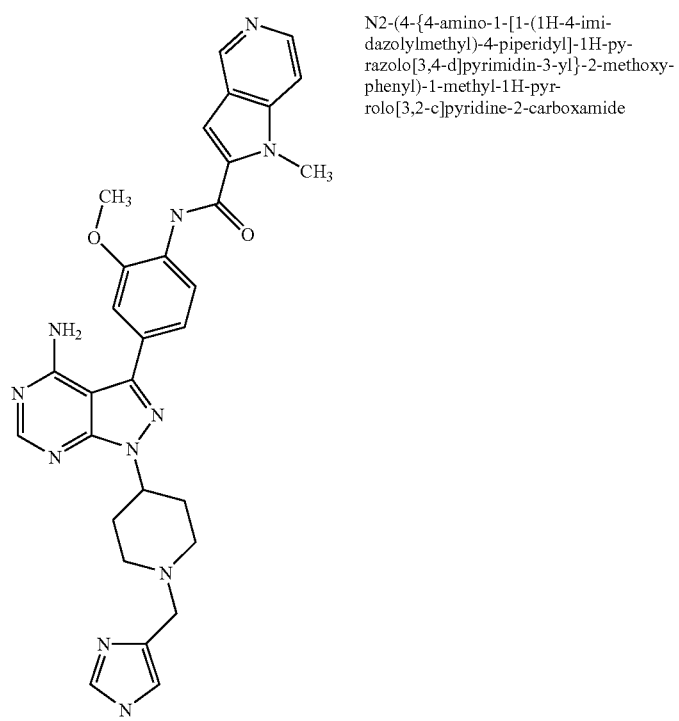 | N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-pyrrolo[3,2-c]pyridine-2-carboxamide |

-continued
| Structure | Name |
|---|---|
| 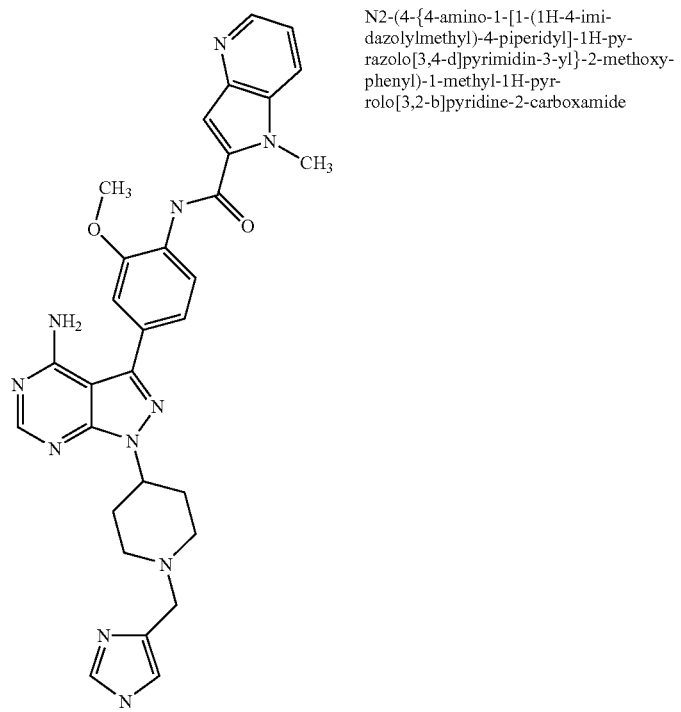 | N2-(4-{4-amino-1-[1-(1H-4-imidazolylmethyl)-4-piperidyl]-1H-pyrazolo[3,4-d]pyrimidin-3-yl}-2-methoxyphenyl)-1-methyl-1H-pyrrolo[3,2-b]pyridine-2-carboxamide |
| 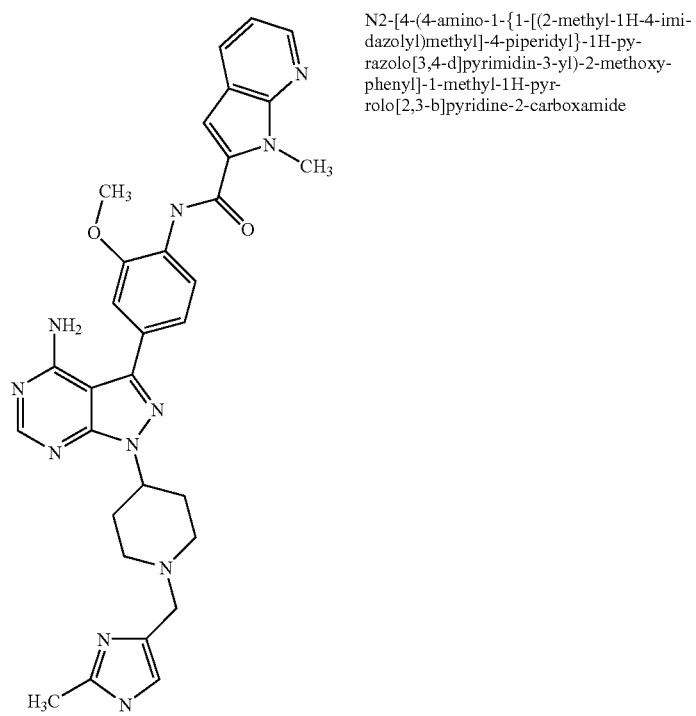 | N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-pyrrolo[2,3-b]pyridine-2-carboxamide |

-continued
| Structure | Name |
|---|---|
| 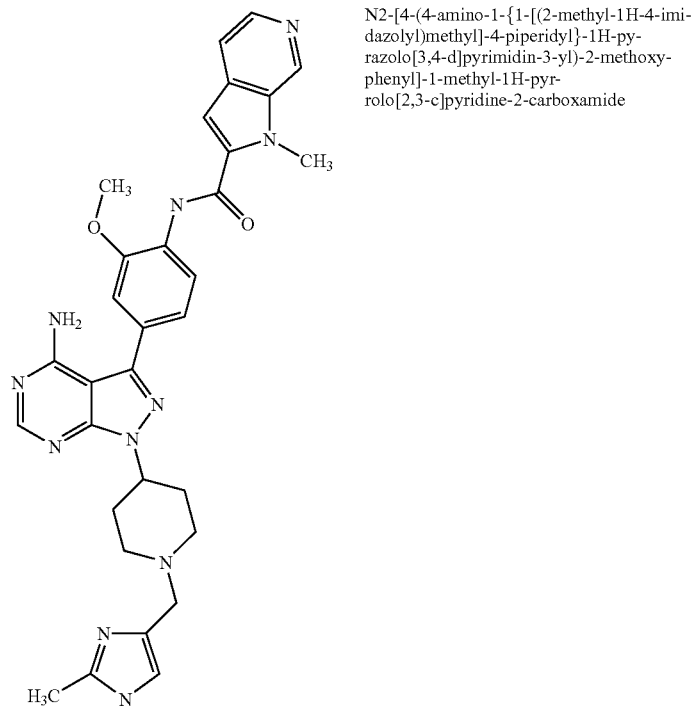 | N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-pyrrolo[2,3-c]pyridine-2-carboxamide |
| 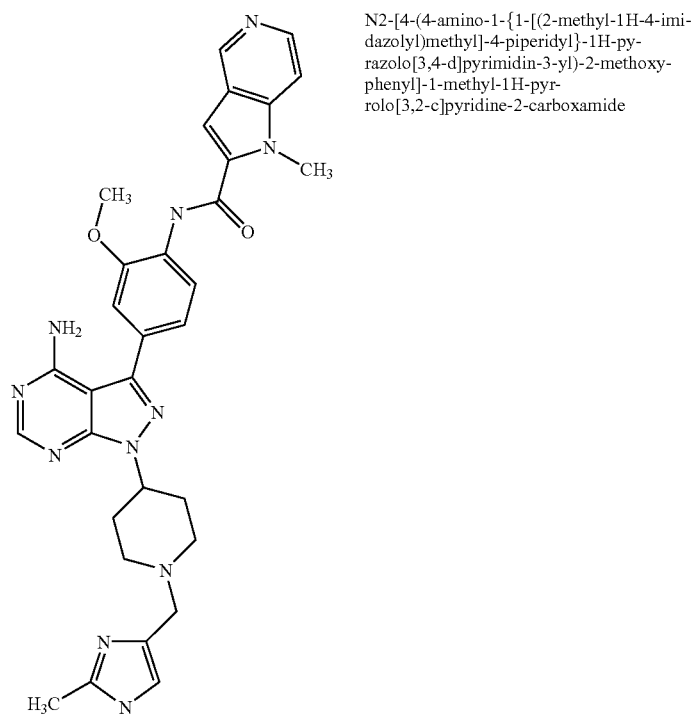 | N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-pyrrolo[3,2-c]pyridine-2-carboxamide |

-continued
| Structure | Name |
|---|---|
| 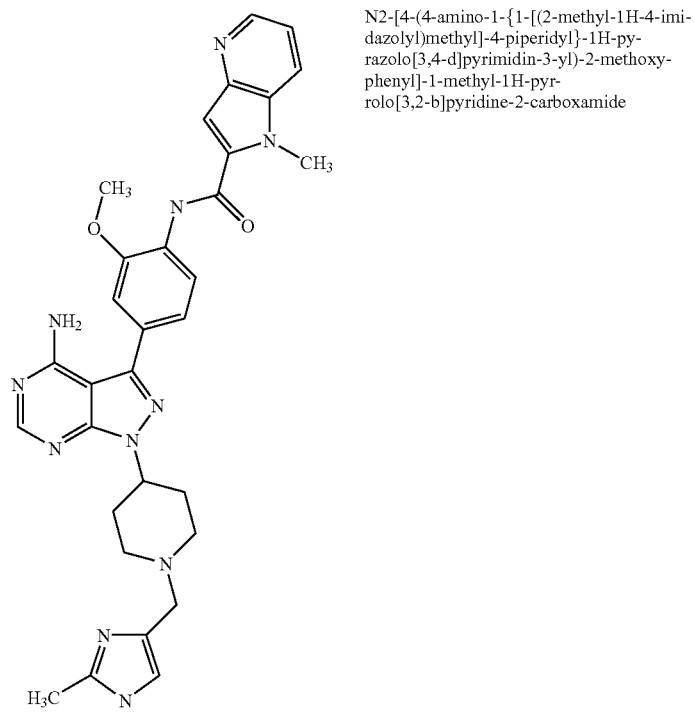 | N2-[4-(4-amino-1-{1-[(2-methyl-1H-4-imidazolyl)methyl]-4-piperidyl}-1H-pyrazolo[3,4-d]pyrimidin-3-yl)-2-methoxyphenyl]-1-methyl-1H-pyrrolo[3,2-b]pyridine-2-carboxamide |
| 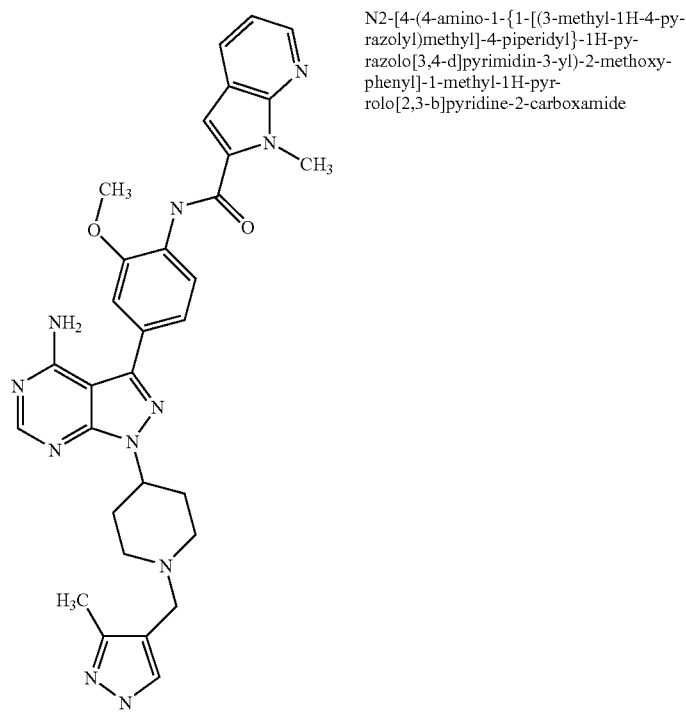 | N2-[4-(4-amino-1-{1-[(3-methyl-1H-4-pyrazolyl)methyl]-4-piperidyl}-1H-pyrazolo[3,4-d]pyrimidin-3-yl)-2-methoxyphenyl]-1-methyl-1H-pyrrolo[2,3-b]pyridine-2-carboxamide |

-continued
| Structure | Name |
|---|---|
| 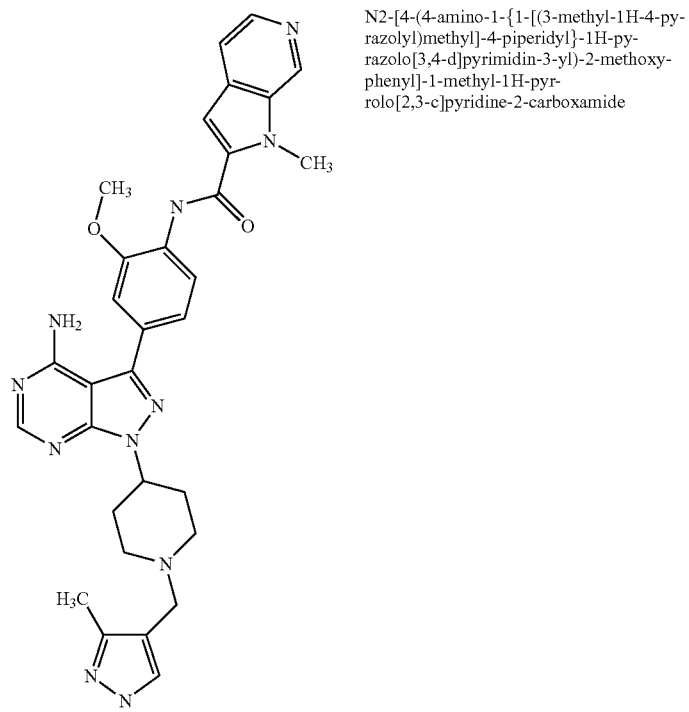 | N2-[4-(4-amino-1-{1-[(3-methyl-1H-4-pyrazolyl)methyl]-4-piperidyl}-1H-pyrazolo[3,4-d]pyrimidin-3-yl)-2-methoxyphenyl]-1-methyl-1H-pyrrolo[2,3-c]pyridine-2-carboxamide |
| 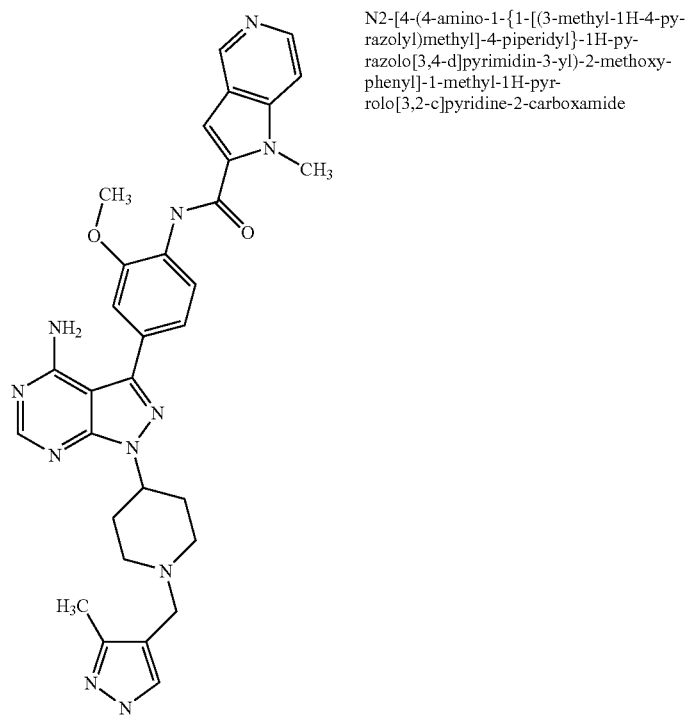 | N2-[4-(4-amino-1-{1-[(3-methyl-1H-4-pyrazolyl)methyl]-4-piperidyl}-1H-pyrazolo[3,4-d]pyrimidin-3-yl)-2-methoxyphenyl]-1-methyl-1H-pyrrolo[3,2-c]pyridine-2-carboxamide |

| Structure | Name |
|---|---|
| 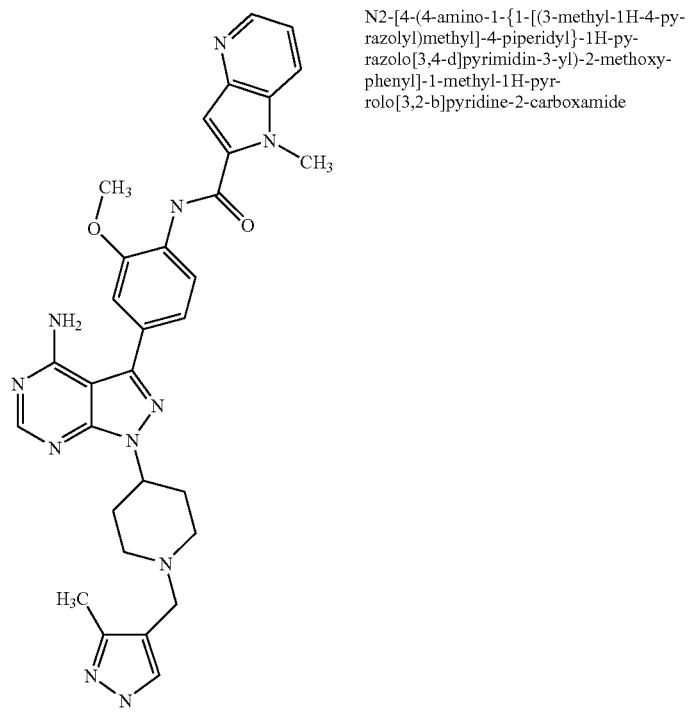 | N2-[4-(4-amino-1-{1-[(3-methyl-1H-4-pyrazolyl)methyl]-4-piperidyl}-1H-pyrazolo[3,4-d]pyrimidin-3-yl)-2-methoxyphenyl]-1-methyl-1H-pyrrolo[3,2-b]pyridine-2-carboxamide |
| 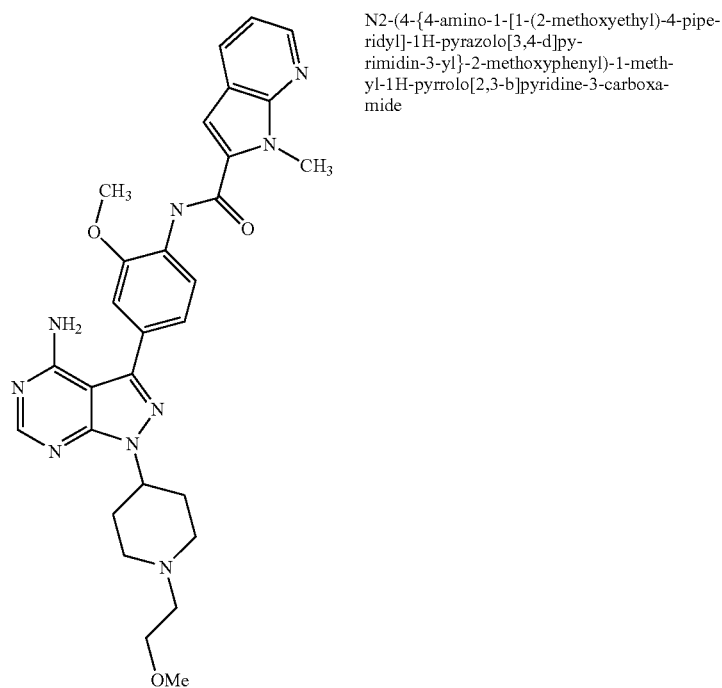 | N2-(4-{4-amino-1-[1-(2-methoxyethyl)-4-piperidyl]-1H-pyrazolo[3,4-d]pyrimidin-3-yl}-2-methoxyphenyl)-1-methyl-1H-pyrrolo[2,3-b]pyridine-3-carboxamide |

| Structure | Name |
|---|---|
| 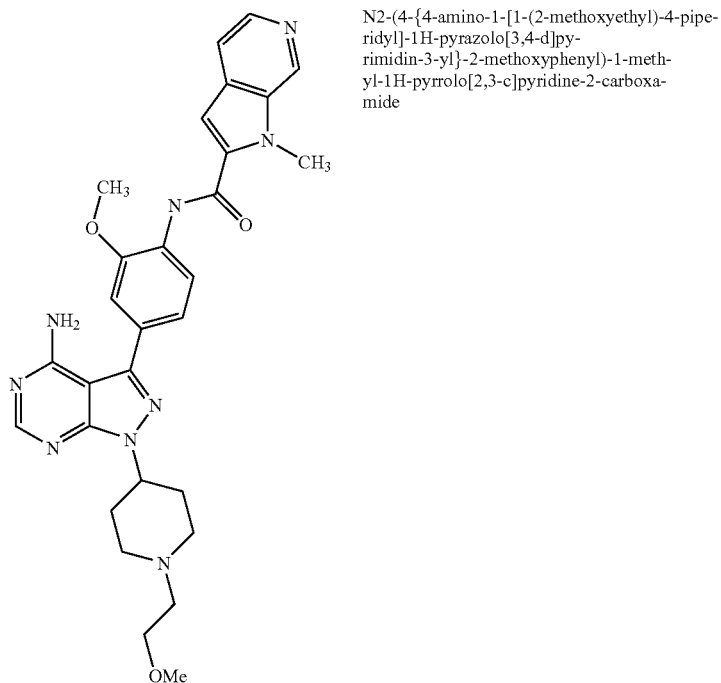 | N2-(4-{4-amino-1-[1-(2-methoxyethyl)-4-piperidyl]-1H-pyrazolo[3,4-d]pyrimidin-3-yl}-2-methoxyphenyl)-1-methyl-1H-pyrrolo[2,3-c]pyridine-2-carboxamide |
| 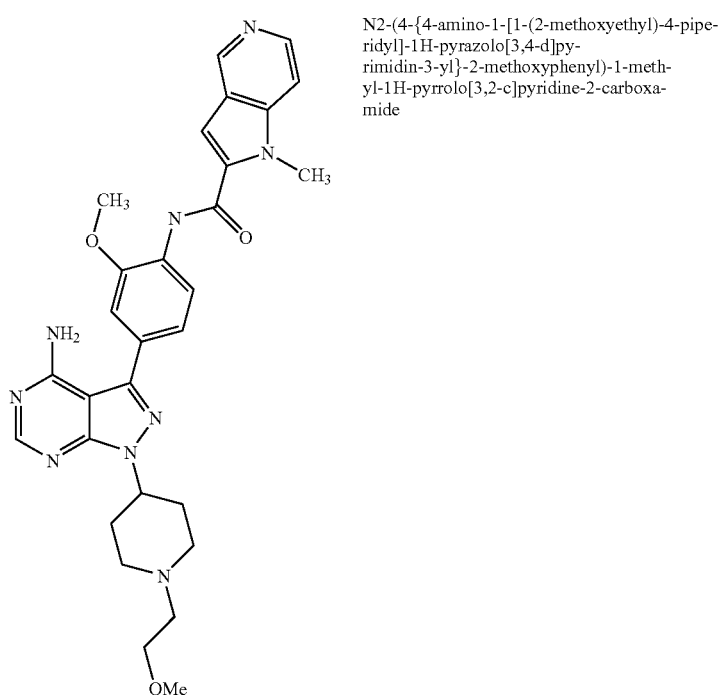 | N2-(4-{4-amino-1-[1-(2-methoxyethyl)-4-piperidyl]-1H-pyrazolo[3,4-d]pyrimidin-3-yl}-2-methoxyphenyl)-1-methyl-1H-pyrrolo[3,2-c]pyridine-2-carboxamide |

-continued
| Structure | Name |
|---|---|
| 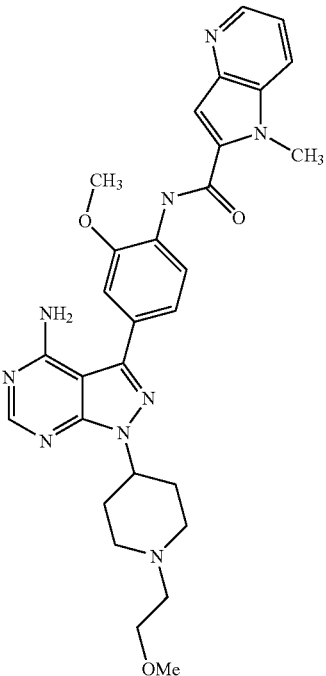 | N2-(4-{4-amino-1-[1-(2-methoxyethyl)-4-piperidyl]-1H-pyrazolo[3,4-d]pyrimidin-3-yl}-2-methoxyphenyl)-1-methyl-1H-pyrrolo[3,2-b]pyridine-2-carboxamide |
| 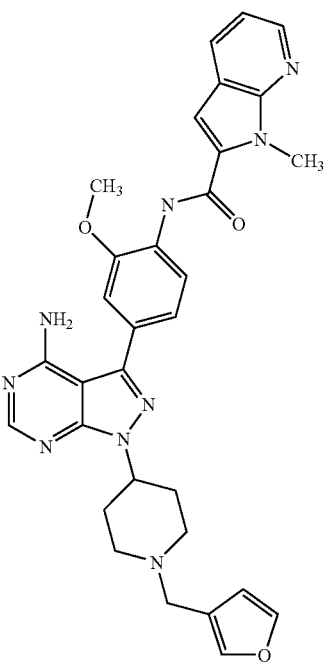 | N2-(4-{4-amino-1-[1-(3-furylmethyl)-4-piperidyl]-1H-pyrazolo[3,4-d]pyrimidin-3-yl}-2-methoxyphenyl)-1-methyl-1H-pyrrolo[2,3-b]pyridine-2-carboxamide |

| Structure | Name |
|---|---|
| 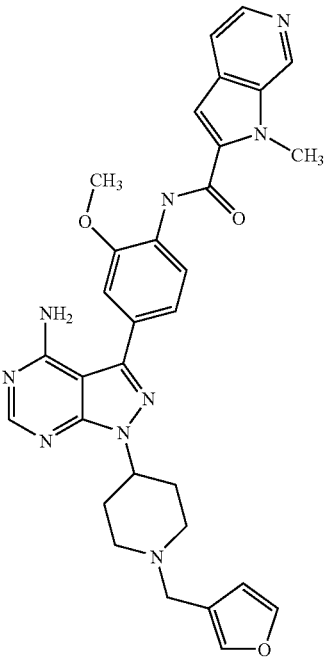 | N2-(4-{4-amino-1-[1-(3-furylmethyl)-4-piperidyl]-1H-pyrazolo[3,4-d]pyrimidin-3-yl}-2-methoxyphenyl)-1-methyl-1H-pyrrolo[2,3-c]pyridine-2-carboxamide |
| 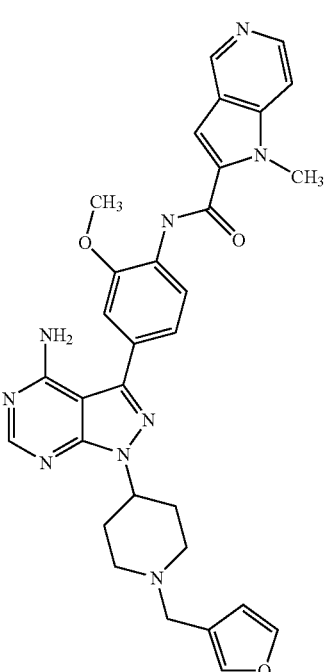 | N2-(4-{4-amino-1-[1-(3-furylmethyl)-4-piperidyl]-1H-pyrazolo[3,4-d]pyrimidin-3-yl}-2-methoxyphenyl)-1-methyl-1H-pyrrolo[3,2-c]pyridine-2-carboxamide |

-continued
| Structure | Name |
|---|---|
| 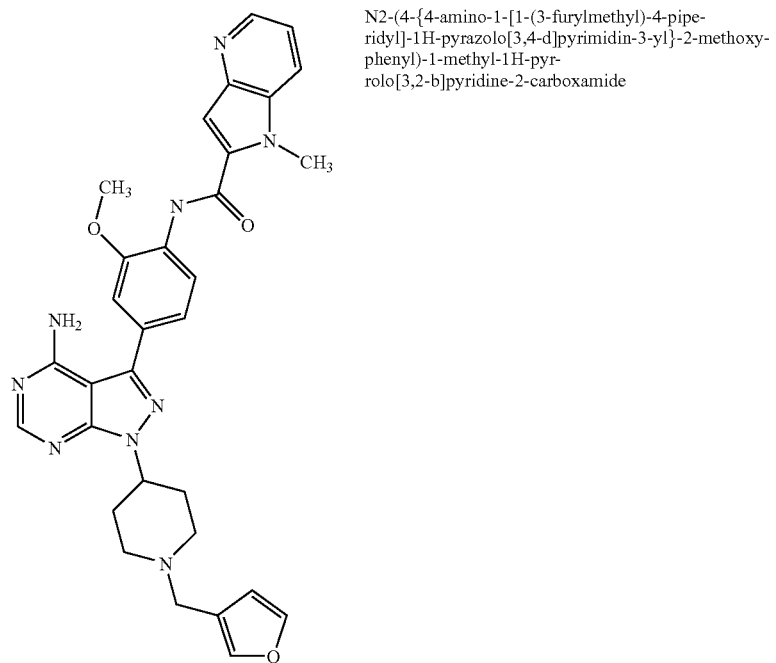 | N2-(4-{4-amino-1-[1-(3-furylmethyl)-4-piperidyl]-1H-pyrazolo[3,4-d]pyrimidin-3-yl}-2-methoxyphenyl)-1-methyl-1H-pyrrolo[3,2-b]pyridine-2-carboxamide |
| 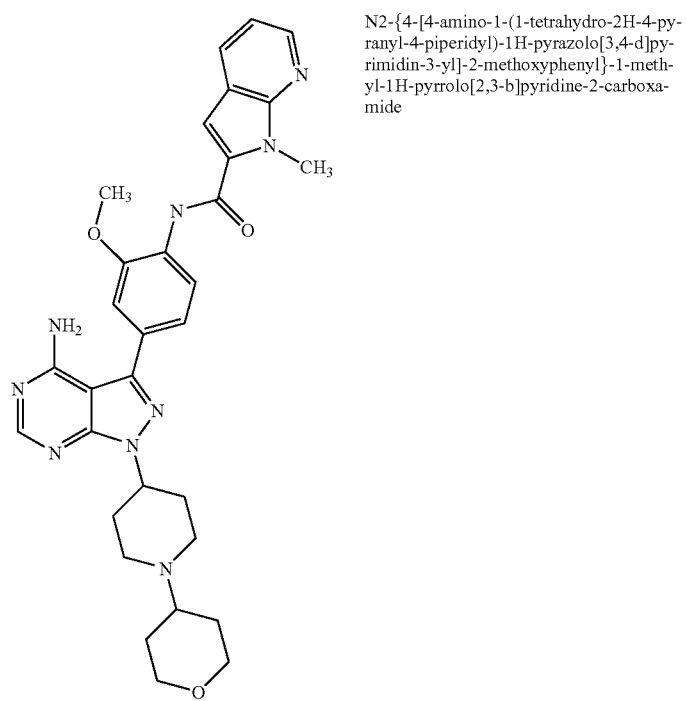 | N2-{4-[4-amino-1-(1-tetrahydro-2H-4-pyranyl-4-piperidyl)-1H-pyrazolo[3,4-d]pyrimidin-3-yl]-2-methoxyphenyl}-1-methyl-1H-pyrrolo[2,3-b]pyridine-2-carboxamide |

| Structure | Name |
|---|---|
| 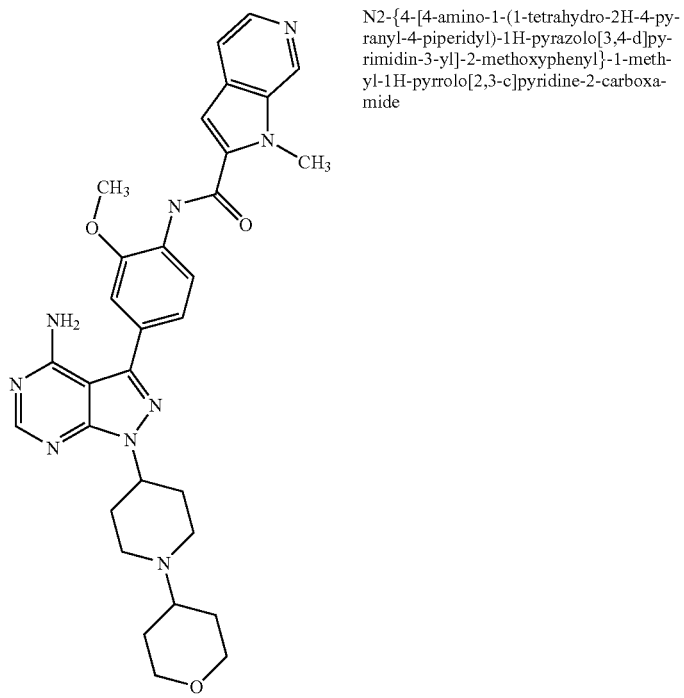 | N2-{4-[4-amino-1-(1-tetrahydro-2H-4-pyranyl-4-piperidyl)-1H-pyrazolo[3,4-d]pyrimidin-3-yl]-2-methoxyphenyl}-1-methyl-1H-pyrrolo[2,3-c]pyridine-2-carboxamide |
| 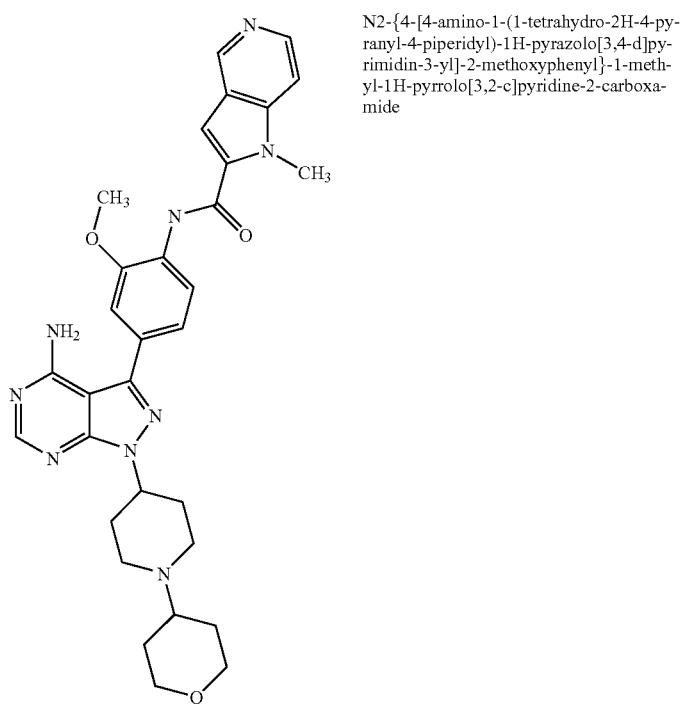 | N2-{4-[4-amino-1-(1-tetrahydro-2H-4-pyranyl-4-piperidyl)-1H-pyrazolo[3,4-d]pyrimidin-3-yl]-2-methoxyphenyl}-1-methyl-1H-pyrrolo[3,2-c]pyridine-2-carboxamide |

| Structure | Name |
|---|---|
| 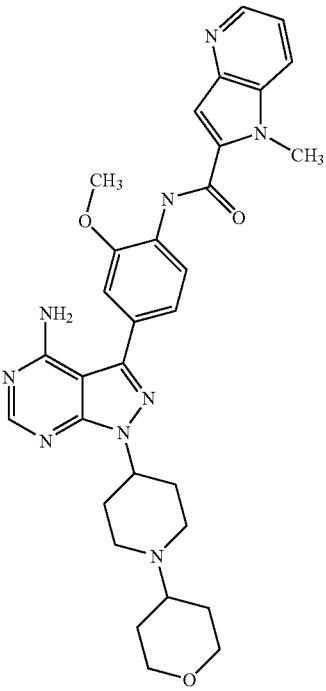 | N2-{4-[4-amino-1-(1-tetrahydro-2H-4-pyranyl-4-piperidyl)-1H-pyrazolo[3,4-d]pyrimidin-3-yl]-2-methoxyphenyl}-1-methyl-1H-pyrrolo[3,2-b]pyridine-2-carboxamide |
| 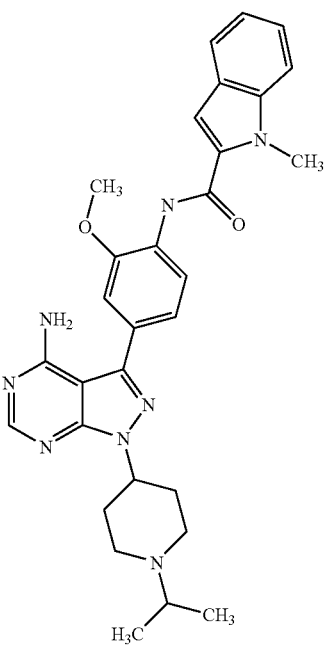 | N2-{4-[4-amino-1-(1-isopropyl-4-piperidyl)-1H-pyrazolo[3,4-d]pyrimidin-3-yl]-2-methoxyphenyl}-1-methyl-1H-2-indolecarboxamide |

| Structure | Name |
|---|---|
| 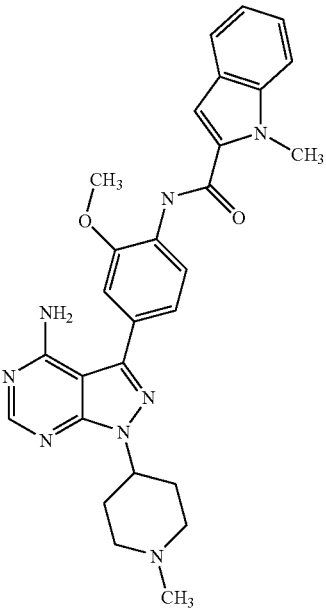 | N2-{4-[4-amino-1-(1-methyl-4-piperidyl)-1H-pyrazolo[3,4-d]pyrimidin-3-yl]-2-methoxyphenyl}-1-methyl-1H-2-indolecarboxamide |
| 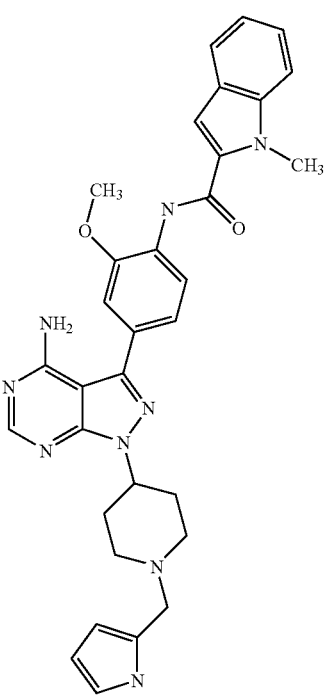 | N2-(4-{4-amino-1-[1-(1H-2-pyrrolylmethyl)-4-piperidyl]-1H-pyraolo[3,4-d]pyrimidin-3-yl}-2-methoxyphenyl)-1-methyl-1H-2-indolecarboxamide |

| Structure | Name |
|---|---|
| 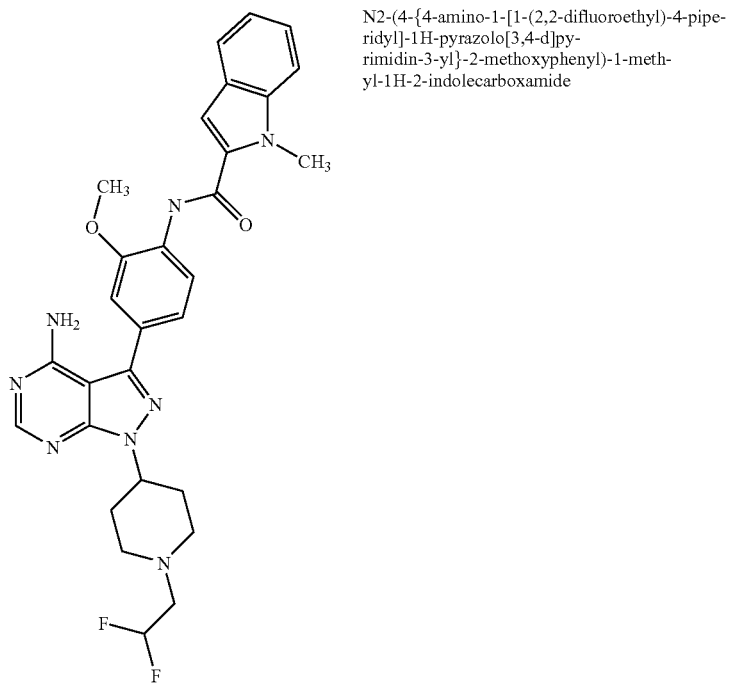 | N2-(4-{4-amino-1-[1-(2,2-difluoroethyl)-4-piperidyl]-1H-pyrazolo[3,4-d]pyrimidin-3-yl}-2-methoxyphenyl)-1-methyl-1H-2-indolecarboxamide |
| 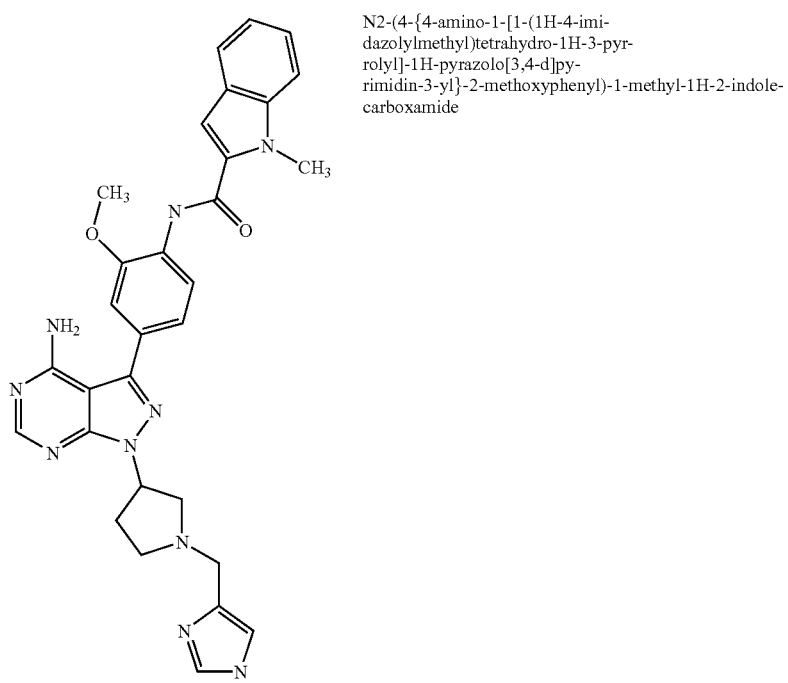 | N2-(4-{4-amino-1-[1-(1H-4-imidazolylmethyl)tetrahydro-1H-3-pyrrolyl]-1H-pyrazolo[3,4-d]pyrimidin-3-yl}-2-methoxyphenyl)-1-methyl-1H-2-indolecarboxamide |

-continued

| Structure | Name |
|---|---|
| 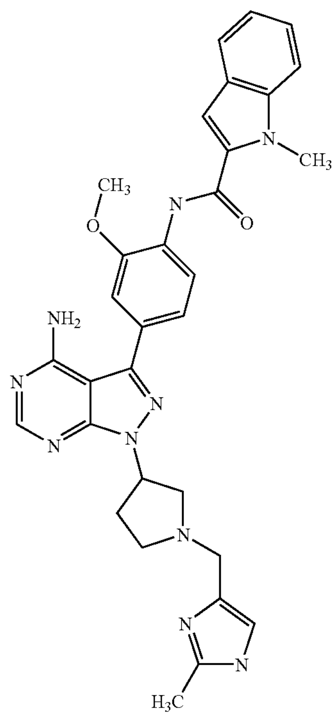 | N2-[4-(4-amino-1-{1-[(2-methyl-1H-4-imidazolyl)methyl]tetrahydro-1H-3-pyrrolyl}-1H-pyrazolo[3,4-d]pyrimidin-3-yl)-2-methoxyphenyl]-1-methyl-1H-2-indolecarboxamide |
| 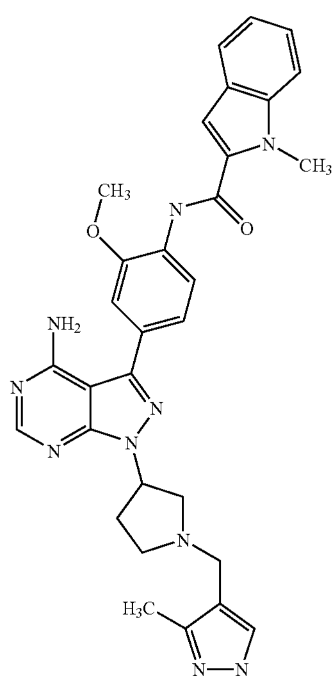 | N2-[4-(4-amino-1-{1-[(3-methyl-1H-4-pyrazolyl)methyl]tetrahydro-1H-3-pyrrolyl}-1H-pyrazolo[3,4-d]pyrimidin-3-yl)-2-methoxyphenyl]-1-methyl-1H-2-indolecarboxamide |

-continued

| Structure | Name |
|---|---|
| 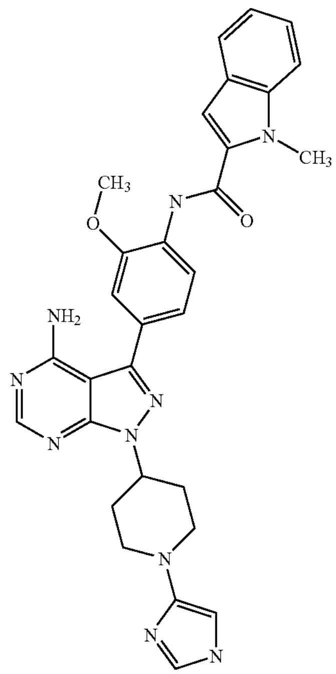 | N2-(4-{4-amino-1-[1-(1H-4-imidazolyl)-4-piperidyl]-1H-pyrazolo[3,4-d]pyrimidin-3-yl}-2-methoxyphenyl)-1-methyl-1H-2-indolecarboxamide |
| 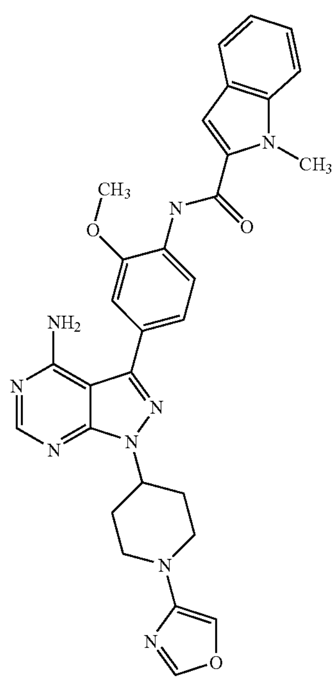 | N2-(4-{4-amino-1-[1-(1,3-oxazol-4-yl)-4-piperidyl]-1H-pyrazolo[3,4-d]pyrimidin-3-yl}-2-methoxyphenyl)-1-methyl-1H-2-indolecarboxamide |

-continued
| Structure | Name |
|---|---|
| 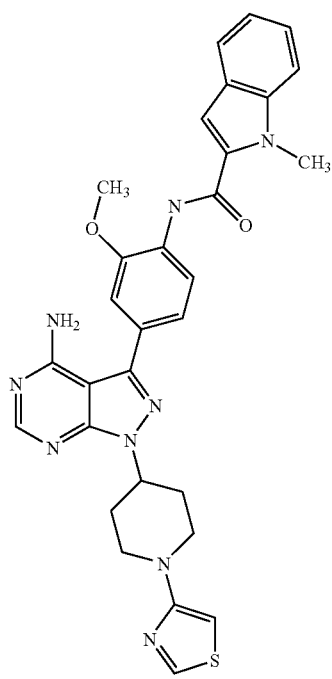 | N2-(4-{4-amino-1-[1-(1,3-thiazol-4-yl)-4-piperidyl]-1H-pyrazolo[3,4-d]pyrimidin-3-yl}-2-methoxyphenyl)-1-methyl-1H-2-indole-carboxamide |
| 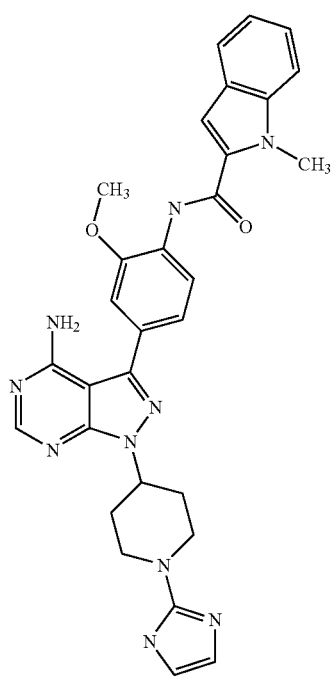 | N2-(4-{4-amino-1-[1-(1H-2-imidazolyl)-4-piperidyl]-1H-pyrazolo[3,4-d]pyrimidin-3-yl}-2-methoxyphenyl)-1-methyl-1H-2-indolecarboxamide |

-continued
| Structure | Name |
|---|---|
| 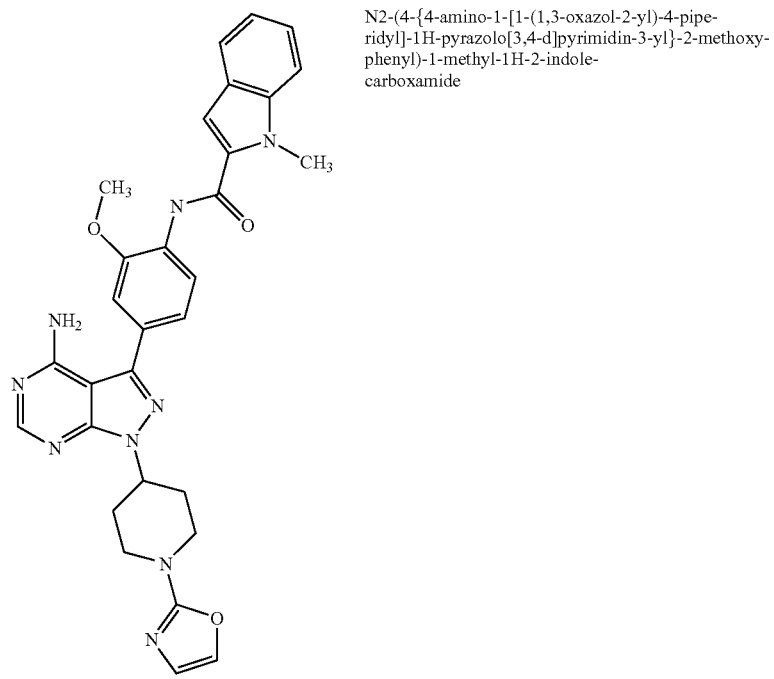 | N2-(4-{4-amino-1-[1-(1,3-oxazol-2-yl)-4-piperidyl]-1H-pyrazolo[3,4-d]pyrimidin-3-yl}-2-methoxyphenyl)-1-methyl-1H-2-indolecarboxamide |
| 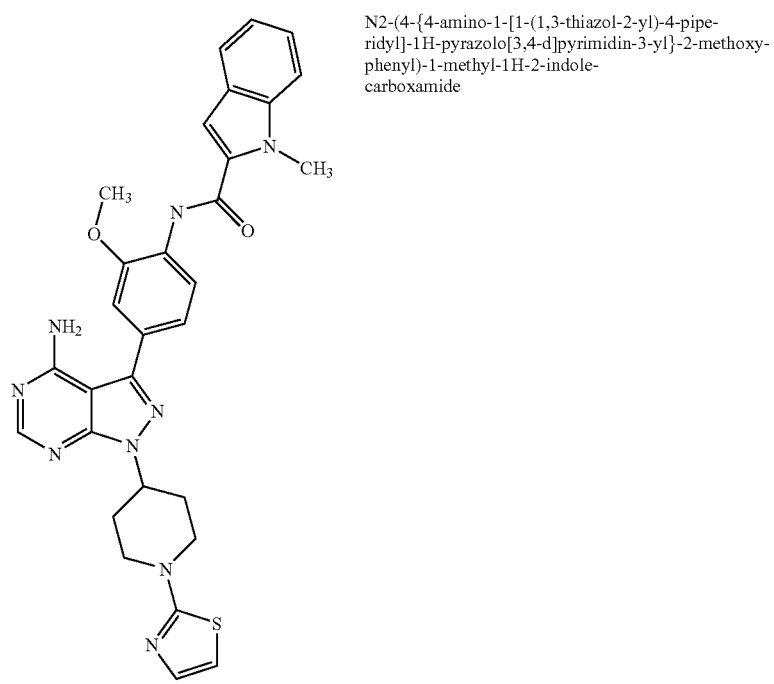 | N2-(4-{4-amino-1-[1-(1,3-thiazol-2-yl)-4-piperidyl]-1H-pyrazolo[3,4-d]pyrimidin-3-yl}-2-methoxyphenyl)-1-methyl-1H-2-indolecarboxamide |

| Structure | Name |
|---|---|
|  | N2-(4-{4-amino-1-[2-hydroxy-3-(4-methyl-piperazino)propyl]-1H-pyrazolo[3,4-d]pyrimidin-3-yl}-2-methoxyphenyl)-1-methyl-1H-2-indolecarboxamide |
| 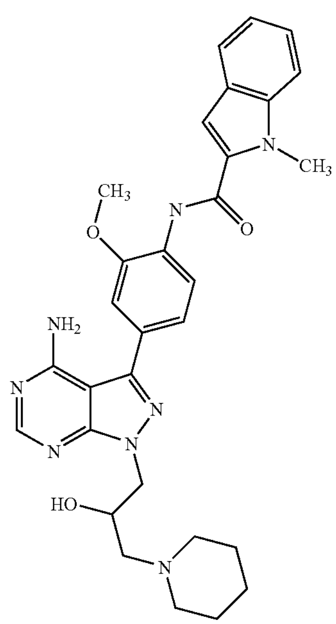 | N2-{4-[4-amino-1-(2-hydroxy-3-piperidinopropyl)-1H-pyrazolo[3,4-d]pyrimidin-3-yl]-2-methoxyphenyl}-1-methyl-1H-2-indolecarboxamide |

-continued

| Structure | Name |
|---|---|
| | N2-{4-[4-amino-1-(2-hydroxy-3-morpholino-propyl)-1H-pyrazolo[3,4-d]py-rimidin-3-yl]-2-methoxyphenyl}-1-meth-yl-1H-2-indolecarboxamide |
| | N2-(4-{4-amino-1-[2-hydroxy-3-(1H-1-imi-dazolyl)propyl]-1H-pyrazolo[3,4-d]py-rimidin-3-yl}-2-methoxyphenyl)-1-meth-yl-1H-2-indolecarboxamide |

We claim:
1. A compound of Formula (I)

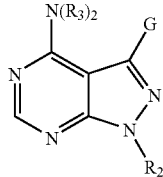

racemic-diastereomeric mixtures, optical isomers or pharmaceutically-acceptable salts thereof wherein:

G is 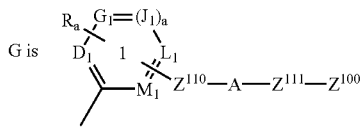

where $Z^{100}$ is

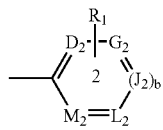

or a group optionally substituted with $R_1$ selected from the group consisting of alkyl, cycloalkyl, pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl, benzothiazolyl,

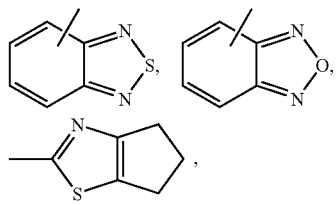

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted $(C_1-C_6)$ which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted $(C_1-C_6)$ or an optionally substituted—$(CH_2)_n$-cycloalkyl-$(CH_2)_n$—; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-$S(O)_p$—, substituted or unsubstituted alkyl-S—, substituted or unsubstituted aryl-$S(O)_p$—, substituted or unsubstituted heteroaryl-$S(O)_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, $-Z^{105}-C(O)N(R)_2$, $-Z^{105}-N(R)-C(O)-Z^{200}$, $-Z^{105}-N(R)-S(O)_2-Z^{200}$, $-Z^{105}-N(R)-C(O)-N(R)-Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—O-alkyl, —W—$(CH_2)_t$—S-alkyl, or —W—$(CH_2)_t$—OH;

$Z^{105}$ for each occurrence is independently a covalent bond or $(C_1-C_6)$;

$Z^{200}$ for each occurrence is independently a substituted or unsubstituted $(C_1-C_6)$, substituted or unsubstituted phenyl or substituted or unsubstituted —$(C_1-C_6)$-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$ wherein $R_f$ for each occurrence is independently H or alkyl; or $R_1$ is a substituted or unsubstituted carbocyclic or heterocyclic ring fused with ring 2;

$R_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

A is —$(C_1-C_6)$—; —O—; —S—; —$S(O)_p$—; —N(R)—; —N(C(O)OR)—; —N(C(O)R)—; —N($SO_2$R)—; —$CH_2$O—; —$CH_2$S—; —$CH_2$N(R)—; —CH(NR)—; —$CH_2$N(C(O)R))—; —$CH_2$N(C(O)OR)—; —$CH_2$N($SO_2$R)—; —CH(NHR)—; —CH(NHC(O)R)—; —CH($NHSO_2$R)—; —CH(NHC(O)OR)—; —CH(OC(O)R)—; —CH(OC(O)NHR)—; —CH═CH—; —C(═NOR)—; —C(O)—; —CH(OR)—; —C(O)N (R)—; —N(R)C(O)—; —N(R)S(O)$_p$—; —OC(O)N(R)—; —N(R)—C(O)—(CH$_2$)$_n$—N(R)—, —N(R)C(O)O—; —N(R)—(CH$_2$)$_{n+1}$—C(O)—, —S(O)$_p$N(R)—; —O—(CR$_2$)$_{n+1}$—C(O)—, —O—(CR$_2$)$_{n+1}$—O—, —N(C(O)R)S(O)$_p$—; —N(R)S(O)$_p$N(R)—; —N(R)—C(O)—(CH$_2$)—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_b$)O—; —N(R)P(OR$_b$)—; —N(R)P(O)(OR$_b$)O—; —N(R)P(O)(OR$_b$)—; —N(C(O)R)P(OR$_b$)O—; —N(C(O)R)P(OR$_b$)—; —N(C(O)R)P(O)(OR$_b$)O—, or —N(C(O)R)P(OR$_b$)—;

where R for each occurrence is independently H, substituted or unsubstituted alkyl, substituted or unsubstituted arylalkyl or substituted or unsubstituted aryl;

R$_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and R$_b$ together form a five- or six-membered heterocyclic ring; or A is NRSO$_2$ and R, R$_a$ and the nitrogen atom together form a substituted or unsubstituted five or -six-membered heterocyclic ring fused to ring 1; or Z$^{110}$-A-Z$^{111}$ taken together is a covalent bond; and R$_2$ is a) hydrogen; b) substituted or unsubstituted trityl; c) substituted or unsubstituted cycloalkenyl; d) azaheteroaryl substituted with a substituted or unsubstituted alkyl; e) azacycloalkyl which is substituted with one or more substituents selected from substituted or unsubstituted —(C$_1$-C$_6$)-alkyl, substituted or unsubstituted —C$_1$-C$_6$-alkyl-OR, substituted or unsubstituted —C(O)—C$_1$-C$_6$-alkyl-N(R)$_2$, substituted or unsubstituted —C$_1$-C$_6$-alkyl-N(R)$_2$, substituted or unsubstituted —C$_1$-C$_6$-alkyl-cycloalkyl, substituted or unsubstituted tetrahydrothienyl, and substituted or unsubstituted tetrahydrothiopyranyl; or f) a group of the formula

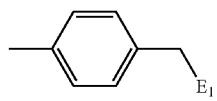

wherein E$_1$ is piperidinyl, piperazinyl, imidazolyl, morpholinyl, pyrrolidinyl, amino, amido, or tetrahydrothiazolyl, and wherein E is optionally substituted with one or more substituents selected from -C$_0$-C$_6$-alkyl-OR, —C$_1$-C$_6$-alkyl-C(O)OR, —C$_1$-C$_6$-alkyl-heteroaryl, —C$_1$-C$_6$-alkyl-heterocycloalkyl, and —C$_1$-C$_6$-alkyl-N(R)$_2$;

a is 1 and D$_1$, G$_1$, J$_1$, L$_1$ and M$_1$ are each independently selected from the group consisting of CR$_a$ and N, provided that at least two of D$_1$, G$_1$, J$_1$, L$_1$ and M$_1$ are CR$_a$; or a is 0, and one of D$_1$, G$_1$, L$_1$ and M$_1$ is NR$_a$, one of D$_1$, G$_1$, L$_1$ and M$_1$ is CR$_a$ and the remainder are independently selected from the group consisting of CR$_a$ and N, wherein R$_a$ is as defined above;

b is 1 and D$_2$, G$_2$, J$_2$, L$_2$ and M$_2$ are each independently selected from the group consisting of CR$_a$ and N, provided that at least two of D$_2$, G$_2$, J$_2$, L$_2$ and M$_2$ are CR$_a$; or b is 0, and one of D$_2$, G$_2$, L$_2$ and M$_2$ is NR$_a$, one of D$_2$, G$_2$, L$_2$ and M$_2$ is CR$_a$ and the remainder are independently selected from the group consisting of CR$_a$ and N, wherein R$_a$ is as defined above; and n for each occurrence is independently an integer from 0 to 6;

provided that when Z$^{110}$-A-Z$^{111}$ taken together are a covalent bond, then Z$^{100}$ is not alkyl; and provided that when Z$^{110}$-A-Z$^{111}$ taken together are a C$_1$-C$_6$ alkyl, then Z$^{100}$ is not phenyl, pyrrolyl, imidazolyl, pyrazolyl, pyridinyl, pyrimidinyl, pyrazinyl, pyridazinyl, furyl or thienyl.

2. The compound of claim 1, wherein R$_2$ is a group represented by the following structural formula:

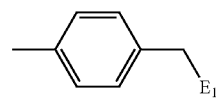

wherein:

E$_1$ is selected from the group consisting of -amino-C$_1$-C$_6$-alkyl-morpholino, -piperidino-C$_1$-C$_6$-alkyl-OR, -imidazolyl-C$_1$-C$_6$-alkyl-C(O)OR, -piperazino-C$_1$-C$_6$-alkyl-OR, -amino-C$_1$-C$_6$-alkyl-OR, -pyrrolidino-OR, -amino-C$_1$-C$_6$-alkyl-imidazolo, -amino-C$_1$-C$_6$-alkyl-N(R)$_2$, -amido-C$_1$-C$_6$-alkyl-N(R)$_2$, tetrahydrothiazolyl, N,N-di-(hydroxy-C$_1$-C$_6$-alkyl)amino-, and -piperizino-OR.

3. The compound of claim 2, wherein:

E$_1$ is selected from the group consisting of 4-(2-hydroxyethyl)morpholino, 3-hydroxymethylpiperidino, 2-[3-(methylcarboxy)propyl]imidizol-4-yl, 4-(2-hydroxyethyl)piperazino, 2-hydroxyethylamino, 3-hydroxypyrrolidino, 3-imidazolopropylamino, 4-hydroxybutylamino, 3-methoxypropylamino, 3-(N,N-dimethylamino)propylamino, N-[2-(N,N-dimethyl)ethyl]amido, tetrahydrothiazolyl, N,N-di-(2-hydroxyethyl)amino, and 4-hydroxypiperazinyl, and 4-hydroxymethylpiperazinyl.

4. The compound of claim 2, wherein Z$^{110}$-A-Z$^{111}$ is —NHC(O)—.

5. The compound of claim 2, wherein G is a group represented by the following structural formula:

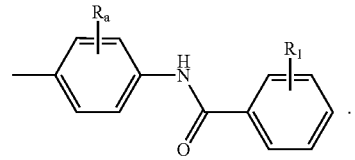

6. The compound of claim 5, wherein G is represented by the following structural formula:

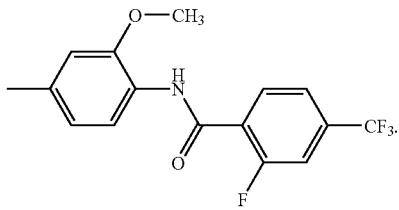

7. The compound of claim 1, wherein R$_2$ is an azaheteroaryl substituted with a C$_1$-C$_6$ alkyl, wherein the alkyl is optionally substituted with with one or more substitutents selected form RO—, —C(O)OR, —C(O)N(R)$_2$, and —N(R)$_2$.

8. The compound of claim 7, wherein R$_2$ is 4-(2-hydroxyethyl)pyridin-2-yl, 3-aminomethylpyridin-4-yl or 2-methylimidazol-4-yl.

9. The compound of claim 8, wherein G is represented by the following formula:

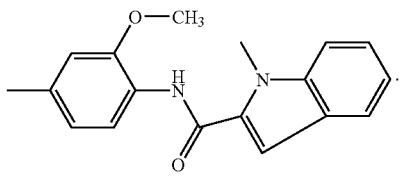

10. The compound of claim 1, wherein R$_2$ is a pyrrolidinyl which is substituted with 2-methoxyethyl, N,N-dimethylaminomethyl, N,N-dimethylamino-1-oxoethyl, or 2-(N-methylamino)-1-oxopropyl.

11. The compound of claim 10 wherein G is represented by the following structural formula:

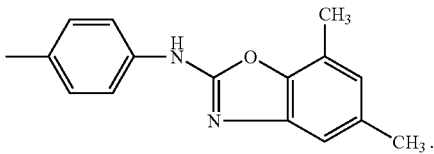

12. The compound of claim 1, wherein R$_2$ is a piperidinyl which is substituted with a tetrahydrothiopyranyl, tetrahydrothienyl, 2-(N-methyl)-2-methyl-1-oxopropyl, 2-methoxyethyl, or cyclopropylmethyl.

13. A compound of Formula (I)

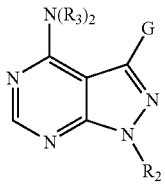

(I)

racemic-diastereomeric mixtures, optical isomers, pharmaceutically-acceptable salts, prodrugs or biologically active metabolites thereof wherein:

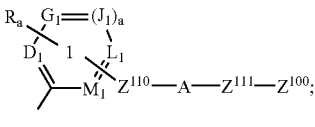

G is wherein Z$^{100}$ is pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, H-pyridinone, 1,1-dioxybenzoisothiazolyl, benzoisoxazolyl, alkyl, imidazo[1,2-a]pyridinyl, pyrrolopyridinyl or

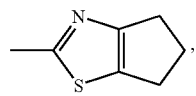

wherein all of the foregoing Z$^{100}$ groups are optionally substituted with R$_1$;

Z$^{110}$ is a covalent bond, or an optionally substituted (C$_1$-C$_6$) which is optionally substituted with one or more substituents selected from the group consisting of alkyl, CN, OH, halogen, NO$_2$, COOH, substituted or unsubstituted amino and substituted or unsubstituted phenyl;

Z$^{11}$ is a covalent bond, an optionally substituted (C$_1$-C$_6$) or an optionally substituted—(CH$_2$)$_n$-cycloalkyl-(CH$_2$)$_n$—; where the optionally substituted groups are optionally substituted with one or more substituents selected from the group consisting of alkyl, CN, OH, halogen, NO$_2$, COOH, substituted or unsubstituted amino and substituted or unsubstituted phenyl;

R$_a$ and R$_1$ each represent one or more substituents for each occurrence independently selected from the group consisting of hydrogen, halogen, —CN, —NO$_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-S(O)$_p$—, substituted or unsubstituted alkyl-S—, substituted or unsubstituted aryl-S(O)$_p$—, substituted or unsubstituted heteroaryl-S(O)$_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, $-Z^{105}-C(O)N(R)_2$, $-Z^{105}-N(R)-C(O)-Z^{200}$, $-Z^{105}-N(R)-S(O)_2-Z^{200}$, $-Z^{105}-N(R)-C(O)-N(R)-Z^{2'}$, $R_c$ and $CH_2OR_c$;

where $R_c$ for each occurrence is independently hydrogen, substituted or unsubstituted alkyl, substituted or unsubstituted aryl, $-CH_2-NR_dR_e$, $-W-(CH_2)_tNR_dR_e$, $-W-(CH_2)_t-O$-alkyl, $-W-(CH_2)_tS$-alkyl, or $-W-(CH_2)_t-OH$;

$Z^{105}$ for each occurrence is independently a covalent bond or $(C_1-C_6)$;

$Z^{200}$ for each occurrence is independently a substituted or unsubstituted $(C_1-C_6)$, substituted or unsubstituted phenyl or substituted or unsubstituted $-(C_1-C_6)$-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$, wherein $R_f$ for each occurrence is independently H or alkyl; or $R_1$ is a substituted or unsubstituted carbocyclic or heterocyclic ring fused with ring 2;

$R_3$ for each occurrence is, independently, hydrogen, hydroxy, substituted or unsubstituted alkyl, substituted or unsubstituted $-C(O)$-alkyl, a substituted or unsubstituted $-C(O)$-aryl, or a substituted or unsubstituted $-C(O)$-heteroaryl or substituted or unsubstituted alkoxy;

A is $-(C_1-C_6)-$, $-O-$; $-S-$; $-S(O)_p-$; $-N(R)-$; $-N(C(O)OR)-$; $-N(C(O)R)-$; $-N(SO_2R)-$; $-CH_2O-$; $-CH_2S-$; $-CH_2N(R)-$; $-CH(NR)-$; $-CH_2N(C(O)R))-$; $-CH_2N(C(O)OR)-$; $-CH_2N(SO_2R)-$; $-CH(NHR)-$; $-CH(NHC(O)R)-$; $-CH(NHSO_2R)-$; $-CH(NHC(O)OR)-$; $-CH(OC(O)R)-$; $-CH(OC(O)NHR)-$; $-CH=CH-$; $-C(=NOR)-$; $-C(O)-$; $-CH(OR)-$; $-C(O)N(R)-$; $-N(R)C(O)-$; $-N(R)S(O)_p-$; $-OC(O)N(R)-$; $-N(R)-C(O)-(CH_2)_n-N(R)-$, $-N(R)C(O)O-$; $-N(R)-(CH_2)_{n+1}-C(O)-$, $-S(O)_pN(R)-$; $-O-(CR_2)_{n+1}-C(O)-$, $-O-(CR_2)_{n+1}-O-$, $-N(C(O)R)S(O)_p-$; $-N(R)S(O)_pN(R)-$; $-N(R)-C(O)-(CH_2)_n-O-$, $-C(O)N(R)C(O)-$; $-S(O)_pN(R)C(O)-$; $-OS(O)_pN(R)-$; $-N(R)S(O)_pO-$; $-N(R)S(O)_pC(O)-$; $-SO_2N(C(O)R)-$; $-N(R)SO_2N(R)-$; $-C(O)O-$; $-N(R)P(OR_b)O-$; $-N(R)P(OR_b)-$; $-N(R)P(O)(OR_b)O-$; $-N(R)P(O)(OR_b)-$; $-N(C(O)R)P(OR_b)O-$; $-N(C(O)R)P(OR_b)-$; $-N(C(O)R)P(O)(OR_b)O-$, or $-N(C(O)R)P(OR_b)-$;

where R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and $R_b$ together form a five- or six-membered heterocyclic ring; or A is $NRSO_2$ and R, $R_a$ and the nitrogen atom together form a substituted or unsubstituted five or -six-membered heterocyclic ring fused to ring 1; or $Z^{110}$-A-$Z^{111}$ taken together is a covalent bond; and $R_2$ is H or a group of the formula $-Z^{101}-Z^{102}$;

$Z^{101}$ is a covalent bond, $-(C_1-C_6)-$, $-(C_1-C_6)-O-$, $-(C_1-C_6)-C(O)-$, $-(C_1-C_6)-C(O)O-$, $-(C_1-C_6)-C(O)-NH-$, $-(C_1-C_6)-C(O)-N((C_1-C_6))-$ or a substituted or unsubstituted phenyl group;

$Z^{102}$ is hydrogen; a substituted or unsubstituted alkyl group; a substituted or unsubstituted cycloalkyl group; a substituted or unsubstituted cycloalkenyl, a substituted or unsubstituted, saturated or unsaturated heterocyclic group; or a substituted or unsubstituted, saturated or unsaturated heterobicyclic group; wherein said substituted alkyl, substituted cycloalkyl, substituted cycloalkenyl, substituted heterocyclic and substituted heterobicyclic group having one or more substituents each independently selected from the group consisting of hydroxyl, cyano, nitro, halo, substituted or unsubstituted $(C_1-C_6)$, substituted or unsubstituted aryl, substituted or unsubstituted $-C(O)$-alkyl, substituted or unsubstituted alkoxy, substituted or unsubstituted $-N(R)-(C_1-C_6)-OR$, substituted or unsubstituted $-N((C_1-C_6)-OR)_2$, substituted or unsubstituted $-N(R)-(C_1-C_6)-C(O)_2R$, substituted or unsubstituted $-(C_1-C_6)-N(R)-(C_1-C_6)-OR$, substituted or unsubstituted $-(C_1-C_6)-N(R)-(C_1-C_6)-N(R)_2$, substituted or unsubstituted $-(C_1-C_6)-C(O)N(R)-(C_1-C_6)-N(R)_2$, substituted or unsubstituted sulfonamido, substituted or unsubstituted ureido, substituted or unsubstituted carboxamido, substituted or unsubstituted amino, substituted or unsubstituted $-N(R)-(C_1-C_6)-OR$, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted $-C(O)N(R)_2$, substituted or unsubstituted $-C(O)-(C_1-C_6)-N(R)_2$, $-C(O)$-alkyl, $-C(O)$-aryl, $-C(O)$-heteroaryl, substituted or unsubstituted arylalkyl group, or substituted or unsubstituted heteroarylalkyl; or $R_2$ is a group of the formula -B-E, wherein B is a substituted or unsubstituted cycloalkyl, substituted or unsubstituted aryl, substituted or unsubstituted heteroaryl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted alkyl, a substituted or unsubstituted cycloalkyl, substituted or unsubstituted azacycloalkyl, a substituted or unsubstituted heterocycloalkyl, substituted or unsubstituted $(C_1-C_6)$-azacycloalkyl-, substituted or unsubstituted azacycloalkylcarbonyl, substituted or unsubstituted azacycloalkylsulfonyl, substituted or unsubstituted azacycloalkylalkyl, substituted or unsubstituted heteroaryl-N(R)-$(C_1-C_6)-$, substituted or unsubstituted aryl-N(R)-$(C_1-C_6)-$, substituted or unsubstituted alkyl-N(R)-$(C_1-C_6)-$, substituted or unsubstituted heteroaryl-$(C_1-C_6)$-N(R)-, substituted or unsubstituted aryl-$(C_1-C_6)$-N(R)-, substituted or unsubstituted alkyl-$(C_1-C_6)$-N (R)—, substituted or unsubstituted heteroaryl, substituted or unsubstituted heteroarylcarbonyl, substituted or unsubstituted alkylcarbonyl, substituted or unsubstituted arylcarbonyl, substituted or unsubstituted heteroarylsulfonyl, substituted or unsubstituted alkylsulfonyl, substituted or unsubstituted arylsulfonyl, substituted or unsubstituted heteroarylalkyl, substituted or unsubstituted arylalkyl, substituted or unsubstituted azacycloalkylcarbonylamino, substituted or unsubstituted heteroarylcarbonylamino, substituted or unsubstituted arylcarbonylamino, substituted or unsubstituted alkylcarbonylamino or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

provided that when A is —N(R)—, $Z^{110}$ and $Z^{111}$ are each a covalent bond, and $R_2$ is a 3,4-dihydroxytetrahydrofur-2-yl or a 3,4-diacyloxytetrahydrofur-2-yl, then $Z^{100}$ is not alkyl, tetrahydropyranyl, tetrahydrofuranyl, piperidinyl or pyrrolidinyl;

provided that when $Z^{110}$ and $Z^{111}$ are each a covalent bond, and $R_2$ is a 3,4-dihydroxytetrahydrofur-2-yl or a 3,4-diacyloxytetrahydrofur-2-yl, $Z^{100}$ is a substituted or unsubstituted alkyl, then A is not alkyl, —O—, —C(O)—, —NHC(O)— or —C(O)O—;

provided that when $Z^{110}$-A-$Z^{111}$ taken together are a covalent bond, then $Z^{100}$ is not alkyl; and provided that when $Z^{110}$-A-$Z^{111}$ taken together are a $C_1$-$C_6$ alkyl, then $Z^{100}$ is not phenyl, pyrrolyl, imidazolyl, pyrazolyl, pyridinyl, pyrimidinyl, pyrazinyl, pyridazinyl, furyl or thienyl; and provided that when $R_2$ is a substituted or unsubstituted cyclopentyl, $Z^{100}$ is substituted or unsubstituted alkyl, $Z^{110}$ and $Z^{111}$ are each a covalent bond, then A is not —O—, —C(O)O—, or —N(R)—.

14. The compound of claim 13, wherein $Z^{100}$ is 2-pyrrolidinyl, benzoisoxazol-3-yl, 1,1-dioxybenzoisothiazol-3-yl, imidazo[1,2-a]pyridin-2-yl or

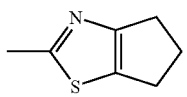

and $R_2$ is 4-(4-methylpiperazino)-cyclohexyl.

15. The compound of claim 14, wherein $Z^{110}$-A-$Z^{111}$ is —NH—.

16. The compound of claim 13, wherein $Z^{100}$ is a pyrrolopyridinyl selected from

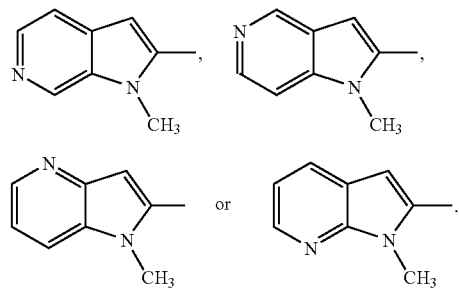

17. The compound of claim 16, wherein $Z^{110}$-A-$Z^{111}$ is —NHC(O)—.

18. The compound of claim 17, wherein $R_2$ is piperdin-4-yl, N-methylpiperidin-4-yl, N-(prop-2-yl)piperidin-4-yl, N-(imidazol-4-yl-methyl)piperidin-4-yl, N-(2-methylimidazol-4-yl-methyl)piperidin-4-yl, N-(pyrazol-4-yl-methyl)piperidin-4-yl, N-(2-methoxyethyl)piperidin-4-yl, N-(fur-3-yl-methyl)piperidin-4-yl, N-(tetrahydropyran-4-yl-methyl)piperidin-4-yl, N-(pyrrol-2-yl-methyl)piperidin-4-yl, or N-(2-difluoroethyl)piperidin-4-yl.

19. A compound of Formula (I)

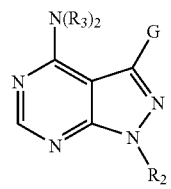

(I)

racemic-diastereomeric mixtures, optical isomers or pharmaceutically-acceptable salts thereof wherein:

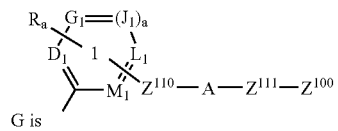

G is where $Z^{100}$ is

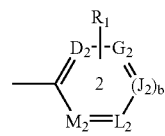

or a group optionally substituted with $R_1$ selected from the group consisting of alkyl, cycloalkyl, pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl,

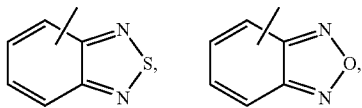

benzothiazolyl

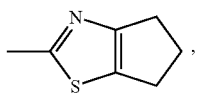, thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted ($C_1$-$C_6$) which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted ($C_1$-$C_6$) or an optionally substituted —$(CH_2)_n$-cycloalkyl-$(CH_2)_n$—; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, —C(O)O-aryl, —C(O)O-heteroaryl, —C(O)-alkyl, —C(O)-aryl, —C(O)-heteroaryl, substituted or unsubstituted cycloalkyl, substituted or unsubstituted heteroaryl, substituted or unsubstituted heteroarylalkoxy, substituted or unsubstituted arylalkoxy, substituted or unsubstituted alkyl-S(O)$_p$—, substituted or unsubstituted alkyl-S—, substituted or unsubstituted aryl-S(O)$_p$—, substituted or unsubstituted heteroaryl-S(O)$_p$—, and wherein at least one of $R_a$ and $R_1$ is not hydrogen;

$R_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

A is —($C_1$-$C_6$)—, —O—; —S—; —S(O)$_p$—; —N(R)—; —N(C(O)OR)—; —N(C(O)R)—; —N(SO$_2$R)—; —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)$_p$—; —OC(O)N(R)—; —N(R)—C(O)—(CH$_2$)$_n$—N(R)—, —N(R)C(O)O—; —N(R)—(CH$_2$)$_{n+1}$—C(O)—, —S(O)$_p$N(R)—; —O—(CR$_2$)$_{n+1}$—C(O)—; —O—(CR$_2$)$_{n+1}$—O—; —N(C(O)R)S(O)$_p$—; —N(R)S(O), N(R)—; —N(R)—C(O)—(CH$_2$)$_n$—O—; —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_b$)O—; —N(R)P(OR$_b$)—; —N(R)P(O)(OR$_b$)O—; —N(R)P(O)(OR$_b$)—; —N(C(O)R)P(OR$_b$)O—; —N(C(O)R)P(OR$_b$)—; —N(C(O)R)P(O)(OR$_b$)O—; or —N(C(O)R)P(OR$_b$)—;

where R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and $R_b$ together form a five- or six-membered heterocyclic ring; or A is NRSO$_2$ and R, $R_a$ and the nitrogen atom together form a substituted or unsubstituted five or -six-membered heterocyclic ring fused to ring 1; or $Z^{110}$-A-$Z^{111}$ taken together is a covalent bond; and $R_2$ is H or a group of the formula $Z^{101}$-$Z^{102}$;

$Z^{101}$ is a covalent bond, —($C_1$-$C_6$)—, —($C_1$-$C_6$)—O—, —($C_1$-$C_6$)—C(O)—, —($C_1$-$C_6$)—C(O)O—, —($C_1$-$C_6$)—C(O)—NH—, —($C_1$-$C_6$)—C(O)—N($C_1$-$C_6$)— or a substituted or unsubstituted phenyl group;

$Z^{102}$ is hydrogen; a substituted or unsubstituted alkyl group; a substituted or unsubstituted cycloalkyl group; a substituted or unsubstituted cycloalkenyl, a substituted or unsubstituted, saturated or unsaturated heterocyclic group; or a substituted or unsubstituted, saturated or unsaturated heterobicyclic group; wherein said substituted alkyl, substituted cycloalkyl, substituted cycloalkenyl, substituted heterocyclic and substituted heterobicyclic group having one or more substituents each independently selected from the group consisting of hydroxyl, cyano, nitro, halo, substituted or unsubstituted ($C_1$-$C_6$), substituted or unsubstituted aryl, substituted or unsubstituted —C(O)-alkyl, substituted or unsubstituted alkoxy, substituted or unsubstituted —N(R)—($C_1$-$C_6$)—OR, substituted or unsubstituted —N(($C_1$-$C_6$)—OR)$_2$, substituted or unsubstituted —N(R)—($C_1$-$C_6$)—C(O)$_2$R, substituted or unsubstituted —($C_1$-$C_6$)—N(R)—($C_1$-$C_6$)—OR, substituted or unsubstituted —($C_1$-$C_6$)—N(R)—($C_1$-$C_6$)—N(R)$_2$, substituted or unsubstituted —($C_1$-$C_6$)—C(O)N(R)—($C_1$-$C_6$)—N(R)$_2$, substituted or unsubstituted sulfonamido, substituted or unsubstituted ureido, substituted or unsubstituted carboxamido, substituted or unsubstituted amino, substituted or unsubstituted —N(R)—($C_1$-$C_6$)—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—($C_1$-$C_6$)—N(R)$_2$, —C(O)-alkyl, —C(O)-aryl, —C(O)-heteroaryl, substituted or unsubstituted arylalkyl group, or substituted or unsubstituted heteroarylalkyl; or $R_2$ is a group of the formula -B-E, wherein B is a substituted or unsubstituted cycloalkyl, substituted or unsubstituted aryl, substituted or unsubstituted heteroaryl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted alkyl, a substituted or unsubstituted cycloalkyl, substituted or unsubstituted azacycloalkyl, a substituted or unsubstituted heterocycloalkyl, substituted or unsubstituted ($C_1$-$C_6$)-azacycloalkyl-, substituted or unsubstituted azacycloalkylcarbonyl, substituted or unsubstituted azacycloalkylsulfonyl, substituted or unsubstituted azacycloalkylalkyl, substituted or unsubstituted heteroaryl-N(R)—($C_1$-$C_6$)—, substituted or unsubstituted aryl-N(R)—($C_1$-$C_6$)—, substituted or unsubstituted alkyl-N(R)—($C_1$-$C_6$)—, substituted or unsubstituted heteroaryl-($C_1$-$C_6$)—N(R)—, substituted or unsubstituted aryl-($C_1$-$C_6$)—N(R)—, substituted or unsubstituted alkyl-($C_1$-$C_6$)—N(R)—, substituted or unsubstituted heteroaryl, substituted or unsubstituted heteroarylcarbonyl, substituted or unsubstituted alkylcarbonyl, substituted or unsubstituted arylcarbonyl, substituted or unsubstituted heteroarylsulfonyl, substituted or unsubstituted alkylsulfonyl, substituted or unsubstituted arylsulfonyl, substituted or unsubstituted heteroarylalkyl, substituted or unsubstituted arylalkyl, substituted or unsubstituted azacycloalkylcarbonylamino, substituted or unsubstituted heteroarylcarbonylamino, substituted or unsubstituted arylcarbonylamino, substituted or unsubstituted alkylcarbonylamino or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

provided that when A is —N(R)—, $Z^{110}$ and $Z^{111}$ are each a covalent bond, and $R_2$ is a 3,4-dihydroxytetrahydrofur-2-yl or a 3,4-diacyloxytetrahydrofur-2-yl, then $Z^{100}$ is not alkyl, tetrahydropyranyl, tetrahydrofuranyl, piperidinyl or pyrrolidinyl;

provided that when $Z^{110}$ and $Z^{111}$ are each a covalent bond, and $R_2$ is a 3,4-dihydroxytetrahydrofur-2-yl or a 3,4-diacyloxytetrahydrofur-2-yl, $Z^{100}$ is a substituted or unsubstituted alkyl, then A is not alkyl, —O—, —C(O)—, —NHC(O)— or —C(O)O—;

provided that when $Z^{110}$-A-$Z^{111}$ taken together are a covalent bond, then $Z^{100}$ is not alkyl;

provided that when $Z^{110}$-A-$Z^{111}$ taken together are a $C_1$-$C_6$ alkyl, then $Z^{100}$ is not phenyl, pyrrolyl, imidazolyl, pyrazolyl, pyridinyl, pyrimidinyl, pyrazinyl, pyridazinyl, furyl or thienyl; and provided that when $R_2$ is a substituted or unsubstituted cyclopentyl, $Z^{100}$ is an substituted or unsubstituted alkyl, $Z^{110}$ and $Z^{111}$ are each a covalent bond, then A is not —O—, —C(O)O—, or —N(R)—.

20. A compound of Formula (I)

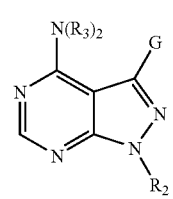

(I)

racemic-diastereomeric mixtures, optical isomers, pharmaceutically-acceptable salts thereof wherein:

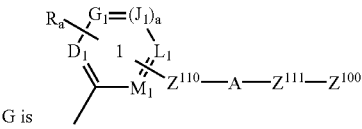

G is where $Z^{100}$ is

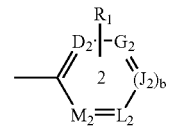

or a group optionally substituted with $R_1$ selected from the group consisting of alkyl, cycloalkyl, pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl, benzothiazolyl,

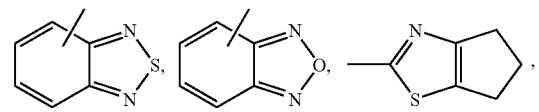

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted ($C_1$-$C_6$) which is optionally substituted with one or more substituents selected from the group consisting of alkyl, CN, OH, halogen, NO$_2$, COOH, substituted or unsubstituted amino and substituted or unsubstituted phenyl;

$Z^{111}$ is a covalent bond, an optionally substituted (C$_1$-C$_6$) or an optionally substituted —(CH$_2$)$_n$-cycloalkyl-(CH$_2$)$_n$—; where the optionally substituted groups are optionally substituted with one or more substituents selected from the group consisting of alkyl, CN, OH, halogen, NO$_2$, COOH, substituted or unsubstituted amino and substituted or unsubstituted phenyl;

R$_a$ and R$_1$ each represent one or more substituents for each occurrence independently selected from the group consisting of hydrogen, halogen, —CN, —NO$_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-S(O)$_p$—, substituted or unsubstituted alkyl-S—, substituted or unsubstituted aryl-S(O)$_p$—, substituted or unsubstituted heteroaryl-S(O)$_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, -Z$^{105}$—C(O)N(R)$_2$, -Z$^{105}$-N(R)—C(O)-Z$^{200}$, -Z$^{105}$-N(R)—S(O)$_2$-Z$^{200}$, -Z$^{105}$-N(R)—C(O)—N(R)Z$^{200}$, R$_c$ and CH$_2$OR$_c$;

where R$_c$ for each occurrence is independently hydrogen, substituted or unsubstituted alkyl, substituted or unsubstituted aryl, —CH$_2$—NR$_d$R$_e$, —W—(CH$_2$)$_t$—NR$_d$R$_e$, —W—(CH$_2$)$_t$—O-alkyl, —W—(CH$_2$)$_t$—S-alkyl, or —W—(CH$_2$)$_t$—OH;

$Z^{105}$ for each occurrence is independently a covalent bond or (C$_1$-C$_6$);

$Z^{200}$ for each occurrence is independently a substituted or unsubstituted (C$_1$-C$_6$), substituted or unsubstituted phenyl or substituted or unsubstituted —(C$_1$-C$_6$)-phenyl;

R$_d$ and R$_e$ for each occurrence are independently H, alkyl, alkanoyl or SO$_2$-alkyl; or R$_d$, R$_e$ and the nitrogen atom to which they are attached together form a five- or six-membered heterocyclic ring;

t for each occurrence is independently an integer from 2 to 6;

W for each occurrence is independently a direct bond or O, S, S(O), S(O)$_2$, or NR$_f$, wherein R$_f$ for each occurrence is independently H or alkyl; or R$_1$ is a substituted or unsubstituted carbocyclic or heterocyclic ring fused with ring 2;

R$_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

A is —(C$_1$-C$_6$)—;

R for each occurrence is independently H, substituted or unsubstituted alkyl, substituted or unsubstituted arylalkyl or substituted or unsubstituted aryl;

p is 1 or 2;

R$_2$ is H or a group of the formula Z$^{101}$-Z$^{102}$;

$Z^{101}$ is a covalent bond, —(C$_1$-C$_6$)—, —(C$_1$-C$_6$)—O—, —(C$_1$-C$_6$)—C(O)—, —(C$_1$-C$_6$)—C(O)O—, —(C$_1$-C$_6$)—C(O)—NH—, —(C$_1$-C$_6$)—C(O)—N((C$_1$-C$_6$))— or a substituted or unsubstituted phenyl group;

$Z^{102}$ is hydrogen; a substituted or unsubstituted alkyl group; a substituted or unsubstituted cycloalkyl group; a substituted or unsubstituted cycloalkenyl; a substituted or unsubstituted, saturated or unsaturated heterocyclic group; or a substituted or unsubstituted, saturated or unsaturated heterobicyclic group; wherein said substituted alkyl, substituted cycloalkyl, substituted cycloalkenyl, substituted heterocyclic and substituted heterobicyclic group having one or more substituents each independently selected from the group consisting of hydroxyl, cyano, nitro, halo, substituted or unsubstituted (C$_1$-C$_6$), substituted or unsubstituted aryl, substituted or unsubstituted —C(O)-alkyl, substituted or unsubstituted alkoxy, substituted or unsubstituted —N(R)—(C$_1$-C$_6$)—OR, substituted or unsubstituted —N((C$_1$-C$_6$)—OR)$_2$, substituted or unsubstituted —N(R)—(C$_1$-C$_6$)—C(O)$_2$R, substituted or unsubstituted —(C$_1$-C$_6$)—N(R)—(C$_1$-C$_6$)—OR, substituted or unsubstituted —(C$_1$-C$_6$)—N(R)—(C$_1$-C$_6$)—N(R)$_2$, substituted or unsubstituted —(C$_1$-C$_6$)—C(O)N(R)—(C$_1$-C$_6$)—N(R)$_2$, substituted or unsubstituted sulfonamido, substituted or unsubstituted ureido, substituted or unsubstituted carboxamido, substituted or unsubstituted amino, substituted or unsubstituted —N(R)—(C$_1$-C$_6$)—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—(C$_1$-C$_6$)—N(R)$_2$, —C(O)-alkyl, —C(O)-aryl, —C(O)-heteroaryl, substituted or unsubstituted arylalkyl group, or substituted or unsubstituted heteroarylalkyl; or R$_2$ is a group of the formula -B-E, wherein B is a substituted or unsubstituted cycloalkyl, substituted or unsubstituted aryl, substituted or unsubstituted heteroaryl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted alkyl, a substituted or unsubstituted cycloalkyl, substituted or unsubstituted azacycloalkyl, a substituted or unsubstituted heterocycloalkyl, substituted or unsubstituted (C$_1$-C$_6$)-azacycloalkyl-, substituted or unsubstituted azacycloalkylcarbonyl, substituted or unsubstituted azacycloalkylsulfonyl, substituted or unsubstituted azacycloalkylalkyl, substituted or unsubstituted heteroaryl-N(R)—($C_1$-$C_6$)—, substituted or unsubstituted aryl-N(R)—($C_1$-$C_6$)—, substituted or unsubstituted alkyl-N(R)—($C_1$-$C_6$)—, substituted or unsubstituted heteroaryl-($C_1$-$C_6$)—N(R)—, substituted or unsubstituted aryl-($C_1$-$C_6$)—N(R)—, substituted or unsubstituted alkyl-($C_1$-$C_6$)—N(R)—, substituted or unsubstituted heteroaryl, substituted or unsubstituted heteroarylcarbonyl, substituted or unsubstituted alkylcarbonyl, substituted or unsubstituted arylcarbonyl, substituted or unsubstituted heteroarylsulfonyl, substituted or unsubstituted alkylsulfonyl, substituted or unsubstituted arylsulfonyl, substituted or unsubstituted heteroarylalkyl, substituted or unsubstituted arylalkyl, substituted or unsubstituted azacycloalkylcarbonylamino, substituted or unsubstituted heteroarylcarbonylamino, substituted or unsubstituted arylcarbonylamino, substituted or unsubstituted alkylcarbonylamino or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

provided that when $Z^{110}$-A-$Z^{111}$ taken together are a $C_1$-$C_6$ alkyl, then $Z^{100}$ is not phenyl, pyrrolyl, imidazolyl, pyrazolyl, pyridinyl, pyrimidinyl, pyrazinyl, pyridazinyl, furyl or thienyl.

21. A compound of Formula (I)

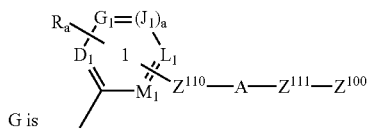

(I)

racemic-diastereomeric mixtures, optical isomers, pharmaceutically-acceptable salts thereof wherein:

G is 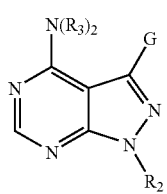

where $Z^{100}$ is

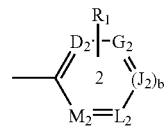

or a group optionally substituted with $R_1$ selected from the group consisting of pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl, benzothiazolyl,

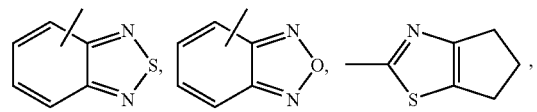

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-S(O)$_p$—, substituted or unsubstituted alkyl-S—, substituted or unsubstituted aryl-S(O)$_p$—, substituted or unsubstituted heteroaryl-S(O)$_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, -$Z^{105}$-C(O)N(R)$_2$, -$Z^{105}$-N(R)—C(O)-$Z^{200}$, -$Z^{105}$-N(R)—S(O)$_2$-$Z^{200}$, -$Z^{105}$-N(R)—C(O)—N(R)-$Z^{200}$, $R_c$ and $CH_2OR_c$;

where $R_c$ for each occurrence is independently hydrogen, substituted or unsubstituted alkyl, substituted or unsubstituted aryl, $CH_2NR_dR_e$, —W—(CH$_2$)$_t$—NR$_d$R$_e$, —W—(CH$_2$)$_t$—O-alkyl, —W—(CH$_2$)$_t$—S-alkyl, or —W—(CH$_2$)$_t$,OH;

$Z^{105}$ for each occurrence is independently a covalent bond or ($C_1$-$C_6$);

$Z^{200}$ for each occurrence is independently a substituted or unsubstituted ($C_1$-$C_6$), substituted or unsubstituted phenyl or substituted or unsubstituted —($C_1$-$C_6$)-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), S(O)$_2$, or $NR_f$, wherein $R_f$ for each occurrence is independently H or alkyl; or $R_1$ is a substituted or unsubstituted carbocyclic or heterocyclic ring fused with ring 2;

$R_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

R for each occurrence is independently H, substituted or unsubstituted alkyl, substituted or unsubstituted arylalkyl or substituted or unsubstituted aryl;

p is 1 or 2;

$Z^{110}$-A-$Z^{111}$ taken together is a covalent bond; and $R_2$ is H or a group of the formula -$Z^{101}$-$Z^{102}$;

$Z^{101}$ is a covalent bond, —($C_1$-$C_6$)—, —($C_1$-$C_6$)—O—, —($C_1$-$C_6$)—C(O)—, —($C_1$-$C_6$)—C(O)O—, —($C_1$-$C_6$)—C(O)—NH—, —($C_1$-$C_6$)—C(O)—N(($C_1$-$C_6$))— or a substituted or unsubstituted phenyl group;

$Z^{102}$ is hydrogen; a substituted or unsubstituted alkyl group; a substituted or unsubstituted cycloalkyl group; a substituted or unsubstituted cycloalkenyl, a substituted or unsubstituted, saturated or unsaturated heterocyclic group; or a substituted or unsubstituted, saturated or unsaturated heterobicyclic group; wherein said substituted alkyl, substituted cycloalkyl, substituted cycloalkenyl, substituted heterocyclic and substituted heterobicyclic group having one or more substituents each independently selected from the group consisting of hydroxyl, cyano, nitro, halo, substituted or unsubstituted ($C_1$-$C_6$), substituted or unsubstituted aryl, substituted or unsubstituted —C(O)-alkyl, substituted or unsubstituted alkoxy, substituted or unsubstituted —N(R)—($C_1$-$C_6$)—OR, substituted or unsubstituted —N(($C_1$-$C_6$)—OR)$_2$, substituted or unsubstituted —N(R)—($C_1$-$C_6$)—C(O)$_2$R, substituted or unsubstituted —($C_1$-$C_6$)—N(R)—(C—$C_6$)—OR, substituted or unsubstituted —($C_1$-$C_6$)—N(R)—($C_1$-$C_6$)—N(R)$_2$, substituted or unsubstituted —($C_1$-$C_6$)—C(O)N(R)—($C_1$-$C_6$)—N(R)$_2$, substituted or unsubstituted sulfonamido, substituted or unsubstituted ureido, substituted or unsubstituted carboxamido, substituted or unsubstituted amino, substituted or unsubstituted —N(R)—($C_1$-$C_6$)—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—($C_1$-$C_6$)—N(R)$_2$, —C(O)-alkyl, —C(O)-aryl, —C(O)-heteroaryl, substituted or unsubstituted arylalkyl group, or substituted or unsubstituted heteroarylalkyl; or $R_2$ is a group of the formula -B-E, wherein B is a substituted or unsubstituted cycloalkyl, substituted or unsubstituted aryl, substituted or unsubstituted heteroaryl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted alkyl, a substituted or unsubstituted cycloalkyl, substituted or unsubstituted azacycloalkyl, a substituted or unsubstituted heterocycloalkyl, substituted or unsubstituted ($C_1$-$C_6$)-azacycloalkyl-, substituted or unsubstituted azacycloalkylcarbonyl, substituted or unsubstituted azacycloalkylsulfonyl, substituted or unsubstituted azacycloalkylalkyl, substituted or unsubstituted heteroaryl-N(R)—($C_1$-$C_6$)—, substituted or unsubstituted aryl-N(R)—($C_1$-$C_6$)—, substituted or unsubstituted alkyl-N(R)—($C_1$-$C_6$)—, substituted or unsubstituted heteroaryl-($C_1$-$C_6$)—N(R)—, substituted or unsubstituted aryl-($C_1$-$C_6$)—N(R)—, substituted or unsubstituted alkyl-($C_1$-$C_6$)—N(R)—, substituted or unsubstituted heteroaryl, substituted or unsubstituted heteroarylcarbonyl, substituted or unsubstituted alkylcarbonyl, substituted or unsubstituted arylcarbonyl, substituted or unsubstituted heteroarylsulfonyl, substituted or unsubstituted alkylsulfonyl, substituted or unsubstituted arylsulfonyl, substituted or unsubstituted heteroarylalkyl, substituted or unsubstituted arylalkyl, substituted or unsubstituted azacycloalkylcarbonylamino, substituted or unsubstituted heteroarylcarbonylamino, substituted or unsubstituted arylcarbonylamino, substituted or unsubstituted alkylcarbonylamino or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6.

22. A compound of Formula (I)

(I)

racemic-diastereomeric mixtures, optical isomers, pharmaceutically-acceptable salts thereof wherein:

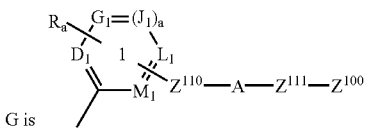

G is where $Z^{100}$ is

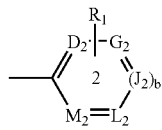

or a group optionally substituted with $R_1$ selected from the group consisting of alkyl, cycloalkyl, pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl, benzothiazolyl,

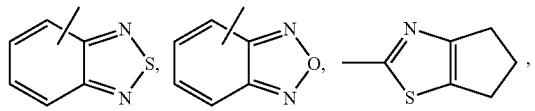

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted $(C_1-C_6)$ which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted $(C_1-C_6)$ or an optionally substituted $—(CH_2)_n$-cycloalkyl-$(CH_2)_n—$; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-$S(O)_p$—, substituted or unsubstituted alkyl-S—, substituted or unsubstituted aryl-$S(O)_p$—, substituted or unsubstituted heteroaryl-$S(O)_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, $-Z^{105}-C(O)N(R)_2$, $-Z^{105}-N(R)—C(O)-Z^2$, $-Z^{105}-N(R)—S(O)_2Z^{200}$, $-Z^{105}-N(R)—C(O)—N(R)-Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—O-alkyl, —W—$(CH_2)_t$-S-alkyl, or —W—$(CH_2)_t$—OH;

$Z^{105}$ for each occurrence is independently a covalent bond or $(C_1-C_6)$;

$Z^{200}$ for each occurrence is independently a substituted or unsubstituted $(C_1-C_6)$, substituted or unsubstituted phenyl or substituted or unsubstituted —$(C_1-C_6)$-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$, wherein $R_f$ for each occurrence is independently H or alkyl; or $R_1$ is a substituted or unsubstituted carbocyclic or heterocyclic ring fused with ring 2;

$R_3$ for each occurrence is, independently, substituted or unsubstituted —C(O)-alkyl, a substituted or unsubstituted —C(O)-aryl, or a substituted or unsubstituted —C(O)-heteroaryl;

A is —$(C_1-C_6)$—; —S—; —$S(O)_p$—; —N(R)—; —N(C(O)R)—; —N(C(O)R)—; —$N(SO_2R)$—; —$CH_2O$—; —$CH_2S$—; —$CH_2N(R)$—; —CH(NR)—; —$CH_2N(C(O)R))$—; —$CH_2N(C(O)OR)$—; —$CH_2N(SO_2R)$—; —CH(NHR)—; —CH(NHC(O)R)—; —$CH(NHSO_2R)$—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —$N(R)S(O)_p$—; —OC(O)N(R)—; —N(R)—C(O)—$(CH_2)_n$—N(R)—; —N(R)C(O)O—; —N(R)—$(CH_2)_{n+1}$—C(O)—; —$S(O)_pN(R)$—; —O—$(CR_2)_{n+1}$—C(O)—, O—$(CR_2)_{n+1}$—O—; —$N(C(O)R)S(O)_p$—; —$N(R)S(O)_pN(R)$—; —N(R)—C(O)—$(CH_2)_n$—O—, —C(O)N(R)C(O)—; —$S(O)_pN(R)C(O)$—; —$OS(O)_pN(R)$—; —$N(R)S(O)_pO$—; —$N(R)S(O)_pC(O)$—; —$SO_pN(C(O)R)$—; —$N(R)SO_pN(R)$—; —C(O)O—; —$N(R)P(OR_b)O$—; —$N(R)P(OR_b)$—; —$N(R)P(O)(OR_b)O$—; —$N(R)P(O)(OR_b)$—; —$N(C(O)R)P(OR_b)O$—; —$N(C(O)R)P(OR_b)$—; —$N(C(O)R)P(O)(OR_b)O$—; or —$N(C(O)R)P(OR_b)$—;

where R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and $R_b$ together form a five- or six-membered heterocyclic ring; or A is $NRSO_2$ and R, $R_a$ and the nitrogen atom together form a substituted or unsubstituted five or -six-membered heterocyclic ring fused to ring 1; or $Z^{110}$-A-$Z^{111}$ taken together is a covalent bond; and $R_2$ is H or a group of the formula -$Z^{101}$-$Z^{102}$;

$Z^{101}$ is a covalent bond, —$(C_1$-$C_6)$—, —$(C_1$-$C_6)$—O—, —$(C_1$-$C_6)$—C(O)—, —$(C_1$-$C_6)$—C(O)O—, —$(C_1$-$C_6)$—C(O)—NH—, —$(C_1$-$C_6)$—C(O)—N$((C_1$-$C_6))$— or a substituted or unsubstituted phenyl group;

$Z^{102}$ is hydrogen; a substituted or unsubstituted alkyl group; a substituted or unsubstituted cycloalkyl group; a substituted or unsubstituted cycloalkenyl, a substituted or unsubstituted, saturated or unsaturated heterocyclic group; or a substituted or unsubstituted, saturated or unsaturated heterobicyclic group; wherein said substituted alkyl, substituted cycloalkyl, substituted cycloalkenyl, substituted heterocyclic and substituted heterobicyclic group having one or more substituents each independently selected from the group consisting of hydroxyl, cyano, nitro, halo, substituted or unsubstituted ($C_1$-$C_6$), substituted or unsubstituted aryl, substituted or unsubstituted —C(O)-alkyl, substituted or unsubstituted alkoxy, substituted or unsubstituted —N(R)—$(C_1$-$C_6)$—OR, substituted or unsubstituted —N$((C_1$-$C_6)$—OR$)_2$, substituted or unsubstituted —N(R)—$(C_1$-$C_6)$—C(O)$_2$R, substituted or unsubstituted —$(C_1$-$C_6)$—N(R)—$(C_1$-$C_6)$—OR, substituted or unsubstituted —$(C_1$-$C_6)$—N(R)—$(C_1$-$C_6)$—N(R)$_2$, substituted or unsubstituted —$(C_1$-$C_6)$—C(O)N(R)—$(C_1$-$C_6)$—N(R)$_2$, substituted or unsubstituted sulfonamido, substituted or unsubstituted ureido, substituted or unsubstituted carboxamido, substituted or unsubstituted amino, substituted or unsubstituted —N(R)—$(C_1$-$C_6)$—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—$(C_1$-$C_6)$—N(R)$_2$, —C(O)-alkyl, —C(O)-aryl, —C(O)-heteroaryl, substituted or unsubstituted arylalkyl group, or substituted or unsubstituted heteroarylalkyl; or $R_2$ is a group of the formula -B-E, wherein B is a substituted or unsubstituted cycloalkyl, substituted or unsubstituted aryl, substituted or unsubstituted heteroaryl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted alkyl, a substituted or unsubstituted cycloalkyl, substituted or unsubstituted azacycloalkyl, a substituted or unsubstituted heterocycloalkyl, substituted or unsubstituted ($C_1$-$C_6$)-azacycloalkyl-, substituted or unsubstituted azacycloalkylcarbonyl, substituted or unsubstituted azacycloalkylsulfonyl, substituted or unsubstituted azacycloalkylalkyl, substituted or unsubstituted heteroaryl-N(R)—$(C_1$-$C_6)$—, substituted or unsubstituted aryl-N(R)—$(C_1$-$C_6)$—, substituted or unsubstituted alkyl-N(R)—$(C_1$-$C_6)$—, substituted or unsubstituted heteroaryl-$(C_1$-$C_6)$—N(R)—, substituted or unsubstituted aryl-$(C_1$-$C_6)$—N(R)—, substituted or unsubstituted alkyl-$(C_1$-$C_6)$—N(R)—, substituted or unsubstituted heteroaryl, substituted or unsubstituted heteroarylcarbonyl, substituted or unsubstituted alkylcarbonyl, substituted or unsubstituted arylcarbonyl, substituted or unsubstituted heteroarylsulfonyl, substituted or unsubstituted alkylsulfonyl, substituted or unsubstituted arylsulfonyl, substituted or unsubstituted heteroarylalkyl, substituted or unsubstituted arylalkyl, substituted or unsubstituted azacycloalkylcarbonylamino, substituted or unsubstituted heteroarylcarbonylamino, substituted or unsubstituted arylcarbonylamino, substituted or unsubstituted alkylcarbonylamino or substituted or unsubstituted aryl;

a is 1 and $D_1$, $G_0$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

provided that when A is —N(R)—, $Z^{110}$ and $Z^{111}$ are each a covalent bond, and $R_2$ is a 3,4-dihydroxytetrahydrofur-2-yl or a 3,4-diacyloxytetrahydrofur-2-yl, then $Z^{100}$ is not alkyl, tetrahydropyranyl, tetrahydrofuranyl, piperidinyl or pyrrolidinyl;

provided that when $Z^{110}$ and $Z^{111}$ are each a covalent bond, and $R_2$ is a 3,4-dihydroxytetrahydrofur-2-yl or a 3,4-diacyloxytetrahydrofur-2-yl, $Z^{100}$ is a substituted or unsubstituted alkyl, then A is not alkyl, —O—, —C(O)—, —NHC(O)— or —C(O)O—;

provided that when $Z^{110}$-A-$Z^{111}$ taken together are a covalent bond, then $Z^{100}$ is not alkyl;

provided that when $Z^{110}$-A-$Z^{111}$ taken together are a $C_1$-$C_6$ alkyl, then $Z^{100}$ is not phenyl, pyrrolyl, imidazolyl, pyrazolyl, pyridinyl, pyrimidinyl, pyrazinyl, pyridazinyl, furyl or thienyl; and provided that when $R_2$ is a substituted or unsubstituted cyclopentyl, $Z^{100}$ is an substituted or unsubstituted alkyl, $Z^{110}$ and $Z^{111}$ are each a covalent bond, then A is not —O—, —C(O)O—, or —N(R)—.

23. A compound of Formula (1)

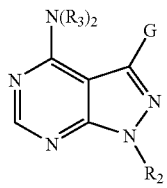

racemic-diastereomeric mixtures, optical isomers, pharmaceutically-acceptable salts thereof wherein:

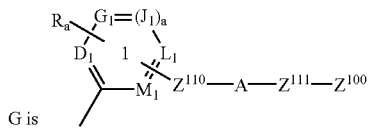

G is where $Z^{100}$ is

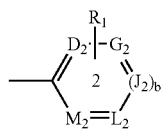

or a group optionally substituted with $R_1$ selected from the group consisting of alkyl, cycloalkyl, pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl, benzothiazolyl,

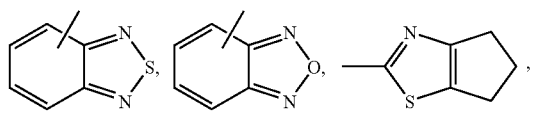

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted $(C_1-C_6)$ which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted $(C_1-C_6)$ or an optionally substituted $-(CH_2)_n$-cycloalkyl-$(CH_2)_n-$; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-$S(O)_p-$, substituted or unsubstituted alkyl-S—, substituted or unsubstituted aryl-$S(O)_p-$, substituted or unsubstituted heteroaryl-$S(O)_p-$, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, $-Z^{105}$-$C(O)N(R)_2$, $-Z^{105}$-$N(R)$—$C(O)$-$Z^{200}$, $-Z^{105}$-$N(R)$—$S(O)$ $Z^{200}$, $-Z^{105}N(R)$—$C(O)$—$N(R)$-$Z^{200}$, $R_c$ and $CH_2OR_c$;

where $R_c$ for each occurrence is independently hydrogen, substituted or unsubstituted alkyl, substituted or unsubstituted aryl, $CH_2NR_dR_e$, —W—$(CH_2)_tNR_dR_e$, —W—$(CH_2)_t$—O-alkyl, —W—$(CH_2)_{r7}$S-alkyl, or —W—$(CH_2)_t$—OH;

$Z^{105}$ for each occurrence is independently a covalent bond or $(C_1-C_6)$;

$Z^{200}$ for each occurrence is independently a substituted or unsubstituted $(C_1-C_6)$, substituted or unsubstituted phenyl or substituted or unsubstituted —$(C_1-C_6)$-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$, wherein $R_f$ for each occurrence is independently H or alkyl; or $R_1$ is a substituted or unsubstituted carbocyclic or heterocyclic ring fused with ring 2;

$R_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

A is —$(C_1-C_6)$—; —O—; —S—; —$S(O)_p$—; —N(R)—; —N(C(O)OR)—; —N(C(O)R)—; —N($SO_2$R)—; —$CH_2$O—; —$CH_2$S—; —$CH_2$N(R)—; —CH(NR)—; —$CH_2$N(C(O)R))—; —$CH_2$N(C(O)OR)—; —$CH_2$N($SO_2$R)—; —CH(NHR)—; —CH(NHC(O)R)—; —CH(NHS$O_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)$_p$—; —OC(O)N(R)—; —N(R)—C(O)—$(CH_2)_n$—N(R)—; —N(R)C(O)O—; —N(R)—$(CH_2)_{n+1}$—C(O)—; —$S(O)_p$N(R)—; —O—$(CR_2)_{n+1}$—C(O)—; —O—$(CR_2)_{n+1}$—

O—; —N(C(O)R)S(O)$_p$—; —N(R)S(O)$_p$N(R)—; —N(R)—C(O)—(CH$_2$)$_n$—O—; —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_2$N(C(O)R)—; —N(R)SO$_p$N(R)—; —C(O)O—; —N(R)P(OR$_b$)O—; —N(R)P(OR$_b$)—; —N(R)P(O)(OR$_b$)O—; —N(R)P(O)(OR$_b$)—; —N(C(O)R)P(OR$_b$)O—; —N(C(O)R)P(OR$_b$)—; —N(C(O)R)P(O)(OR$_b$)O—, or —N(C(O)R)P(OR$_b$)—;

where R for each occurrence is independently H. substituted or unsubstituted alkyl, substituted or unsubstituted arylalkyl or substituted or unsubstituted aryl;

R$_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and R$_b$ together form a five- or six-membered heterocyclic ring; or A is NRSO$_2$ and R, R$_a$ and the nitrogen atom together form a substituted or unsubstituted five or -six-membered heterocyclic ring fused to ring 1; or $Z^{110}$-A-$Z^{111}$ taken together is a covalent bond; and R$_2$ is a group of the formula -$Z^{101}$-$Z^{102}$;

$Z^{101}$ is a covalent bond, —(C$_1$-C$_6$)—, —(C$_1$-C$_6$)—O—, —(C$_1$-C$_6$)—C(O)—, —(C$_1$-C$_6$)—C(O)O—, —(C$_1$-C$_6$)—C(O)—NH—, —(C$_1$-C$_6$)—C(O)—N((C$_1$-C$_6$))— or a substituted or unsubstituted phenyl group;

$Z^{102}$ is a substituted or unsubstituted cycloalkenyl, wherein said substituted cycloalkenyl has one or more substituents each independently selected from the group consisting of hydroxyl, cyano, nitro, halo, substituted or unsubstituted (C$_1$-C$_6$), substituted or unsubstituted aryl, substituted or unsubstituted —C(O)-alkyl, substituted or unsubstituted alkoxy, substituted or unsubstituted —N(R)—(C$_1$-C$_6$)—OR, substituted or unsubstituted —N((C$_1$-C$_6$)—OR)$_2$, substituted or unsubstituted —N(R)—(C$_1$-C$_6$)—C(O)$_2$R, substituted or unsubstituted —(C$_1$-C$_6$)—N(R)—(C$_1$-C$_6$)—OR, substituted or unsubstituted —(C$_1$-C$_6$)—N(R)—(C$_1$-C$_6$)—N(R)$_2$, substituted or unsubstituted —(C$_1$-C$_6$)—C(O)N(R)—(C$_1$-C$_6$)—N(R)$_2$, substituted or unsubstituted sulfonamido, substituted or unsubstituted ureido, substituted or unsubstituted carboxamido, substituted or unsubstituted amino, substituted or unsubstituted —N(R)—(C$_1$-C$_6$)—OR, oxo, and a saturated, unsaturated or aromatic, substituted or unsubstituted heterocyclic group comprising one or more heteroatoms selected from the group consisting of N, O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—(C$_1$-C$_6$)—N(R)$_2$, —C(O)-alkyl, —C(O)-aryl, —C(O)-heteroaryl, substituted or unsubstituted arylalkyl group, or substituted or unsubstituted heteroarylalkyl;

a is 1 and D$_1$, G$_1$, J$_1$, L$_1$ and M$_1$ are each independently selected from the group consisting of CR$_a$ and N, provided that at least two of D$_1$, G$_1$, J$_1$, L$_1$ and M$_1$ are CR$_a$; or a is 0, and one of D$_1$, G$_1$, L$_1$ and M$_1$ is NR$_a$, one of D$_1$, G$_1$, L$_1$ and M$_1$ is CR$_a$ and the remainder are independently selected from the group consisting of CR$_a$ and N, wherein R$_a$ is as defined above;

b is 1 and D$_2$, G$_2$, J$_2$, L$_2$ and M$_2$ are each independently selected from the group consisting of CR$_a$ and N, provided that at least two of D$_2$, G$_2$, J$_2$, L$_2$ and M$_2$ are CR$_a$; or b is 0, and one of D$_2$, G$_2$, L$_2$ and M$_2$ is NR$_a$, one of D$_2$, G$_2$, L$_2$ and M$_2$ is CR$_a$ and the remainder are independently selected from the group consisting of CR$_a$ and N, wherein R$_a$ is as defined above; and n for each occurrence is independently an integer from 0 to 6.

24. A compound of Formula (I)

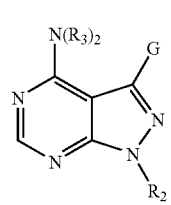

(I)

racemic-diastereomeric mixtures, optical isomers, pharmaceutically-acceptable salts thereof wherein:

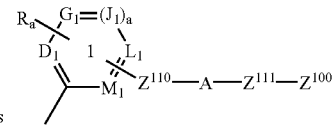

G is where $Z^{100}$ is

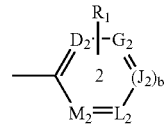

or a group optionally substituted with R$_1$ selected from the group consisting of alkyl, cycloalkyl, pyrrolidinyl, quinolinyl, quinoxalinyl, quinazolinyl, isoquinolinyl, phthalazinyl, imidazo[1,2-a]pyrimidinyl, 1H-imidazo[1,2-a]imidazolyl, imidazo[2,1-b][1,3]thiazolyl, naphthyl, tetrahydronaphthyl, benzothienyl, furanyl, thienyl, benzoxazolyl, benzoisoxazolyl, benzothiazolyl,

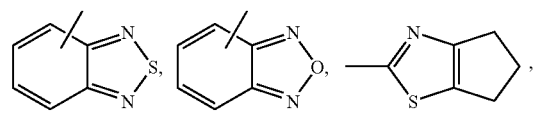

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, pyrrolopyridinyl, H-pyridinone, oxazolyl, isothiazolyl, oxadiazolyl, thiadiazolyl, indolinyl, indazolyl, imidazo[1,2-a]pyridinyl, benzoisothiazolyl, 1,1-dioxybenzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted (C$_1$-C$_6$) which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted ($C_1$-$C_6$) or an optionally substituted —$(CH_2)_n$-cycloalkyl-$(CH_2)_n$—; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, —C(O)O-aryl, —C(O)O-heteroaryl, —C(O)-alkyl, —C(O)-aryl, —C(O)-heteroaryl, substituted or unsubstituted carboxamido, tetrazolyl, trifluoromethylcarbonylamino, trifluoromethylsulfonamido, substituted or unsubstituted alkyl, substituted or unsubstituted cycloalkyl, substituted or unsubstituted alkoxy, substituted or unsubstituted aryl, substituted or unsubstituted heteroaryl, substituted or unsubstituted alkenyl, substituted or unsubstituted aryloxy, substituted or unsubstituted heteroaryloxy, substituted or unsubstituted heteroarylalkoxy, substituted or unsubstituted arylalkoxy, substituted or unsubstituted alkyl-$S(O)_p$—, substituted or unsubstituted alkyl-S—, substituted or unsubstituted aryl-$S(O)_p$—, substituted or unsubstituted heteroaryl-$S(O)_p$—, substituted or unsubstituted arylalkyl, substituted or unsubstituted heteroarylalkyl, substituted or unsubstituted cycloalkylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, -$Z^{105}$-C(O)N(R)$_2$, -$Z^{105}$-N(R)—C(O)-$Z^{200}$, -$Z^{105}$-N(R)—$S(O)_2$-$Z^{200}$, -$Z^{105}$-N(R)—C(O)—N(R)-$Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—O-alkyl, —W—$(CH_2)_t$—S-alkyl, or —W—$(CH_2)_t$—OH;

$Z^{105}$ for each occurrence is independently a covalent bond or ($C_1$-$C_6$);

$Z^{200}$ for each occurrence is independently a substituted or unsubstituted ($C_1$-$C_6$), substituted or unsubstituted phenyl or substituted or unsubstituted —($C_1$-$C_6$)-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring;

t for each occurrence is independently an integer from 2 to 6;

W for each occurrence is independently a direct bond or O, S, S(O), $S(O)_2$, or $NR_f$, wherein $R_f$ for each occurrence is independently H or alkyl; or $R_1$ is a substituted or unsubstituted carbocyclic or heterocyclic ring fused with ring 2;

$R_3$ for each occurrence is, independently, hydrogen, hydroxy, substituted or unsubstituted alkyl, substituted or unsubstituted —C(O)-alkyl, a substituted or unsubstituted —C(O)-aryl, or a substituted or unsubstituted —C(O)-heteroaryl or substituted or unsubstituted alkoxy;

A is —($C_1$-$C_6$)—; —O—; —S—; —$S(O)_p$—; —N(R)—; —N(C(O)OR)—; —N(C(O)R)—; —N($SO_2R$)—;
—$CH_2O$—; —$CH_2S$—; —$CH_2N(R)$—; —CH(NR)—; —$CH_2N(C(O)R))$—; —$CH_2N(C(O)OR)$—; —$CH_2N(SO_2R)$—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)$S(O)_p$—; —OC(O)N(R)—; —N(R)—C(O)—$(CH_2)_n$—N(R)—; —N(R)C(O)O—; —N(R)—$(CH_2)_{n+1}$—C(O)—; —$S(O)_pN(R)$—; —O—$(CR_2)_{n+1}$—C(O)—; —O—$(CR_2)_{n+1}$—O—; —N(C(O)R)$S(O)_p$—; —N(R)$S(O)_pN(R)$—; —N(R)—C(O)—$(CH_2)_n$—O—; —C(O)N(R)C(O)—; —$S(O)_pN(R)C(O)$—; —$OS(O)_pN(R)$—; —N(R)$S(O)_pO$—; —N(R)$S(O)_pC(O)$—; —$SO_pN(C(O)R)$—; —N(R)$SO_pN(R)$—; —C(O)O—; —N(R)P(OR$_b$)O—; —N(R)P(OR$_b$)—; —N(R)P(O)(OR$_b$)O—; —N(R)P(O)(OR$_b$)—; —N(C(O)R)P(OR$_b$)O—; —N(C(O)R)P(OR$_b$)—; —N(C(O)R)P(O)(OR$_b$)O—, or —N(C(O)R)P(OR$_b$)—;

where R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2; or in a phosphorus containing group, the nitrogen atom, the phosphorus atom, R and $R_b$ together form a five- or six-membered heterocyclic ring; or A is $NRSO_2$ and R, $R_a$ and the nitrogen atom together form a substituted or unsubstituted five or -six-membered heterocyclic ring fused to ring 1; or $Z^{110}$-A-$Z^{111}$ taken together is a covalent bond; and $R_2$ is a group of the formula -$Z^{101}$-$Z^{102}$;

$Z^{101}$ is a covalent bond, —($C_1$-$C_6$)—, —($C_1$-$C_6$)—O—, —($C_1$-$C_6$)—C(O)—, —($C_1$-$C_6$)—C(O)O—, —($C_1$-$C_6$)—C(O)—NH—, —($C_1$-$C_6$)—C(O)—N(($C_1$-$C_6$))— or a substituted or unsubstituted phenyl group;

$Z^{102}$ is a substituted, saturated or unsaturated heterocyclic group; or a substituted, saturated or unsaturated heterobicyclic group; wherein said substituted heterocyclic and substituted heterobicyclic group have one or more substituents each independently selected from the group consisting of nitro, halo, substituted or unsubstituted ($C_1$-$C_6$), substituted or unsubstituted aryl, substituted or unsubstituted —C(O)-alkyl, substituted or unsubstituted —N(R)—($C_1$-$C_6$)—OR, substituted or unsubstituted —N(($C_1$-$C_6$)—OR)$_2$, substituted or unsubstituted —N(R)—($C_1$-$C_6$)—C(O)$_2$R, substituted or unsubstituted —($C_1$-$C_6$)—N(R)—($C_1$-$C_6$)—OR, substituted or unsubstituted —($C_2$-$C_6$)—N(R)—(C—$C_6$)—N(R)$_2$, substituted or unsubstituted —($C_1$-$C_6$)—C(O)N(R)—($C_1$-$C_6$)—N(R)$_2$, substituted or unsubstituted —N(R)—($C_1$-$C_6$)—OR, and a substituted or unsubstituted heterocyclic group comprising one or more heteroatoms selected from the group consisting of O, and S; wherein the nitrogen atoms of said heterocyclic group or heterobicyclic group are independently optionally substituted by oxo, substituted or unsubstituted alkyl, substituted or unsubstituted aryl, substituted or unsubstituted heteroaryl, substituted or unsubstituted —C(O)N(R)$_2$, substituted or unsubstituted —C(O)—($C_1$-$C_6$)—N(R)$_2$, —C(O)-alkyl, —C(O)-aryl, —C(O)-heteroaryl, substituted or unsubstituted arylalkyl group, or substituted or unsubstituted heteroarylalkyl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6;

provided that when A is —N(R)—, $Z^{110}$ and $Z^{111}$ are each a covalent bond, and $R_2$ is a 3,4-diacyloxytetrahydrofur-2-yl, then $Z^{100}$ is not alkyl, tetrahydropyranyl, tetrahydrofuranyl, piperidinyl or pyrrolidinyl;

provided that when $Z^{110}$ and $Z^{111}$ are each a covalent bond, and $R_2$ is a 3,4-diacyloxytetrahydrofur-2-yl, $Z^{100}$ is a substituted or unsubstituted alkyl, then A is not alkyl, —O—, —C(O)—, —NHC(O)— or —C(O)O—;

provided that when $Z^{110}$-A-$Z^{111}$ taken together are a covalent bond, then $Z^{100}$ is not alkyl; and provided that when $Z^{110}$-A-$Z^{111}$ taken together are a $C_1$-$C_6$ alkyl, then $Z^{100}$ is not phenyl, pyrrolyl, imidazolyl, pyrazolyl, pyridinyl, pyrimidinyl, pyrazinyl, pyridazinyl, furyl or thienyl.

* * * * *

UNITED STATES PATENT AND TRADEMARK OFFICE
CERTIFICATE OF CORRECTION

PATENT NO. : 7,332,497 B2  
APPLICATION NO. : 10/104140  
DATED : February 19, 2008  
INVENTOR(S) : Gavin C. Hirst et al.

Page 1 of 2

It is certified that error appears in the above-identified patent and that said Letters Patent is hereby corrected as shown below:

Column 418, line 35 - replace "$Z^{11}$" with --$Z^{111}$--

Column 419, line 3 - replace "$Z^{2b}$" with --$Z^{200}$--

Column 419, line 7 - replace "-W-(CH$_2$)S-alkyl" with -- -W-(CH$_2$)-S-alkyl--

Column 419, line 31 - delete "-O-"

Column 420, line 1-2 - replace "-(C$_1$-C$_6$)- -O-," with -- -(C$_1$-C$_6$)-O-,--

Column 420, line 2 - replace "-(C$_1$-C$_6$)- -C(O)-," with -- -(C$_1$-C$_6$)-C(O)-,--

Column 420, line 21 - replace "_substituted" with --substituted--

Column 423, line 58 - replace "-CH$_2$N(C(O)R))-" with -- -CH$_2$N(C(O)R)- --

Column 423, line 67 - replace "-N(R)S(O), N(R)-" with -- -N(R)S(O)$_p$N(R)- --

Column 424, line 27-28 - replace "-(C$_1$-C$_6$)- -O-" with -- -(C$_1$-C$_6$)-O- --

Column 424, line 28 - replace "-(C$_1$-C$_6$)- -C(O)-" with -- -(C$_1$-C$_6$)-C(O)- --

Column 424, line 46 - replace "_substituted" with --substituted--

Column 428, line 8 - replace "-(C$_1$-C$_6$)- -C(O)-" with -- -(C$_1$-C$_6$)-C(O)- --

Column 428, line 8-9 - replace "-(C$_1$-C$_6$)- -C(O)O-" with -- -(C$_1$-C$_6$)-C(O)O- --

Column 428, line 27 - replace "_substituted" with --substituted--

Column 434, line 11 - replace "-$Z^{105}$-N(R)-C(O)-$Z^{2}$" with -- -$Z^{105}$-N(R)-C(O)-$Z^{200}$--

Column 438, line 59 - replace "-CH$_2$N(C(O)R))-" with -- -CH$_2$N(C(O)R)- --

Column 439, line 10 - replace "H." with --H,--

Column 442, line 37 - replace "-(C$_1$-C$_6$) –C(O)O-" with -- -(C$_1$-C$_6$)-C(O)O- --

UNITED STATES PATENT AND TRADEMARK OFFICE
CERTIFICATE OF CORRECTION

PATENT NO. : 7,332,497 B2
APPLICATION NO. : 10/104140
DATED : February 19, 2008
INVENTOR(S) : Gavin C. Hirst et al.

It is certified that error appears in the above-identified patent and that said Letters Patent is hereby corrected as shown below:

Column 442, line 52-53 -    replace "-$(C_2$-$C_6)$-$N(R)$-$(C$-$C_6)$-$N(R)_2$" with
-- -$(C_1$-$C_6)$-$N(R)$-$(C_1$-$C_6)$-$N(R)_2$--

Signed and Sealed this

Third Day of June, 2008

JON W. DUDAS
*Director of the United States Patent and Trademark Office*